US008815834B2

(12) United States Patent
Majoral et al.

(10) Patent No.: US 8,815,834 B2
(45) Date of Patent: Aug. 26, 2014

(54) USE OF DENDRIMERS TO STIMULATE CELL GROWTH

(75) Inventors: Jean-Pierre Majoral, Ramonville Saint Agne (FR); Anne-Marie Jeannine Jacqueline Caminade, Toulouse (FR); Jean-Jacques Fournie, Corronsac (FR); Laurent Griffe, Carcassonne (FR); Mary Poupot-Marsan, Aigrefeuille (FR); Rémy Poupot, Aigrefeuille (FR); Cédric-Olivier Turrin, Toulouse (FR)

(73) Assignees: Centre National de la Recherche Scientifique, Paris (FR); Institut National de la Sante et de la Recherche Medicale, Paris (FR); Rhodia UK Limited, Watford (GB)

( * ) Notice: Subject to any disclaimer, the term of this patent is extended or adjusted under 35 U.S.C. 154(b) by 1840 days.

(21) Appl. No.: 11/658,858

(22) PCT Filed: Jul. 29, 2005

(86) PCT No.: PCT/FR2005/002003
§ 371 (c)(1),
(2), (4) Date: May 31, 2007

(87) PCT Pub. No.: WO2006/024769
PCT Pub. Date: Mar. 9, 2006

(65) Prior Publication Data
US 2009/0142316 A1    Jun. 4, 2009

(30) Foreign Application Priority Data

Jul. 30, 2004  (FR) ..................................... 04 08426

(51) Int. Cl.
*A61K 31/66*    (2006.01)
*A61K 31/663*   (2006.01)
*A61K 31/675*   (2006.01)

(52) U.S. Cl.
CPC ............. *A61K 31/663* (2013.01); *A61K 31/675* (2013.01)
USPC .......................................................... 514/141

(58) Field of Classification Search
CPC ........................... A61K 31/663; A61K 31/675
USPC ......................................................... 514/141
See application file for complete search history.

(56) References Cited

FOREIGN PATENT DOCUMENTS

| WO | 01/38335  | 5/2001  |
| WO | 01/91816  | 12/2001 |
| WO | 02/067908 | 9/2002  |
| WO | 03/091304 | 11/2003 |

OTHER PUBLICATIONS

Launay et al (J Organometallic Chem 529:51-58, 1997).*
Prevote et al (J Org Chem 62:4834-4841, 1997).*
Baten et al (Carcinogenesis 10:1595-1598, 1989).*
"Phosphate-, phosphite-, ylide-, and phosphonate-terminated dendrimers", Journal of Organic Chemistry, vol. 62, No. 14, pp. 4834-4841, Jul. 11, 1997, XP002144559.
"Enhancement of thermal stability of polystyrene and poly(methyl methacrylate) by cyclotriphosphazene derivatives," Polymer Degradation and Stability, pp. 87-93, Apr. 2004, XP002320475.

* cited by examiner

*Primary Examiner* — Paul Zarek
(74) *Attorney, Agent, or Firm* — Young & Thompson

(57) ABSTRACT

The present invention relates to the use of dendrimers with monophosphonic or bisphosphonic terminations in order to stimulate the growth of cell cultures or to activate cells in culture.

18 Claims, 12 Drawing Sheets

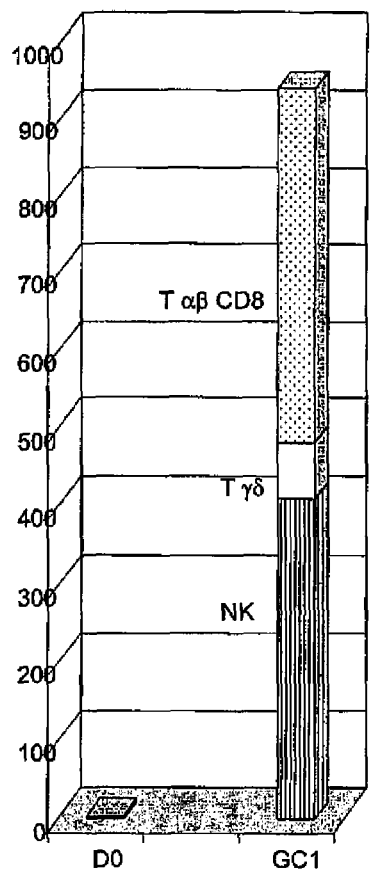
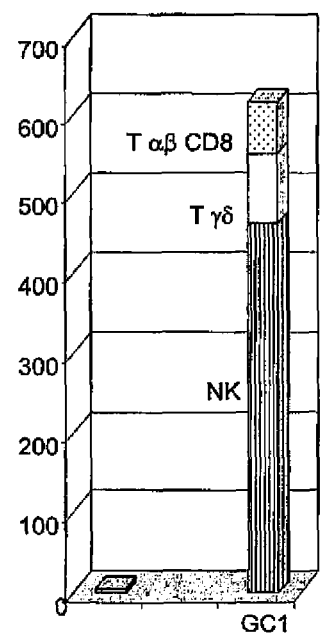
Figure 2A
Figure 2B
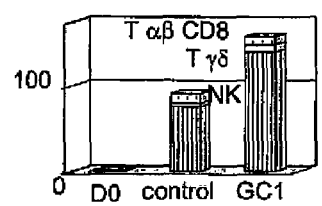
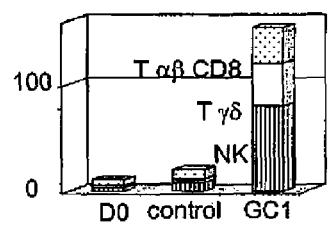
Figure 2C
Figure 2D

USE OF DENDRIMERS TO STIMULATE CELL GROWTH

FIELD OF THE INVENTION

The present invention relates to the use of dendrimers to stimulate cell growth.

Dendrimers are macromolecules constituted by monomers which combine according to a tree-like process around a plurifunctional central core.

BACKGROUD OF THE INVENTION

Dendrimers, also called "cascade molecules", are highly branched functional polymers with a defined structure. These macromolecules are effectively polymers since they are based on the combination of repeating units. However, dendrimers differ fundamentally from standard polymers to the extent that they have specific properties due to their tree-like construction. The molecular weight and the form of the dendrimers can be precisely controlled and all the functions are situated at the termination of the tree-like structures, forming a surface, which makes them easily accessible.

The dendrimers are constructed stage by stage, by the repetition of a sequence of reactions allowing the multiplication of each repeating unit and terminal functions. Each sequence of reactions forms what is called a "new generation". The tree-like construction is carried out by the repetition of a sequence of reactions which makes it possible to obtain a new generation and a growing number of identical branches at the end of each reaction cycle. After a few generations, the dendrimer generally assumes a highly branched and plurifunctionalized globular form due to the numerous terminal functions present at the periphery.

Such polymers have in particular been described by Launay et al., *Angew. Chem. Int. Ed. Engl.,* 1994, 33, 15/16, 1589-1592, or also Launay et al., *Journal of Organometallic Chemistry,* 1997, 529, 51-58.

At present, the proliferation of cells, in particular of cytotoxic cells, in particular of the NK type, is essentially induced, in vitro or in vivo, by cytokines, such as IL-2, IL-7, IL-15, IL-18, IL-21 or IFNα/β, as described in particular by Vivier et al., Immunologie des Cancers (2003) eds Médecine-Sciences Flammarion. These cytokines are in general used in the form of recombinant proteins. However, several obstacles limit their use. First of all, these compounds have a relatively high genetic engineering production cost. Moreover, their use in vivo, in particular in therapy in humans, comes up against high toxicity, linked to their pleiotropic action.

Compounds of plant or bacterial origin for example could optionally be sought in order to stimulate the growth of cells of the lymphoid line. However, the difficulties in obtaining pure natural molecules in significant quantities and the problems linked to the use of natural substances would limit their use in human therapy.

SUMMARY OF THE INVENTION

Thus one of the purposes of the present invention is to propose a novel process for the stimulation of cell growth using synthetic and essentially non-toxic compounds with low production costs.

Another purpose of the invention is to propose new synthetic compounds, which can be used for the stimulation of cell growth.

Another purpose of the invention is also to propose novel pharmaceutical compositions containing cells the cell growth of which has been stimulated by synthetic and essentially non-toxic compounds with low production costs.

Thus, the present invention relates to the use of dendrimers with monophosphonic or bisphosphonic terminations to stimulate the growth of cell cultures or to activate cells in culture.

The dendrimers used according to the invention are constituted by a core §, to which linkage chains are attached in a tree-like structure, said linkage chains being themselves constituted by generation chains, an intermediate chain being optionally attached to the end of each generation chain the furthest from the central core, monophosphonic or bisphosphonic groups being present at the ends not linked to the core of the linkage chains. For the sake of clarity, these elements are diagrammatically represented in FIG. 9.

According to the invention, the dendrimers with monophosphonic terminations, or monophosphonic dendrimers, have a terminal function —$PO(OX)_2$, and the dendrimers with bisphosphonic terminations, or bisphosphonic dendrimers, have two terminal functions —$PO(OX)_2$, at the termination of each tree-like structure, where X represents —H or an -alkyl, -aryl, -alkaryl or -aralkyl radical, or the corresponding salts, said salts being formed by the combination of monophosphonic or bisphosphonic terminations and cations. For a given phosphonic group the X groups can be identical or different.

The salts of the dendrimers can be prepared in situ during the final isolation and purification of the compounds. The salts can be prepared by separately reacting the purified compound in its acid form with an organic or inorganic base and by isolating the salt thus formed. The salts comprise aminated and metal salts. Suitable metal salts include sodium, potassium, copper, calcium, barium, zinc, magnesium and aluminium salts. Sodium and potassium salts are preferred. Suitable basic inorganic salts are prepared from metallic bases which include sodium hydride, sodium hydroxide, potassium hydroxide, calcium hydroxide, aluminium hydroxide, lithium hydroxide, magnesium hydroxide, zinc hydroxide.

Advantageously, according to a particular embodiment, the salts of the monophosphonic or bisphosphonic dendrimers used in the present invention are pharmaceutically acceptable.

According to the invention, the expression "to stimulate cell culture growth" means that the addition of the abovementioned dendrimers to a cell culture makes it possible to obtain a larger quantity of cells on completion of the culture than when this culture is carried out under the same conditions in the absence of said dendrimers.

Advantageously, the dendrimers with monophosphonic or bisphosphonic terminations can also cause, directly or indirectly, a cell differentiation and lead to the obtaining of novel cells, said novel cells being able in particular to be characterized by a specific combination of membrane markers and/or by a specific combination of level of expression of membrane markers. This phenomenon is known as "activation of the cells in culture".

In a particular embodiment of the use defined above, the cells in question are hematopoietic cells, i.e. cells originating from the differentiation of hematopoietic stem cells.

The present invention relates more particularly to the use, as defined above, of dendrimers with monophosphonic or bisphosphonic terminations for the preparation of cell compositions enriched with cells of the lymphoid line expressing the receptor NKG2D, from biological samples.

The enriched cell compositions according to the invention are characterized in that they contain a larger proportion of cells of the lymphoid line expressing the receptor NKG2D compared with the proportion of these same cells in the biological sample from which they originate.

Not all the cells of the lymphoid lines express this receptor, it is found more particularly at the surface of the cells involved in innate immunity and in particular at the surface of cells of NK (natural killer) type, of γδ T lymphocyte type, of CD8αβ T lymphocyte type (S. Bauer et al., *Science,* 1999, 285, 727-729; J. Wu, *Science,* 1999, 285, 730-732).

According to the invention, by "biological sample" is meant any sample of tissue taken from a living being. In particular whole blood and whole blood cell fractions, such as peripheral blood mononuclear cells (PBMC), are considered biological samples.

The main cell types found in PBMCs are T and B lymphocytes, NK cells, and monocyte type cells.

According to a particular embodiment of the invention, the dendrimers with monophosphonic or bisphosphonic terminations are of generation n and comprise a central core § with a valency of m which can establish m−2 bonds, providing that m is greater than 2, or m−1 bonds, providing that m is greater than 1, or m bonds with linkage chains, preferably identical to each other, which linkage chains are constituted by:
  generation chains attached in a tree-like structure around the core on each of the bonds, at least one intermediate chain being optionally attached to the end of each chain generation furthest from the central core, and a terminal group being attached to the end of each chain generation the furthest from the central core or if appropriate to the end of each intermediate chain, or
  intermediate chains attached around the core on each of the bonds, a terminal group being attached to the end of each intermediate chain;
said terminal group being represented by the formula:

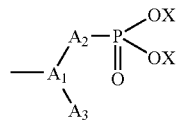

where
  $A_1$ represents N; a P=Y group, where Y represents O, S, or any atom; an N—R group; or a C—R group; R representing H or a linear, branched or cyclic hydrocarbon chain with 1 to 16 members, optionally containing one or more heteroatoms, said heteroatoms being preferably chosen from oxygen, sulphur, nitrogen, phosphorus, silicon and/or one or more double or triple bonds, each of said members being optionally substituted by at least one substituent chosen from a hydroxyl group, an —NR'R" group, an alkoxy group of 1 to 16 carbon atoms, an alkyl group of 1 to 16 carbon atoms, a halogen atom, an —NO$_2$ group, a —CN group, a —CF$_3$ group, an aryl group of 6 to 24 carbon atoms, an aralkyl group of 7 to 16 carbon atoms, R' and R" representing independently of each other H or an alkyl group of 1 to 16 carbon atoms, an aryl group of 6 to 24 carbon atoms or an aralkyl group of 7 to 16 carbon atoms;
  $A_2$ represents a single bond or a linear, branched or cyclic hydrocarbon chain with 1 to 6 members, each of said members optionally containing one or more heteroatoms, said heteroatoms being preferably chosen from a sulphur, oxygen, phosphorus or nitrogen atom, more preferably nitrogen, and being optionally substituted by at least one substituent chosen from H, an alkyl group of 1 to 16 carbon atoms, a halogen, an —NO$_2$ group, an —NRR' group, a —CN group, a —CF3 group, a hydroxyl group, an alkoxy group of 1 to 16 carbon atoms, an aryl or heteroaryl group of 1 to 24 carbon atoms, the heteroelement being preferably chosen from oxygen, nitrogen or sulphur, an aralkyl group of 7 to 16 carbon atoms, R and R' representing independently of each other H or a linear, branched or cyclic hydrocarbon chain with 1 to 16 members, optionally containing one or more heteroatoms, said heteroatoms being preferably chosen from oxygen, sulphur, nitrogen, phosphorus, silicon and/or one or more double or triple bonds, each of said members being optionally substituted by at least one substituent chosen from a hydroxyl group, an —NR"R'" group, an alkoxy group of 1 to 16 carbon atoms, an alkyl group of 1 to 16 carbon atoms, a halogen atom, an —NO$_2$ group, a —CN group, a —CF$_3$ group, an aryl group of 6 to 24 carbon atoms, an aralkyl group of 7 to 16 carbon atoms, R" and R'" representing independently of each other H or an alkyl group of 1 to 16 carbon atoms, an aryl group of 6 to 24 carbon atoms or an aralkyl group of 7 to 16 carbon atoms;
  $A_3$ represents H, or a linear, branched or cyclic hydrocarbon chain with 1 to 6 members, each of said members being optionally chosen from a heteroatom, said heteroatom being preferably chosen from sulphur, nitrogen, phosphorus or silicon, more preferably nitrogen, each member being able to be optionally substituted by at least one group chosen from a hydroxyl group, an —NR"R'" group, an alkoxy group of 1 to 16 carbon atoms, an alkyl group of 1 to 16 carbon atoms, a halogen atom, an —NO$_2$ group, a —CN group, a —CF$_3$ group, an aryl group of 6 to 24 carbon atoms, an aralkyl group of 7 to 16 carbon atoms, R" and R" representing independently of each other H or an alkyl group of 1 to 16 carbon atoms, an aryl group of 6 to 24 carbon atoms, or an aralkyl group of 7 to 16 carbon atoms or

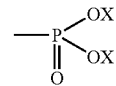

in particular $A_3$ can represent

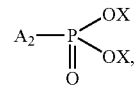

each $A_2$ being identical or different;
  each OX, identical or different for each phosphonic group, represents OH, Oalkyl, where the alkyl group comprises from 1 to 16 carbon atoms, Oaryl, where the aryl group comprises from 6 to 24 carbon atoms, Oaralkyl, where the aralkyl group comprises from 7 to 24 carbon atoms, Oalkylaryl, where the alkylaryl group comprises from 7 to 24 carbon atoms, OSiR'$_1$R'$_2$R'$_3$, where R'$_1$, R'$_2$ and R'$_3$, identical or different, represent an alkyl group of 1 to 16 carbon atoms, or O$^-$M$^+$, where M$^+$ is a cation of elements of group IA, IB, IIA, IIB or IIIA, IIIB of the periodic table of the elements, preferably M$^+$ is chosen from the cations of the sodium, potassium, copper, calcium, barium, zinc, magnesium, lithium and aluminium atoms, or hydrocarbon groups of 1 to 100 carbon atoms, or nitrogenous groups of 0 to 100 carbon atoms, such as $NR_1R_2R_3R_4^+$, where, independently of each other $R_1$, $R_2$, $R_3$ and $R_4$ represent H or a linear, branched or cyclic hydrocarbon chain with 1 to 16 members, optionally containing one or more heteroatoms, said heteroatoms being preferably chosen from oxygen, sulphur, nitrogen, phosphorus, silicon and/or one or more double or triple bonds, each of said members being optionally substituted by at least one substituent chosen from a hydroxyl group, an —NR"R"' group, an alkoxy group of 1 to 16 carbon atoms, an alkyl group of 1 to 16 carbon atoms, a halogen atom, an —$NO_2$ group, a —CN group, a —$CF_3$ group, an aryl group of 6 to 24 carbon atoms, an aralkyl group of 7 to 16 carbon atoms, R" and R"' representing independently of each other H or an alkyl group of 1 to 16 carbon atoms, an aryl group of 6 to 24 carbon atoms or an aralkyl group of 7 to 16 carbon atoms;

m represents an integer from 1 to 20, in particular of 1 to 10 and more particularly of 1 to 8;

n represents an integer from 0 to 12;

said central core § representing a group comprising from 1 to 500 atoms, and optionally containing one or more heteroatoms, said heteroatoms being preferably chosen from oxygen, sulphur, nitrogen, phosphorus or silicon.

According to a particular embodiment of the invention, the dendrimers with monophosphonic or bisphosphonic terminations are of generation n and include a central core § with a valency of m which can establish m−2 bonds, providing that m is greater than 2, or m−1 bonds, providing that m is greater than 1, or m bonds with linkage chains, preferably identical to each other, m representing an integer from 1 to 20, in particular of 1 to 10 and more particularly of 1 to 8, and n representing an integer from 0 to 12, which linkage chains are constituted by:

generation chains attached in a tree-like structure around the core on each of the bonds, when n is greater than or equal to 1, a generation chain of a given generation being linked to a generation chain of the generation immediately below the given generation, or to the core when the given generation is 1, and to at least 2 generation chains of the generation immediately above the given generation, or optionally to at least one intermediate chain when the given generation is n, a terminal group being attached to the end of each generation chain of generation n, or if appropriate to the end of each intermediate chain, or intermediate chains attached around the core on each of the bonds, when n is 0, a terminal group being attached to the end of each intermediate chain;

said terminal group being represented by the formula:

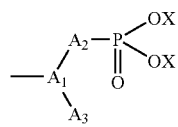

where $A_1$ represents N; a P=Y group, where Y represents O, S, or any atom; an N—R group; or a C—R group; R representing H or a linear, branched or cyclic hydrocarbon chain with 1 to 16 members, optionally containing one or more heteroatoms, said heteroatoms being preferably chosen from oxygen, sulphur, nitrogen, phosphorus, silicon and/or one or more double or triple bonds, each of said members being optionally substituted by at least one substituent chosen from a hydroxyl group, an —NR'R" group, an alkoxy group of 1 to 16 carbon atoms, an alkyl group of 1 to 16 carbon atoms, a halogen atom, an —$NO_2$ group, a —CN group, a —$CF_3$ group, an aryl group of 6 to 24 carbon atoms, an aralkyl group of 7 to 16 carbon atoms, R' and R" representing independently of each other H or an alkyl group of 1 to 16 carbon atoms, an aryl group of 6 to 24 carbon atoms or an aralkyl group of 7 to 16 carbon atoms;

$A_2$ represents a single bond or a linear, branched or cyclic hydrocarbon chain with 1 to 6 members, each of said members optionally containing one or more heteroatoms, said heteroatoms being preferably chosen from a sulphur, oxygen, phosphorus or nitrogen atom, more preferably nitrogen, and being optionally substituted by at least one substituent chosen from H, an alkyl group of 1 to 16 carbon atoms, a halogen, an —$NO_2$ group, an —NRR' group, a —CN group, a —$CF_3$ group, a hydroxyl group, an alkoxy group of 1 to 16 carbon atoms, an aryl or heteroaryl group of 1 to 24 carbon atoms, the heteroelement being preferably chosen from oxygen, nitrogen or sulphur, an aralkyl group of 7 to 16 carbon atoms, R and R' representing independently of each other H or a linear, branched or cyclic hydrocarbon chain with 1 to 16 members, optionally containing one or more heteroatoms, said heteroatoms being preferably chosen from oxygen, sulphur, nitrogen, phosphorus, silicon and/or one or more double or triple bonds, each of said members being optionally substituted by at least one substituent chosen from a hydroxyl group, an —NR"R"' group, an alkoxy group of 1 to 16 carbon atoms, an alkyl group of 1 to 16 carbon atoms, a halogen atom, an —$NO_2$ group, a —CN group, a —$CF_3$ group, an aryl group of 6 to 24 carbon atoms, an aralkyl group of 7 to 16 carbon atoms, R" and R"' representing independently of each other H or an alkyl group of 1 to 16 carbon atoms, an aryl group of 6 to 24 carbon atoms or an aralkyl group of 7 to 16 carbon atoms;

$A_3$ represents H, or a linear, branched or cyclic hydrocarbon chain with 1 to 6 members, each of said members being optionally chosen from a heteroatom, said heteroatom being preferably chosen from sulphur, nitrogen, phosphorus or silicon, more preferably nitrogen, each member being able to be optionally substituted by at least one group chosen from a hydroxyl group, an —NR"R"' group, an alkoxy group of 1 to 16 carbon atoms, an alkyl group of 1 to 16 carbon atoms, a halogen atom, an —$NO_2$ group, a —CN group, a —$CF_3$ group, an aryl group of 6 to 24 carbon atoms, an aralkyl group of 7 to 16 carbon atoms, R" and R"' representing independently of each other H or an alkyl group of 1 to 16 carbon atoms, an aryl group of 6 to 24 carbon atoms, or an aralkyl group of 7 to 16 carbon atoms or

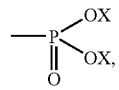

in particular $A_3$ can represent

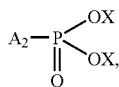

each $A_2$ being identical or different;
each OX, identical or different for each phosphonic group, represents OH, Oalkyl, where the alkyl group comprises from 1 to 16 carbon atoms, Oaryl, where the aryl group comprises from 6 to 24 carbon atoms, Oaralkyl, where the aralkyl group comprises from 7 to 24 carbon atoms, Oalkylaryl, where the alkylaryl group comprises from 7 to 24 carbon atoms, $OSiR'_1R'_2R'_3$, where $R'_1$, $R'_2$ and $R'_3$, identical or different, represent an alkyl group of 1 to 16 carbon atoms, or $O^-M^+$, where $M^+$ is a cation of elements of group IA, IB, IIA, IIB or IIIA, IIIB of the periodic table of the elements, preferably $M^+$ is chosen from the cations of the sodium, potassium, copper, calcium, barium, zinc, magnesium, lithium and aluminium atoms, or hydrocarbon groups of 1 to 100 carbon atoms, or nitrogenous groups of 0 to 100 carbon atoms, such as $NR_1R_2R_3R_4^+$, where, independently of each other $R_1$, $R_2$, $R_3$ and $R_4$ represent H or a linear, branched or cyclic hydrocarbon chain with 1 to 16 members, optionally containing one or more heteroatoms, said heteroatoms being preferably chosen from oxygen, sulphur, nitrogen, phosphorus, silicon and/or one or more double or triple bonds, each of said members being optionally substituted by at least one substituent chosen from a hydroxyl group, an —NR"R"' group, an alkoxy group of 1 to 16 carbon atoms, an alkyl group of 1 to 16 carbon atoms, a halogen atom, an —$NO_2$ group, a —CN group, a —$CF_3$ group, an aryl group of 6 to 24 carbon atoms, an aralkyl group of 7 to 16 carbon atoms, R" and R"' representing independently of each other H or an alkyl group of 1 to 16 carbon atoms, an aryl group of 6 to 24 carbon atoms or an aralkyl group of 7 to 16 carbon atoms;
said central core § representing a group comprising from 1 to 500 atoms, and optionally containing one or more heteroatoms, said heteroatoms being preferably chosen from oxygen, sulphur, nitrogen, phosphorus or silicon.

The linkage chains are of two types depending on whether or not they contain generation chains. In the same molecule, all the linkage chains are identical or different. The generation chains make it possible in particular to multiply the number of terminal functions, and to control the size of the dendrimer.

By "dendrimer of generation n" is meant a dendrimer comprising n generations of generation chains. Each generation chain can then be characterized by the generation to which it belongs.

Thus, a dendrimer of generation 0 comprises no generation chain, the intermediate chains are directly linked to the core.

A dendrimer of generation 1 comprises only one generation of generation chains, which generation chains are linked, on the one hand, to the core and, on the other hand, to optionally at least 1 intermediate chain.

For the dendrimers of generation 2, the generation chains of generation 1 are linked, on the one hand, to the core and, on the other hand, to at least 2 generation chains of generation 2, each generation chain 2 being linked to a generation chain 1 and optionally to at least 1 intermediate chain.

Finally, in a general manner, for a dendrimer of generation n, n varying from 3 to 12, i being an integer from 2 to n−1, a generation chain of a given generation i is linked to a generation chain of generation i−1, i.e. of a generation immediately below the given generation, and to at least two generation chains of generation i+1, i.e. of a generation immediately above the given generation. When i is n then the generation chain of generation i is linked to a generation chain of generation n−1 and optionally to at least 1 intermediate chain.

If appropriate, for a generation chain of a given generation, by "coefficient of divergence" is meant the number of generation chains of the generation immediately above the given generation which are linked to the latter.

According to a preferred embodiment of the invention, the coefficient of divergence is from 2 to 5.

According to a particular embodiment of the invention, the coefficient of divergence is identical for a given generation of generation chains, on the other hand it can vary from one generation to another.

In a particular embodiment of the invention, the coefficient of divergence is identical for each generation of a given dendrimer.

According to a yet more particular embodiment of the invention, the coefficient of divergence is 2.

According to another particular embodiment of the invention, a generation chain of generation n is linked to a number of terminal groups or intermediate chains corresponding to the coefficient of divergence.

Advantageously, a high coefficient of divergence makes it possible to have a large number of terminal groups at the surface of a dendrimer of a given generation.

According to a particular embodiment of the invention, the generation chains are identical to each other for the same generation but can be different from one generation to another.

According to another particular embodiment of the invention, the generation chains are all identical to each other.

According to another particular embodiment of the invention, the core § establishes m bonds with m identical linkage chains constituted:
either by generation chains attached in a tree-like structure around the core on each of the bonds, the end of each chain generation furthest from the central core being attached either to a terminal group or to an intermediate chain, the end of each intermediate chain being attached to a terminal group,
or by intermediate chains attached around the core on each of the bonds, the end of each intermediate chain being attached to a terminal group.

According to this embodiment, for a given dendrimer, all of the generation chains of the generation furthest from the central core are attached to an identical substituent which can be either to a terminal group or to an intermediate chain.

According to an alternative embodiment of the invention, the core establishes m−2 or m−1 bonds, m representing an integer from 3 to 20, in particular from 3 to 10 and more particularly from 3 to 8, with respectively m−2 or m−1 identical linkage chains constituted:
either by generation chains attached in a tree-like structure around the core on each of the bonds, the end of each chain generation furthest from the central core being attached either to a terminal group or to an intermediate chain, and the end of each intermediate chain being attached to a terminal group,
or by intermediate chains attached around the core on each of the bonds, the end of each intermediate chain being attached to a terminal group;
the 1 or 2 remaining bonds being attached to linkage groups, identical or different, optionally linked together, in particular by means of a covalent bond, constituted:

either by part of the linkage chains defined above,
or by a hydrogen atom,
or by hydrocarbon groups comprising from 1 to 500 carbon atoms, said hydrocarbon groups being in particular constituted by H or by a linear, branched or cyclic hydrocarbon chain with 1 to 200 members, optionally containing one or more double or triple bonds, each of said members being optionally chosen from a heteroatom, said heteroatom being preferably chosen from a nitrogen, oxygen, phosphorus, silicon or sulphur atom, an aryl group of 6 to 24 carbon atoms, a heteroaryl group of 1 to 24 carbon atoms, a carboxyl group, a >C=NR group, each member being able to be optionally substituted by at least one substituent chosen from a hydroxyl group, an —NR"R'" group, an alkoxy group of 1 to 16 carbon atoms, an alkyl group of 1 to 16 carbon atoms, a halogen atom, an —NO$_2$ group, a —CN group, a —CF$_3$ group, an aryl group of 6 to 24 carbon atoms, an aralkyl group of 7 to 16 carbon atoms, R" and R'" representing independently of each other H or an alkyl group of 1 to 16 carbon atoms, an aryl group of 6 to 24 carbon atoms or an aralkyl group of 7 to 16 carbon atoms, the first member of said hydrocarbon chain preferably being oxygen or nitrogen.

In particular the hydrocarbon groups comprising from 1 to 500 carbon atoms defined above can be fluorophores, or any functional chemical group.

According to another particular embodiment of the invention, the generation chains are chosen from any linear, branched or cyclic hydrocarbon chain with 1 to 12 members, optionally containing one or more double or triple bonds, each of said members being optionally chosen from a heteroatom, said heteroatom being preferably chosen from nitrogen, oxygen, sulphur, phosphorus or silicon, an aryl group of 6 to 24 carbon atoms, a heteroaryl group of 1 to 24 carbon atoms, the heteroelement being preferably chosen from oxygen, nitrogen or sulphur, a carboxyl group, a >C=NR group, each member being able to be optionally substituted by at least one substituent chosen from an alkyl group of 1 to 16 carbon atoms, a halogen atom, an —NO$_2$ group, an —NRR' group, a —CN group, a —CF$_3$ group, a hydroxyl group, an alkoxy group of 1 to 16 carbon atoms, an aryl group of 6 to 24 carbon atoms, or an aralkyl group of 7 to 16 carbon atoms, R and R' representing independently of each other H or an alkyl group of 1 to 16 carbon atoms, an aryl group of 6 to 24 carbon atoms, or an aralkyl group of 7 to 16 carbon atoms.

According to yet another particular embodiment of the invention, the intermediate chains are chosen from the groups corresponding to the formula:

-J-K-L- where
  J represents an oxygen or sulphur atom, or an —NR— group;
  K represents an aryl group of 6 to 24 carbon atoms, a heteroaryl group of 1 to 24 carbon atoms, the heteroelement being preferably chosen from oxygen, nitrogen or sulphur, an alkyl group of 1 to 16 carbon atoms, each being able to be optionally substituted by a halogen atom or an —NO$_2$, —NRR', —CN, —CF$_3$, —OH group, an alkyl group of 1 to 16 carbon atoms, an aryl group of 6 to 24 carbon atoms, an aralkyl group of 7 to 16 carbon atoms;
  L represents a linear, branched or cyclic hydrocarbon chain with 0 to 10 members, in particular with 0 to 6 members, optionally containing one or more double or triple bonds, each of said members optionally being able to be a heteroatom, said heteroatom being preferably chosen from oxygen, sulphur, nitrogen, phosphorus, silicon, each member being able to be optionally substituted by at least one substituent chosen from an alkyl group of 1 to 16 carbon atoms, a halogen, an oxygen atom, —NO$_2$, —NRR', —CN, —CF$_3$, —OH, an alkoxy group of 1 to 16 carbon atoms, an aryl group of 6 to 24 carbon atoms, an aralkyl group of 7 to 16 carbon atoms;
  R and R' representing independently of each other H or an alkyl group of 1 to 16 carbon atoms, an aryl group of 6 to 24 carbon atoms, or an aralkyl group of 7 to 16 carbon atoms.

According to a more particular embodiment of the invention, the core is chosen from:
  a nitrogen or silicon atom;
  a group of formula

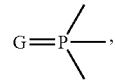

in which G represents an oxygen, nitrogen, sulphur, selenium, tellurium atom or an =NR group, R representing H or an alkyl group of 1 to 16 carbon atoms, an aryl group of 6 to 24 carbon atoms, or an aralkyl group of 7 to 16 carbon atoms, such as the thiophosphoryl group of formula

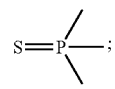

a bis-phenyloxy group of formula

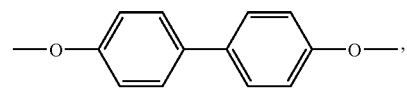

a 1,2-diamino-ethane group of formula

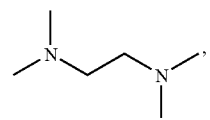

a 1,4-diamino-butane group of formula

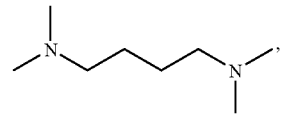

a cyclotriphosphazene group of formula

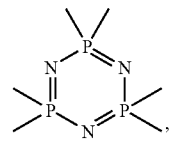

also denoted $N_3P_3$ or $P_3N_3$, a cyclotetraphosphazene group of formula

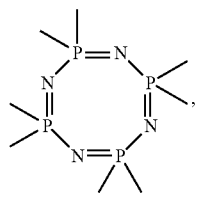

also denoted $N_4P_4$ or $P_4N_4$.

The present invention relates in particular to the use as defined above, of dendrimers of structure PAMAM, DAB or PMMH.

The dendrimers of structure PAMAM are in particular described by D. A. Tomalia, H. Baker, J. Dewald, M. Hall, G. Kallos, S. Martin, J. Roeck, J. Ryder, P. S. Smith, Polym. J. (Tokyo) 1985, 17, 117; D. A. Tomalia, H. Baker, J. Dewald, M. Hall, G. Kallos, S. Martin, J. Roeck, J. Ryder, P. S. Smith, Macromolecules, 1986, 19, 2466.

The dendrimers of structure DAB are in particular described by E. M. M. de Brabander-van den Berg, E. W. Meijer *Angew. Chem.* Int. Ed. Engl. 1993, 32, 1308.

The dendrimers of structure PMMH are in particular described in "A general synthetic strategy for neutral phosphorus containing dendrimers" Launay N., Caminade A. M., Lahana R., Majoral J. P., *Angew. Chem.* 1994, 106, 1682. *Angew. Chem. Int. Ed. Engl.* 1994, 33, 1589 and in "Synthesis of bowl-shaped dendrimers from generation 1 to generation 8" Launay N., Caminade A. M., Majoral J. P., *J. Organomet. Chem.* 1997, 529,51.

An example of a dendrimer of type PAMAM for which n=4 and m=4 is represented below:

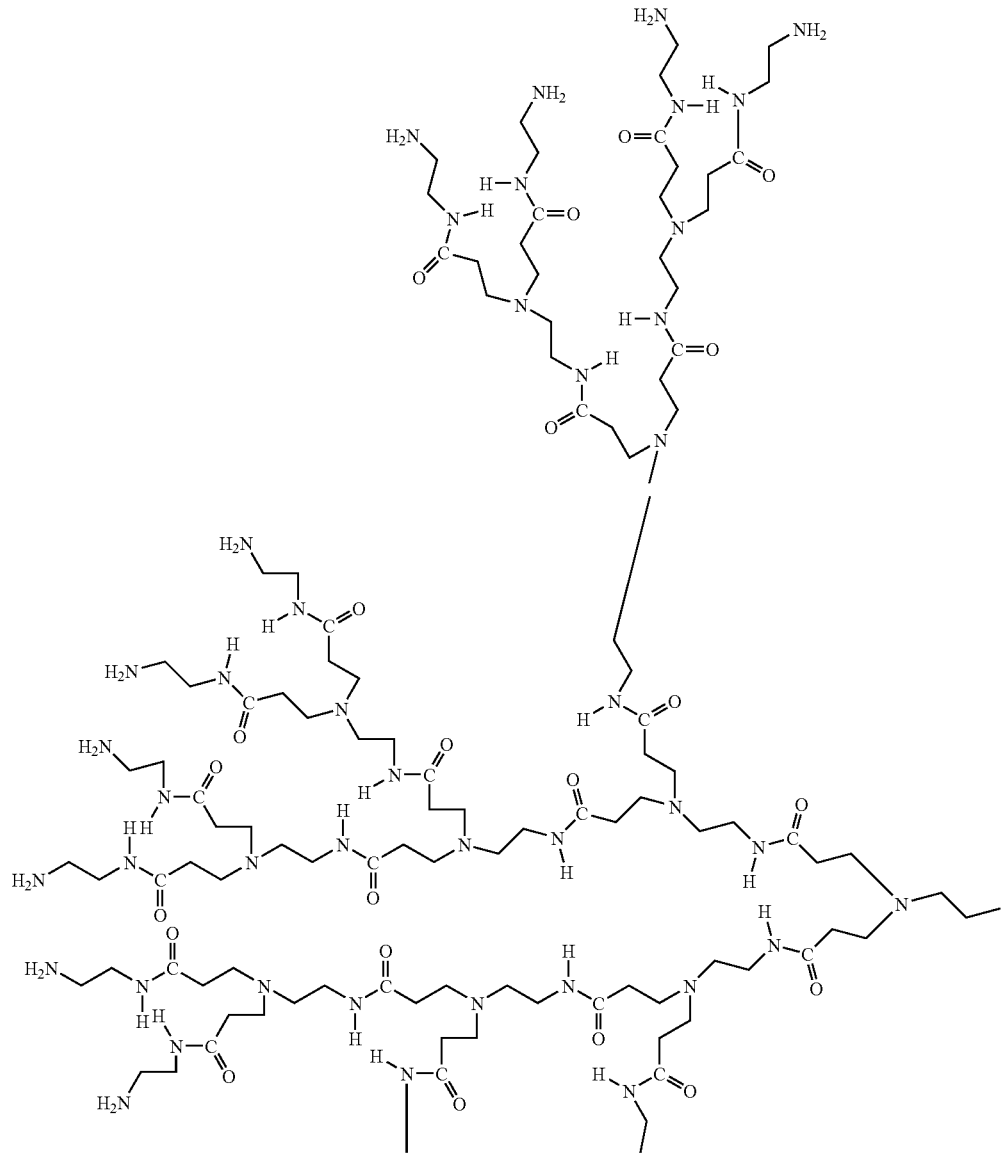

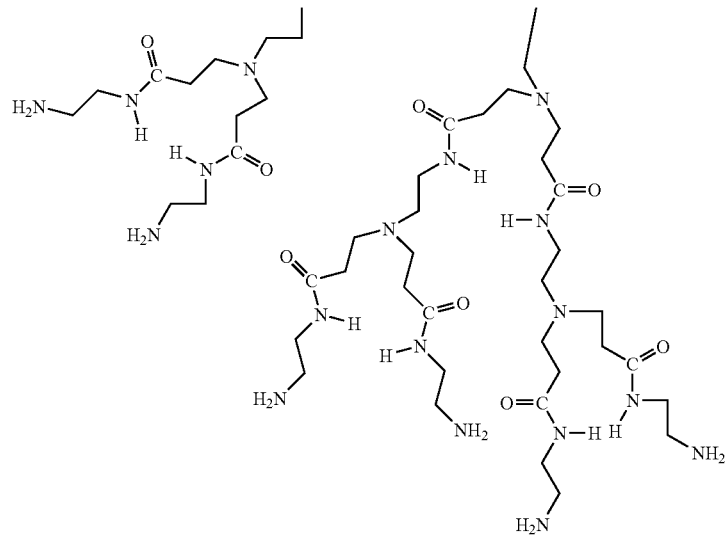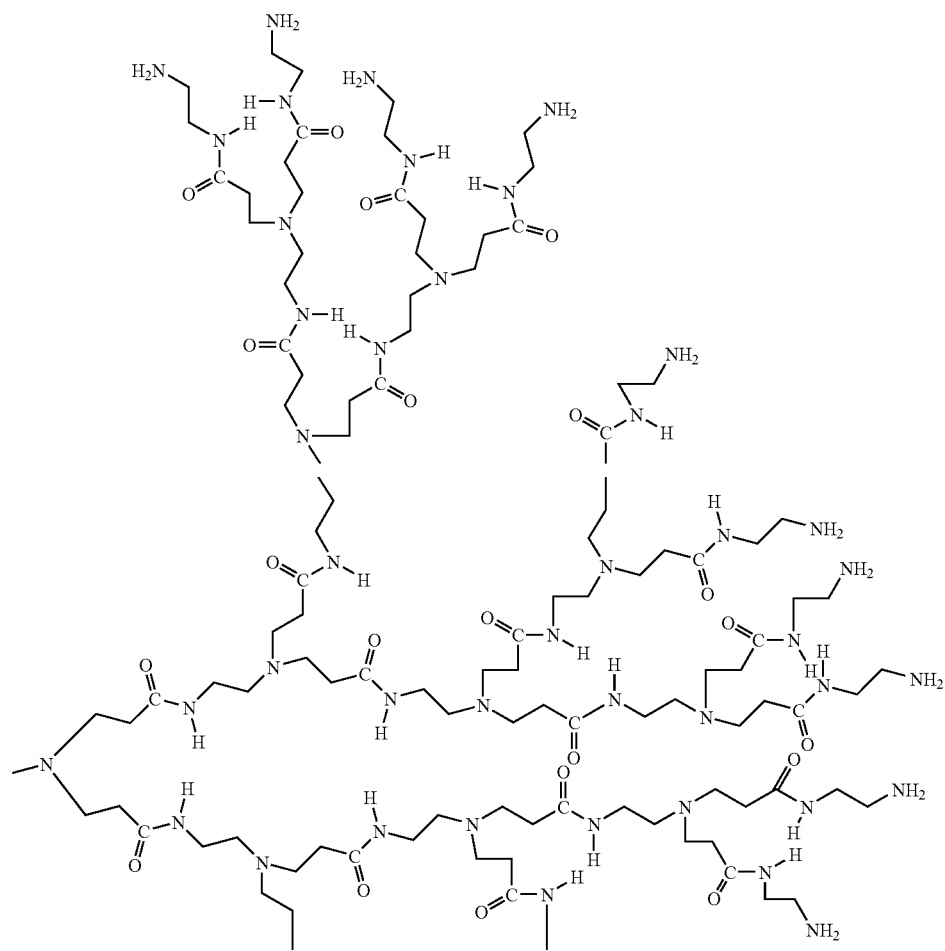

-continued
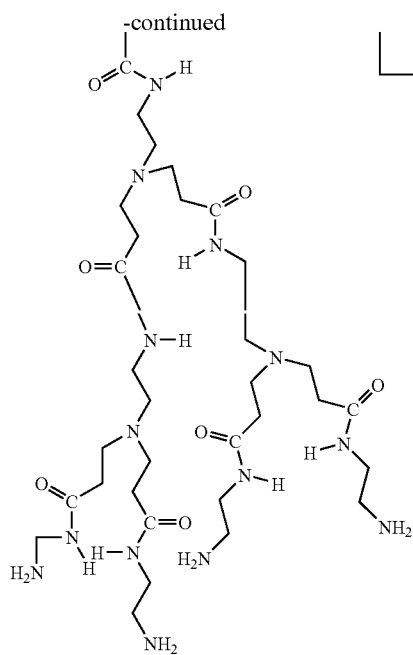
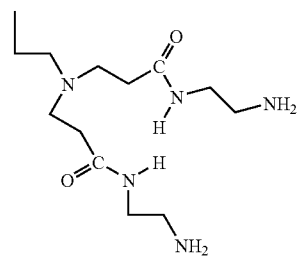
An example of a dendrimer of type DAB, for which n=5 and m=4 is represented below:
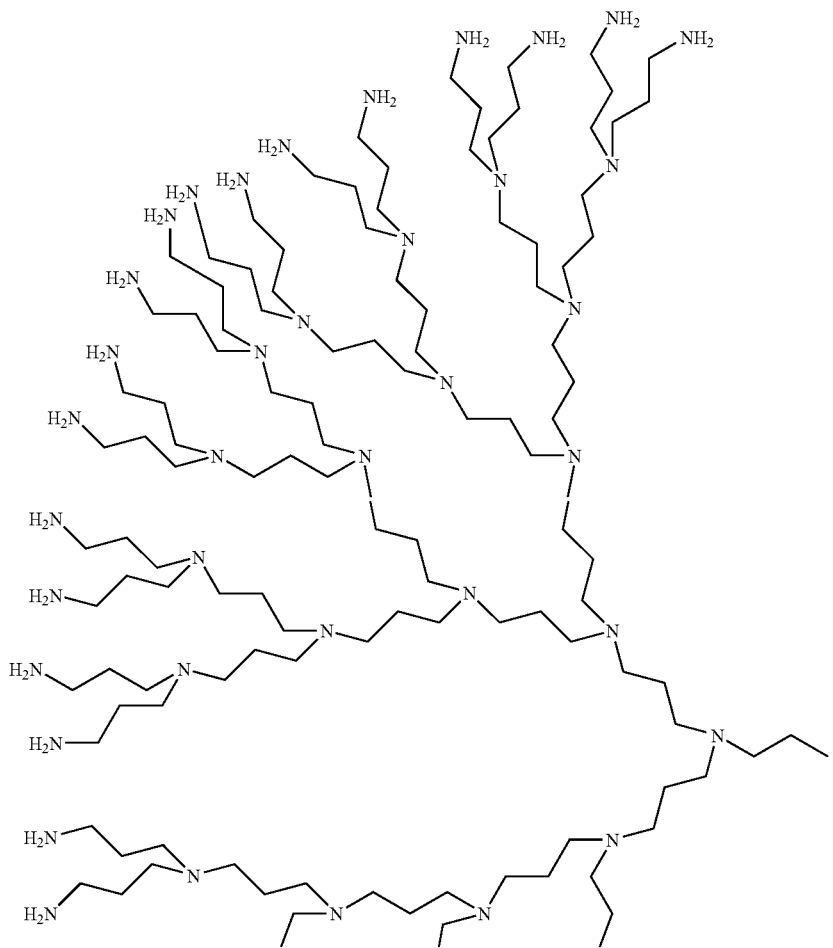

-continued
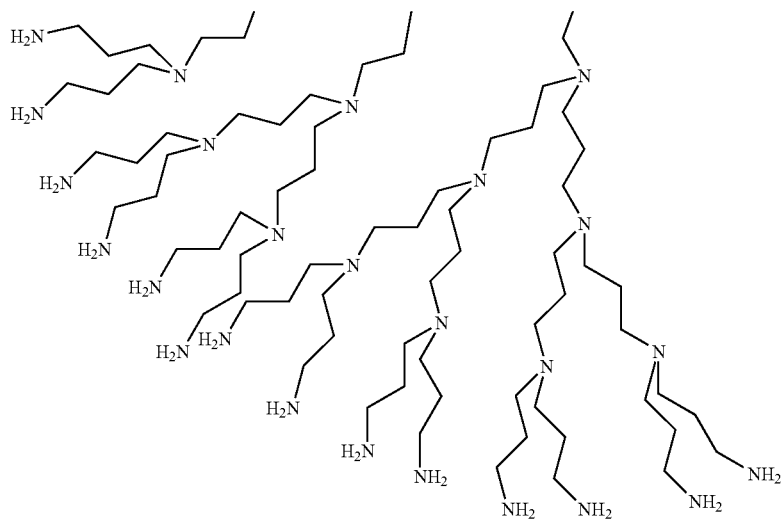
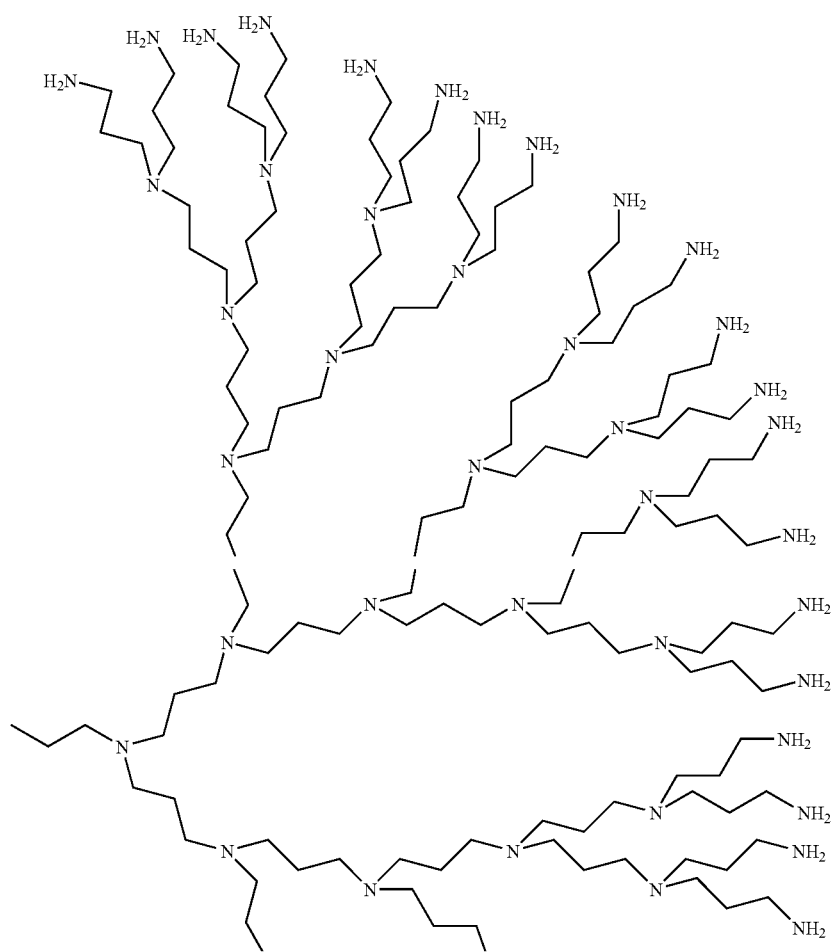

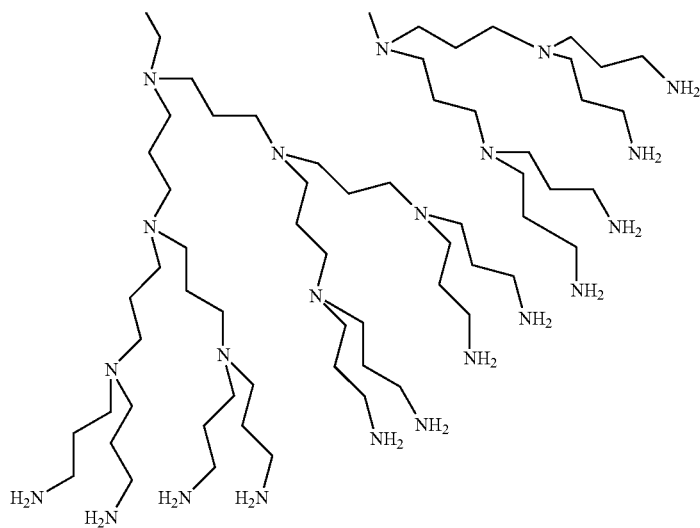
An example of a dendrimer of type PMMH with a thiophosphoryl core, for which n=4 and m=3 is represented below:
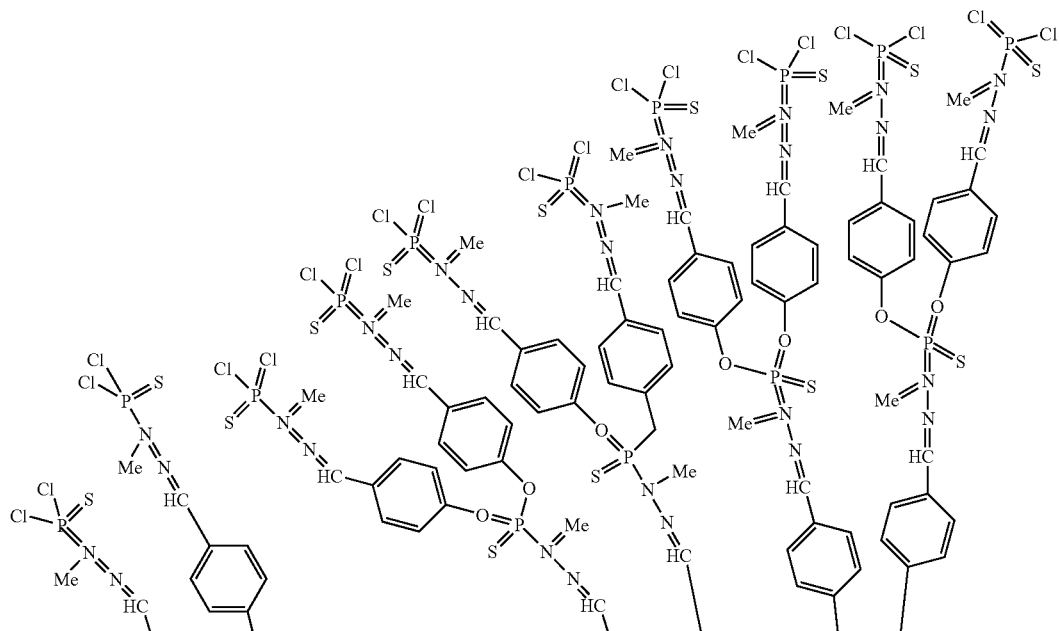

21 22
-continued
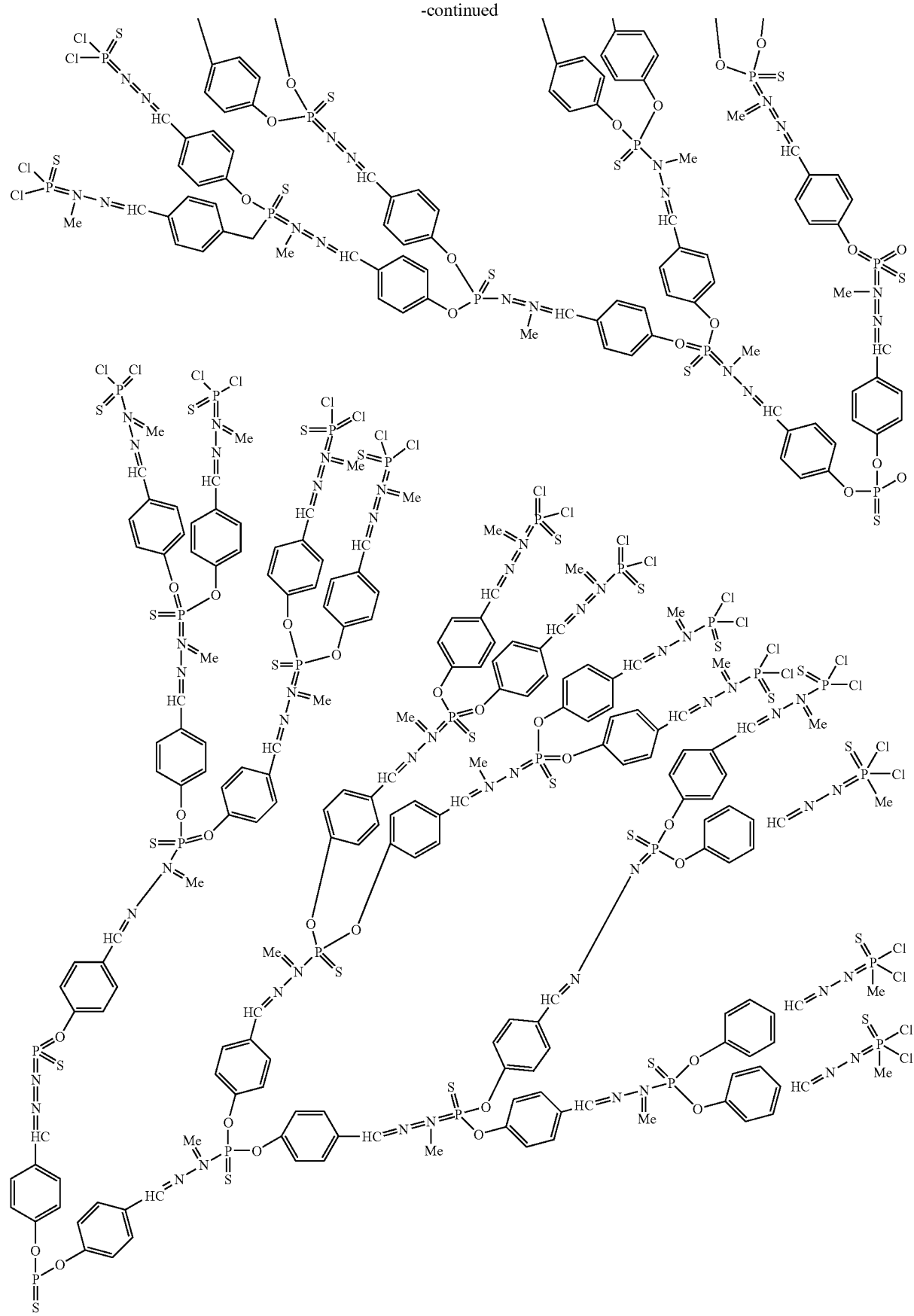

An example of a dendrimer of type PMMH with a cyclotriphosphazene core, for which n=2 and m=6, without an intermediate chain, is represented below:

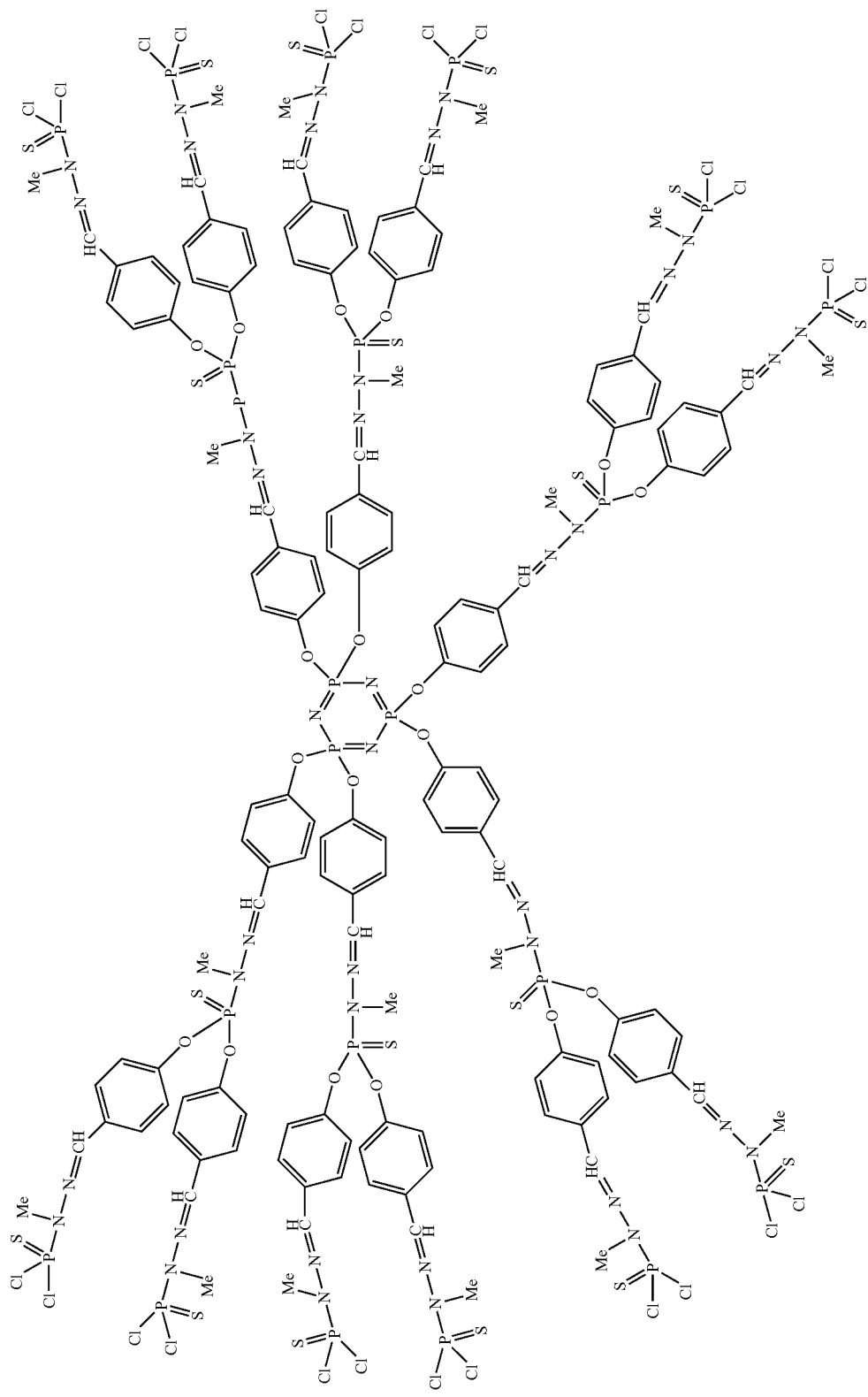

Another example of a dendrimer of type PMMH with a cyclotriphosphazene core, for which n=2 and m=6, with an intermediate chain, is represented below:
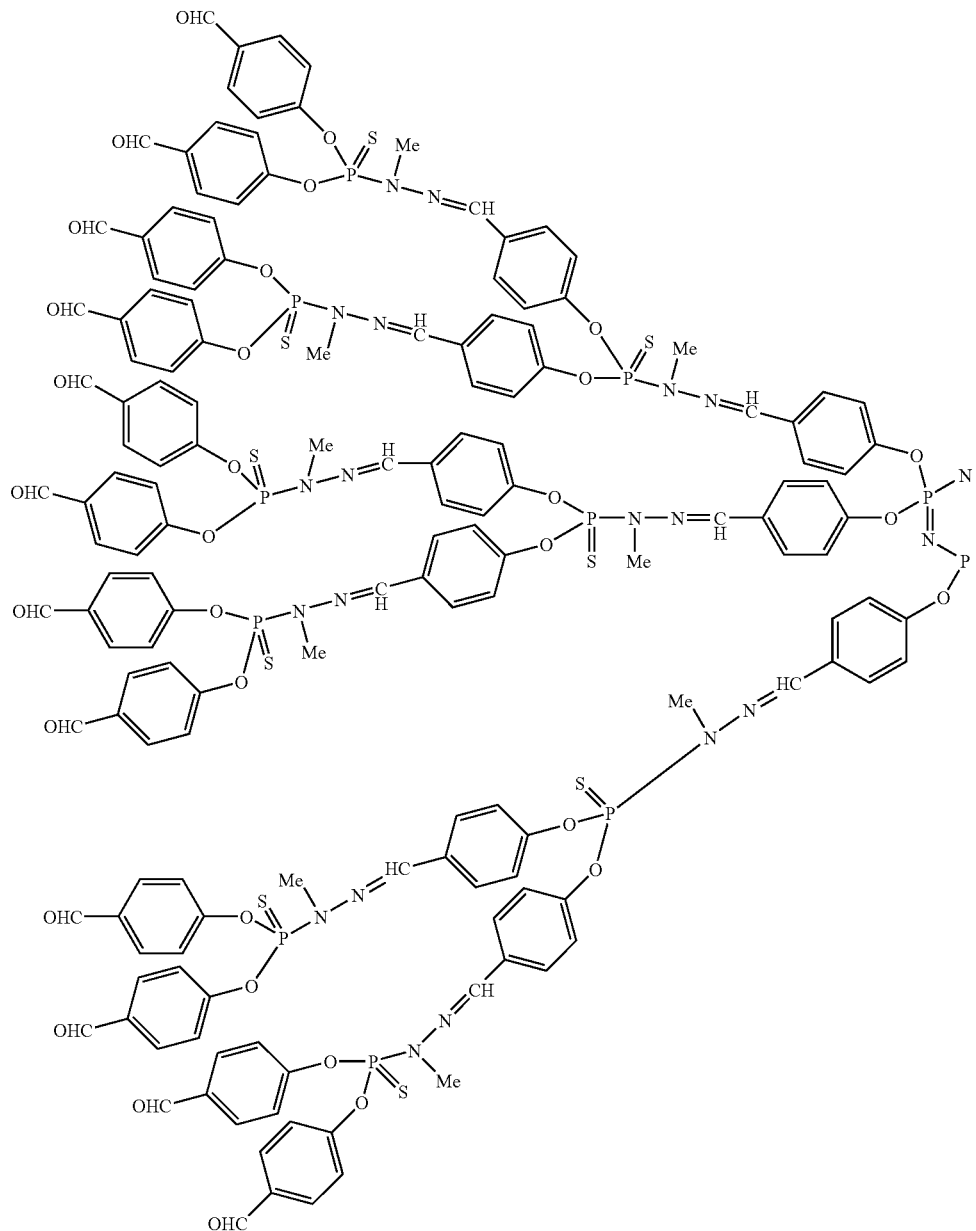

-continued

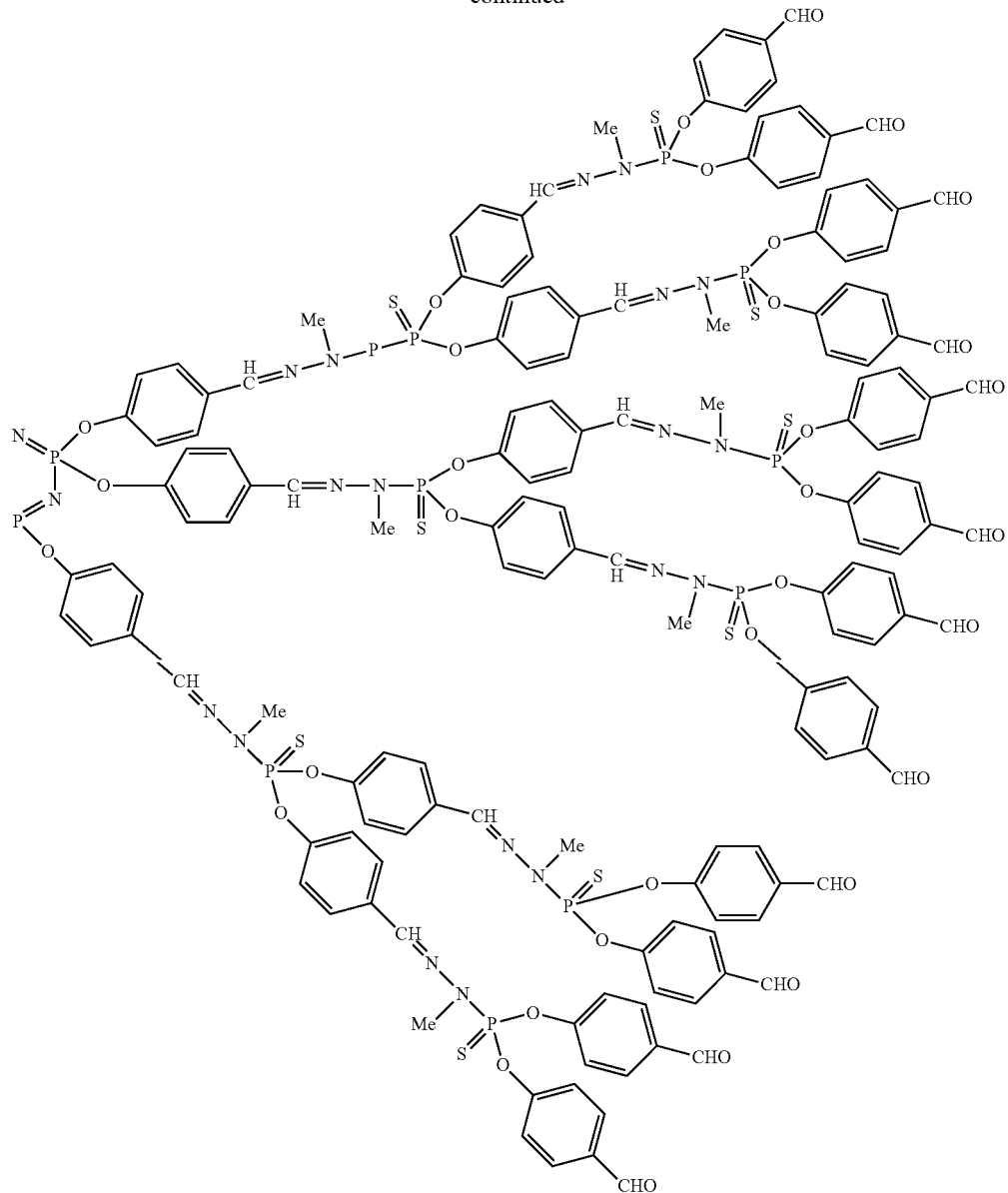

In a particular embodiment, the invention relates to the use as defined above, of dendrimers with monophosphonic or bisphosphonic terminations corresponding to the following general formula (1a):

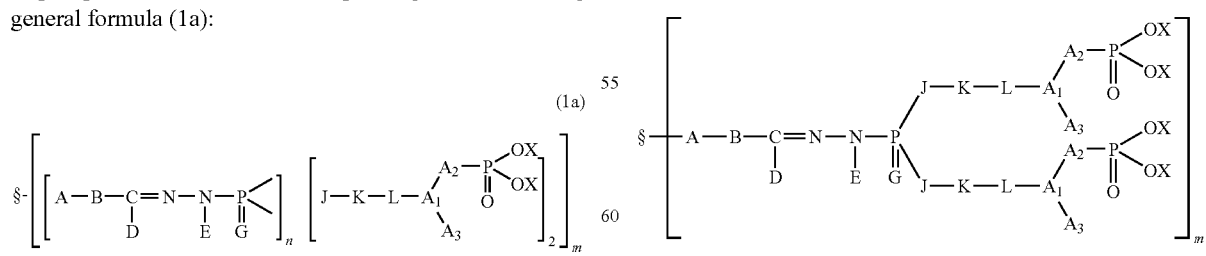

where n represents an integer from 0 to 3, namely:

when n=0, formula (1a) corresponds to the following formula (2a), when n=1, formula (1a) corresponds to the following formula (3a),

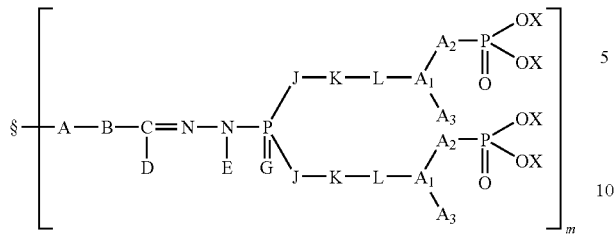
when n=2, formula (1a) corresponds to the following formula (4a),
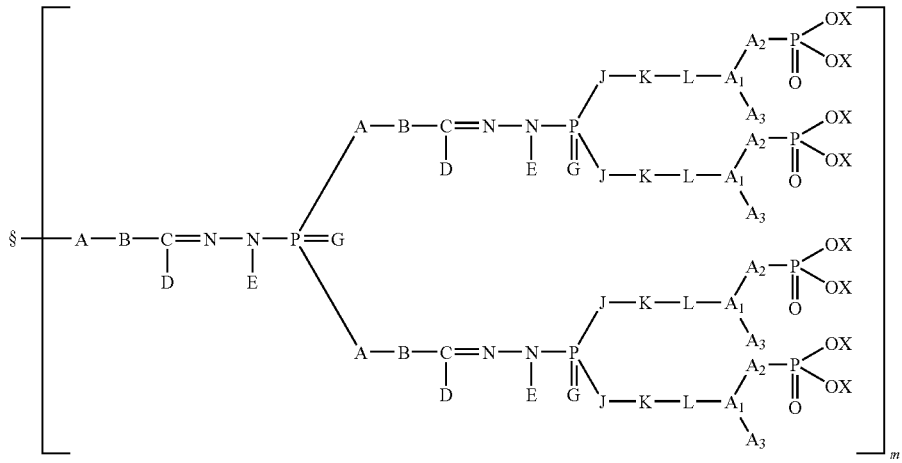
and when n=3, formula (1a) corresponds to the following formula (5a),
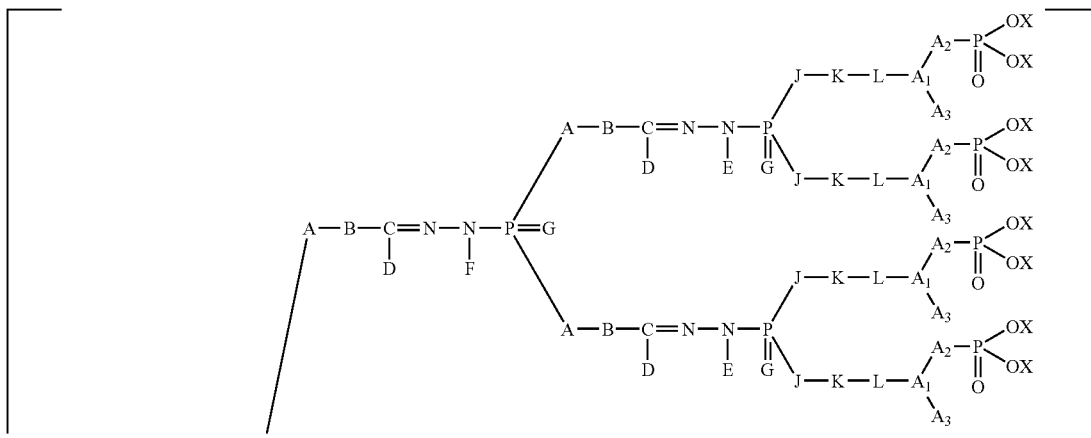

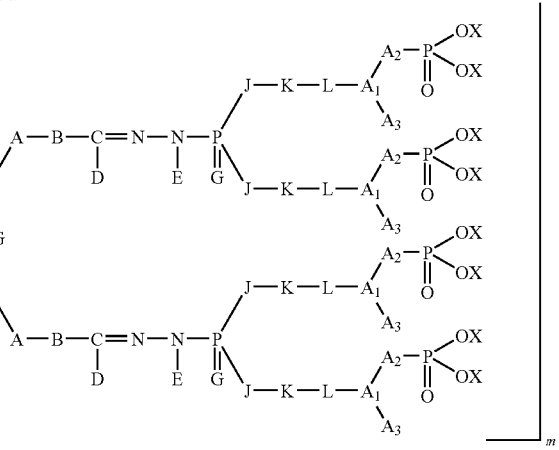

and in which formulae:

the central core § is chosen from the following groups:

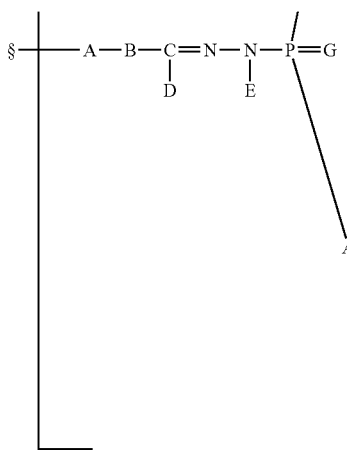

m represents 3, 6 or 8;
the generation chain corresponds to the formula:

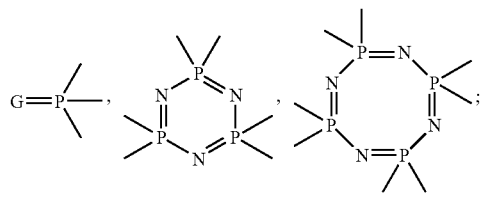

where
A represents an oxygen, sulphur, phosphorus atom or an —NR— group;
B represents an aryl group of 6 to 24 carbon atoms, a heteroaryl group of 1 to 24 carbon atoms, an alkyl group of 1 to 16 carbon atoms, each being able to be optionally substituted by a halogen atom or an —NO$_2$, —NRR', —CN, —CF$_3$, —OH group, an alkyl group of 1 to 16 carbon atoms, an aryl group of 6 to 24 carbon atoms, an aralkyl group of 7 to 16 carbon atoms;
D represents a hydrogen atom, an alkyl group of 1 to 16 carbon atoms, an alkoxy group of 1 to 16 carbon atoms, an aryl group of 6 to 24 carbon atoms, an aralkyl group of 7 to 16 carbon atoms, each being able to be optionally substituted by a halogen atom or an —NO$_2$, —NRR', —CN, —CF$_3$, —OH group, an alkyl group of 1 to 16 carbon atoms, an aryl group of 6 to 24 carbon atoms, an aralkyl group of 7 to 16 carbon atoms;
E represents a hydrogen atom, an alkyl group of 1 to 16 carbon atoms, an alkoxy group of 1 to 16 carbon atoms, an aryl group of 6 to 24 carbon atoms, an aralkyl group of 7 to 16 carbon atoms, each being able to be optionally substituted by a halogen atom or an —NO$_2$, —NRR', —CN, —CF$_3$, —OH group, an alkyl group of 1 to 16 carbon atoms, an aryl group of 6 to 24 carbon atoms, an aralkyl group of 7 to 16 carbon atoms;
G represents an oxygen, nitrogen, sulphur, selenium, tellurium atom or an =NR group; R and R' representing independently of each other H or an alkyl group of 1 to 16 carbon atoms, an aryl group of 6 to 24 carbon atoms, or an aralkyl group of 7 to 16 carbon atoms;
the intermediate chain corresponds to the formula:

-J-K-L- where
J represents an oxygen, sulphur atom, or an —NR— group;
K represents an aryl group of 6 to 24 carbon atoms, a heteroaryl group of 1 to 24 carbon atoms, the heteroelement being preferably chosen from oxygen, nitrogen or sulphur, an alkyl group of 1 to 16 carbon atoms, each being able to be optionally substituted by a halogen atom or an —NO$_2$, —NRR', —CN, —CF$_3$, —OH group, an alkyl group of 1 to 16 carbon atoms, an aryl group of 6 to 24 carbon atoms, an aralkyl group of 7 to 16 carbon atoms;
L represents a linear, branched or cyclic hydrocarbon chain with 0 to 10 members, optionally containing one or more double or triple bonds, each of said members being able to be optionally a heteroatom, said heteroatom being preferably chosen from oxygen, sulphur, nitrogen, phosphorus, silicon, each member being able to be optionally substituted by at least one substituent chosen from an alkyl group of 1 to 16 carbon atoms, a halogen, an oxygen atom, —NO$_2$, —NRR', —CN, —CF$_3$, —OH, an alkoxy group of 1 to 16 carbon atoms, an aryl group of 6 to 24 carbon atoms, an aralkyl group of 7 to 16 carbon atoms;
R and R' representing independently of each other H or an alkyl group of 1 to 16 carbon atoms, an aryl group of 6 to 24 carbon atoms, or an aralkyl group of 7 to 16 carbon atoms;
the terminal group corresponds to the formula:

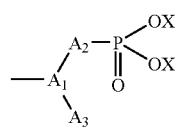

where $A_1$, $A_3$ and X have been defined previously, each X being identical or different.

In a more particular embodiment, the invention relates to the use as defined above of a dendrimer of general formula (1a) in which $A_3$ represents:

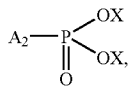

said general formula (1a) then corresponding to the following general formula (1):

(1)

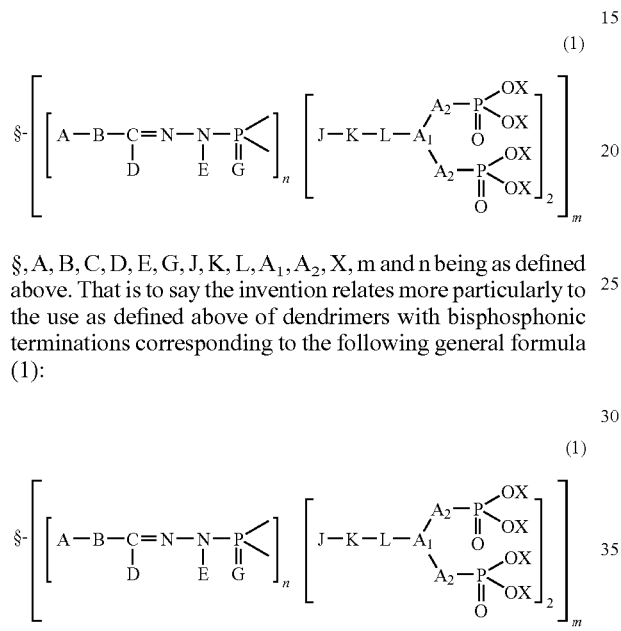

§, A, B, C, D, E, G, J, K, L, $A_1$, $A_2$, X, m and n being as defined above. That is to say the invention relates more particularly to the use as defined above of dendrimers with bisphosphonic terminations corresponding to the following general formula (1):

(1)

where n represents an integer from 0 to 3, namely:

when n=0, formula (1) corresponds to the following formula (2),

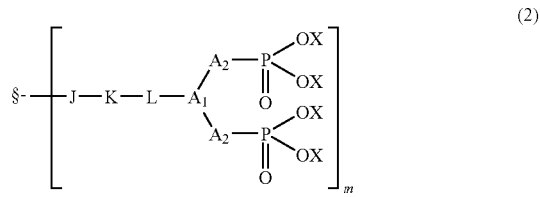

when n=1, formula (1) corresponds to the following formula (3),

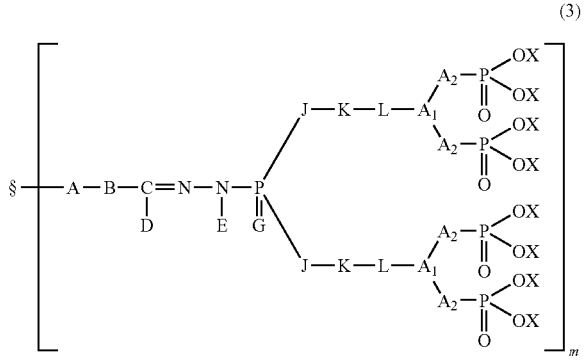

when n=2, formula (1) corresponds to the following formula (4),

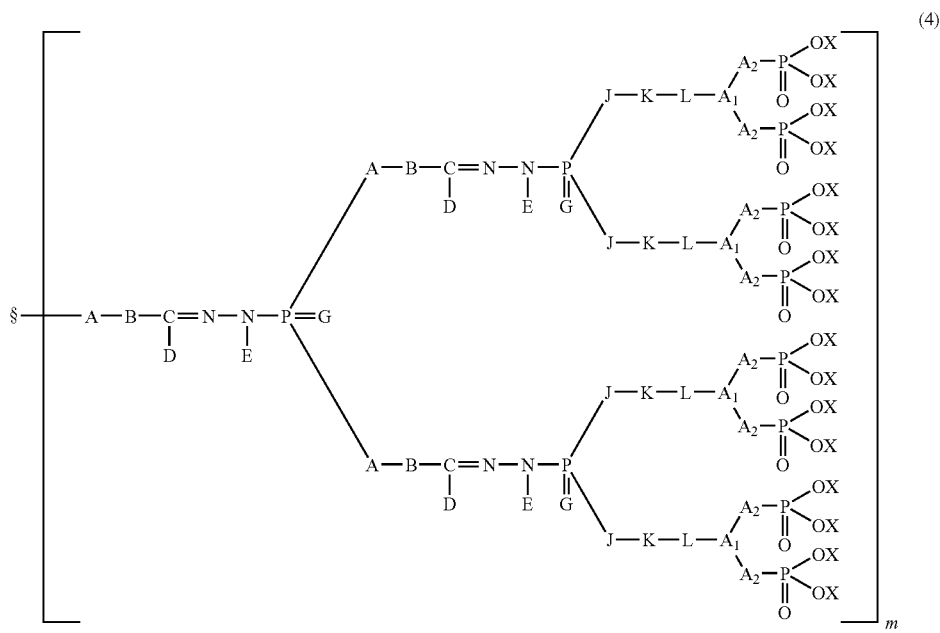

and when n=3, formula (1) corresponds to the following formula (5),
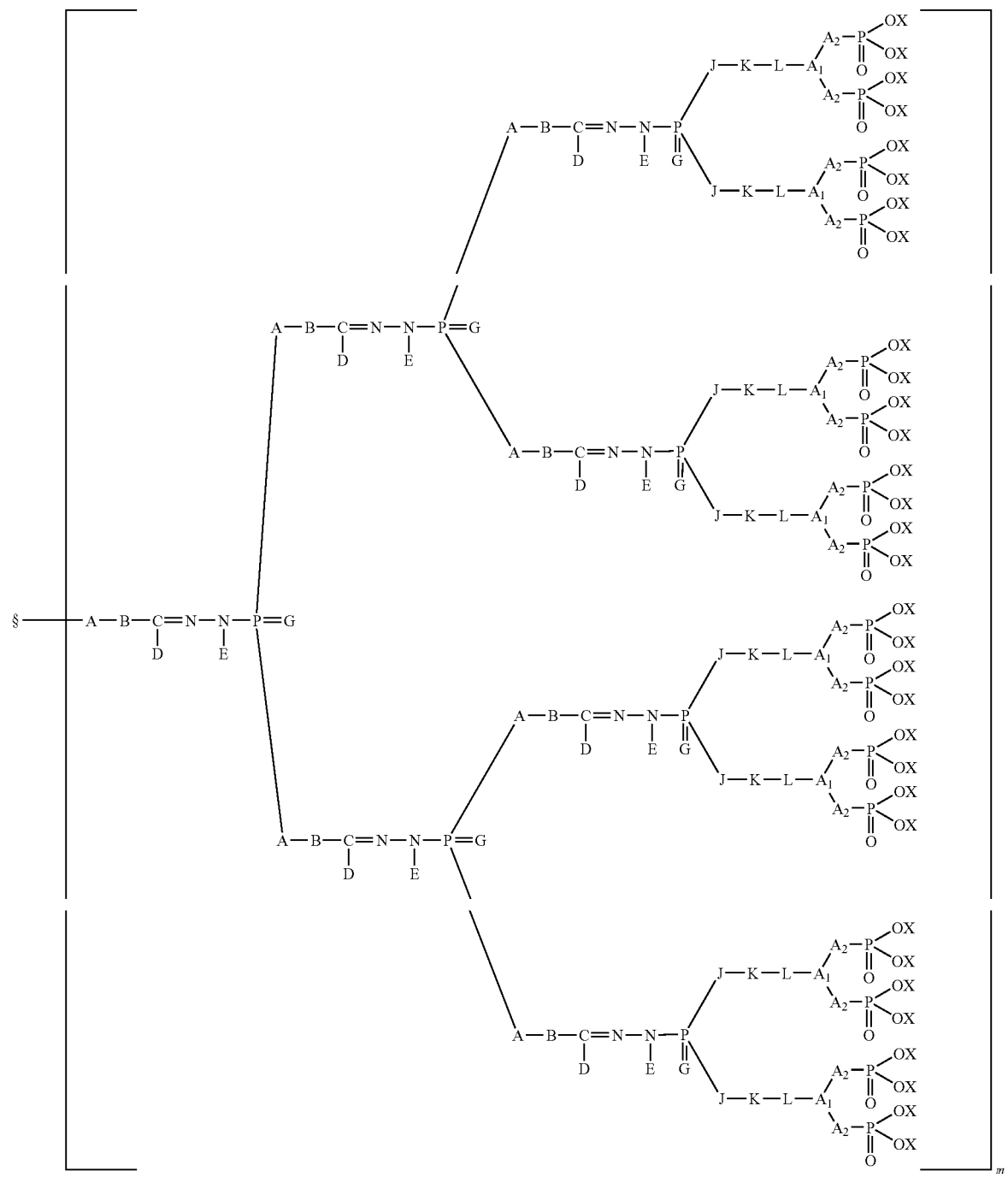
(5)

and in which formulae:

the central core § is chosen from the following groups:

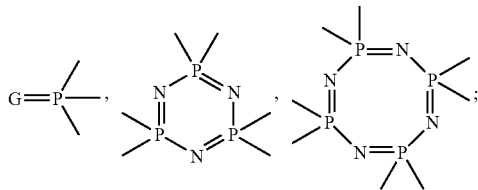

the generation chain corresponds to the formula:

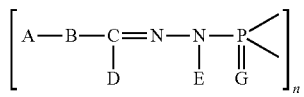

where
A represents an oxygen, sulphur, phosphorus atom or an —NR— group;
B represents an aryl group of 6 to 24 carbon atoms, a heteroaryl group of 1 to 24 carbon atoms, an alkyl group of 1 to 16 carbon atoms, each being able to be optionally substituted by a halogen atom or an —NO$_2$, —NRR', —CN, —CF$_3$, —OH group, an alkyl group of 1 to 16 carbon atoms, an aryl group of 6 to 24 carbon atoms, an aralkyl group of 7 to 16 carbon atoms;
D represents a hydrogen atom, an alkyl group of 1 to 16 carbon atoms, an alkoxy group of 1 to 16 carbon atoms, an aryl group of 6 to 24 carbon atoms, an aralkyl group of 7 to 16 carbon atoms, each being able to be optionally substituted by a halogen atom or an —NO$_2$, —NRR', —CN, —CF$_3$, —OH group, an alkyl group of 1 to 16 carbon atoms, an aryl group of 6 to 24 carbon atoms, an aralkyl group of 7 to 16 carbon atoms;
E represents a hydrogen atom, an alkyl group of 1 to 16 carbon atoms, an alkoxy group of 1 to 16 carbon atoms, an aryl group of 6 to 24 carbon atoms, an aralkyl group of 7 to 16 carbon atoms, each being able to be optionally substituted by a halogen atom or an —NO$_2$, —NRR', —CN, —CF$_3$, —OH group, an alkyl group of 1 to 16 carbon atoms, an aryl group of 6 to 24 carbon atoms, an aralkyl group of 7 to 16 carbon atoms;
G represents an oxygen, nitrogen, sulphur, selenium, tellurium atom or an =NR group;
R and R' representing independently of each other H or an alkyl group of 1 to 16 carbon atoms, an aryl group of 6 to 24 carbon atoms, or an aralkyl group of 7 to 16 carbon atoms;
the intermediate chain corresponds to the formula:
-J-K-L- where
J represents an oxygen or sulphur atom, or an —NR— group;
K represents an aryl group of 6 to 24 carbon atoms, a heteroaryl group of 1 to 24 carbon atoms, the heteroelement being preferably chosen from oxygen, nitrogen or sulphur, an alkyl group of 1 to 16 carbon atoms, each being able to be optionally substituted by a halogen atom or an —NO$_2$, —NRR', —CN, —CF$_3$, —OH group, an alkyl group of 1 to 16 carbon atoms, an aryl group of 6 to 24 carbon atoms, an aralkyl group of 7 to 16 carbon atoms;

L represents a linear, branched or cyclic hydrocarbon chain with 0 to 10 members, in particular with 0 to 6 members, optionally containing one or more double or triple bonds, each of said members optionally being able to be a heteroatom, said heteroatom being preferably chosen from oxygen, sulphur, nitrogen, phosphorus, silicon, each member being able to be optionally substituted by at least one substituent chosen from an alkyl group of 1 to 16 carbon atoms, a halogen, an oxygen atom, —NO$_2$, —NRR', —CN, —CF$_3$, —OH, an alkoxy group of 1 to 16 carbon atoms, an aryl group of 6 to 24 carbon atoms, an aralkyl group of 7 to 16 carbon atoms;
R and R' representing independently of each other H or an alkyl group of 1 to 16 carbon atoms, an aryl group of 6 to 24 carbon atoms, or an aralkyl group of 7 to 16 carbon atoms;
the terminal group corresponds to the formula:

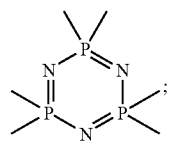

where $A_1$, $A_2$ and X have been defined previously, each X being identical or different.

According to a preferred embodiment, the invention relates to the use as defined above of a dendrimer of general formula (1) of structure PMMH, in which § represents

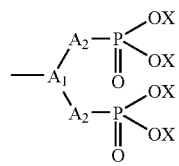

m represents 6;
n represents 0, 1, or 2;
A represents an oxygen atom;
B represents a benzene group;
D represents hydrogen;
E represents a methyl group;
G represents a sulphur atom;
J represents an oxygen atom;
K represents a benzene group;
L represents a non-substituted linear saturated hydrocarbon chain with two carbon atoms;
$A_1$ represents a nitrogen atom;
$A_2$ represents a CH$_2$ group;
X represents a methyl group, or a hydrogen or sodium atom;
said dendrimer being designated GCn, n being defined above.

According to a particularly preferred embodiment, the invention relates to the use as defined above of compounds of the following formulae:

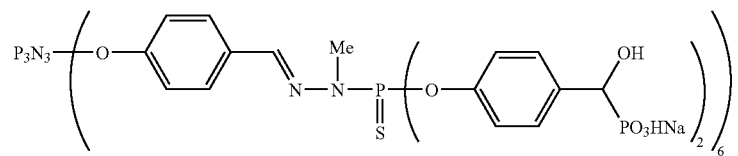
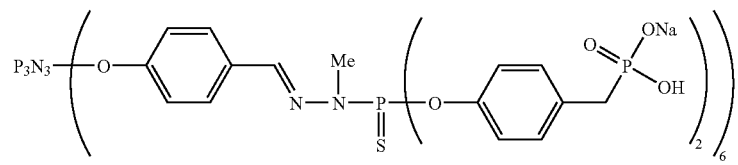
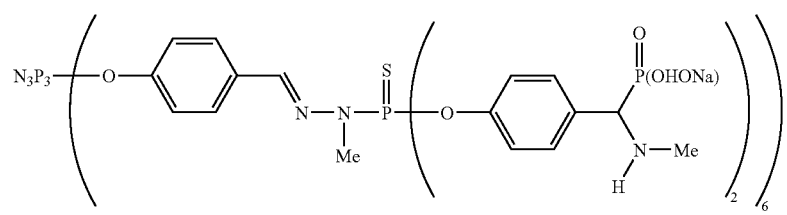
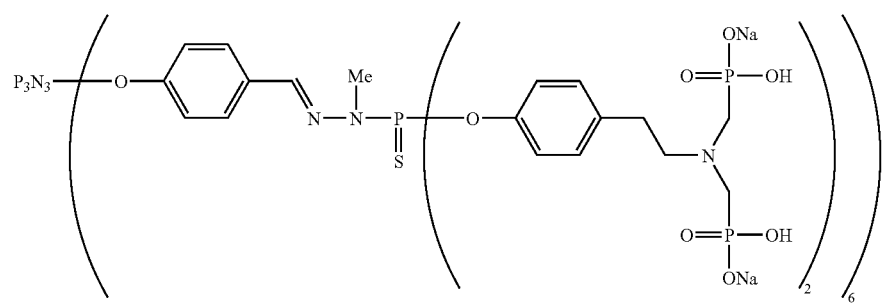
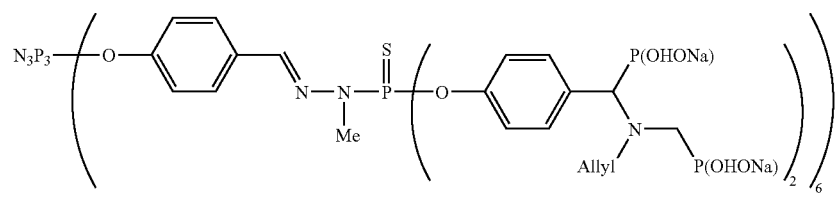
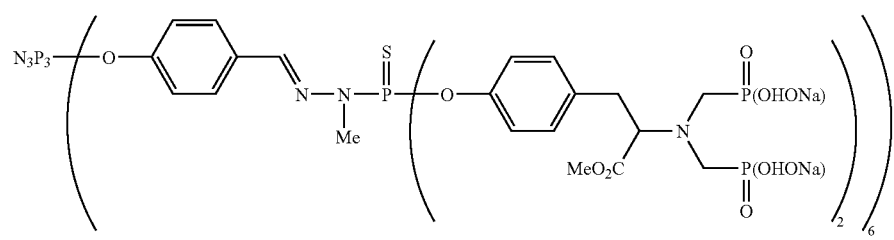
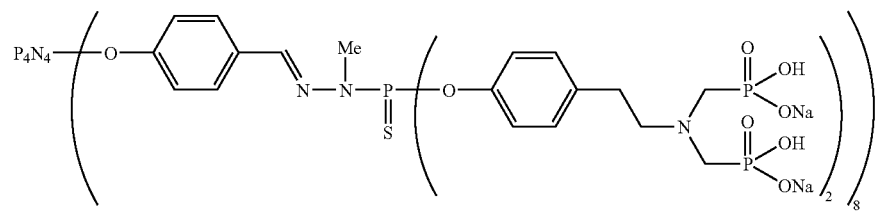

or of GC1 compounds of the following formulae:
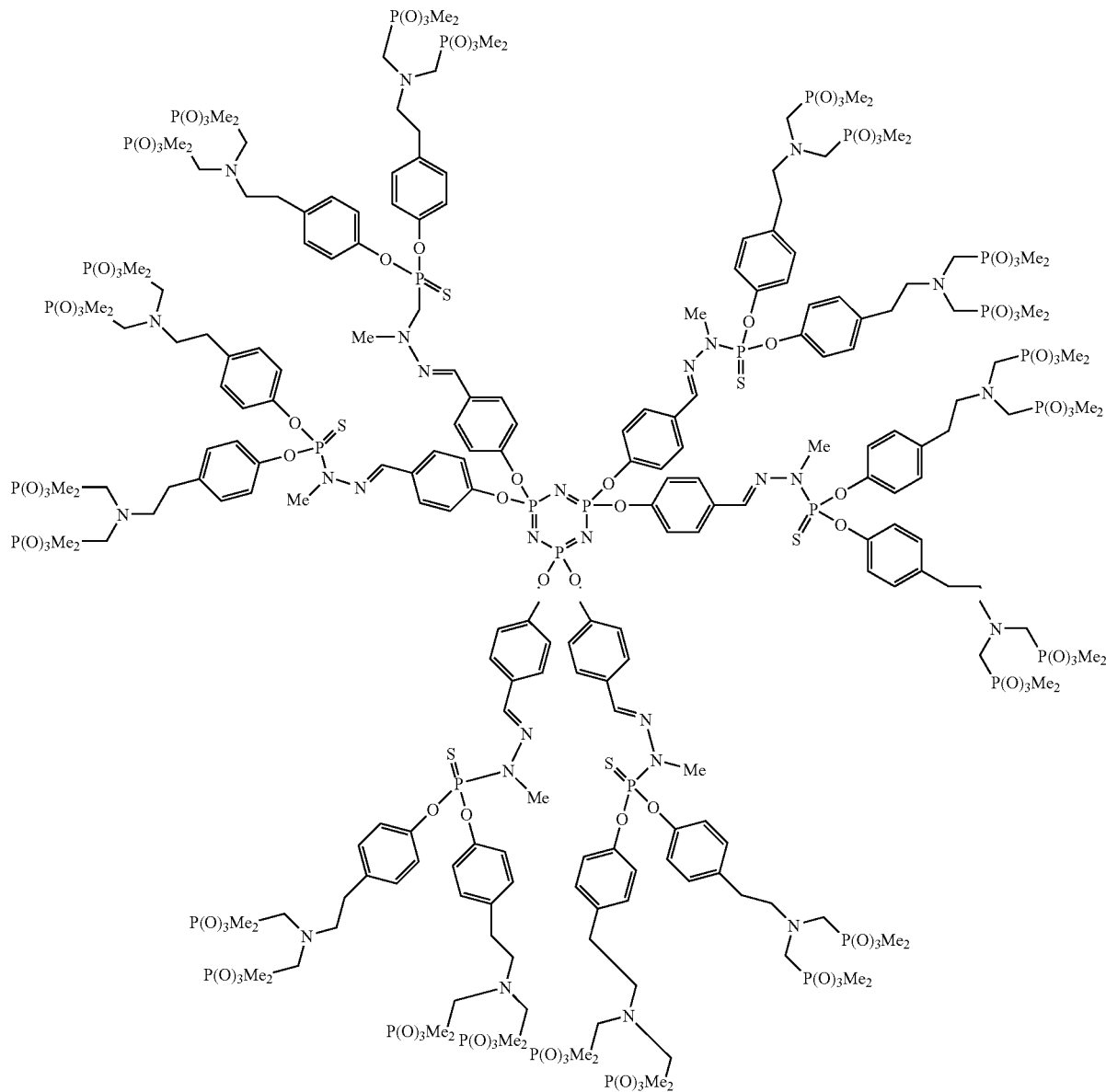

-continued
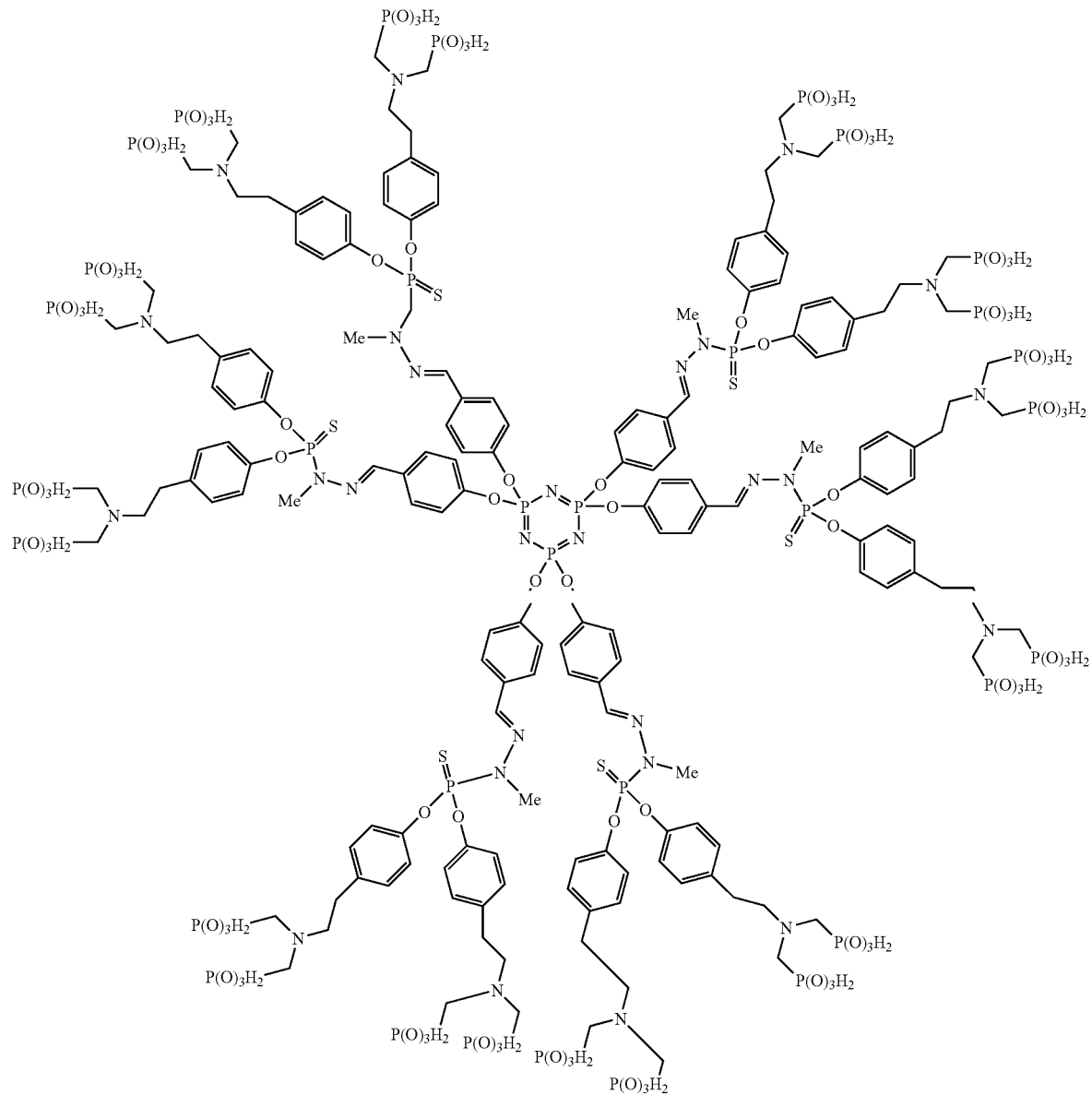

-continued
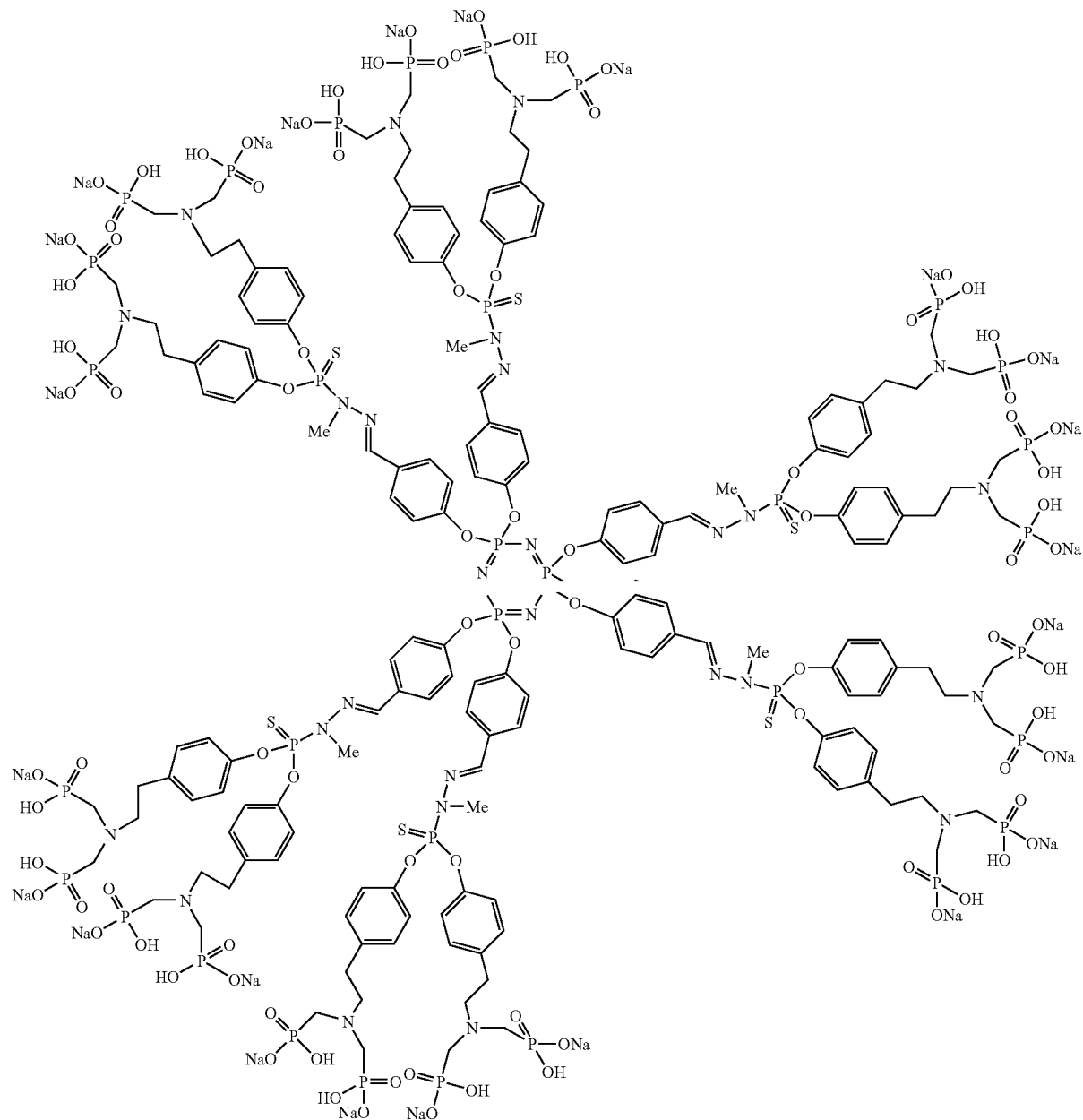

and in particular of the following formula (6):

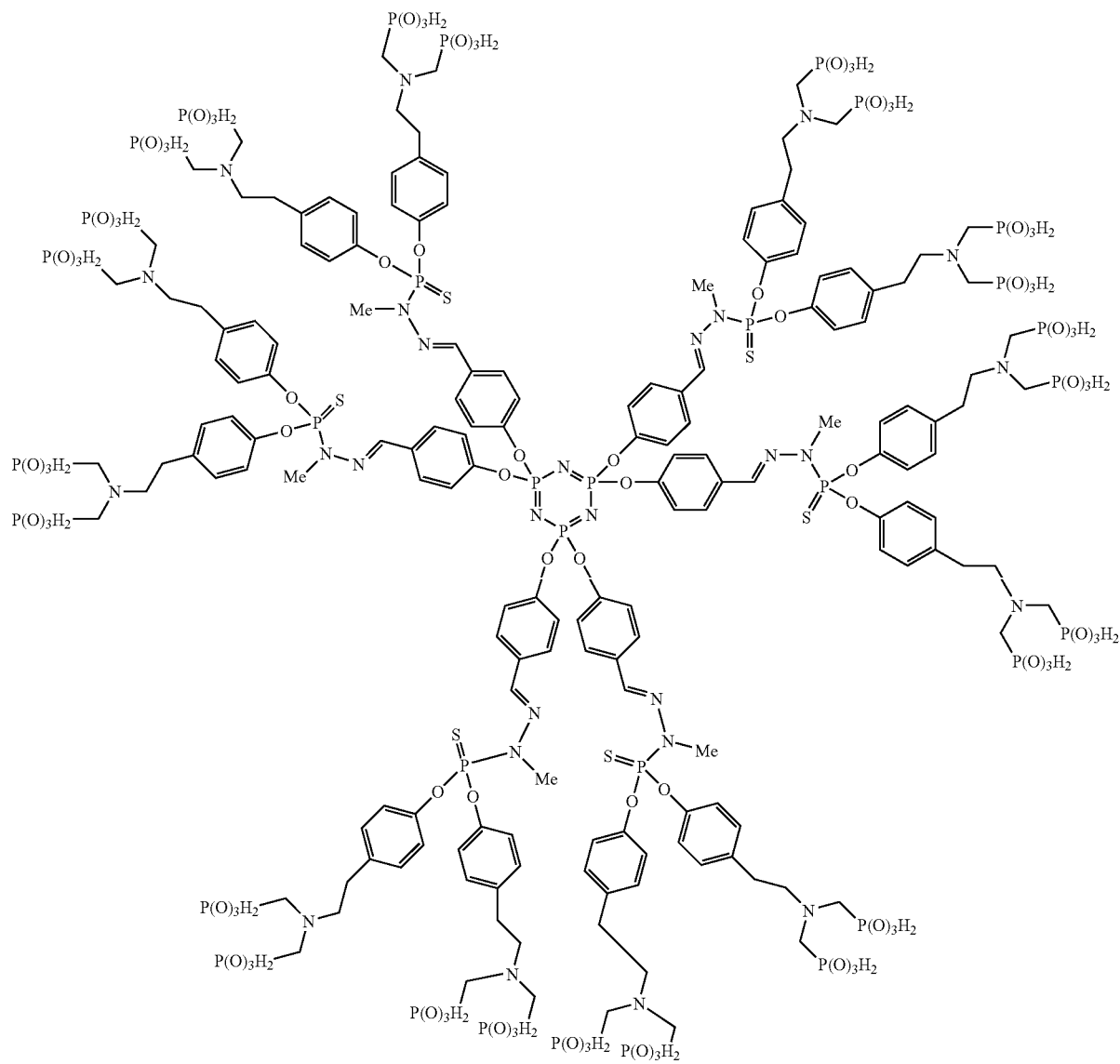

(6)

The present invention also relates to the use as defined above, of dendrimers with bisphosphonic terminations corresponding to the following general formula (7):

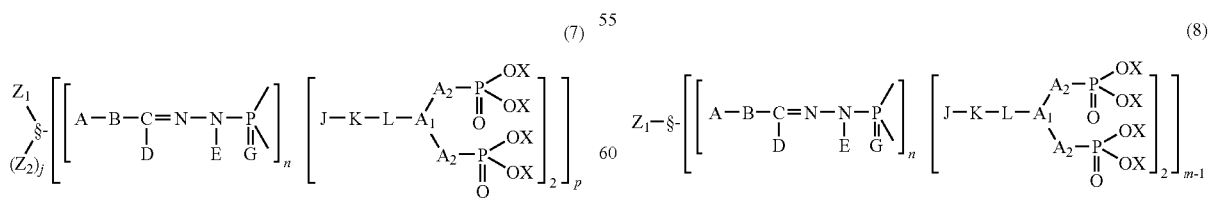

where n represents an integer from 0 to 3, m represents 3, 6 or 8, p represents m−1 or m−2, and j represents 0 when p represents m−1 and 1 when p represents m−2, namely:

when p=m−1, formula (7) corresponds to the following formula (8):

when p=m−2, formula (7) corresponds to the following formula (9):

(9)

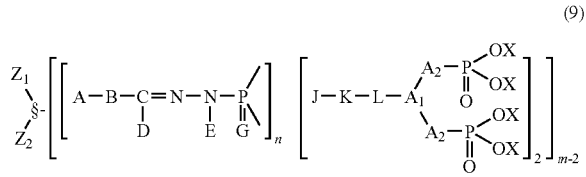

and in which formulae:
the central core § is chosen from the following groups:

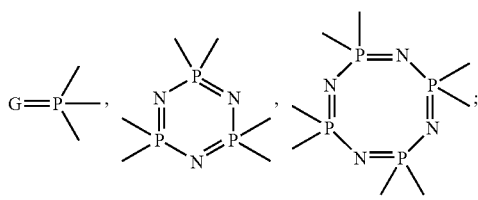

the generation chain corresponds to the formula:

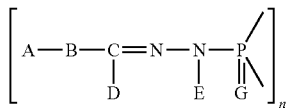

where
A represents an oxygen, sulphur, phosphorus atom or an —NR— group;

B represents an aryl group of 6 to 24 carbon atoms, a heteroaryl group of 1 to 24 carbon atoms, an alkyl group of 1 to 16 carbon atoms, each being able to be optionally substituted by a halogen atom or an —NO$_2$, —NRR', —CN, —CF$_3$, —OH group, an alkyl group of 1 to 16 carbon atoms, an aryl group of 6 to 24 carbon atoms, an aralkyl group of 7 to 16 carbon atoms;

D represents a hydrogen atom, an alkyl group of 1 to 16 carbon atoms, an alkoxy group of 1 to 16 carbon atoms, an aryl group of 6 to 24 carbon atoms, an aralkyl group of 7 to 16 carbon atoms, each being able to be optionally substituted by a halogen atom or an —NO$_2$, —NRR', —CN, —CF$_3$, —OH group, an alkyl group of 1 to 16 carbon atoms, an aryl group of 6 to 24 carbon atoms, an aralkyl group of 7 to 16 carbon atoms;

E represents a hydrogen atom, an alkyl group of 1 to 16 carbon atoms, an alkoxy group of 1 to 16 carbon atoms, an aryl group of 6 to 24 carbon atoms, an aralkyl group of 7 to 16 carbon atoms, each being able to be optionally substituted by a halogen atom or an —NO$_2$, —NRR', —CN, —CF$_3$, —OH group, an alkyl group of 1 to 16 carbon atoms, an aryl group of 6 to 24 carbon atoms, an aralkyl group of 7 to 16 carbon atoms;

G represents an oxygen, nitrogen, sulphur, selenium, tellurium atom or an =NR group;

R and R' representing independently of each other H or an alkyl group of 1 to 16 carbon atoms, an aryl group of 6 to 24 carbon atoms, or an aralkyl group of 7 to 16 carbon atoms;

the intermediate chain corresponds to the formula:

-J-K-L- where
J represents an oxygen or sulphur atom, or an —NR— group;

K represents an aryl group of 6 to 24 carbon atoms, a heteroaryl group of 1 to 24 carbon atoms, the heteroelement being preferably chosen from oxygen, nitrogen or sulphur, an alkyl group of 1 to 16 carbon atoms, each being able to be optionally substituted by a halogen atom or an —NO$_2$, —NRR', —CN, —CF$_3$, —OH group, an alkyl group of 1 to 16 carbon atoms, an aryl group of 6 to 24 carbon atoms, an aralkyl group of 7 to 16 carbon atoms;

L represents a linear, branched or cyclic hydrocarbon chain with 0 to 10 members, in particular with 0 to 6 members, optionally containing one or more double or triple bonds, each of said members optionally being able to be a heteroatom, said heteroatom being preferably chosen from oxygen, sulphur, nitrogen, phosphorus, silicon, each member being able to be optionally substituted by at least one substituent chosen from an alkyl group of 1 to 16 carbon atoms, a halogen, an oxygen atom, —NO$_2$, —NRR', —CN, —CF$_3$, —OH, an alkoxy group of 1 to 16 carbon atoms, an aryl group of 6 to 24 carbon atoms, an aralkyl group of 7 to 16 carbon atoms;

R and R' representing independently of each other H or an alkyl group of 1 to 16 carbon atoms, an aryl group of 6 to 24 carbon atoms, or an aralkyl group of 7 to 16 carbon atoms;

the terminal group corresponds to the formula:

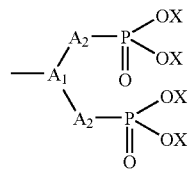

where A1, A2 and X have been defined previously, each X being identical or different;

$Z_1$ and $Z_2$ being identical or different, optionally linked together, in particular by means of a covalent bond, and representing H or a linear, branched or cyclic hydrocarbon chain with 1 to 16 members, optionally containing one or more double or triple bonds, each of said members being optionally chosen from a heteroatom, said heteroatom being preferably chosen from a nitrogen, oxygen, phosphorus, silicon or sulphur atom, an aryl group of 6 to 24 carbon atoms, a heteroaryl group of 1 to 24 carbon atoms, a carboxyl group, a >C═NR group, each member being able to be optionally substituted by at least one substituent chosen from a hydroxyl group, an —NR"R'" group, an alkoxy group of 1 to 16 carbon atoms, an alkyl group of 1 to 16 carbon atoms, a halogen atom, an —NO$_2$ group, a —CN group, a —CF$_3$ group, an aryl group of 6 to 24 carbon atoms, an aralkyl group of 7 to 16 carbon atoms, R" and R'" representing independently of each other H or an alkyl group of 1 to 16 carbon atoms, an aryl group of 6 to 24 carbon atoms or an aralkyl group of 7 to 16 carbon atoms, the first member of said hydrocarbon chain preferably being oxygen or nitrogen.

The invention relates more particularly to the use as defined above, of a dendrimer of general formula (8) of structure PMMH, in which § represents

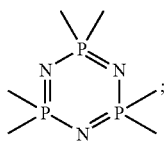

m represents 6;
p represents 5;
n represents 0, 1, or 2;
A represents an oxygen atom;
B represents a benzene group;
D represents hydrogen;
E represents a methyl group;
G represents a sulphur atom;
J represents an oxygen atom;
K represents a benzene group;
L represents a non-substituted linear saturated hydrocarbon chain with two carbon atoms;
$A_1$ represents a nitrogen atom;
$A_2$ represents a CH$_2$ group;
X represents a methyl group, or a hydrogen or sodium atom;
$Z_1$ represents a phenyloxy group;
said dendrimer being designated GCn', n being defined above.

Preferably, the present invention relates in particular to the use as defined above:
of the compounds of the following formulae:

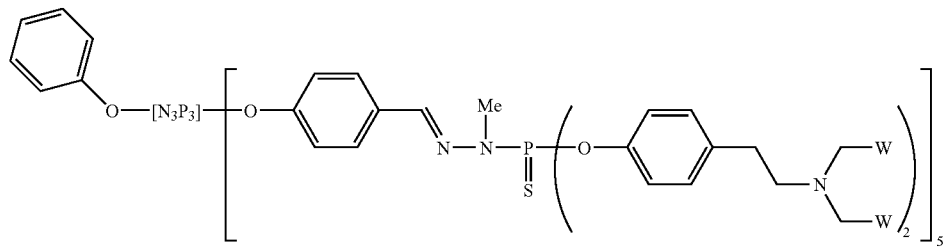

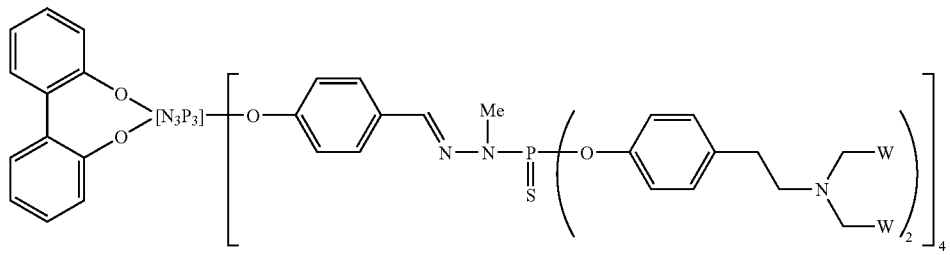

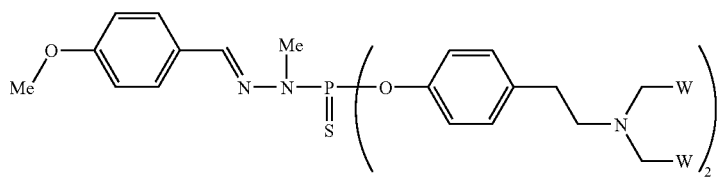

in which W represents $PO_3Me_2$, $PO_3HNa$, $PO_3H_2$, said compounds corresponding, in particular, to compound GC1' of the following formula (10):
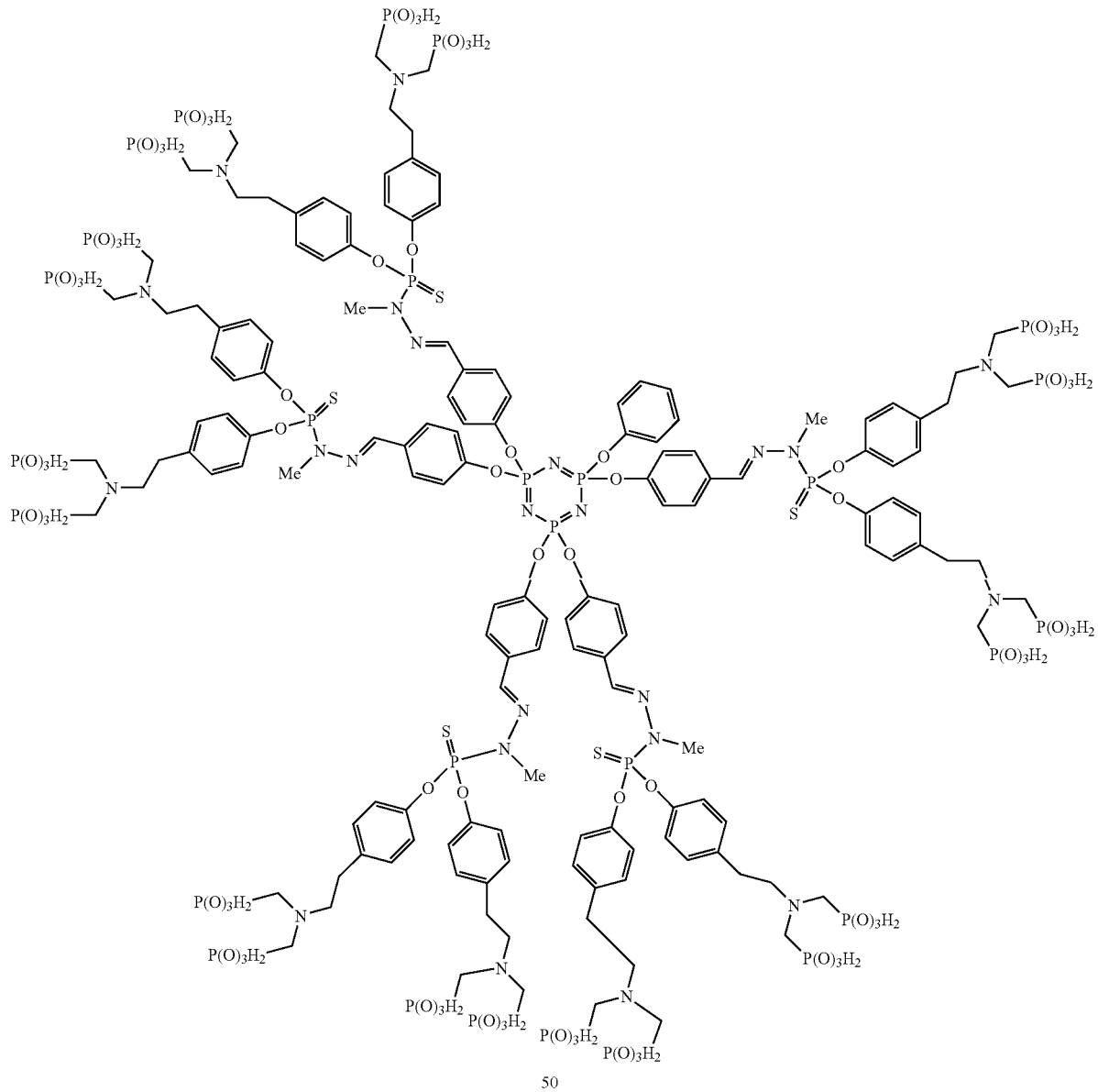
(10)
or compounds of the following formula:
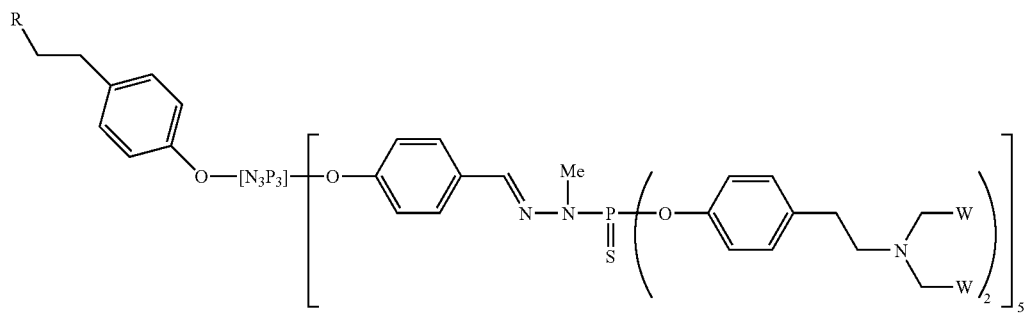

in which W represents PO₃Me₂, PO₃HNa, or PO₃H₂ and R represents a fluorescent group chosen from:
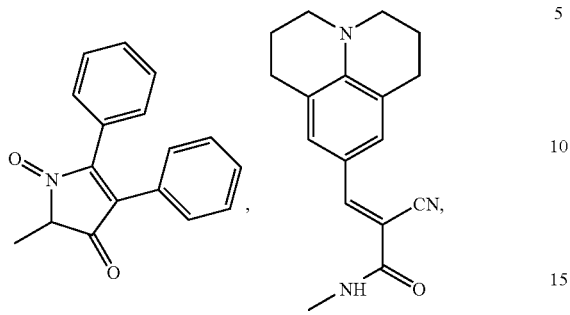
said compounds corresponding in particular to the compounds of the following formulae:
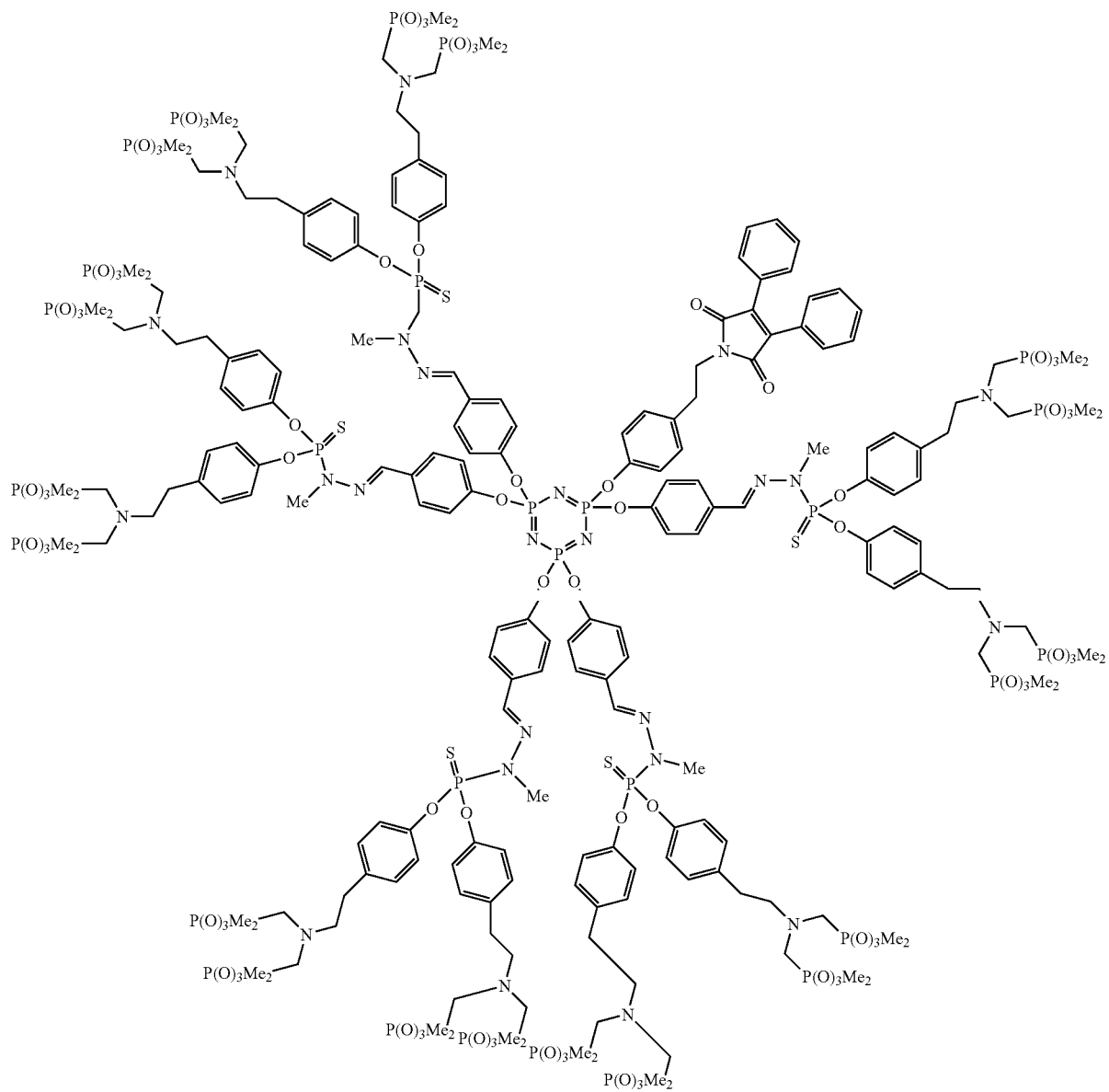

-continued
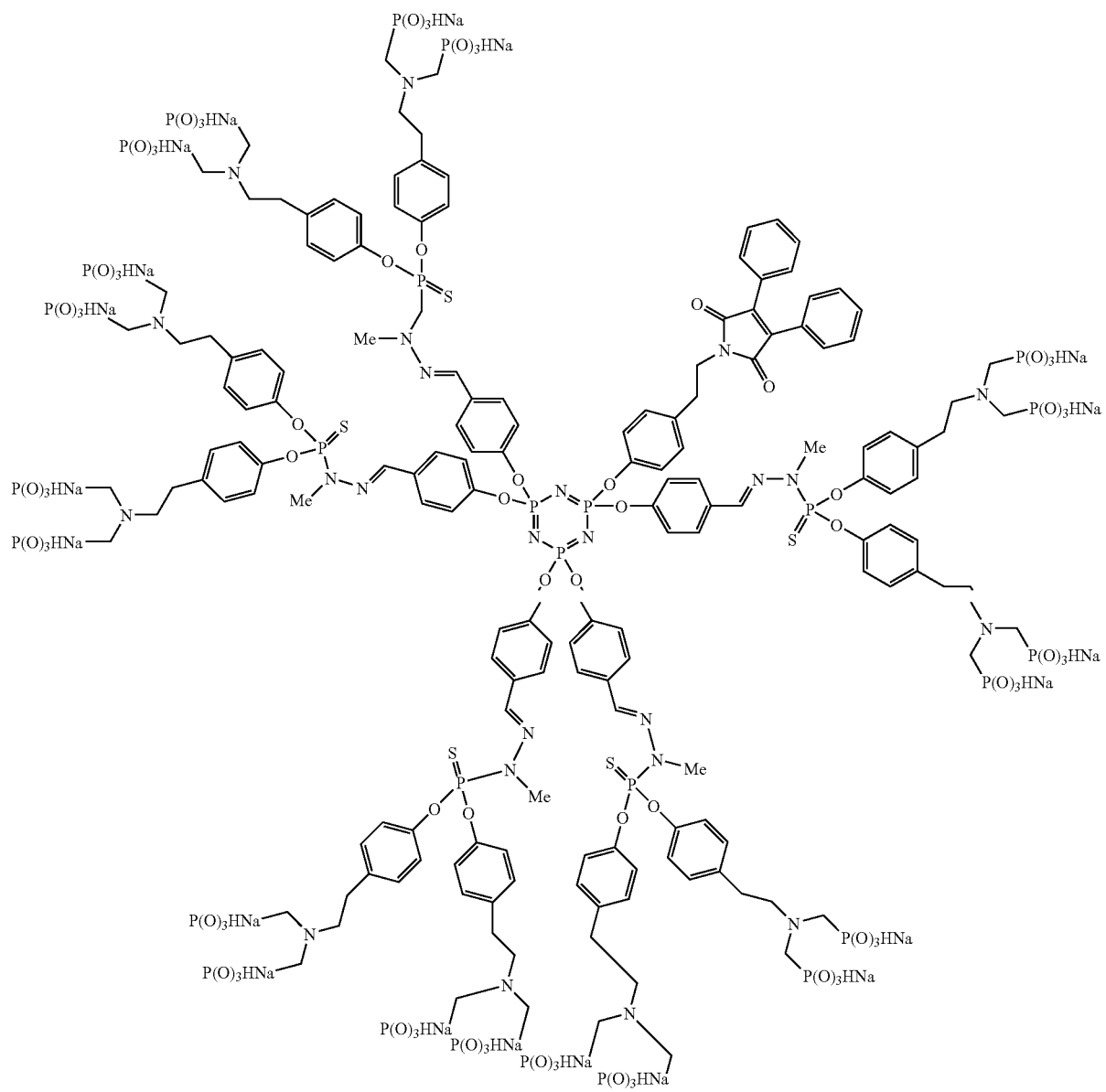

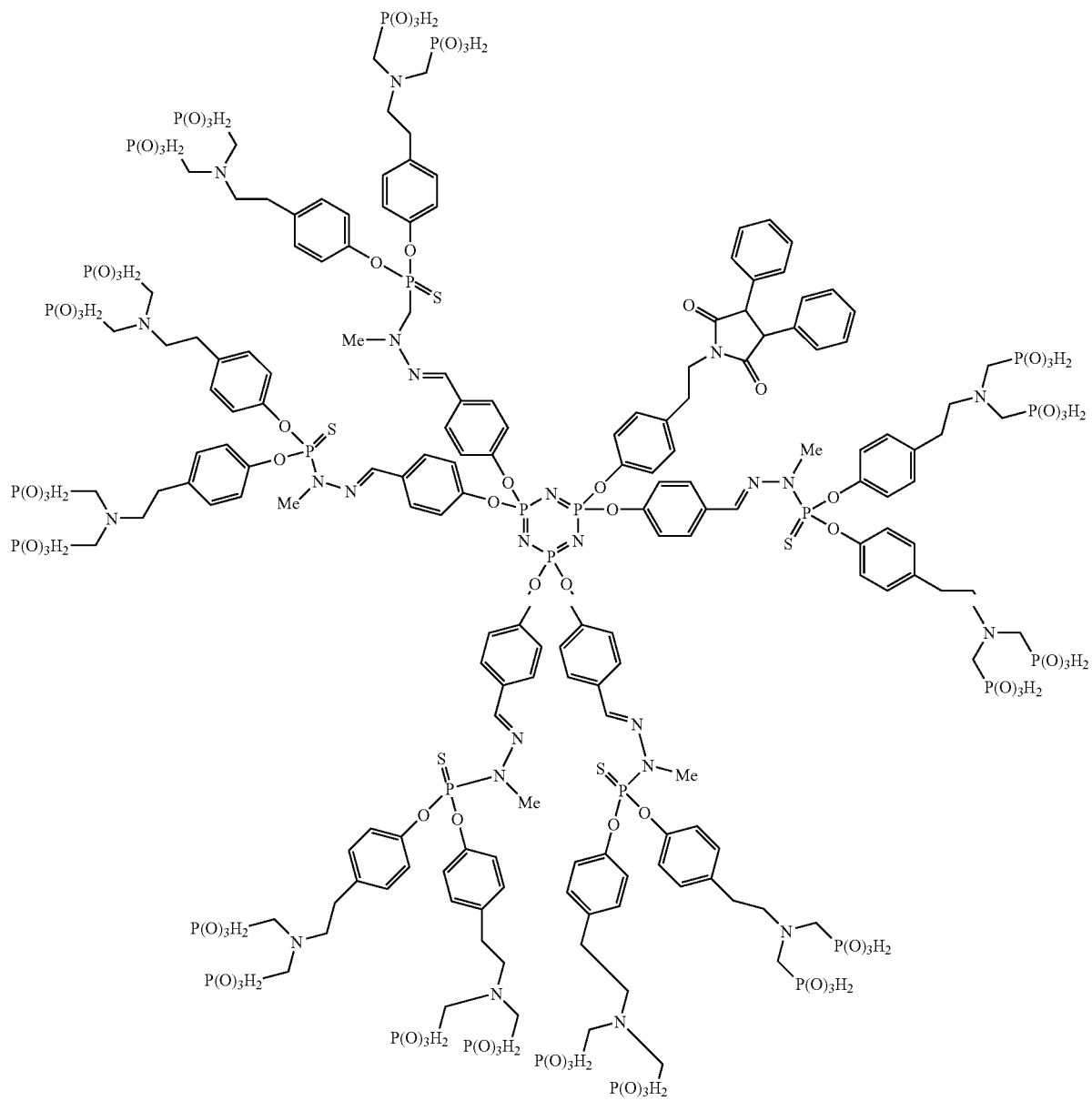

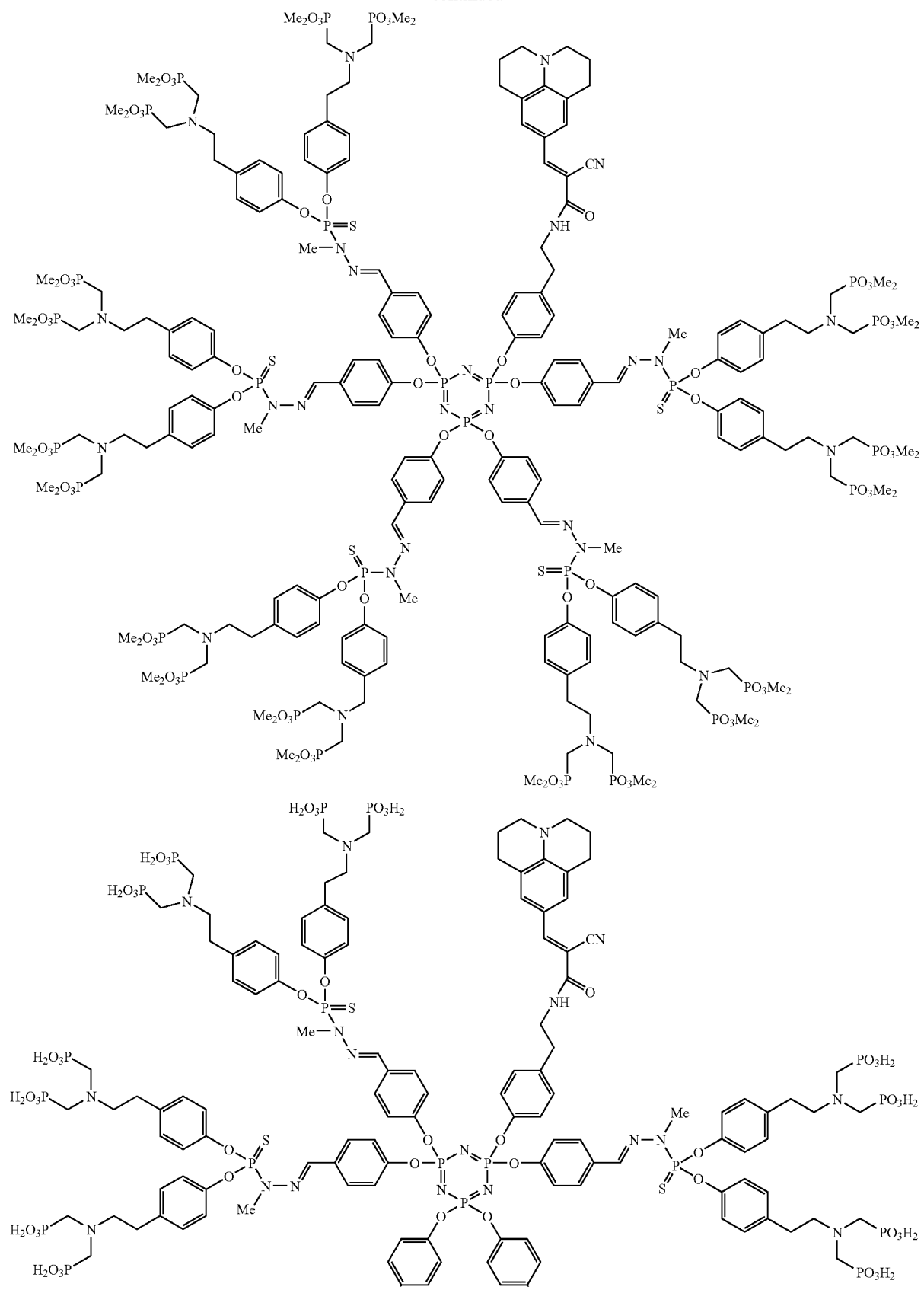

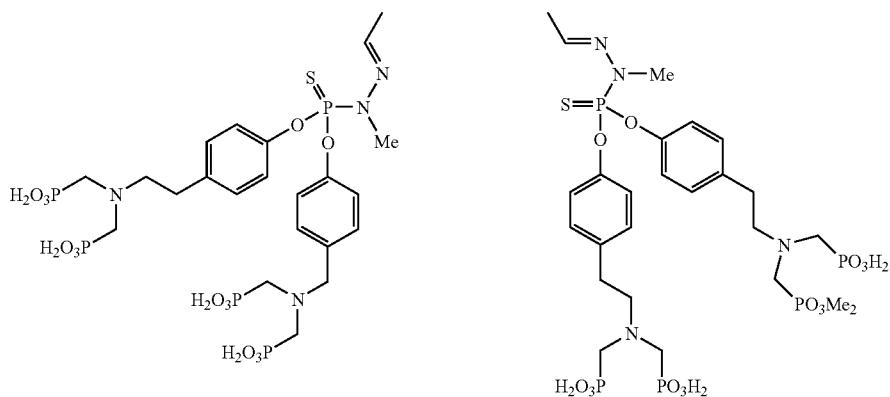
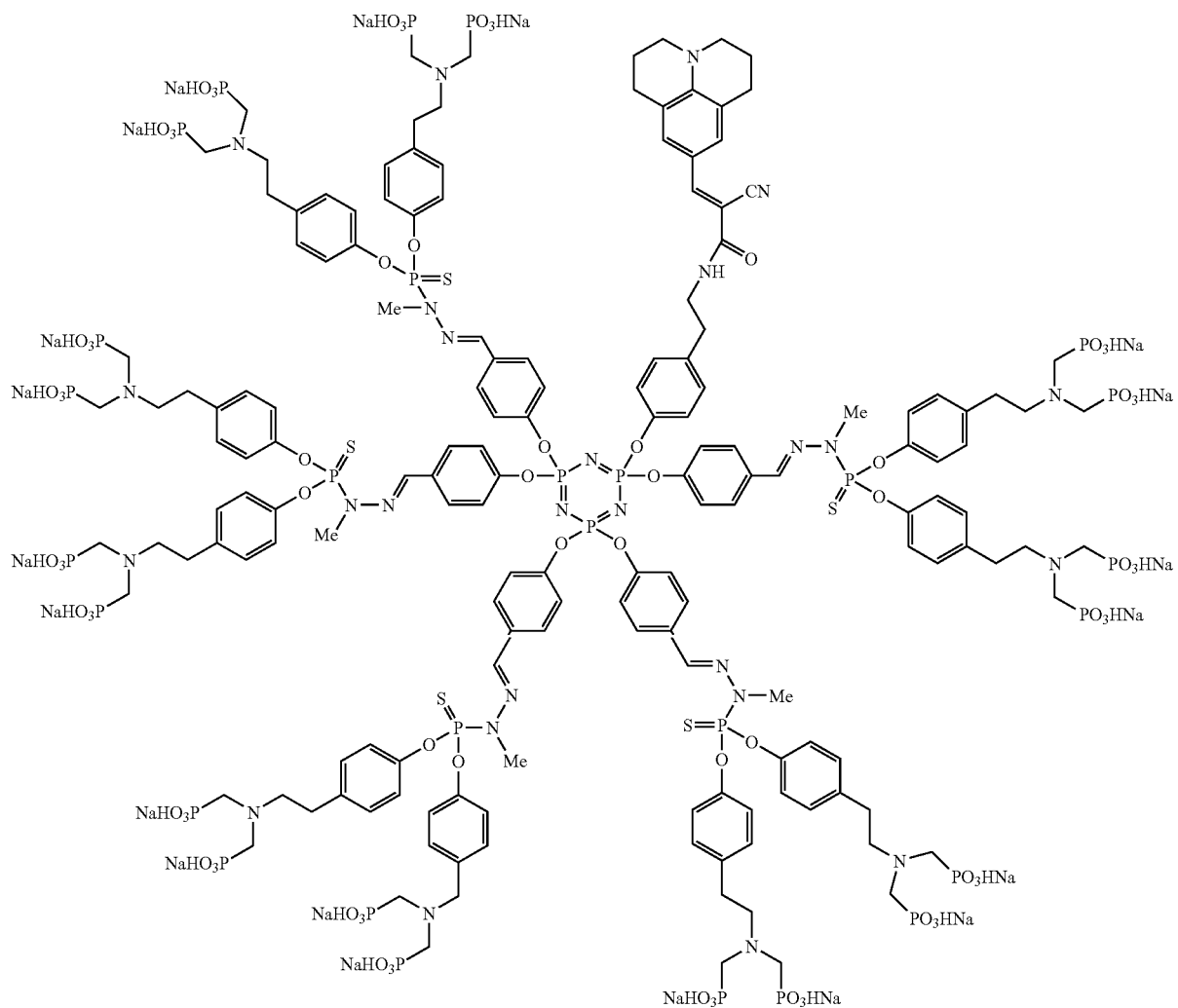
Advantageously, the latter dendrimers are fluorescent. They can in particular be used within the framework of the detection of cells binding to the dendrimers and/or for the identification of the binding site of the dendrimers at the surface of the cells.

The present invention also relates to the use as defined above of dendrimers with bisphophonic terminations of the following formula:

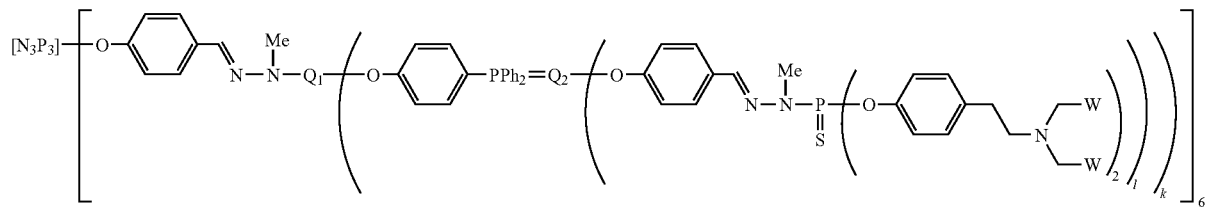

in which W represents $PO_3Me_2$, $PO_3HNa$, or $PO_3H_2$, $Q_1$ and $Q_2$, identical or different, represent P=S or cyclotriphosphazene ($N_3P_3$), l represents 2 when $Q_2$ represents P=S or 5 when $Q_2$ represents $N_3P_3$ and k represents 2 when $Q_1$ represents P=S or 5 when $Q_1$ represents $N_3P_3$, said dendrimers being in particular represented by the following formulae:

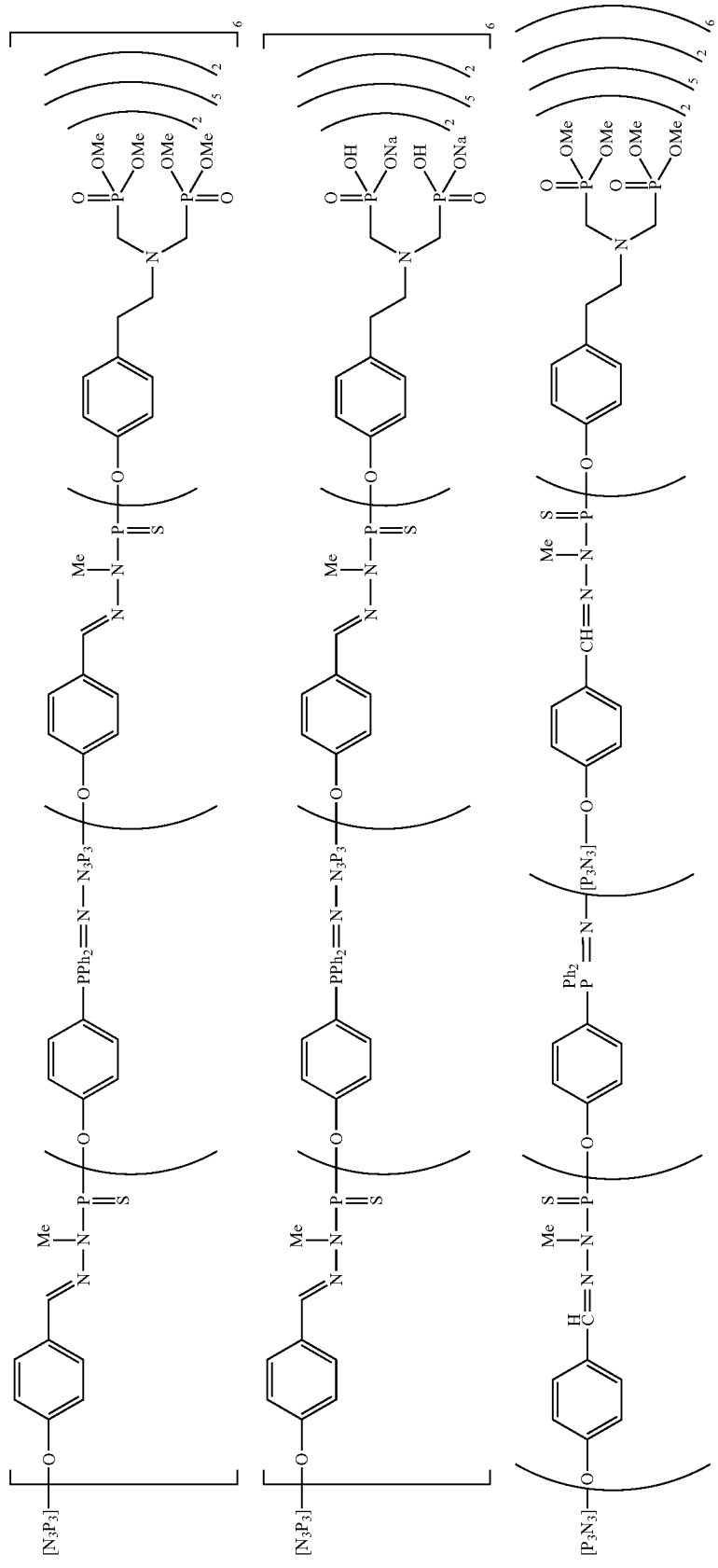

-continued
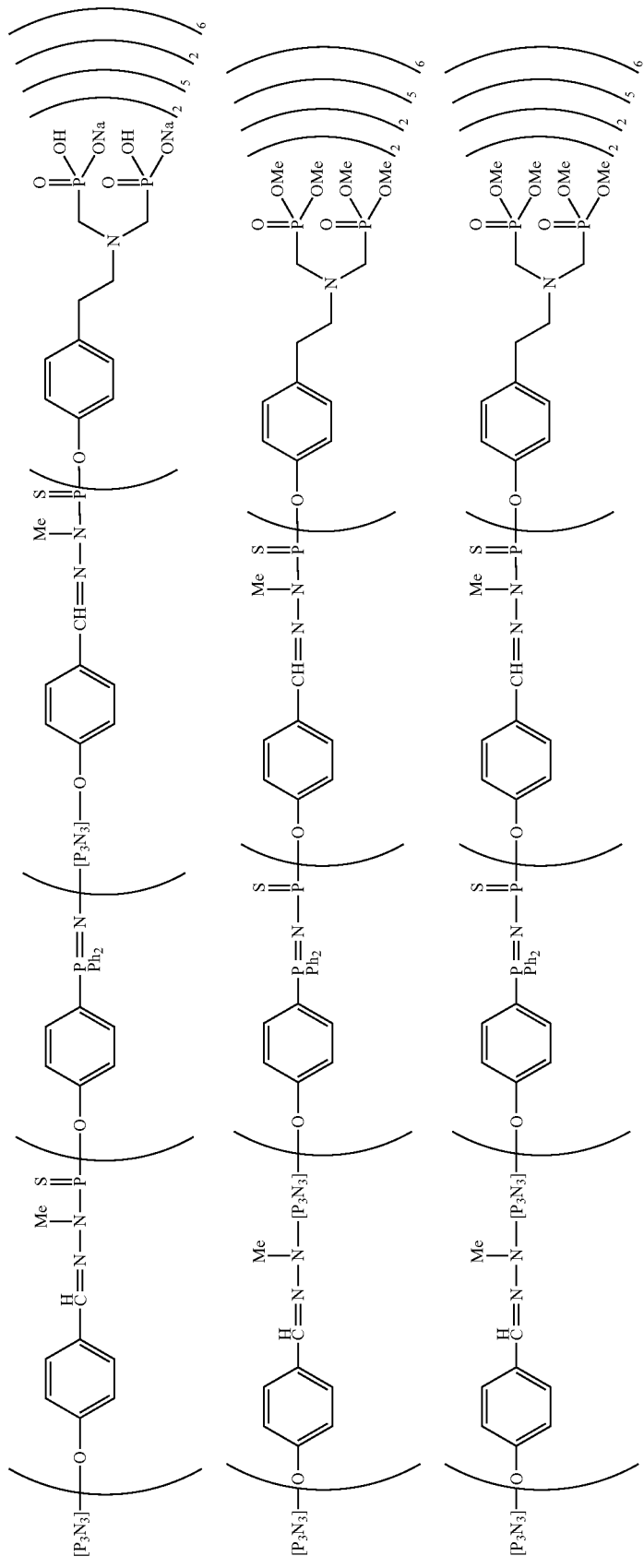

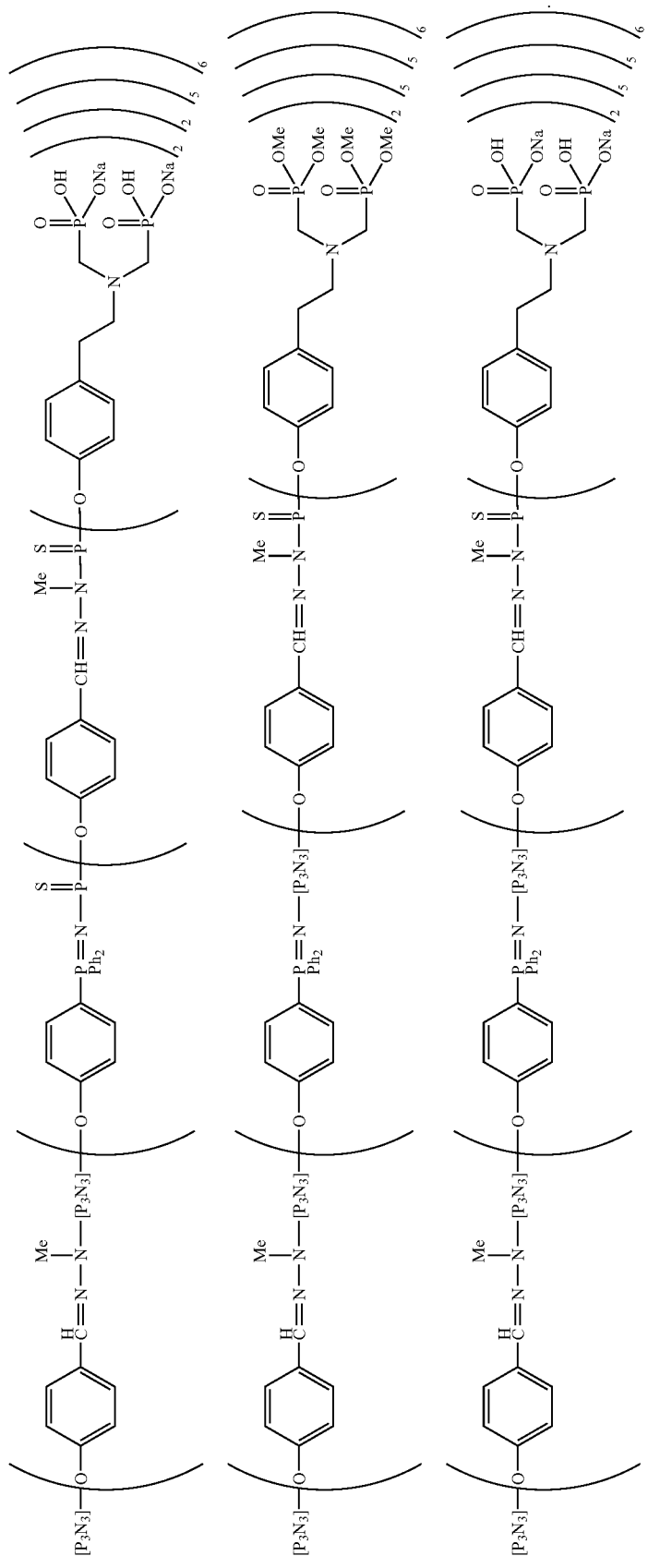

The present invention also relates to the use as defined above of dendrimers with monophosphonic or bisphosphonic terminations of the following formula:

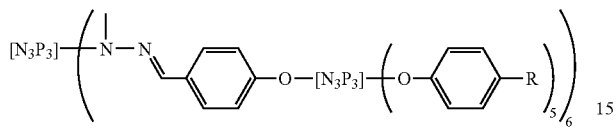

in which R represents a group chosen from

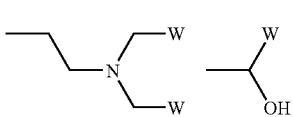

where W represents $PO_3Me_2$, $PO_3HNa$, or $PO_3H_2$.

The present invention also relates to the use as defined above of dendrimers with bisphosphonic terminations of the following formula:

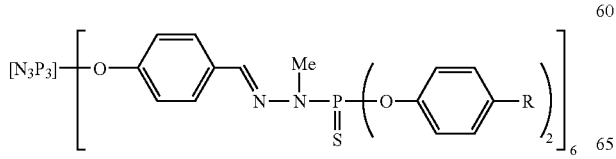

in which R represents a group chosen from:

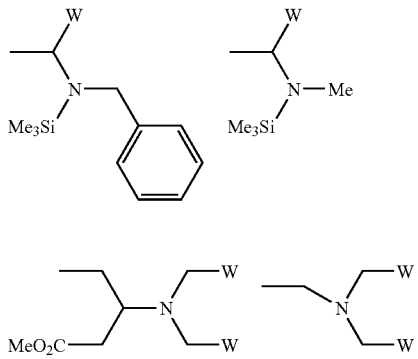

where W represents $PO_3Si_2Me_6$, $PO_3Me_2$, $PO_3HNa$, or $PO_3H_2$.

The present invention also relates to the use as defined above of dendrimers with monophosphonic terminations of the following formula:

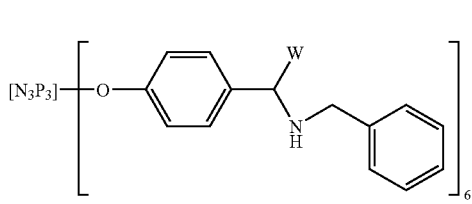

in which W represents $PO_3Me_2$, $PO_3HNa$, or $PO_3H_2$.

The present invention also relates to the use as defined above of dendrimers with bisphosphonic terminations of the following formula:

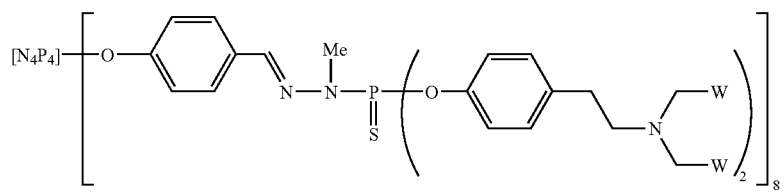

in which W represents $PO_3Me_2$, $PO_3HNa$, or $PO_3H_2$.

The present invention also relates to the use as defined above of dendrimers with bisphosphonic terminations of the following formula:

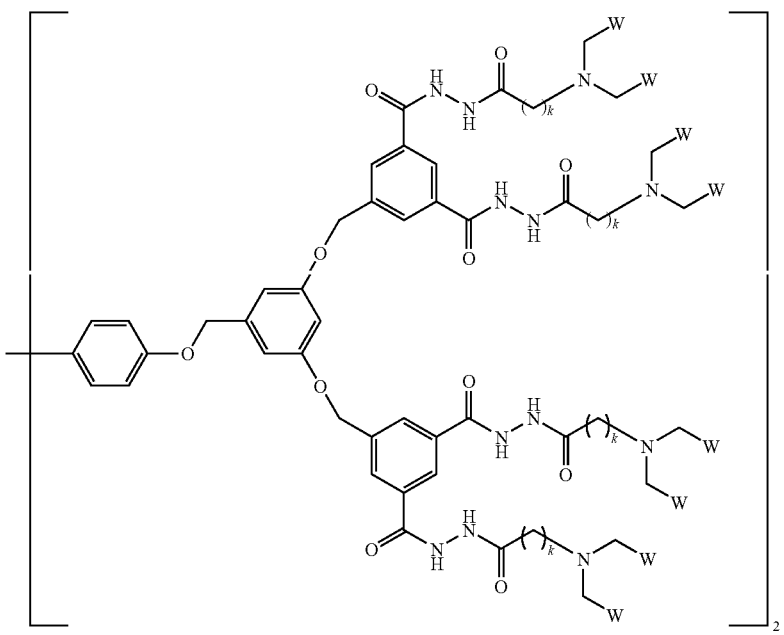

in which W represents $PO_3Me_2$, $PO_3HNa$, or $PO_3H_2$ and k represents 1, 2 or 3.

The present invention also relates to the use as defined above of dendrimers with bisphosphonic terminations of the following formula:

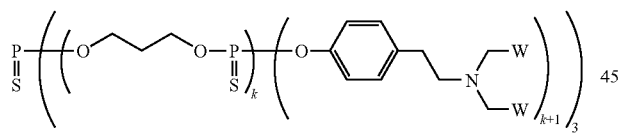

in which W represents $PO_3Me_2$, $PO_3HNa$, or $PO_3H_2$ and k represents 0 or 1.

The present invention also relates to the use as defined above of dendrimers with bisphosphonic terminations of the following formula:

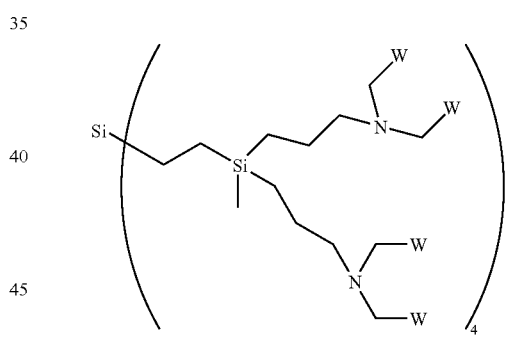

in which W represents $PO_3Me_2$, $PO_3HNa$, or $PO_3H_2$.

The present invention also relates to the use as defined above of dendrimers with bisphosphonic terminations of the following formula:

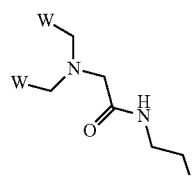

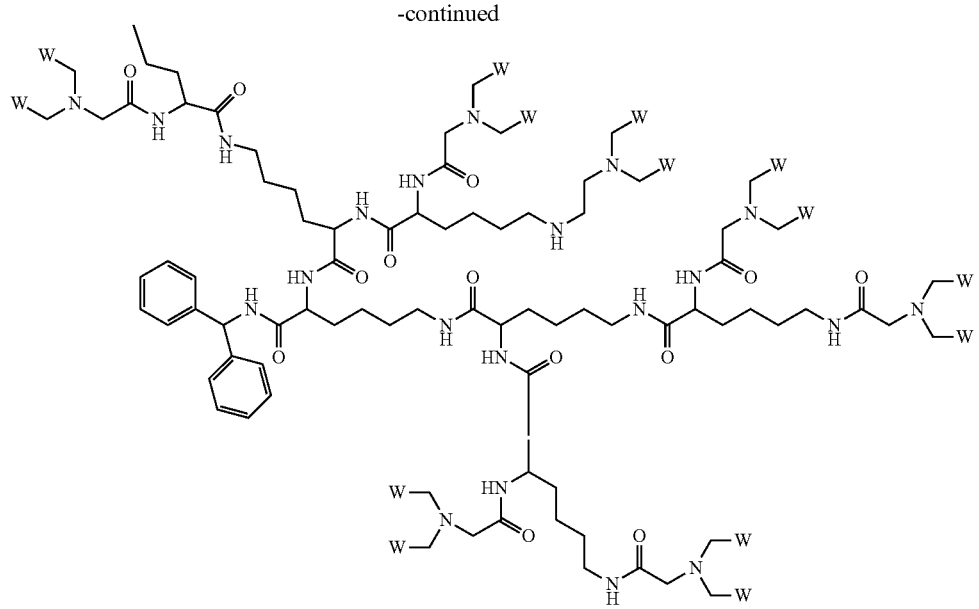
25
in which W represents $PO_3Me_2$, $PO_3HNa$, or $PO_3H_2$.
In a particular manner, the present invention relates in particular to the use, as defined above, of the compounds of the following formulae:
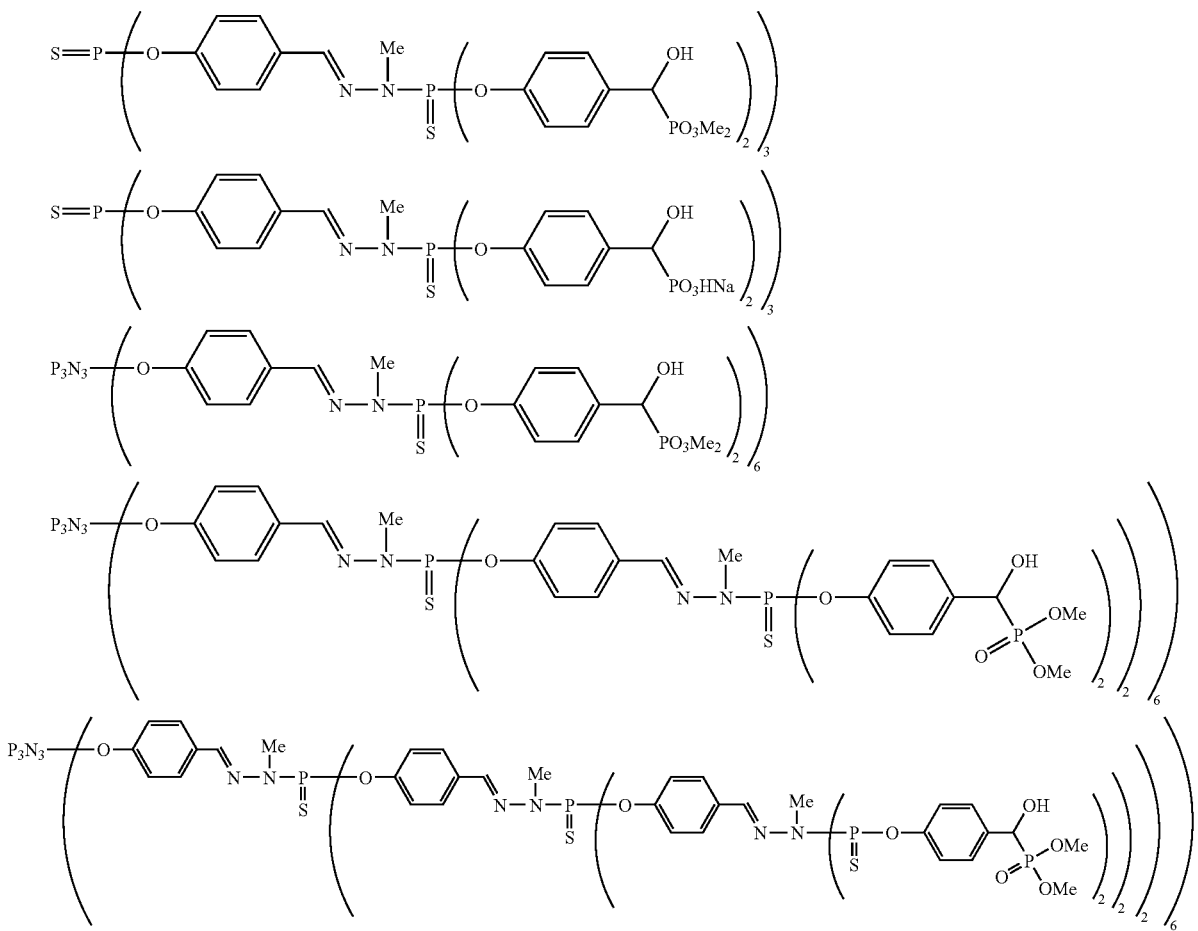

-continued
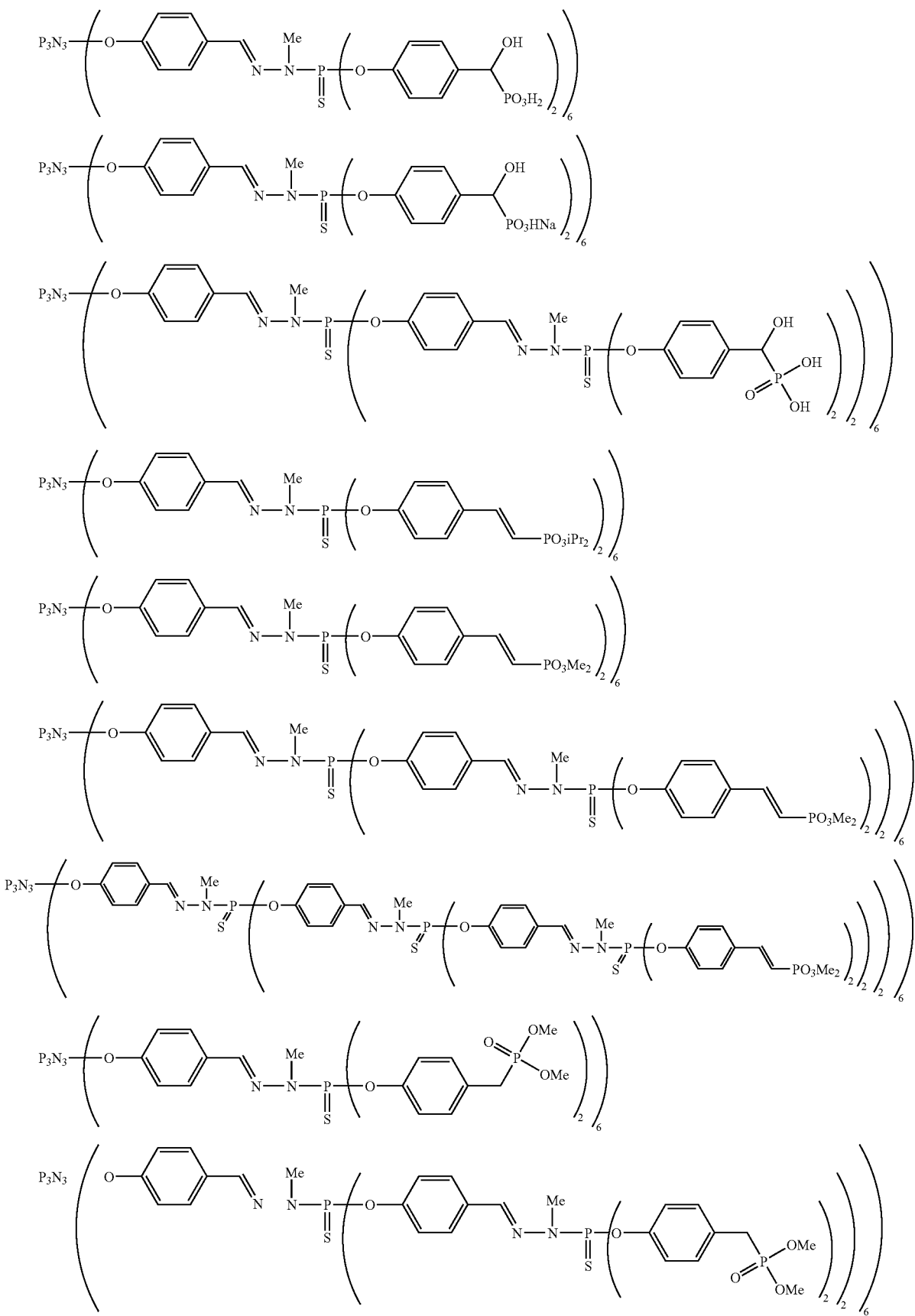

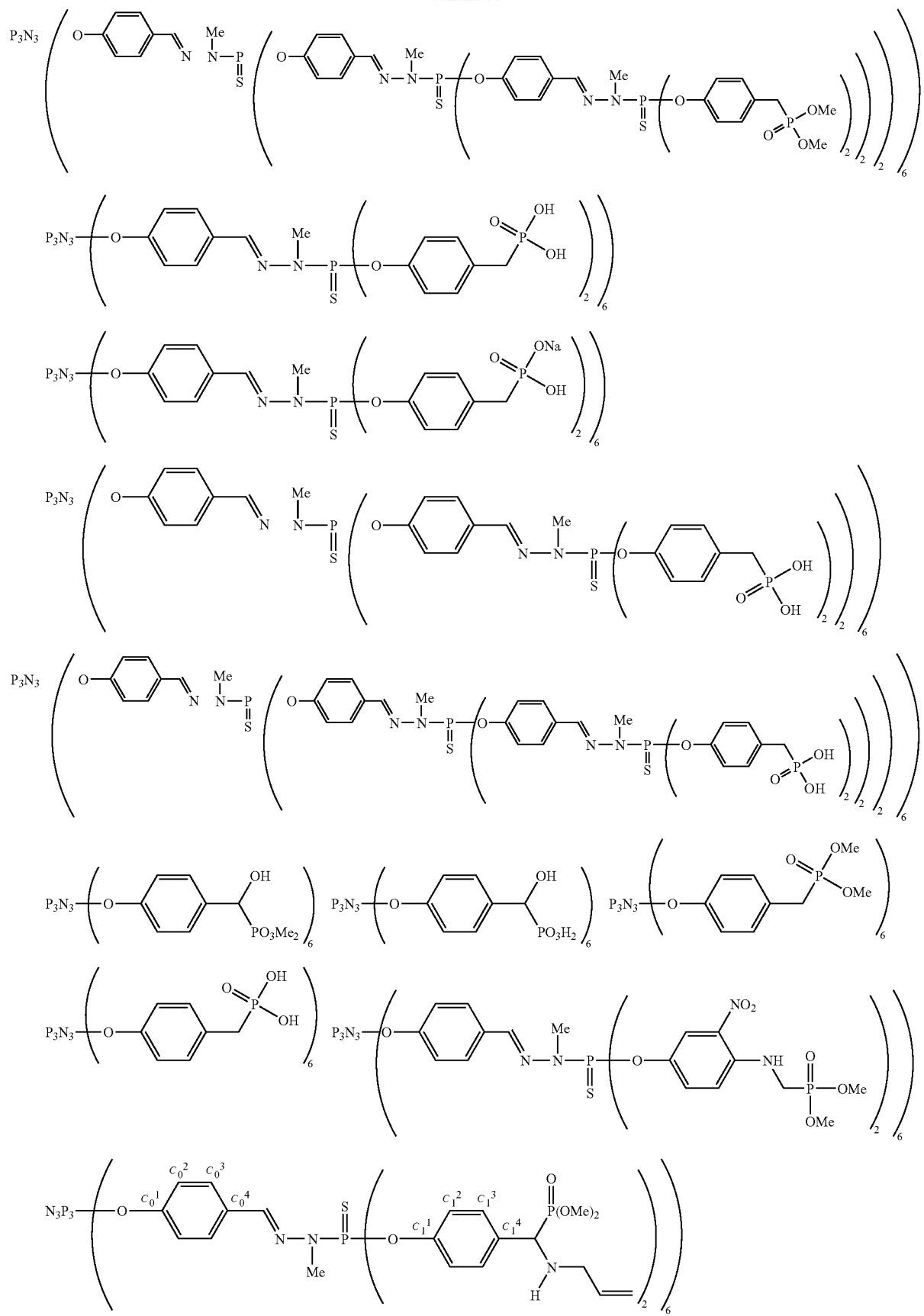

-continued
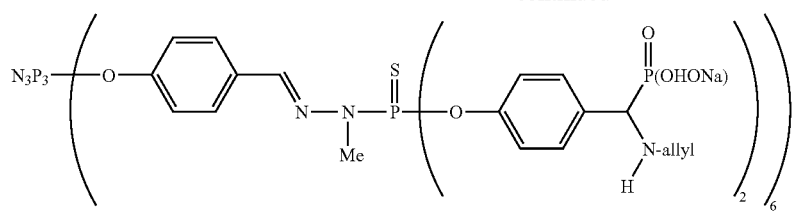
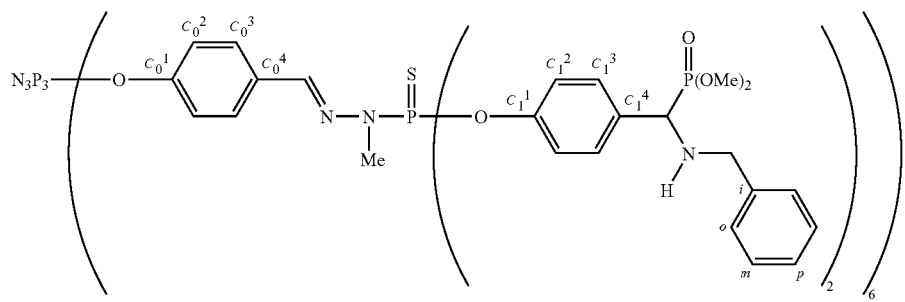
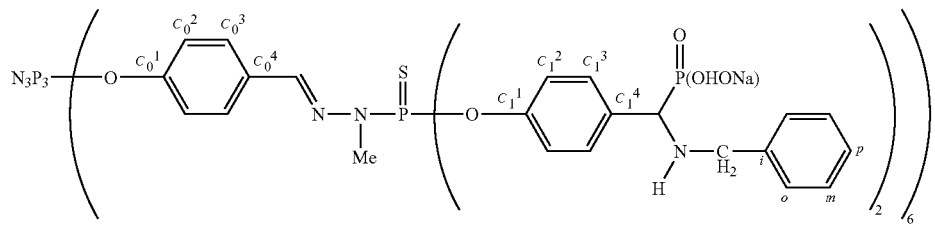
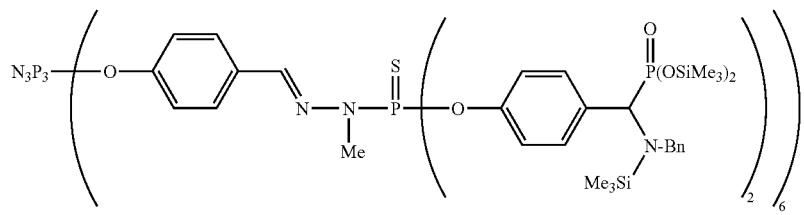
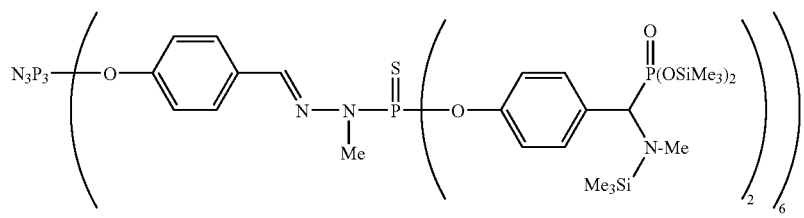
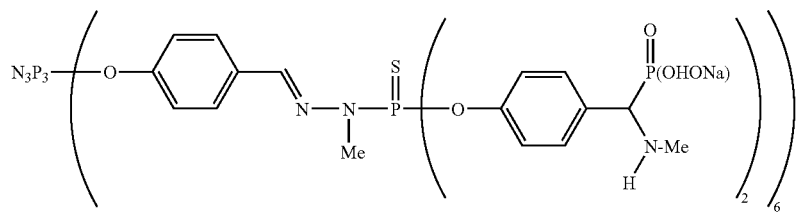
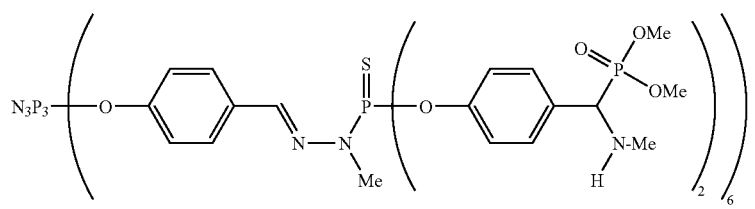

-continued
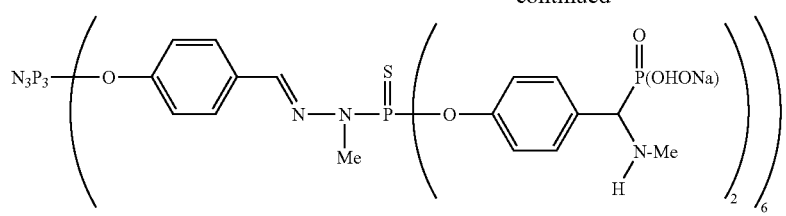
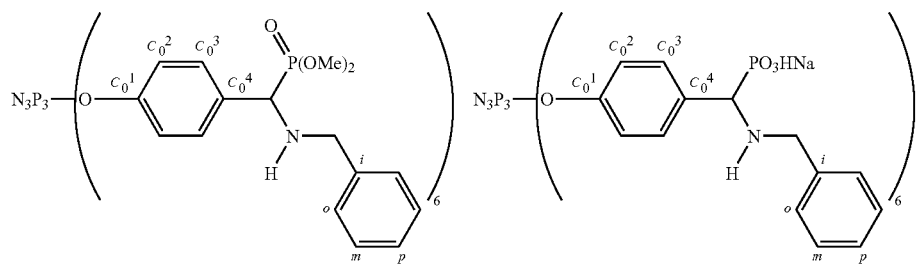
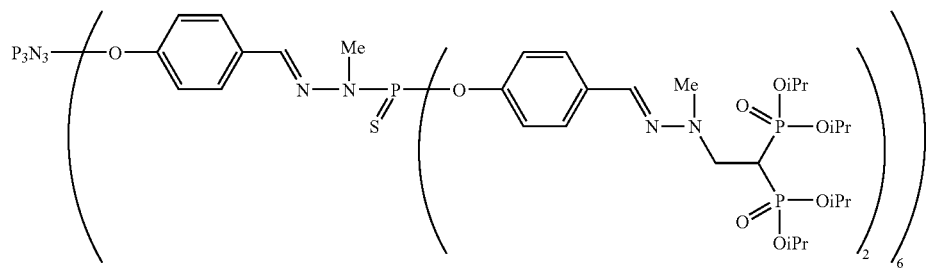
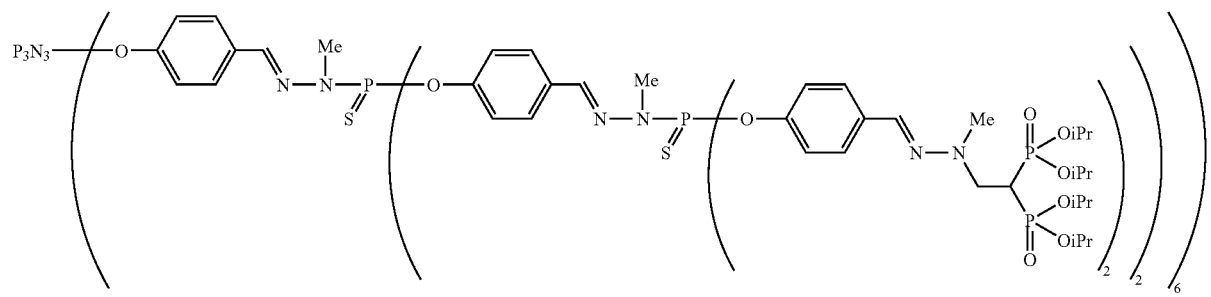
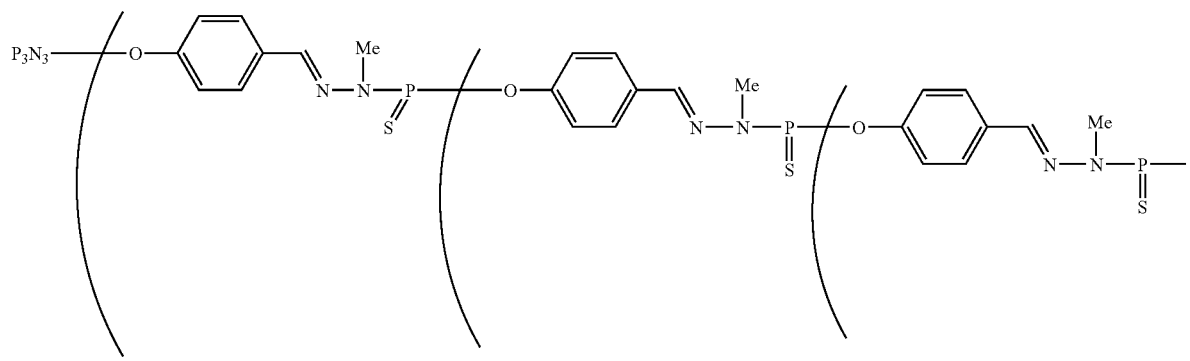

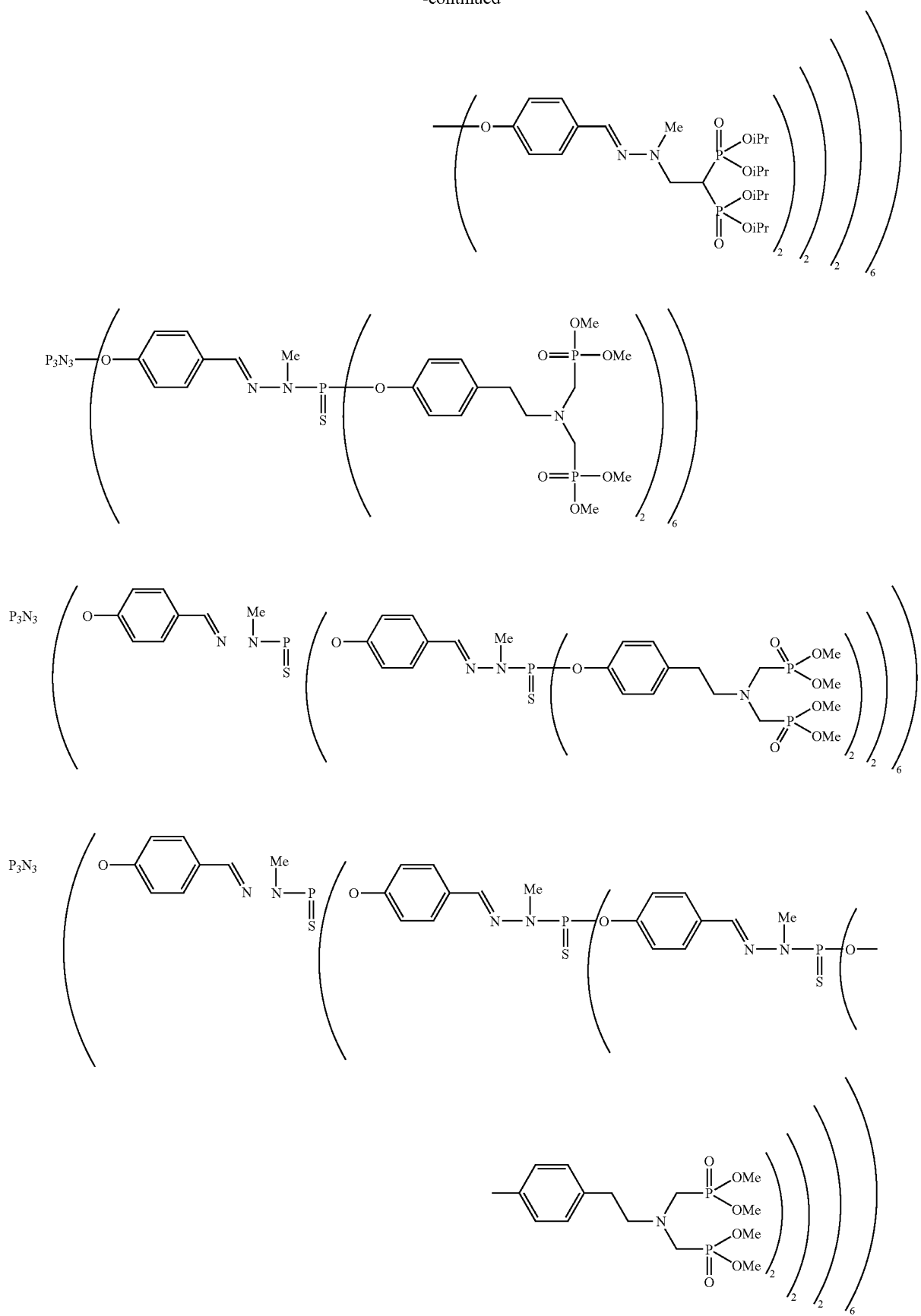

-continued
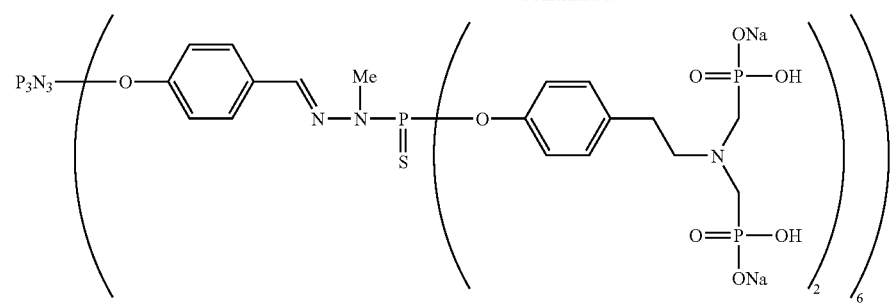
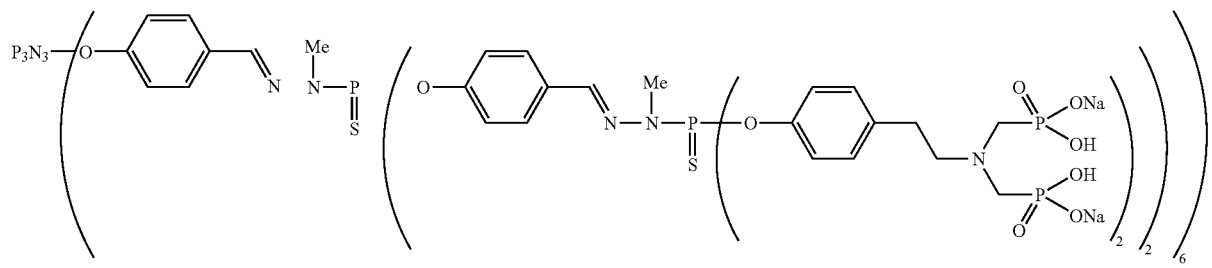
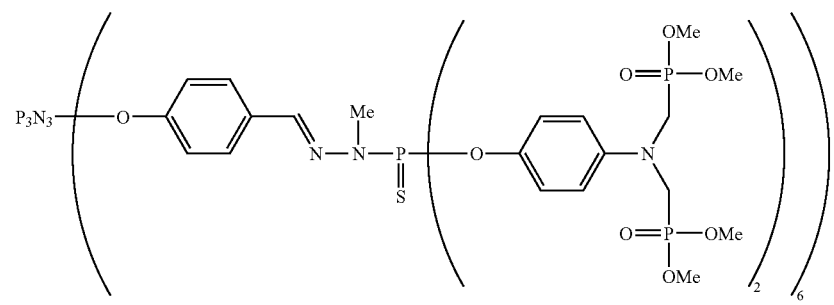
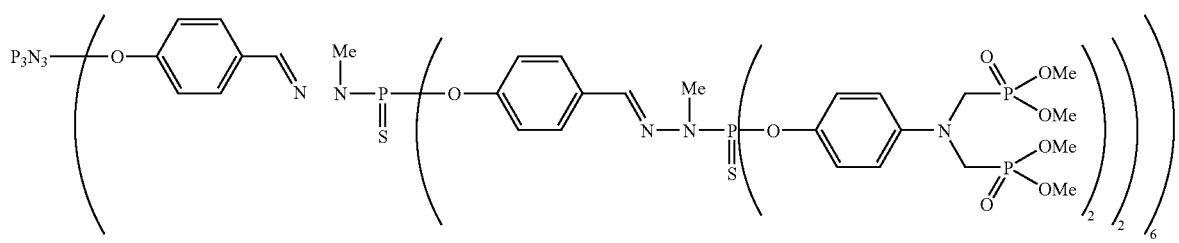
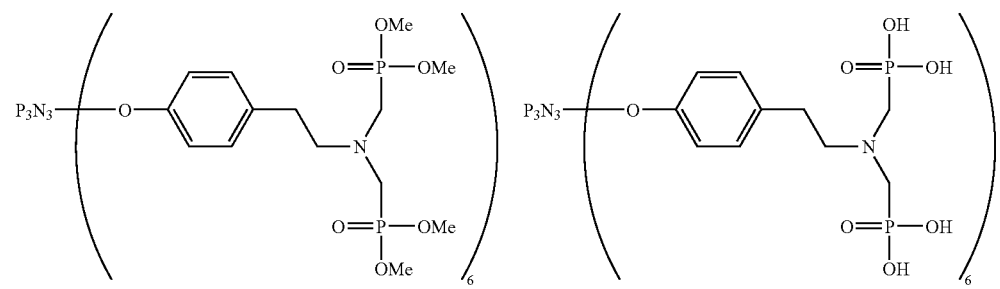
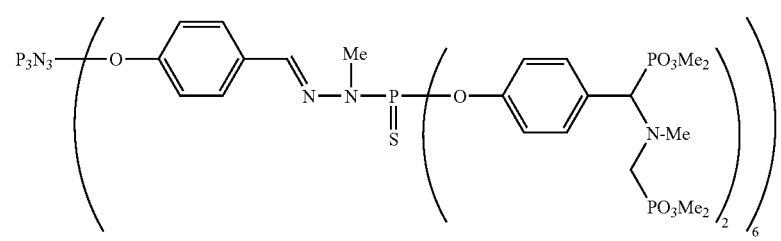

-continued
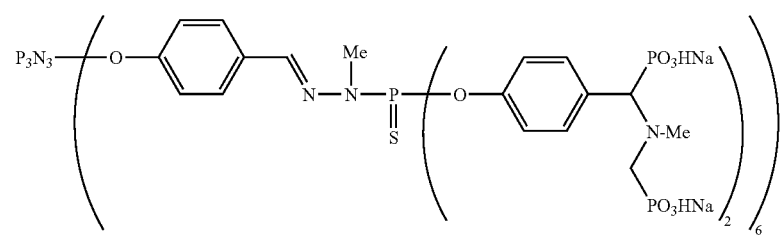
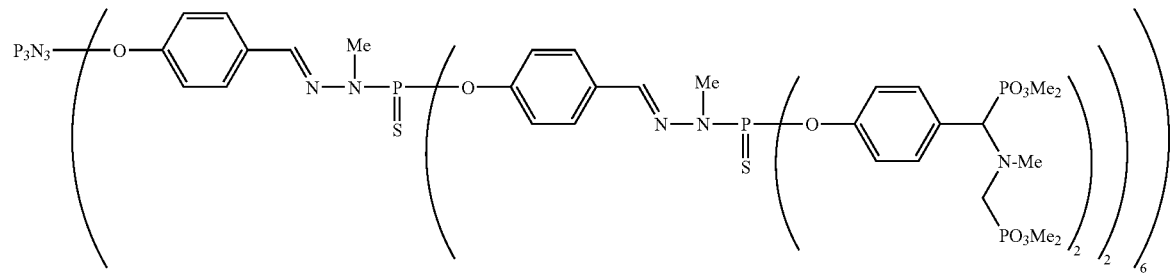
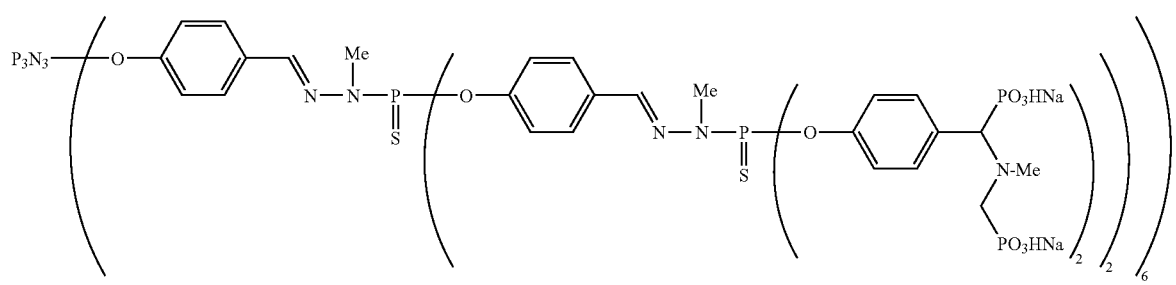
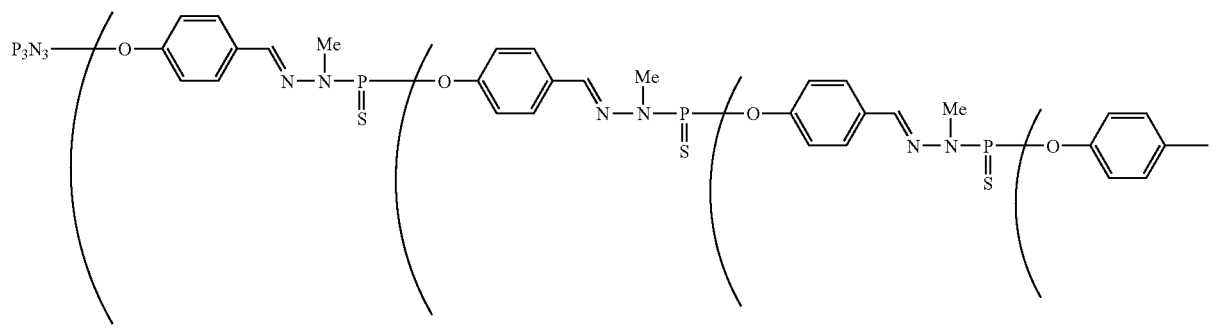
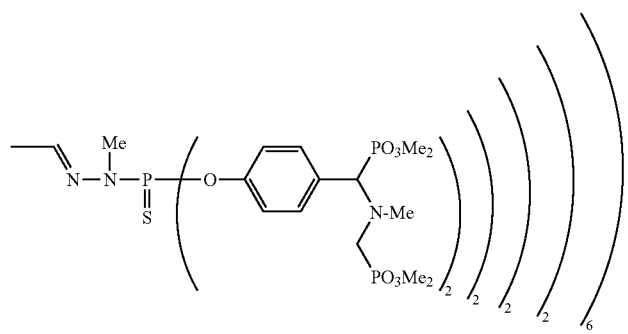
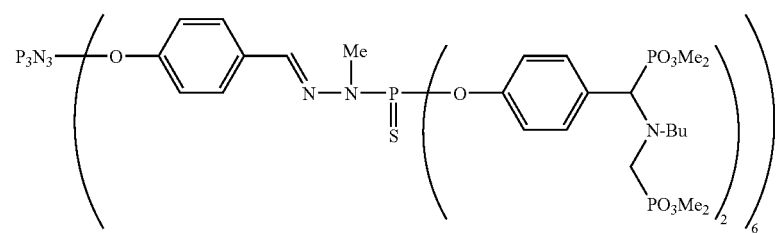

-continued
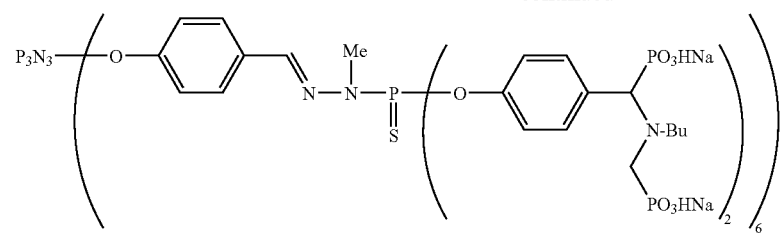
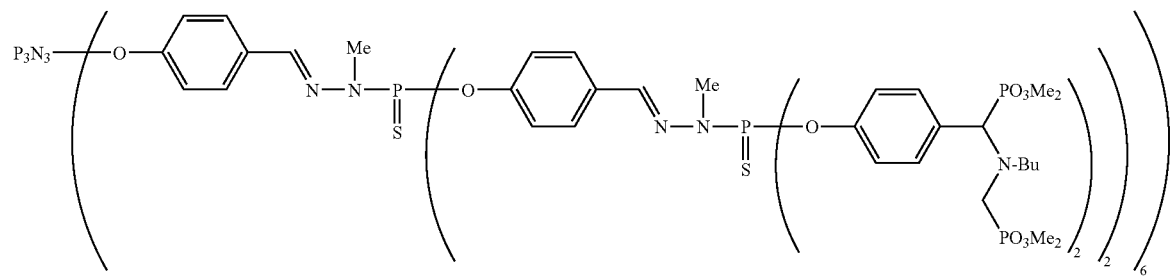
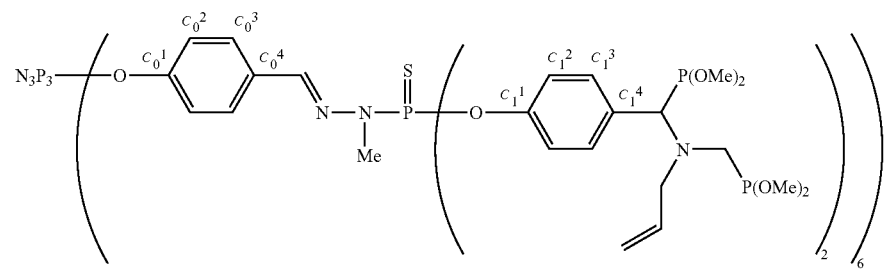
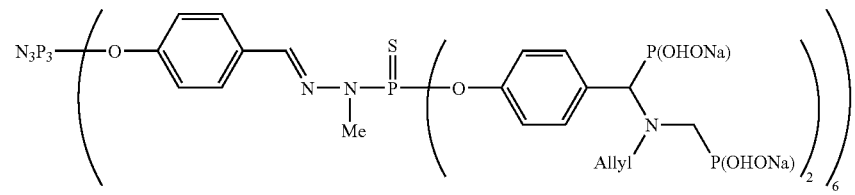
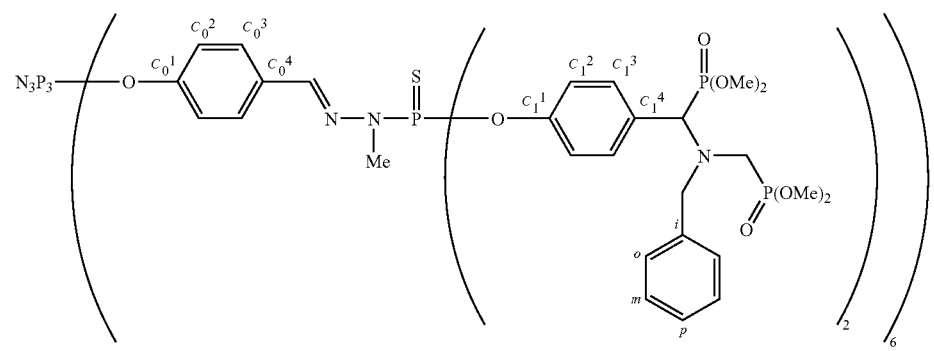
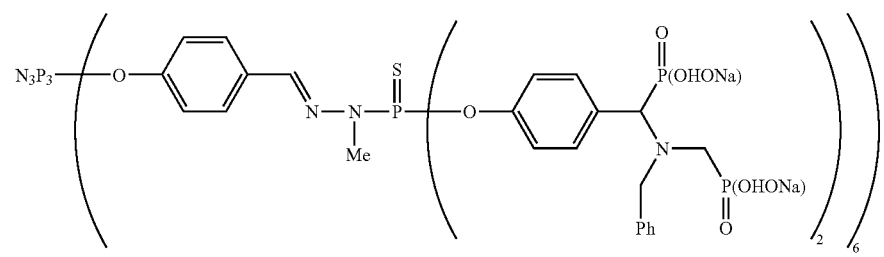
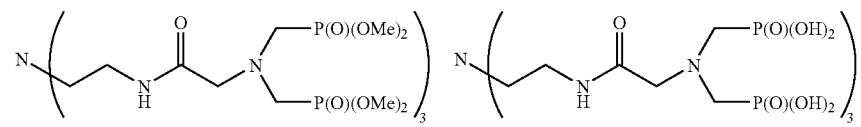

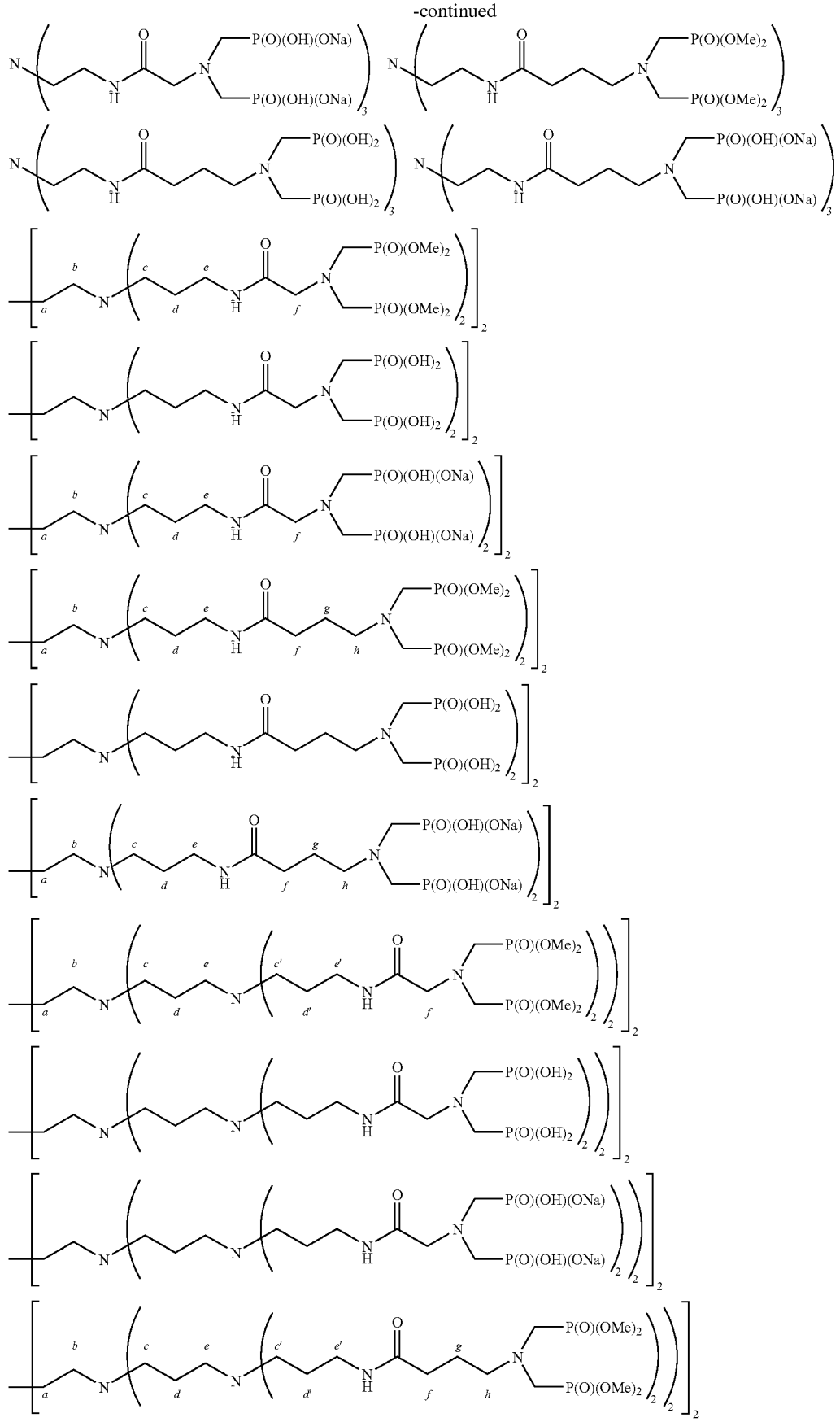

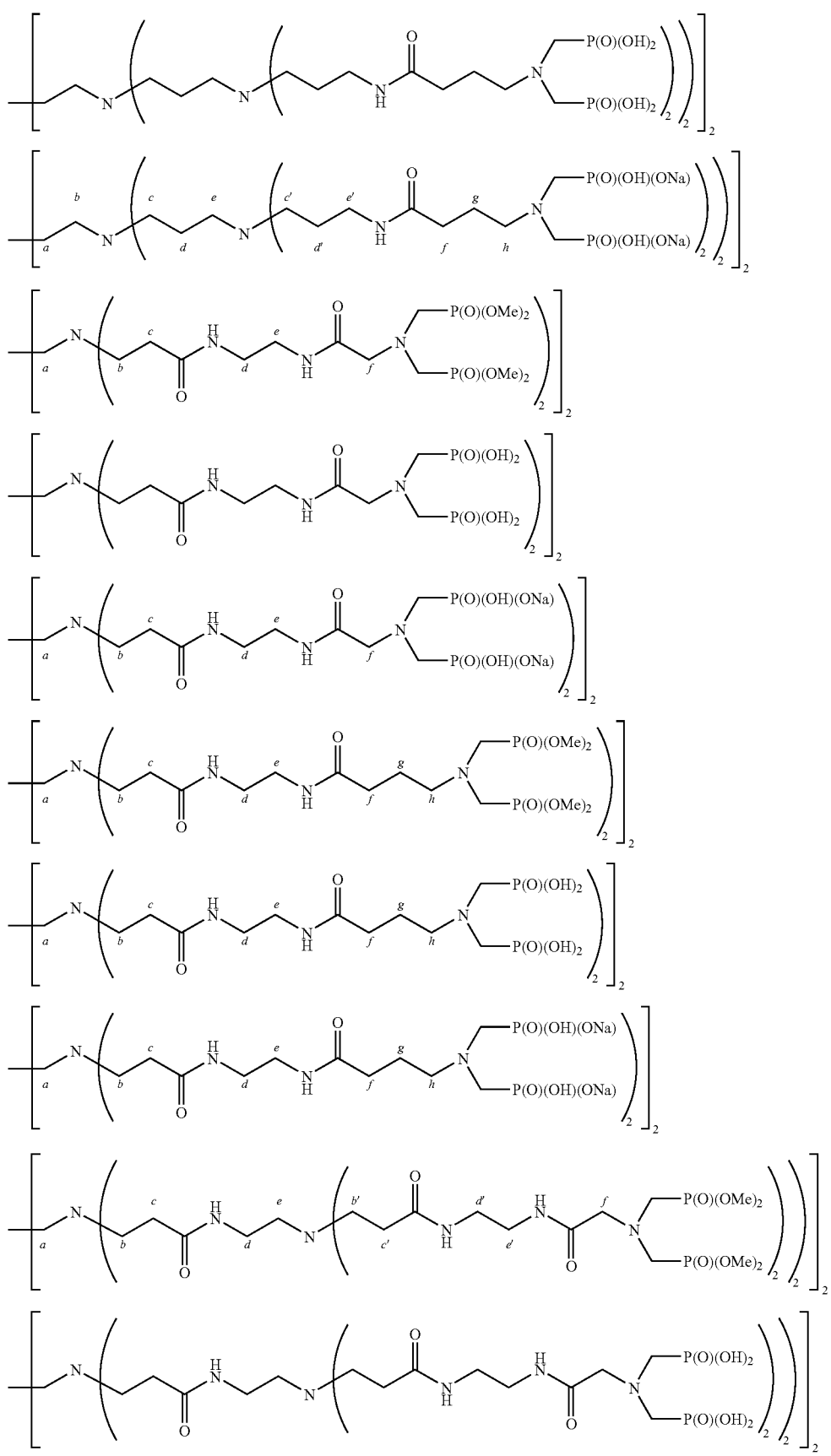

-continued
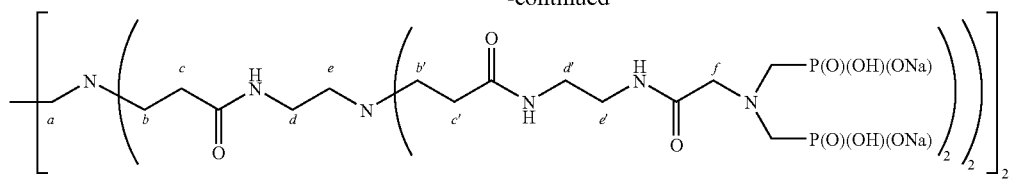
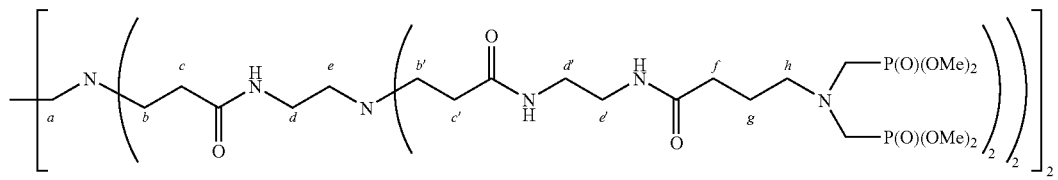
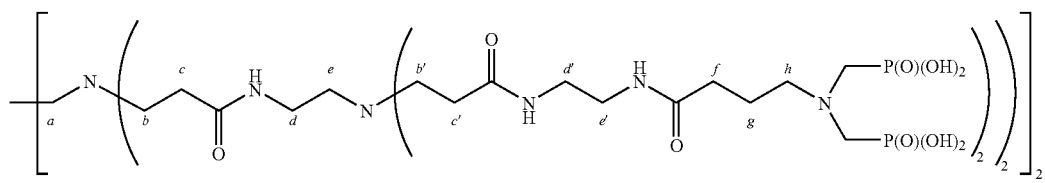
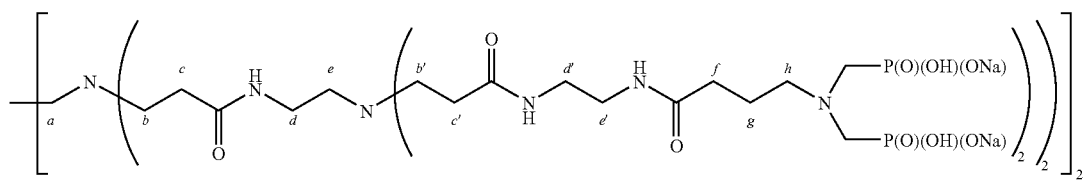
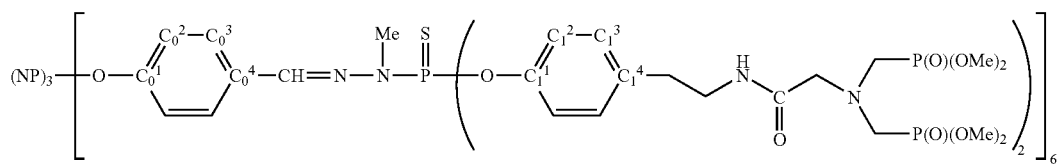
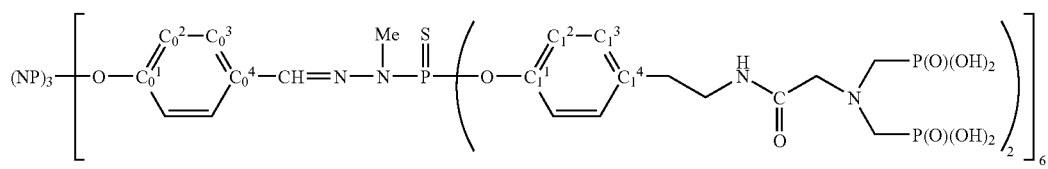
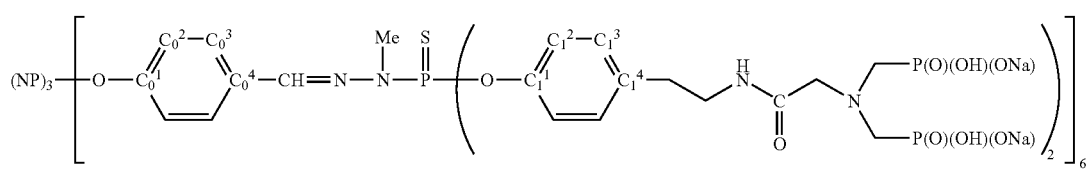

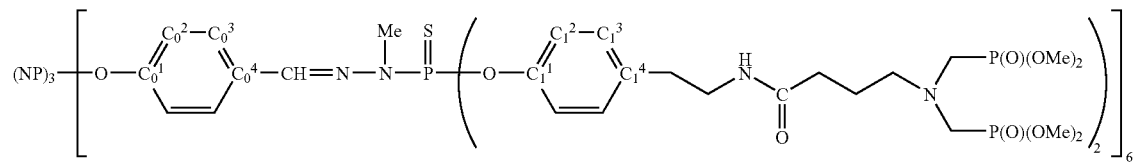
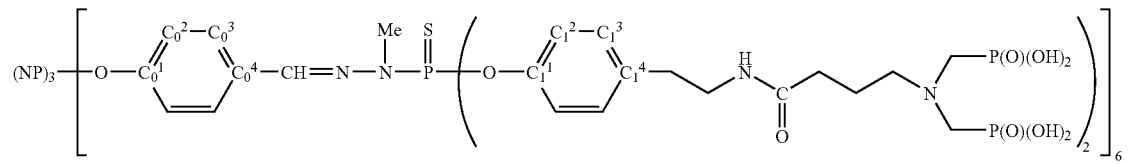
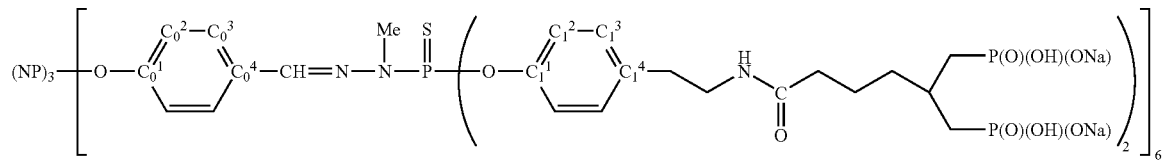
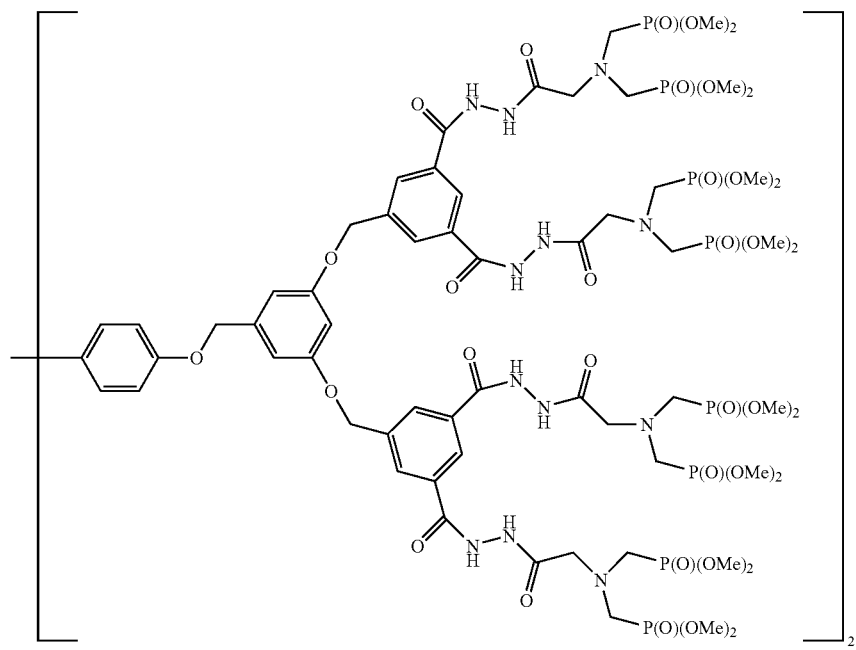

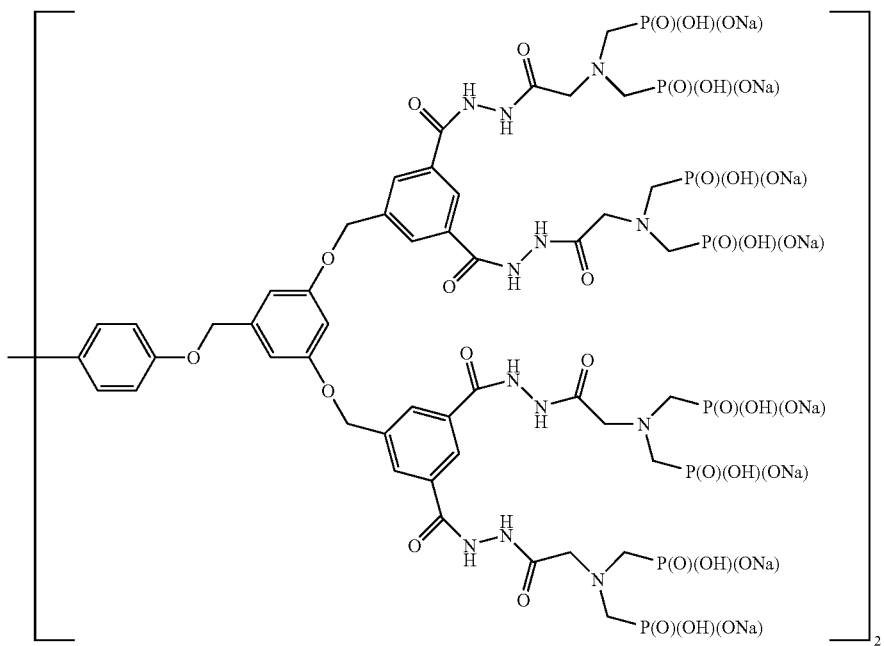
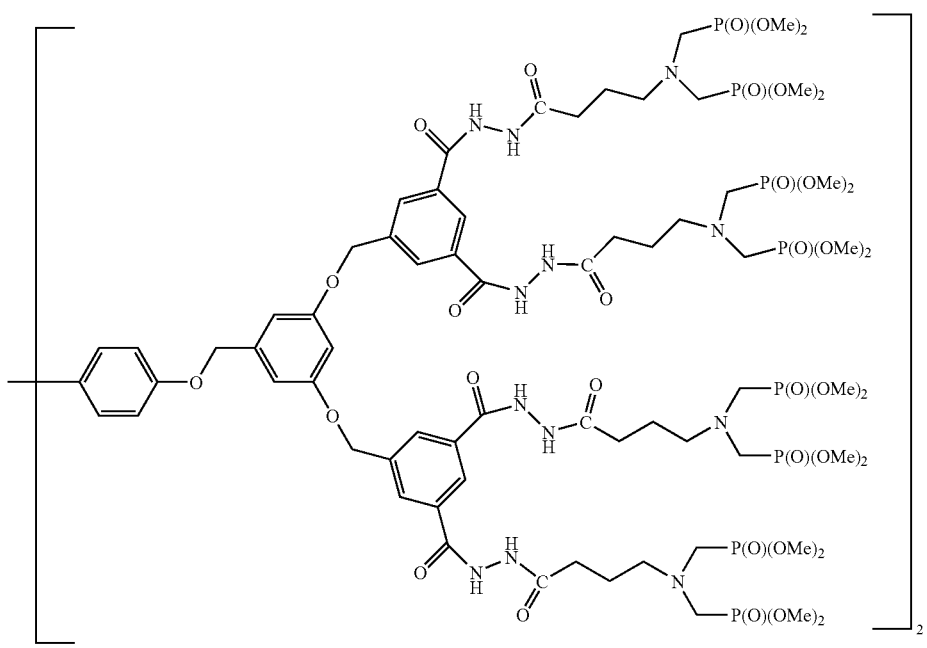

-continued
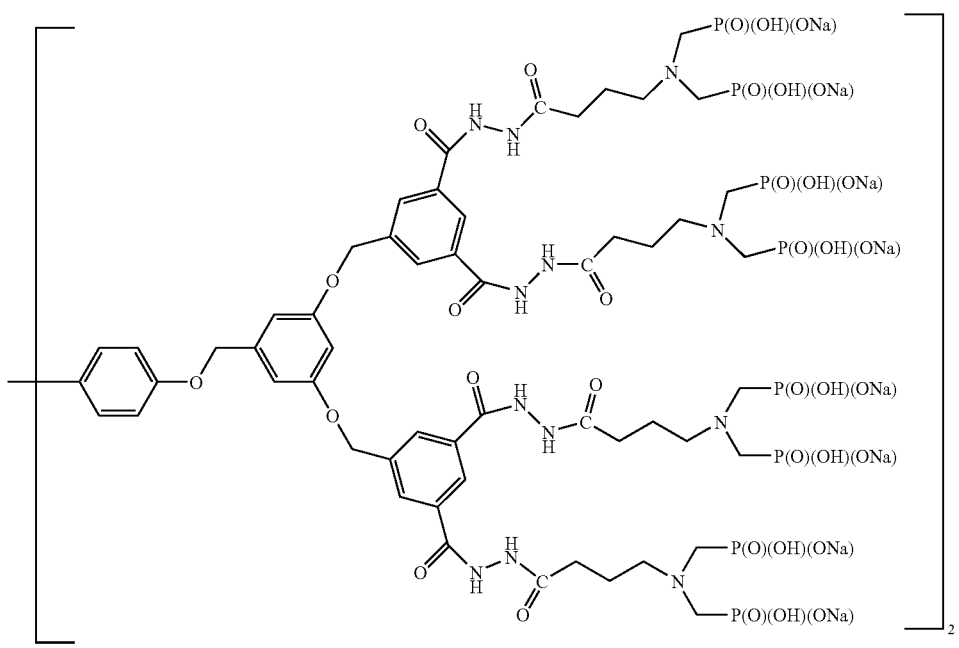
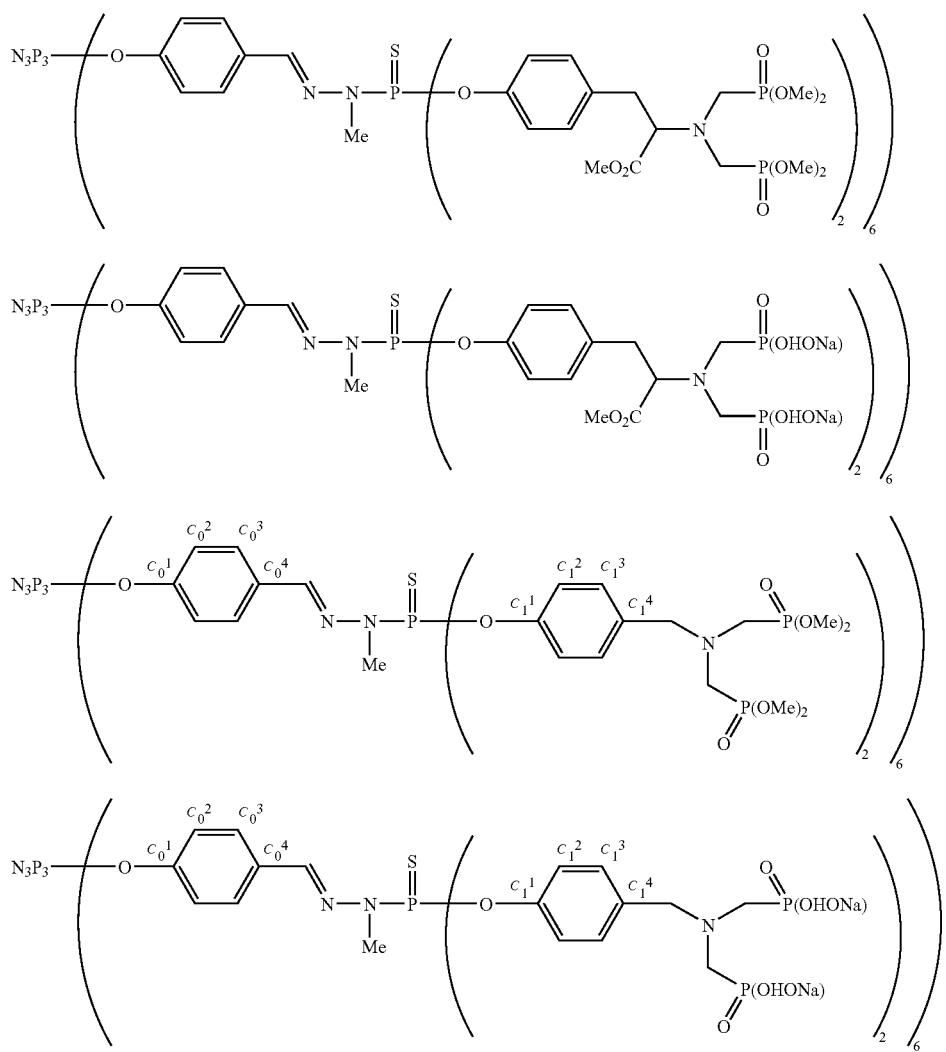

-continued
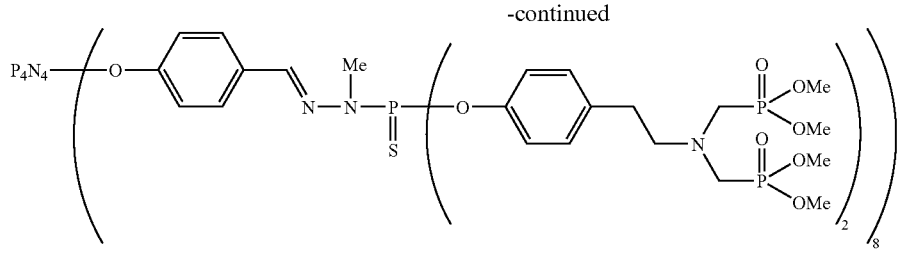
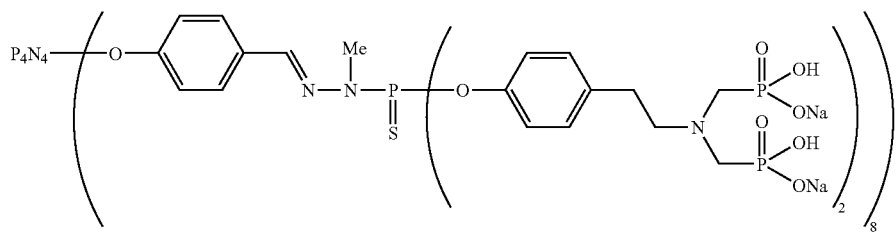
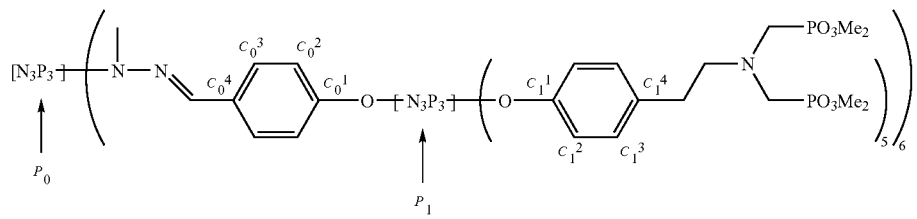
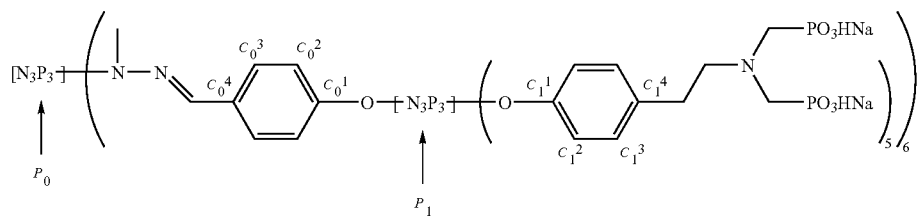
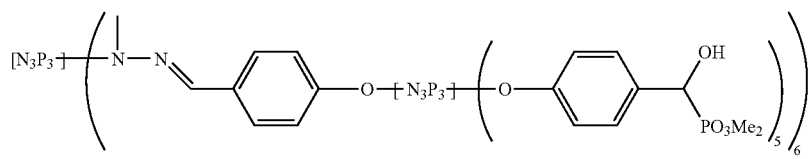
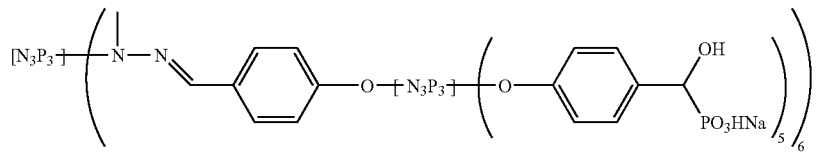
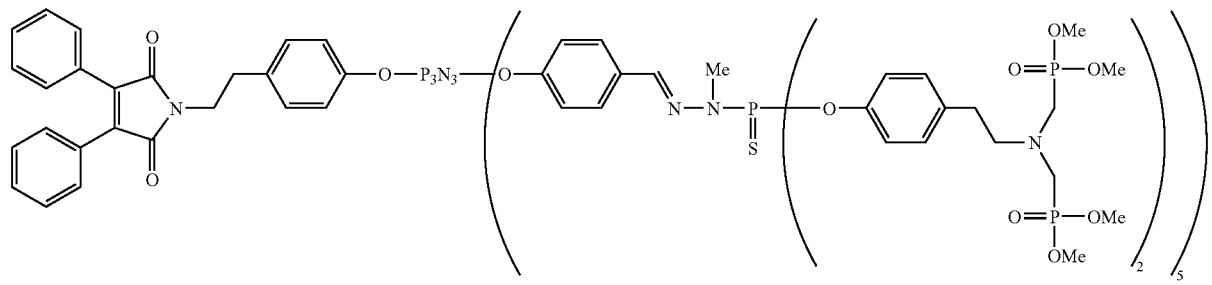

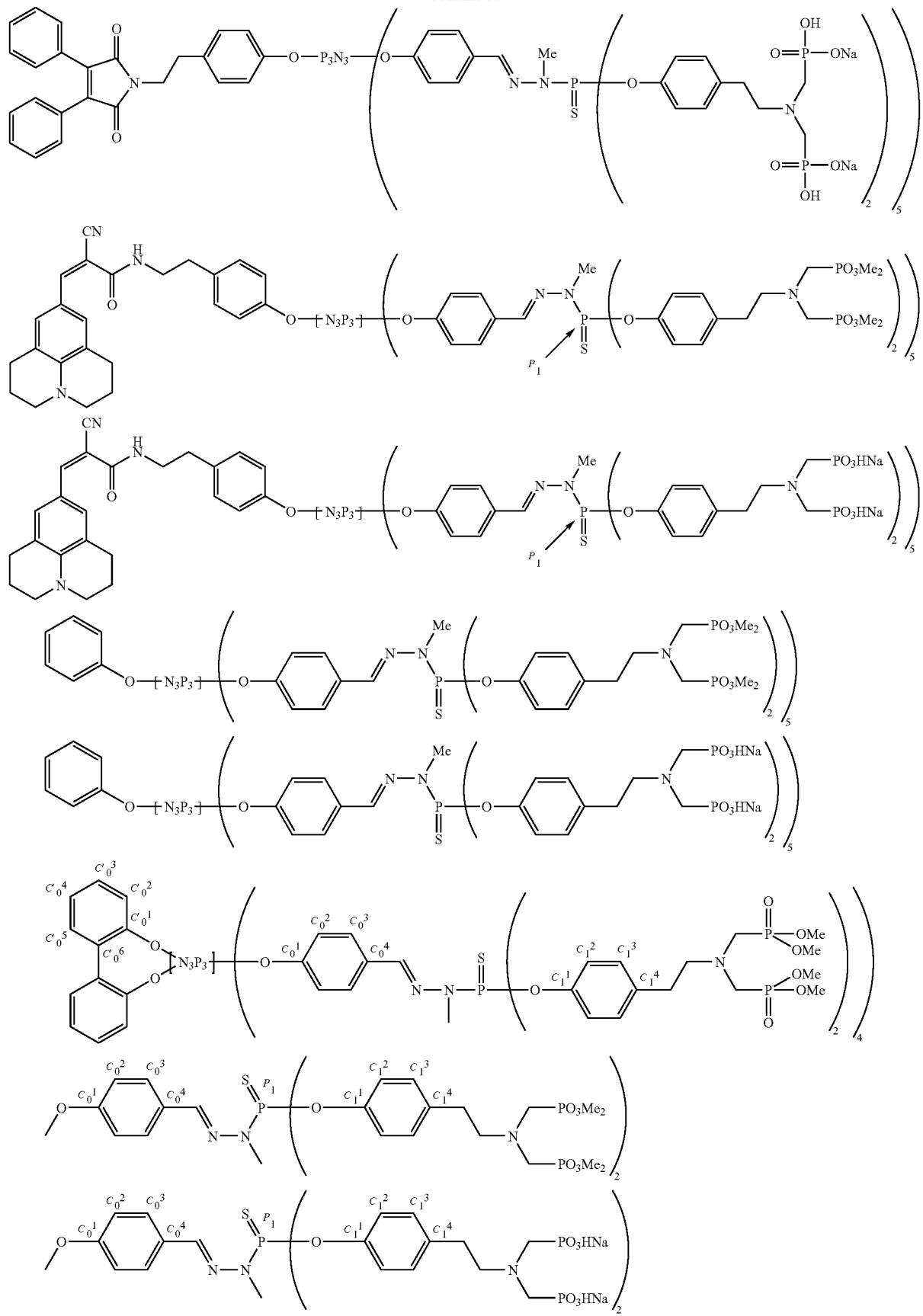

113 114
-continued
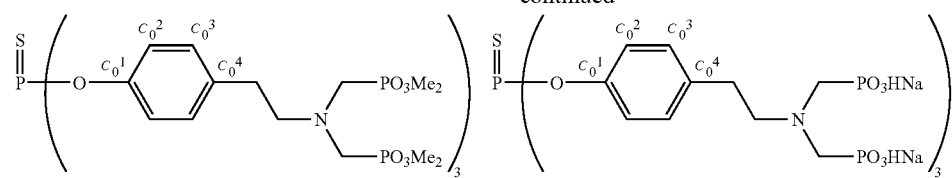
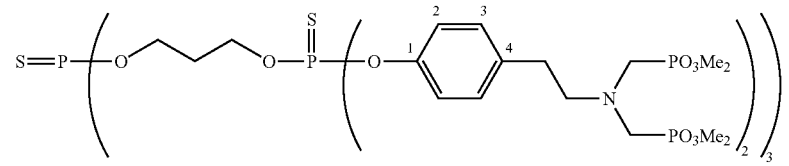
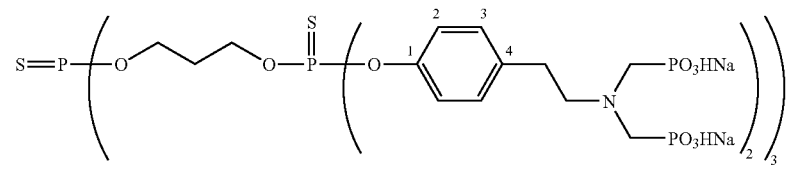
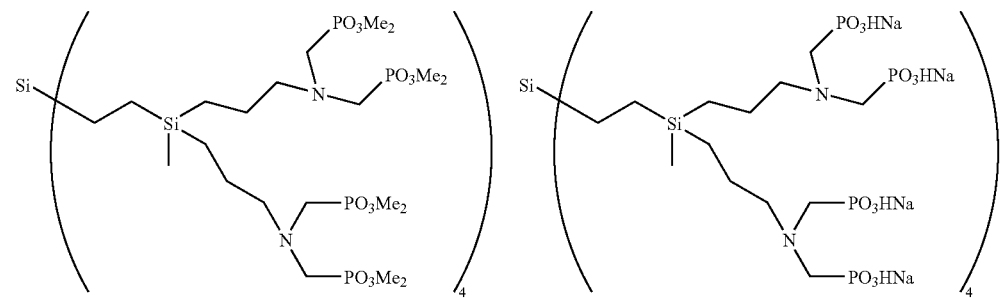
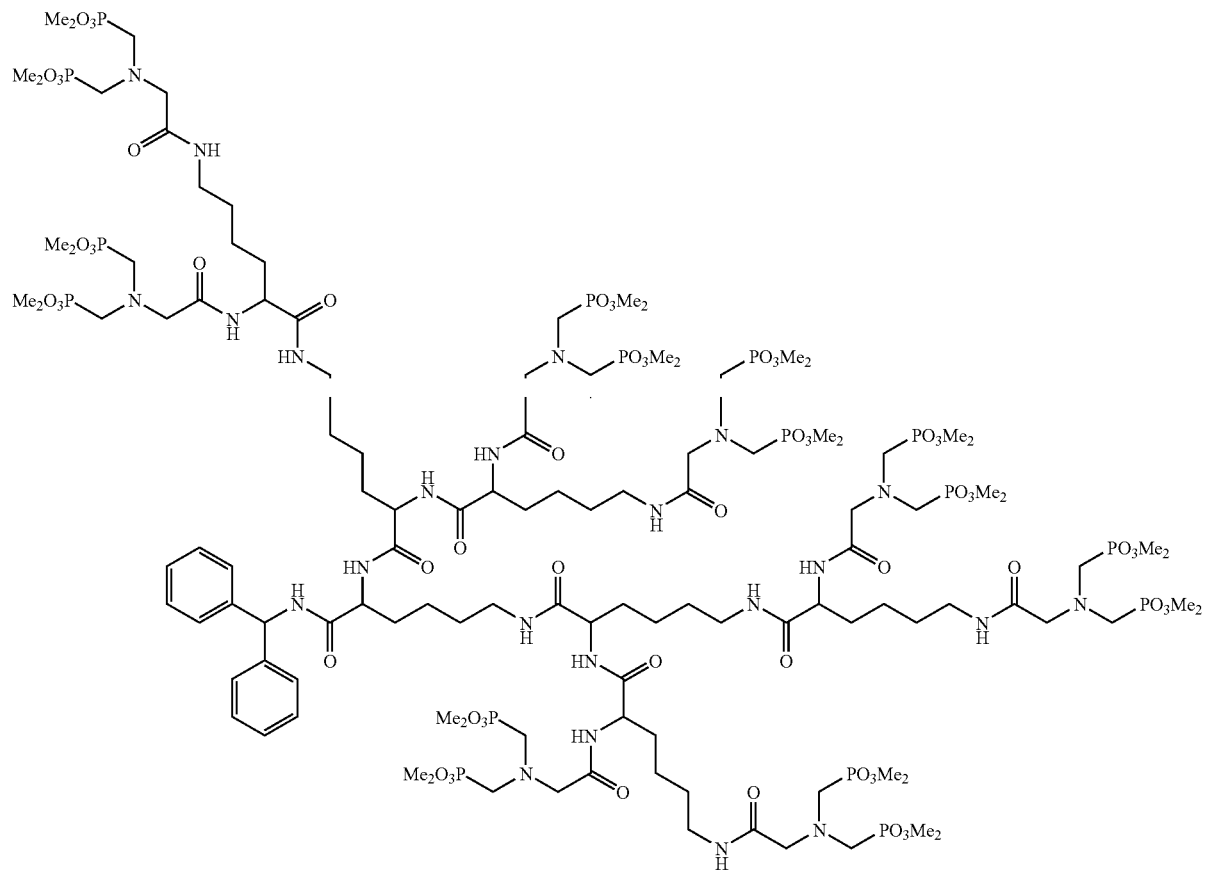

-continued
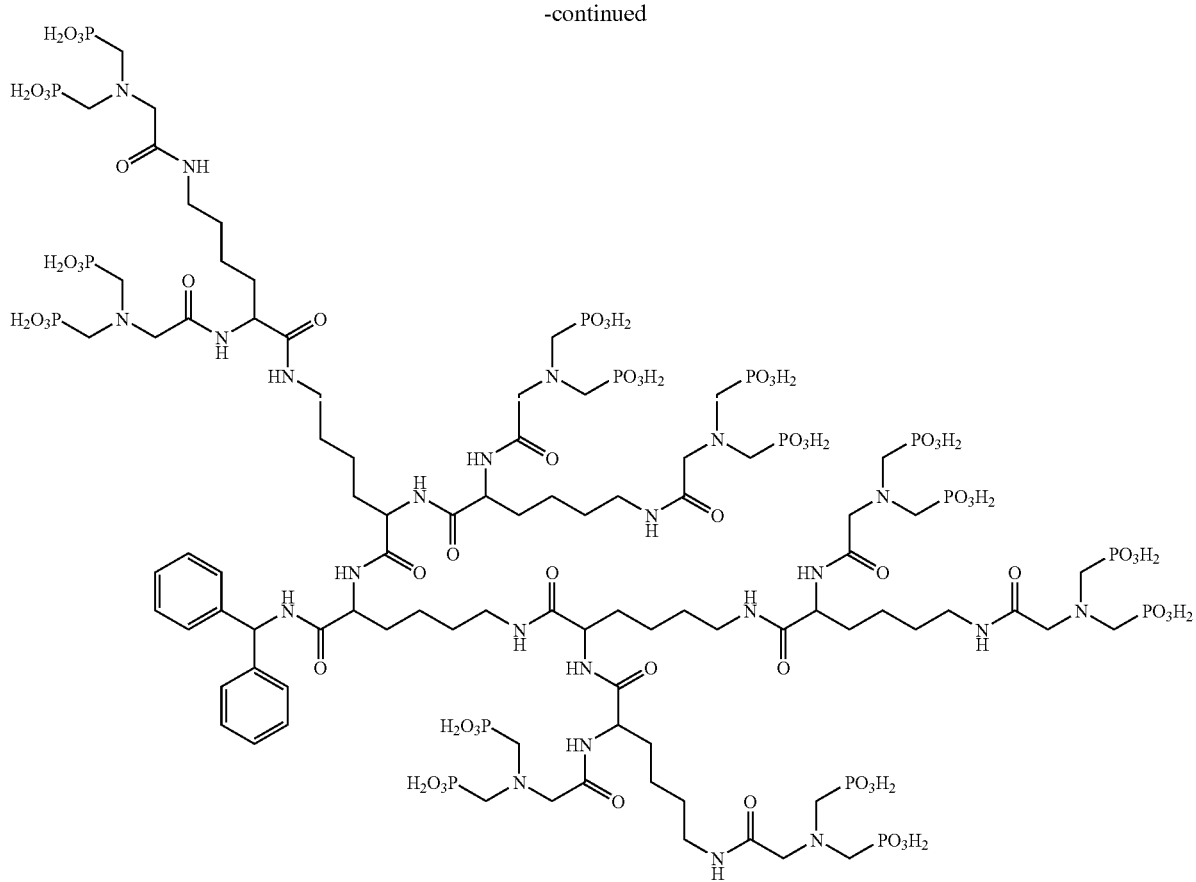
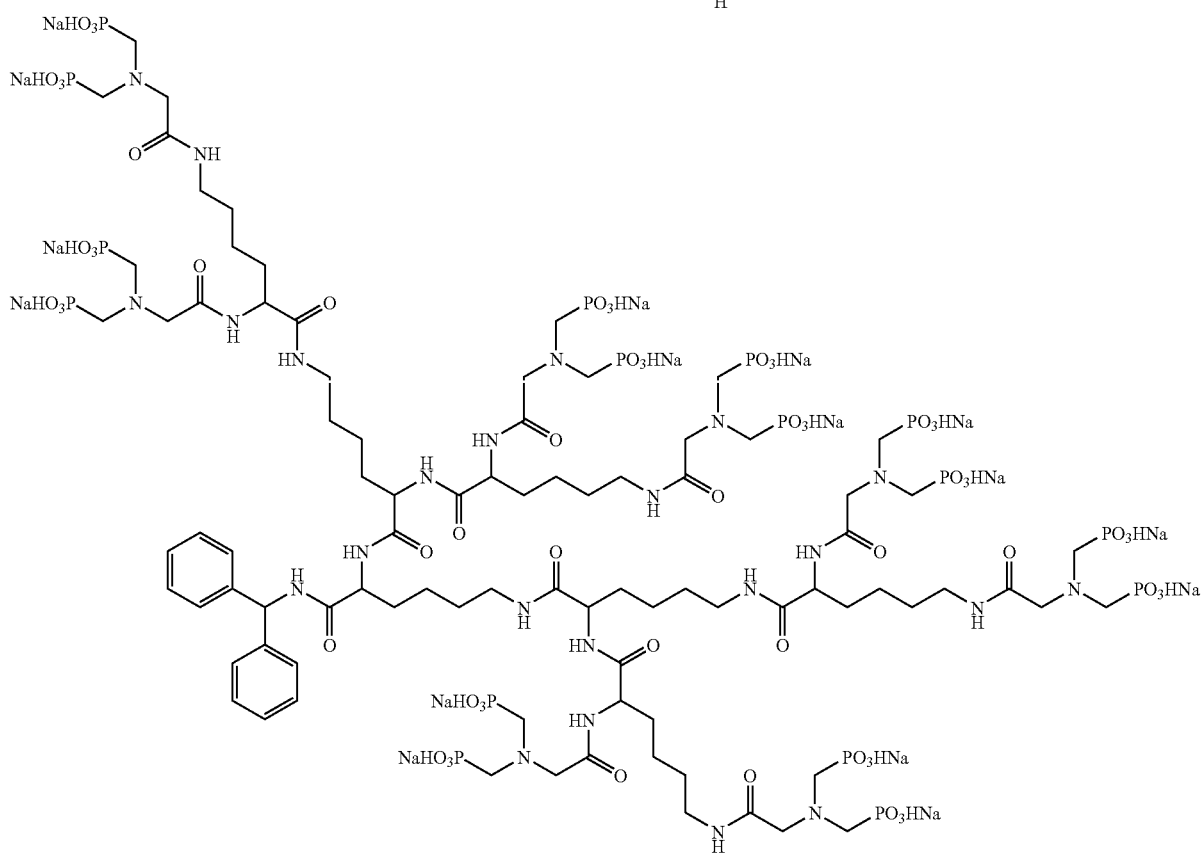

According to another particular embodiment of the invention, cells of the lymphoid line expressing the receptor NKG2D are derived from NK cells, from CD8+ αβ T lymphocytes or from γδ T lymphocytes, in particular from NK cells.

The expression "derived" signifies that the cells of the invention are in particular obtained by stimulation of the growth of NK cells, CD8+ αβ T lymphocytes or γδ T lymphocytes.

In another particular embodiment of the invention, cells of the monocyte line in culture are activated by the dendrimers with monophosphonic or bisphosphonic terminations, the activation of the cells of the monocyte line corresponding in particular:
- to an increase in the size of the activated cells compared with the non-activated cells, and/or
- to a reduction in the expression of MHC class I and class II molecules, or of the molecule CD14 compared with the non-activated cells, and/or
- to an increase in the nuclear translocation of the factor NFκB.

In another particular embodiment of the invention, the cells of the monocyte line in culture exhibit reduced apoptosis compared with cells of the monocyte line cultured in the absence of dendrimers with monophosphonic or bisphosphonic terminations.

The present invention also relates to a cell culture medium, characterized in that it contains at least one dendrimeric compound with monophosphonic or bisphosphonic terminations.

By cell culture medium is meant a solid or liquid medium, containing all of the elements necessary for the growth of cells (nutrients, growth factors etc.), in particular of eukaryotic cells. Such media are well known to a person skilled in the art.

According to a particular embodiment of the invention, the culture medium defined above also comprises at least one growth and/or NK cell activation factor.

Such growth and/or NK cell activation factors can be interleukins, but also type α or β interferons.

According to another preferred embodiment of the invention, the culture medium defined above comprises at least one interleukin chosen from the group comprising: IL-2, IL-7, IL-12, IL-15, IL-18, or IL-21.

These interleukins are commonly used for the culture of cells, in particular of NK cells. Advantageously, in the presence of dendrimers of the invention, the concentration of these compounds in the culture media can be reduced relative to standard culture media, which makes it possible in particular to reduce the cost of said media.

According to another preferred embodiment of the invention, the culture medium defined above comprises at least one dendrimeric compound with monophosphonic or bisphosphonic terminations in combination with IL-2.

Preferably, the IL-2 used is recombinant human IL-2, produced in a prokaryotic (*Escherichia coli* for example) or eukaryotic system (human or insect cell lines for example).

According to yet another preferred embodiment of the invention, the dendrimeric compound included in the culture medium as defined above corresponds to the dendrimers as defined above.

According to a particularly preferred embodiment of the invention, the dendrimeric compound included in the culture medium as defined above corresponds to the dendrimers defined below:

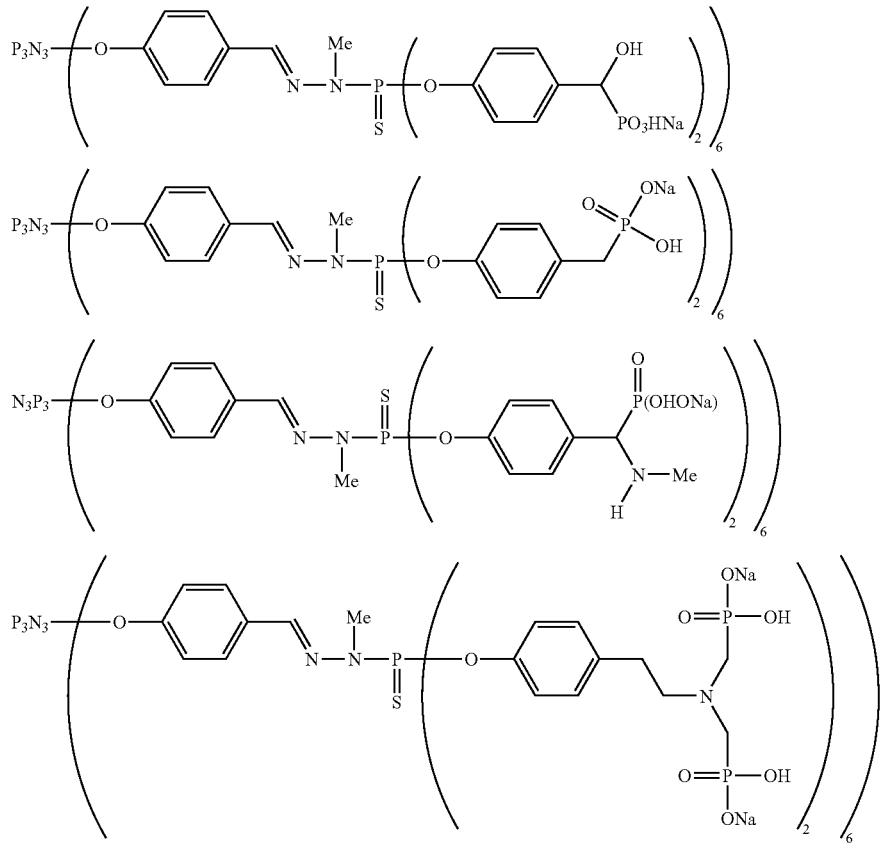

119 120
-continued
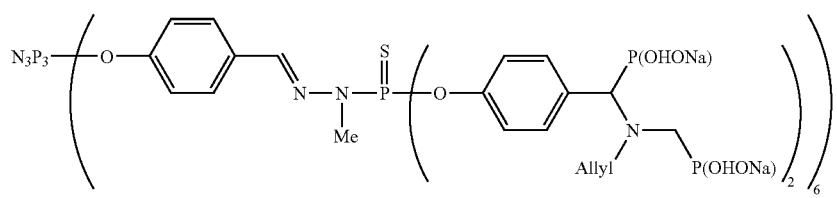
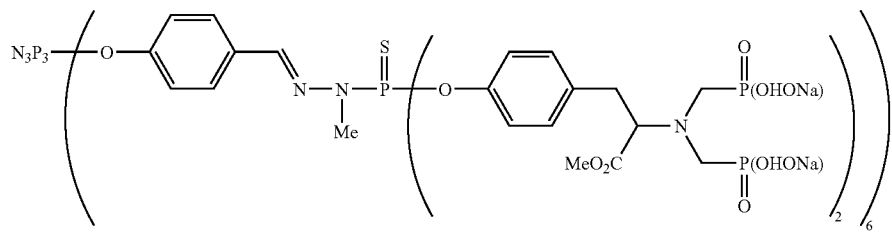
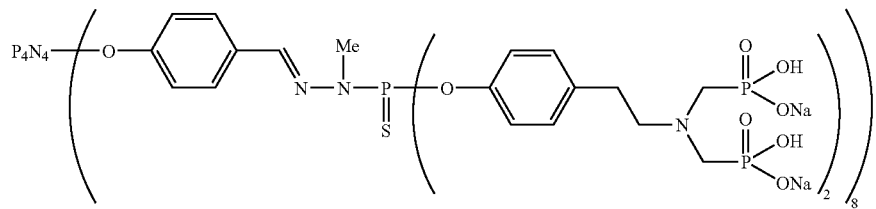
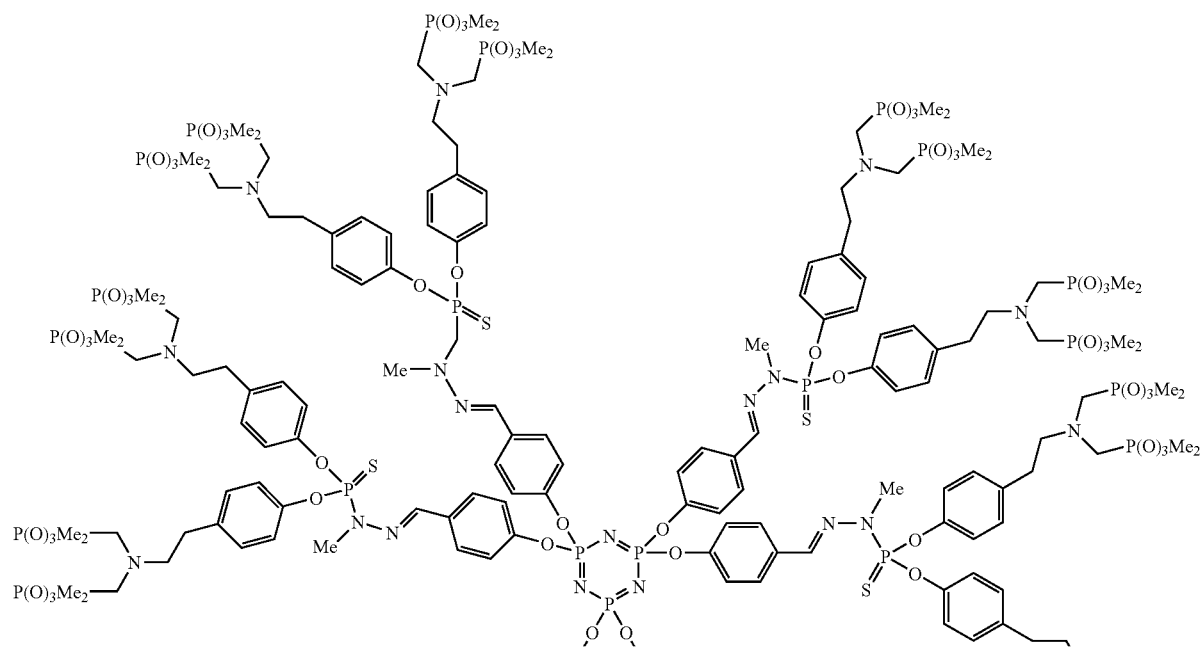

121
-continued
122
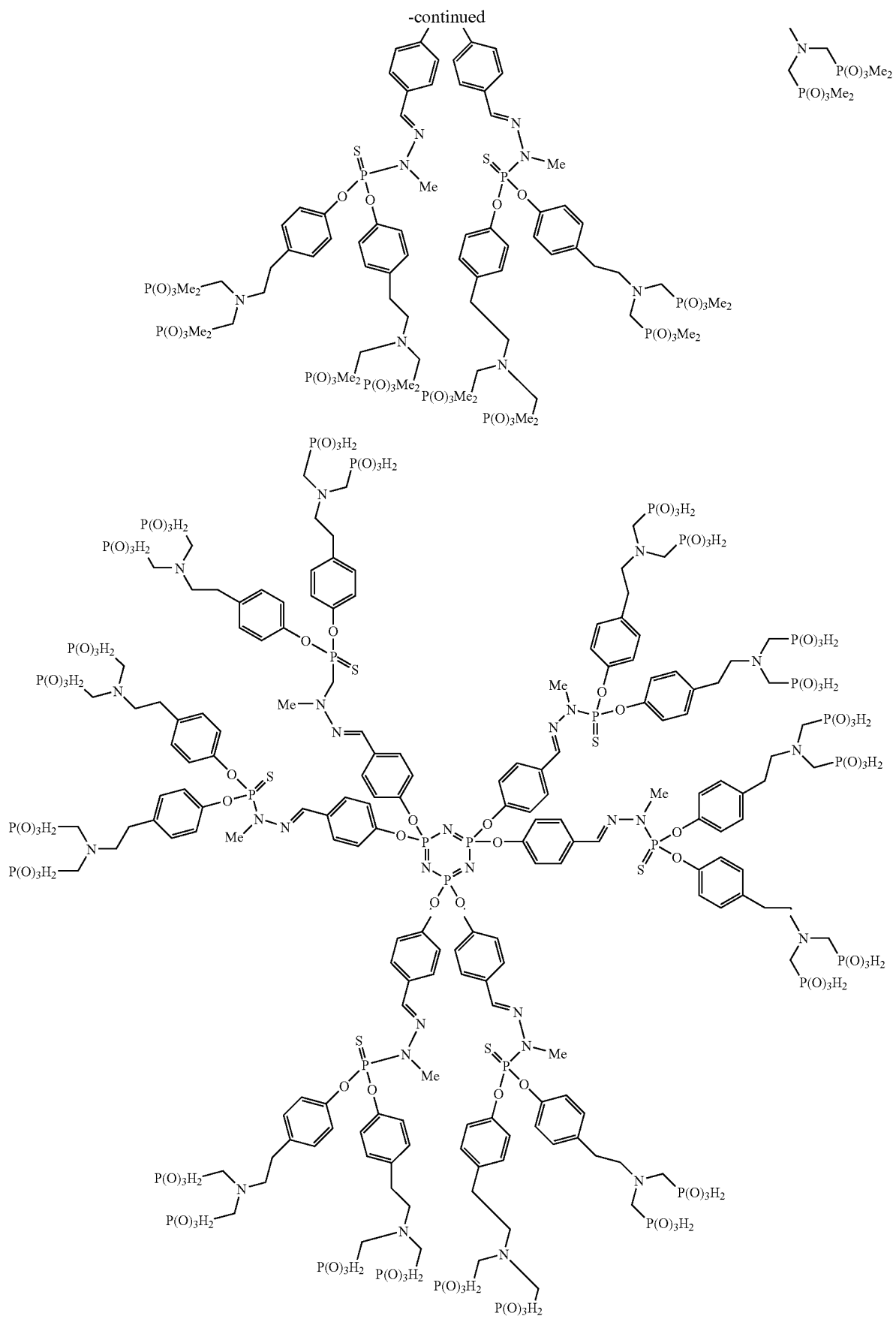

-continued

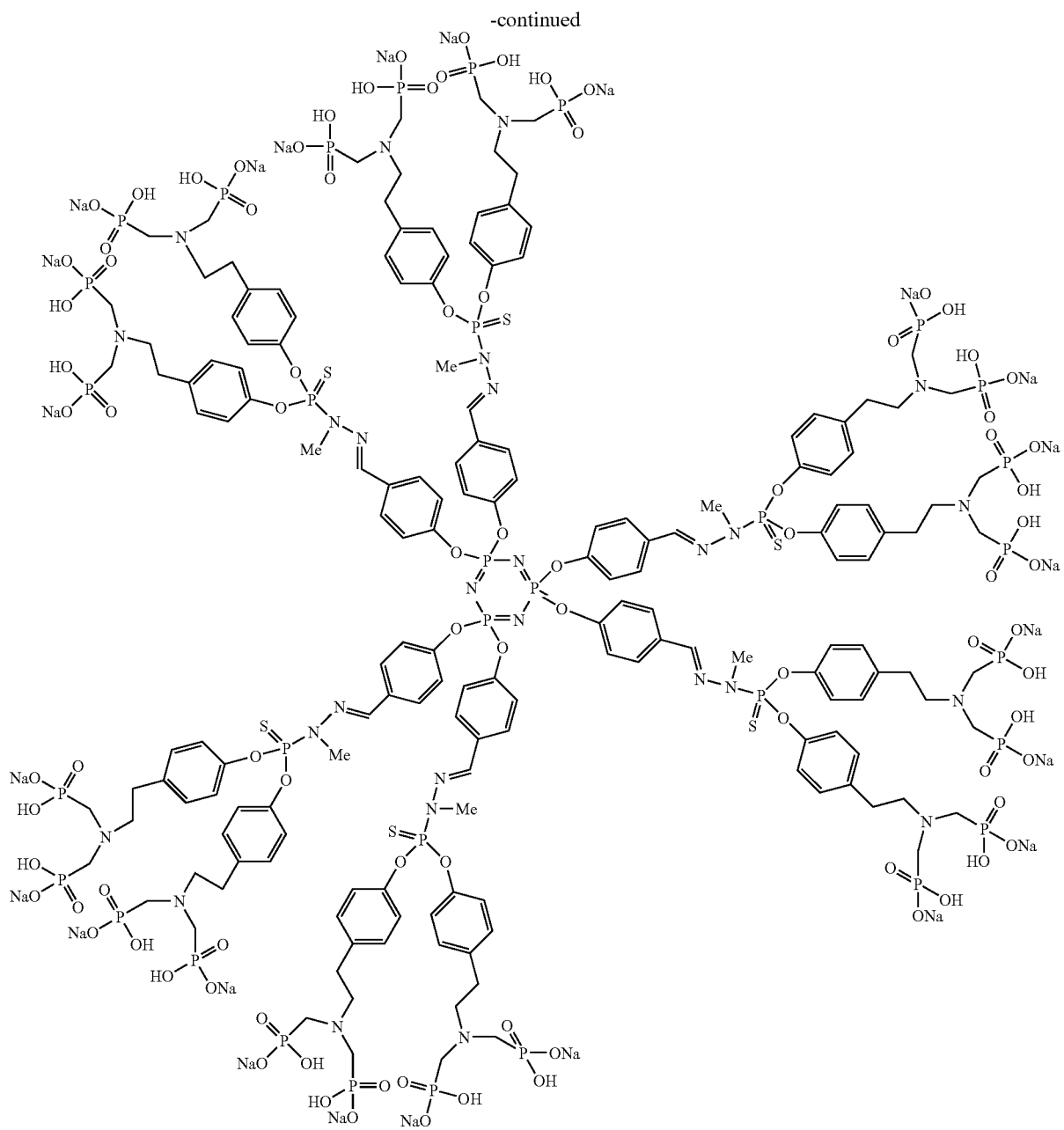

or to GC0, GC1 or GC2, in particular to GC1.

According to a quite particularly preferred embodiment of the invention, the culture medium as defined above is characterized in that it comprises the compound GC1 at a concentration of approximately 10 to approximately 50 µM, in particular approximately 20 µM, in combination with IL-2 at a concentration of approximately 100 to approximately 1000 units per ml, corresponding to a concentration of approximately 4 to approximately 40 ng per ml, in particular approximately 400 units per ml, corresponding to approximately 16 ng/ml, and in that the IL-2 corresponds to human recombinant IL-2.

The present invention also relates to a process for the preparation of cell compositions enriched with cells of the lymphoid line expressing the receptor NKG2D, in particular NK cells, characterized in that it comprises a stage of bringing a biological sample together with a dendrimer with monophosphonic or bisphosphonic terminations.

In a particular embodiment, the above process is characterized in that it comprises cells of the lymphoid line and/or cells of the monocyte line.

According to a preferred embodiment of the process as defined above, the biological sample is constituted by human blood, in particular by a mononuclear cell fraction of a sample of human peripheral blood.

The peripheral blood mononuclear cell (PBMC) fractions are prepared according to methods well known to a person skilled in the art and in particular by density gradient centrifugation, as described in the examples.

According to another preferred embodiment of the process as defined above the dendrimer with monophosphonic or bisphosphonic terminations corresponds to the dendrimers as defined above.

According to a quite particularly preferred embodiment of the process as defined above the dendrimer with monophosphonic or bisphosphonic terminations corresponds to the dendrimers of the following formulae:
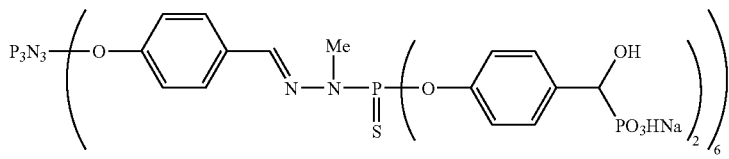
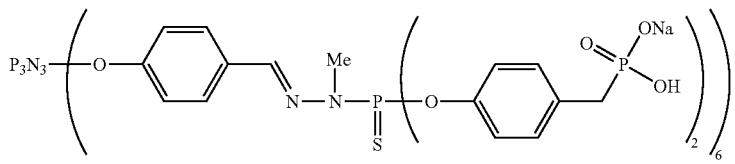
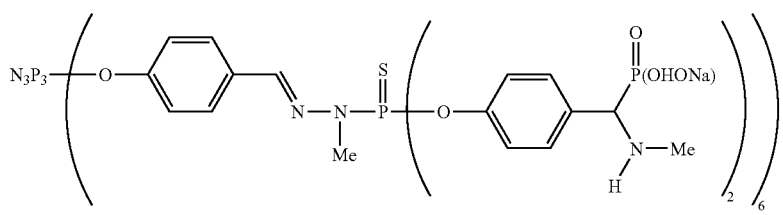
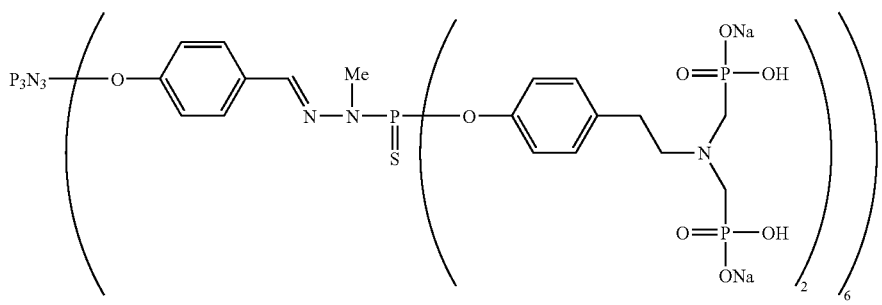
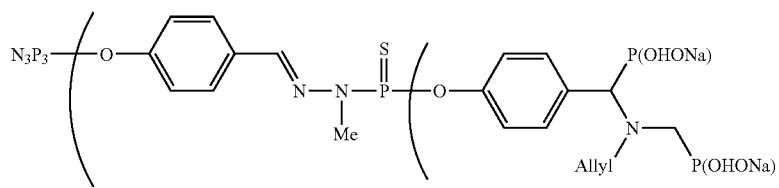
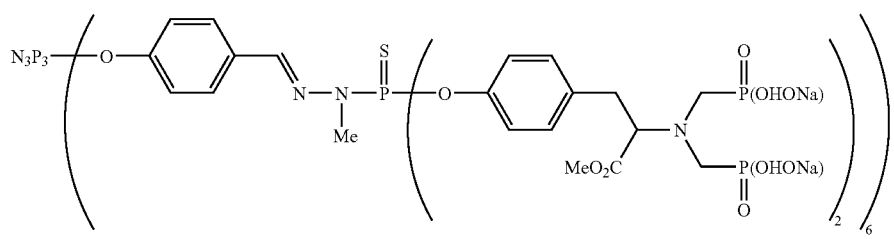
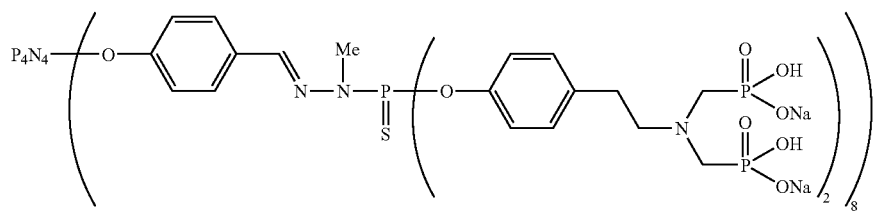

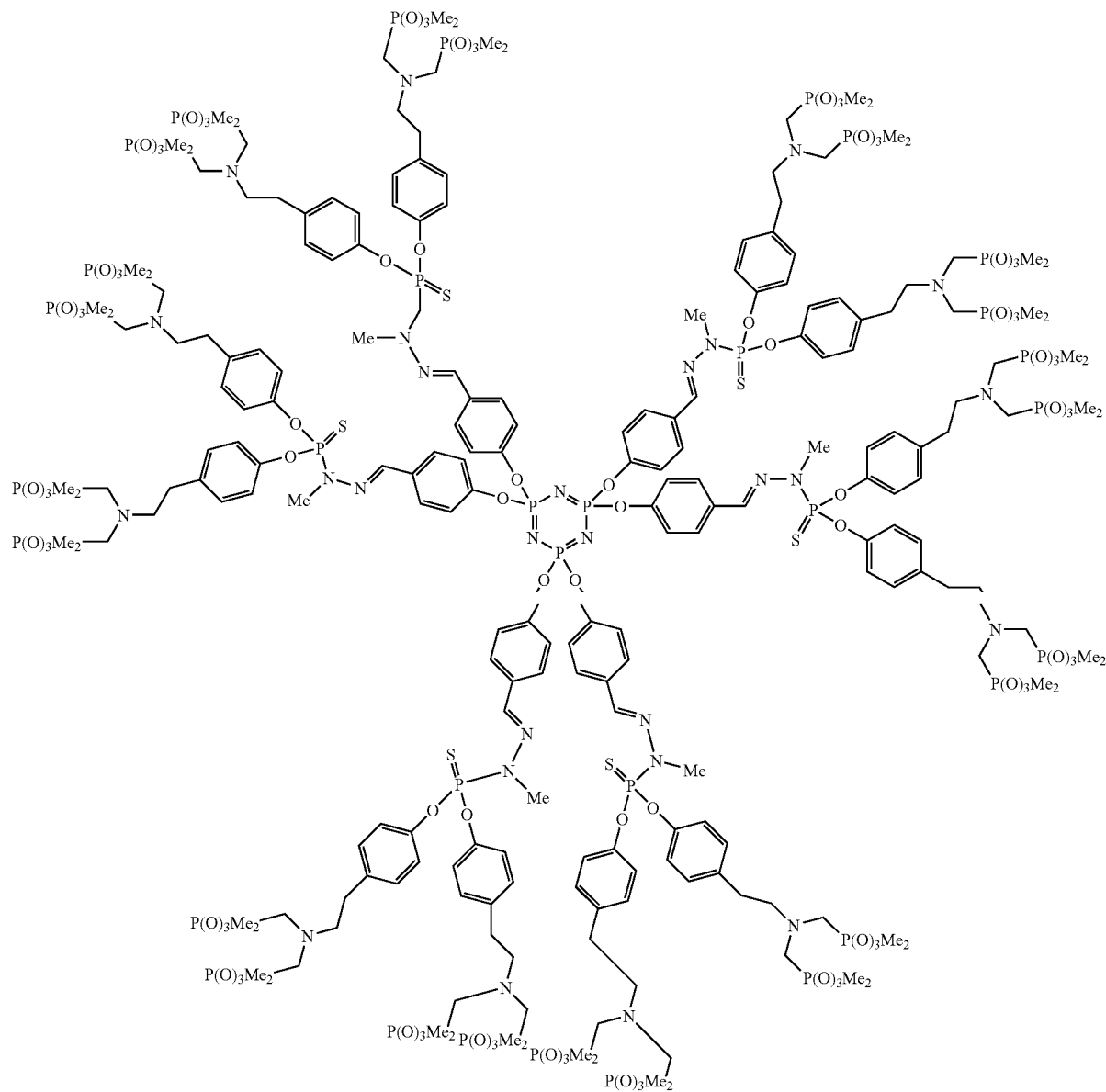

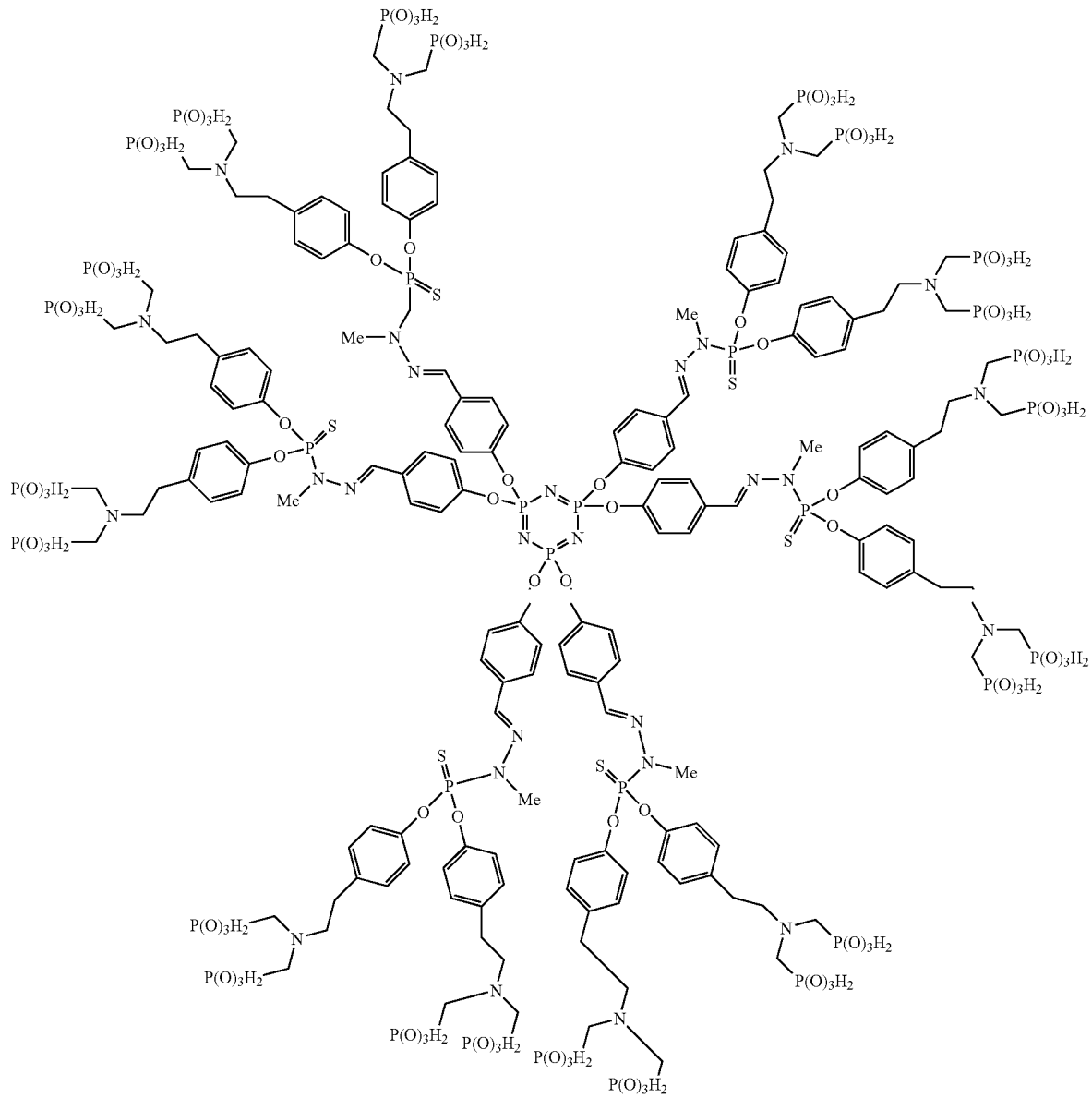

-continued

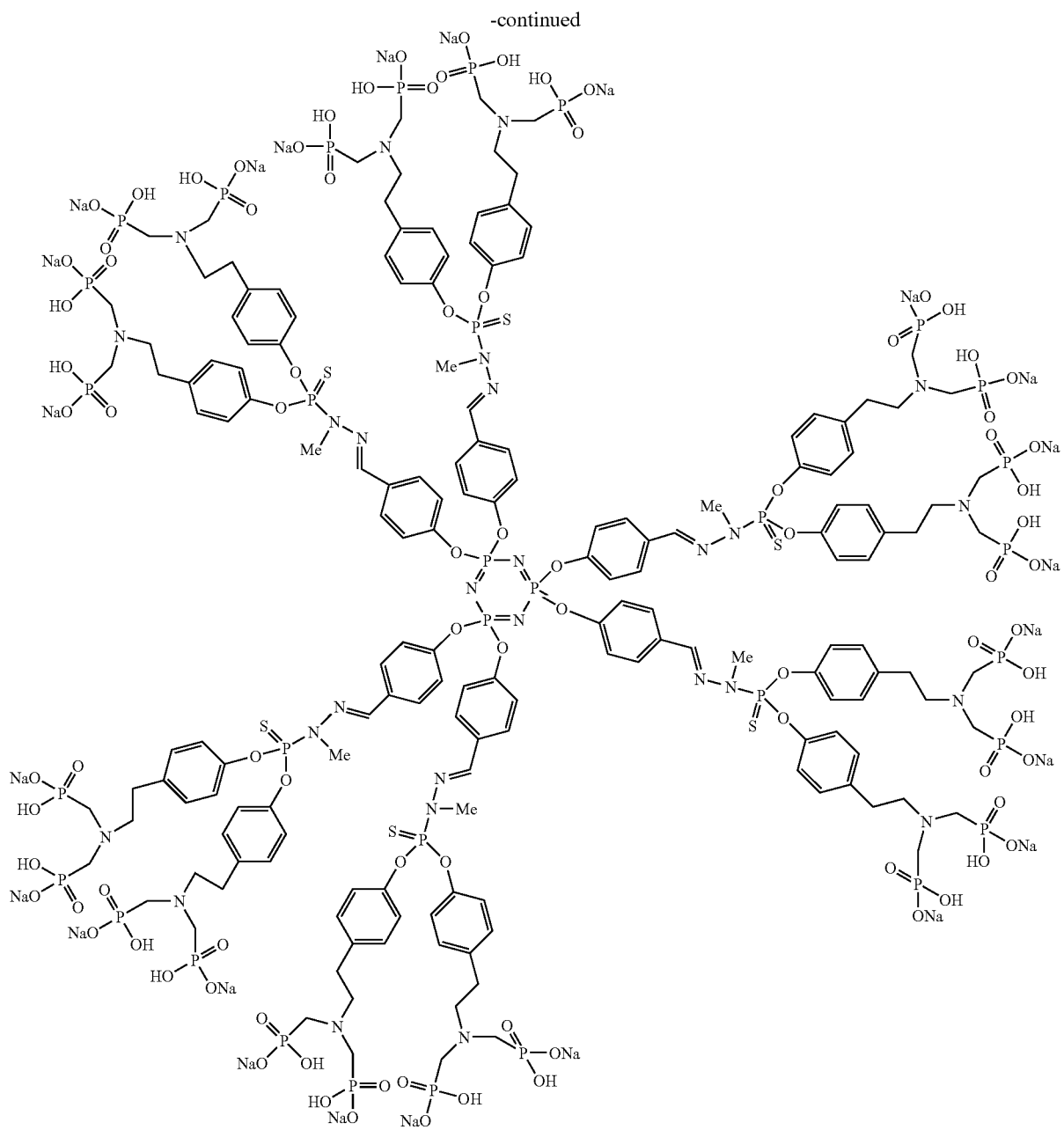

or to GC0, GC1 or GC2, in particular to GC1.

The present invention also relates to cell compositions enriched with cells of the lymphoid line expressing the receptor NKG2D, in particular NK cells, as obtained by the process defined above.

According to a preferred embodiment of the invention, the cell compositions defined above also include a dendrimer with monophosphonic or bisphosphonic terminations, in particular GC1.

The present invention also relates to a process for the preparation of activated monocytes or of cell compositions comprising activated monocytes, characterized in that it comprises a stage of bringing a biological sample comprising monocytes together with a dendrimer with monophosphonic or bisphosphonic terminations.

In a preferred embodiment of the process for the preparation of activated monocytes or of cell compositions comprising the above activated monocytes, the biological sample is constituted by human blood, in particular by a mononuclear cell fraction of a sample of human peripheral blood.

In a preferred embodiment of the process for the preparation of activated monocytes or of cell compositions comprising the above activated monocytes, the dendrimer with monophosphonic or bisphosphonic terminations corresponds to the dendrimers as defined above.

In a preferred embodiment of the process for the preparation of activated monocytes or of cell compositions comprising the above activated monocytes, the dendrimer with monophosphonic or bisphosphonic terminations corresponds to the dendrimers of the following formulae:

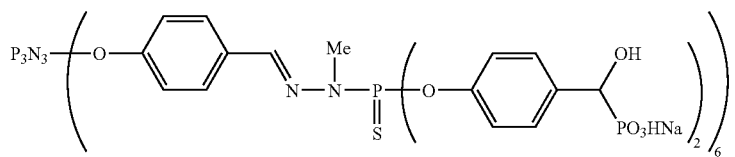
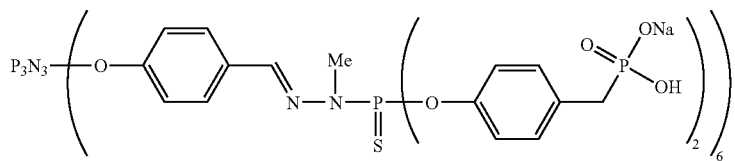
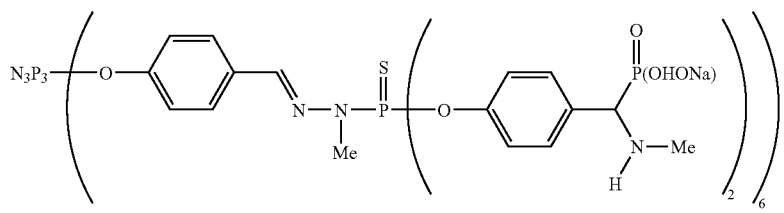
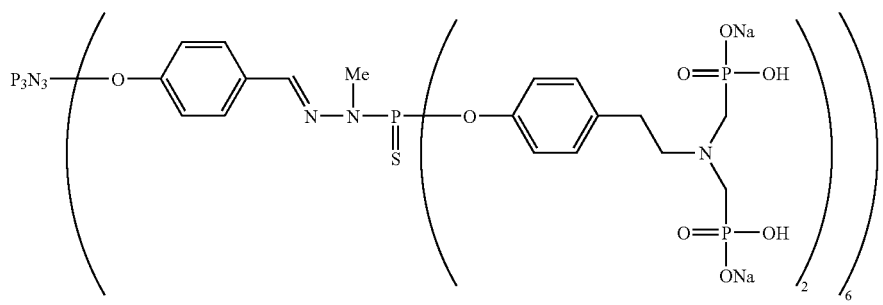
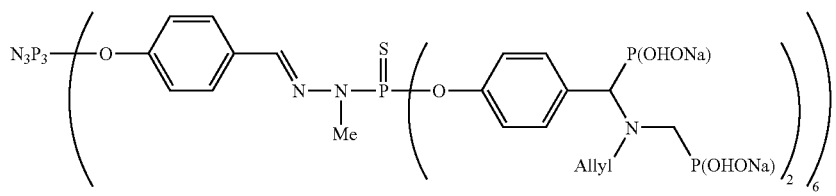
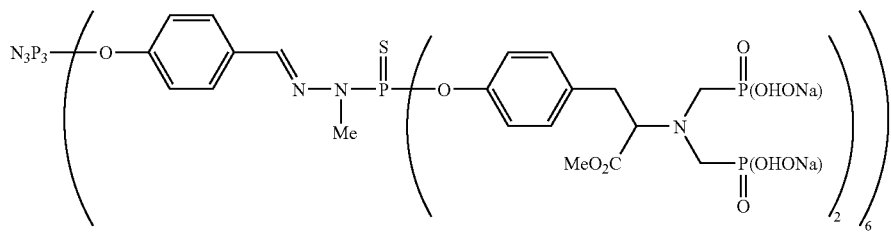
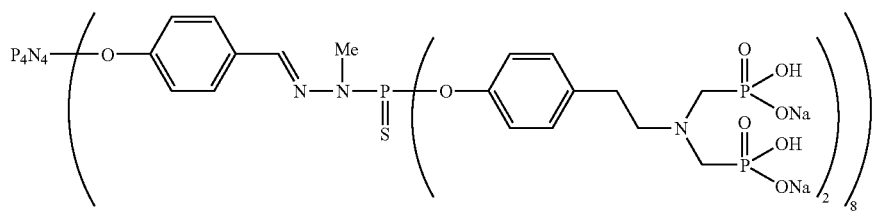

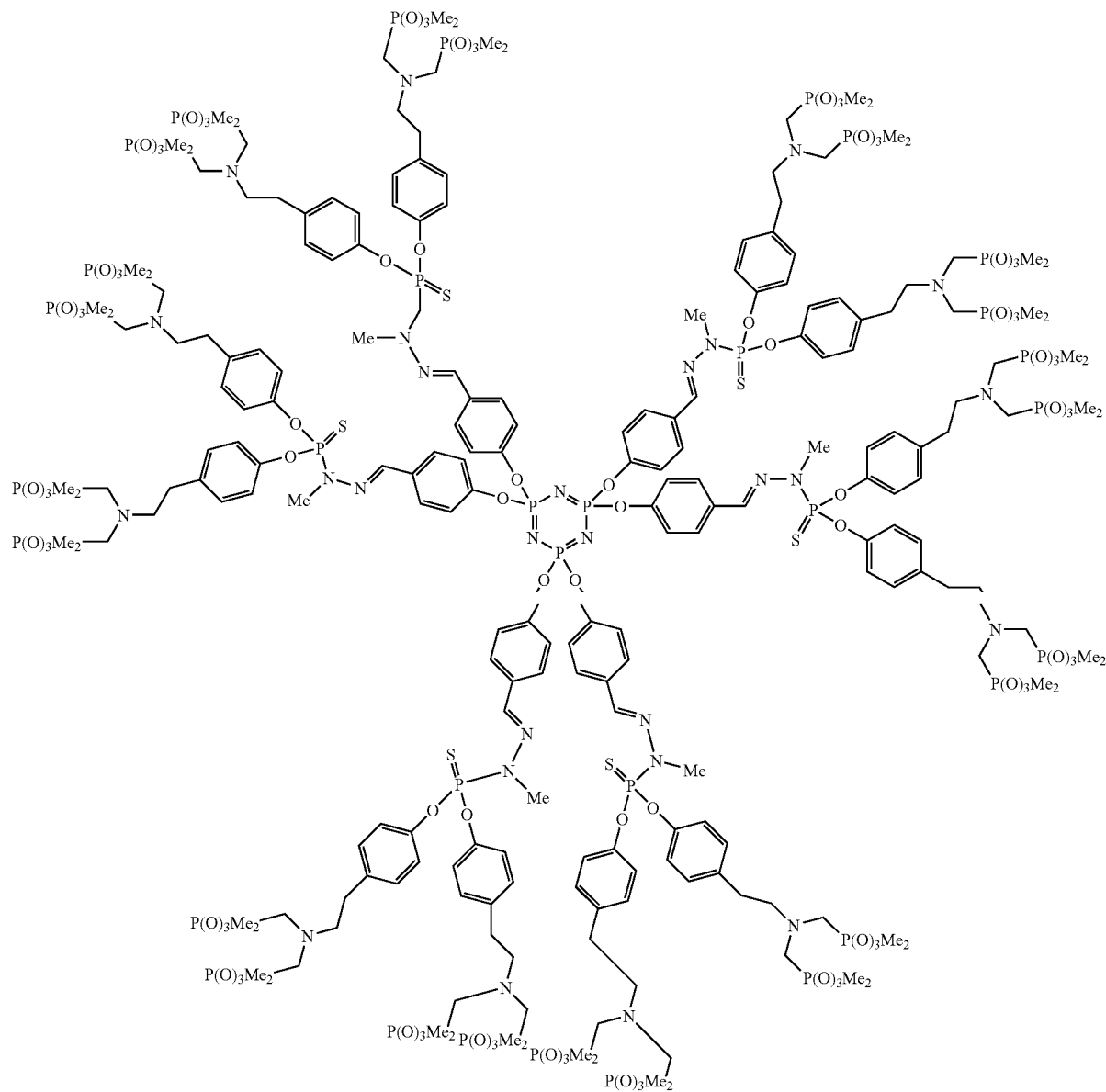

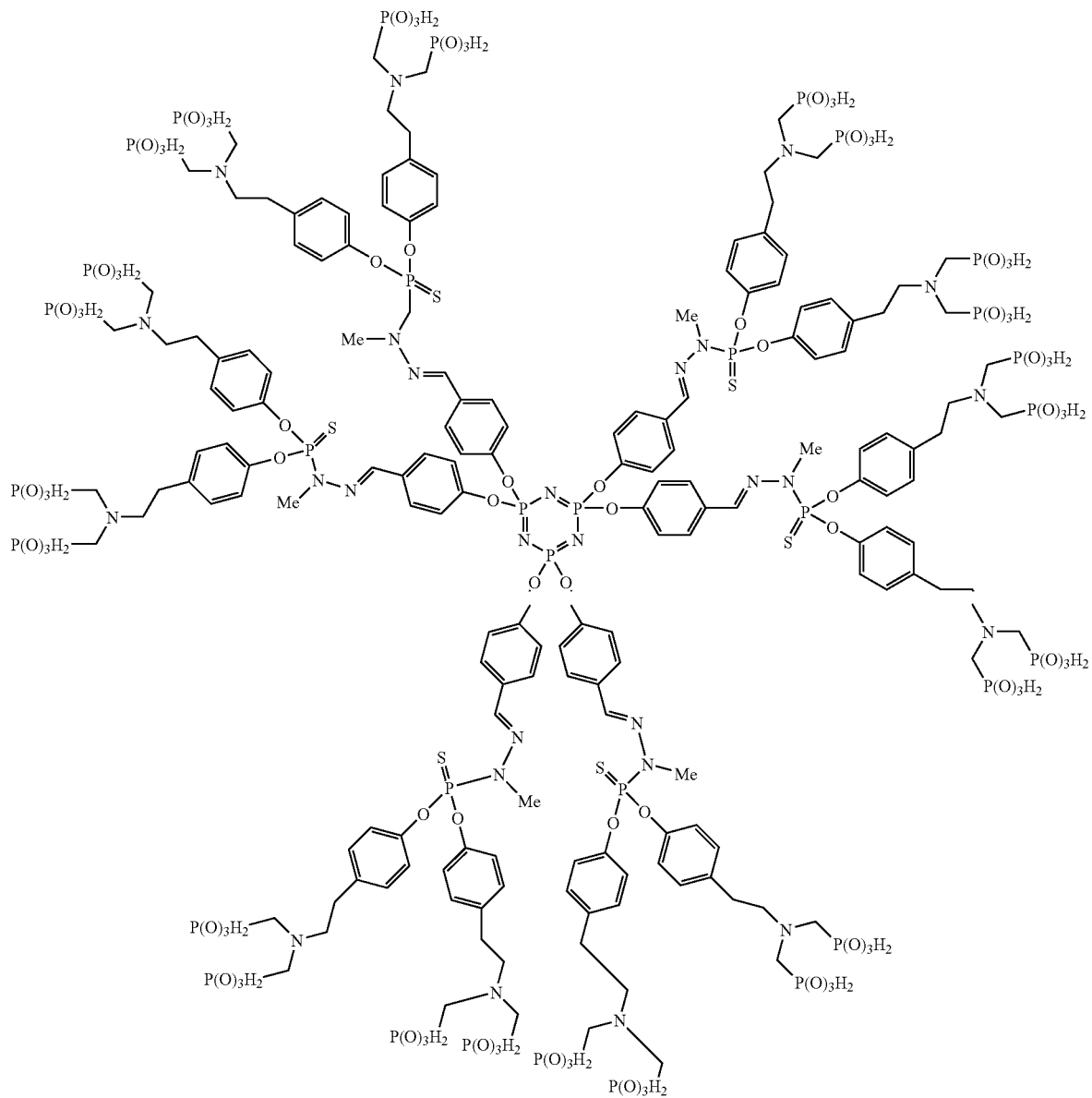

-continued

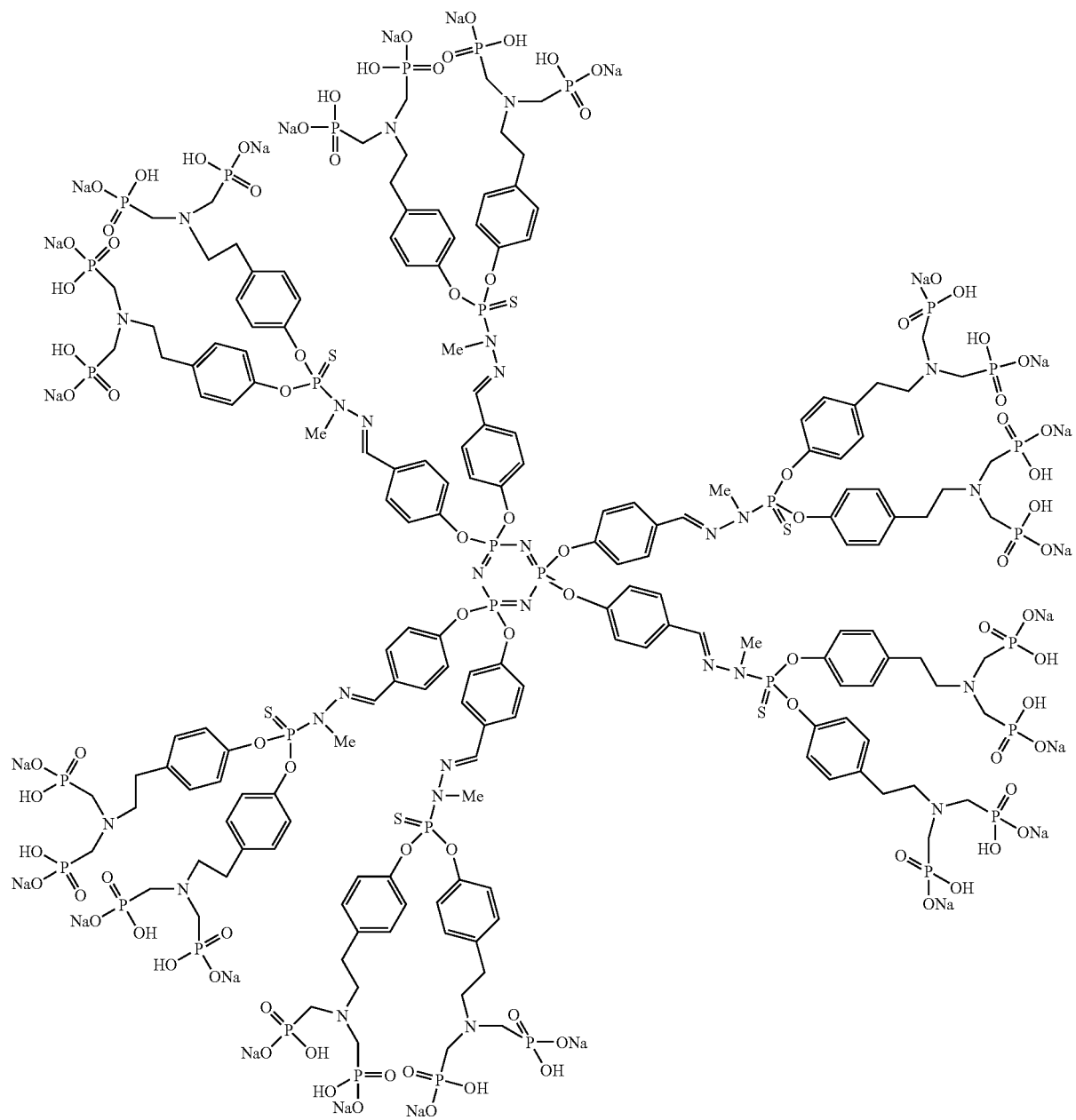

or to GC0, GC1 or GC2, in particular to GC1.

In a particular embodiment, the process defined above comprises an additional stage of purification of the activated monocytes starting with a cell composition comprising activated monocytes.

The present invention also relates to activated monocytes or cell compositions comprising activated monocytes as obtained by the process defined above.

The present invention also relates to a pharmaceutical composition characterized in that it comprises, as active ingredient, lymphoid cells expressing the receptor NKG2D, in particular NK cells, and at least one dendrimer with monophosphonic or bisphosphonic terminations, in combination with a pharmaceutically acceptable vehicle.

According to a preferred embodiment of the pharmaceutical composition, the dendrimer with monophosphonic or bisphosphonic terminations corresponds to the dendrimers as defined above.

According to another preferred embodiment of the pharmaceutical composition defined above, the dendrimer with monophosphonic or bisphosphonic terminations corresponds to the dendrimers of the following formulae:

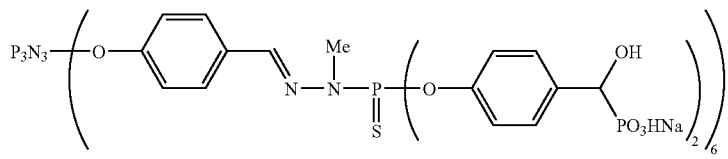
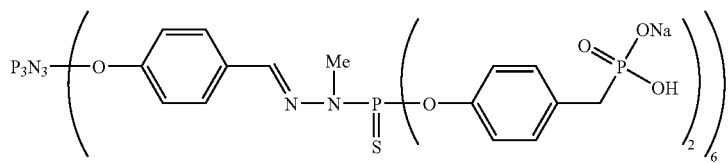
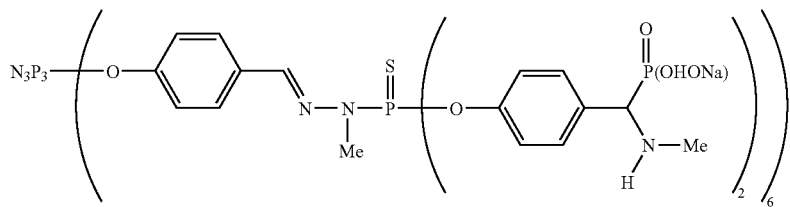
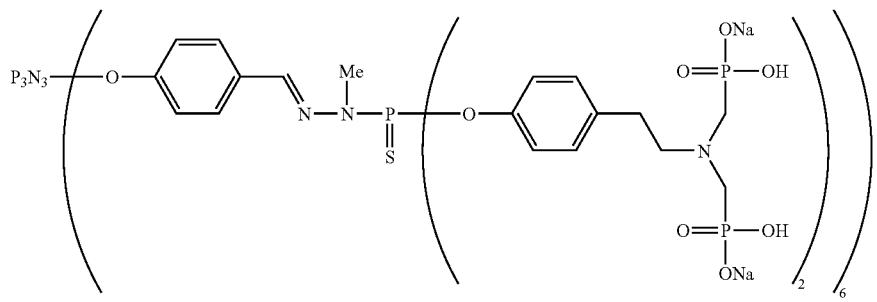
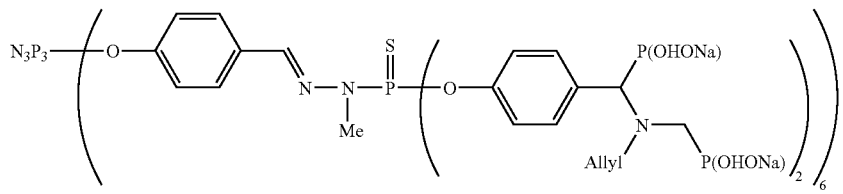
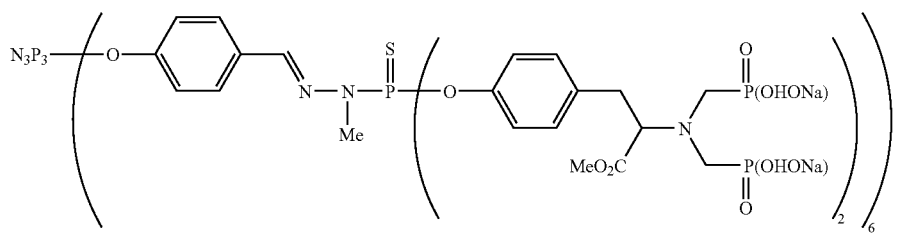
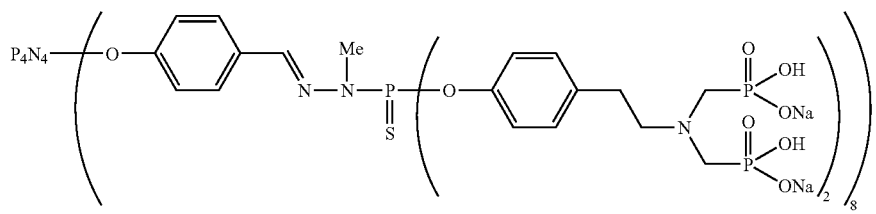

-continued
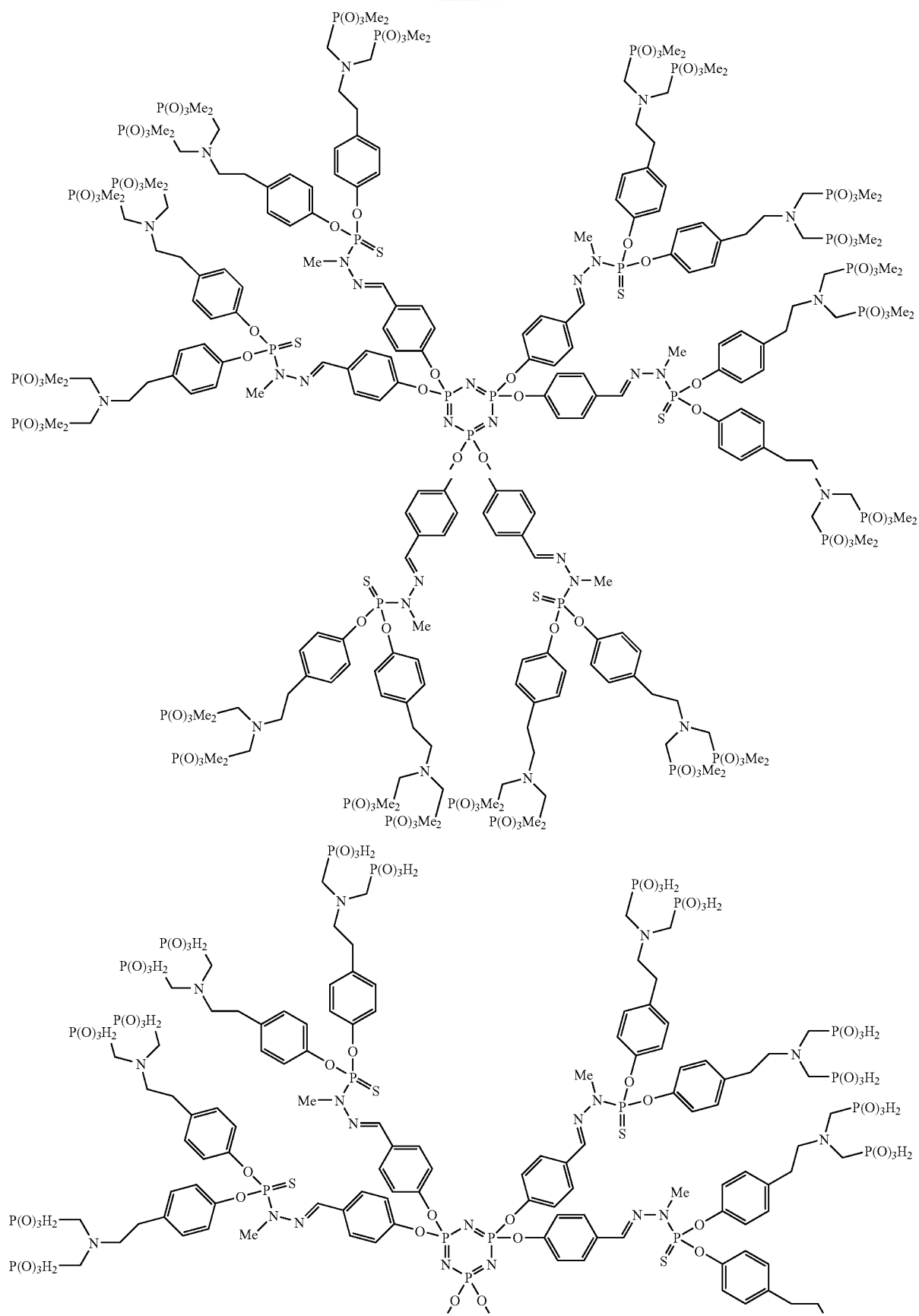

145
-continued
146
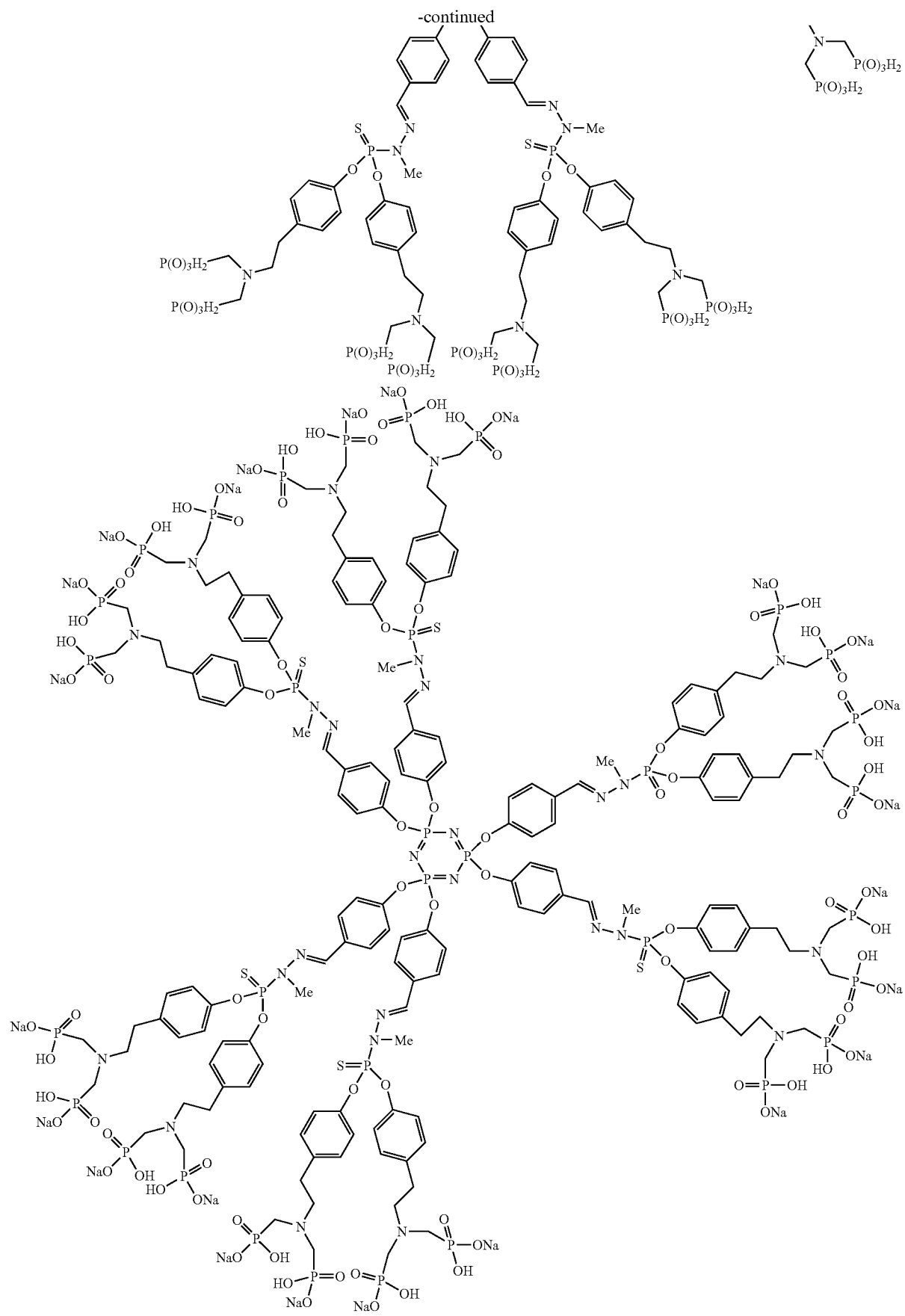

or to GC0, GC1 or GC2, in particular to GC1.

According to another preferred embodiment of the pharmaceutical composition defined above, it contains, as active ingredient, a cell composition enriched with cells of the lymphoid line expressing the receptor NKG2D as defined above and/or activated monocytes or a cell composition comprising activated monocytes as defined above, in combination with a pharmaceutically acceptable vehicle.

According to yet another particular embodiment of the pharmaceutical composition defined above, it is suitable for the administration to an individual of a single dose of approximately $10^5$ to approximately $5 \cdot 10^9$ lymphoid cells expressing the receptor NKG2D, in particular NK cells.

The present invention also relates to the use of lymphoid cells expressing the receptor NKG2D, in particular of NK cells, and of GC1 for the preparation of medicaments intended to treat and/or prevent cancers, including tumours of hematopoietic tissues, such as myeloid leukemias or anaplastic lymphomas, and melanomas.

The cells according to the invention possess cytolytic activity directed against cancer cells. These cells can therefore be administered to a cancer patient in order to destroy in vivo the tumours carried by the latter. Advantageously, these cells can be prepared, either from biological samples originating from the patient himself, or from a healthy donor.

The invention relates more particularly to the use of a cell composition enriched with cells of the lymphoid line expressing the receptor NKG2D as defined above and/or activated monocytes or a cell composition comprising activated monocytes as defined above for the preparation of medicaments intended to treat and/or prevent cancers, including tumours of hematopoietic tissues, such as myeloid leukemias or anaplastic lymphomas, and melanomas.

The present invention also relates to a pharmaceutical composition containing as active ingredient at least one dendrimer with monophosphonic or bisphosphonic terminations in combination with a pharmaceutically acceptable vehicle.

The present invention relates more particularly to a pharmaceutical composition containing as active ingredient at least one dendrimer with monophosphonic or bisphosphonic terminations as defined above, characterized in that the dendrimer with monophosphonic or bisphosphonic terminations corresponds to the dendrimers as defined above.

According to a preferred embodiment of the pharmaceutical composition containing as active ingredient at least one dendrimer with monophosphonic or bisphosphonic terminations as defined above, the dendrimer with monophosphonic or bisphosphonic terminations corresponds to the dendrimers of the following formulae:

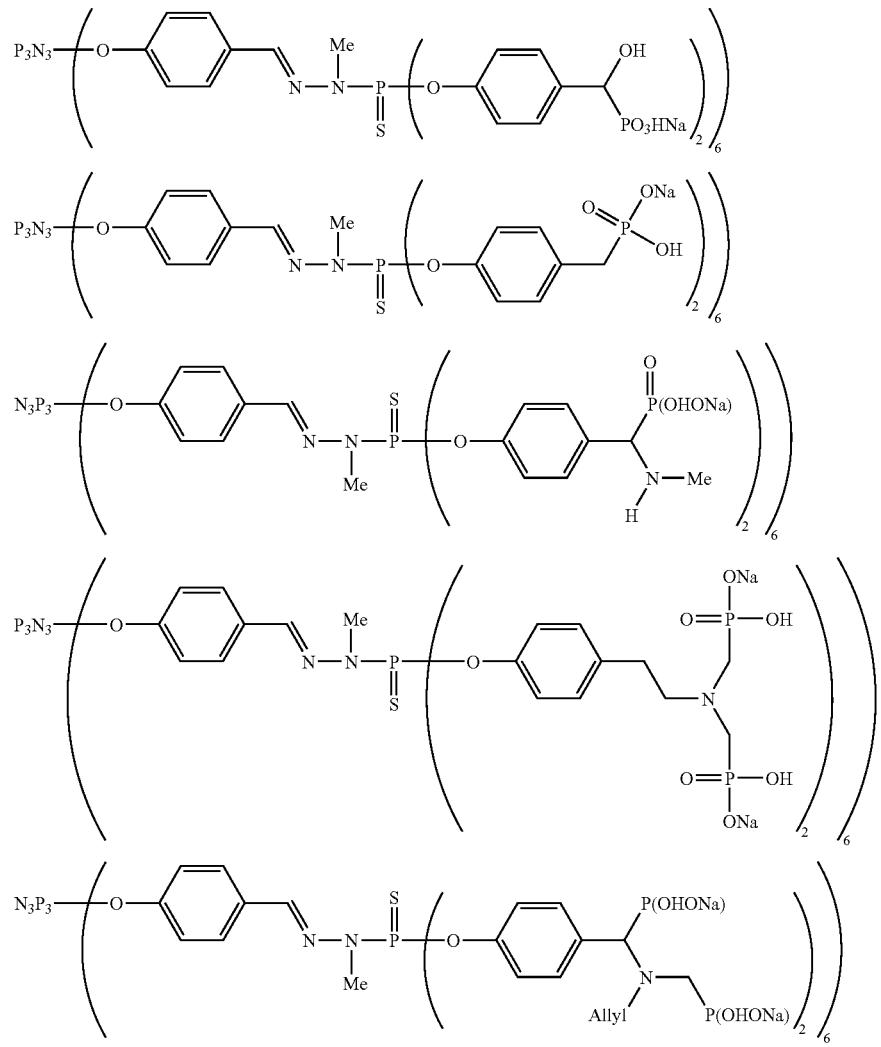

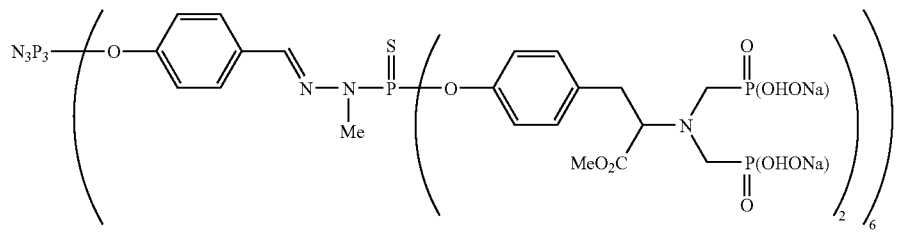
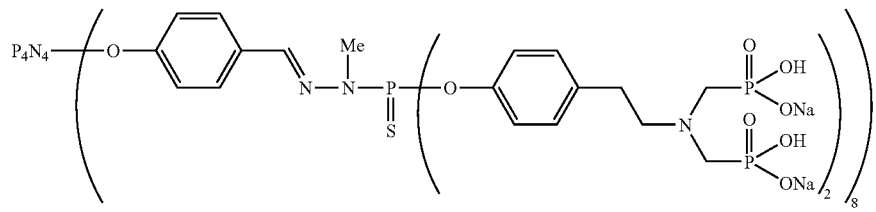
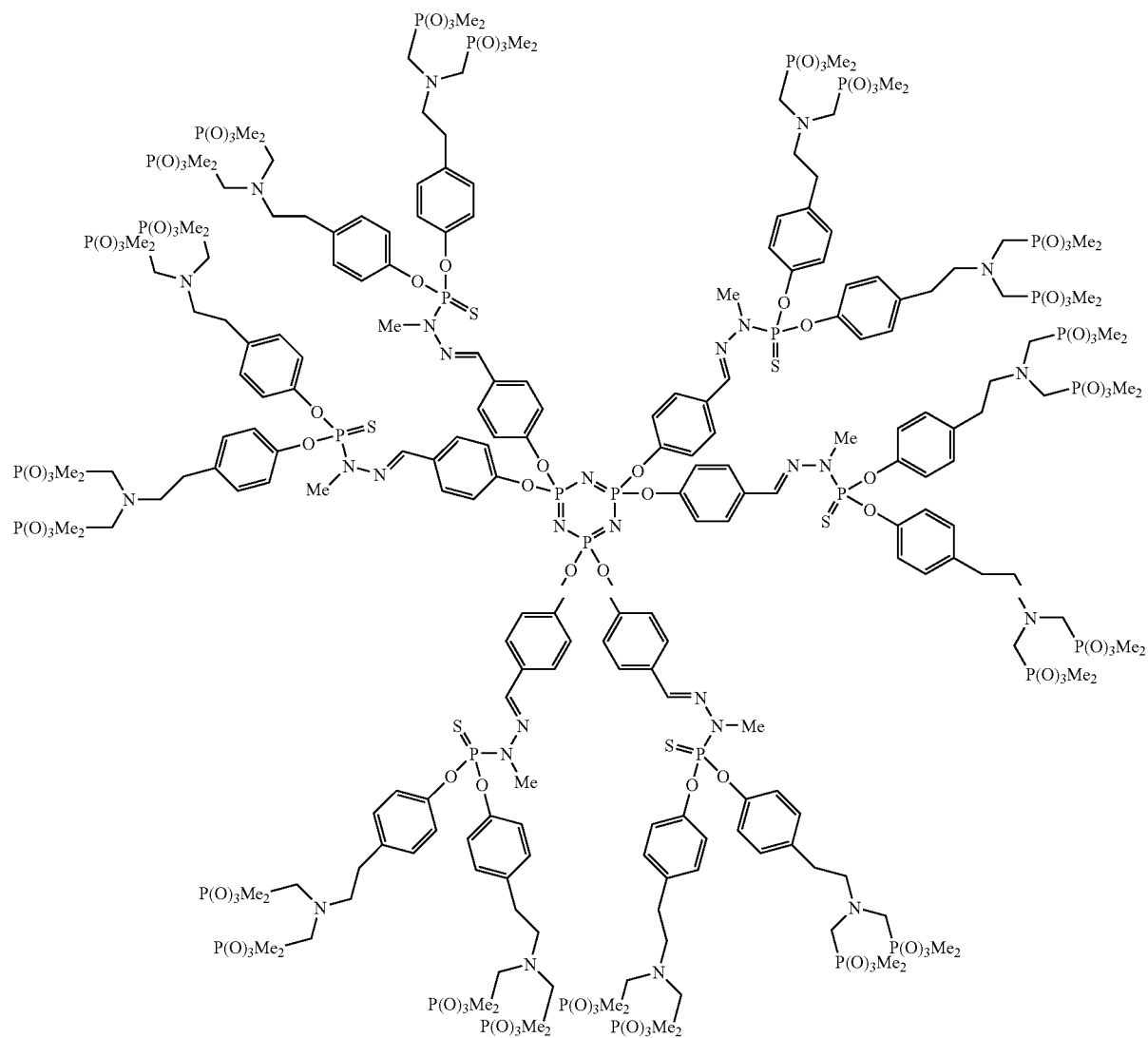

151 152
-continued
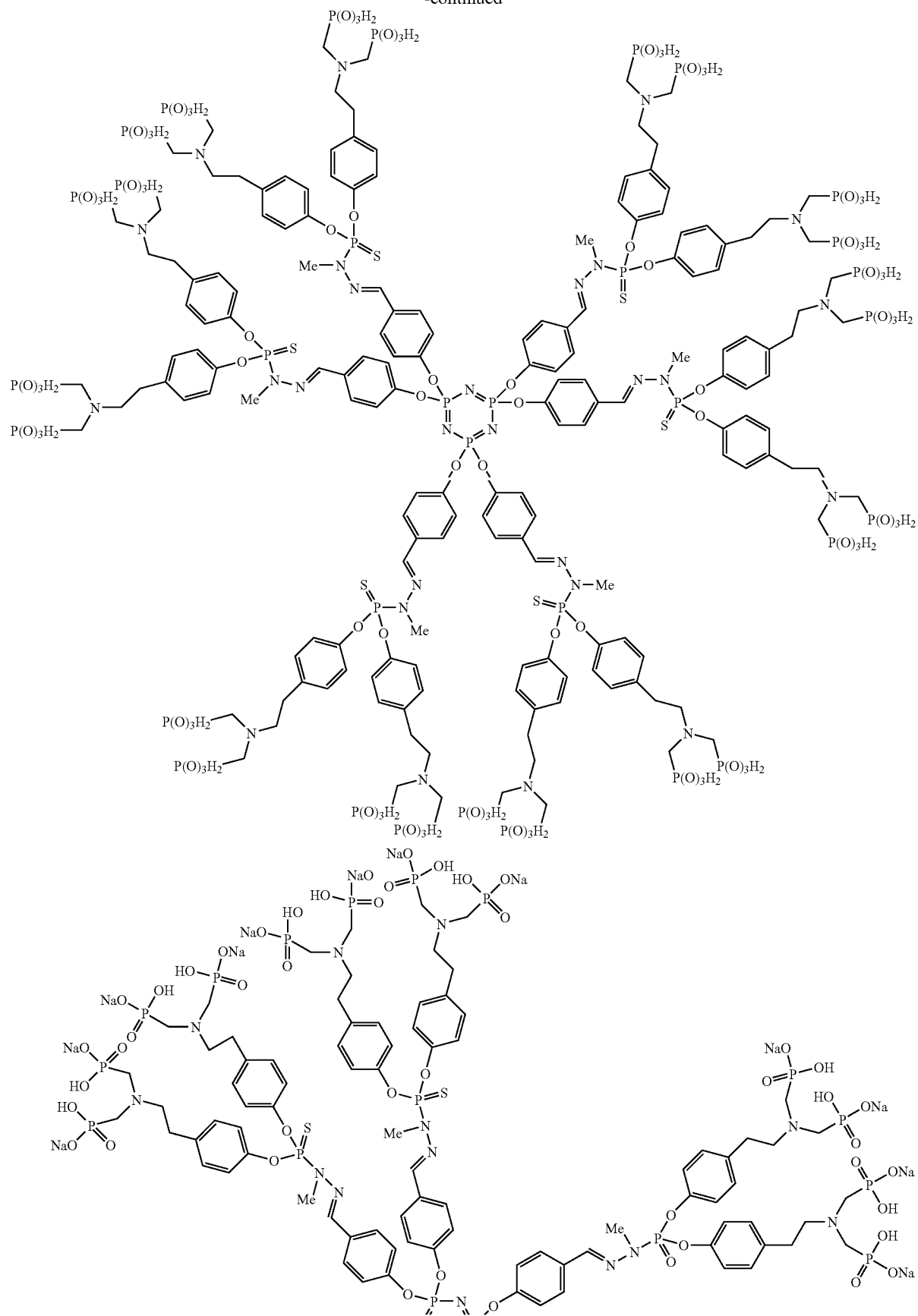

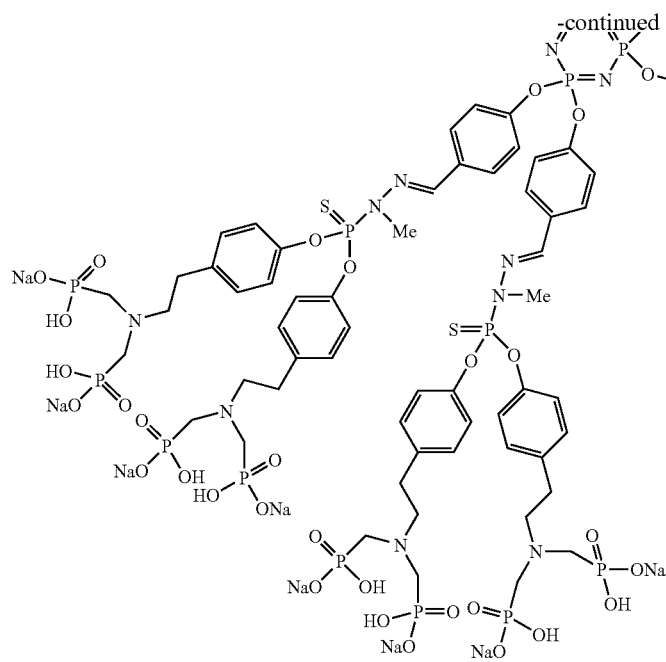
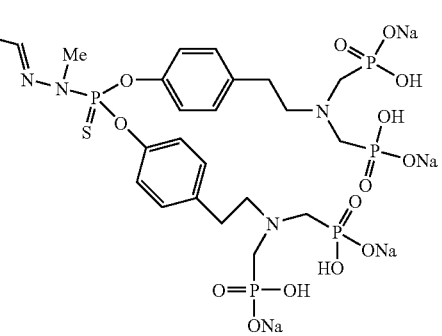

or to GC0, GC1 or GC2, in particular to GC1.

In order to produce their effects in vivo, the dendrimers of the invention can advantageously be administered directly to a patient. These effects can take place in particular by the selective stimulation of the growth of the NK cells within the organism, thus allowing the anti-cancer defences of said patient to be reinforced.

The dendrimers used within the scope of the invention and in which one or two bonds capable of being established by the central core are linked to identical or different linkage groups, constituted either on the one hand by the linkage chains defined above, or by a hydrogen atom, or by hydrocarbon groups comprising from 1 to 500 carbon atoms, are novel.

Thus, the present invention also relates to dendrimers with generation n monophosphonic or bisphosphonic terminations comprising a central core § of valency m, m representing an integer from 3 to 20, in particular from 3 to 10 and more particularly from 3 to 8, the core establishing m−2 or m−1 bonds with respectively m−2 or m−1 identical linkage chains, constituted:

either by generation chains attached in a tree-like structure around the core on each of the bonds, at least one intermediate chain being optionally attached to the end of each chain of the generation furthest from the central core, and a terminal group being attached to the end of the chain of the generation furthest from the central core or if appropriate to the end of each intermediate chain, or by intermediate chains attached around the core on each of the bonds, a terminal group being attached to the end of each intermediate chain;

said terminal group being represented by the formula:

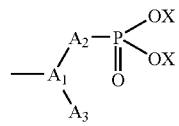

where $A_1$ represents N; a P=Y group, where Y represents O, S, or any atom; an N—R group; or a C—R group; R representing H or a linear, branched or cyclic hydrocarbon chain with 1 to 16 members, optionally containing one or more heteroatoms, said heteroatoms preferably being chosen from oxygen, sulphur, nitrogen, phosphorus, silicon and/or one or more double or triple bonds, each of said members optionally being substituted by at least one substituent chosen from a hydroxyl group, an —NR'R" group, an alkoxy group of 1 to 16 carbon atoms, an alkyl group of 1 to 16 carbon atoms, a halogen atom, an —NO$_2$ group, a —CN group, a —CF$_3$ group, an aryl group of 6 to 24 carbon atoms, an aralkyl group of 7 to 16 carbon atoms, R' and R" representing independently of each other H or an alkyl group of 1 to 16 carbon atoms, an aryl group of 6 to 24 carbon atoms or aralkyl group of 7 to 16 carbon atoms;

$A_2$ represents a single bond or a linear, branched or cyclic hydrocarbon chain with 1 to 6 members, each of said members optionally containing one or more heteroatoms, said heteroatoms preferably being chosen from a sulphur, oxygen, phosphorus or nitrogen atom, more preferably nitrogen, and optionally being substituted by at least one substituent chosen from H, an alkyl group of 1 to 16 carbon atoms, a halogen, an —NO$_2$ group, an —NRR' group, a —CN group, a —CF$_3$ group, a hydroxyl group, an alkoxy group of 1 to 16 carbon atoms, an aryl or heteroaryl group of 1 to 24 carbon atoms, the heteroelement preferably being chosen from oxygen, nitrogen or sulphur, an aralkyl group of 7 to 16 carbon atoms, R and R' representing independently of each other H or a linear, branched or cyclic hydrocarbon chain with 1 to 16 members, optionally containing one or more heteroatoms, said heteroatoms preferably being chosen from oxygen, sulphur, nitrogen, phosphorus, silicon and/or one or more double or triple bonds, each of said members optionally being substituted by at least one substituent chosen from a hydroxyl group, an —NR"R'" group, an alkoxy group of 1 to 16 carbon atoms, an alkyl group of 1 to 16 carbon atoms, a halogen atom, an —NO$_2$ group, a —CN group, a —CF$_3$ group, an aryl group of 6 to 24 carbon atoms, an aralkyl group of 7 to 16 carbon atoms, R" and R'" representing independently of each other H or an alkyl group of 1 to 16 carbon atoms, an aryl group of 6 to 24 carbon atoms or an aralkyl group of 7 to 16 carbon atoms;

A$_3$ represents H, or a linear, branched or cyclic hydrocarbon chain with 1 to 6 members, each of said members optionally being chosen from a heteroatom, said heteroatom preferably being chosen from sulphur, nitrogen, phosphorus, or silicon, more preferably nitrogen, each member being able to be optionally substituted by at least one group chosen from a hydroxyl group, an —NR"R'" group, an alkoxy group of 1 to 16 carbon atoms, an alkyl group of 1 to 16 carbon atoms, a halogen atom, an —NO$_2$ group, a —CN group, a —CF$_3$ group, an aryl group of 6 to 24 carbon atoms, an aralkyl group of 7 to 16 carbon atoms, R" and R'" representing independently of each other H or an alkyl group of 1 to 16 carbon atoms, an aryl group of 6 to 24 carbon atoms, or an aralkyl group of 7 to 16 carbon atoms or

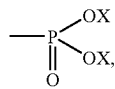

in particular A$_3$ can represent

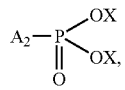

each A$_2$ being identical or different;
each OX, identical or different for each phosphonic group, represents OH, Oalkyl, where the alkyl group comprises 1 to 16 carbon atoms, Oaryl, where the aryl group comprises 6 to 24 carbon atoms, Oaralkyl, where the aralkyl group comprises 7 to 24 carbon atoms, Oalkylaryl, where the alkylaryl group comprises 7 to 24 carbon atoms, OSiR'$_1$R'$_2$R'$_3$, where R'$_1$, R'$_2$ and R'$_3$, identical or different, represent an alkyl group of 1 to 16 carbon atoms, or O$^-$M$^+$, where M$^+$ is a cation of elements of the group IA, IB, IIA, IIB or IIIA, IIIB of the periodic table of the elements, M$^+$ is preferably chosen from the cations of sodium, potassium, copper, calcium, barium, zinc, magnesium, lithium and aluminium atoms, or hydrocarbon groups of 1 to 100 carbon atoms, or nitrogenous groups of 0 to 100 carbon atoms, such as NR$_1$R$_2$R$_3$R$_4$$^+$, where, independently of one another R$_1$, R$_2$, R$_3$ and R$_4$ represent H or a linear, branched or cyclic hydrocarbon chain with 1 to 16 members, optionally containing one or more heteroatoms, said heteroatoms preferably being chosen from oxygen, sulphur, nitrogen, phosphorus, silicon and/or one or more double or triple bonds, each of said members optionally being substituted by at least one substituent chosen from a hydroxyl group, an —NR"R'" group, an alkoxy group of 1 to 16 carbon atoms, an alkyl group of 1 to 16 carbon atoms, a halogen atom, an —NO$_2$ group, a —CN group, a —CF$_3$ group, an aryl group of 6 to 24 carbon atoms, an aralkyl group of 7 to 16 carbon atoms, R" and R'" representing independently of each other H or an alkyl group of 1 to 16 carbon atoms, an aryl group of 6 to 24 carbon atoms or an aralkyl group of 7 to 16 carbon atoms;

n represents an integer from 0 to 12;
the 1 or 2 remaining bonds being attached to identical or different linkage groups, optionally linked together, in particular by a covalent bond, constituted either on the one hand by linkage chains defined above,
or by a hydrogen atom,
or by hydrocarbon groups comprising from 1 to 500 carbon atoms,
said hydrocarbon groups being constituted in particular by H or by a linear, branched or cyclic hydrocarbon chain with 1 to 16 members, optionally containing one or more double or triple bonds, each of said members optionally being able to be chosen from a heteroatom, said heteroatom preferably being chosen from a nitrogen, oxygen, phosphorus, silicon or sulphur atom, an aryl group of 6 to 24 carbon atoms, a heteroaryl group of 1 to 24 carbon atoms, a carboxyl group, a >C=NR group, each member being able to be optionally substituted by at least one substituent chosen from a hydroxyl group, an —NR"R'" group, an alkoxy group of 1 to 16 carbon atoms, an alkyl group of 1 to 16 carbon atoms, a halogen atom, an —NO$_2$ group, a —CN group, a —CF$_3$ group, an aryl group of 6 to 24 carbon atoms, an aralkyl group of 7 to 16 carbon atoms, R" and R'" representing independently of each other H or an alkyl group of 1 to 16 carbon atoms, an aryl group of 6 to 24 carbon atoms or an aralkyl group of 7 to 16 carbon atoms, the first member of said hydrocarbon chain preferably being oxygen or nitrogen.

said central core § representing a group comprising from 1 to 500 atoms, and optionally containing one or more heteroatoms, said heteroatoms preferably being chosen from oxygen, sulphur, nitrogen, phosphorus or silicon.

In particular the hydrocarbon groups comprising from 1 to 500 atoms defined above can be fluorophores, or any functional chemical group.

The present invention also relates to dendrimers with monophosphonic or bisphosphonic terminations of generation n, n representing an integer from 0 to 12, comprising a central core § of valency m, m representing an integer from 3 to 20, in particular 3 to 10 and more particularly 3 to 8, the core establishing m−2 or m−1 bonds with respectively m−2 or m−1 identical linkage chains constituted by:

generation chains attached in a tree-like structure around the core on each of the bonds, when n is greater than or equal to 1, a generation chain of a given generation being linked to
a generation chain of the generation immediately below the given generation, or to the core when the given generation is 1, and to
at least 2 generation chains of the generation immediately above the given generation, or optionally to at least one intermediate chain when the given generation is n,
a terminal group being attached to the outside of each generation chain of generation n, or if appropriate to the end of each intermediate chain, or intermediate chains attached around the core on each of the bonds, when n is 0, a terminal group being attached to the end of each intermediate chain;

said terminal group being represented by the formula:

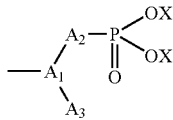

where

A$_1$ represents N; a P=Y group, where Y represents O, S, or any atom; an N—R group; or a C—R group; R representing H or a linear, branched or cyclic hydrocarbon chain with 1 to 16 members optionally containing one or more heteroatoms, said heteroatoms preferably being chosen from oxygen, sulphur, nitrogen, phosphorus, silicon and/or one or more double or triple bonds, each of said members optionally being substituted by at least one substituent chosen from a hydroxyl group, an —NR'R" group, an alkoxy group of 1 to 16 carbon atoms, an alkyl group of 1 to 16 carbon atoms, a halogen atom, an —NO$_2$ group, a —CN group, a —CF$_3$ group, an aryl group of 6 to 24 carbon atoms, an aralkyl group of 7 to 16 carbon atoms, R' and R" representing independently of each other H or an alkyl group of 1 to 16 carbon atoms, an aryl group of 6 to 24 carbon atoms or an aralkyl group of 7 to 16 carbon atoms;

A$_2$ represents a single bond or a linear, branched or cyclic hydrocarbon chain with 1 to 6 members, each of said members optionally containing one or more heteroatoms, said heteroatoms preferably being chosen from a sulphur, oxygen, phosphorus, or nitrogen atom, more preferably nitrogen, and optionally being substituted by at least one substituent chosen from H, an alkyl group of 1 to 16 carbon atoms, a halogen, an —NO$_2$ group, an —NRR' group, a —CN group, a —CF$_3$ group, a hydroxyl group, an alkoxy group of 1 to 16 carbon atoms, an aryl or heteroaryl group of 1 to 24 carbon atoms, the heteroelement preferably being chosen from oxygen, nitrogen or sulphur, an aralkyl group of 7 to 16 carbon atoms, R and R' representing independently of each other H or a linear, branched or cyclic hydrocarbon chain with 1 to 16 members, optionally containing one or more heteroatoms, said heteroatoms preferably being chosen from oxygen, sulphur, nitrogen, phosphorus, silicon and/or one or more double or triple bonds, each of said members optionally being substituted by at least one substituent chosen from a hydroxyl group, an —NR"R"' group, an alkoxy group of 1 to 16 carbon atoms, an alkyl group of 1 to 16 carbon atoms, a halogen atom, an —NO$_2$ group, a —CN group, a —CF$_3$ group, an aryl group of 6 to 24 carbon atoms, an aralkyl group of 7 to 16 carbon atoms, R" and R"' representing independently of each other H or an alkyl group of 1 to 16 carbon atoms, an aryl group of 6 to 24 carbon atoms or an aralkyl group of 7 to 16 carbon atoms;

A$_3$ represents H, or a linear, branched or cyclic hydrocarbon chain with 1 to 6 members, each of said members optionally being chosen from a heteroatom, said heteroatom preferably being chosen from sulphur, nitrogen, phosphorus, or silicon, more preferably nitrogen, each member being able to be optionally substituted by at least one group chosen from a hydroxyl group, an —NR"R"' group, an alkoxy group of 1 to 16 carbon atoms, an alkyl group of 1 to 16 carbon atoms, a halogen atom, an —NO$_2$ group, a —CN group, a —CF$_3$ group, an aryl group of 6 to 24 carbon atoms, an aralkyl group of 7 to 16 carbon atoms, R" and R"' representing independently of each other H or an alkyl group of 1 to 16 carbon atoms, an aryl group of 6 to 24 carbon atoms, or an aralkyl group of 7 to 16 carbon atoms or

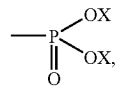

in particular A$_3$ can represent

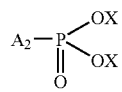

each A$_2$ being identical or different;

each OX, identical or different for each phosphonic group, represents OH, Oalkyl, where the alkyl group comprises from 1 to 16 carbon atoms, Oaryl, where the aryl group comprises from 6 to 24 carbon atoms, Oaralkyl, where the aralkyl group comprises from 7 to 24 carbon atoms, Oalkylaryl, where the alkylaryl group comprises from 7 to 24 carbon atoms, OSiR'$_1$R'$_2$R'$_3$, where R'$_1$, R'$_2$ and R'$_3$, identical or different, represent an alkyl group from 1 to 16 carbon atoms, or O$^-$M$^+$, where M$^+$ is a cation of elements of the group IA, IB, IIA, IIB or IIIA, IIIB of the periodic table of the elements, M$^+$ is preferably chosen from the cations of sodium, potassium, copper, calcium, barium, zinc, magnesium, lithium and aluminium atoms, or from hydrocarbon groups of 1 to 100 carbon atoms, or nitrogenous groups of 0 to 100 carbon atoms, such as NR$_1$R$_2$R$_3$R$_4^+$, where, independently of one another R$_1$, R$_2$, R$_3$ and R$_4$ represent H or a linear, branched or cyclic hydrocarbon chain with 1 to 16 members, optionally containing one or more heteroatoms, said heteroatoms preferably being chosen from oxygen, sulphur, nitrogen, phosphorus, silicon and/or one or more double or triple bonds, each of said members optionally being substituted by at least one substituent chosen from a hydroxyl group, an —NR"R"' group, an alkoxy group of 1 to 16 carbon atoms, an alkyl group of 1 to 16 carbon atoms, a halogen atom, an —NO$_2$ group, a —CN group, a —CF$_3$ group, an aryl group of 6 to 24 carbon atoms, an aralkyl group of 7 to 16 carbon atoms, R" and R"' representing independently of each other H or an alkyl group of 1 to 16 carbon atoms, an aryl group of 6 to 24 carbon atoms or an aralkyl group of 7 to 16 carbon atoms;

the 1 or 2 remaining bonds being attached to the identical or different linkage groups, optionally linked together, in particular by a covalent bond, constituted either on the one hand by linkage chains defined above, or by a hydrogen atom, or by hydrocarbon groups comprising from 1 to 500 carbon atoms, said hydrocarbon groups being constituted in particular by H or a linear, branched or cyclic hydrocarbon chain with 1 to 16 members, optionally containing one or more double or triple bonds, each of said members optionally being able to be chosen from a heteroatom, said heteroatom preferably being chosen from a nitrogen, oxygen, phosphorus, silicon or sulphur atom, an aryl group of 6 to 24 carbon atoms, a heteroaryl group of 1 to 24 carbon atoms, a carboxyl group, a >C═NR group, each member being able to be optionally substituted by at least one substituent chosen from a hydroxyl group, an —NR″R‴ group, an alkoxy group of 1 to 16 carbon atoms, an alkyl group of 1 to 16 carbon atoms, a halogen atom, an —NO₂ group, a —CN group, a —CF₃ group, an aryl group of 6 to 24 carbon atoms, an aralkyl group of 7 to 16 carbon atoms, R″ and R‴ representing independently of each other H or an alkyl group of 1 to 16 carbon atoms, an aryl group of 6 to 24 carbon atoms or an aralkyl group of 7 to 16 carbon atoms, the first member of said hydrocarbon chain preferably being oxygen or nitrogen;

said central core § representing a group comprising from 1 to 500 atoms, and optionally containing one or more heteroatoms, said heteroatoms preferably being chosen from oxygen, sulphur, nitrogen, phosphorus or silicon.

In particular the hydrocarbon groups comprising from 1 to 500 atoms defined above can be fluorophores or any functional chemical group.

According to a particular embodiment of the dendrimers defined above, the generation chains are chosen from any linear, branched or cyclic hydrocarbon chain with 1 to 12 members, optionally containing one or more double or triple bonds, each of said members optionally being able to be chosen from a heteroatom, said heteroatom preferably being chosen from nitrogen, oxygen, sulphur, phosphorus or silicon, an aryl group of 6 to 24 carbon atoms, a heteroaryl group of 1 to 24 carbon atoms, the heteroelement preferably being chosen from oxygen, nitrogen or sulphur, a carboxyl group, a >C═NR group, each member optionally being able to be substituted by at least one substituent chosen from an alkyl group of 1 to 16 carbon atoms, a halogen atom, an —NO₂ group, an —NRR' group, a —CN group, a —CF₃ group, a hydroxyl group, an alkoxy group of 1 to 16 carbon atoms, an aryl group of 6 to 24 carbon atoms, or an aralkyl group of 7 to 16 carbon atoms, R and R' representing independently of each other H or an alkyl group of 1 to 16 carbon atoms, an aryl group of 6 to 24 carbon atoms, or an aralkyl group of 7 to 16 carbon atoms.

According to another preferred embodiment of the dendrimers defined above, the intermediate chains are chosen from the groups corresponding to the formula:

-J-K-L- where

J represents an oxygen or sulphur atom, or an —NR— group;

K represents an aryl group of 6 to 24 carbon atoms, a heteroaryl group of 1 to 24 carbon atoms, the heteroelement preferably being chosen from oxygen, nitrogen or sulphur, an alkyl group of 1 to 16 carbon atoms, each being able to be optionally substituted by a halogen atom or an —NO₂, —NRR', —CN, —CF₃, —OH group, an alkyl group of 1 to 16 carbon atoms, an aryl group of 6 to 24 carbon atoms, an aralkyl group of 7 to 16 carbon atoms;

L represents a linear, branched or cyclic hydrocarbon chain with 0 to 10 members, in particular 0 to 6 members, optionally containing one or more double or triple bonds, each of said members optionally being able to be a heteroatom, said heteroatom preferably being chosen from oxygen, sulphur, nitrogen, phosphorus, silicon, each member being able to be optionally substituted by at least one substituent chosen from an alkyl group of 1 to 16 carbon atoms, a halogen, an oxygen atom, —NO₂, —NRR', —CN, —CF₃, —OH, an alkoxy group of 1 to 16 carbon atoms, an aryl group of 6 to 24 carbon atoms, an aralkyl group of 7 to 16 carbon atoms;

R and R' representing independently of each other H or an alkyl group of 1 to 16 carbon atoms, an aryl group of 6 to 24 carbon atoms, or an aralkyl group of 7 to 16 carbon atoms.

According to yet another embodiment of the dendrimers as defined above, the core is chosen from:

a nitrogen atom or a silicon atom, a group of formula

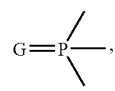

in which G represents an oxygen, nitrogen, sulphur, selenium, tellurium atom or an ═NR group, R representing H or an alkyl group of 1 to 16 carbon atoms, an aryl group of 6 to 24 carbon atoms, or an aralkyl group of 7 to 16 carbon atoms, such as the thiophosphoryl group of formula

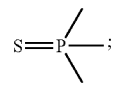

a bis-phenyloxy group of formula

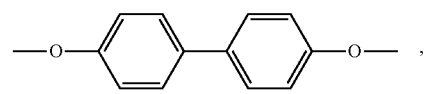

a 1,2-diamino-ethane group of formula

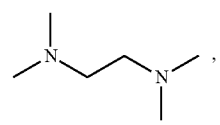

a 1,4-diamino-butane group of formula

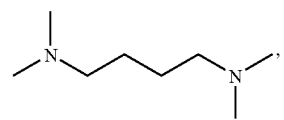

a cyclotriphosphazene group of formula

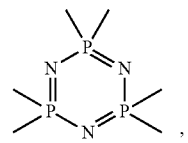

a cyclotetraphosphazene group of formula

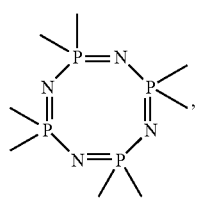

According to a particularly preferred embodiment of the invention, the dendrimers defined above have the structure PMMH, PAMAM or DAB.

According to another particularly preferred embodiment of the invention, the dendrimers defined above have bisphosphonic terminations corresponding to the following general formula (7):

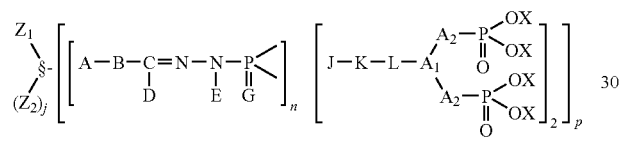

where n represents an integer from 0 to 3, m represents 3, 6 or 8, p represents m−1 or m−2, and j represents 0 when p represents m−1 and 1 when p represents m−2, namely:

when p=m−1, formula (7) corresponds to the following formula (8):

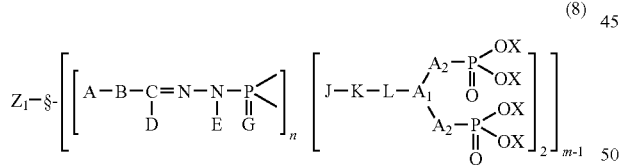

when p=m−2, formula (7) corresponds to the following formula (9)

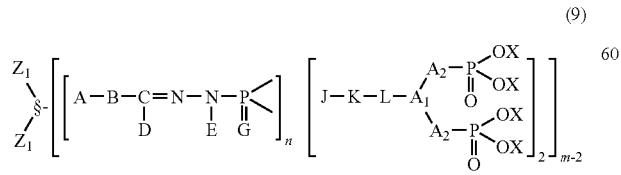

and in which formulae:
the central core § is chosen from the following groups:

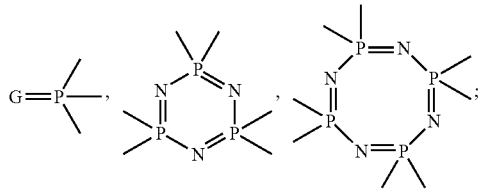

the generation chain corresponds to the formula:

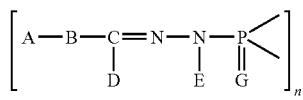

where
A represents an oxygen, sulphur, phosphorus atom or an —NR— group;
B represents an aryl group of 6 to 24 carbon atoms, a heteroaryl group of 1 to 24 carbon atoms, an alkyl group of 1 to 16 carbon atoms, each being able to be optionally substituted by a halogen atom or an —NO$_2$, —NRR', —CN, —CF$_3$, —OH group, an alkyl group of 1 to 16 carbon atoms, an aryl group of 6 to 24 carbon atoms, an aralkyl group of 7 to 16 carbon atoms;
D represents a hydrogen atom, an alkyl group of 1 to 16 carbon atoms, an alkoxy group of 1 to 16 carbon atoms, an aryl group of 6 to 24 carbon atoms, an aralkyl group of 7 to 16 carbon atoms, each being able to be optionally substituted by a halogen atom or an —NO$_2$, —NRR', —CN, —CF$_3$, —OH group, an alkyl group of 1 to 16 carbon atoms, an aryl group of 6 to 24 carbon atoms, an aralkyl group of 7 to 16 carbon atoms;
E represents a hydrogen atom, an alkyl group of 1 to 16 carbon atoms, an alkoxy group of 1 to 16 carbon atoms, an aryl group of 6 to 24 carbon atoms, an aralkyl group of 7 to 16 carbon atoms, each being able to be optionally substituted by a halogen atom or an —NO$_2$, —NRR', —CN, —CF$_3$, —OH group, an alkyl group of 1 to 16 carbon atoms, an aryl group of 6 to 24 carbon atoms, an aralkyl group of 7 to 16 carbon atoms;
G represents an oxygen, nitrogen, sulphur, selenium, tellurium atom or an =NR group;
R and R' representing independently of each other H or an alkyl group of 1 to 16 carbon atoms, an aryl group of 6 to 24 carbon atoms, or an aralkyl group of 7 to 16 carbon atoms;
the intermediate chain corresponds to the formula:

-J-K-L- where
J represents an oxygen, sulphur atom, or an —NR— group;
K represents an aryl group of 6 to 24 carbon atoms, a heteroaryl group of 1 to 24 carbon atoms, the heteroelement preferably being chosen from oxygen, nitrogen or sulphur, an alkyl group of 1 to 16 carbon atoms, each being able to be optionally substituted by a halogen atom or an —NO$_2$, —NRR', —CN, —CF$_3$, —OH group, an alkyl group of 1 to 16 carbon atoms, an aryl group of 6 to 24 carbon atoms, an aralkyl group of 7 to 16 carbon atoms;

L represents a linear, branched or cyclic hydrocarbon chain with 0 to 10 members, in particular 0 to 6 members, optionally containing one or more double or triple bonds, each of said members optionally being able to be a heteroatom, said heteroatom preferably being chosen from oxygen, sulphur, nitrogen, phosphorus, silicon, each member being able to be optionally substituted by at least one substituent chosen from an alkyl group of 1 to 16 carbon atoms, a halogen, an oxygen atom, —NO$_2$, —NRR', —CN, —CF$_3$, —OH, an alkoxy group of 1 to 16 carbon atoms, an aryl group of 6 to 24 carbon atoms, an aralkyl group of 7 to 16 carbon atoms;

R and R' representing independently of each other H or an alkyl group of 1 to 16 carbon atoms, an aryl group of 6 to 24 carbon atoms, or an aralkyl group of 7 to 16 carbon atoms;

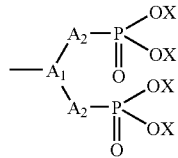

the terminal group corresponds to the formula:

where A1, A2 and X have been defined previously, each X being identical or different;

Z$_1$ and Z$_2$ being identical or different, optionally linked together, in particular by a covalent bond, and representing H or a linear, branched or cyclic hydrocarbon chain with 1 to 16 members, optionally containing one or more double or triple bonds, each of said members optionally being chosen from a heteroatom, said heteroatom preferably being chosen from a nitrogen, oxygen, phosphorus, silicon or sulphur atom, an aryl group of 6 to 24 carbon atoms, a heteroaryl group of 1 to 24 carbon atoms, a carboxyl group, a >C=NR group, each member being able to be optionally substituted by at least one substituent chosen from a hydroxyl group, an —NR"R'" group, an alkoxy group of 1 to 16 carbon atoms, an alkyl group of 1 to 16 carbon atoms, a halogen atom, an —NO$_2$ group, a —CN group, a —CF$_3$ group, an aryl group of 6 to 24 carbon atoms, an aralkyl group of 7 to 16 carbon atoms, R" and R'" representing independently of each other H or an alkyl group of 1 to 16 carbon atoms, an aryl group of 6 to 24 carbon atoms or an aralkyl group of 7 to 16 carbon atoms, the first member of said hydrocarbon chain preferably being oxygen or nitrogen.

According to yet another particularly preferred embodiment of the invention, the dendrimers as defined above have the structure PMMH, and correspond to general formula (8), in which § represents

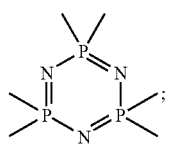

m represents 6;
p represents 5;
n represents 0, 1, or 2;
A represents an oxygen atom;
B represents a benzene group;
D represents hydrogen;
E represents a methyl group;
G represents a sulphur atom;
J represents an oxygen atom;
K represents a benzene group;
L represents a non substituted saturated linear hydrocarbon chain with two carbon atoms;
A$_1$ represents a nitrogen atom;
A$_2$ represents a CH$_2$ group;
X represents a methyl group, or a hydrogen or sodium atom;
Z$_1$ represents a phenyloxy group;
said dendrimer being designated GCn', n being defined above.

According to a quite particularly preferred embodiment of the invention, the dendrimers defined above correspond to the compounds of the following formulae:

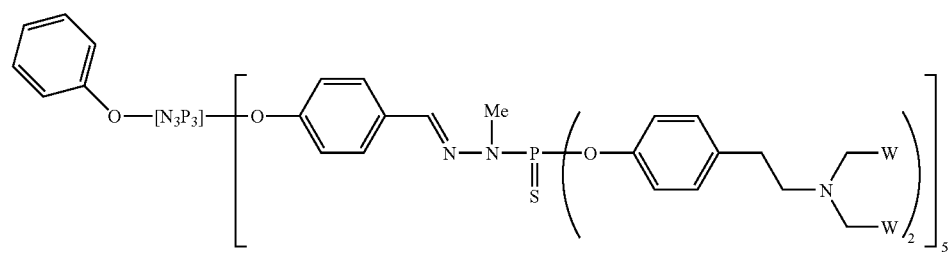

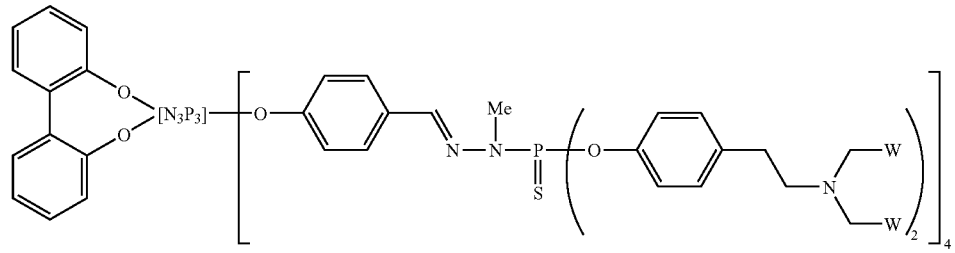

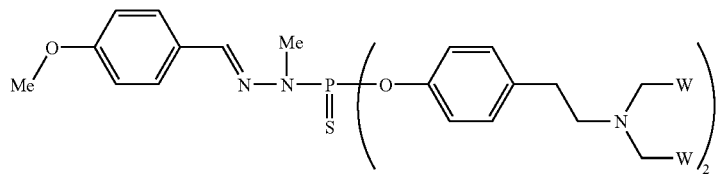
in which W represents $PO_3Me_2$, $PO_3HNa$, or $PO_3H_2$, said dendrimers corresponding in particular to compound GC1' of the following formula (10):
(10)
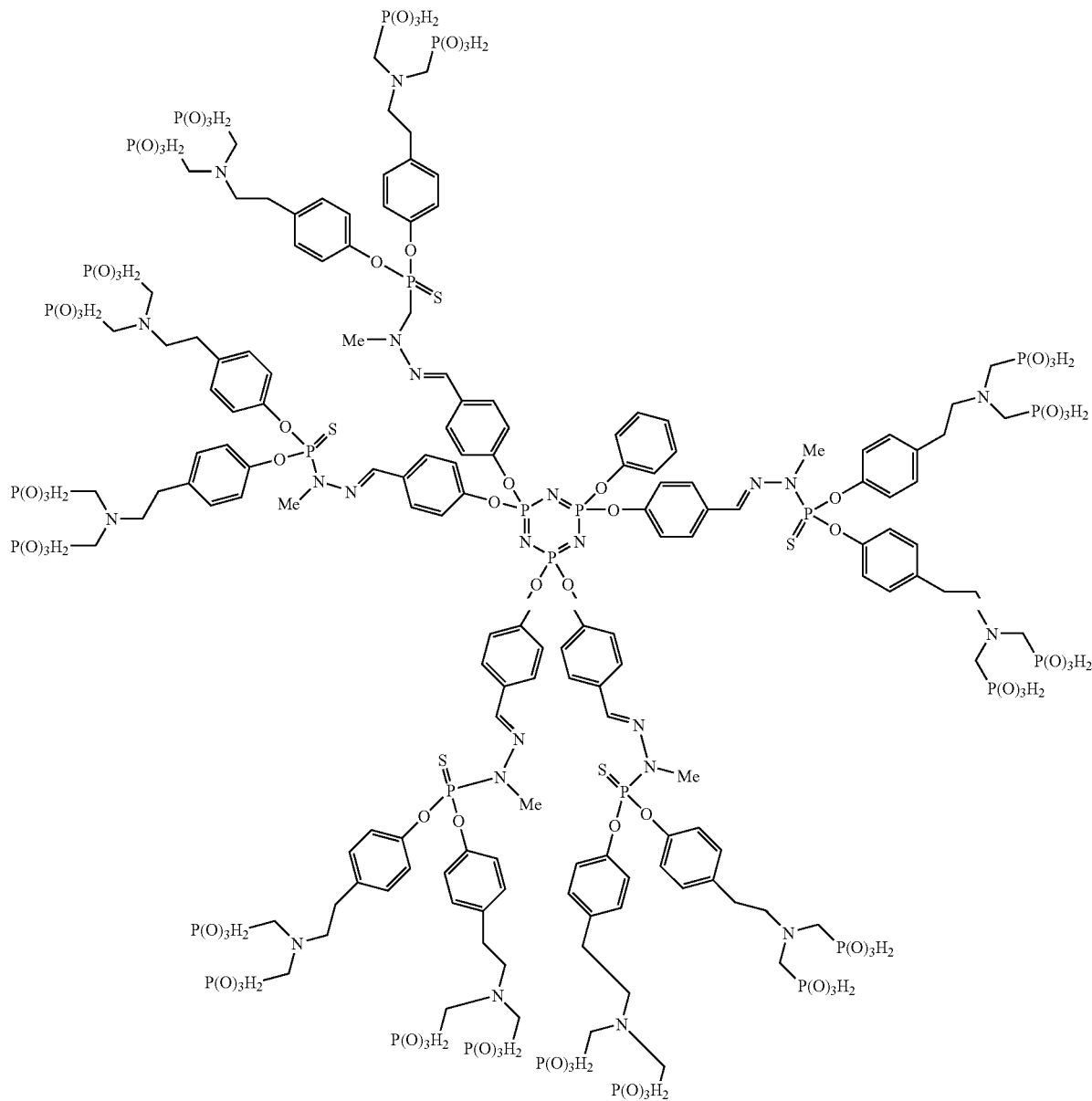

According to another particularly preferred embodiment of the invention, the dendrimers defined above correspond to the compound of the following formula:
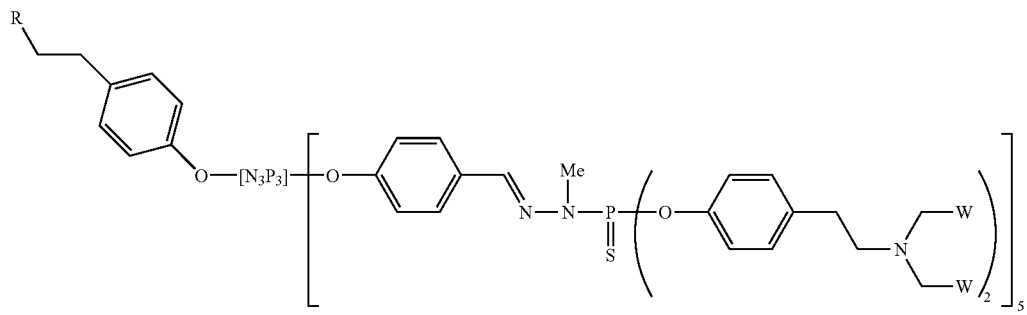
in which W represents $PO_3Me_2$, $PO_3HNa$, or $PO_3H_2$ and R represents a fluorescent group chosen from:
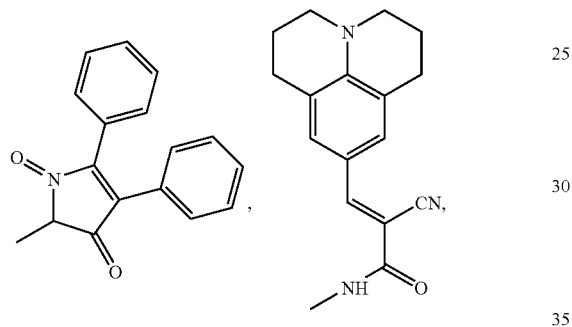
said dendrimers corresponding in particular to the compounds of the following formulae:
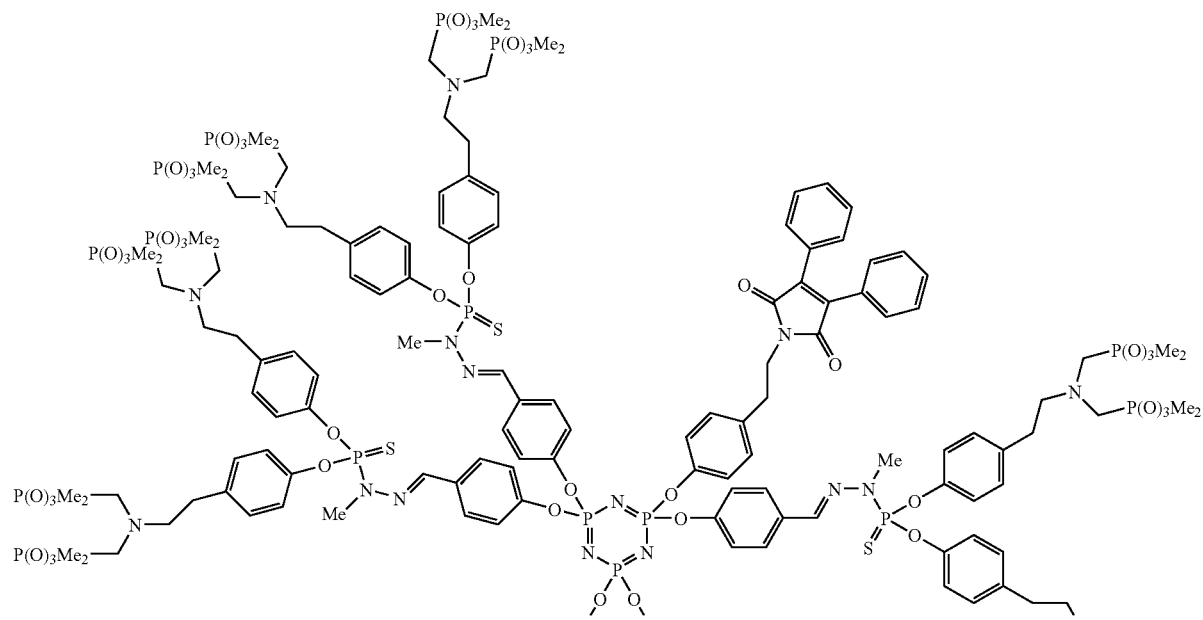

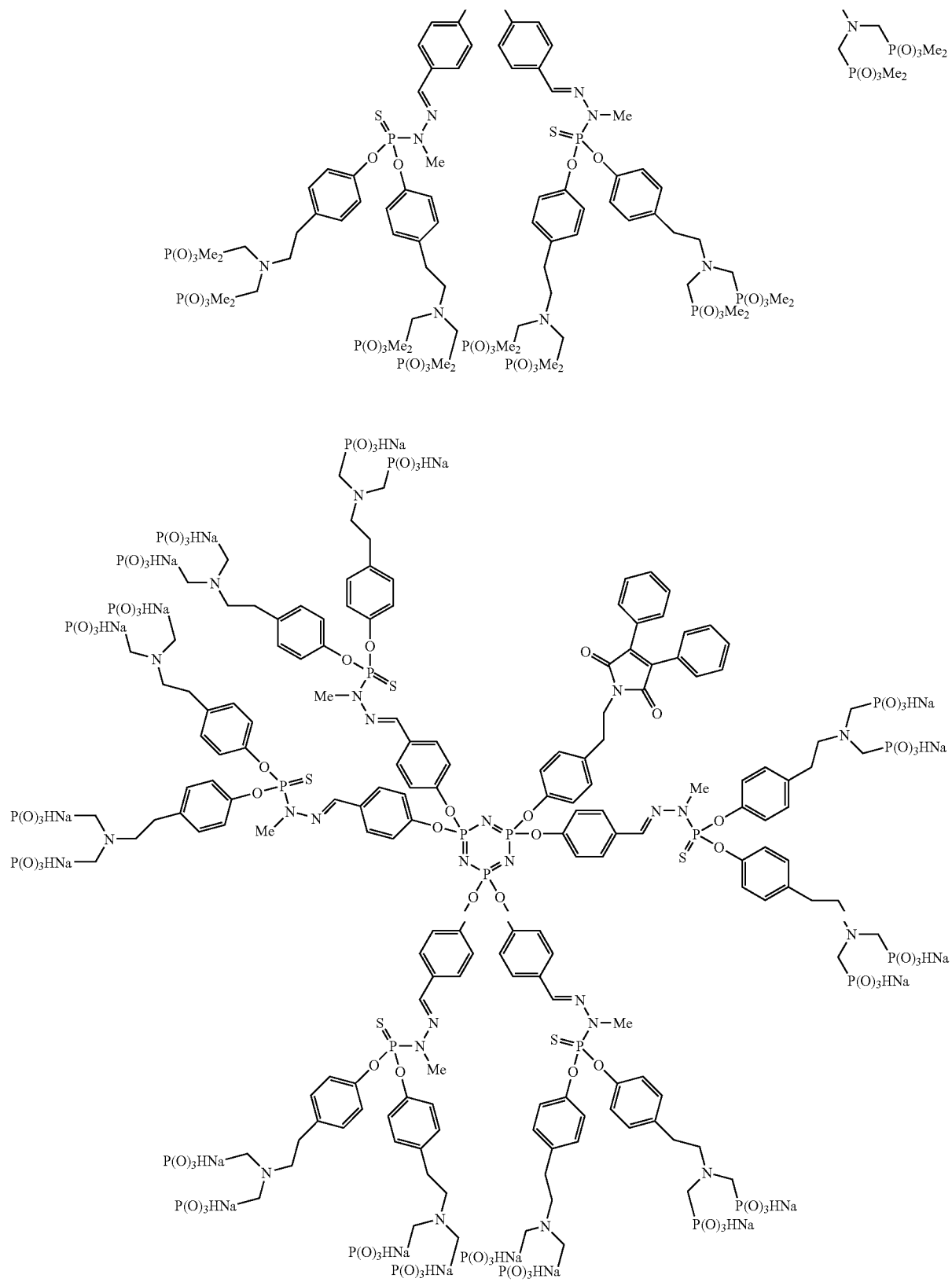

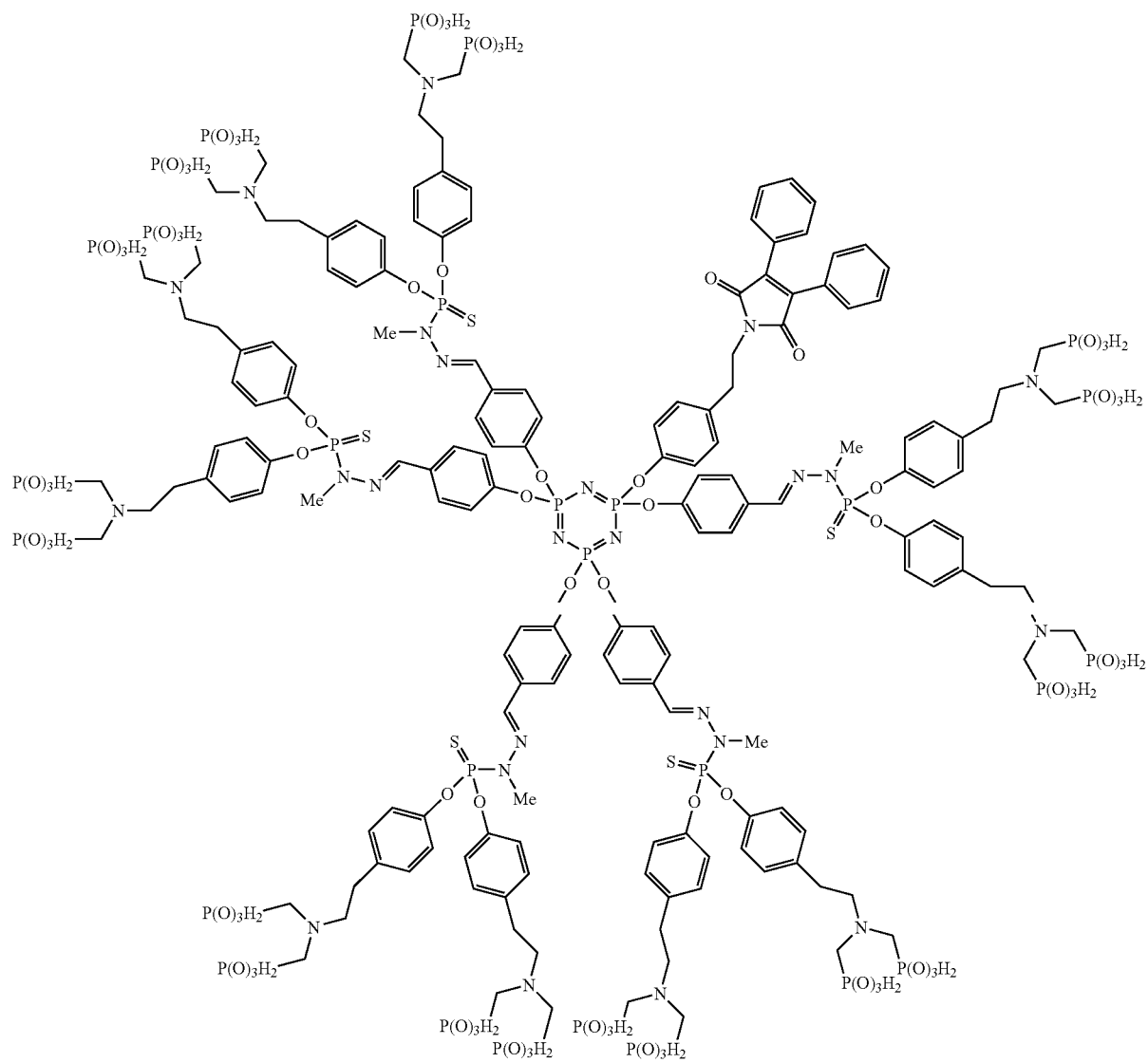

173
174
-continued
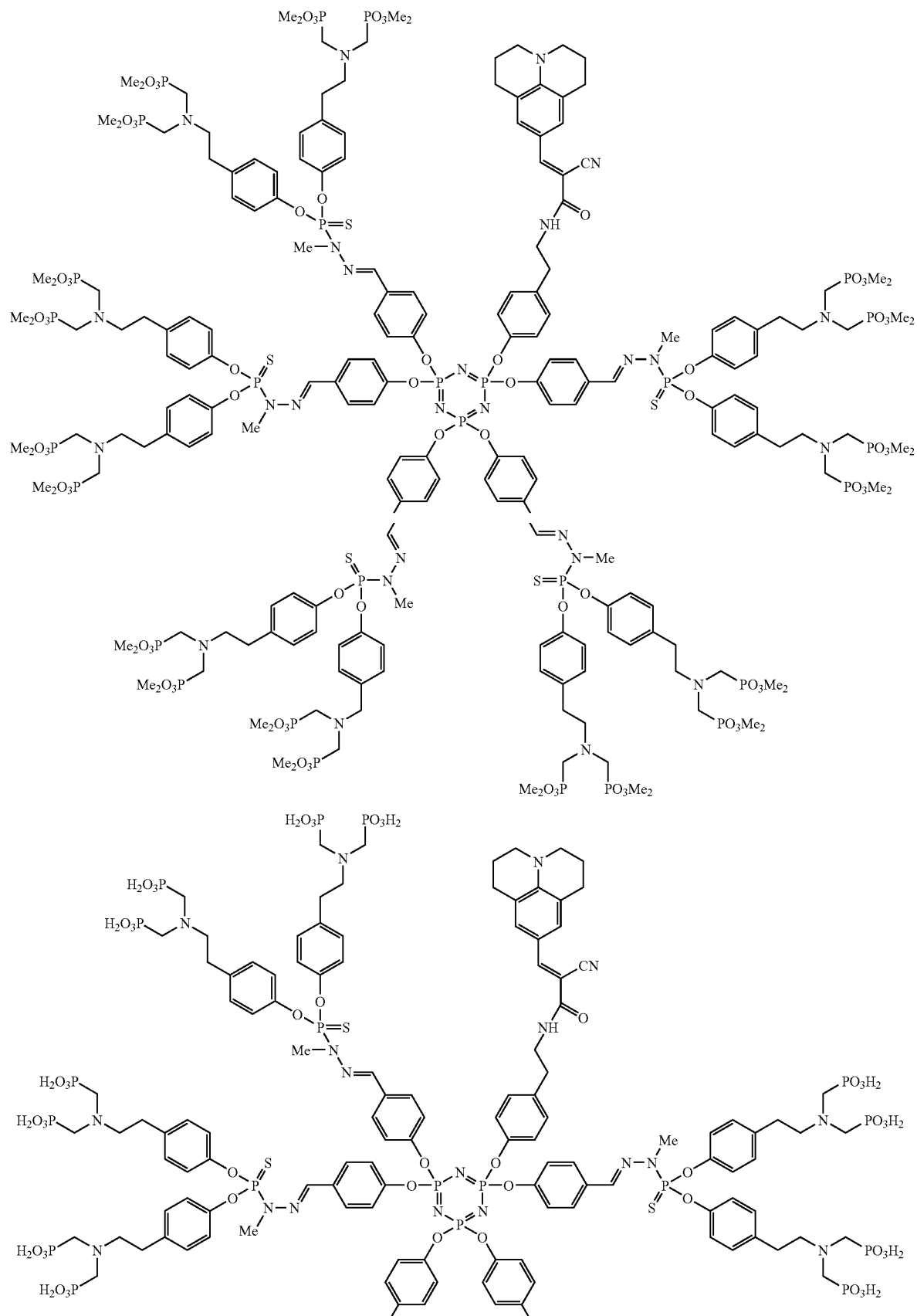

-continued
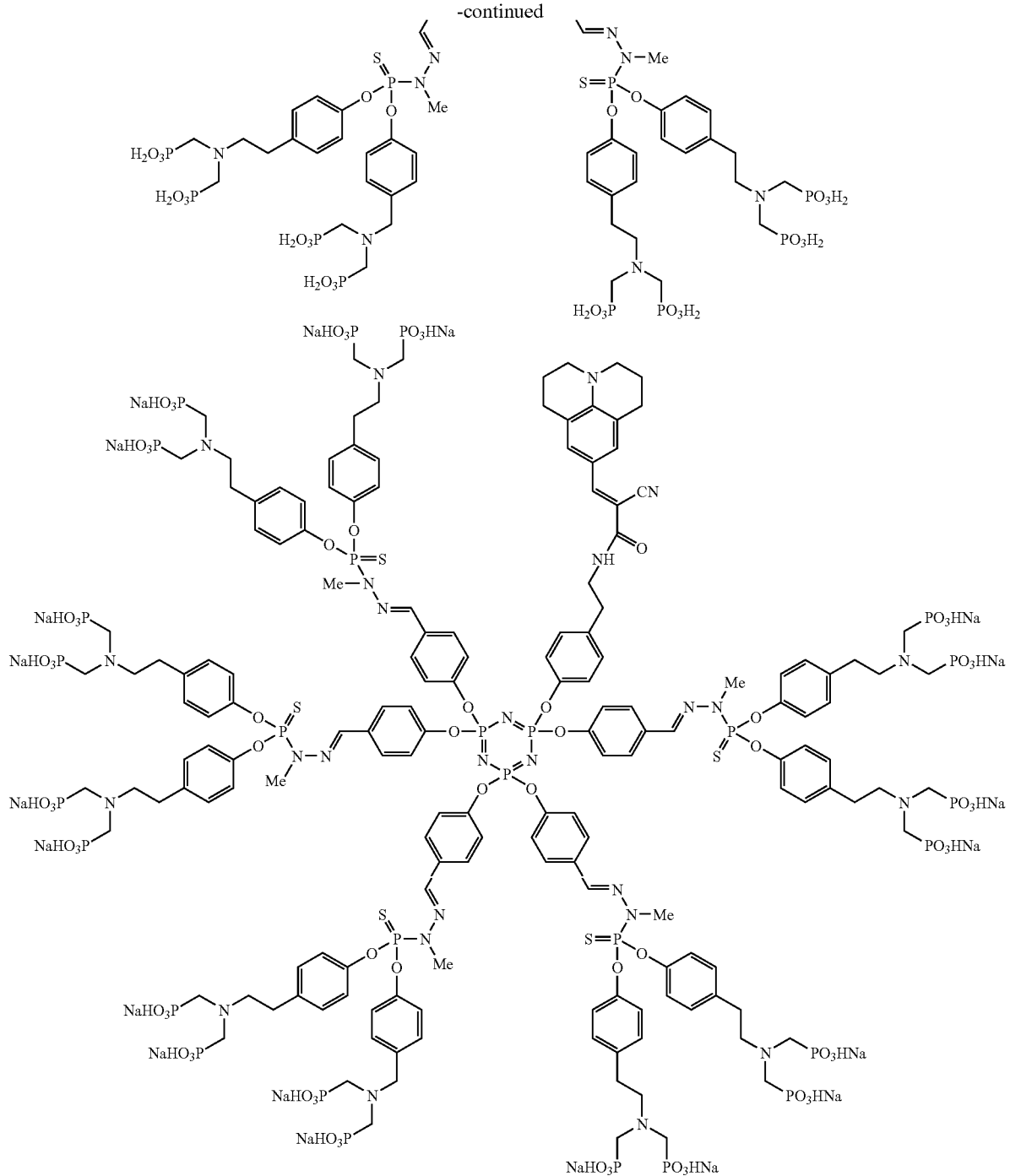
These compounds are advantageously fluorescent. Their synthesis is described in Examples 88 to 90.
The present invention also relates to the dendrimers with bisphosphonic terminations of the following formula:
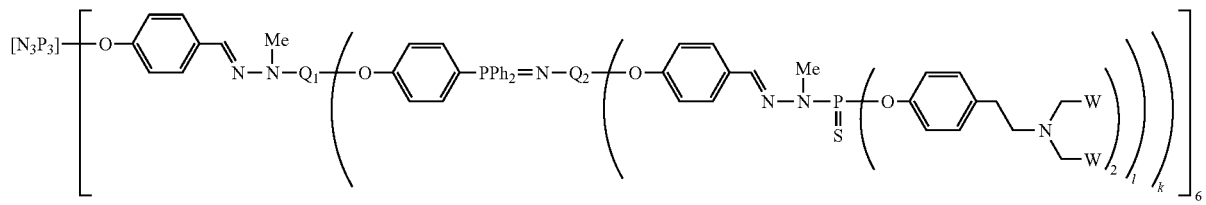

in which W represents PO$_3$Me$_2$, PO$_3$HNa, or PO$_3$H$_2$, Q$_1$ and Q$_2$, identical or different, represent P=S or the cyclotriphosphazene (N$_3$P$_3$), 1 represents 2 when Q$_2$ represents P=S or 5 when Q$_2$ represents N$_3$P$_3$ and k represents 2 when Q$_1$ represents P=S or 5 when Q$_1$ represents N$_3$P$_3$, said dendrimers being represented in particular by the following formulae:
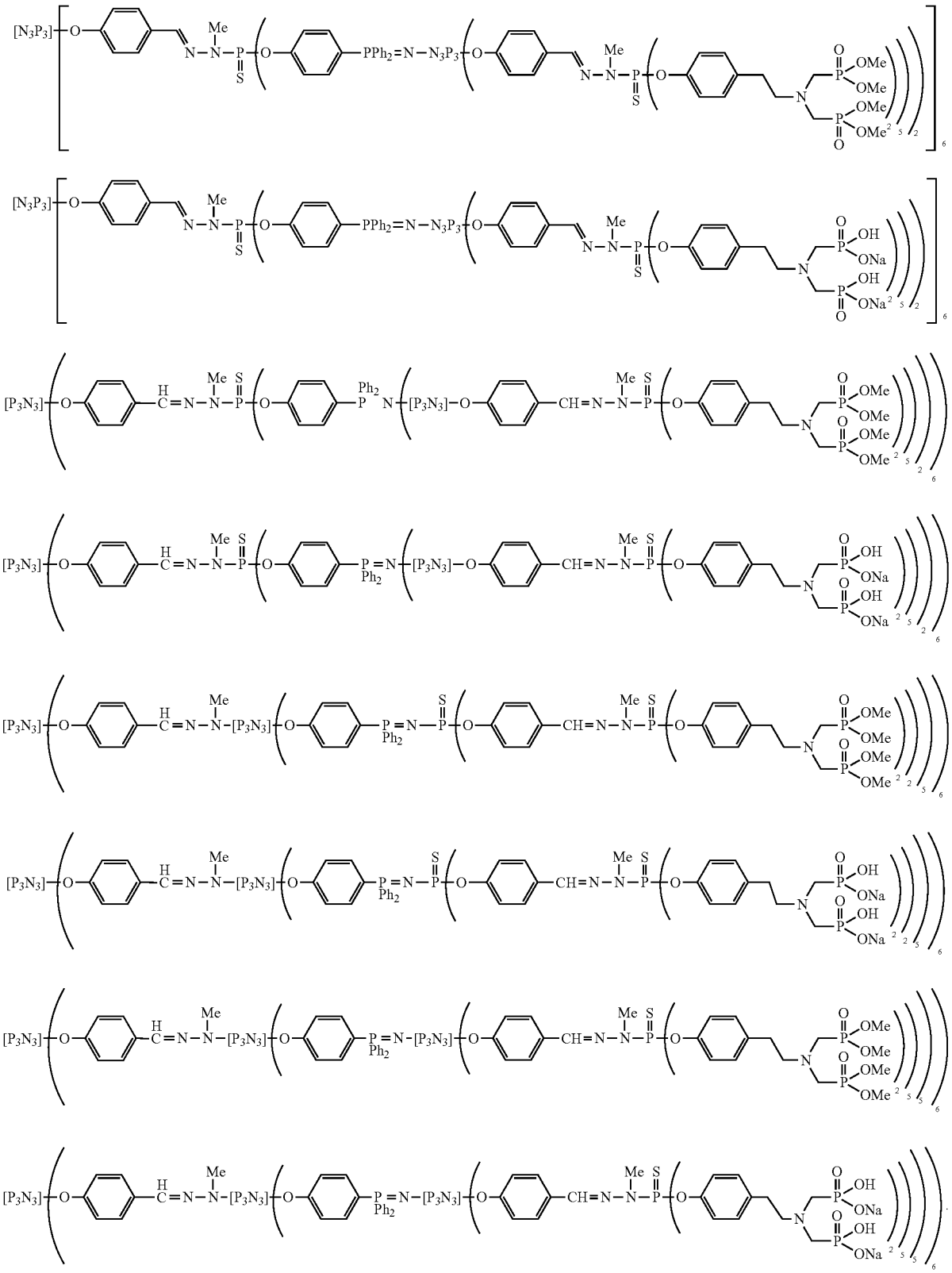

In these dendrimer formulae, $P_3N_3$ represents the cyclotriphosphazene core.

These dendrimers with bisphosphonic terminations are characterized in particular in that the coefficient of divergence varies from one generation to the other for a given dendrimer. Moreover, for each of these dendrimers, at least one generation corresponds to a coefficient of divergence greater than 2.

The compounds of formulae:

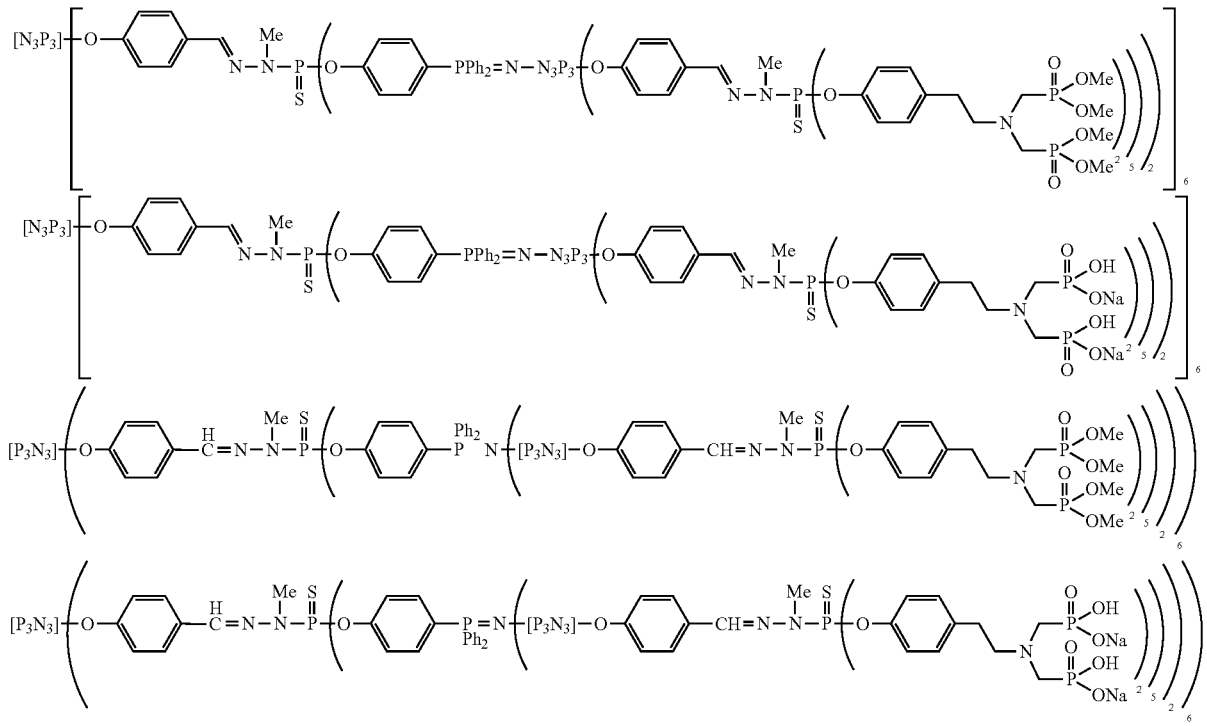

can be synthesized from the compound of formula:

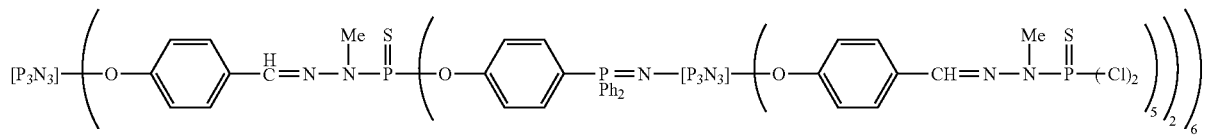

which can itself be synthesized from compound 6-2-5 defined in Example 40 and described in V. Maraval et al. *Angew. Chem. Int. Ed.* (2003) 42, 1822.

The compounds of formulae:

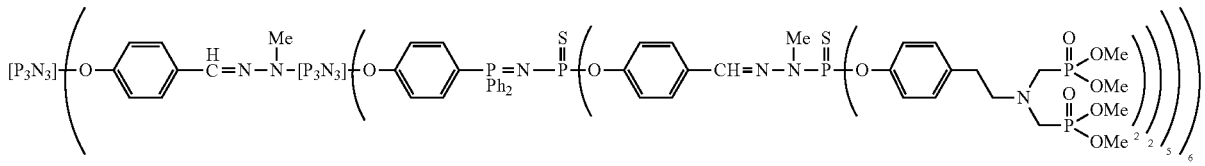

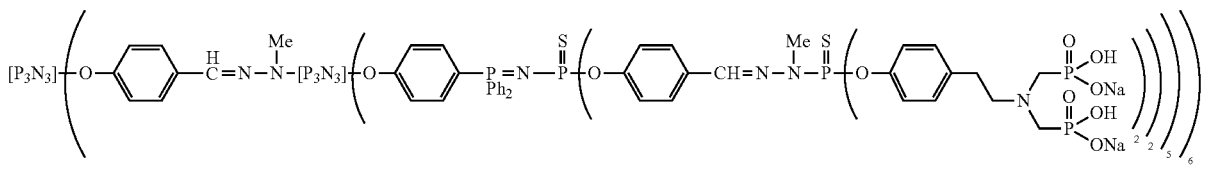

can be synthesized from the compound of formula:

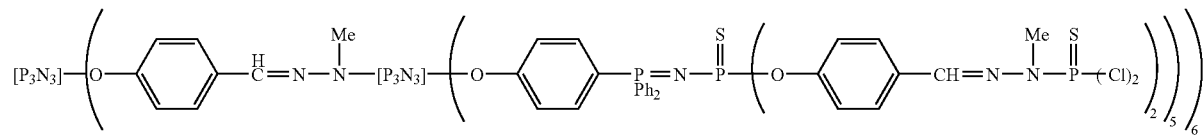

which can itself be synthesized from compound 6-5-2 defined in Example 40 and described in V. Maraval et al. *Angew. Chem. Int. Ed.* (2003) 42, 1822.

The compounds of formulae:

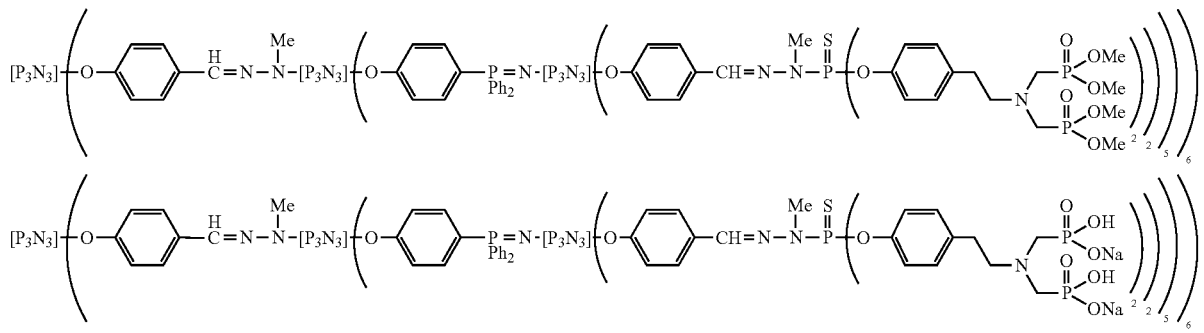

can be synthesized from the compound of formula:

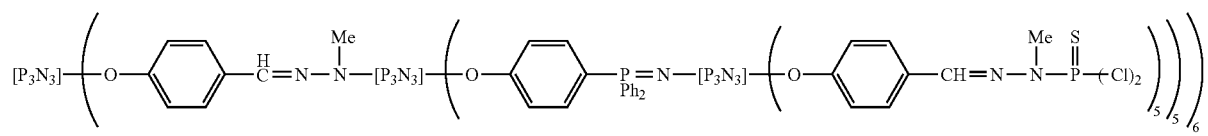

which can itself be synthesized from compound 6-5-5 defined in Example 40 and described in V. Maraval et al. *Angew. Chem. Int. Ed.* (2003) 42, 1822.

The synthesis of the compounds of the invention is described in more detail in Examples 77 to 85.

The present invention also relates to dendrimers with monophosphonic or bisphosphonic terminations of the following formula:

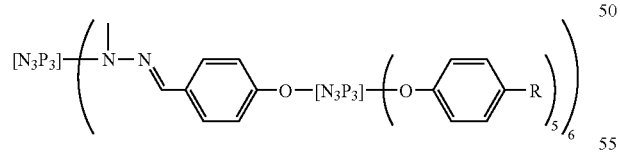

in which R represents a group chosen from

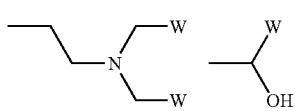

where W represents $PO_3Me_2$, $PO_3HNa$, or $PO_3H_2$.

The present invention also relates to dendrimers with bisphosphonic terminations of the following formula:

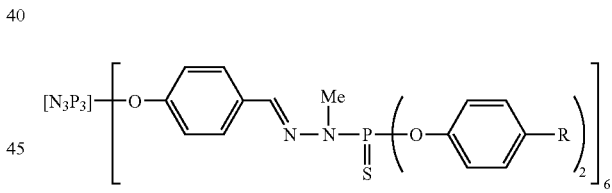

in which R represents a group chosen from:

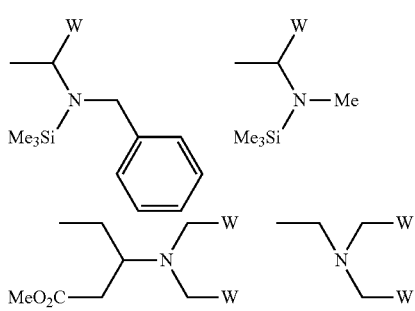

where W represents $PO_3Si_2Me_6$, $PO_3Me_2$, $PO_3HNa$, or $PO_3H_2$.

The present invention also relates to dendrimers with monophosphonic terminations of the following formula:

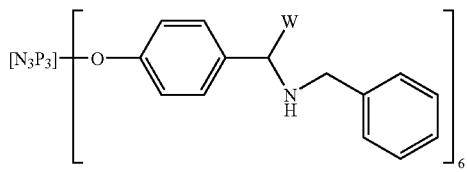

in which W represents $PO_3Me_2$, $PO_3HNa$, or $PO_3H_2$.

The present invention also relates to dendrimers with bis-phosphonic terminations of the following formula:

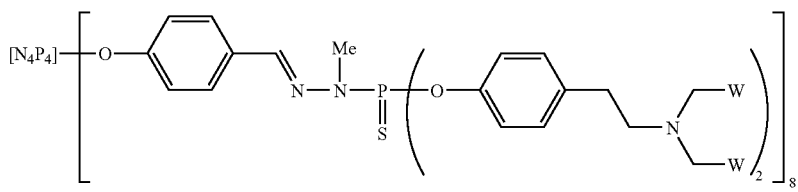

in which W represents $PO_3Me_2$, $PO_3HNa$, or $PO_3H_2$.

The present invention also relates to dendrimers with bis-phosphonic terminations of the following formula:

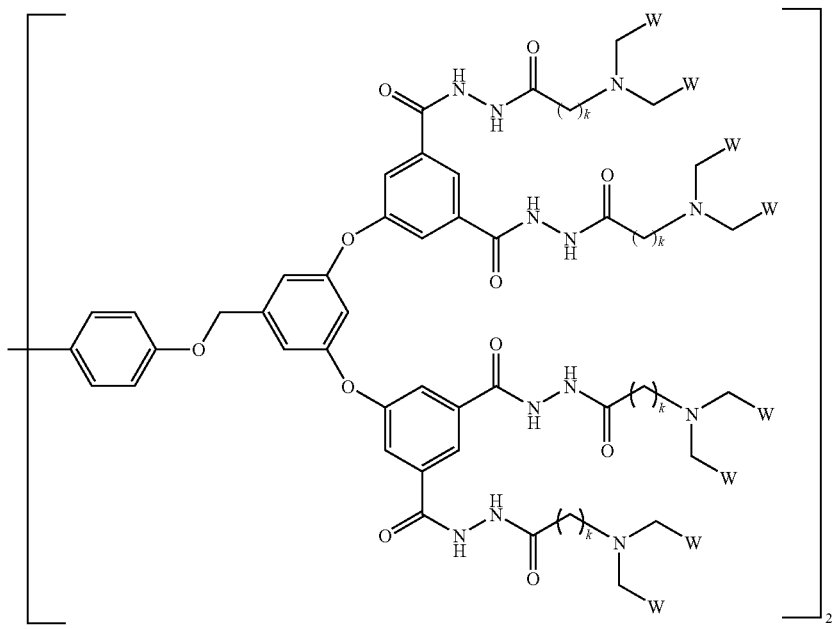

in which W represents $PO_3Me_2$, $PO_3HNa$, or $PO_3H_2$ and k represents 1, 2 or 3

The present invention also relates to dendrimers with bis-phosphonic terminations of the following formula:

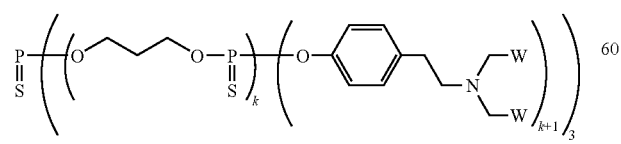

in which W represents $PO_3Me_2$, $PO_3HNa$, or $PO_3H_2$ and k represents 0 or 1.

The present invention also relates to dendrimers with bis-phosphonic terminations of the following formula:

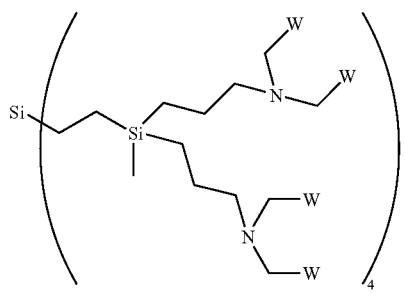

in which W represents $PO_3Me_2$, $PO_3HNa$, or $PO_3H_2$.

The present invention also relates to dendrimers with bisphosphonic terminations of the following formula:

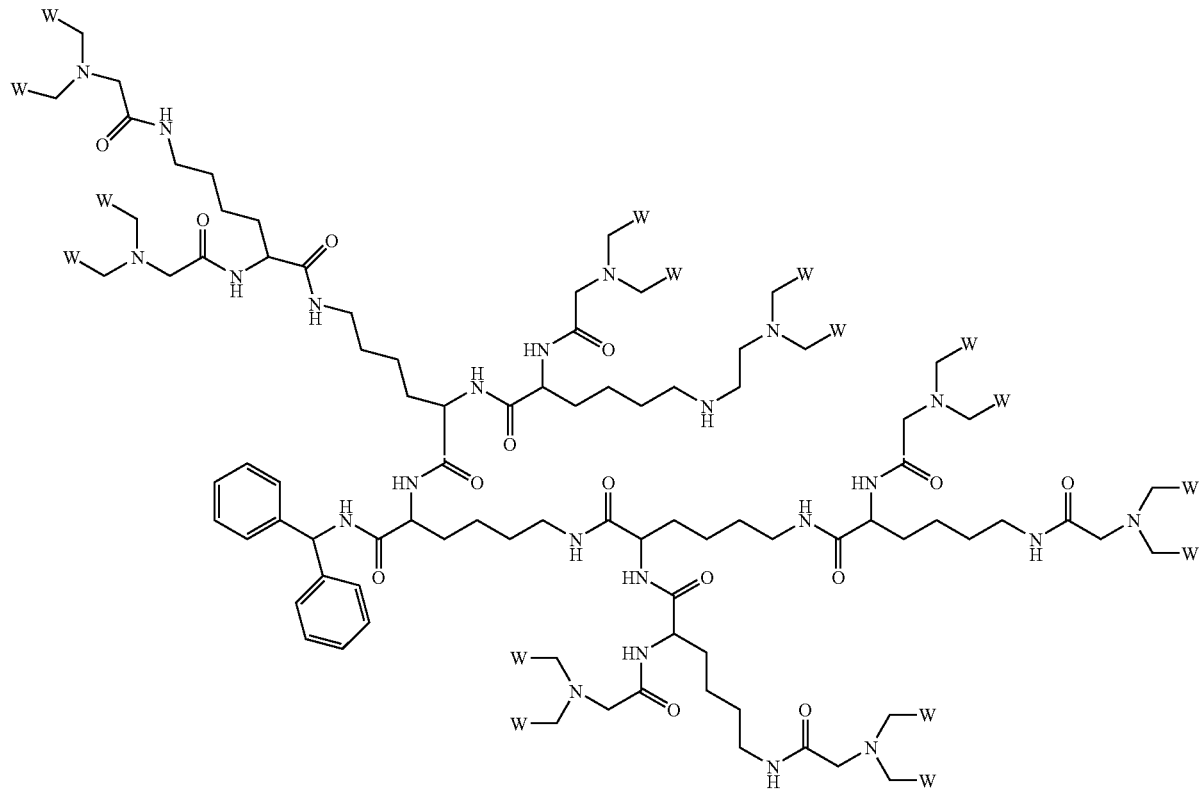

in which W represents $PO_3Me_2$, $PO_3HNa$, or $PO_3H_2$.

The present invention also relates to cells of the lymphoid line, characterized in that they express the receptor NKG2D more strongly than cells of the lymphoid line expressing the receptor NKG2D and originating from biological samples and/or cultured under standard conditions.

According to a particular embodiment, the invention relates in particular to cells of the lymphoid line defined above, characterized in that the level of expression of the receptor NKG2D is 2 to 5 times greater than that of the cells of the lymphoid line expressing the receptor NKG2D and originating from biological samples and/or cultured under standard conditions.

According to another particular embodiment, the invention relates in particular to cells of the lymphoid line defined above, characterized in that the level of expression of the receptor NKG2D corresponds to a mean fluorescent intensity (MFI) comprised from approximately 5 to approximately 20 as measured on a Coulter Epics XL device using the Beckman-Coulter-Immunotech anti-NKG2D antibody (clone ON72) labelled with phycoerythrin.

According to yet another particular embodiment of the invention, the cells of the lymphoid line defined above are derived from NK cells, $CD8^+$ $\alpha\beta$ T lymphocytes or $\gamma\delta$ T lymphocytes.

According to a preferred embodiment of the invention, the cells of the lymphoid line defined above are derived from NK cells.

According to another preferred embodiment of the invention, the cells of the lymphoid line defined above express the receptor TLR2.

According to a particularly preferred embodiment of the invention, the cells of the lymphoid line defined above are characterized in that the level of expression of the receptor TLR2 corresponds to a mean fluorescent intensity (MFI) comprised from approximately 1 to approximately 3 as measured on a Coulter Epics XL device using the BioLegend anti-TLR2 antibody (clone TL2.1) labelled with phycoerythrin.

The present invention also relates to a pharmaceutical composition, characterized in that it comprises, as active ingredient, cells of the lymphoid line as defined above, combined with a pharmaceutically acceptable vehicle.

According to a particular embodiment of the invention, the pharmaceutical composition defined above, comprising, as active ingredient, cells of the lymphoid line as defined above, is characterized in that it is suitable for the administration to an individual of a single dose of approximately $10^5$ to approximately $5·10^9$ cells of the lymphoid line as defined above.

The present invention also relates to the use of cells of the lymphoid line as defined above, for the preparation of medicaments intended for the treatment and/or prevention of cancers, including hematopoietic tissue tumors, such as myeloid leukemia or anaplastic lymphomas, and melanomas.

In general, the mono- and bisphosphonic dendrimers of the invention can be prepared as indicated in the international applications WO 2005/0052032 and WO 2005/0052031 respectively. In particular, the monophosphonic dendrimers used in the invention can be prepared as indicated below. They are defined below in order to facilitate the description of the preparation processes. The monophosphonic dendrimers can be constituted by:

a central core § of valency m;
optionally generation chains in a tree-like structure around the core;
an intermediate chain on the end of each bond around the core or optionally on the end of each generation chain, if necessary; and
a terminal group in a tree-like structure on the end of each intermediate chain, of formula:

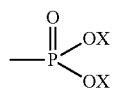 (T)

where each X, identical or different for a given terminal group, represents an -Me, —H, or /M⁺ radical where M⁺ is a cation,
n represents the generation of the dendrimer in question; it represents an integer between 0 and 12.
m represents an integer greater than or equal to 1.
The central core § is constituted by at least one atom of valency m.
The central core § preferably presents at least one phosphorus atom. The core § is preferably chosen from the following groups: $SPCl_3$, $P_3N_3Cl_6$, $P_4N_4Cl_8$,

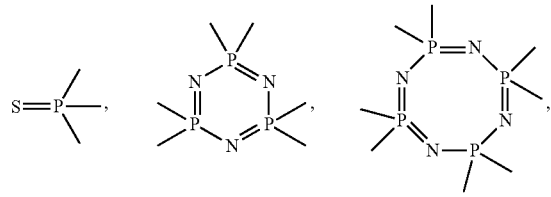

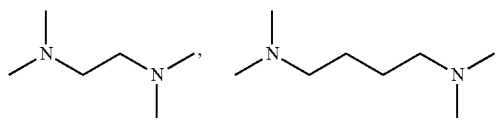

The central core § is preferably of formula:

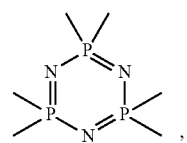

n is preferably between 0 and 3.

m is preferably chosen from 3, 4 and 6.

The monophosphonic dendrimers preferably correspond to the commercial dendrimers to which the terminal group —P(=O)(OX)₂ has been grafted.

Said commercial dendrimers are chosen in particular from dendrimers of type DAB-AM, PAMAM (Starbust® in particular) having the terminal functions —NH₂, —OH or —COOH, or also from dendrimers of type PMMH, such as cyclophosphazene- or thiophosphoryl-PMMH, in particular:

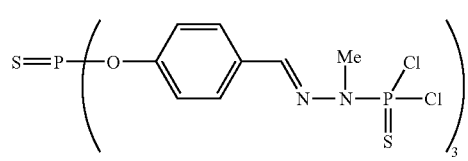

G₁

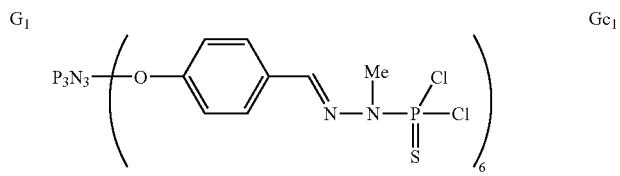

Gc₁

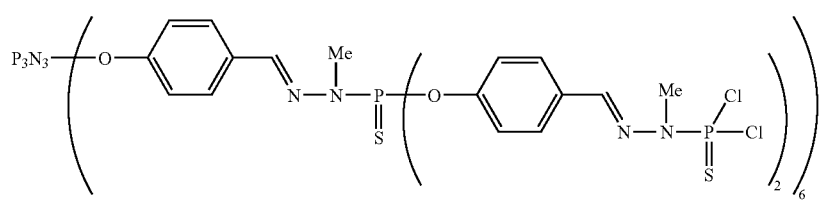

Gc₂

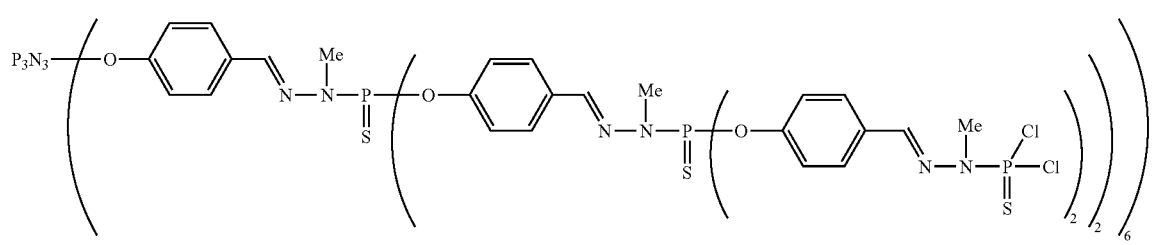

Gc₃

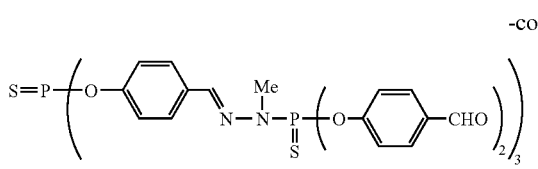
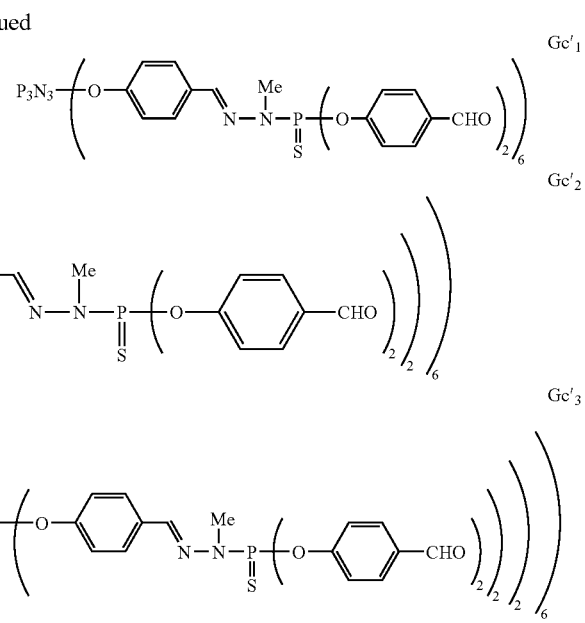

as well as dendrimers of the later generation.

All these dendrimers are marketed by Aldrich.

M preferably represents an element of the group IA, IB, IIA, IIB or IIIA, IIIB of the periodic table; M is preferably chosen from sodium, potassium, copper, calcium, barium, zinc, magnesium, lithium and aluminium atoms, even more preferably sodium, lithium and potassium atoms.

$M^+$ is a cation of an atom, for example a metal atom, or a cation derived from any radical capable of being stable in cation form. Said cation can be chosen in particular from ammonium salts, alone or in a mixture, in particular with cationic surfactants.

$M^+$ preferably represents the cation of a nitrogenous base, such as $HNEt_3^+$.

The generation chains are chosen from any linear or branched hydrocarbon chain with 1 to 12 members, optionally containing one or more double or triple bonds, each of said members optionally being chosen from a heteroatom, an aryl, heteroaryl, >C=O, >C=NR group, each member being able to be optionally substituted by one or more substituents chosen from -alkyl, -Hal, —$NO_2$, —NRR', —CN, —$CF_3$, —OH, —Oalkyl, -aryl, -aralkyl.
where
R and R', identical or different, represent independently a hydrogen atom or a -alkyl, -aryl, -aralkyl radical;

The identical or different generation chains are preferably represented by the formula:

-A-B-C(D)=N—N(E)-(P(=G))<     (C1)

where:

A represents an oxygen, sulphur, phosphorus atom or an —NR— radical;

B represents an -aryl-, -heteroaryl-, -alkyl- radical, each being able to be optionally substituted by a halogen atom or an —$NO_2$, —NRR', —CN, —$CF_3$, —OH, -alkyl, -aryl, -aralkyl radical;

C represents a carbon atom,

D and E, identical or different, represent independently a hydrogen atom, an -alkyl, —Oalkyl, -aryl, -aralkyl radical, each being able to be optionally substituted by a halogen atom or an —$NO_2$, —NRR', —CN, —$CF_3$, —OH, -alkyl, -aryl, -aralkyl radical;

G represents a sulphur, oxygen, selenium, tellurium atom or an =NR radical;

N represents a nitrogen atom;

P represents a phosphorus atom;

< represents the 2 bonds situated at the end of each generation chain.

In general formula (C1) above, A preferably represents an oxygen atom.

In general formula (C1) above, B preferably represents a phenyl core, optionally substituted by a halogen atom or an —$NO_2$, —NRR', —CN, —$CF_3$, —OH, -alkyl, -aryl, -aralkyl radical; still more preferably, B represents a non-substituted phenyl core.

In general formula (C1) above, D preferably represents a hydrogen atom.

In general formula (C1) above, E preferably represents an -alkyl radical.

In general formula (C1) above, G preferably represents a sulphur atom.

According to another preferred aspect, the generation chains are represented by the formula:

-A'-(C=O)—N(R)-B'-N<     (C1')

where

A' and B' represent independently an -alkyl, -alkenyl, -alkynyl radical, each being able to be optionally substituted by one or more substituents chosen from -alkyl, -Hal, —$NO_2$, —NRR', —CN, —$CF_3$, —OH, —Oalkyl, -aryl, -aralkyl;

R, R' are as defined previously.

A' preferably represents -alkyl-, still more preferably -ethyl-.

B' preferably represents -alkyl-, still more preferably -ethyl-.

R preferably represents a hydrogen atom.

According to another preferred aspect, the generation chains are represented by the formula:

-A"-N<     (C1")

where

A" represents an -alkyl-, -alkenyl-, -alkynyl- radical, each being able to be optionally substituted by one or more substituents chosen from -alkyl, -Hal, —NO$_2$, —NRR', —CN, —CF$_3$, —OH, —Oalkyl, -aryl, -aralkyl, where RR' are as defined previously.

A" preferably represents -alkyl-, still more preferably -propyl-.

According to another preferred aspect, the dendrimers according to the invention of generation 0 do not include generation chains. In particular, in the case where the generation chain is represented by formulae (C1') or (C1"), the corresponding dendrimers of generation 0 do not include generation chains.

The intermediate chains are chosen from any linear or branched hydrocarbon chain with 1 to 12 members, optionally containing one or more double or triple bonds, each of said members optionally being able to be chosen from a heteroatom, an aryl group, heteroaryl, >C=O, >C=NR, each member being able to be optionally substituted by one or more substituents chosen from -alkyl, -Hal, —NO$_2$, —NRR', —CN, —CF$_3$, —OH, —Oalkyl, -aryl, -aralkyl, where R, R' are as defined previously.

The intermediate chains preferably have a single bond at their end.

The intermediate chains, identical or different, are represented by the formula:

-J-K-L-                (C2)

where

J represents an oxygen, sulphur atom, or an —NR— radical;

K represents an -aryl-, -heteroaryl-, -alkyl- radical, each being able to be optionally substituted by a halogen atom or an —NO$_2$, —NRR', —CN, —CF$_3$, —OH, -alkyl, -aryl, -aralkyl radical;

L represents a linear or branched hydrocarbon chain with 1 to 6 members, optionally containing one or more heteroatoms, and/or optionally containing one or more double or triple bonds, each of said linkages optionally being able to be substituted by one or more substituents chosen from —OH, —NRR', —Oalkyl, -alkyl, -Hal, —NO$_2$, —CN, —CF$_3$, -aryl, -aralkyl.

R and R', identical or different, represent independently a hydrogen atom or an -alkyl, -aryl, -aralkyl radical.

In formula (C2) above, J preferably represents an oxygen atom.

In formula (C2) above, K preferably represents a phenyl core, optionally substituted; Still more preferably, K represents a non-substituted phenyl core.

In formula (C2) above, L represents an -alkyl-, -alkenyl- or -alkynyl- radical, each being able to be optionally substituted by one or more substituents chosen from —OH, —NRR', —Oalkyl; still more preferably, L represents an -alkyl- radical, optionally substituted by an —OH radical, or an -alkenyl- radical; still more preferably, L represents an -alkyl- radical optionally substituted by an —OH radical.

According to another preferred aspect, the intermediate chains can be represented by formula (C2'):

-L"-                (C2')

where L" represents an -alkyl- chain with 1 to 6 members, optionally substituted by one or more substituents chosen from —OH, —NRR', —Oalkyl; still more preferably, L represents an -alkyl-, preferably -methyl- radical.

The generation chains are preferably identical.

In formulae (C1) and (C2) cited above, J and K are respectively preferably equal to A, B.

The dendrimers can preferably be represented by the following formula (I):

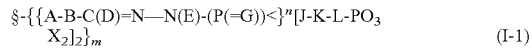

§-{{A-B-C(D)=N—N(E)-(P(=G))<}$^n$[J-K-L-PO$_3$X$_2$]$_2$}$_m$    (I-1)

in which:

§, A, B, C, D, E, G, N, P, J, K, L, X, m, n, < are as defined previously.

According to another preferred aspect, the dendrimers can be represented by the following formula (I-2):

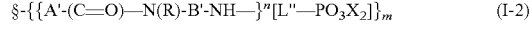

§-{{A'-(C=O)—N(R)-B'-NH—}$^n$[L"—PO$_3$X$_2$]}$_m$    (I-2)

in which:

§, A', B', C, N, P, X, L", m, n are as defined previously.

According to another preferred aspect, the dendrimers can be represented by the following formula (I-3):

§-{{A"-NH-}$^n$[L"—PO$_3$X$_2$]}$_m$    (I-3)

in which:

§, A", N, P, X, L", m, n are as defined previously.

In the formula above, { }$^n$ designates the tree-like structure of generation n of said radical.

The -alk, -alkyl or -alkyl- radical represents an alkyl radical, i.e. a saturated hydrocarbon radical, in straight or branched chains, with 1 to 20 carbon atoms, preferably 1 to 5 carbon atoms.

There can be mentioned in particular, when they are linear, the methyl, ethyl, propyl, butyl, pentyl, hexyl, octyl, nonyl, decyl, dodecyl, hexadecyl, and octadecyl radicals.

There can be mentioned in particular, when they are branched or substituted by one or more alkyl radicals, the isopropyl, tert-butyl, 2-ethylhexyl, 2-methylbutyl, 2-methylpentyl, 1-methylpentyl and 3-methylheptyl radicals.

-Alkenyl or -alkenyl- designates an aliphatic hydrocarbon group which contains at least one carbon-carbon double bond and which can be linear or branched having approximately 2 to approximately 15 carbon atoms in the chain. Preferred alkenyl groups have 2 to approximately 12 carbon atoms in the chain; and still more preferably approximately 2 to approximately 4 carbon atoms in the chain. <<Branched>> denotes that one or more lower alkyl groups, such as methyl, ethyl or propyl, are linked to a linear alkenyl chain. Examples of types of alkenyl groups include ethenyl, propenyl, n-butenyl, i-butenyl, 3-methylbut-2-enyl, n-pentenyl, heptenyl, octenyl, cyclohexylbutenyl and decenyl.

Alkynyl or -alkynyl- designates an aliphatic hydrocarbon group which contains at least one carbon-carbon triple bond and which can be linear or branched having 2 to approximately 15 carbon atoms in the chain. Preferred alkynyl groups have 2 to approximately 12 carbon atoms in the chain; and still more preferably approximately 2 to approximately 4 carbon atoms in the chain. <<Branched>> denotes that one or more lower alkyl groups, such as methyl, ethyl or propyl, are linked to a linear alkynyl chain. Examples of types of alkynyl groups include ethynyl, propynyl, n-butynyl, 2-butynyl, 3-methylbutynyl, n-pentynyl, heptynyl, octynyl and decynyl.

Among the halogen atoms, there can be mentioned more particularly fluorine, chlorine, bromine and iodine, preferably fluorine, atoms.

The -aryl or -aryl- radical represents an aryl radical, i.e. a mono or bicyclic, aromatic hydrocarbon system with 6 to 10 carbon atoms.

Among the aryl radicals, there can be mentioned in particular phenyl or naphthyl radicals, more particularly substituted by at least one halogen atom.

Among the aralkyl (-arylalkyl) radicals, there can be mentioned in particular benzyl or phenethyl radicals.

The term <<heteroatom>> designates a nitrogen, oxygen, silicon, phosphorus or sulphur atom.

-Heteroaryl or -heteroaryl- designates a heteroaryl radical, i.e. a mono or bicyclic aromatic system comprising one or more heteroatoms chosen from nitrogen, oxygen or sulphur with 5 to 10 carbon atoms. Among the heteroaryl radicals, there can be mentioned pyrazinyl, thienyl, oxazolyl, furazanyl, pyrrolyl, 1,2,4-thiadiazolyl, naphthhyridinyl, pyridazinyl, quinoxalinyl, phtalazinyl, imidazo{1,2-a}pyridine, imidazo[2,1-b]thiazolyl, cinnolinyl, triazinyl, benzofurazanyl, azaindolyl, benzimidazolyl, benzothienyl, thienopyridyl, thienopyrimidinyl, pyrrolopyridyl, imidazopyridyl, benzoazaindole, 1,2,4-triazinyl, benzothiazolyl, furanyl, imidazolyl, indolyl, triazolyl, tetrazolyl, indolizinyl, isoxazolyl, isoquinolinyl, isothiazolyl, oxadiazolyl, pyrazinyl, pyridazinyl, pyrazolyl, pyridyl, pyrimidinyl, purinyl, quinazolinyl, quinolinyl, isoquinolyl, 1,3,4-thiadiazolyl, thiazolyl, triazinyl, isothiazolyl, carbazolyl, as well as the corresponding groups originating from their fusion or fusion with the phenyl core. Preferred heteroaryl groups include thienyl, pyrrolyl, quinoxalinyl, furanyl, imidazolyl, indolyl, isoxazolyl, isothiazolyl, pyrazinyl, pyridazinyl, pyrazolyl, pyridyl, pyrimidinyl, quinazolinyl, quinolinyl, thiazolyl, carbazolyl, thiadiazolyl, and groups originating from fusion with a phenyl core, and more particularly quinolynyl, carbazolyl, thiadiazolyl.

By <<corresponding dendrimer>> is meant a dendrimer of the same generation having the same cores, generation chains, intermediate chains and distinct terminal groups.

The monophosphonic dendrimers can be prepared by applying or adapting any method known per se and/or within the scope of a person skilled in the art which allows —$PO_3X_2$ functions to be grafted, in particular those described by Larock in *Comprehensive Organic Transformations*, VCH Pub., 1989, or by applying or adapting the processes described in the following examples.

In the reactions described hereafter, it may be necessary to protect the reactive functional groups, for example the hydroxy, amino, imino, thio, carboxy groups, when they are desired in the final product, in order to prevent their undesired participation in the reactions. The usual protective groups can be used according to standard practice, for examples see T. W. Green and P. G. M. Wuts in *Protective Groups in Organic Chemistry*, John Wiley and Sons, 1991; J. F. W. McOmie in *Protective Groups in Organic Chemistry*, Plenum Press, 1973.

The process for the preparation of a dendrimer according to the invention comprising the —$P(=O)(OX)_2$ terminal group comprises:

(i) the reaction of the corresponding dendrimer having a terminal function capable of reacting with a corresponding compound having a —$PO_3Me_2$ functionality. The terminal function of the dendrimer can be for example: —CHO, —CH=NR, or —$P(=G)Cl_2$;

(ii) followed optionally, when X represents H or M, by the stage consisting of converting the dendrimer obtained in (i) having a —$PO_3Me_2$ termination to the corresponding dendrimer having a —$P(=O)(OH)_2$ termination, (iii) followed optionally, when X represents M, by the stage consisting of converting the dendrimer obtained in (ii) having a $P(=O)(OH)_2$ termination to the salt of the corresponding dendrimer having a $P(=O)(OM)_2$ or $P(=O)(OH)(OM)$ termination.

Stage (i) comprises the reaction of the corresponding dendrimer of the same generation n having a —CHO, —CH=NR, or —$P(=S)Cl_2$ terminal function with a compound of formula Z—$PO_3Me_2$, where Z represents respectively:

either —H when the function is —CHO or —CH=NR,
or the intermediate chain defined previously when said function represents —$P(=S)Cl_2$;

According to a first alternative, stage (i) comprises the action of $HPO_3Me_2$ on the corresponding dendrimer having a —CHO or —CH=NR termination by applying or adapting the method described in J. Org. Chem. 1997, 62, 4834.

More precisely, this reaction is carried out under stirring, in solution in an aprotic, polar solvent such as THF, chloroform, dichloromethane, acetonitrile, preferably without solvent, in the presence of an organic or inorganic base, preferably a nitrogenous base, such as triethylamine, at a temperature comprised between –80° C. and 100° C., preferably at ambient temperature.

The compound of formula $HPO_3Me_2$ is commercially available (Aldrich) or can be prepared according to methods known per se.

According to a second alternative, stage (i) comprises the action of a compound of formula Z—$PO_3Me_2$, where Z represents the intermediate chain previously defined on a starting dendrimer having the —$P(=S)Cl_2$ terminal function.

This reaction is carried out under stirring, in solution in an aprotic, polar solvent such as THF, chloroform, dichloromethane, acetonitrile, acetone, DMF, preferably THF, in the presence of an organic or inorganic base, preferably a carbonate type, such as cesium carbonate, at a temperature comprised between –80° C. and 100° C., preferably at ambient temperature.

(ii) followed optionally, when X represents H or M, by the stage consisting of converting the dendrimer obtained in (i) having a —$PO_3Me_2$ termination to the corresponding dendrimer having a —$PO_3H_2$ termination, by the action of trimethylsilane halide, preferably trimethylsilane bromide ($Me_3SiBr$), in an organic aprotic, polar solvent such as chloroform, dichloromethane, acetonitrile, preferably acetonitrile. The operation is preferably carried out by slowly adding trimethylsilane halide, keeping the reaction mixture at a temperature comprised between –80° C. and 100° C., preferably at approximately 0° C.

followed by the action of anhydrous MeOH added to the reaction mixture;

(iii) followed optionally, when X represents M, by the stage consisting of converting the dendrimer obtained in (ii) having a —$PO_3H_2$ termination to the salt of the corresponding dendrimer having a —$PO_3M_2$ termination.

More precisely, when the dendrimer is of formula (I-1)

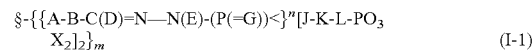
(I-1)

in which §, A, B, C, D, E, G, N, P, J, K, L, X, m, n, < are as defined previously, stage (i) comprises the reaction on the corresponding dendrimer n of formula

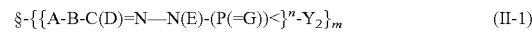
(II-1)

where Y represents:
either -J-K-L', where L' represents a —CHO or —CH=NR radical;
or —Cl;
of a compound of formula Z—$PO_3Me_2$, where Z represents respectively:
either H— when Y represents -J-K-L';
or H-J-K-L- when Y represents Cl;

(ii) followed optionally, when X represents H or M, by the stage consisting of converting the dendrimer of formula (III-1) obtained in (i) in which X represents a methyl radical to the dendrimer corresponding to formula (I-1) in which X represents a hydrogen atom, according to the following reaction diagram:

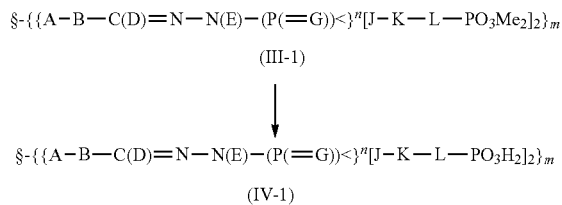

in which §, A, B, C, D, E, G, N, P, J, K, L, n, m, < are as defined previously, (iii) followed optionally, when X represents M, by the stage consisting of converting the dendrimer of formula (IV-1) obtained in (ii) to the corresponding salt.

The product of formula (III-1) is obtained according to stage (i) by one of the following methods:

According to a first alternative of stage (i), the product of formula (III-1) is obtained according to the following reaction:

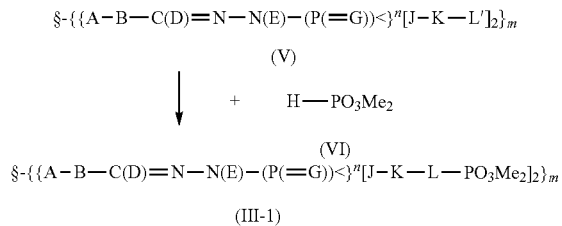

where

§, A, B, C, D, E, G, N, P, J, K, L, L', m, n, < are as defined previously.

This reaction can be carried out by applying or adapting the method described in *J. Org. Chem.* 1997, 62, 4834.

More precisely, this reaction is carried out under stirring, optionally in solution in an aprotic, polar solvent such as THF, dichloromethane, chloroform or acetonitrile, preferably without solvent, in the presence of an organic or inorganic base, preferably nitrogenous, such as triethylamine, at a temperature comprised between −80° C. and 100° C., preferably at ambient temperature.

The compound of formula (VI) is commercially available (Aldrich) or can be prepared according to the methods known per se.

The dendrimers of formula (V) are commercially available (Aldrich) or can be prepared according to the methods known per se.

According to a second alternative, the compound of formula (III-1) is obtained according to the following reaction:

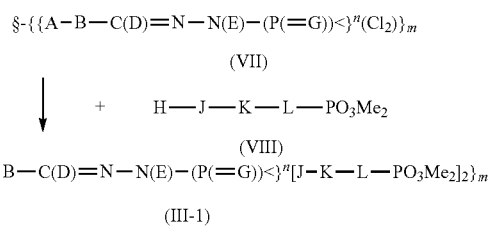

where

§, A, B, C, D, E, G, N, P, J, K, L, m, n are as defined previously.

This reaction is carried out under stirring, in solution in an aprotic, polar solvent such as THF, chloroform, dichloromethane, acetonitrile, acetone, DMF, preferably THF, in the presence of an organic or inorganic base, preferably carbonate type, such as cesium carbonate, at a temperature comprised between −80° C. and 100° C., preferably at ambient temperature.

The dendrimers of formula (VII) are commercially available (Aldrich) or can be prepared according to methods known per se.

The dendrimers of formula (V) and (VII) can be chosen in particular from:

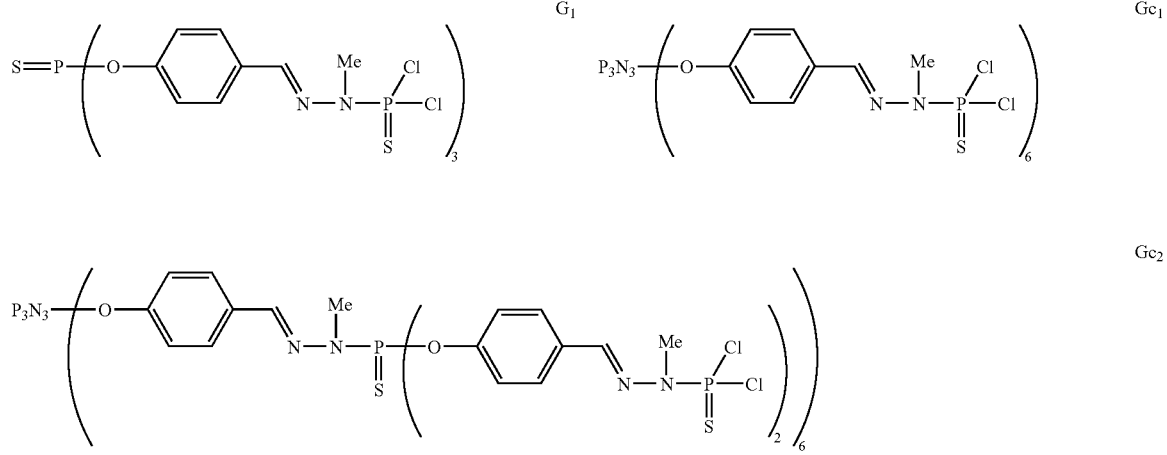

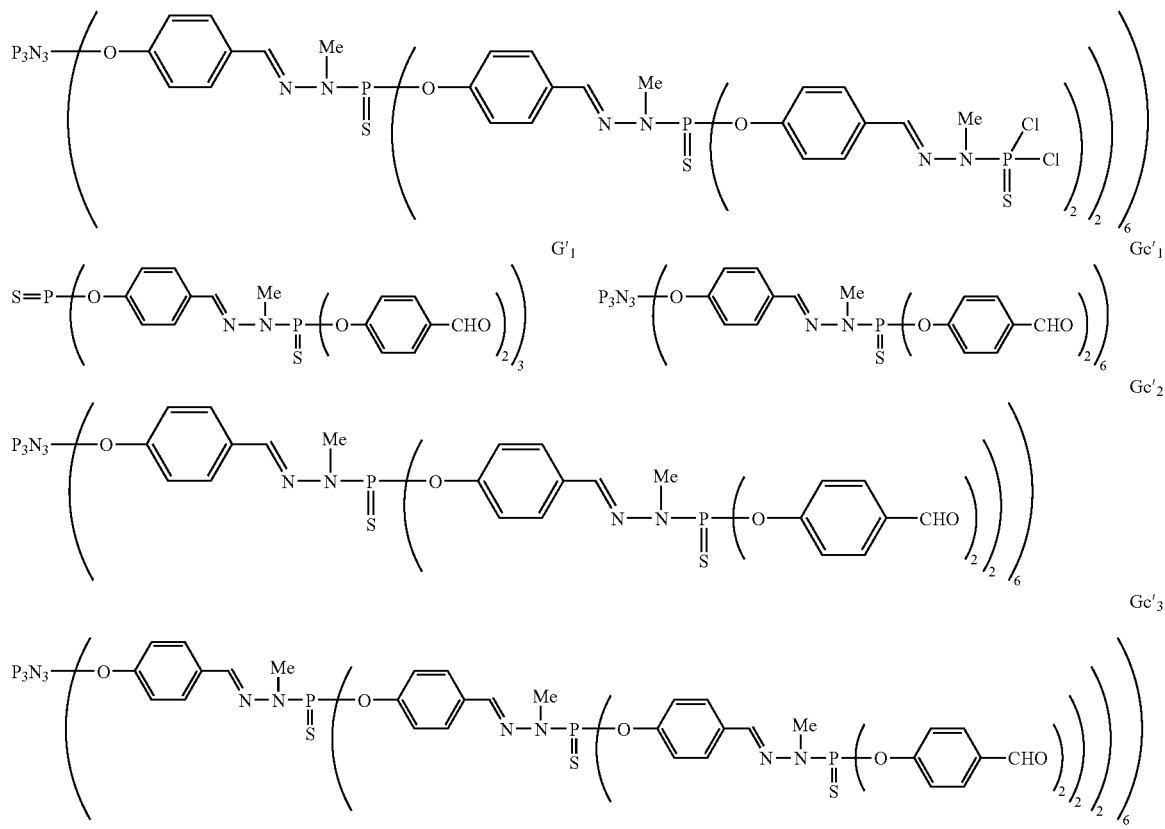

More precisely, when the dendrimers according to the invention are represented by the following formula (I-2):

$$\S-\{\{A'-(C=O)-N(R)-B'-NH-\}^n[L''-PO_3X_2]\}_m \quad (I-2)$$

in which §, A', B', C, N, P, X, L", m, n are as defined previously.

Or the following formula (I-3):

$$\S-\{\{A''-NH-\}^n[L''-PO_3X_2]_2\}_m \quad (I-3)$$

in which §, A", N, P, X, L", m, n are as defined previously, the process comprises:

stage (i) comprising the reaction on the corresponding dendrimer n of formula $$\S-\{\{A'-(C=O)-N(R)-B'-N=R\}^n\}_m \quad (II-2)$$

or $\S-\{\{A''-N=R\}_n\}_m$ (I-3)

where R is an >alkyl radical, with a compound of formula $$H-PO_3Me_2 \quad (VI).$$

This reaction can be carried out by applying or adapting the method described in *J. Org. Chem.* 1997, 62, 4834.

More precisely, this reaction is carried out under stirring, optionally in solution in an aprotic, polar solvent such as THF, chloroform, dichloromethane, acetonitrile, preferably without solvent, in the presence of an organic or inorganic base, preferably nitrogenous, such as triethylamine, at a temperature comprised between −80° C. and 100° C., preferably at ambient temperature.

The compound of formula (VI) is commercially available (Aldrich) or can be prepared according to the methods known per se.

The dendrimers of formula $$\S-\{\{A'-(C=O)-N(R)-B'-N=R\}^n\}_m \quad (II-2)$$

or $\S-\{\{A''-N=R\}^n\}_m$ (II-3)

can be obtained from the corresponding commercial dendrimers of formula $$\S-\{\{A'-(C=O)-N(R)-B'-NH_2\}^n\}_m \quad (XVI)$$

or $\S-\{\{A''-NH_2\}^n\}_m$ (XVII)

by applying or adapting any reaction known per se, allowing the terminal —NH$_2$ group to be converted to the required —N=R terminal function. Such methods, within the scope of a person skilled in the art, have been described in particular by Larock et al (supra).

The dendrimers of formula (XVI) and (XVII) are commercially available and can be chosen in particular from the DAB or PAMAM type dendrimers.

(ii) followed optionally, when X represents H or M, by the stage consisting of converting the dendrimer of formula (III-2) or (III-3) obtained in (i) in which X represents a methyl radical to the corresponding dendrimer of formula (I) in which X represents a hydrogen atom, according to the following reaction diagram:

§-{{A'―(C=O)―N(R)―B'―NH―}$^n$[L''―PO$_3$Me$_2$]}$_m$ (III-2)

or

§-{{A''―NH―}$^n$[L''―PO$_3$Me$_2$]}$_m$ (III-3)

↓

§-{{A'―(C=O)―N(R)―B'―NH―}$^n$[L''―PO$_3$H$_2$]}$_m$ (IV-2)

or

§-{{A''―NH―}$^n$[L''―PO$_3$H$_2$]}$_m$ (IV-3)

(iii) followed optionally, when X represents M, by the stage consisting of converting the dendrimer of formula (IV) obtained in (ii) to the corresponding salt.

In all cases, reaction (ii) is carried out:

by the action of trimethylsilane halide, preferably trimethylsilane bromide (Me$_3$SiBr), in an organic aprotic, polar solvent such as acetonitrile, chloroform or dichloromethane, preferably acetonitrile. The operation is preferably carried out by slowly adding trimethylsilane halide, keeping the reaction mixture at a temperature comprised between −80° C. and 100° C., preferably at approximately 0° C.

followed by the action of anhydrous MeOH, added to the reaction mixture.

In stage (iii), the acid salts of the dendrimers can be obtained from the dendrimers having a terminal chain in which Z represents a hydrogen atom, by applying or adapting known processes by adding a base. The operation is preferably carried out in solution, under stirring, in an appropriate protic or aprotic, polar solvent such as alcohols, water, THF, dichloromethane, chloroform, acetonitrile, DMF, preferably water, in the presence of an organic or inorganic base, such as hydroxides, carbonates, nitrogenous bases, preferably sodium, lithium or potassium hydroxide, according to the desired salt.

When starting dendrimers are used having different terminal groups of the terminal functions described above for the dendrimers of formula (II-1), (II-2) or (II-3), the process comprises the additional preliminary stage allowing said groups to be converted to said required functions. For example, in the case of dendrimers having terminal groups of carboxylic acid or hydroxyl type, it is sufficient to carry out any reaction allowing said carboxylic acid or hydroxyl type groups to be converted to the functions of —NH$_2$, —CHO, —C=NR or —PSCl$_2$ type corresponding to the dendrimers of formula (II-1), (II-2) or (II-3). Such reactions are known to a person skilled in the art and/or can be carried out by applying or adapting those discussed by Larock et al (supra).

In order to obtain a dendrimer of generation 0, the above reactions can be carried out in the same manner operating from the core, having the required functionality. For example, the generation reactions can be carried out operating from a PSCl$_3$, P$_3$N$_3$Cl$_6$, P$_4$N$_4$Cl$_8$, or

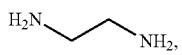 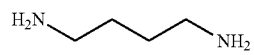

core.

With regard to the compounds of formula (VIII):

Z-J-K-L-PO$_3$Me$_2$ (VIII)

in which

Z represents H or a protective group of the -JH function; these protective groups are known per se and can be identified in particular in Green et al or McOmie et al. mentioned above. Preferably, when J represents an oxygen atom, Z represents the TBDMS group (tert-butyl-dimethyl-silyl radical).

J represents an oxygen, sulphur atom, or an —NR— radical;

K represents an -aryl-, -heteroaryl-, -alkyl- radical, each being able to be optionally substituted by a halogen atom or an —NO$_2$, —NRR', —CN, —CF$_3$, —OH, -alkyl, -aryl, -aralkyl radical;

L represents a linear or branched hydrocarbon chain with 1 to 6 members, each of said members optionally being able to be chosen from a heteroatom, preferably nitrogen, and/or optionally containing one or more double or triple bonds, each of said linkages optionally being substituted by one or more substituents chosen from —OH, —NRR', —Oalkyl, -alkyl, -Hal, —NO$_2$, —CN, —CF$_3$, -aryl, -aralkyl.

R, R', identical or different, represent independently of each other a hydrogen atom or an -alkyl, -aryl, -aralkyl radical, in formula (VIII) above, J preferably represents an oxygen atom, in formula (VIII) above, K preferably represents a phenyl core, optionally substituted;

still more preferably, K represents a non-substituted phenyl core, in formula (VIII) above, L preferably represents an -alkyl- radical, optionally substituted by an —OH radical, or an -alkenyl- radical; still more preferably, L represents an -alkyl- radical, they can be obtained as follows:

Z-J-K-L-Hal (IX) → Z-J-K-L-PO$_3$Me$_2$ (VIII)

where Z, J, K, L are as defined previously, Hal represents a halogen atom, preferably bromine.

In the case where, in formula (VIII), Z=H, the product of formula (VIII) is obtained from the product of formula (VIII) where Z is a protective group, by applying or adapting any known method for the deprotection of the protective group Z, in particular those described in Green et al. or McOmie et al. (supra). In particular, in the case where J=O and Z=TBDMS, the process is carried out by the action of tetrabutylammonium fluoride, preferably 2 equivalents, under stirring, in solution in an aprotic, polar solvent such as THF, chloroform, dichloromethane, acetonitrile, DMF, preferably THF, at a temperature comprised between −80° C. and 100° C., preferably at ambient temperature.

The product of formula (VIII) where Z is a protective group is obtained from the product of formula (IX) by applying or adapting the Arbuzov reaction described in particular in B. A. Arbuzov, Pure appl. Chem. 1964, 9, 307, or any equivalent reaction. In particular, the product of formula (IX) is reacted in the presence of trimethylphosphite of formula P(OMe)$_3$ (X)

under stirring, in solution in an aprotic, polar solvent such as THF, chloroform, dichloromethane, acetonitrile, preferably without solvent, at a temperature comprised between −80° C. and 150° C., preferably at approximately 80° C.

The product of formula (IX) can be obtained by applying or adapting the method described by Olszewski et al in *J. Org Chem.* 1994, 59, 4285-4296.

In particular, the process can be carried out as follows:

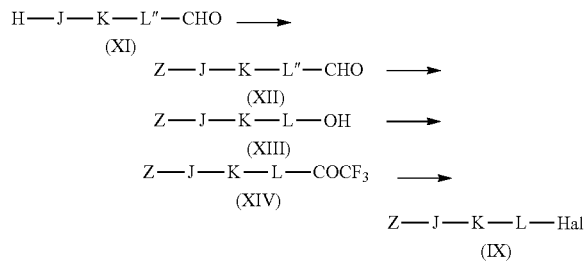

where Z, J, K, L, Hal are as defined above and L" represents a radical corresponding to L where a hydrogen and carbon atom have been formally eliminated.

The product of formula (IX) is obtained from the product of formula (XIV) by applying or adapting any known reaction for substituting the trifluoroacetate group by a halogen atom, in particular bromine, for example by the action of LiBr under stirring, in solution in an aprotic, polar solvent such as THF, chloroform, dichloromethane, acetonitrile, DMF, preferably THF, under reflux, for a period of time necessary to obtain an acceptable reaction yield, for example between 5 and 20 hours.

The product of formula (XIV) is obtained from the product of formula (XIII) by applying or adapting any known reaction for substituting the hydroxy function by a trifluoroacetate radical, in particular by the action of trifluoroacetic anhydride $(CF_3CO)_2O$ under stirring, in solution in an aprotic, polar solvent such as THF, chloroform, dichloromethane, acetonitrile, DMF, preferably THF, under reflux, for a period of time necessary to obtain an acceptable reaction yield, for example between 5 minutes and 5 hours.

The product of formula (XIII) is obtained from the product of formula (XII) by applying or adapting any known reaction for the reduction of the aldehyde function to a hydroxy function, in particular by the action of a reducing agent such as $NaBH_4$ or any equivalent agent, in solution in a protic or aprotic, polar solvent such as ether, THF, alcohols, water, preferably a THF/EtOH mixture (5/1), under reflux, for a period of time necessary to obtain an acceptable reaction yield, for example between 1 hour and 10 days.

The product of formula (XII) is obtained from the product of formula (XI) by applying or adapting any known reaction for the protection of the -JH function by a protective group Z or any other appropriate protective group, by applying or adapting the methods described by Green et al. or Wuts et al. mentioned above. In the case of protection by TBDMS, the operation is carried out in particular by the action of Cl-TBDMS (XV) under stirring, in solution in an aprotic, polar solvent such as THF, chloroform, dichloromethane, acetonitrile, DMF, preferably dichloromethane, in the presence of a base such as triethylamine (2 equivalents), at a temperature comprised between −80° C. and 100° C., preferably at ambient temperature.

The product of formula (XI) is commercially available and can be obtained in particular from Aldrich.

In the description of the process above, two groups are said to be <<corresponding>> when they are included in a starting and end product respectively, and their structure is identical and one can be obtained from the other.

Optionally, said process can also comprise the stage consisting of isolating the product obtained or the final intermediate product formed in stages (i), (ii) or (iii).

The compound prepared in this way can be recovered from the reaction mixture by usual means. For example, the compounds can be recovered by distilling the solvent from the reaction mixture or if necessary after distillation of the solvent from the solution mixture by pouring the remainder into water followed by extraction with an organic solvent immiscible in water, and by distilling the solvent from the extract. Moreover, if desired, the product can also be purified by various techniques such as recrystallization, reprecipitation or various chromatography techniques, in particular column chromatography or preparative thin-layer chromatography.

The base or intermediate products can be prepared by applying or adapting known processes, for example processes as described in the reference examples or their obvious chemical equivalents.

The bisphosphonic dendrimers used in the present invention can be prepared as indicated below. They are defined below to facilitate the description of the preparation processes.

The bisphosphonic dendrimers of generation n can be characterized as comprising:
  a central core § of valency m;
  optionally generation chains in a tree-like structure around the core;
  an intermediate chain at the end of each generation chain or at the end of each bond around the core, if appropriate; and
  a terminal group at the end of each intermediate chain, if appropriate,
characterized in that said terminal group is represented by the formula:

where
-A1< represents the —CR< radical or -heteroatom<;
each A2, identical or different, represents independently a single bond or a linear or branched hydrocarbon chain with 1 to 6 members, each of said members optionally being chosen from a heteroatom, preferably nitrogen, each member being able to be optionally substituted by one or more substituents chosen from -alkyl, -Hal, —$NO_2$, —NRR', —CN, —$CF_3$, —OH, —Oalkyl, -aryl, -aralkyl;
each X, identical or different for each of the phosphonic groups, represents an -alkyl, -aryl radical, —H, or /$M^+$ where $M^+$ is a cation,
m represents an integer greater than or equal to 1;
n represents an integer between 0 and 12;
< represents two bonds situated on A1.

Preferably, the dendrimers used correspond to the commercially available dendrimers to the surface of which has been grafted the -(A1)<[A2-P(=O)(OX)$_2$]$_2$ terminal group.

Said commercially available dendrimers are chosen in particular from those mentioned above.

A1 preferably represents the —CH< or —N< radical.
The —P(=O)(OX)$_2$ groups are preferably in position gem.
X preferably represents an -alkyl radical such as -methyl.
A2 preferably represents -Me-.
The central core § is constituted by at least one atom of valency m.
The central core § can be chosen from any atom or radical having a valency m greater than or equal to 1. § preferably contains at least one heteroatom.

$M^+$ is a cation of an atom, for example a metal atom, or a cation derived from any radical capable of being stable in cation form. Said cation can be chosen in particular from nitrogenous base salts, in particular ammonium salts, alone or in a mixture, in particular with cationic surfactants.

$M^+$ preferably represents a cation of an element of the group IA, IB, HA, JIB or MA, IIB of the periodic table; M is preferably chosen from sodium, potassium, copper, calcium, barium, zinc, magnesium, lithium and aluminium, still more preferably sodium, lithium and potassium atoms.

According to another preferred aspect, $M^+$ represents the cation of a nitrogenous base such as $HNEt_3^+$.

The core § is preferably chosen from the following groups:

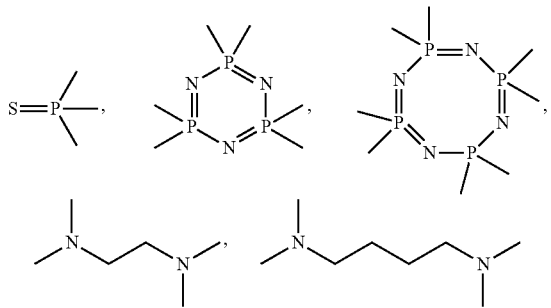

The central core § is preferably of formula:

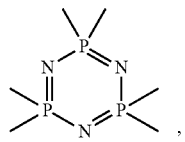

m represents an integer comprised between 1 and 20, in particular 1 to 10, more particularly 1 to 8, still more preferably comprised between 3 and 8, and more particularly 3, 4 or 6;

n represents the number of generations of the dendrimer; it represents an integer comprised between 0 and 12; preferably comprised between 0 and 3;

The generation chains are chosen from those defined above according to the definitions given for monophosphonic dendrimers.

The generation chains, identical or different, are preferably represented by the formula:

-A-B-C(D)=N—N(E)-(P(=G))<     (C1)

where:

A represents an oxygen, sulphur, phosphorus atom or an —NR— radical;

B represents an -aryl-, -heteroaryl-, -alkyl- radical, each being able to be optionally substituted by a halogen atom or an —$NO_2$, —NRR', —CN, —$CF_3$, —OH, -alkyl, -aryl, -aralkyl radical;

C represents a carbon atom,

D and E, identical or different, represent independently a hydrogen atom, an -alkyl, —Oalkyl, -aryl, -aralkyl radical, each being able to be optionally substituted by a halogen atom or an —$NO_2$, —NRR', —CN, —$CF_3$, —OH, -alkyl, -aryl, -aralkyl radical;

G represents a sulphur, oxygen, nitrogen, selenium, tellurium atom or an =NR radical;

N represents a nitrogen atom;

P represents a phosphorus atom.

In general formula (C1) above, A preferably represents an oxygen atom.

In general formula (C1) above, B preferably represents a phenyl core, optionally substituted by a halogen atom or an —$NO_2$, —NRR', —CN, —$CF_3$, —OH, -alkyl, -aryl, -aralkyl radical; still more preferably, B represents a non-substituted phenyl core.

In general formula (C1) cited above, D preferably represents a hydrogen atom.

In general formula (C1) cited above, E preferably represents an -alkyl radical.

In general formula (C1) above, G preferably represents a sulphur atom.

According to another preferred aspect, the generation chains are represented by the formula:

-A'-(C=O)—N(R)-B'-N<     (C1')

where

A' and B' represent independently an -alkyl-, -alkenyl-, -alkynyl- radical, each optionally substituted by one or more substituents chosen from -alkyl, -Hal, —$NO_2$, —NRR', —CN, —$CF_3$, —OH, —Oalkyl, -aryl, -aralkyl;

R, R' are as defined previously.

A' preferably represents -alkyl-, still more preferably -ethyl-. B' preferably represents -alkyl-, still more preferably -ethyl-.

R preferably represents a hydrogen atom.

According to another preferred aspect, the generation chains are represented by the formula:

-A"-N<     (C1")

where

A" represents an -alkyl-, -alkenyl-, -alkynyl- radical, each optionally substituted by one or more substituents chosen from -alkyl, -Hal, —$NO_2$, —NRR', —CN, —$CF_3$, —OH, —Oalkyl, -aryl, -aralkyl, where RR' are as defined previously.

A" preferably represents -alkyl-, still more preferably -propyl-.

According to another preferred aspect, the dendrimers of generation 0 do not comprise a generation chain. In particular, where the generation chain is represented by formulae (C1') or (C1"), the corresponding dendrimers of generation 0 do not comprise a generation chain. The intermediate chains are chosen from those defined with regard to the monophosphonic dendrimers.

The intermediate chains preferably have a single bond at their end.

The intermediate chains, identical or different, are preferably represented by the formula:

-J-K-L-     (C2)

defined above.

In formula (C2) above, J preferably represents an oxygen atom.

In formula (C2) above, K preferably represents a phenyl core, optionally substituted; still more preferably, K represents a non-substituted phenyl core.

In formula (C2) above, L preferably represents an -(alk)$_a$- radical, or L represents the —C(D)=N—N(E)-(alk)$_a$- radical, where C represents a carbon atom, D and E, identical or different, represent independently a hydrogen atom, an -alkyl, —Oalkyl, -aryl, -aralkyl radical, each being able to be optionally substituted by a halogen atom or an —$NO_2$, —NRR', —CN, —$CF_3$, —OH, -alkyl, -aryl, -aralkyl radical;

a represents 0 or 1;

R, R' are as defined previously.

According to another preferred aspect, the intermediate chains are represented by the formula

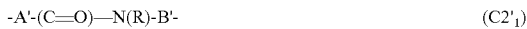

where A', B', R, R' are as defined previously.

A' preferably represents -alkyl-; still more preferably -ethyl-.

B' preferably represents -alkyl-; still more preferably -ethyl-.

R preferably represents a hydrogen atom.

According to another preferred aspect, the intermediate chains are represented by the formula

where

A" is as defined previously.

A" preferably represents an -alkyl- radical; still more preferably -propyl-.

The generation chains are preferably identical.

In formulae (C1) and (C2) cited above, J and K are preferably equal to A, B respectively.

The bisphosphonic dendrimers can preferably be represented by the following formula (I-1i):

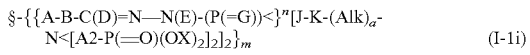

in which:

§, A, B, C, D, E, G, N, P, J, K, X, A2, m, n are as defined previously, { }$^n$ designates the tree-like structure of the generation chains n of said dendrimer, and a represents 0 or 1; A2 preferably represents an -alkyl- radical.

The bisphosphonic dendrimers can preferably be represented by the following formula (I-1ii):

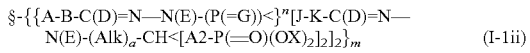

in which:

§, A, B, C, D, E, G, N, P, J, K, X, A2, m, n are as defined previously, { }$^n$ designates the tree-like structure of the generation chains n of said dendrimer, and a represents 0 or 1; A2 preferably represents a single bond.

According to another preferred aspect, the bisphosphonic dendrimers can be represented by the following formula (I-2):

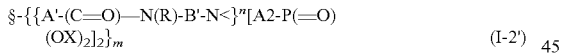

in which:

§, A', B', C, N, P, X, A2, m, n are as defined previously and { }$^n$ designates the tree-like structure of the generation chains n of said dendrimer.

According to another preferred aspect, the bisphosphonic dendrimers can be represented by the following formula (I-3):

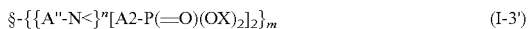

in which:

§, A", N, P, X, A2, m, n are as defined previously and { }$^n$ designates the tree-like structure of the generation chains n of said dendrimer.

The -alk, -alkyl or -alkyl-, -alkenyl or -alkenyl-, -alkynyl or -alkynyl- radicals have the meanings mentioned above.

Among the halogen atoms (Hal), there can be mentioned more particularly fluorine, chlorine, bromine and iodine, preferably fluorine, atoms.

The -aryl or -aryl-, -aralkyl (-alkylaryl), -heteroaryl or -heteroaryl- radicals, have the meanings mentioned above.

By «corresponding dendrimer» is meant the dendrimer of the same generation having the same cores, generation chains, intermediate chains and distinct terminal groups.

Bisphosphonic dendrimers can be prepared by applying or adapting any method known per se and/or within the scope of a person skilled in the art allowing the grafting of $-PO_3X_2$ functions, particularly $-(A1)<[A2-P(=O)(OX)_2]_2$, in particular those described by Larock in *Comprehensive Organic Transformations*, VCH Pub., 1989, or by applying or adapting the processes described in the following examples.

In the reactions described below, it may be necessary to protect the reactive functional groups, for example the hydroxy, amino, imino, thio, carboxy groups, when they are desired in the final product, in order to prevent their undesired participation in the reactions. The usual protective groups can be used according to standard practice, for examples see T. W. Green and P. G. M. Wuts in *Protective Groups in Organic Chemistry*, John Wiley and Sons, 1991; J. F. W. McOmie in *Protective Groups in Organic Chemistry*, Plenum Press, 1973.

The process for the preparation of a dendrimer according to the invention comprising the $-A_1<[A2-P(=O)(OX)_2]_2$ terminal group comprises:

(i) the reaction of the corresponding dendrimer having a $-CHO$, $-CH=NR$, $-NH_2$ or $-P(=G)Cl_2$ terminal function with a corresponding compound having one or two $-PO_3X_2$ functionalities;

(ii) followed optionally, when X represents H or M, by the stage consisting of converting the dendrimer obtained in (i) having a $-PO_3Me_2$ termination to the corresponding dendrimer having an $-A1<[A2-P(=O)(OH)_2]_2$ termination, (iii) followed optionally, when X represents M, by the stage consisting of converting the dendrimer obtained in (ii) having an $-A1<[A2-P(=O)(OH)_2]_2$ termination to the salt of the corresponding dendrimer having an $-A1<[A2-P(=O)(OM)_2]_2$ termination.

The corresponding starting dendrimers are commercially available (Aldrich) or can be prepared according to methods known per se.

More precisely, stage (i) can be carried out according to the following alternatives:

According to a first alternative, when the bisphosphonic dendrimer is represented by formula (I-1i)

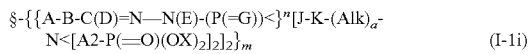

in which §, A, B, C, D, E, G, N, P, J, K, A2, Alk, X, a, m, n, < are as defined previously, stage (i) comprises the reaction on the corresponding dendrimer of the same generation n of formula

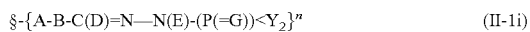

where Y represents $-Cl$;

of a compound of formula

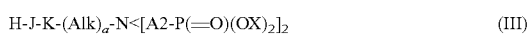

This reaction is carried out under stirring, in solution in an aprotic, polar solvent such as THF, acetonitrile, chloroform, dichloromethane, DMF or acetone, preferably THF, in the presence of an organic or inorganic base, such as cesium carbonate, at a temperature comprised between −80° C. and 100° C., preferably at ambient temperature.

In formula (II-1i), G preferably represents S.

The dendrimers of formula (II-1i) are preferably chosen from: $SPCl_3$, $P_3N_3Cl_6$,

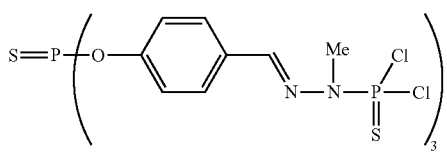 $G_1$

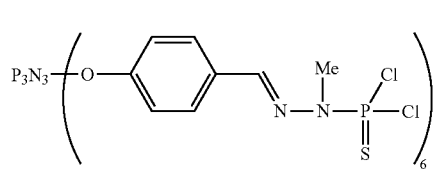 $Gc_1$

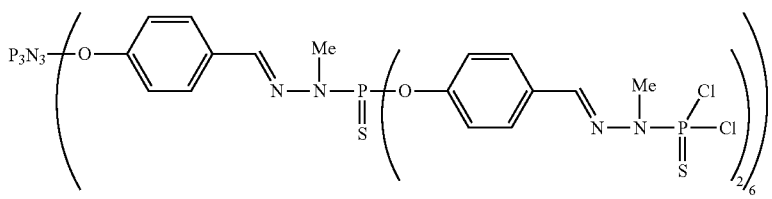 $Gc_2$

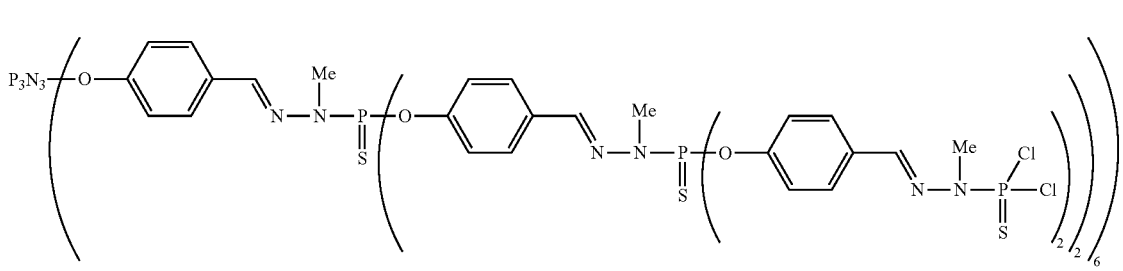 $Gc_3$

According to a second alternative, when the dendrimer is represented by formula (I-2') or (I-3):

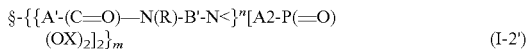  (I-2')

or

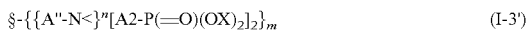  (I-3')

in which §, A', A", B', B", C, N, P, A2, X, m, n, < are as defined previously, stage (i) comprises the reaction on the corresponding dendrimer of the same generation n of formula

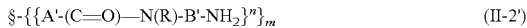  (II-2')

or

  (II-3)

of a compound of formula

  (IV), in the presence of a corresponding compound of formula

  (V').

This reaction is carried out under stirring, optionally diluted in aqueous solution, at a temperature comprised between −5° C. and the reflux temperature of the mixture.

The compounds of formula (IV) and (V') are commercially available (Aldrich) or can be prepared according to the methods known per se.

The dendrimers of formula (II-2') and (II-3) are commercially available (Aldrich). They are preferably of DAB or PAMAM type mentioned above.

According to a third alternative, when the dendrimer is represented by formula (I-1ii)

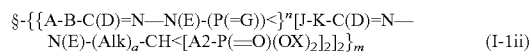  (I-1ii)

in which:
§, A, B, C, D, E, G, N, P, J, K, L, X, A2, m, n, a are as defined previously,
stage (i) comprises the reaction on the corresponding dendrimer of formula

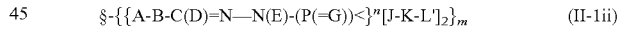  (II-1ii)

where L' represents a —CHO radical;
of a compound of formula

  (VI')

where alk corresponding to alk defined previously in formula (I-1ii) represents an alkenyl radical in the presence of a compound of formula

  (VII')

This reaction can be carried out by applying or adapting the method described in J. Org. Chem., 1997, 62, 4834.

Preferably, the operation is carried out in a polar, aprotic solvent medium such as THF, chloroform, dichloromethane, or acetonitrile, preferably $CH_2Cl_2$, by simultaneous addition of (VI') and (VII') to the dendrimer at a temperature between −80° C. and 50° C., preferably approximately 0° C.

The compounds of formula (VI') and (VII') are commercially available or can be prepared according to the methods known per se.

The dendrimers of formula (II-1ii) are preferably chosen from: $SPCl_3$, $P_3N_3Cl_6$,

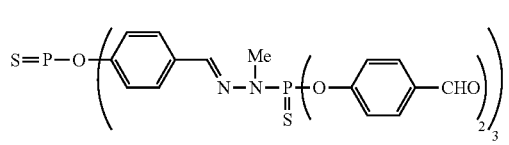

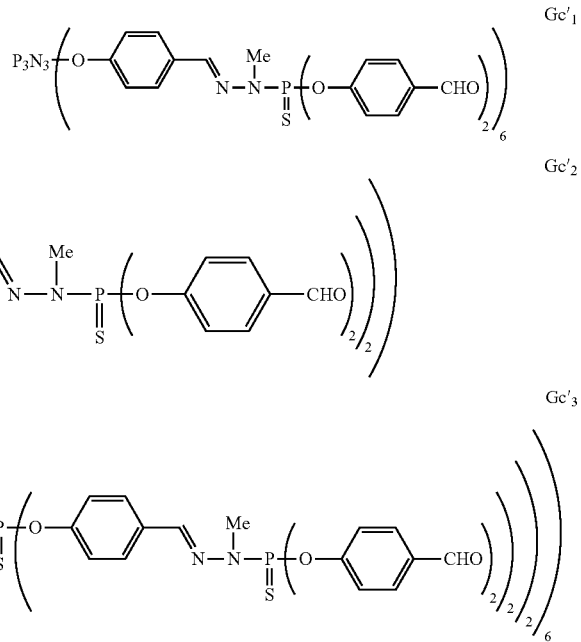

In order to obtain a dendrimer compound where X=H or M, stage (i) is preferably carried out with a reagent of formula (III), (IV) or (VI) where X=Me. Stage (ii) is then carried out starting from the compound of formula (I-1i), (I-2'), (I-3'), (I-1ii) obtained in (i) where X=Me.

Stage (ii) is preferably carried out:

by the action of trimethylsilane halide, preferably trimethylsilane bromide (Me$_3$SiBr), in an organic aprotic, polar solvent such as acetonitrile, chloroform or dichloromethane, preferably acetonitrile. The operation is preferably carried out by slowly adding trimethylsilane halide, keeping the reaction mixture at a temperature comprised between −80° C. and 50° C., preferably at approximately 0° C.

followed by the action of anhydrous MeOH, added to the reaction mixture.

In stage (iii), the acid salts of bisphosphonic dendrimers can be obtained from the bisphosphonic dendrimers having a terminal group in which X represents a hydrogen atom, by applying or adapting known processes by adding a base. The operation is preferably carried out in solution, under stirring, in an appropriate polar, protic or aprotic solvent such as THF, chloroform, dichloromethane, DMF, acetonitrile, alcohols, water, preferably water, in the presence of an organic or inorganic base, such as sodium, lithium or potassium hydroxide, according to the desired salt.

When starting dendrimers are used having different terminal groups of the terminal functions described above for the dendrimers of formula (II-1i), (II-1ii), (II-2') or (II-3), the process comprises the additional preliminary stage of allowing said groups to be converted to said required functions. For example, in the case of dendrimers having carboxylic acid or hydroxyl type terminal groups, it is sufficient to carry out any reaction allowing said carboxylic acid or hydroxyl type groups to be converted to —NH$_2$, —CHO, —CH=NR or —PSCl$_2$ type functions corresponding to the dendrimers of formula (II-1i), (II-1ii), (II-2') or (II-3). Such reactions are known to a person skilled in the art and/or can be carried out by applying or adapting those discussed by Larock et al (supra).

In order to obtain a dendrimer of generation 0, the above reactions can be carried out in the same manner by operating from the core having the required functionality. For example, the generation reactions can be carried out by operating from a PSCl$_3$, P$_3$N$_3$Cl$_6$, P$_4$N$_4$Cl$_8$, or

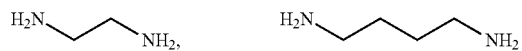

core.

With regard to the compounds of formula (III):

$$\text{H-J-K-(Alk)}_a\text{-N<[A2-P(=O)(OX)}_2]_2 \quad \text{(III)}$$

in which

X represents H, an -alkyl, -aryl or M$^+$ radical where M$^+$ represents a cation;

J represents an oxygen, sulphur atom, or an —NR— radical;

K represents an -aryl-, -heteroaryl-, -alkyl- radical, each being able to be optionally substituted by a halogen atom or an —NO$_2$, —NRR', —CN, —CF$_3$, —OH, -alkyl, -aryl, -aralkyl radical;

each A2, identical or different, represents independently a single bond or a linear or branched hydrocarbon chain with 1 to 6 members, each of said members optionally being able to be chosen from a heteroatom, preferably nitrogen, each member being able to be optionally substituted by one or more substituents chosen from -alkyl, -Hal, —NO$_2$, —NRR', —CN, —CF$_3$, —OH, —Oalkyl, -aryl, -aralkyl;

-alk- represents an alkyl radical;

a represents 0 or 1, in which in formula (III) above, J preferably represents an oxygen atom;

in formula (III) above, K preferably represents a phenyl core, optionally substituted; still more preferably, K represents a non-substituted phenyl core;

in formula (III) above, -alk- preferably represents an -ethyl- radical;

in formula (III) above, A2 preferably represents an -alkyl- radical, still more preferably, -methyl-;

in formula (III) above, X preferably represents —H or -Me; they can be obtained from a compound of formula (VIII') as follows:

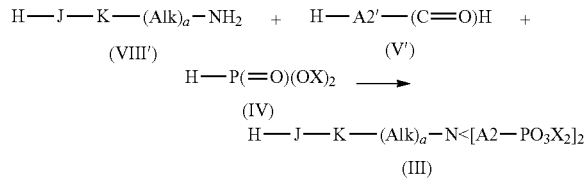

where, in formula (V'), -A2'- is a radical corresponding to A2.

This reaction is carried out by applying or adapting a method known per se, in particular described in I. Linzaga et al., Tetrahedron 2002, 58, 8973-8978. The operation is carried out in particular by slowly adding compounds (VIII') and (IV), then compound (V'), optionally diluted in aqueous solution, preferably at a temperature between −5 and 25° C., preferably at approximately 0° C. The reaction mixture is then left to adjust to ambient temperature, then optionally reacted under reflux.

In the description of the process above, two groups are said to be <<corresponding>> when they are each included in a starting and end product, and their structure is identical and they can be derived from each other.

Optionally, said process can also comprise the stage consisting of isolating the product obtained in stages (i), (ii), and/or (iii).

The compound prepared in this way can be recovered from the reaction mixture by usual means. For example, the compounds can be recovered by distilling the solvent from the reaction mixture or if necessary after distillation of the solvent from the solution mixture by pouring the remainder into water followed by extraction with an organic solvent immiscible in water, and by distilling the solvent from the extract. Moreover, if desired the product can also be purified by various techniques such as recrystallization, reprecipitation or various chromatography techniques, in particular column chromatography or preparative thin-layer chromatography.

It is understood that the compounds used according to the present invention can contain asymmetrical centres. These asymmetrical centres can be independently in R or S configuration. It is clear to a person skilled in the art that certain compounds used according to the invention can also have a geometric isomerism. It must be understood that the present invention comprises individual geometric isomers and stereoisomers and mixtures of same, including racemic mixtures, of compounds of formula (I) above. These isomers can be separated from their mixtures by applying or adapting known processes, for example chromatography techniques or recrystallization techniques, or they are prepared separately starting from appropriate isomers of their intermediates.

For the purpose of this text, it is understood that the tautomeric forms are comprised in the citation of a given group, for example thio/mercapto or oxo/hydroxy.

The compounds used according to the present invention can be prepared easily, or formed during the process of the invention in the form of solvates (for example hydrates).

The hydrates of the compounds used according to the present invention can be prepared easily by recrystallization from a mixture of aqueous/organic solvents, using organic solvents such as dioxane, tetrahydrofuran or methanol.

The base products or the intermediates can be prepared by applying or adapting known processes, for example processes as described in the reference examples or their obvious chemical equivalents.

The monophosphonic or bisphosphonic dendrimers according to the invention for which one or two core bonds are not occupied by generation chains, i.e. monophosphonic or bisphosphonic dendrimers having one or two branches missing, are prepared as described in Example 91. In brief, one or two groups which do not allow the elongation of the generation chains (such as phenol, for example) are attached to the core before implementing the process for elongating the dendrimer already described above for monophosphonic or bisphosphonic dendrimers.

BRIEF DESCRIPTION OF THE FIGURES

FIG. 1A represents the fluorescence intensity of cells separated by flow cytometry originating from an initial PBMC population labelled with an anti-CD3-FITC antibody (X-axis) and by an anti-CD56-PC5 antibody (Y-axis). Section 1 corresponds to $CD3^-CD56^+$ cells (23%), section 2 corresponds to $CD3^+CD56^+$ cells (6%), section 3 corresponds to $CD3^-CD56^-$ cells and section 4 correspond to $CD3^+CD56^-$ cells (50%).

FIG. 1B represents the fluorescence intensity of cells separated by flow cytometry originating from an initial PMBC population cultured in the presence of dendrimer GC1, labelled with an anti-CD3-FITC antibody (X-axis) and by an anti-CD56-PC5 antibody (Y-axis). Section 1 corresponds to $CD3^-CD56^+$ cells (76%), section 2 corresponds to $CD3^+CD56^+$ cells (14%), section 3 corresponds to $CD3^-CD56^-$ cells and section 4 corresponds to $CD3^+CD56^-$ cells (8%).

FIG. 1C represents the fluorescence intensity of cells separated by flow cytometry originating from an initial PMBC population cultured in the presence of dendrimer GC1, labelled with an anti-CD16-PE antibody (X-axis) and by an anti-CD56-PC5 antibody (Y-axis). Section 1 corresponds to $CD16^-CD56^+$ cells, section 2 corresponds to $CD16^+CD56^+$ cells, section 3 corresponds to $CD16^-CD56^-$ cells and section 4 corresponds to $CD16^+CD56^-$ cells.

FIG. 1D represents the fluorescence intensity of cells separated by flow cytometry originating from an initial PMBC population cultured in the presence of dendrimer GC1, labelled with an anti-NKG2D antibody tagged with a GAM (Goat Anti-Mouse)-FITC antibody (X-axis) and by an anti-CD56-PC5 antibody (Y-axis). Section 1 corresponds to $NKG2D^-CD56^+$ cells, section 2 corresponds to $NKG2D^+CD56^+$ cells, section 3 corresponds to $NKG2D^-CD56^-$ cells and section 4 corresponds to $NKG2D^+CD56^-$ cells.

FIG. 1E represents the fluorescence intensity of cells separated by flow cytometry originating from an initial PMBC population cultured in the presence of dendrimer GC1, labelled with an anti-NKp30 antibody tagged with a GAM (Goat Anti-Mouse)-FITC antibody (X-axis) and by an anti-CD56-PC5 antibody (Y-axis). Section 1 corresponds to $NKp30^-CD56^+$ cells, section 2 corresponds to $NKp30^+CD56^+$ cells, section 3 corresponds to $NKp30^-CD56^-$ cells and section 4 corresponds to $NKp30^+CD56^-$ cells.

FIG. 1F represents the fluorescence intensity of cells separated by flow cytometry originating from an initial PMBC population cultured in the presence of dendrimer GC1, labelled with an anti-NKp44-PE antibody (X-axis) and by an anti-CD56-PC5 antibody (Y-axis). Section 1 corresponds to NKp44$^-$CD56$^+$ cells, section 2 corresponds to NKp44$^+$CD56$^+$ cells, section 3 corresponds to NKp44$^-$CD56$^-$ cells and section 4 corresponds to NKp44$^+$CD56$^-$ cells.

FIG. 1G represents the fluorescence intensity of cells separated by flow cytometry originating from an initial PMBC population cultured in the presence of dendrimer GC1, labelled with an anti-CD8 5j (ILT2) antibody tagged with a GAM (Goat Anti-Mouse)-FITC antibody (X-axis) and by an anti-CD56-PC5 antibody (Y-axis). Section 1 corresponds to CD85j$^-$CD56$^+$ cells, section 2 corresponds to CD85j$^+$CD56$^+$ cells, section 3 corresponds to CD85j$^-$CD56$^-$ cells and section 4 corresponds to CD85j$^+$CD56$^-$ cells.

FIG. 2A, FIG. 2B, FIG. 2C, FIG. 2D

FIGS. 2A, 2B, 2C and 2D represent respectively the lymphocytic compositions of PBMC cultures in the presence of GC1 originating from four different donors. The Y-axis represents the number of cells in millions. The bar DO represents the number of cells at the start of the experiment, the bar GC1 represents the number of cells present after 15 days of culture in the presence of GC1 (NK cells (vertical lines), T γδ cells (white) and T αβ cells (dots)), and the control bar represents the number of cells present after 15 days of culture in the presence of a standard culture medium (NK cells (vertical lines), T γδ cells (white) and T αβ cells (dots)).

FIG. 3 represents the number of NK cells obtained after culture of PBMC from 4 different donors (white circle, black circle, white triangle, black triangle) in the presence (+GC1) or in absence (−GC1) of GC1. The X-axis represents the number of cells in millions and the Y-axis represents the culture time (in weeks).

FIG. 4A represents the number of NK cells obtained (Y-axis, in millions) by culture of PBMC in the presence of variable concentrations of GC1 (X-axis, in μM).

FIG. 4B represents the number of NK cells obtained (Y-axis, in millions) by culture of PBMC from different donors (white circle, black circle) in the presence of a standard culture medium (0), GC0, GC1, GC2 or an azabisphosphonic group alone (monomer).

FIGS. 5A and 5B represent the fluorescence transmitted to NK cells obtained using GC1 (fluorescence intensity, Y-axis) by lymphoma cells B (FIG. 5A) or colic carcinoma (FIG. 5B) labelled with a fluorescent membrane label, as a function of time (X-axis, in minutes). FIG. 5C represents a photograph taken under confocal microscope in which the trogocytosis (arrows) of cancerous cells (target) by an NK cell is visible.

FIG. 6A represents diagrammatically the redirected lysis experiment in which NK cells cause the lysis of target cells (P815) following the stimulation of receptors of the NK cells carried out by the (Ig) antibody attached using FcR to said target cells.

FIG. 6B represents the results of a redirected lysis experiment carried out using NK cells obtained with GC1 (Y-axis, percentage of specific lysis) as a function of the E:T ratio (number of effective cells:number of target cells) (X-axis) in the presence of any antibody (white triangles), a control antibody (black triangles), an anti-NKG2D antibody (black circles) or an anti-NKp30 antibody (white circles).

FIGS. 7A-7C represent the lysis by NK cells obtained with GC1 (percentage of specific lysis, Y-axis) of Burkitt lymphoma cell (FIG. 7A), LMC K562 cells (FIG. 7B) or PBMC autologues (FIG. 7C) as a function of the E:T ratio (X-axis).

Figure 8:
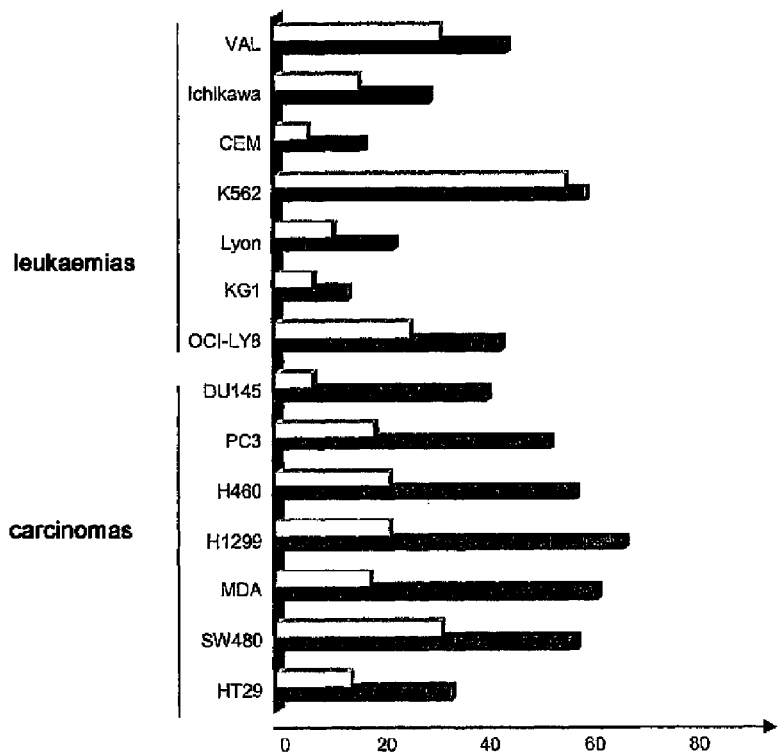
FIG. 8

The FIG. 8 represents the cytotoxicity exerted by NK1 cells obtained with GC1 (X-axis, percentage of specific lysis) vis-à-vis leukaemia or carcinoma cell line cells as a function of an E:T ratio of 1:1 (white bars) or 10:1 (grey bars).

FIG. 9

Figure 9:
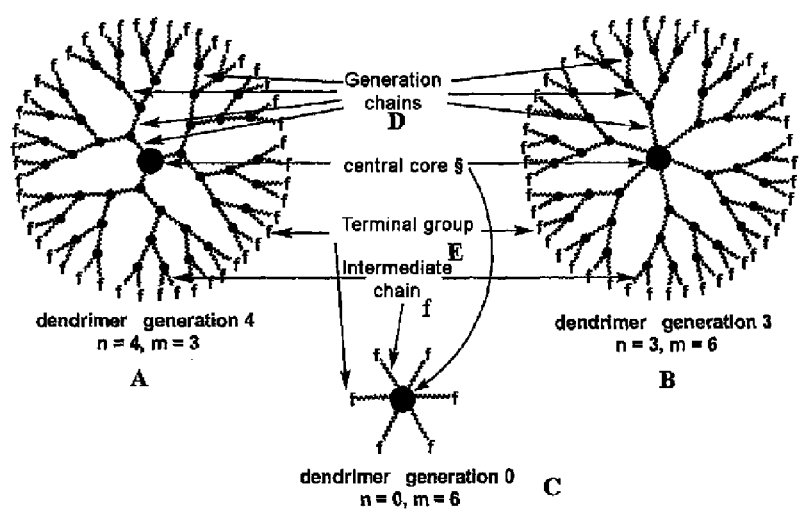

FIG. 9 represents diagrammatic examples of three dendrimers, a dendrimer of generation 4, for which n=4 and m=3 (A, left), a dendrimer of generation 3, for which n=3 and m=6 (B, right) and a dendrimer of generation 0, for which n=0 and m=6 (C, below). The constitutive elements of a dendrimer are represented: a core (§) to which generation chains (D) are attached for dendrimers of generation greater than or equal to 1, or directly the intermediate chains (E) for dendrimers of generation 0, intermediate chains (E) attached to the end of the generation chains, the intermediate chains also being linked to terminal groups (f), the mixture of terminal groups forming the surface of the dendrimer. The linkage chains are constituted by a group of generation chains comprising one generation chain attached to the core and the set of the other generation chains which are linked to this chain either directly or via other generation chains.

Figure 10A:
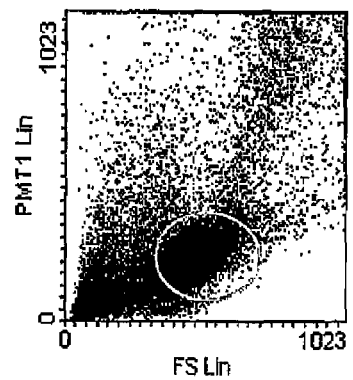
Figure 10B:
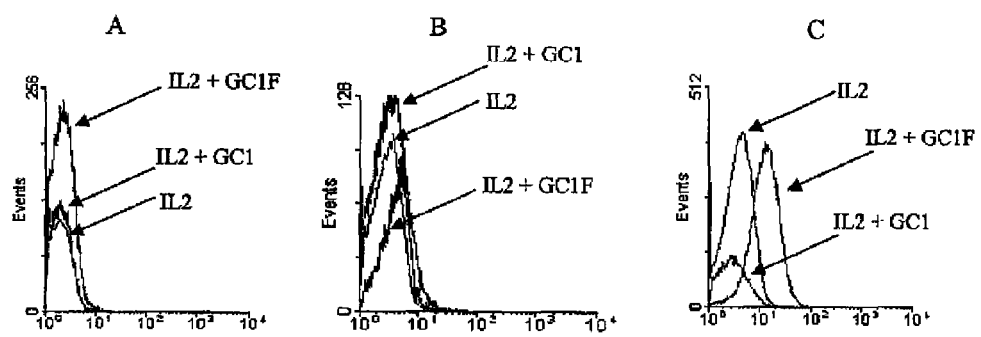

FIG. 10A and FIG. 10B

FIG. 10A represents a population of total lymphocytes separated by flow cytometry as a function of their size (X-axis, FS lin) and their granularity (PMT1 lin), as well as those selected to be incubated in the presence of fluorescent dendrimers (circle).

FIG. 10B represents the results of cultures of the above lymphocytes in the presence of IL2, or fluorescent dendrimer (GC1F) and IL2, or GC1 and IL2, after 4 h (A), 24 h (B) or 15 days (C). The X-axis represents the fluorescence intensity (arbitrary units) and the Y-axis the number of cells (arbitrary units).

FIG. 11

Figure 11:
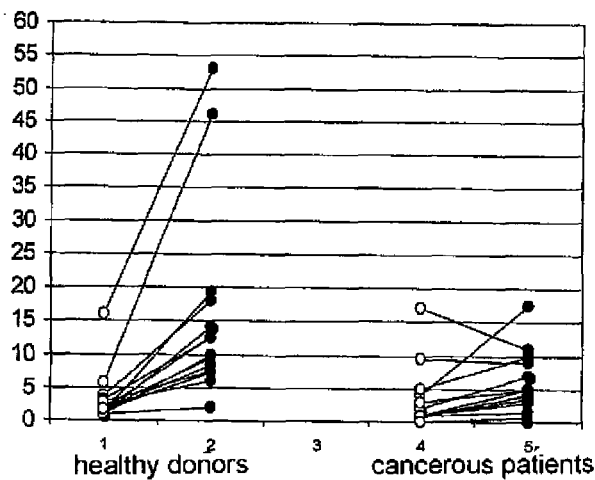

FIG. 11 represents the number of NK cells (Y-axis, in millions) obtained after culture, in the presence of GC1 over 2.5 weeks, of PBMC originating from healthy donors and from cancerous patients affected by multiple myeloma (filled circles) with respect to the number of NK cells present at the start of the culture (empty circles).

Figure 12A:
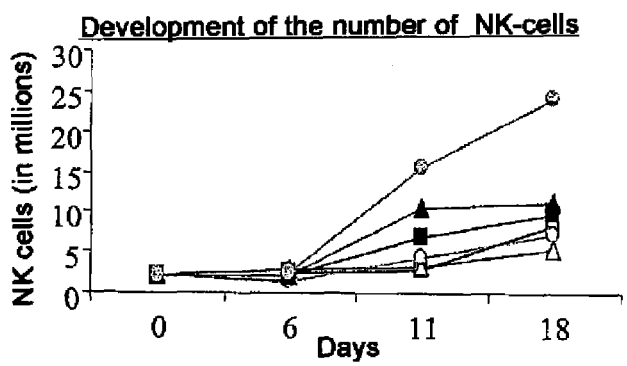
Figure 12B:
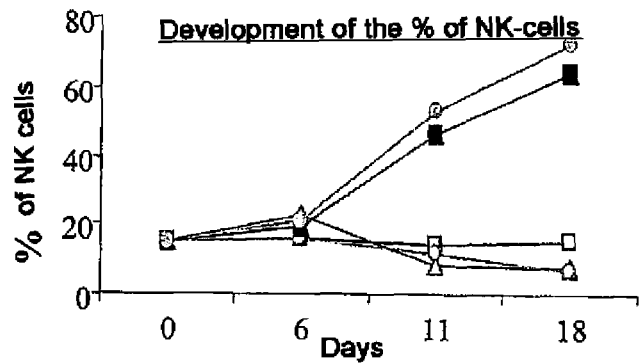

FIG. 12A and FIG. 12B

FIG. 12A represents the number of NK cells obtained (Y-axis, in millions) as a function of the duration of culture (X-axis, in days) of PBMC from healthy donors in the presence of IL2 (empty squares), IL15 (empty triangles), IL2+IL15 (empty circles), IL2+GC1 (full squares), IL15+GC1 (full triangles) and IL2+IL15+GC1 (full circles).

FIG. 12B represents the percentage of NK cells (Y-axis) in a culture of PBMC of healthy donors as a function of the duration of the culture (X-axis, in days), in the presence of IL2 (empty squares), IL15 (empty triangles), IL2+IL15 (empty circles), IL2+GC1 (full squares), IL15+GC1 (full triangles) and IL2+IL15+GC1 (full circles).

FIG. 13

Figure 13:
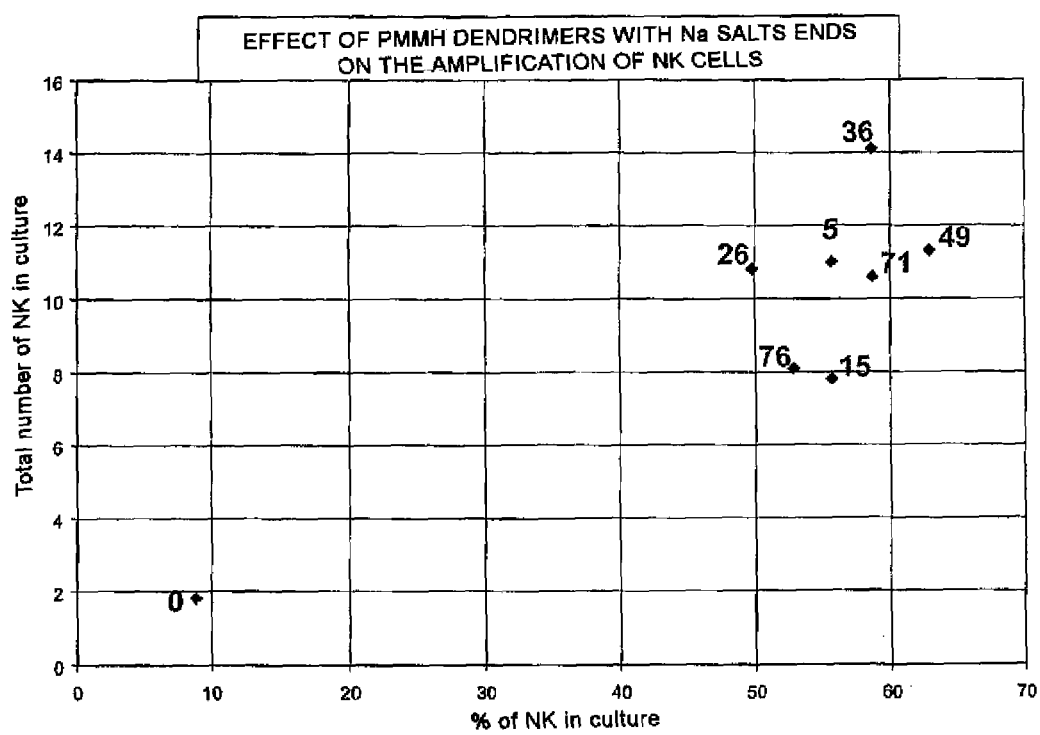

FIG. 13 represents the effect of PMMH-type phosphorus-containing dendrimers with Na salt ends on the amplification of NK cells. 0 corresponds to the amplification in culture medium by IL2 alone (without dendrimer). The other numbers correspond to the numbers of examples of the dendrimers in question, in their form of sodium salts.

FIG. 14A, FIG. 14B, FIG. 14C and FIG. 14D

Figure 14A:
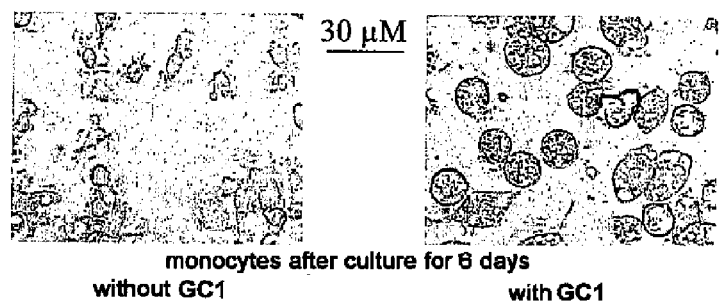

FIG. 14A represents photographs of slides, observed under an optical microscope, of monocytes cultured in the absence (left) or in the presence (right) of the dendrimer GC1. The horizontal bar represents 30 μm.

Figure 14B:
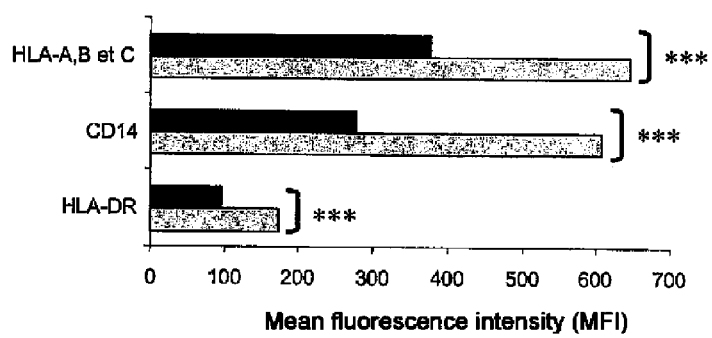

FIG. 14B represents the flow cytometry analysis (X-axis, mean fluorescence intensity (MFI)) of the expression of the labels HLA-A, B, C, CD14 and HLA-DR on monocytes in culture in the presence (black bars) or in the absence (grey bars) of GC1. The asterisk symbol (***) represents a significant difference in MFI in a Student test ($p<0.001$). The results are representative of 3 donors.

Figure 14C:
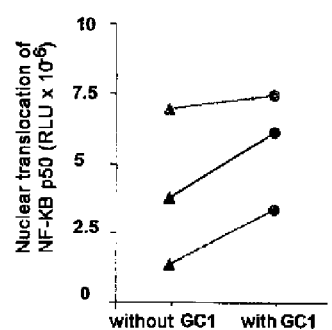

FIG. 14C represents the nuclear translocation of NFκB p50 (Y-axis, RLU×$10^6$) (RLU: relative luminescence unit) within monocytes cultured in the absence (triangles) or in the presence (circles) of GC1.

Figure 14D:
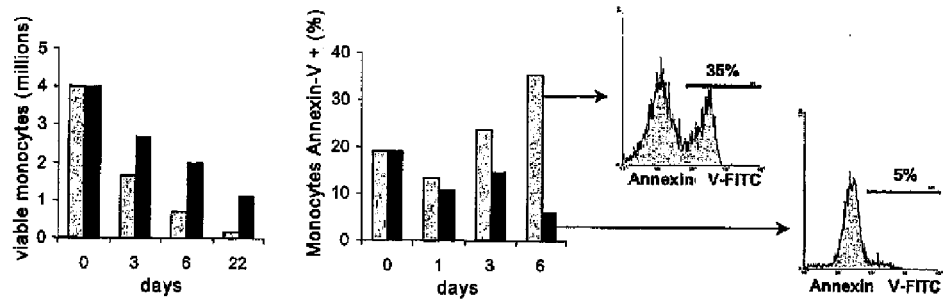

FIG. 14D represents the number of viable monocytes (Y-axis, in millions) as a function of the duration of culture (X-axis, in days) of monocytes cultured in the absence (grey bars) or in the presence (black bars) of GC1 (first graph from the left) and the percentage of monocytes positive to annexin-V (Y-axis) as a function of the duration of culture of monocytes cultured in the absence (grey bars) or in the presence (black bars) of GC1 (second graph from the left). The percentage of monocytes positive to annexin-V is determined by flow cytometry using an anti-annexin-V antibody labelled with FITC. Examples of the determination of the percentage of monocytes positive to annexin-V for monocytes cultured for 6 days in the absence of GC1 (third graph from the left: 35% monocytes positive to annexin-V) and for monocytes cultured for 6 days in the presence of GC1 (fourth graph from the left: 5% monocytes positive to annexin-V).

DETAILED DESCRIPTION OF THE INVENTION

EXAMPLES

General Points

The reactions were carried out under a dry argon atmosphere (argon U, Air Liquide). The following solvents were dried and distilled under argon immediately before use according to the techniques described by Perrin et al, *Purification of Laboratory Chemicals, Third Edition*; Press, P., Ed.: Oxford, 1988: tetrahydrofuran, dichloromethane, acetonitrile, pentane, toluene, diethyl ether, chloroform, triethylamine, pyridine.

Thin layer chromatography analyses were carried out on aluminium plates coated with silica of the Merck Kieselgel $60F_{254}$ type.

The NMR spectra were recorded on Brüker devices (AC200, AM250, DPX 300). The chemical shifts are expressed in parts per million (ppm) relative to phosphoric acid at 85% in water for the $^{31}P$ NMR and relative to tetramethylsilane for the $^1H$ and $^{13}C$ NMR. The following abbreviations were used in order to express the multiplicity of signals: s (singlet), d (doublet), bd (broad doublet), dd (doublet of doublets), AB syst. (AB system), t (triplet), dt (doublet of triplets), q (quadruplet), hept (heptuplet), m (unresolved multiplet).

Infrared vibrational spectroscopy was carried out on a Perkin Elmer FT 1725x spectrometer. The UV-visible spectroscopy was carried out on an HP 4852A device. The thermogravimetric measurements were carried out on a Netzch DSC 204 or Setaram TGA 92-16.18 device.

Numbering Used for the NMR Attribution:

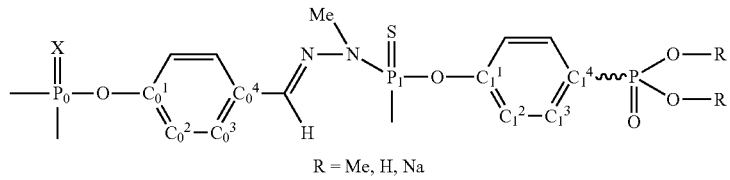

R = Me, H, Na

Example of Numbering for a First-Generation Dendrimer

Structures of the Dendrimers Used as Starting Product

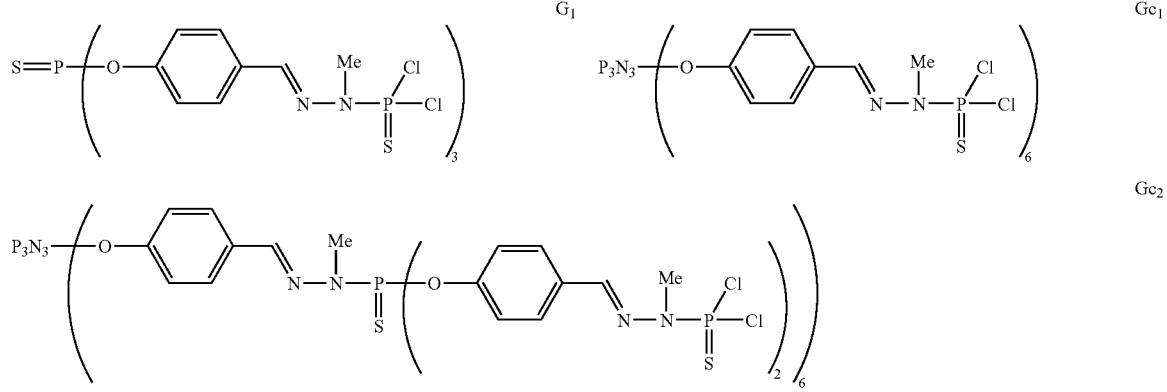

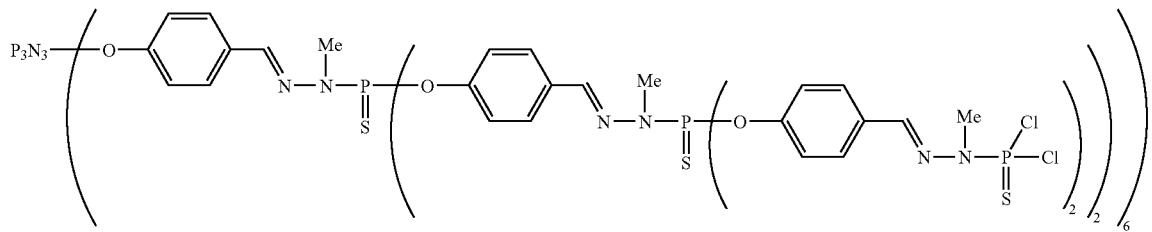

Gc₃

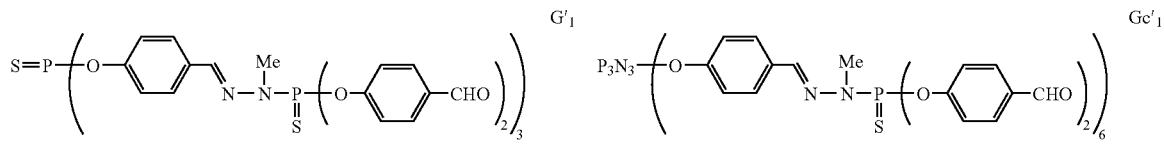

G'₁          Gc'₁

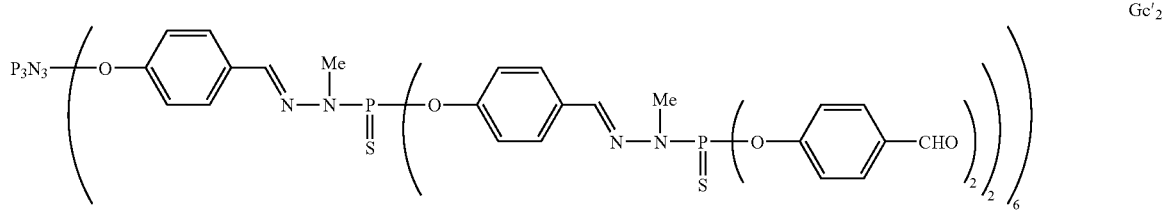

Gc'₂

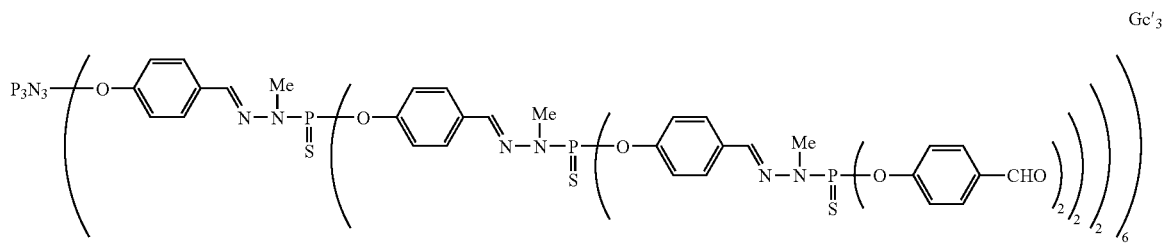

Gc'₃

Example 1

Synthesis of First-Generation Dendrimer (Core P=S) with α-Hydroxy-Dimethylphosphonic Acid Ends Stage 1: Synthesis of First-Generation Dendrimer (Core P=S) with α-Hydroxy-Dimethylphosphonic Ends

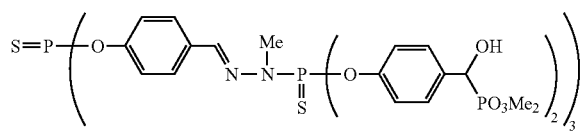

The dendrimer G'₁ (0.14 mmol, 200 mg) is placed in solution in 0.2 ml of THF with distilled triethylamine (0.126 mmol, 4.5 μL), and dimethylphosphite (1.26 mmol, 115 μL). The mixture is left for 12 hours with magnetic stirring. The paste obtained is then washed with a THF/Et₂O: mixture 1/1, in order to produce a white powder. The final product is isolated with a yield of 72%.

NMR $^{31}$P-{$^1$H} (DMSO d6): δ=27.10 (s, P(O)(O—CH₃)₂), 56.10 (s, P₀), 65.91 (s, P₁) ppm.

NMR $^1$H (DMSO d6): δ=3.34 (d, $^3J_{HP}$=9.8 Hz, 9H, CH₃—N—P₁), 3.52 (d, 18H, $^3J_{HP}$=10.3 Hz, P(O)—O—CH₃), 3.57 (d, 18H, $^3J_{HP}$=11.6 Hz, P(O)—O—CH₃), 5.01 (dd, $^3J_{HH}$=4.5 Hz, $^2J_{HP}$=13.0 Hz, 6H, CH—P(O)), 6.33 (dd, $^3J_{HH}$=5.6 Hz, $^3J_{HP}$=15.7 Hz, 6H, OH), 7.18-7.93 (m, 39H, H$_{arom}$, CH=N) ppm.

NMR $^{13}$C—{$^1$H} (DMSO d6): δ=33.9 (d, $^2J_{CP}$=12.1 Hz, CH₃—N—P₁), 53.7 (d, $^2J_{CP}$=6.8 Hz, CH₃—O—P(O)), 54.2 (d, $^2J_{CP}$=7.0 Hz, CH₃—O—P(O)), 70.0 (d, $^1J_{CP}$=162.8 Hz, C—OH), 121.3 (broad s, C₁²), 122.4 (d, $^3J_{CP}$=3.8 Hz, C₀²), 129.4 (s, C₀³), 129.8 (d, $^3J_{CP}$=5.6 Hz, C₁³), 133.6 (s, C₀⁴), 136.4 (s, $C_1^4$), 141.4 (d, $^3J_{CP}$=14.5 Hz, CH=N), 150.3 (dd, $^1J_{CP}$=3.4 Hz, $^2J_{CP}$=6.6 Hz, $C_1^1$), 151.4 (d, $^2J_{CP}$=8.0 Hz, $C_0^1$) ppm.

Stage 2: Synthesis of Dendrimer G′$_1$ with α-Hydroxy-Phosphonic Acid Ends (Na Salt)

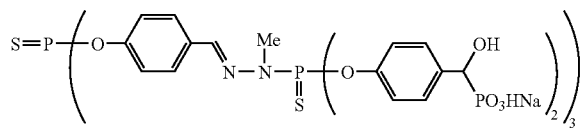

Bromotrimethylsilane (15.8 mmol) is added slowly to a solution of first-generation dendrimer G′$_1$ with α-hydroxy-dimethyl-phosphonate ends (0.8 mmol, 1 g) obtained in Stage 1 at 0° C. in acetonitrile (5 mL) with distilled triethylamine (4.8 mmol). Once the addition is finished the mixture is allowed to return to room temperature over 12 hours. The mixture is then evaporated to dryness then 1 mL of anhydrous methanol is added at room temperature and the mixture is left for one hour under stirring. After evaporation to dryness, the residue is washed several times with ether. Since the product is totally insoluble in organic solvents it is converted to its monosodium salt in the presence of a previously titrated sodium hydroxide solution. The resulting solution is lyophilized in order to produce the dendrimer in the form of a white powder. The final product is isolated with a yield of 48%.

NMR $^{31}$P-$\{^1H\}$ (D$_2$O/CD$_3$CN): δ=10.1 (s, P(O)(OH)(ONa)), 56.10 (s, P$_0$), 66.91 (s, P$_1$) ppm.

Example 2

Synthesis of First-Generation Dendrimer (Core P$_3$N$_3$) with α-Hydroxy-Dimethylphosphonate Ends

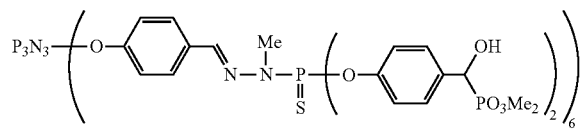

1 g of Gc′$_1$ (0.35 mmol) is placed in solution in 1 ml of THF then distilled triethylamine (10 μl or 0.84·10$^{-3}$ mol) and dimethylphosphite (382 μL or 4.2·10$^{-3}$ mol) (1 equiv per —CHO) are added. The mixture is left for 12 hours under stirring. The paste obtained is then washed with a THF/Et$_2$O: mixture 1/1, in order to produce a white powder. The final product is isolated with a yield of 72%.

NMR $^{31}$P-$\{^1H\}$ (DMSO d6): δ=11.46 (s, P$_0$), 27.10 (s, P(O)(O—CH$_3$)$_2$), 66.07 (s, P$_1$) ppm.

NMR $^1$H (DMSO d6): δ=3.35 (d, $^3J_{HP}$=10.5 Hz, 18H, CH$_3$—N—P$_1$), 3.54 (d, $^3J_{HP}$=10.3 Hz, 36H, P(O)—O—CH$_3$), 3.59 (d, $^3J_{HP}$=10.4 Hz, 36H, P(O)—O—CH$_3$), 5.01 (dd, $^3J_{HH}$=5.2 Hz, $^2J_{HP}$=13.5 Hz, 12H, CH—P(O)), 6.41 (dd, $^3J_{HH}$=5.6 Hz, $^3J_{HP}$=15.5 Hz, 12H, OH), 7.18-7.93 (m, 78H, H$_{arom}$, CH=N) ppm.

NMR $^{13}$C-$\{^1H\}$ (DMSO d6): δ=32.8 (d, $^2J_{CP}$=11.9 Hz, CH$_3$—N—P$_1$), 52.7 (d, $^2J_{CP}$=6.9 Hz, CH$_3$—O—P(O)), 53.2 (d, $^2J_{CP}$=6.9 Hz, CH$_3$—O—P(O)), 68.2 (d, $^1J_{CP}$=162.3 Hz, C—OH), 120.4 (broad s, $C_1^2$), 120.8 (s, $C_0^2$), 128.2 (s, $C_0^3$), 128.7 (d, $^3J_{CP}$=5.7 Hz, $C_1^3$), 132.0 (s, $C_0^4$), 135.5 (s, $C_1^4$), 140.2 (d, $^3J_{CP}$=13.8 Hz, CH=N), 149.4 (d, $^2J_{CP}$=6.3 Hz, $C_1^1$), 150.5 (s, $C_0^1$) ppm.

IR: Absence of ν(CHO) at 1670 cm$^{-1}$; ν(OH) at 3271 cm$^{-1}$.

Example 3

Synthesis of Second-Generation Dendrimer with α-Hydroxy-Dimethylphosphonate Ends

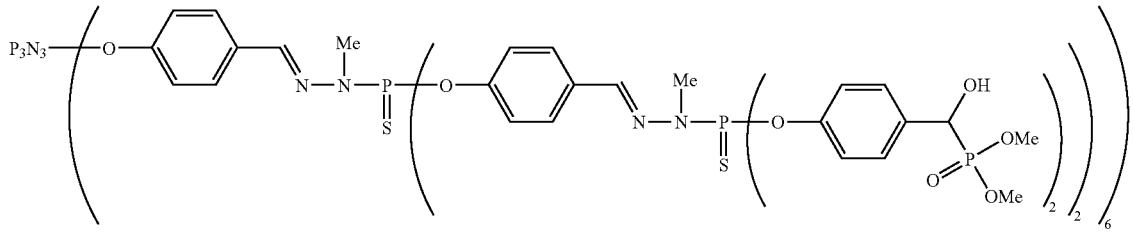

The dendrimer Gc′$_2$ (0.146 mmol, 1 g) is placed in solution in 1 ml of THF with distilled triethylamine (1.3 mmol, 15 μL), and dimethylphosphite (3.5 mmol, 319 μL). The mixture is left for 12 hours with magnetic stirring. The paste obtained is then washed with a THF/Et$_2$O: mixture 1/1, in order to produce a white powder. The final product is isolated with a yield of 80%.

NMR $^{31}$P-$\{^1H\}$ (DMSO d6): δ=11.7 (s, P$_0$), 27.10 (s, P(O)(O—CH$_3$)$_2$), 66.1 (broad s, P$_{1,2}$) ppm.

NMR $^1$H (DMSO d6): δ=3.29 (broad d, $^3J_{HP}$=9.2 Hz, 54H, CH$_3$—N—P$_1$, CH$_3$—N—P$_2$), 3.49 (d, $^2J_{CP}$=10.9 Hz, 72H, P(O)—O—CH$_3$), 3.55 (d, $^2J_{CP}$=10.6 Hz, 72H, P(O)—O—CH$_3$), 5.00 (dd, $^3J_{HH}$=5.4 Hz, $^2J_{HP}$=15.7 Hz, 24H, CH—P(O)), 6.30 (dd, $^3J_{HH}$=5.4 Hz, $^2J_{HP}$=15.7 Hz, 24H, OH), 7.0-8.0 (m, 186H, H$_{arom}$, CH=N) ppm.

NMR $^{13}$C-$\{^1H\}$ (DMSO d6): δ=32.8 (broad d, $^2J_{CP}$=11.3 Hz, CH$_3$—N—P$_{1,2}$), 52.7 (d, $^2J_{CP}$=6.2 Hz, CH$_3$—O—P(O)), 53.2 (d, $^2J_{CP}$=6.3 Hz, CH$_3$—O—P(O)), 68.2 (d, $^1J_{CP}$=163.0 Hz, C—OH), 120.4 (broad s, $C_2^2$), 120.8 (broad s, $C_0^2$), 121.4 (s, $C_1^2$), 128.2 (s, $C_0^3$), 128.2 (s, $C_1^3$), 128.7 (d, $^3J_{CP}$=3.7 Hz, $C_2^3$), 132.1 (s, $C_0^4$), 132.1 (s, $C_1^4$), 135.4 (s, $C_2^4$), 140.2 (broad s, CH=N—N(Me)-P$_{1,2}$), 149.4 (d, $^2J_{CP}$=3.8 Hz, $C_2^1$), 150.4 (s, $C_0^1$) 150.7 (d, $^2J_{CP}$=6.4 Hz, $C_1^1$) ppm.

IR: Absence of ν(CHO) at 1670 cm$^{-1}$; ν(OH) at 3271 cm$^{-1}$.

Example 4

Synthesis of Third-Generation Dendrimer with α-Hydroxy-Dimethylphosphonate Ends

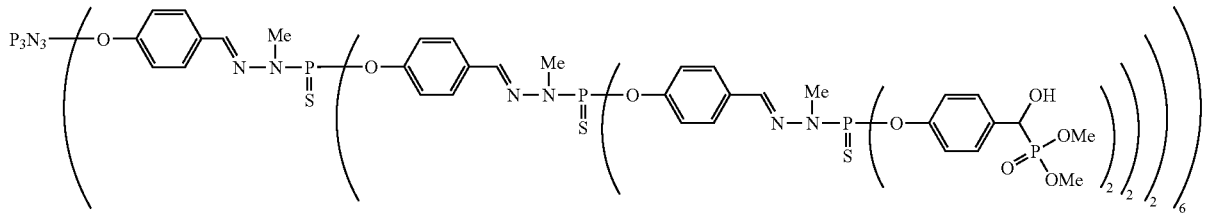

The dendrimer Gc'$_3$ (1.35·10$^{-2}$ mmol, 0.2 g) is placed in solution in 0.2 ml of THF with distilled triethylamine (0.8 mmol, 10 μL), and dimethylphosphite (0.648 mmol, 59 μL). The mixture is left for 12 hours with magnetic stirring. The paste obtained is then washed with a THF/Et$_2$O: mixture 1/1, in order to produce a white powder. The final product is isolated with a yield of 85%.

NMR $^{31}$P-{$^1$H} (DMSO d6): δ=11.7 (s, P$_0$), 28.6 (s, P(O)(O—CH$_3$)$_2$), 66.4 (broad s, P$_{1,2,3}$) ppm.

NMR $^1$H (DMSO d6): δ=3.40 (broad d, $^3J_{HP}$=10.7 Hz, 126H, CH$_3$—N—P$_1$, CH$_3$—N—P$_2$, CH$_3$—N—P$_3$), 3.60 (d, $^2J_{CP}$=13.15 Hz, 144H, P(O)—O—CH$_3$), 3.65 (d, $^2J_{CP}$=13.16 Hz, 144H, P(O)—O—CH$_3$), 5.10 (dd, $^3J_{HH}$=4.3 Hz, $^2J_{HP}$=15.3 Hz, 48H, CH—P(O)), 6.4 (dd, $^3J_{HH}$=4.3 Hz, $^2J_{HP}$=15.3 Hz, 48H, OH), 7.0-8.1 (m, 402H, H$_{arom}$, CH=N) ppm.

NMR $^{13}$C-{$^1$H} (DMSO d6): δ=32.8 (broad s, CH$_3$—N—P$_{1,2,3}$), 52.7 (d, $^2J_{CP}$=6.3 Hz, CH$_3$—O—P(O)), 53.2 (d, $^2J_{CP}$=7.4 Hz, CH$_3$—O—P(O)), 68.1 (d, $^1J_{CP}$=162.8 Hz, C—OH), 119.5 (s, C$_1^2$), 120.4 (broad s, C$_3^2$, C$_0^2$), 121.4 (s, C$_2^2$), 128.3 (broad s, C$_0^3$, C$_1^3$, C$_2^3$), 128.6 (d, $^3J_{CP}$=4.2 Hz, C$_3^3$), 132.1 (s, C$_0^4$, C$_1^4$, C$_2^4$), 135.5 (s, C$_3^4$), 140.2 (broad s, CH=N—N(Me)-P$_{1,2,3}$), 149.4 (d, $^2J_{CP}$=8.3 Hz, C$_3^1$), 150.6 (broad s, C$_0^1$, C$_1^1$, C$_2^1$) ppm.

IR: Absence of ν(CHO) at 1670 cm$^{-1}$; ν(OH) at 3271 cm$^{-1}$.

Example 5

Synthesis of First-Generation Dendrimer with α-Hydroxy-Phosphonic Acid Ends

Stage 1: Dendrimer with α-Hydroxy-Phosphonic Acid Ends

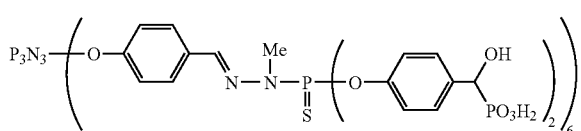

The first-generation dendrimer (4.78·10$^{-2}$ mmol, 200 mg) with α-hydroxy-dimethylphosphonate ends obtained in Example 2 is suspended in acetonitrile (4 mL) with triethylamine (0.575 mmol, 20.5 μL) at 0° C. Then trimethylsilane bromide (1.72 mmol, 229 μL) is added slowly at 0° C., the mixture slowly returns to room temperature over 6 hours. Then anhydrous methanol (1 mL) is added. After 2 hours of stirring the reaction mixture is dried under reduced pressure. Then the powder is suspended in a minimum amount of water for 30 minutes with vigorous stirring. After filtration, the product is dried then thoroughly washed with ether. Preferably, in order to obtain a soluble dendrimer, the final dendrimer must not be totally desolvated. The final product is isolated with a yield of 51%.

NMR $^{31}$P-{$^1$H} (DMSO d6): δ=11.40 (s, P$_0$), 22.0 (m, P(O)(OH)$_2$), 66.05 (s, P$_1$) ppm.

NMR $^1$H (DMSO d6): δ=3.29 (d, $^3J_{HP}$=10.5 Hz, 18H, CH$_3$—N—P$_1$), 4.67 (d, $^3J_{HP}$=13.9 Hz, 12H, —CH—OH), 4.7-5.7 (m, 36H, —OH), 7.0-8.0 (m, 78H, H$_{arom}$, CH=N) ppm.

NMR $^{13}$C-{$^1$H} (DMSO d6): δ=32.9 (d, $^2J_{CP}$=15.7 Hz, CH$_3$—N—P$_1$), 69.5 (d, $^1J_{CP}$=163.5 Hz, C—OH), 120.0 (broad s, C$_1^2$), 120.7 (s, C$_0^2$), 128.2 (s, C$_0^3$), 128.6 (s, C$_1^3$), 132.0 (s, C$_0^4$), 137.1 (s, C$_1^4$), 140.2 (broad s, CH=N), 148.8 (s, C$_1^1$), 150.4 (s, C$_0^1$) ppm.

IR: Absence of ν(CHO) at 1670 cm$^{-1}$; ν(OH) at 3271 cm$^{-1}$.

Stage 2: Dendrimer with α-Hydroxy-Phosphonic Acid Sodium Salt Ends

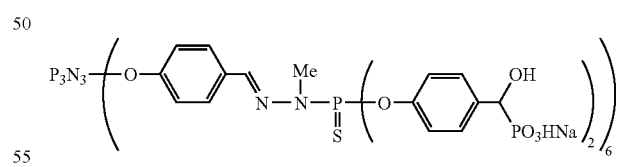

The dendrimer obtained in the preceding stage is dissolved in a solution of titrated soda (0.1966 M, 12 eq.). The solution obtained is filtered on a Millipore filter then freeze-dried. The first-generation dendrimer with monosodium salt ends of alpha-hydroxy-phosphonic acid is obtained in the form of a white powder with a yield of 82%.

NMR $^{31}$P{$^1$H} (D$_2$O/CD$_3$CN, 81 MHz): δ=12.5 (s1, N$_3$P$_3$), 17.8 (s1, P=O), 67.5 (s1, P=S).

Example 6

Synthesis of Second-Generation Dendrimer with α-Hydroxy-Phosphonic Acid Ends

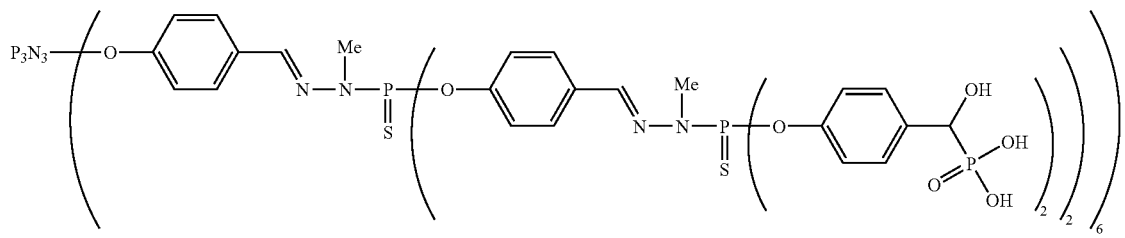

The second-generation dendrimer (3.16·10$^{-2}$ mmol, 300 mg) with α-hydroxy-dimethylphosphonate ends obtained in Example 3 is suspended in acetonitrile (1.5 mL) with triethylamine (0.86 mmol, 30 μL) at 0° C. Then trimethylsilane bromide (2.3 mmol, 304 μL) is added slowly at 0° C., the mixture slowly returns to room temperature over 6 hours. Then anhydrous methanol (1 mL) is added. After 2 hours of stirring the reaction mixture is dried under reduced pressure. Then the powder is suspended in a minimum amount of water for 30 minutes with vigorous stirring. After filtration, the product is dried then thoroughly washed with ether. Preferably, if a soluble product is desired, the final dendrimer must not be totally desolvated. The final product is isolated with a yield of 62%.

NMR $^{31}$P-{$^1$H} (DMSO d6): δ=11.9 (s, P$_0$), 21.5 (m, P(O)(OH)$_2$), 66.00 (broad s, P$_{1,2}$) ppm.

NMR $^1$H (DMSO d6): δ=3.06 (broad s, 54H, CH$_3$—N—P$_{1,2}$), 4.66 (d, $^3J_{HP}$=14.0 Hz, 24H, —CH—OH), 3.7-5.2 (m, 72H, —OH), 6.7-8.0 (m, 186H, H$_{arom}$, CH=N) ppm.

NMR $^{13}$C-{$^1$H} (DMSO d6): δ=33.6 (broad s, CH$_3$—N—P$_{1,2}$), 70.2 (d, $^1J_{CP}$=158.5 Hz, C—OH), 121.0 (broad s, C$_2^2$, C$_0^2$), 122.0 (s, C$_1^2$), 129.5 (broad s, C$_0^3$, C$_1^3$, C$_2^3$), 132.8 (s, C$_0^4$, C$_1^4$), 137.4 (s, C$_2^4$), 141.0 (broad s, CH=N), 149.8 (broad s, C$_2^1$), 151.2 (broad s, C$_0^1$, C$_1^1$) ppm.

IR: Absence of ν(CHO) at 1670 cm$^{-1}$; ν(OH) at 3271 cm$^{-1}$.

The derivatives with phosphonic acid terminations can be obtained by application or adaptation of this method using the compounds of Examples 1 to 5 and 8 to 10 having a dimethyl phosphonate group. This reaction does not work starting with the compound having a diisopropyl phosphonate group of Example 7.

Example 7

Synthesis of First-Generation Dendrimer with Vinyl-Diisopropyl-Phosphonate Terminations Tetraisopropyl-methylene-gem-diphosphonate (3 mmol) as well as sodium hydride (3 mmol, 75 mg) are placed in 2 mL of distilled THF. This mixture is left under vigorous stirring for 2 hours at room temperature. Once the evolution of hydrogen has finished, it is slowly added to the dendrimer Gc'$_1$ (0.17 mmol, 500 mg) which has been previously placed in solution in 3 mL of distilled THF. The addition is carried out at 0° C. then the mixture is allowed to return to room temperature overnight. After evaporation of the THF, the white solid is washed with a pentane/ether mixture 1/1 in order to remove the excess of tetraisopropyl-methylene-gem-diphosphonate. Then the dendrimer is suspended in the minimum amount of water, the cloudy solution obtained is centrifuged. A white powder is recovered after centrifugation but it can sometimes be necessary to repeat the operation (centrifugation) a second time still with the minimum amount of water. The final product is isolated with a yield of 55%.

NMR $^{31}$P-{$^1$H} (CDCl$_3$): δ=11.66 (s, P$_0$); 65.73 (s, P$_1$); 20.31 (s, P=O) ppm.

NMR (CDCl$_3$): δ=1.26 (d, $^3J_{HH}$=6.2 Hz, 72H, CH$_3$—CH); 1.32 (d, $^3J_{HH}$=6.2 Hz, 72H CH$_3$—CH); 3.27 (d, $^3J_{HP}$=10.4 Hz, 18H, N-Me); 4.66 (hept, $^3J_{HH}$=5.9 Hz, 24H, O—CH—(CH$_3$)$_2$); 6.14 (dd, $^3J_{HH\ trans}$=$^2J_{HP(O)}$=17.1 Hz, 12H, —CH=CH—P(O)); 6.9-7.7 (m, 90H, CH$_{arom}$, CH=N, —CH=CH—P(O)) ppm.

NMR $^{13}$C-{$^1$H} (CDCl$_3$): δ=24.0 (d, $^3J_{CP}$=5.0 Hz, CH$_3$—CH); 32.9 (d, $^2J_{CP}$=12 Hz, CH$_3$—N—P$_1$); 70.5 (d, $^2J_{CP}$=5.0 Hz, —O—CH—CH$_3$); 116.1 (d, $^1J_{CP}$=192.52 Hz, —CH=CH—P(O)(OiPr)$_2$); 121.4 (broad s, C$_0^2$); 121.8 (d, $^3J_{CP}$=4.9 Hz, C$_1^2$); 128.3 (s, C$_0^3$); 129.0 (s, C$_1^3$); 132.2 (d, $^3J_{CP}$=18.7 Hz, C$_1^4$); 132.7 (s, C$_0^4$); 139.0 (d, $^3J_{CP}$=14.46 Hz, CH=N); 146.3 (d, $^2J_{CP}$=6.3 Hz, —CH=CH—P(O)(OiPr)$_2$); 151.3 (broad s, C$_0^1$); 151.6 (d, $^2J_{CP}$=5.7 Hz, C$_1^1$) ppm.

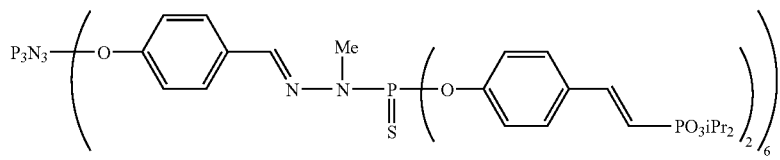

Example 8

Synthesis of First-Generation Dendrimer with Vinyl-Dimethyl-Phosphonate Terminations

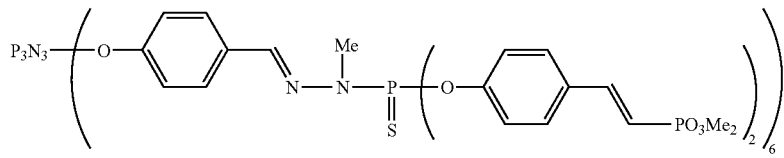

Tetramethyl-methylene-gem-diphosphonate (11.7 mmol, 2.7 g) as well as sodium hydride (11.7 mmol, 281 mg) are placed in 10 mL of distilled THF. This mixture is left under vigorous stirring for 2 hours at room temperature. Once the evolution of hydrogen has finished, it is slowly added to the dendrimer Gc'$_2$ (0.7 mmol, 1 g) which has been previously placed in solution in 5 mL of distilled THF. The addition is carried out at 0° C. then the mixture is allowed to return to room temperature overnight. After evaporation of the THF, the white solid is washed with a pentane/ether mixture 1/1 in order to remove the excess of tetramethyl-methylene-gem-diphosphonate. Then the dendrimer is suspended in the minimum amount of water, the cloudy solution obtained is centrifuged. A white powder is recovered after centrifugation but it can sometimes be necessary to repeat the operation (centrifugation) a second time still with the minimum amount of water. The final product is isolated with a yield of 63%.

NMR $^{31}$P-{$^1$H} (CDCl$_3$): δ=11.7 (s, P$_0$); 65.5 (s, P$_1$); 25.43 (s, P=O) ppm.

NMR $^1$H (CDCl$_3$): δ=3.27 (d, $^3J_{HP}$=9.5 Hz, 18H, N-Me); 3.72 (d, $^3J_{HP}$=10.6 Hz, 72H, O—C$\underline{H}_3$); 6.08 (dd, $^3J_{HH\ trans}$=$^2J_{HP(O)}$=16.9 Hz, 12H, —CH=C$\underline{H}$—P(O)); 6.9-7.8 (m, 90H, CH$_{arom}$, CH=N, —C$\underline{H}$=CH—P(O)) ppm.

NMR $^{13}$C-{$^1$H} (CDCl$_3$): δ=32.9 (d, $^2J_{CP}$=12.13 Hz, CH$_3$—N—P$_1$); 52.4 (d, $^2J_{CP}$=5.6 Hz, —O—C$\underline{H}_3$); 112.7 (d, $^1J_{CP}$=191.64 Hz, —CH=C$\underline{H}$—P(O)(OMe)$_2$); 121.3 (broad s, C$_0^2$); 121.7 (d, $^3J_{CP}$=3.2 Hz, C$_1^2$); 128.2 (s, C$_0^3$); 129.1 (s, C$_1^3$); 131.9 (s, C$_0^4$); 132.1 (d, $^3J_{CP}$=16.9 Hz, C$_1^4$); 139.0 (d, $^3J_{CP}$=13.4 Hz, CH=N); 148.03 (d, $^2J_{CP}$=6.8 Hz, —CH=CH—P(O)(OMe$_2$); 151.2 (broad s, C$_0^1$); 151.8 (d, $^2J_{CP}$=6.3 Hz, C$_1^1$) ppm.

Example 9

Synthesis of Second-Generation Dendrimer with Vinyl-Dimethyl-Phosphonate Terminations Tetramethyl-methylene-gem-diphosphonate (0.77 mmol, 0.18 g) as well as sodium hydride (0.78 mmol, 19 mg) are placed in 4 mL of distilled THF, this mixture is left under vigorous stirring for 2 hours at room temperature. Once the evolution of hydrogen has finished, it is slowly added to the dendrimer Gc'$_2$ (2.9·10$^{-2}$ mmol, 0.2 mg) which has been previously placed in solution in 2 mL of distilled THF. The addition is carried out at 0° C. then the mixture is allowed to return to room temperature overnight. After evaporation of the THF, the white solid is washed with a pentane/ether mixture 1/1 in order to remove the excess of tetramethyl-methylene-gem-diphosphonate. Then, the dendrimer is suspended in the minimum amount of water, the cloudy solution obtained is centrifuged. A white powder is recovered after centrifugation but it can sometimes be necessary to repeat the operation (centrifugation) a second time still with the minimum amount of water. The final product is isolated with a yield of 68%.

NMR $^{31}$P-{$^1$H} (CDCl$_3$): δ=11.8 (s, P$_0$); 65.4 (s, P$_2$); 65.9 (s, P$_1$); 25.4 (s, P=O) ppm.

NMR (CDCl$_3$): δ=3.26 (broad d, $^3J_{HP}$=10.2 Hz, 54H, N-Me); 3.66 (d, $^3J_{HP}$=10.4 Hz, 144H, O—C$\underline{H}_3$); 6.06 (dd, $^3J_{HH\ trans}$=$^2J_{HP(O)}$=16.9 Hz, 24H, —CH=C$\underline{H}$—P(O)); 6.9-7.8 (m, 210H, CH$_{arom}$, CH=N, —C$\underline{H}$=CH—P(O)) ppm.

NMR $^{13}$C-{$^1$H} (CDCl$_3$): δ=33.0 (d, $^2J_{CP}$=12.5 Hz, CH$_3$—N—P$_{1,2}$); 52.5 (d, $^2J_{CP}$=5.3 Hz, —O—C$\underline{H}_3$); 112.6 (d, $^1J_{CP}$=192.08 Hz, —CH=C$\underline{H}$—P(O)(OMe)$_2$); 121.4 (broad s, C$_0^2$); 121.9 (broad s, C$_1^2$, C$_2^2$); 128.4 (broad s, C$_0^3$, C$_1^3$); 129.2 (s, C$_2^3$); 132.0 (s, C$_1^4$); 132.4 (broad s, C$_0^4$, C$_2^4$); 139.2 (d, $^3J_{CP}$=13.6 Hz, CH=N); 148.1 (d, $^2J_{CP}$=5.4 Hz, —CH=CH—P(O)(OMe)$_2$); 151.2 (s, C$_0^1$); 151.3 (d, $^2J_{CP}$=6.9 Hz, C$_1^1$); 151.8 (d, $^2J_{CP}$=6.4 Hz, C$_2^1$) ppm.

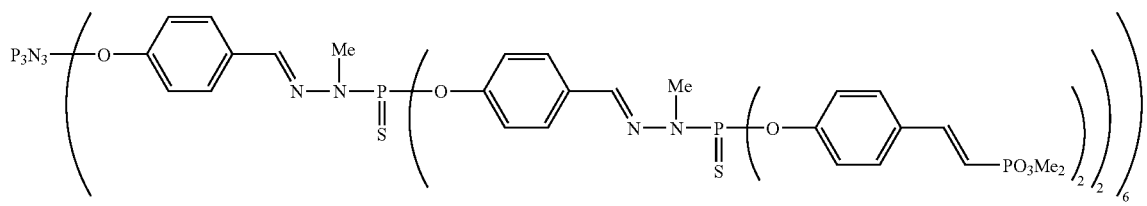

Example 10

Synthesis of Third-Generation Dendrimer with
Vinyl-Dimethyl-Phosphonate Terminations

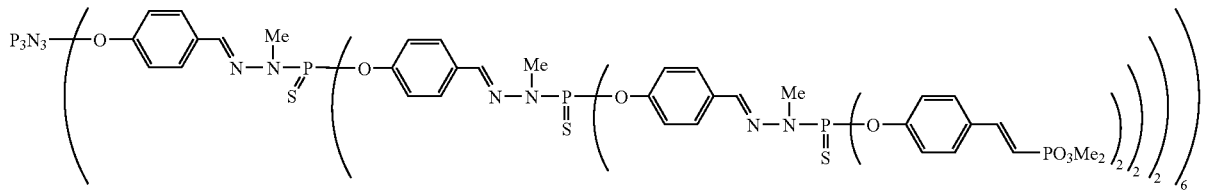

Tetramethyl-methylene-gem-diphosphonate (0.71 mmol, 165 mg) as well as sodium hydride (0.71 mmol, 17.1 mg) are placed in 5 mL of distilled THF, this mixture is left under vigorous stirring for 2 hours at room temperature. Once the evolution of hydrogen has finished, it is slowly added to the dendrimer Gc'$_3$ (1.35·10$^{-2}$ mmol, 200 mg) which has been previously placed in solution in 3 mL of distilled THF. The addition is carried out at 0° C. then the mixture is allowed to return to room temperature overnight. After evaporation of the THF, the white solid is washed with a pentane/ether mixture 1/1 in order to remove the excess of tetramethyl-methylene-gem-diphosphonate. Then, the dendrimer is suspended in the minimum amount of water, the cloudy solution obtained is centrifuged. A white powder is recovered after centrifugation but it can sometimes be necessary to repeat the operation (centrifugation) a second time still with the minimum amount of water. The final product is isolated with a yield of 72%.

NMR $^{31}$P-{$^1$H} (CDCl$_3$): δ=11.7 (s, P$_0$); 65.3 (s, P$_3$); 66.0 (s, P$_{1,2}$); 25.5 (s, P=O) ppm.

NMR $^1$H (CDCl$_3$): δ=3.29 (broad s, 126H, N-Me); 3.68 (d, $^3J_{HP}$=7.7 Hz, 288H, O—CH$_3$); 6.08 (dd, $^3J_{HH\ trans}$=$^2J_{HP(O)}$=17.6 Hz, 48H, —CH=CH—P(O)); 6.9-7.8 (m, 450H, CH$_{arom}$, CH=N, —CH=CH—P(O)) ppm.

NMR $^{13}$C-{$^1$H} (CDCl$_3$): δ=33.0 (d, $^2J_{CP}$=13.1 Hz, CH$_3$—N—P$_{1,2,3}$); 52.5 (d, $^2J_{CP}$=5.5 Hz, —O—CH$_3$); 112.6 (d, $^1J_{CP}$=192.2 Hz, —CH=CH—P(O)(OMe)$_2$); 121.9 (broad d, $^3J_{CP}$=2.7 Hz, C$_0^2$, C$_1^2$, C$_2^2$, C$_3^2$); 128.3 (broad s, C$_0^3$, C$_1^3$, C$_2^3$); 129.1 (s, C$_3^3$); 131.9 (broad s, C$_0^4$, C$_2^4$); 132.1 (s, C$_1^4$); 132.2 (s, C$_3^4$); 139.2 (d, $^3J_{CP}$=13.2 Hz, CH=N); 148.3 (broad s, —CH=CH—P(O)(OMe)$_2$); 151.3 (s, C$_1^1$, C$_0^1$); 151.8 (s, C$_3^1$); 152.0 (s, C$_2^1$) ppm.

Example 11

4-Hydroxybenzyl-Dimethyl-Phosphonate Synthesis

Stages a) to d) of this multi-stage synthesis were already described by J. D. Olsjewski et al *J. Org. Chem.* 1994, 59, 4285-4296.

a) Synthesis of
4-Tertiobutyldimethylsiloxy-Benzaldehyde

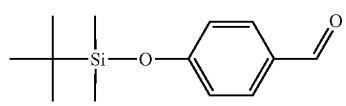

4-hydroxy-benzaldehyde (10 g, 0.082 mol) is placed in solution in 100 mL of dichloromethane. Chlorotrimethylsilane (11.72 g, 0.078 mol) as well as N,N-dimethylaminopyridine (1 g, 0.008 mol) and triethylamine (23 mL, 0.164 mol) are added to this solution at room temperature. The mixture is left at room temperature for 48 hours with magnetic stirring then the solvent is evaporated under reduced pressure. The solid obtained is stirred in pure pentane (3×200 mL), and the silylated product is thus extracted.

b) Synthesis of 4-Tertiobutyldimethylsiloxy-Benzyl Alcohol

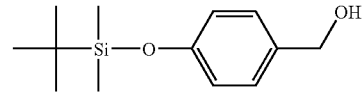

4-tertiobutyldimethylsiloxy-benzaldehyde (28 g, 0.118 mol) is placed in solution in a THF/ethanol mixture (50 mL/10 mL). Sodium borohydride (9 g, 0.237 mol) is added to this solution at room temperature and this suspension is stirred under argon and at room temperature for 4 days. Then all the solvents of the reaction medium are evaporated under reduced pressure and a very compact white gel is thus obtained. The latter is suspended in ether then a solution of saturated ammonium hydrochloride is very slowly added, until a more homogeneous solution is obtained in the two phases. When the two phases are homogeneous the final product is separated by simple water/ether decantation. The ether phase is evaporated then the product obtained is taken up in pentane and washed once with water.

c) Synthesis of 4-Tertiobutyldimethylsiloxy-Benzyl Trifluoroacetate

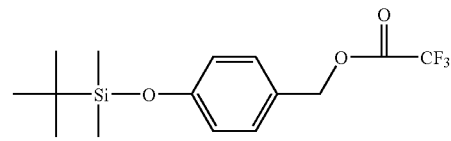 [SMILES: CC(C)(C)[Si](C)(C)Oc1ccc(COC(=O)C(F)(F)F)cc1]

The benzylic alcohol obtained in b) (27 g, 0.113 mol) is placed in solution in THF (100 mL); trifluoroacetic anhydride (19.2 mL, 0.136 mol) is added to this solution at room temperature. Then the mixture is refluxed in the THF for one hour.

Then the mixture is left to slowly return to room temperature, and 75% of the THF is evaporated then the mixture is taken up in ether and washed firstly with a solution of sodium hydrogen carbonate (2×100 mL) and once with water (100 mL).

d) Synthesis of 4-Tertiobutyldimethylsiloxy-Benzyl Bromide

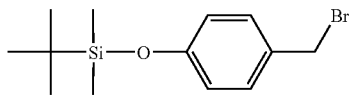 [SMILES: CC(C)(C)[Si](C)(C)Oc1ccc(CBr)cc1]

The trifluoroacetate obtained in c) (35 g, 0.105 mol) is placed in solution in THF (100 mL), lithium bromide (11 g, 0.126 mol) is added to this solution and the mixture is refluxed in the THF for 18 hours. The THF is evaporated under reduced pressure then the product is taken up in 40 mL of acetonitrile and a decantation is carried out with hexane (4×100 mL). The hexane is evaporated and a whitish oil is obtained containing white crystals. The oil must then be recovered again using hexane but by filtering these crystals. The product is isolated with a yield of 84%.

e) Synthesis of 4-Tertiobutyldimethylsiloxy-Benzyl-Dimethyl-Phosphonate

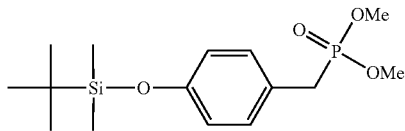 [SMILES: COP(=O)(Cc1ccc(O[Si](C)(C)C(C)(C)C)cc1)OC]

Trimethylphosphite (4 mmol, 0.47 mL) is added to the benzyl bromide of 4-tertiobutyldimethylsiloxane obtained in d) (2.72 mmol, 800 mg). The trimethylphosphite is added in several goes: firstly the first equivalent is added (0.32 mL) then the mixture is taken to 80° C. with stirring and without solvent. The reaction releases methyl bromide which must be eliminated under reduced pressure in order to allow the reaction to be complete. After 4 hours of reflux the excess of trimethylphosphite is added (0.15 mL). The reaction mixture is again taken to 80° C. for 2 hours. The final mixture contains traces of trimethylphosphite and methyl-dimethylphosphite, by-product caused by the formation of methyl bromide, which can be eliminated under reduced pressure at 80° C. The final product is obtained in the form of an oil, with a yield of 90%.

NMR $^{31}$P-{$^1$H} (CDCl$_3$): δ=32.6 (s, P) ppm.
NMR $^1$H (CDCl$_3$): δ=0.17 (s, 6H, Si—CH$_3$); 0.97 (s, 9H, Si-tBu); 3.09 (d, $^2J_{HP}$=21.2 Hz, 2H, —CH$_2$—); 3.63 (d, $^2J_{HP}$=10.7 Hz, 6H, O-Me); 6.78 (d, $^3J_{HH}$=8.5 Hz, 2H, CH$_{arom}$); 7.15 (dd, $^3J_{HH}$=8.5 Hz, $^4J_{HP}$=2.5 Hz, 2H, CH$_{arom}$) ppm.

Synthesis of 4-Hydroxy-Benzyl-Dimethyl-Phosphonate

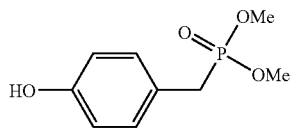 [SMILES: COP(=O)(Cc1ccc(O)cc1)OC]

The siloxane obtained in e) (2.72 mmol) is placed in solution in 5 mL anhydrous THF, then tetrabutylammonium fluoride in anhydrous solution at 1 M in THF is added (5.4 mmol, 5.5 mL). The mixture is left for 48 hours at room temperature. A few drops of water are added to this reaction mixture; after 1 hour of stirring the product is washed with pentane. The product is then purified by filtration on silica using a solvent gradient: firstly pure ether, then with a pentane/THF mixture 1/1.

The final product is recrystallized from dichloromethane, for this it is dissolved in a minimum amount of hot dichloromethane then it is left to very slowly return to room temperature. It is cooled again to −20° C., and the product is recovered totally pure, in the form of white crystals with a yield of 50%.

NMR $^{31}$P-{$^1$H} (CDCl$_3$): δ=32.4 (s, P) ppm.
NMR $^1$H (CDCl$_3$): δ=3.07 (d, $^2J_{HP}$=22.0 Hz, 2H, —CH$_2$—); 3.68 (d, $^2J_{HP}$=10.8 Hz, 6H, O-Me); 6.64 (dd, $^3J_{HH}$=8.6 Hz, $^5J_{HP}$=0.78 Hz, 2H, CH$_{arom}$); 7.04 (dd, $^3J_{HH}$=8.6 Hz, $^4J_{HP}$=2.8 Hz, 2H, CH$_{arom}$); 7.68 (broad s, 1H, OH) ppm.
NMR $^{13}$C-{$^1$H} (CDCl$_3$): δ=31.7 (d, $^1J_{CP}$=139.6 Hz, —CH$_2$—P); 53.1 (d, $^2J_{CP}$=6.9 Hz, —OMe); 116.0 (s, C$_2$); 120.8 (d, $^2J_{CP}$=8.17 Hz, C$_4$); 130.7 (d, $^3J_{CP}$=7.54 Hz, C$_3$), 156.0 (d, $^5J_{CP}$=3.14 Hz, C$_1$) ppm.

Example 12

Synthesis of a First-Generation Dendrimer with Benzyl-Dimethyl-Phosphonate Ends

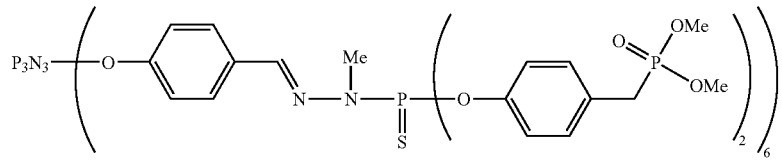

The first-generation dendrimer with dichlorothiophosphine ends Gc$_1$ (0.109 mmol, 200 mg) is placed in solution in THF (2 mL). Cesium carbonate (2.6 mmol, 853 mg) and 4-hydroxy-benzyl-dimethyl-phosphonate (1.3 mmol, 282 mg) are added to this solution. The mixture is left under stirring for 24 hours at room temperature. After filtration, the sample is placed under vacuum until a white powder is obtained which is washed with a pentane/ether mixture (1/1). The final product is isolated with a yield of 73%.

NMR $^{31}$P-{$^1$H} (CDCl$_3$): δ=66.2 (s, P$_1$); 31.9 (s, P(O)(OMe)$_2$); 12.3 (s, P$_0$) ppm.

NMR $^1$H ((CD$_3$)$_2$CO): δ=3.15 (d, $^2J_{HP}$=21.5 Hz, 24H, CH$_2$); 3.32 (d, $^3J_{HP}$=10.5 Hz, 18H, CH$_3$—N—P$_1$); 3.58 (d, $^3J_{HP}$=10.9 Hz, 72H, P(O)—O—CH$_3$); 6.90-7.90 (m, 78H, H$_{arom}$, CH=N) ppm.

NMR $^1$H (CD$_3$)$_2$CO): δ=3.15 (d, $^2J_{HP}$=22.2 Hz, 48H, CH$_2$); 3.25 (d, $^3J_{HP}$=11.2 Hz, 54H, CH$_3$—N—P$_{1,2}$); 3.55 (d, $^3J_{HP}$=10.8 Hz, 144H, P(O)—O—CH$_3$); 6.70-7.90 (m, 186H, H$_{arom}$, CH=N) ppm.

NMR $^{13}$C-{$^1$H} (CDCl$_3$): δ=32.1 (d, $^1J_{CP}$=138.6 Hz, —CH$_2$—P(O)(OMe)$_2$); 33.0 (d, $^2J_{CP}$=12.2 Hz, CH$_3$—N—P$_{1,2}$); 52.9 (d, $^2J_{CP}$=6.3 Hz, —O—CH$_3$); 121.4 (s, C$_0^2$); 121.5 (s, C$_1^2$); 121.6 (broad d, $^3J_{CP}$=3.5 Hz, C$_2^2$); 128.3 (s, C$_0^3$, C$_1^3$); 128.4 (d, $^2J_{CP}$=8.9 Hz, C$_2^4$); 130.8 (d, $^2J_{CP}$=6.5 Hz, C$_2^3$); 132.1 (s, C$_0^4$); 132.3 (s, C$_1^4$); 138.6 (d, $^3J_{CP}$=13.7 Hz, CH=N—N(Me)-P$_2$); 139.1 (d, $^3J_{CP}$=12.8 Hz, CH=N—N(Me)-P$_1$); 149.6 (dd, $^2J_{CP}$=6.1 Hz, $^5J_{CP}$=3.8 Hz, C$_2^1$); 151.1 (s, C$_0^1$); 151.2 (d, $^2J_{CP}$=7.6 Hz, C$_1^1$) ppm.

Example 14

Synthesis of a Third-Generation Dendrimer with Benzyl-Dimethyl-Phosphonate Ends

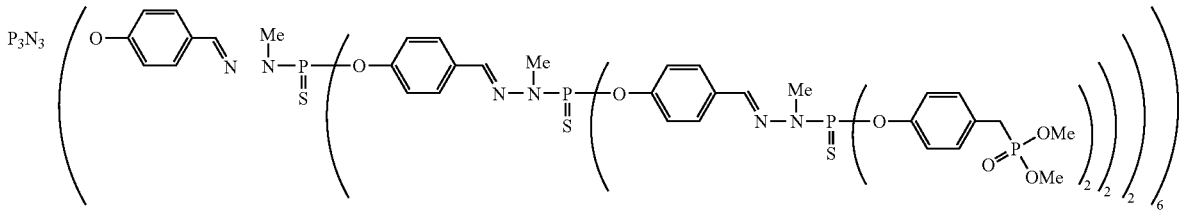

NMR $^{13}$C-{$^1$H} ((CD$_3$)$_2$CO): δ=31.85 (d, $^1J_{CP}$=136.4 Hz, —CH$_2$—P(O)(OMe)$_2$); 33.4 (d, $^2J_{CP}$=16.8 Hz, CH$_3$—N—P$_1$); 52.8 (d, $^2J_{CP}$=6.8 Hz, —O—CH$_3$); 121.9 (broad s, C$_0^2$ and C$_1^2$); 129.1 (s, C$_0^3$); 130.3 (d, $^2J_{CP}$=8.6 Hz, C$_1^4$); 131.8 (d, $^2J_{CP}$=6.18 Hz, C$_1^3$); 133.3 (s, C$_0^4$); 140.4 (d, $^3J_{CP}$=14.04 Hz, CH=N); 150.3 (broad d, $^2J_{CP}$=3.8 Hz, C$_1^1$); 152.0 (broad d, C$_0^1$) ppm.

Example 13

Synthesis of a Second-Generation Dendrimer with Benzyl-Dimethyl-Phosphonate Ends The third-generation dendrimer with dichlorothiophosphine ends Gc$_3$ (0.014 mmol, 150 mg) is placed in solution in THF (2 mL). Cesium carbonate (1.4 mmol, 460 mg) and 4-hydroxy-benzyl-dimethyl-phosphonate (0.71 mmol, 153 mg) are added to this solution. The mixture is left under stirring for 24 hours at room temperature. After filtration, the sample is placed under vacuum until a white powder is obtained which is washed with a pentane/ether mixture (1/1). The final product is isolated with a yield of 80%.

NMR $^{31}$P-{$^1$H} (CDCl$_3$): δ=66.0 (s, P$_{1,2,3}$); 31.9 (s, P(O)(OMe)$_2$); 11.5 (s, P$_0$) ppm.

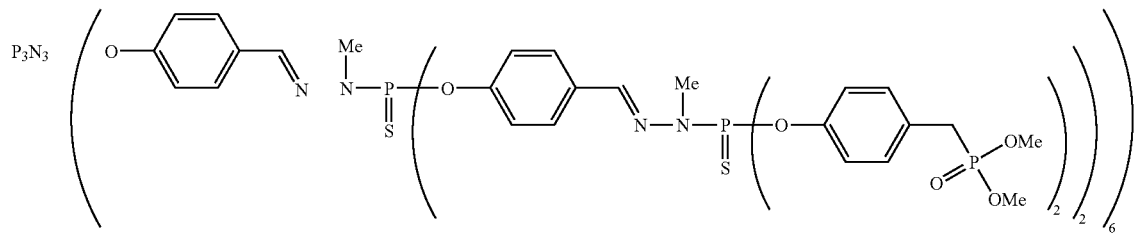

The second-generation dendrimer with dichlorothiophosphine ends Gc$_2$ (0.02 mmol, 100 mg) is placed in solution in THF (2 mL). Cesium carbonate (1.5 mmol, 490 mg) and 4-hydroxy-benzyl-dimethyl-phosphonate (0.53 mmol, 113 mg) are added to this solution. The mixture is left under stirring for 24 hours at room temperature. After filtration, the sample is placed under vacuum until a white powder is obtained which is washed with a pentane/ether mixture (1/1). The final product is isolated with a yield of 78%.

NMR $^{31}$P-{$^1$H} (CDCl$_3$): δ=66.0 (s, P$_2$); 65.9 (s, P$_1$); 31.8 (s, P(O)(OMe)$_2$); 11.8 (s, P$_0$) ppm.

NMR $^1$H (CDCl$_3$): δ=3.03 (d, $^2J_{HP}$=21.5 Hz, 96H, CH$_2$); 3.23 (d, $^3J_{HP}$=9.7 Hz, 126H, CH$_3$—N—P$_{1,2,3}$); 3.54 (d, $^3J_{HP}$=10.8 Hz, 288H, P(O)—O—CH$_3$); 6.70-7.90 (m, 402H, H$_{arom}$, CH=N) ppm.

NMR $^{13}$C-{$^1$H} (CDCl$_3$): δ=31.8 (d, $^1J_{CP}$=122.5 Hz, —CH$_2$—P(O)(OMe)$_2$); 33.1 (s, CH$_3$—N—P$_{1,2,3}$); 52.9 (d, $^2J_{CP}$=7.4 Hz, —O—CH$_3$); 121.2 (s, C$_1^2$); 121.5 (s, C$_3^2$); 121.7 (broad s, C$_2^2$, C$_0^2$); 128.3 (s, C$_0^3$, C$_1^3$, C$_2^3$); 128.4 (d, $^2J_{CP}$=10.1 Hz, C$_3^4$); 130.5 (s, C$_0^4$); 130.6 (s, C$_1^4$); 130.8 (d, $^2J_{CP}$=6.2 Hz, C$_3^3$) 132.2 (s, C$_2^4$); 138.7 (broad d, $^3J_{CP}$=13.6

Hz, $\underline{CH}=N\!-\!N(Me)\text{-}P_{1,2,3}$); 148.3 (broad s, $C_0^1$); 149.6 (dd, $^2J_{CP}$=4.3 Hz, $^5J_{CP}$=4.3 Hz, $C_3^1$); 151.2 (d, $^2J_{CP}$=7.1 Hz, $C_1^1$, $C_2^1$) ppm.

Example 15

Synthesis of a First-Generation Dendrimer with Benzyl-Phosphonic Ends

Stage 1: Dendrimer with Benzyl Phosphonic Acid Ends

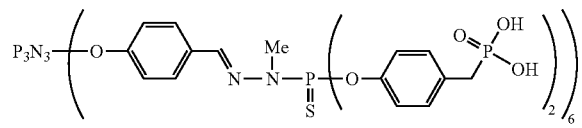

$C_1^3$, $^2J_{CP}$=6.8 Hz); 131.1 (s, $C_1^4$); 132.1 (s, $C_0^4$); 139.8 (broad d, $^3J_{CP}$=10.8 Hz, $\underline{CH}=N$); 148.3 (d, $^2J_{CP}$=7.2 Hz, $C_1^1$); 150.4 (s, $C_0^1$) ppm.

Stage 2: Dendrimer with Benzyl Phosphonic Acid Sodium Salt Ends

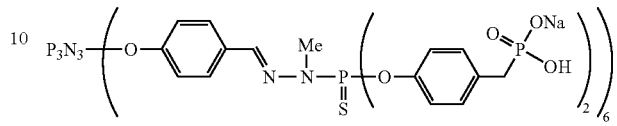

The dendrimer obtained in the preceding stage is dissolved in a solution of titrated soda (0.1966 M, 12 eq.). The solution obtained is filtered on a Millipore filter then freeze-dried. The first-generation dendrimer with benzylphosphonic acid monosodium salt ends is obtained in the form of a white powder with a yield of 89%. NMR $^{31}P\{^1H\}$ ($D_2O/CD_3CN$, 81 MHz): $\delta$=12.0 (s1, $N_3P_3$), 21.3 (s1, P=O), 65.8 (m, P=S).

Example 16

Synthesis of a Second-Generation Dendrimer with Benzyl-Phosphonic Ends

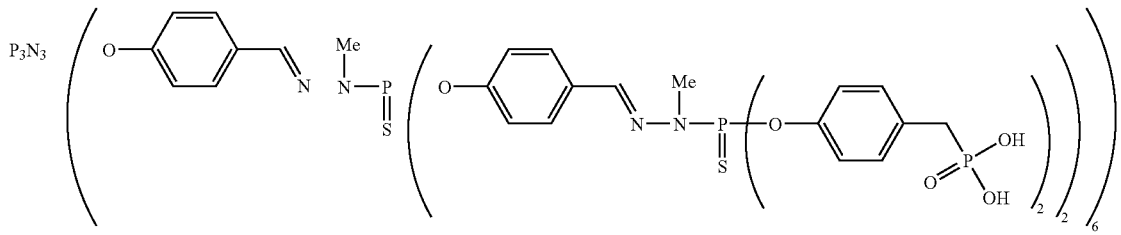

The first-generation dendrimer with benzyl-dimethylphosphonate ends obtained in Example 12 (400 mg, 0.1 mmol) is placed in solution in acetonitrile (1 mL). The mixture is cooled to 0° C. then bromotrimethylsilane (386 μl, 2.9 mmol) or 1.2 equivalents of silane per methyl end is slowly added. The mixture is left for 16 hours at room temperature. Then the sample is placed under vacuum for two hours. After a powder is obtained, anhydrous methanol (1 mL) is added, the suspension is stirred for 2 hours, finally the product is placed under vacuum again for 1 hour. The powder obtained is washed several times with water and with ether. The final product is isolated with a yield of 70%.

NMR $^{31}P\text{-}\{^1H\}$ (DMSO d6): $\delta$=66.1 (s, $P_1$); 25.2 (s, P(O)(OH)$_2$); 11.7 (s, $P_0$) ppm.

NMR $^1H$ (DMSO d6): $\delta$=2.89 (d, $^2J_{HP}$=20.7 Hz, 24H, $CH_2$); 3.22 (d, $^3J_{HP}$=10.6 Hz, 18H, $CH_3\!-\!N\!-\!P_1$); 4.0-5.2 (m, 24H, $-PO_3H_2$); 6.70-7.90 (m, 78H, $H_{arom}$, $CH=N$) ppm.

NMR $^{13}C\text{-}\{^1H\}$ (DMSO d6): $\delta$=32.8 (d, $^2J_{CP}$=11.3 Hz, $CH_3\!-\!N\!-\!P$); 34.3 (d, $^1J_{CP}$=132.7 Hz, $-\underline{CH_2}\!-\!P(O)(OH)_2$); 120.4 (s, $C_1^2$); 120.9 (s, $C_0^2$); 128.2 (s, $C_0^3$); 130.9 (d, The second-generation dendrimer with benzyl-dimethylphosphonate ends obtained in Example 13 (130 mg, 0.014 mmol) is placed in solution in acetonitrile (1 mL). The mixture is cooled to 0° C. then bromotrimethylsilane (101 μl, 0.76 mmol) or 1.2 equivalents of silane per methyl end is slowly added. The mixture is left for 16 hours at room temperature. Then the sample is left under vacuum for two hours. After a powder is obtained, anhydrous methanol (1 mL) is added, the suspension is stirred for 2 hours, finally the product is placed under vacuum again for one hour. The powder obtained is washed several times with water and with ether. The final product is isolated with a yield of 63%.

NMR $^{31}P\text{-}\{^1H\}$ (DMSO d6/$D_2O$): $\delta$=66.1 (s, $P_{1,2}$); 25.5 (s, P(O)(OH)$_2$); 11.9 (s, $P_0$) ppm.

NMR $^1H$ (DMSO d6/$D_2O$): $\delta$=2.95 (broad s, 48H, $CH_2$); 3.40-3.75 (m, 54H, $CH_3\!-\!N\!-\!P_{1,2}$); 6.50-7.30 (m, 186H, $H_{arom}$, $CH=N$) ppm.

NMR $^{13}C\text{-}\{^1H\}$ (DMSO d6/$D_2O$): $\delta$=32.9 (d, $^2J_{CP}$=11.5 Hz, $CH_3\!-\!N\!-\!P_{1,2}$); 34.5 (d, $^1J_{CP}$=133.7 Hz, $-\underline{CH_2}\!-\!P(O)(OH)_2$); 119.5 (s, $C_0^2$); 120.4 (s, $C_2^2$); 121.4 (s, $C_1^2$); 128.2 (s, $C_0^3$, $C_1^3$); 131.0 (broad s, $C_2^4$, $C_2^3$); 132.1 (s, $C_0^4$, $C_1^4$); 140.3 (broad d, $^3J_{CP}$=11.1 Hz, $CH=N$); 148.3 (d, $^2J_{CP}$=3.6 Hz, $C_2^1$); 150.3 (s, $C_0^1$); 150.7 (s, $^2J_{CP}$=6.0 Hz, $C_1^1$) ppm.

Example 17

Synthesis of a Third-Generation Dendrimer with Benzyl-Phosphonic Ends

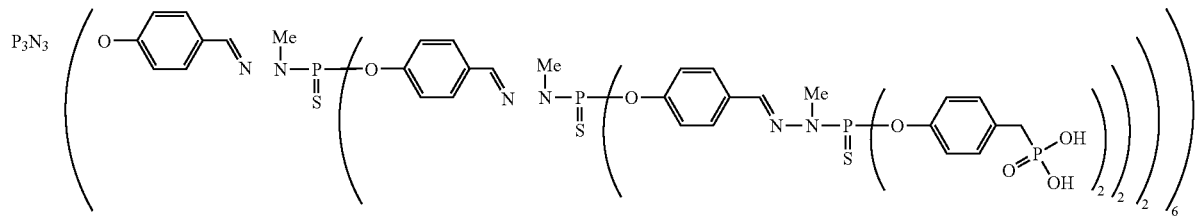

The third-generation dendrimer with benzyl-dimethyl-phosphonate ends obtained in Example 14 (200 mg, 0.01 mmol) is placed in solution in acetonitrile (1 mL). The mixture is cooled to 0° C. then bromotrimethylsilane (146 μl, 1.09 mmol) or 1.1 equivalents of silane per methyl end is slowly added. The mixture is left for 16 hours at room temperature. Then, the sample is placed under vacuum for two hours. After a powder is obtained, anhydrous methanol (1 mL) is added, the suspension is stirred for 2 hours, finally the product is placed under vacuum again for one hour. The powder obtained is washed several times with water and with ether. The final product is isolated with a yield of 81%.

NMR $^{31}$P-{$^1$H} (DMSO d6): δ=66.1 (s, $P_{1,2,3}$); 25.1 (s, $P(O)(OH)_2$); 11.7 (s, $P_0$) ppm.

NMR $^1$H (DMSO d6): δ=2.94 (d, $^2J_{HP}$=23.1 Hz, 96H, $CH_2$); 3.10-3.40 (m, 126H, $CH_3$—N—$P_{1,2,3}$); 5.2-6.2 (m, 96H, —$PO_3H_2$); 7.00-8.10 (m, 402H, $H_{arom}$, CH=N) ppm.

NMR $^{13}$C-{$^1$H} (DMSO d6): δ=32.9 (d, $^2J_{CP}$=12.2 Hz, $CH_3$—N—$P_{1,2,3}$); 34.5 (d, $^1J_{CP}$=132.1 Hz, —$CH_2$—$P(O)(OH)_2$); 119.5 (s, $C_0^2$); 120.4 (s, $C_3^2$); 120.6 (s, $C_2^2$); 121.4 (s, $C_1^2$); 128.3 (s, $C_0^3$, $C_1^3$, $C_2^3$); 131.0 (broad s, $C_3^4$, $C_3^3$); 132.1 (broad s, $C_0^4$, $C_1^4$, $C_2^4$); 140.3 (broad d, $^3J_{CP}$=10.4 Hz, CH=N); 148.3 (d, $^2J_{CP}$=6.2 Hz, $C_3^1$); 150.6 (broad d, $^2J_{CP}$=7.2 Hz, $C_0^1$, $C_1^1$, $C_2^1$) ppm.

Example 18

Synthesis of a Zero-Generation Dendrimer ($P_3N_3$ Core) with α-Hydroxy-Dimethylphosphonate Ends

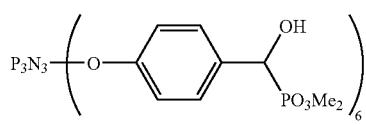

Distilled triethylamine (5 μl or 0.42·10$^{-3}$ mol), and dimethylphosphite (196 μL or 2.1·10$^{-3}$ mol) (1 equiv per —CHO) is added to 301 mg of $P_3N_3(OC_6H_4$—CHO)$_6$ (0.35 mmol) in solution in 1 ml of THF. The mixture is left for 12 hours under stirring. The paste obtained is then washed with a THF/Et$_2$O mixture 1/1, in order to produce a white powder. The final product is isolated with a yield of 78%.

NMR $^{31}$P-{$^1$H} (DMSO d6): δ=11.5 (s, $P_0$), 27.2 (s, P(O)(O—$CH_3$)$_2$) ppm.

Example 19

Synthesis of a Zero-Generation Dendrimer with α-Hydroxy-Phosphonic Acid Ends

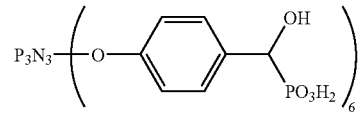

The zero-generation dendrimer of Example 18 (4.78·10$^{-2}$ mmol, 72 mg) with α-hydroxy-dimethylphosphonate ends is suspended in acetonitrile (4 mL) with triethylamine (0.288 mmol, 10.25 μL) at 0° C. Then trimethylsilane bromide (0.86 mmol, 115 μL) is added slowly at 0° C., the mixture slowly returns to room temperature over 6 hours, then anhydrous methanol (1 mL) is added. After 2 hours of stirring the reaction mixture is dried under reduced pressure. Then the powder is suspended in a minimum amount of water for 30 minutes with vigorous stirring. After filtration, the product is dried then thoroughly washed with ether. Preferably, in order to obtain a soluble dendrimer, the final dendrimer must not be totally desolvated. The final product is isolated with a yield of 60%.

NMR $^{31}$P-{$^1$H} (DMSO d6): δ=11.3 (s, $P_0$), 22.0 (m, P(O)(OH)$_2$) ppm.

IR: Absence of ν(CHO) at 1670 cm$^{-1}$; ν(OH) at 3271 cm$^{-1}$.

Example 20

Synthesis of a Zero-Generation Dendrimer with Benzyl-Dimethyl-Phosphonate Ends

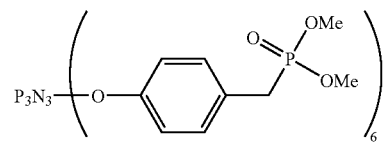

Cesium carbonate (1.3 mmol, 427 mg) and 4-hydroxy-benzyl-dimethyl-phosphonate (0.65 mmol, 141 mg) are added to a solution of hexachlorocyclotriphosphazene (0.109 mmol, 38 mg) in 2 mL of THF. The mixture is left under stirring for 24 hours at room temperature. After filtration, the sample is placed under vacuum until a white powder is obtained which is washed with a pentane/ether mixture (1/1). The final product is isolated with a yield of 61%.

NMR $^{31}$P-{$^1$H} (CDCl$_3$): δ=12.2 (s, P$_0$); 31.8 (s, P(O)(OMe)$_2$) ppm.

Example 21

Synthesis of a Zero-Generation Dendrimer with Benzyl-Phosphonic Ends

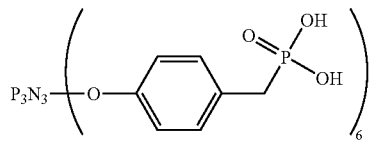

The zero-generation dendrimer with benzyl-dimethyl-phosphonate ends of Example 20 (126 mg, 0.1 mmol) is placed in solution in acetonitrile (1 mL). The mixture is cooled to 0° C. then bromotrimethylsilane (198 μl, 1.45 mmol) or 1.2 equivalents of silane per methyl end is slowly added. The mixture is left for 16 hours at room temperature, then the sample is placed under vacuum for two hours. After a powder is obtained, anhydrous methanol (1 mL) is added, the suspension is stirred for 2 hours, finally the product is placed under vacuum again for 1 hour. The powder obtained is washed several times with water and with ether. The final product is isolated with a yield of 79%.

NMR $^{31}$P-{$^1$H} (DMSO d$^6$): δ=11.8 (s, P$_0$); 25.1 (m, P(O)(OH)$_2$) ppm.

Example 22

Synthesis of (4-Hydroxy-2-Nitrophenylamino)Methyl-Dimethylphosphonate

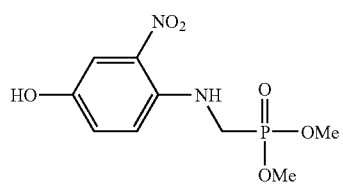

500 mg of 2-nitro-4-hydroxy-aniline, 1 mL of 37% solution of formaldehyde in water and 1.2 mL of dimethylphosphite are mixed at room temperature. The resulting red solution is stirred at room temperature for 96 hours. The crude residue is directly purified by silica gel chromatography (eluent: diethyl ether then ethyl acetate). The red residue obtained after column chromatography is diluted in 300 mL of ethyl acetate then washed with 50 mL of water. The organic phase is then dried over magnesium sulphate then evaporated to dryness in order to produce the expected product in the form of a red powder with a yield of 71%.

NMR $^{31}$P-{$^1$H} (Acetone): δ=28.7 (s, P(O)(OMe)$_2$) ppm.

NMR $^1$H (Acetone): δ=3.8 (d, $^3$J$_{HP}$=10.8 Hz, 6H, —OMe); 3.90 (d, $^2$J$_{HP}$=12.6 Hz, 2H, N—CH$_2$—P); 5.9 (broad s, 1H, —NH); 7.0-8.0 (m, 3H, CH$_{arom}$) ppm.

NMR $^{13}$C-{$^1$H} (Acetone): δ=38.5 (d, $^1$J$_{CP}$=154.7 Hz, CH$_2$); 52.9 (d, $^2$J$_{CP}$=6.0 Hz, OMe); 110.1 (s, C$_{arom}$); 116.5 (s, C$_{arom}$); 126.8 (s, C$_{arom}$); 132.6 (s, C$_{arom}$); 139.8 (s, C$_{arom}$); 148.3 (s, C$_{arom}$) ppm.

[M+Na]$^+$=299.2 g·mol$^{-1}$.

Example 23

Synthesis of a First-Generation Dendrimer with a Cyclotriphosphazene Core and with a 2-Nitrophenylaminomethyl-Dimethylphosphonate Surface

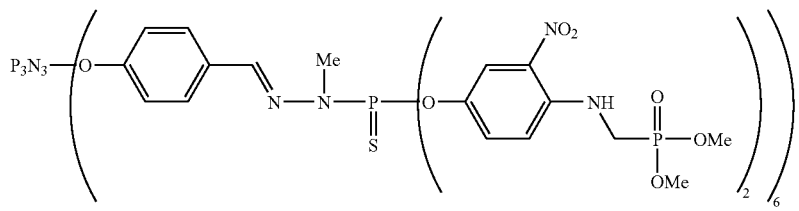

90 mg of phenol (4-hydroxy-2-nitrophenylamino)methyl-dimethyl-phosphonate of Example 22 is added at room temperature to a suspension of NaH (7 mg) in THF. After one hour of stirring, 30 mg of Gc$_1$ dendrimer in solution in 5 mL of anhydrous THF are added. The mixture is left under stirring for 24 hours at room temperature then filtered on celite and the final mixture is centrifuged in order to separate the salts. Finally the final product is washed by precipitation in pentane and isolated with a yield of 82%.

NMR $^{31}$P-{$^1$H} (CDCl$_3$): δ=66.1 (s, P$_1$); 28.6 (s, P(O)(OMe)$_2$); 11.9 (s, P$_0$) ppm.

NMR $^1$H (CDCl$_3$): δ=3.6 (d, $^3$J$_{HP}$=14.6 Hz, 18H, CH$_3$—N—P$_1$); 3.78 (d, $^3$J=10.7 Hz, 72H, —P(O)(O—CH$_3$)$_2$); 3.9 (d, $^2$J$_{HP}$=12.6 Hz, 24H, —CH$_2$—P(O)(OCH$_3$)$_2$); 7.0-8.1 (m, 66H, CH$_{arom}$, CH=N) ppm.

Example 24

Synthesis of a First-Generation Dendrimer with a Cyclotriphosphazene Core with an Aza-Mono-Phosphonic Surface Derived from Allylamine Stage 1: Allylimine on the Surface of Phosphorus-Containing Dendrimers

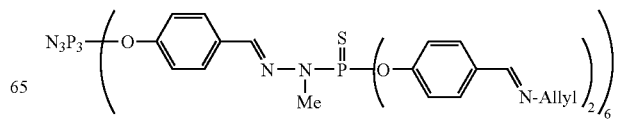

Allylamine (400 μL, 66 eq., 5.33 mmol) and a few grams of MgSO$_4$ are added to a solution of Gc'1 (230 mg, 80.5 μmol) in CH$_2$Cl$_2$ (10 mL). The suspension is stirred for 24 hours at room temperature then diluted with 10 mL of CH$_2$Cl$_2$ and filtered. The solid is rinsed with 10 mL of CH$_2$Cl$_2$ and the solution is evaporated under reduced pressure. The viscous residue is washed with ether then with a THF/pentane mixture and with acetonitrile. The solid obtained is solubilized in CH$_2$Cl$_2$, the solution is then filtered and concentrated under reduced pressure in order to produce the dendrimer with an 3.78 (d, 36H, $^3J_{HP}$=11.9 Hz, POMe); 4.06 (d, 12H, $^2J_{HP}$=19.8 Hz, PCH); 5.08 (m, 24H, CH$_2$=); 5.78 (m, 12H, CH=); 7.04 (d, 12H, $^3J_{HH}$=8.3 Hz, C$_0^2$—H); 7.19 (d, 24H, $^3J_{HH}$=7.9 Hz, C$_1^2$—H); 7.35 (d, 24H, $^3J_{HH}$=6.9 Hz, C$_1^3$—H); 7.61 (m, 18H, C$_0^3$—H, CH=N).

Stage 3a: First-Generation Phosphorus-Containing Dendrimer with Monophosphonic Acid (Na Salt) Ends

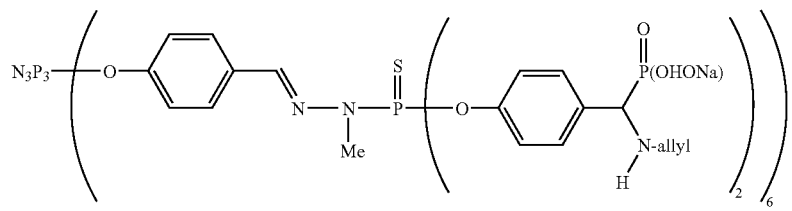

N-allylamine surface in the form of a pale yellow powder with a yield of 75%.

NMR $^{31}$P{$^1$H} (CDCl$_3$, 81.01 MHz): δ=11.7 (s, N$_3$P$_3$); 65.3 (s, P=S).

$^1$H (CDCl$_3$, 200.13 MHz): δ=3.25 (d, 18H, $^3J_{HP}$=10.5 Hz, NCH$_3$); 4.19 (d, 24H, $^3J_{HH}$=5.6 Hz, CH$_2$CH=); 5.21 (m, 24H, CH$_2$=); 6.02 (m, 12H, CH=); 6.98 (d, 12H, $^3J_{HH}$=8.5 Hz, C$_0^2$—H); 7.21 (m, 24H, C$_1^2$—H); 7.60 (m, 42H, C$_0^3$—H, C$_1^3$—H and CH=NN); 8.17 (bs, 12H, CH=N).

Stage 2: First-Generation Phosphorus-Containing Dendrimer with Monophosphonate Ends

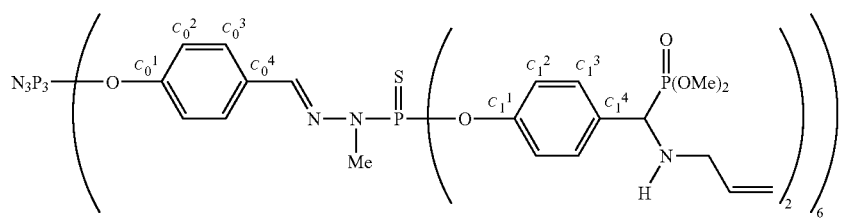

Dimethyl phosphite (1 mL, 10.9 mmol) in a large excess (205 eq.) is added to the dendrimer with N-allylimine terminations (200 mg, 60.4 μmol) without solvent. The solution obtained is stirred for 72 hours at room temperature then diluted with 2 mL of THF. The dendrimer is precipitated by addition of a large volume of pentane and the solid obtained is washed twice with a THF/pentane mixture then 3 times with ether then dried in order to produce a white powder with a yield of 70%.

NMR $^{31}$P{$^1$H} (CDCl$_3$, 81.01 MHz): δ=11.5 (s, N$_3$P$_3$); 28.9 (s, P=O); 65.6 (s, P=S).

NMR $^1$H (CDCl$_3$, 250.13 MHz): δ=2.90-3.01 (m, 12H, CHHN); 3.10-3.20 (m, 12H, CHHN); 3.30 (d, 18H, $^3J_{HP}$=10.1 Hz, NCH$_3$); 3.68 (d, 36H, $^3J_{HP}$=10.5 Hz, POMe);

The solid is dried under reduced pressure until a powder is obtained. A soda solution (0.1966 M, 12 eq.) is slowly added to the solid. The solution obtained is filtered then freeze-dried. The dendrimer with aminophosphonic acid terminations is obtained in the form of a white powder with a yield of 65%.

NMR $^{31}$P{$^1$H} (D$_2$O/CD$_3$CN, 81.01 MHz): 12.1 (s, N$_3$P$_3$), 14.5 (s, P=O), 66.7 (s, P=S).

Stage 3b: The Same Compound can be Obtained According to the Following Alternative Procedure 36 equivalents of N(Et)$_3$ (118 μL, 0.846 mmol) then 90 equivalents (280 μL, 2.11 mmol) of bromotrimethylsilane are added at 0° C. under an argon flow to a solution of dendrimer 13 equivalents of HCl 1M in ether are added at 0° C. under an argon flow to a solution of dendrimer with dimethyl phosphonate terminations (220 mg, 46.9 μmol) in acetonitrile. The heterogeneous solution is stirred for 2 hours at room temperature then concentrated under reduced pressure. The residue is suspended in distilled acetonitrile and 30 equivalents of bromo-trimethylsilane are added under argon at 0° C. The solution is stirred for 20 hours at room temperature then concentrated under reduced pressure. 5 mL of methanol are added and the mixture is vigorously stirred for 2 hours. The methanol is eliminated under reduced pressure and the residue is washed with distilled ether, then water and methanol.

with dimethyl N-allylphosphonate terminations obtained in Stage 2 (110 mg, 23.5 µmol) in a CH$_3$CN/CH$_2$Cl$_2$ mixture (5/5 mL). The solution is stirred for 20 hours at room temperature then concentrated under reduced pressure. 3 mL of methanol are added and the mixture is vigorously stirred for 2 hours. The methanol is eliminated under reduced pressure and the residue is washed with distilled ether, then water and methanol. The solid is dried under reduced pressure until a powder is obtained. A soda solution (0.1966 M, 12 eq.) is slowly added to the solid. The solution obtained is filtered then freeze-dried. The dendrimer with aminophosphonic acid terminations is obtained in the form of a white powder.

Example 25

Synthesis of a First-Generation Dendrimer with a Cyclotriphosphazene Core with an Aza-Mono-Phosphonic Surface Derived from Benzylamine Stage 1: Benzylimine on the Surface of Phosphorus-Containing Dendrimers CH$_2$Cl$_2$ (15 mL). The suspension is stirred for 24 hours at room temperature then diluted with 10 mL of CH$_2$Cl$_2$ and filtered. The solid is rinsed with 10 mL of CH$_2$Cl$_2$ and the solution is evaporated under reduced pressure. The viscous residue is washed with ether then with a THF/pentane mixture and with acetonitrile. The solid obtained is solubilized in CH$_2$Cl$_2$, then the resulting solution is filtered and concentrated under reduced pressure in order to produce a pale yellow solid with a yield of 92%.

NMR $^{31}$P{$^1$H} (CDCl$_3$, 81.01 MHz): δ=11.8 (s, N$_3$P$_3$); 65.3 (s, P=S).

NMR $^1$H (CDCl$_3$, 200.13 MHz): δ=3.20 (d, 18H, $^3J_{HP}$=10.4 Hz, NCH$_3$); 4.75 (s, 24H, CH$_2$Ph); 6.98 (d, 12H, $^3J_{HH}$=8.6 Hz, C$_0^2$—H); 7.30 (m, 84H, C$_1^2$—H and C$_6$H$_5$); 7.64 (s, 6H, CH=NN); 7.65 (d, 12H, $^3J_{HH}$=8.8 Hz, C$_0^3$—H); 7.68 (d, 24H, $^3J_{HH}$=8.6 Hz, C$_1^3$—H); 8.27 (s, 12H, CH=N).

NMR $^{13}$C{$^1$H} (CDCl$_3$, 50.3 MHz): δ=32.9 (d, $^2J_{CP}$=12.1 Hz, NMe); 64.0 (s, NCH$_2$); 121.5 (d, $^2J_{CP}$=4.5 Hz, C$_0^2$ and C$_1^2$); 127.1 (s, C$_p$); 127.9 (s, C$_m$); 128.3 (s, C$_0^3$); 128.5 (s, C$_o$); 129.6 (s, C$_1^3$); 132.0 (s, C$_0^4$); 133.6 (s, C$_1^4$); 138, 8 (bs, CH=N—N); 139.1 (s, C$_i$); 151.2 (bs, C$_0^1$); 152.3 (d, $^2J_{CP}$=7.5 Hz, C$_1^1$); 160.5 (s, CH=N).

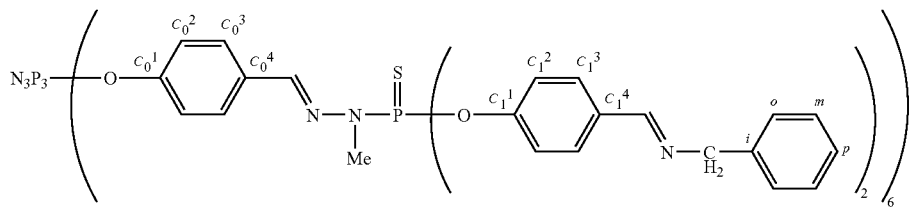

Benzylamine (450 µL, 38 eq, 4.1 mmol) and 4 grams of MgSO$_4$ are added to a solution of Gc'1 (310 mg, 108 µmol) in Stage 2a: Dendrimer with a Dimethyl Benzylamino Mono-Phosphonate Surface

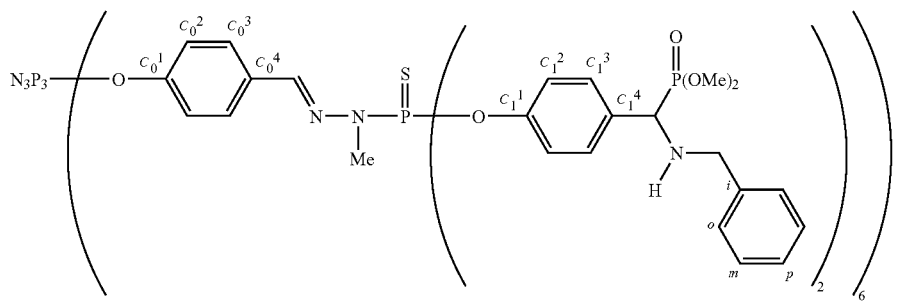

Dimethyl phosphite (1 mL, 10.9 mmol) in a large excess (195 eq) is then added to the dendrimer with N-benzylimine terminations described above (210 mg, 53 μmol) without solvent. The solution obtained is stirred for 72 hours at room temperature then diluted with 2 mL of THF. The dendrimer is precipitated by addition of a large volume of pentane and the solid obtained is washed twice with a THF/pentane mixture then 3 times with ether. After drying under reduced pressure, a white solid is obtained with a yield of 61%.

NMR $^{31}$P{$^1$H} (CDCl$_3$, 81.01 MHz): δ=11.5 (s, N$_3$P$_3$); 28.7 (s, P=O); 65.6 (s, P=S).

NMR $^1$H (CDCl$_3$, 200.13 MHz): δ=2.17 (bs, 12H, NH); 3.30 (d, 18H, $^3J_{HP}$=10.2 Hz, NMe); 3.46 (d, 12H, $^2J_{HH}$=13.6 Hz, NCHH); 3.47 (d, 36H, $^3J_{HP}$=10.6 Hz, POMe); 3.65 (d, 36H, $^3J_{HP}$=10.6 Hz, POMe); 3.71 (d, 12H, $^2J_{HH}$=13.6 Hz, NCHH); 3.98 (d, 12H, $^2J_{HP}$=20.8 Hz, PCH); 7.04 (d, 12H, $^3J_{HH}$=8.5 Hz, $C_0^2$—H); 7.25 (m, 84H, $C_1^2$—H and $C_6H_5$); 7.31 (d, 24H, $^3J_{HH}$=6.8 Hz, $C_1^3$—H); 7.60 (s, 6H, CH=N); 7.61 (d, 12H, $^3J_{HH}$=8.5 Hz, $C_0^3$—H).

NMR $^{13}$C{$^1$H} (CDCl$_3$, 62.89 MHz): δ=32.9 (d, $^2J_{CP}$=12.3 Hz, NMe); 51.1 (d, $^3J_{CP}$=17.0 Hz, NCH$_2$); 53.5 (d, $^2J_{CP}$=6.9 Hz, POMe); 53.8 (d, $^2J_{CP}$=7.2 Hz, POMe); 58.5 (d, $^1J_{CP}$=154.2 Hz, PCH); 121.2 (bs, $C_0^2$); 121.4 (bs, $C_1^2$); 127.2 (s, $C_p$); 128.3 (s, $C_0^3$ and $C_m$); 128.4 (s, $C_o$); 129.8 (d, $^3J_{CP}$=5.5 Hz, $C_1^3$); 132.1 (s, $C_0^4$); 132.6 (bs, $C_1^4$); 138.9 (bs, CH=N and $C_i$); 150.4 (d, $^2J_{CP}$=5.9 Hz, $C_1^1$); 151.3 (bs, $C_0^1$).

Stage 2b: The Same Compound can be Obtained According to the Alternative Procedure Described Below 12.2 equivalents (500 mg, 1.55 mmol) of functionalized phenol synthesized in Stage 1 of Example 50 (solubilized in acetonitrile or THF) and 15 equivalents (623 mg, 1.91 nimbi) of Cs$_2$CO$_3$ are added to a solution of Gc1 dendrimer (233 mg, 0.127 mmol) with S=PCl$_2$ terminations in THF or acetonitrile. The resulting suspension is stirred until the chlorines are completely substituted ($^{31}$P and $^1$H NMR monitoring). The mixture is decanted, the supernatant is collected and the residual solid is washed with THF. The supernatants are combined and centrifuged. The clear solution obtained is concentrated under reduced pressure. The residue is dissolved in a minimum amount of THF then precipitated with pentane and finally purified by washing (THF/pentane and THF/Et$_2$O) in order to produce a white solid with a yield of 92%.

The characteristics of this product are given above, in Stage 2.

Stage 3a: First-Generation Phosphorus-Containing Dendrimer with a Monophosphonic Acid (Na Salt) Surface 13 equivalents of HCl 1M in ether (0.545 mL, 0.54 mmol) is added at 0° C. under an argon flow to a solution of dendrimers with dimethyl phosphonate terminations obtained in Stage 2a or 2b above (220 mg, 41.9 μmol) in acetonitrile. The heterogeneous solution is stirred for 2 hours at room temperature then concentrated under reduced pressure. The residue is suspended in distilled acetonitrile and 30 equivalents (82 μL, 0.628 mmol) of bromotrimethylsilane are added under argon at 0° C. The solution is stirred for 20 hours at room temperature then concentrated under reduced pressure. 5 mL of methanol are added and the mixture is vigorously stirred for 2 hours. The methanol is eliminated under reduced pressure and the residue is washed with distilled ether, then water and methanol. The solid is dried under reduced pressure until a powder is obtained. A soda solution (0.1966 M, 2.55 mL, 12 eq.) is slowly added to the solid. The solution obtained is filtered then freeze-dried. The dendrimer with aminophosphonic acid terminations is obtained in the form of a white powder with a yield of 65%.

NMR $^{31}$P{$^1$H} (D$_2$O/CD$_3$CN, 81.01 MHz): 12.3 (s, N$_3$P$_3$), 14.6 (s, P=O), 66.6 (s, P=S).

NMR $^1$H (D$_2$O/CD$_3$CN, 200.13 MHz): 3.39-3.65 (m, 30H, CH$_2$Ph and NCH$_3$); 3.86 (m, 12H, CH$_2$Ph); 4.03 (d, 12H, $^2J_{HP}$=17 Hz, PCH); 6.91 (m, 12H, $C_0^2$—H); 7.25 (m, 24H, $C_1^2$—H); 7.38 (m, 60H, $C_6H_5$); 7.57 (m, 30H, $C_1^3$—H and CH=N), 7.97 (bs, 12H, $C_0^3$—H).

Stage 3b: The Same Compound can be Obtained According to the Alternative Procedure Described Below 36 equivalents of N(Et)$_3$ (106 μL, 0.755 mmol) then 90 equivalents (250 μL, 1.89 mmol) of bromo-trimethylsilane are added at 0° C. under an argon flow to a solution of dendrimer with dimethyl phosphonate terminations obtained in Stage 2 or 2b above (110 mg, 20.9 μmol) in a CH$_3$CN/CH$_2$Cl$_2$ mixture (5/5 mL). The solution is stirred for 20 hours at room temperature then concentrated under reduced pressure. 3 mL of methanol are added and the mixture is vigorously stirred for 2 hours. The methanol is eliminated under reduced pressure and the residue is washed with distilled ether, then water and methanol. The solid is dried under reduced pressure until a powder is obtained. A soda solution (0.1966 M, 1.28 mL, 12 eq.) is slowly added to the solid. The solution obtained is filtered then freeze-dried. The dendrimer with aminophosphonic acid terminations is obtained in the form of a white powder. Its characteristics are given in Stage 3 above.

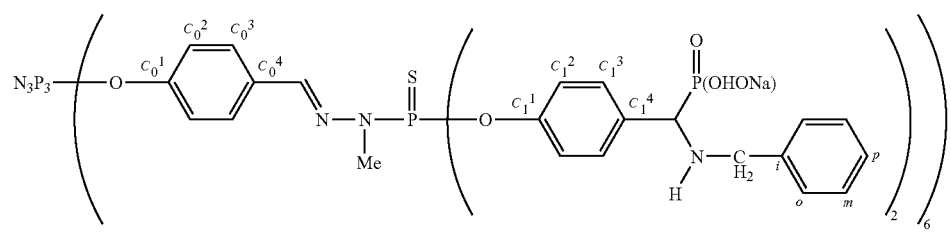

Stage 3c: The Same Compound can be Obtained According to Another Alternative Procedure Described Below

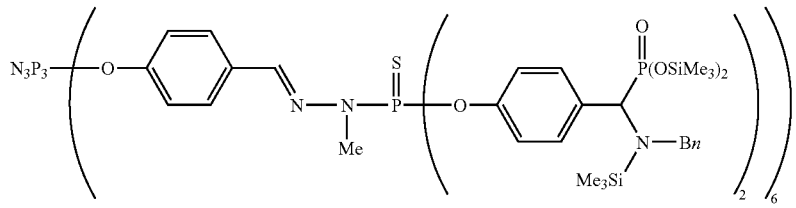

20 equivalents (360 µL, 1.019 mmol) of P(OSiMe$_3$)$_3$ and 12 equivalents of ClTMS (80 µL, 0.61 mmol) are added to a solution of dendrimer with imine terminations obtained in Stage 1 above (200 mg, 50.9 µmol) in solution in 5 mL of dichloromethane or anhydrous chloroform. The solution is stirred at room temperature or heated to 50° C. until the imine completely disappears (24 to 96 hours, $^{31}$P and $^1$H NMR monitoring). The silylated product is not isolated but characterized by $^{31}$P NMR NMR $^{31}$P{$^1$H} (CDCl$_3$, 81.01 MHz): 9.2 (s, O=P(OSiMe$_3$)$_2$), 11.4 (s, N$_3$P$_3$), 66.2 (s, P=S).

The reaction mixture is then concentrated under reduced pressure then 5 mL of methanol are added and the suspension is stirred vigorously for 2 hours. The methanol is evaporated and the residue is washed with distilled water (until washing water at pH=approximately 6 is obtained). The solid is washed with 3 times 5 mL of distilled ether then dried under vacuum. A soda solution (0.1966 M, 3.11 mL, 12 eq.) is added to the solid, the solution obtained is filtered then freeze-dried. The dendrimer with aminophosphonic acid terminations is obtained in the form of a white powder with a yield of 87%. Its characteristics are given in Stage 3 above.

Example 26

Synthesis of a First-Generation Dendrimer with a Cyclotriphosphazene Core with an Aza-Mono-Phosphonic Surface Derived from Methylamine Stage 1: Methylimine at the Surface of a First-Generation Phosphorus-Containing Dendrimer Methylamine (8 M in ethanol, 110 µL, 17.4 eq, 0.88 mmol) and 2 grams of MgSO$_4$ are added to a solution of Gc'1 (145 mg, 50.7 µmol) in THF (10 mL). The suspension is stirred for 24 hours at room temperature then filtered. The solid is rinsed with 10 mL of THF and the solution is evaporated under reduced pressure. The viscous residue is washed with ether then with a THF/pentane mixture. The solid obtained is solubilized in CH$_2$Cl$_2$, the resulting solution is then filtered and concentrated under reduced pressure in order to produce a white solid with a yield of 100%.

NMR $^{31}$P{$^1$H} (CDCl$_3$, 81.01 MHz): δ=11.7 (s, N$_3$P$_3$); 65.2 (s, P=S).

NMR $^1$H (CDCl$_3$, 200.13 MHz): δ=3.24 (d, 18H, $^3J_{HP}$=10.4 Hz, NNCH$_3$); 3.44 (bs, 36H, NMe); 6.97 (d, 12H, $^3J_{HH}$=8.5 Hz, C$_0^2$—H); 7.21 (d, 24H, $^3J_{HH}$=8.5 Hz, C$_1^2$—H); 7.58 (m, 42H, C$_0^3$—H, C$_1^3$—H and CH=NN); 8.16 (bs, 12H, CH=NMe).

NMR $^{13}$C{$^1$H} (CDCl$_3$, 62.89 MHz): δ=32.9 (d, $^2J_{CP}$=13.0 Hz, NNCH$_3$); 48.2 (s, NCH$_3$); 121.5 (s, C$_0^2$); 121.6 (d, $^4J_{CP}$=3.8 Hz, C$_1^2$); 128.3 (s, C$_0^3$); 129.2 (s, C$_1^3$); 131.9 (s, C$_0^4$); 133.6 (s, C$_1^4$); 139.0 (m, CH=NN); 151.3 (bs, C$_0^1$); 152.1 (bs, C$_1^1$); 161.0 (s, CH=NMe).

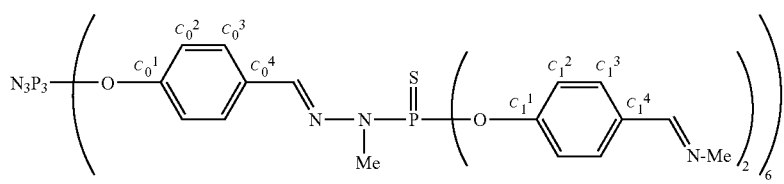

Stage 2: First-Generation Phosphorus-Containing Dendrimer with Silylphosphonate Ends

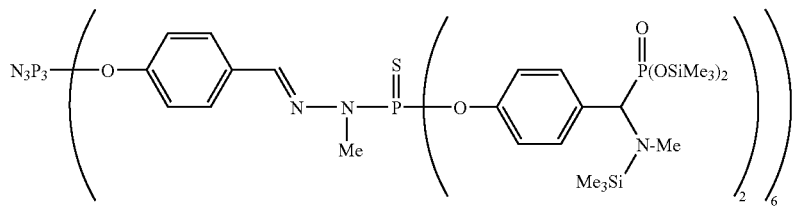

20 equivalents (481 µL, 1.44 mmol) of P(OSiMe$_3$)$_3$ are added to a solution of dendrimer with imine terminations (217 mg, 72.0 µmol) in solution in 5 mL of dichloromethane or anhydrous chloroform. The solution is stirred at room temperature or heated to 50° C. until the imine disappears completely (24 to 96 hours, $^{31}$P and NMR monitoring). This product is not isolated, but used directly in the following stage NMR $^{31}$P{$^1$H} (C$_6$D$_6$, 81.01 MHz): 9.0 (s, O=P(OSiMe$_3$)$_2$), 11.8 (s, N$_3$P$_3$), 66.4 (s, P=S).

Stage 3a: First-Generation Phosphorus-Containing Dendrimer with Monophosphonic Acid (Na Salt) Ends

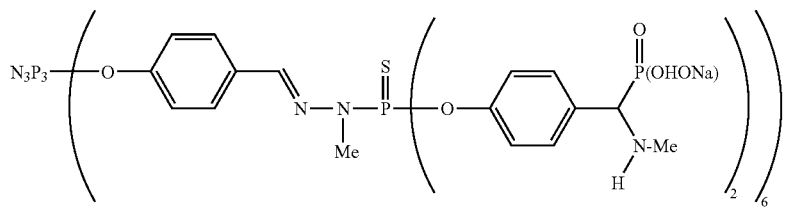

The reaction mixture obtained in Stage 2 above is concentrated under reduced pressure then 5 mL of methanol are added and the suspension is stirred vigorously for 2 hours. The methanol is evaporated and the residue is washed with distilled water (until washing water at approximately pH 6 is obtained). The solid is washed with 3 times 5 mL of distilled ether then dried under vacuum.

A soda solution (0.1966 M, 4.39 mL, 12 eq) is added to the solid, the solution obtained is filtered then freeze-dried. The dendrimer with aminophosphonic acid terminations is obtained in the form of a white powder with a yield of 92%.

NMR $^{31}$P {$^1$H} (D$_2$O/CD$_3$CN, 81.01 MHz): δ=8.9 (s, P=O); 10.5 (s, N$_3$P$_3$); 65.1 (s, P=S).

The same product can be obtained by the following alternative method:

Stage 2a: First-Generation Phosphorus-Containing Dendrimer with Methylphosphonate Ends

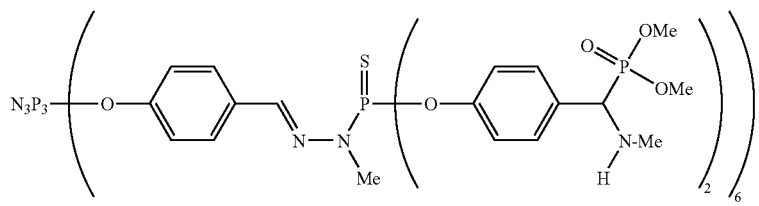

The dendrimer with imine terminations obtained in Stage 1 is solubilized in a large excess of dimethyl phosphite. The homogeneous solution is stirred for 72 hours at RT then 10 mL of distilled ether are added. After decantation, the solvent is eliminated and the solid is washed with 3 times 10 mL of ether. The residue is solubilized in a minimum amount of THF then precipitated by addition of pentane. The solid obtained is dried under reduced pressure and the dendrimer with a dimethyl N-(methyl)-methylphosphonate termination is obtained pure with a yield of 80% (white powder).

NMR $^{31}$P-{$^1$H} (CDCl$_3$): δ=11.5 (s); 29.0 (s); 65.2 (s).

Stage 3b: First-Generation Phosphorus-Containing Dendrimer with Monophosphonic (Na Salt) Acid Ends

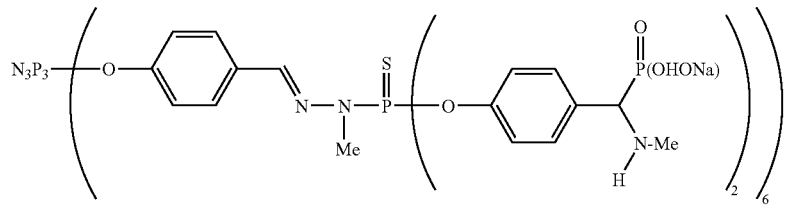

46 equivalents of BrTMS (230 μL) are added slowly at 0° C. to a solution of 160 mg (37 μmol) of dendrimer obtained in Stage 2a in acetonitrile (5 mL). The solution is then stirred for 20 hours at room temperature. The solvent is evaporated under reduced pressure and the residue is treated with 10 mL of methanol. After 1 hour of vigorous stirring in methanol, the solid is dried under reduced pressure. The phosphonic acid is washed with twice 20 mL of distilled ether. The solvent is eliminated and the dendrimer with pure phosphonic acid ends is slowly treated with an aqueous soda solution 0.1955 M (2.3 mL). The homogeneous solution is lyophilized and the dendrimer with an N-(methyl)-methylphosphonic acid (monosodium salt) termination is isolated with a quantitative yield in the form of a white powder.

NMR $^{31}$P-{$^1$H} (CD$_3$CN/D$_2$O): δ=8.9 (s); 10.5 (s); 65.1 (bs).

Example 27

Synthesis of a Generation 0 Dendrimer with a Cyclotriphosphazene Core with a Mono-Phosphonic Surface Derived from Benzylamine

Stage 1: Generation 0 Dendrimer with a Monophosphonate Surface

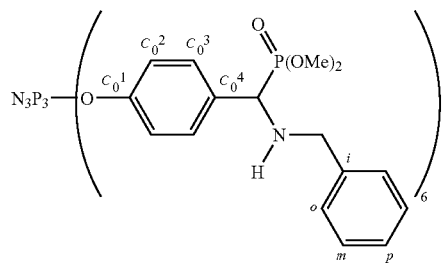

Cesium carbonate (1.3 g, 3.99 mmol) and dimethyl phenol amino-phosphonate (1 g, 3.11 mmol) are added to a solution of hexachloro-cyclotriphosphazene (N$_3$P$_3$Cl$_6$, 175 mg, 0.502 mmol) in distilled acetonitrile (10 mL). The suspension is stirred at room temperature for 24 hours. After decantation the supernatant is cannulated, the salts are washed with 10 mL of THF and the combined organic phases are centrifuged. The supernatants are collected and concentrated under reduced pressure. The residue is precipitated several times in a THF/pentane mixture then the solid is washed with ether and dried under reduced pressure. The product is obtained in the form of a white powder with a yield of 87%.

NMR $^{31}$P{$^1$H} (CDCl$_3$, 81.01 MHz): δ=11.3 (s, N$_3$P$_3$); 28.9 (s, P=O).

NMR $^1$H (CDCl$_3$, 200.13 MHz): δ=2.28 (bs, 6H, NH); 3.43 (d, 6H, $^2J_{HH}$=13 Hz, CHHPh); 3.48 (d, 18H, $^3J_{HP}$=10.2 Hz, POMe); 3.67 (d, 18H, $^3J_{HP}$=9.2 Hz, POMe); 3.73 (d, 6H, $^2J_{HH}$=13 Hz, CHHPh); 3.98 (d, 6H, $^2J_{HP}$=19.9 Hz, PCH); 7.2-7.50 (m, 54H, H$_{arom}$).

NMR $^{13}$C{$^1$H} (CDCl$_3$, 50.3 MHz): δ=50.9 (d, $^3J_{CP}$=17.2 Hz, CH$_2$Ph); 53.3 (d, $^2J_{CP}$=6.5 Hz, POMe); 53.7 (d, $^2J_{CP}$=7.0 Hz, POMe); 56.4 (d, $^1J_{CP}$=154.5 Hz, PCH); 120.9 (s, C$_o^2$); 127.2 (s, C$_p$); 128.2 (s, C$_m$); 128.4 (s, C$_o$); 129.8 (d, $^3J_{CP}$=5.9 Hz, C$_o^3$); 132.5 (d, $^2J_{CP}$=3.9 Hz, C$_o^4$); 138.9 (s, C$_i$); 150.3 (bs, C$_o^1$).

Stage 2: Generation 0 Dendrimer with a Phosphonic Acid (Na Salt) Surface

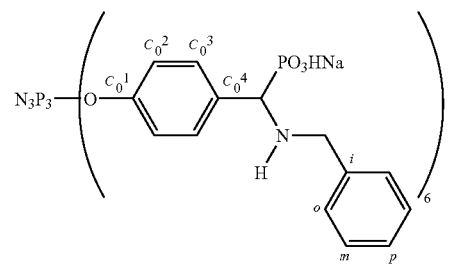

18 equivalents of N(Et)$_3$ then 45 equivalents of bromotrimethylsilane are added at 0° C. under an argon flow to a solution of dendrimers with dimethyl phosphonate terminations obtained in the preceding stage (200 mg, 1 eq) in a CH$_3$CN/CH$_2$Cl$_2$ mixture (5/5 mL). The solution is stirred for 20 hours at room temperature then concentrated under reduced pressure. 3 mL of methanol are added and the mixture is vigorously stirred for 2 hours. The methanol is eliminated under reduced pressure and the residue is washed with distilled ether, then water and methanol. The solid is dried under reduced pressure until a powder is obtained. A soda solution (0.1966 M, 6 eq.) is slowly added to the solid. The solution obtained is filtered then freeze-dried. The dendrimer with aminophosphonic acid terminations is obtained in the form of a white powder.

NMR $^{31}$P{$^1$H} (D$_2$O/CD$_3$CN, 81.01 MHz): 12.1 (s, N$_3$P$_3$), 14.3 (s, P=O).

Stage 2 a: The Same Compound can be Obtained According to the Following Alternative Procedure 7 equivalents of HCl 1M in ether are added at 0° C. under an argon flow to a solution of dendrimers with dimethyl phosphonate terminations synthesized in Stage 1 (200 mg, 1 eq) in acetonitrile (5 mL). The heterogeneous solution is stirred for 2 hours at room temperature then concentrated under reduced pressure. The residue is suspended in distilled acetonitrile and 15 equivalents of bromotrimethylsilane are added under argon at 0° C. The solution is stirred for 20 hours at room temperature then concentrated under reduced pressure. 5 mL of methanol are added and the mixture is vigorously stirred for 2 hours. The methanol is eliminated under reduced pressure and the residue is washed with distilled ether, then water and methanol. The solid is dried under reduced pressure until a powder is obtained. A soda solution (0.1966 M, 6 eq.) is slowly added to the solid. The solution obtained is filtered then freeze-dried. The dendrimer with aminophosphonic acid terminations is obtained in the form of a white powder with a yield of 63%.

Example 28

Synthesis of the First-Generation Dendrimer with a Tetraisopropyl-Gem-Diphosphonate Surface 24 hours. The evaporation of the solvent under reduced pressure, followed by 3 washings with 50 mL of pure pentane, make it possible to eliminate all the by-products of the reaction as well as the impurities contained in the starting tetraisopropyl-vinyl-gem-diphosphonate. The final product is isolated with a yield of 70%.

NMR $^{31}$P-{$^1$H} (CDCl$_3$): δ=66.5 (s, P$_1$); 23.5 (s, P(O)(OiPr)$_2$); 11.9 (s, P$_0$) ppm.

NMR (CDCl$_3$): δ=1.29 (d, $^3J_{HH}$=6.1 Hz, 288H, —O—CH—(CH$_3$)$_2$); 2.91 (s, 36H, N—N(CH$_3$)—CH$_2$—); 3.00 (tt, $^2J_{HP}$=23.6 Hz, $^3J_{HH}$=6.0 Hz, 12H, —CH—(P(O)(OiPr)$_2$)$_2$); 3.23 (d, $^3J_{HP}$=8.8 Hz, 18H, CH$_3$—N—P$_1$); 3.78 (dt, $^3J_{HP}$=14.7 Hz, $^3J_{HH}$=6.2 Hz, 24H, —CH$_2$—CH—(P(O)(OiPr)$_2$)$_2$); 4.74 (hept, $^3J_{HH}$=6.1 Hz, 48H, —O—CH—(CH$_3$)$_2$); 6.8-7.8 (m, 90H, CH$_{arom}$, and CH=N) ppm.

NMR $^{13}$C-{$^1$H} (CDCl$_3$): δ=23.7 (d, $^3J_{CP}$=3.1 Hz, —O—CH—(CH$^3$)$_2$); 23.8 (d, $^3J_{CP}$=2.5 Hz, —O—CH—(CH$_3$)$_2$); 24.0 (d, $^3J_{CP}$=3.0 Hz, —O—CH—(CH$_3$)$_2$); 24.2 (d, $^3J_{CP}$=2.9 Hz, —O—CH—(CH$_3$)$_2$); 32.9 (d, $^2J_{CP}$=11.7 Hz, CH$_3$—N—P$_1$), 37.7 (t, $^1J_{CP}$=132.2 Hz, —CH—(P(O)(OiPr)$_2$)$_2$); 38.8 (s, N—N(CH$_3$)—CH$_2$—); 55.1 (s, —CH$_2$—CH—(P(O)(OiPr)$_2$)$_2$); 70.9 (d, $^2J_{CP}$=6.6 Hz, —O—CH—(CH$_3$)$_2$); 71.3 (d, $^2J_{CP}$=6.8 Hz, —O—CH—(CH$_3$)$_2$); 121.2 (broad s, C$_0^2$, C$_1^2$); 126.3 (s, C$_1^3$); 128.2 (s, C$_0^3$); 129.4 (s, CH=N—N(Me)-CH$_2$); 132.1 (s, C$_0^4$),

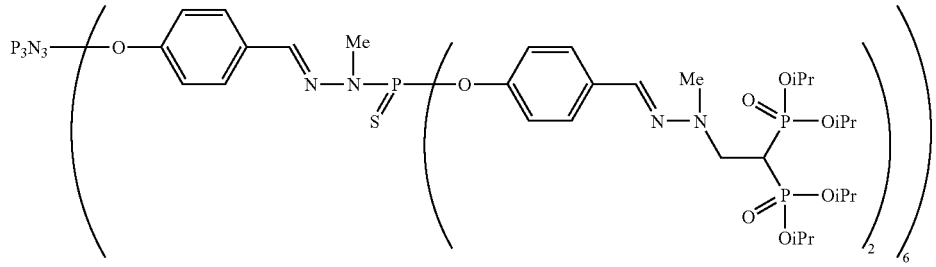

Gc'$_1$ dendrimer (7.0·10$^{-2}$ mmol, 200 mg) is placed in solution in CH$_2$Cl$_2$ (10 mL) then monomethylhydrazine is added at 0° C. (1.3 mmol, 66 μL) as well as tetraisopropyl-vinyl-gem-diphosphonate (0.7 g understanding that it is pure only at 65%); this addition must be simultaneous and slow in order to avoid the formation of an insoluble aggregate. Once the addition is finished, the mixture is stirred at room temperature for 134.5 (s, C$_1^4$), 138.8 (broad s, CH=N—N(Me)-P$_1$), 149.4 (d, $^2J_{CP}$=7.5 Hz, C$_1^1$), 151.1 (s, C$_0^1$) ppm.

Example 29

Synthesis of the Second-Generation Dendrimer with a Tetraisopropyl-Gem-Diphosphonate Surface

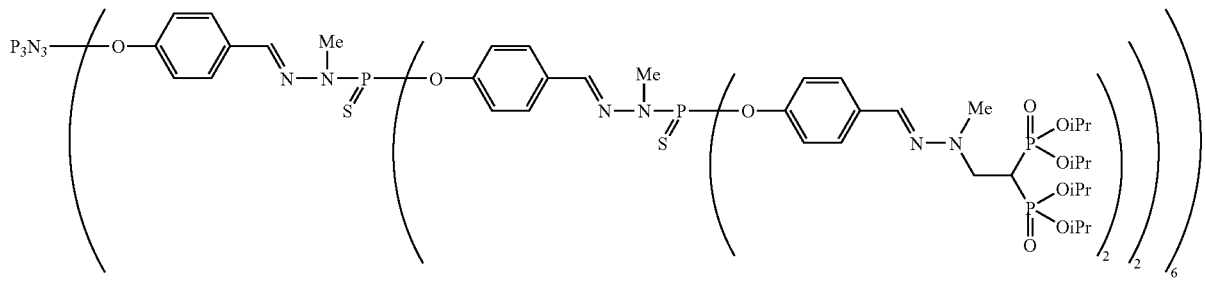

Gc'₂ dendrimer (2.9·10⁻² mmol, 200 mg) is placed in solution in CH₂Cl₂ (10 mL) then monomethylhydrazine is added at 0° C. (1.05 mmol, 56 µL) as well as tetraisopropyl-vinyl-gem-diphosphonate (0.575 g understanding that it is pure only at 65%); this addition must be simultaneous and slow in order to avoid the formation of an insoluble aggregate. Once the addition is finished, the mixture is stirred at room temperature for 24 hours. The evaporation of the solvent under reduced pressure, followed by 3 washings with 100 mL of pentane/ether 1/1, make it possible to eliminate all the by-products of the reaction as well as the impurities contained in the starting tetraisopropyl-vinyl-gem-diphosphonate. The final product is isolated with a yield of 79%.

NMR $^{31}$P-{$^1$H} (CDCl₃): δ=66.4 (s, P₂); 66.1 (s, P₁); 23.5 (s, P(O)(OiPr)₂); 11.8 (s, P₀) ppm.

NMR $^1$H (CDCl₃): δ=1.25 (d, $^3J_{HH}$=6.0 Hz, 576H, —O—CH—(CH₃)₂); 2.87 (s, 72H, N—N(CH₃)—CH₂—); 2.97 (tt, $^2J_{HP}$=23.6 Hz, $^3J_{HH}$=6.6 Hz, 24H,

Example 30

Synthesis of the Third-Generation Dendrimer with a Tetraisopropyl-Gem-Diphosphonate Surface Gc'₃ dendrimer (1.35·10⁻² mmol, 200 mg) is placed in solution in CH₂Cl₂ (10 mL) then monomethylhydrazine is added at 0° C. (0.97 mmol, 52 µL) as well as tetraisopropyl-vinyl-gem-diphosphonate (0.532 g understanding that it is pure only at 65%); this addition must be simultaneous and slow in order to avoid the formation of an insoluble aggregate. Once the addition is finished, the mixture is stirred at room temperature for 24 hours. The evaporation of the solvent under reduced pressure, followed by 3 washings with 100 mL of pentane/ether 1/1, make it possible to eliminate all the by-products of the reaction as well as the impurities contained in the starting tetraisopropyl-vinyl-gem-diphosphonate. The final product is isolated with a yield of 80%.

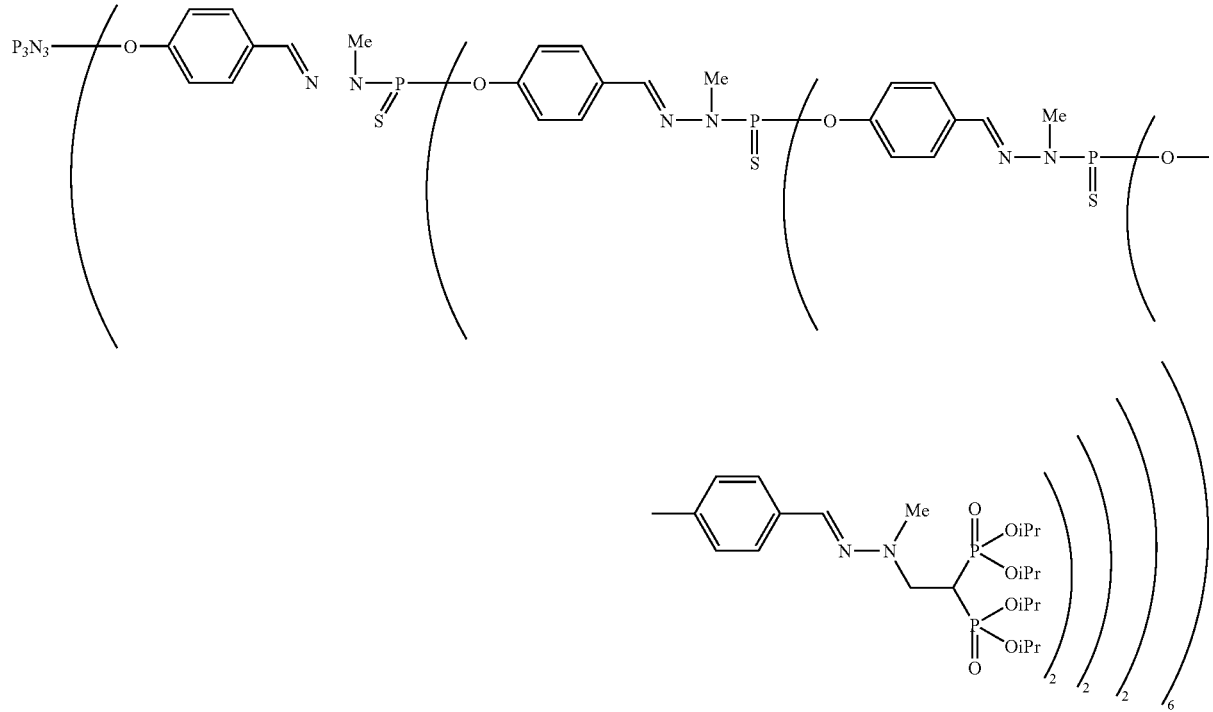

—CH—(P(O)(OiPr)₂)₂); 3.24 (broad d, $^3J_{HP}$=9.5 Hz, 54H, CH₃—N—P₁,₂); 3.74 (dt, $^3J_{HP}$=13.9 Hz, $^3J_{HH}$=6.2 Hz, 48H, —CH₂—CH—(P(O)(OiPr)₂)₂); 4.71 (hept, $^3J_{HH}$=5.9 Hz, 96H, —O—CH—(CH₃)₂); 6.8-7.8 (m, 210H, CH$_{arom}$ and CH=N) ppm.

NMR $^{13}$C-{$^1$H} (CDCl₃): δ=23.8 (d, $^3J_{CP}$=3.1 Hz, —O—CH—(CH₃)₂); 24.2 (d, $^3J_{CP}$=3.0 Hz, —O—CH—(CH₃)₂); 32.9 (d, $^2J_{CP}$=11.8 Hz, CH₃—N—P₁,₂), 38.3 (t, $^1J_{CP}$=132.1 Hz, —CH—(P(O)(OiPr)₂)₂); 38.8 (s, N—N(CH₃)—CH₂—); 55.2 (s, —CH₂—CH—(P(O)(OiPr)₂)₂); 70.9 (d, $^2J_{CP}$=6.8 Hz, —O—CH—(CH₃)₂); 71.3 (d, $^2J_{CP}$=6.8 Hz, —O—CH—(CH₃)₂); 121.4 (broad s, C₀², C₁², C₂²); 126.4 (s, C₂³); 128.3 (broad s, C₀³, C₁³); 129.5 (s, CH=N—N(Me)-CH₂); 132.1 (s, C₀⁴), 132.4 (s, C₁⁴), 134.5 (s, C₂⁴), 138.7 (broad s, CH=N—N(Me)-P₁,₂), 149.5 (d, $^2J_{CP}$=7.4 Hz, C₂¹), 151.2 (s, C₀¹, C₁¹) ppm.

NMR $^{31}$P-{$^1$H} (CDCl₃): δ=66.3 (s, P₃); 66.0 (s, P₁,₂); 23.5 (s, P(O)(OiPr)₂); 11.4 (s, P₀) ppm.

NMR $^1$H (CDCl₃): δ=1.26 (d, $^3J_{HH}$=6.0 Hz, 1152H, —O—CH—(CH₃)₂); 2.88 (s, 144H, N—N(CH₃)—CH₂—); 2.98 (tt, $^2J_{HP}$=23.9 Hz, $^3J_{HH}$=6.6 Hz, 48H, —CH—(P(O)(OiPr)₂)₂); 3.26 (broad d, $^3J_{HP}$=9.5 Hz, 126H, CH₃—N—P₁,₂,₃); 3.74 (m, 96H, —CH₂—CH—(P(O)(OiPO₂)₂); 4.70 (hept, $^3J_{HH}$=5.9 Hz, 192H, —O—CH—(CH₃)₂); 6.8-7.8 (m, 450H, CH$_{arom}$ and CH=N) ppm.

NMR $^{13}$C-{$^1$H} (CDCl₃): δ=23.9 (d, $^3J_{CP}$=2.9 Hz, —O—CH—(CH₃)₂); 24.2 (d, $^3J_{CP}$=2.5 Hz, —O—CH—(CH₃)₂); 32.9 (d, $^2J_{CP}$=12.3 Hz, CH₃—N—P₁,₂,₃), 38.4 (t, $^1J_o$=132.3 Hz, —CH—(P(O)(OiPr)₂)₂); 38.9 (s, N—N(CH₃)—CH₂—); 55.2 (s, —CH₂—CH—(P(O)(OiPr)₂)₂); 70.9 (d, $^2J_{CP}$=6.9 Hz, —O—CH—(CH₃)₂); 71.3 (d, $^2J_{CP}$=6.9 Hz, —O—CH—(CH₃)₂); 121.4 (s, C₃²); 121.8 (broad s, C₀², C₁², C₂²); 126.4 (s, C₃³); 128.3 (broad s, C₀³, C₁³, C₂³); 129.6

(s, CH=N—N(Me)-CH$_2$); 131.3 (s, C$_0^4$); 132.4 (broad s, C$_1^4$, C$_2^4$); 134.5 (s, C$_3^4$); 138.7 (broad s, CH=N—N(Me)-P$_{1,2,3}$); 149.5 (d, $^2J_{CP}$=8.1 Hz, C$_3^1$); 151.2 (broad s, C$_0^1$, C$_1^1$, C$_2^1$) ppm.

Example 31

Synthesis of Phenol Aza-Bis-Dimethyl-Phosphonate Derived from Tyramine

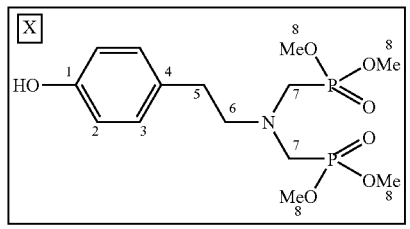 [SMILES: COP(=O)(CN(CCc1ccc(O)cc1)CP(=O)(OC)OC)OC]

Tyramine (6 g, 43.7 mmol) and dimethyl-phosphite (10.32 ml, 112.5 mmol) are mixed at 0°, then a 37% solution of formaldehyde in water (12.6 ml) is slowly added, still at 0° C. The mixture is taken to room temperature for 30 minutes and refluxed for 1 hour with magnetic stirring. Finally the crude reaction product is placed under reduced pressure in order to evaporate the excess of formaldehyde. The product is extracted with a chloroform/water mixture (4/1) (3×100 ml of chloroform). The organic phase is recovered then subjected to chromatography on silica using acetone as eluent. The final product is isolated with a yield of 65%.

NMR $^{31}$P-{$^1$H} (CDCl$_3$): δ=30.2 (s, P(O)(OMe)$_2$) ppm.

NMR $^1$H (CDCl$_3$): δ=2.68 (deformed t, $^3J_{HH}$=7.2 Hz, 2H, —CH$_2$—CH$_2$—N); 3.05 (deformed t, $^3J_{HH}$=7.2 Hz, 2H, —CH$_2$—CH$_2$—N—); 3.20 (d, $^2J_{HP}$=8.9 Hz, 4H, N—CH$_2$—P); 3.75 (d, $^3J_{HP}$=10.7 Hz, 12H, —OMe); 6.6-7.1 (m, 4H, CH$_{arom}$); 8.16 (broad s, 1H, —OH) ppm.

NMR $^{13}$C-{$^1$H} (CDCl$_3$): δ=32.7 (s, C$_5$); 49.4 (dd, $^3J_{CP}$=6.8 Hz, $^1J_{CP}$=158.5 Hz, C$_7$); 52.8 (d, $^2J_{CP}$=3 Hz, C$_8$); 58.8 (t, $^3J_{CP}$=7.5 Hz, C$_6$); 115.4 (s, C$_3$); 129.8 (s, C$_2$); 129.8 (s, C$_4$); 155.9 (s, C$_1$) ppm.

Example 32

Synthesis of Phenol Aza-Bis-Dimethyl-Phosphonate Derived from 4-Hydroxyaniline

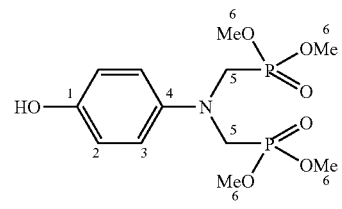

4-hydroxyaniline (5 g, 46 mmol) and dimethyl-phosphite (10.5 ml, 115 mmol) are mixed at 0° C., then a 37% solution of formaldehyde in water (10.6 ml) is slowly added, still at 0° C. The mixture is taken to room temperature for 30 minutes and refluxed for 1 hour with magnetic stirring. Finally the crude reaction product is placed under reduced pressure in order to evaporate the excess of formaldehyde. The product is extracted with a chloroform/water mixture (4/1) (3×100 ml of chloroform). The organic phase is recovered then subjected to chromatography on silica using acetone as eluent. The final product is isolated with a yield of 30%.

NMR $^{31}$P-{$^1$H} (CDCl$_3$): δ=29.8 (s, P(O)(OMe)$_2$) ppm.

NMR $^1$H (CDCl$_3$): δ=3.67 (d, $^3J_{HP}$=10.6 Hz, 12H, —OMe); 3.84 (d, $^2J_{HP}$=5.7 Hz, 4H, N—CH$_2$—P); 6.6-6.9 (m, CH$_{arom}$, 4H); 8.05 (broad s, 1H, —OH) ppm.

NMR $^{13}$C-{$^1$H} (CDCl$_3$): δ=47.6 (d, $^1J_{CP}$=157.1 Hz, C$_5$); 52.6 (d, $^2J_{CP}$=3.8 Hz, C$_6$); 52.7 (d, $^2J_{CP}$=3.3 Hz, C$_6$); 115.8 (s, C$_3$); 117.3 (s, C$_2$); 141.0 (s, C$_4$); 150.9 (s, C$_1$) ppm.

Example 33

Synthesis of First-Generation Dendrimer with an Aza-Bis-Dimethyl-Phosphonate Surface Derived from Tyramine

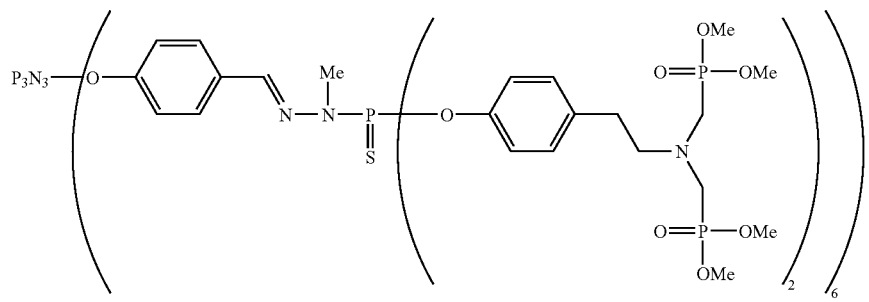

Cesium carbonate (6.898 mmol, 2.25 g) is added to a solution of Gc$_1$ dendrimer (0.273 mmol, 500 mg) in solution in anhydrous THF (10 mL) then phenol aza-bis-dimethyl-phosphonate derived from the tyramine obtained in Example 31 is added (3.449 mmol, 1.31 g). The mixture is left under stirring for 24 hours at room temperature then the final mixture is filtered on celite in order to separate the salts. Finally the final product is washed by precipitation in pentane and isolated with a yield of 70%.

NMR $^{31}$P-{$^{1}$H} (CDCl$_3$): δ=68.7 (s, P$_1$); 31.9 (s, P(O)(OMe)$_2$); 13.7 (s, P$_0$) ppm.

NMR $^{1}$H (CDCl$_3$): δ=2.69 (t, $^{3}J_{HH}$=6.8 Hz, 24H, CH$_2$—CH$_2$—N); 2.99 (t, $^{3}J_{HH}$=6.8 Hz, 24H, CH$_2$—CH$_2$—N); 3.13 (d, $^{2}J_{HP}$=9.17 Hz, 48H, —CH$_2$—P(O)(OCH$_3$)$_2$); 3.2 (d, $^{3}J_{HP}$=11.8 Hz, 18H, CH$_3$—N—P$_1$); 3.67 (d, $^{3}J_{HP}$=10.2 Hz, 144H, —P(O)(O—CH$_3$)$_2$); 6.8-7.8 (m, 78H, CH$_{arom}$, CH=N) ppm.

NMR $^{13}$C-{$^{1}$H} (CDCl$_3$): δ=32.9 (d, $^{2}J_{CP}$=11 Hz, CH$_3$—N—P$_1$); 32.95 (s, CH$_2$—CH$_2$—N) 49.5 (dd, $^{1}J_{CP}$=157.5 Hz, $^{3}J_{CP}$=6.8 Hz, —CH$_2$—P(O)(OCH$_3$)$_2$); 52.6 (d, $^{2}J_{CP}$=4.0 Hz, —P(O)(O—CH$_3$)$_2$); 57.8 (t, $^{3}J_{CP}$=7.2 Hz, CH$_2$—CH$_2$—N); 120.8 (s, C$_0^2$); 120.8 (d, $^{3}J_{CP}$=4.1 Hz, C$_1^2$); 128.3 (s, C$_0^3$); 129.6 (s, C$_1^3$); 131.9 (s, C$_0^4$); 136.3 (s, C$_1^4$); 138.4 (d, $^{3}J_{CP}$=14.1 Hz, CH=N); 148.5 (d, $^{2}J_{CP}$=7.0 Hz, C$_1^1$); 150.8 (d, $^{2}J_{CP}$=3.0 Hz, C$_0^1$) ppm.

Example 34

Synthesis of Second-Generation Dendrimer with an Aza-Bis-Dimethyl-Phosphonate Surface Derived from Tyramine Cesium carbonate (5.28 mmol, 1.72 g) is added to a solution of Gc$_2$ dendrimer (0.104 mmol, 500 mg) in solution in anhydrous THF (10 mL) then phenol aza-bis-dimethyl-phosphonate derived from the tyramine obtained in Example 31 is added (2.6 mmol, 1.00 g). The mixture is left under stirring for 24 hours at room temperature then the final mixture is filtered on celite in order to separate the salts. Finally the final product is washed by precipitation in pentane and isolated with a yield of 78%. NMR $^{31}$P-{$^{1}$H} (CDCl$_3$): δ=66.5 (s, P$_2$); 66.2 (s, P$_1$); 30.1 (s, P(O)(OMe)$_2$); 12.1 (s, P$_0$) ppm.

NMR $^{1}$H (CDCl$_3$): δ=2.69 (broad s, 48H, CH$_2$—CH$_2$—N); 2.99 (broad s, 48H, CH$_2$—CH$_2$—N); 3.12 (d, $^{2}J_{HP}$=9.51 Hz, 96H, —CH$_2$—P(O)(OCH$_3$)$_2$); 3.24 (d, $^{3}J_{HP}$=8.5 Hz, 54H, CH$_3$—N—P); 3.66 (d, $^{3}J_{HP}$=10.4 Hz, 288H, —P(O)(O—CH$_3$)$_2$); 6.6-7.7 (m, 186H, CH$_{arom}$, CH=N) ppm.

NMR $^{13}$C-{$^{1}$H} (CDCl$_3$): δ=32.95 (s, CH$_2$—CH$_2$—N); 33.0 (d, $^{2}J_{CP}$=11.2 Hz, CH$_3$—N—P); 49.4 (dd, $^{1}J_{CP}$=157.5 Hz, $^{3}J_{CP}$=6.6 Hz, —CH$_2$—P(O)(OCH$_3$)$_2$); 52.7 (d, $^{2}J_{CP}$=4.2 Hz, —P(O)(O—CH$_3$)$_2$); 58.0 (t, $^{3}J_{CP}$=7.1 Hz, CH$_2$—CH$_2$—N); 121.2 (s, C$_0^2$); 121.7 (s, C$_1^2$); 121.2 (d, $^{3}J_{CP}$=3.9 Hz, C$_2^2$) 128.3 (s, C$_1^3$); 129.65 (s, C$_0^3$); 129.9 (s, C$_2^3$); 132.1 (s, C$_0^4$); 132.4 (s, C$_1^4$); 136.5 (s, C$_2^4$); 138.6 (d, $^{3}J_{CP}$=13.3 Hz, CH=N); 148.8 (s, C$_0^1$); 148.9 (d, $^{2}J_{CP}$=7.5 Hz, C$_2^1$); 151.2 (d, $^{2}J_{CP}$=7.4 Hz, C$_1^1$) ppm.

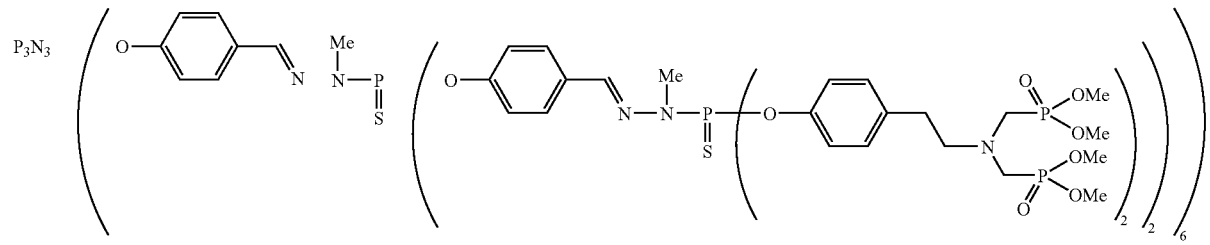

Example 35

Synthesis of Third-Generation Dendrimer with an Aza-Bis-Dimethyl-Phosphonate Surface Derived from Tyramine

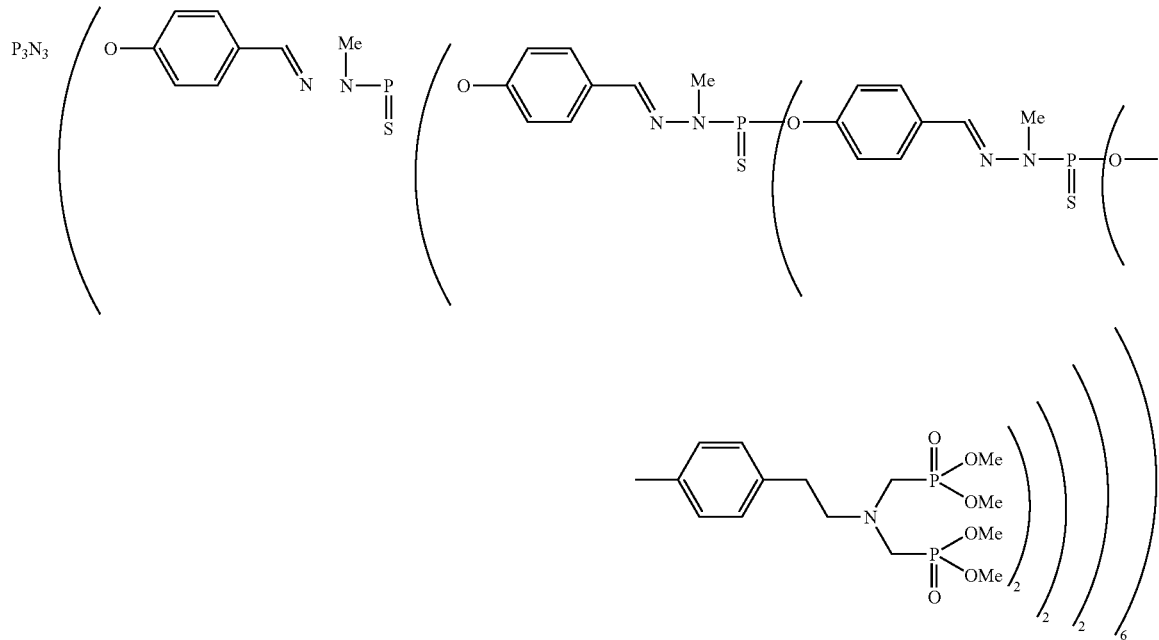

Cesium carbonate (0.941 mmol, 0.306 g) is added to a solution of Gc₃ dendrimer (9.3·10⁻³ mmol, 100 mg) in solution in anhydrous THF (2 mL) then phenol aza-bis-dimethyl-phosphonate derived from the tyramine obtained in Example 31 is added (0.471 mmol, 180 mg). The mixture is left under stirring for 24 hours at room temperature then the final mixture is filtered on celite in order to separate the salts. Finally the final product is washed by precipitation in pentane and isolated with a yield of 80%.

NMR $^{31}$P-{$^{1}$H} (CDCl₃): δ=66.6 (s, P₃); 66.3 (s, P₂); 65.8 (s, P₁); 30.2 (s, P(O)(OMe)₂); 12.0 (s, P₀) ppm.

NMR $^{1}$H (CDCl₃): δ=2.67 (broad s, 96H, C$\underline{H_2}$—CH₂—N); 2.97 (broad s, 96H, CH₂—C$\underline{H_2}$—N); 3.10 (d, $^{2}J_{HP}$=9.60 Hz, 192H, —C$\underline{H_2}$—P(O)(OCH₃)₂); 3.25 (broad s, 126H, CH₃—N—P); 3.63 (d, $^{3}J_{HP}$=10.25 Hz, 576H, —P(O)(O—C$\underline{H_3}$)₂); 6.5-7.7 (m, 402H, CH$_{arom.}$ CH=N) ppm.

NMR $^{13}$C-{$^{1}$H} (CDCl₃): δ=32.9 (s, C$\underline{H_2}$—CH₂—N); 32.9 (s, CH₃—N—P); 49.3 (dd, $^{1}J_{CP}$=157.5 Hz, $^{3}J_{CP}$=6.5 Hz, —C$\underline{H_2}$—P(O)(OCH₃)₂); 52.6 (d, $^{2}J_{CP}$=3.6 Hz, —P(O)(O—C$\underline{H_3}$)₂); 58.0 (t, $^{3}J_{CP}$=6.9 Hz, CH₂—C$\underline{H_2}$—N); 120.5 (s, C₀²); 121.2 (d, $^{3}J_{CP}$=3.1 Hz, C₃²); 121.5 (s, C₁²); 121.8 (s, C₂²); 128.2 (s, C₀³); 128.2 (s, C₁³); 129.6 (s, C₂³); 129.9 (s, C₃³); 132.3 (s, C₀⁴); 132.3 (s, C₁⁴); 132.3 (s, C₂⁴); 136.5 (s, C₃⁴); 138.6 (d, $^{3}J_{CP}$=13.0 Hz, CH=N); 148.9 (broad d, $^{2}J_{CP}$=6.3 Hz, C₀¹, C₁¹, C₃¹); 151.2 (d, $^{2}J_{CP}$=6.1 Hz, C₂¹) ppm.

Example 36

Synthesis of First-Generation Dendrimer with an Aza-Bis-Phosphonic Surface Derived from Tyramine (GC1)

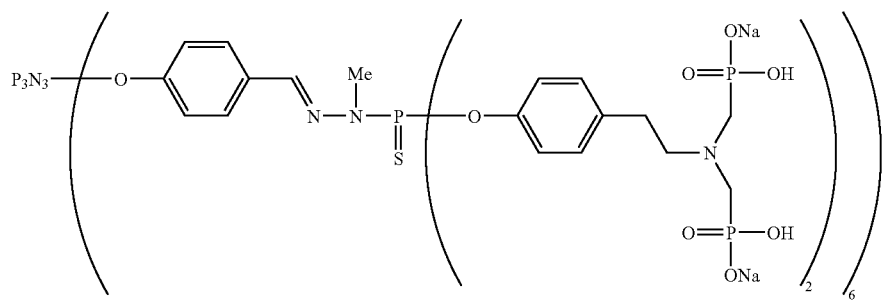

Bromotrimethylsilane (1.04 mmol; 138 μl) is added slowly to a solution of first-generation dendrimer with aza-bis-dimethyl-phosphonate ends derived from the tyramine obtained in Example 33 (1.68·10$^{-2}$ mmol, 100 mg) at 0° C. in acetonitrile (5 mL). Once the addition is finished the mixture is allowed to return to room temperature over 12 hours. The mixture is then evaporated to dryness then 1 ml of anhydrous methanol is added at room temperature and the mixture is left for one hour under stirring. After evaporation to dryness, the residue is washed several times with pure ether. As the product is totally insoluble in organic solvents it is converted to its monosodium salt in the presence of soda (36.3 mg of soda, for 100 mg of dendrimer). The resulting solution is lyophilized in order to produce the dendrimer in the form of a white powder. The final product is isolated with a yield of 58%.

NMR $^{31}$P-{$^1$H} (CD$_3$CN/D$_2$O): δ=67.9 (s, P$_1$); 14.4 (s, P(O)(ONa)$_2$); 12.9 (s, P$_0$) ppm.

NMR $^{13}$C-{$^1$H} (CD$_3$CN/D$_2$O): δ=31.95 (s, CH$_2$—CH$_2$—N); 35.5 (d, $^2J_{CP}$=10.9 Hz, CH$_3$—N—P$_1$); 57.0 (d, $^1J_{CP}$=136.8 Hz, —CH$_2$—P(O)(OH)$_2$); 60.7 (s, CH$_2$—CH$_2$—N); 124.1 (s, C$_0^2$); 124.1 (s, C$_1^2$); 131.3 (s, C$_0^3$); 133.5 (s, C$_1^3$); 135.3 (s, C$_0^4$); 139.0 (s, C$_1^4$); 143.2 (broad s, CH=N); 151.7 (d, $^2J_{CP}$=7.0 Hz, C$_1^1$); 153.3 (s, C$_0^1$) ppm.

Example 37

Synthesis of Second-Generation Dendrimer with an Aza-Bis-Phosphonic Surface Derived from Tyramine (GC2)

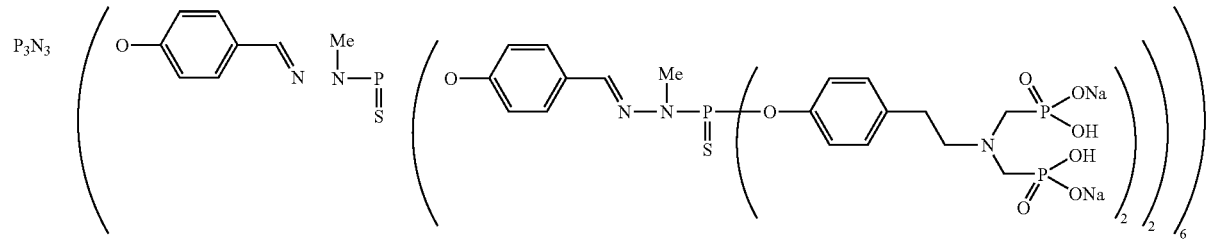

Bromotrimethylsilane (10 mmol, 1.34 ml) is slowly added to a solution of second-generation dendrimer with aza-bis-dimethyl-phosphonate ends derived from the tyramine obtained in Example 34 (8.27·10$^{-2}$ mmol, 1.08 g) at 0° C. in acetonitrile (10 mL). Once the addition is finished the mixture is allowed to return to room temperature over 12 hours. The mixture is then evaporated to dryness then 3 ml of anhydrous methanol is added at room temperature and the mixture is left for one hour under stirring. After evaporation to dryness, the residue is washed several times with pure ether. As the product is totally insoluble in organic solvents it is converted to its monosodium salt in the presence of soda (8.2 mg of soda, for 50 mg of dendrimer). The resulting solution is lyophilized in order to produce the dendrimer in the form of a white powder. The final product is isolated with a yield of 62%.

NMR $^{31}$P-{$^1$H} (CD$_3$CN/D$_2$O): δ=67.8 (s, P$_2$); 67.6 (s, P$_1$); 10.5 (s, P(O)(ONa)(OH)); 10.0 (s, P$_0$) ppm.

NMR $^{13}$C-{$^1$H} (CD$_3$CN/D$_2$O): δ=31.6 (s, CH$_3$—N—P$_1$); 35.3 (s, CH$_2$—CH$_2$—N); 55.2 (d, $^1J_{CP}$=128.2 Hz, —CH$_2$—P(O)(OH)$_2$); 60.4 (s, CH$_2$—CH$_2$—N); 124.3 (s, C$_0^2$); 124.3 (s, C$_1^2$); 124.3 (s, C$_2^2$); 131.3 (s, C$_0^3$); 131.3 (s, C$_1^3$); 133.3 (s, C$_2^3$); 135.0 (s, C$_0^4$); 135.0 (s, C$_1^4$); 136.0 (s, C$_2^4$); 142.5 (broad s, CH=N); 151.8 (broad s, C$_2^1$); 153.3 (broad s, C$_1^1$); 153.3 (s, C$_0^1$) ppm.

The dendrimers with an aza-bis-phosphonic surface cannot be prepared by application or adaptation of the above method using dendrimers with a tetraisopropyl-gem-diphosphonate surface of Examples 28 to 30.

The dendrimers with an aza-bis-phosphonic surface can be prepared by application or adaptation of the method above using dendrimers with an aza-bis-dimethyl-phosphonate surface derived from 4-hydroxyaniline of Examples 38 and 39 below:

Example 38

Synthesis of First-Generation Dendrimer with an Aza-Bis-Dimethyl-Phosphonate Surface Derived from 4-Hydroxyaniline

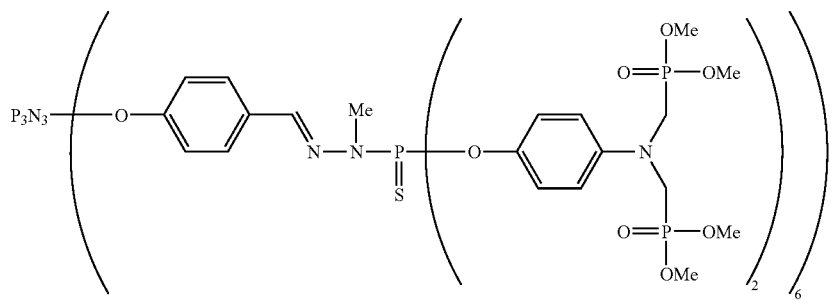

Cesium carbonate (2.94 mmol, 955 mg) is added to a solution of Gc$_1$ dendrimer (0.116 mmol, 214 mg) in solution in anhydrous THF (10 mL) then the phenol obtained in Example 32 is added (1.47 mmol, 520 mg). The mixture is left under stirring for 24 hours at room temperature then the final mixture is filtered on celite in order to separate the salts. Finally the final product is precipitated in pentane, then washed with ether. The final product is isolated with a yield of 76%.

NMR $^{31}$P-{$^1$H} (C$_6$D$_6$/THF): δ=67.9 (s, P$_1$); 29.3 (s, P(O)(OMe)$_2$); 12.3 (s, P$_0$) ppm. NMR $^1$H (CDCl$_3$): δ=3.20 (d, $^3J_{HP}$=10.4 Hz, 18H, CH$_3$—N—P$_1$); 3.70 (d, $^3J_{HP}$=10.5 Hz, 144H, —P(O)(O—CH$_3$)$_2$); 3.9 (d, $^2J_{HP}$=4.8 Hz, 48H, —CH$_2$—P(O)(OCH$_3$)$_2$); 6.7-7.8 (m, 78H, CH$_{arom}$, CH=N) ppm.

NMR $^{13}$C-{$^1$H} (CDCl$_3$): δ=33.0 (d, $^2J_{CP}$=11.8 Hz, CH$_3$—N—P$_1$); 46.4 (d, $^1J_{CP}$=158.3 Hz, —CH$_2$—P(O)(OCH$_3$)$_2$); 52.6 (d, $^2J_{CP}$=3.7 Hz, —P(O)(O—CH$_3$)$_2$); 52.7 (d, $^2J_{CP}$=3.9 Hz, —P(O)(O—CH$_3$)$_2$); 114.4 (s, C$_1^2$); 121.2 (s, C$_0^2$); 122.0 (s, C$_1^3$); 128.3 (s, C$_0^3$); 132.2 (s, C$_0^4$); 138.5 (d, $^3J_{CP}$=14.1 Hz, CH=N); 142.9 (d, $^3J_{CP}$=6.5 Hz, C$_1^4$); 145.1 (s, C$_1^1$); 151.1 (broad s, C$_0^1$) ppm.

Example 39

Synthesis of the Second-Generation Dendrimer with an Aza-Bis-Dimethyl-Phosphonate Surface Derived from 4-Hydroxyaniline

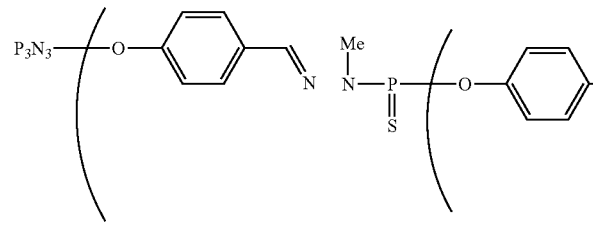

Cesium carbonate (2.00 mmol, 652 mg) is added to a solution of Gc$_2$ dendrimer (4.2·10$^{-2}$ mmol, 200 mg) in solution in anhydrous THF (5 mL) then the phenol obtained in Example 32 is added (1.05 mmol, 372 mg). The mixture is left under stirring for 24 hours at room temperature then the final mixture is filtered on celite in order to separate the salts. Finally the final product is precipitated in pentane, then washed with ether. The final product is isolated with a yield of 81%.

NMR $^{31}$P-{$^1$H} (CDCl$_3$): δ=68.1 (s, P$_1$); 66.2 (s, P$_1$); 29.2 (s, P(O)(OMe)$_2$); 11.7 (s, P$_0$) ppm.

NMR $^1$H (CDCl$_3$): 3.25 (d, $^3J_{HP}$=10.2 Hz, 54H, CH$_3$—N—P$_1$, CH$_3$—N—P$_2$); 3.65 (d, $^3J_{HP}$=10.3 Hz, 288H, —P(O)(O—CH$_3$)$_2$; 3.88 (d, $^2J_{HP}$=4.7 Hz, 96H, —CH$_2$—P(O)(OCH$_3$)$_2$); 6.7-7.8 (m, 186H, CH$_{arom}$, CH=N) ppm.

NMR $^{13}$C-{$^1$H} (CDCl$_3$): δ=32.9 (broad d, $^2J_{CP}$=11.7 Hz, CH$_3$—N—P$_1$, CH$_3$—N—P$_2$); 46.3 (d, $^1J_{CP}$=158.5 Hz, —CH$_2$—P(O)(OCH$_3$)$_2$); 52.6 (broad s, —P(O)(O—CH$_3$)$_2$); 114.3 (broad s, C$_0^2$, C$_1^2$, C$_2^2$); 121.8 (s, C$_2^3$); 128.1 (s, C$_1^3$); 131.3 (s, C$_0^3$); 131.7 (s, C$_0^4$); 132.1 (s, C$_1^4$); 138.4 (broad s, CH=N); 142.6 (d, $^3J_{CP}$=6.8 Hz, C$_2^4$); 145.0 (s, C$_2^1$); 151.0 (broad s, C$_0^1$, C$_1^1$) ppm.

Example 40

Synthesis of Zero-Generation Dendrimer with an Aza-Bis-Dimethyl-Phosphonate Surface Derived from Tyramine

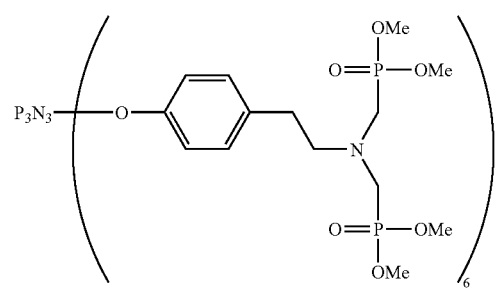

Cesium carbonate (31.2 mmol, 10.16 g) is added to a solution of hexachlorocyclotriphosphazene (2.4 mmol, 834 mg) in solution in anhydrous THF (5 mL) then phenol aza-his-dimethyl-phosphonate derived from the tyramine obtained in Example 31 is added (15.6 mmol, 5.96 g). The mixture is left under argon and with magnetic stirring for 3 days at room temperature. After filtration on celite, the product is precipitated in pentane. The isolated product can contain [0-5%] of phenol aza-bis-dimethyl-phosphonate in excess. The final product is isolated with a yield of 85%.

NMR $^{31}$P-{$^1$H} (CDCl$_3$): δ=30.2 (s, P(O)(OMe)$_2$); 12.9 (s, P$_0$) ppm.

NMR $^1$H (CDCl$_3$): δ=2.72 (deformed t, $^3J_{HH}$=8.4 Hz, 2H, —CH$_2$—CH$_2$—N); 3.00 (deformed t, $^3J_{HH}$=8.2 Hz, 2H, —CH$_2$—CH$_2$—N—); 3.18 (d, $^2J_{HP}$=8.9 Hz, 4H, N—CH$_2$—P); 3.70 (d, $^3J_{HP}$=7.8 Hz, 12H, —OMe); 6.7-7.2 (m, 4H, CH$_{arom}$) ppm.

NMR $^{13}$C-{$^1$H} (CDCl$_3$): δ=32.90 (s, —CH$_2$—CH$_2$—N); 49.4 (dd, $^1J_{CP}$=157.3 Hz, $^3J_{CP}$=6.6 Hz, —CH$_2$—P(O)(OCH$_3$)$_2$); 52.6 (d, $^2J_{CP}$=3.0 Hz, —P(O)(O—CH$_3$)$_2$); 58.3 (t, $^3J_{CP}$=7.8 Hz, CH$_2$—CH$_2$—N); 120.7 (s, C$_0^2$); 129.7 (s, C$_0^3$); 135.9 (s, C$_0^4$); 149.0 (d, $^2J_{CP}$=3.9 Hz, C$_0^1$) ppm.

Example 41

Synthesis of Zero-Generation Dendrimer with an Aza-Bis-Dimethyl-Phosphonic Surface Derived from Tyramine (GC0)

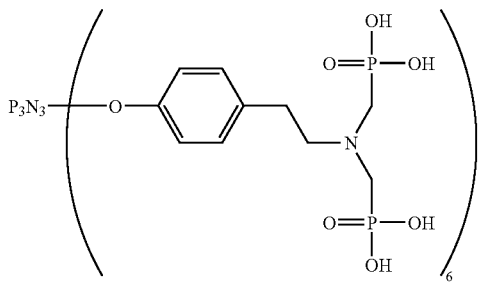

Bromotrimethylsilane (165 mmol, 22 mL) is added slowly to a solution of zero-generation dendrimer with aza-bis-dimethyl-phosphonate ends obtained in Example 40 (4.9 mmol, 11.84 g) at 0° C. in acetonitrile (5 mL). Once the addition is finished the mixture is allowed to return to room temperature over 24 hours. The mixture is then evaporated to dryness then 5 ml of water are added slowly at room temperature and the mixture is left for one hour under stirring. After filtration, the residue is washed several times with pure ether. The final product is isolated with a yield of 50%.

NMR $^{31}$P-{$^1$H} (D$_2$O): δ=12.9 (s, P$_0$); 11.4 (s, P(O)(OH)$_2$) ppm.

NMR $^{13}$C-{$^1$H} (D$_2$O): δ=31.40 (s, CH$_2$—CH$_2$—N); 53.9 (d, $^1J_{CP}$=140.07 Hz, —CH$_2$—P(O)(OH)$_2$); 59.7 (s, CH$_2$—CH$_2$—N); 123.9 (s, C$_0^2$); 132.9 (s, C$_0^3$); 135.7 (s, C$_0^4$); 151.4 (broad s, C$_0^1$) ppm.

Example 42

Synthesis of Dendrimer with an Aza-Bis-Phosphonic Surface with a DAB Structure

DAB G$_3$ dendrimer (180 mg) (Aldrich) (E. M. M. de Brabander-van den Berg, E. W. Meijer Angew. Chem. Int. Ed. Engl. 1993, 32, 1308), dimethyl phosphite (0.4 mL) and 37% solution of formaldehyde in water (0.5 mL) are stirred at 0° C. for 30 minutes. The reaction mixture is then stirred at a temperature comprised between 0° C. and 80° C. and under autogeneous pressure until the reaction is complete. After cooling, the crude reaction product is concentrated under reduced pressure and the crude residue washed with a suitable solvent, preferably ether, in order to produce the expected product in the form of a white powder.

Example 43

Synthesis of Dendrimer with an Aza-Bis-Phosphonic Surface with a PAMAM Structure PAMAM G$_3$ dendrimer (400 mg) (Aldrich) (D. A. Tomalia, H. Baker, J. Dewald, M. Hall, G. Kallos, S. Martin, J. Roeck, J. Ryder, P. S. Smith, Polym. J. (Tokyo) 1985, 17, 117; D. A. Tomalia, H. Baker, J. Dewald, M. Hall, G. Kallos, S. Martin, J. Roeck, J. Ryder, P. S. Smith, Macromolecules, 1986, 19, 2466), dimethyl phosphite (0.43 mL) and 37% solution of formaldehyde in water (0.55 mL) are stirred at 0° C. for 30 minutes. The reaction mixture is then stirred at a temperature comprised between 0° C. and 80° C. and under autogeneous pressure until the reaction is complete. After cooling, the crude reaction product is concentrated under reduced pressure and the crude residue washed with a suitable solvent, preferably ether in order to produce the expected product in the form of a white powder.

Example 44

Synthesis of First-Generation Dendrimer with a Cyclotriphosphazene Core Derived from Amino-Methyl Bis-Phosphonate Stage 1: Synthesis of the Imine Derived from Methylamine

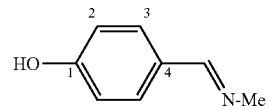

Methylamine (25 mmol, 3 mL) in solution at 33% in absolute ethanol (8 mol·L$^{-1}$) as well as 4-hydroxybenzaldehyde (20 mmol, 2.5 g) are mixed without solvent at room temperature. The mixture is left under magnetic stirring for 24 hours at room temperature. The ethanol is evaporated under reduced pressure in order to obtain an oil which is dissolved in a minimum amount of ether then precipitated in pentane. This imine has not been isolated since it is directly used in the following stage.

Stage 2: Synthesis of Amino-Methyl Mono-Phosphonate

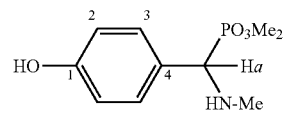

The phenol carrying the imine function of Stage 1 above (17.0 mmol, 2.3 g) is mixed without solvent and at room temperature with a few drops of triethylamine as well as dimethylphosphite (18.7 mmol, 1.7 ml). The mixture is left for 12 hours at room temperature then it is evaporated to dryness. The powder obtained is placed in solution in acetone then passed over a silica "patch". Finally the eluent is evaporated in order to obtain the final product with a yield of 68%.

NMR $^{31}$P-{$^1$H} (CDCl$_3$): δ=29.6 (s, P(O)(OMe)$_2$) ppm.

NMR $^1$H (CDCl$_3$): δ=2.29 (s, 3H, N—CH$_3$); 3.54 (d, $^3J_{HP}$=Hz, 3H, —OMe); 3.72 (d, 3H, $^3J_{HP}$=Hz, 3H, —OMe); 3.84 (d, $^2J_{HP}$=23.9 Hz, 1H, H); 6.73 (d, $^3J_{HH}$=Hz, CH$_{arom}$, 2H); 7.14 (dd, CH$_{arom}$, 2H) ppm.

NMR $^{13}$C-{$^1$H} (CDCl$_3$): δ=43.3 (t, $^3J_{CP}$=6.8 Hz, N-Me); 53.6 (d, $^2J_{CP}$=7.7 Hz, OMe); 54.1 (d, $^2J_{CP}$=6.4 Hz, OMe);

63.2 (dd, $^1J_{CP}$=159.6 Hz, $^3J_{CP}$=14.5 Hz, CH); 115.6 (s, C$_2$); 121.1 (d, $^2J_{CP}$=3.8 Hz, C$_4$); 132.0 (d, $^3J_{CP}$=8.9 Hz, C$_3$); 157.1 (s, C$_1$) ppm.

Stage 3: Synthesis of Amino-Methyl Bis-Phosphonate

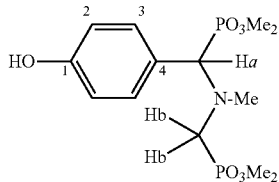

The secondary amine of Stage 2 above (6.1 mmol, 1.5 g) is placed in solution at room temperature in 37% aqueous formaldehyde solution (12.2 mmol, 1 ml) and dimethylphosphite (24.4 mmol, 2.24 mL) without solvent. The mixture is left under magnetic stirring and at room temperature for 12 hours. Then the final mixture is washed several times with an ether/pentane mixture 1/1. Finally the product is purified by chromatography on silica gel using ethyl acetate as solvent (Rf=0.35), the final product is isolated with a yield of 65%.

NMR $^{31}$P-{$^1$H} (CDCl$_3$): δ=28.1 (s, P(O)(OMe)$_2$); 30.9 (s, P(O)(OMe)$_2$) ppm.

NMR $^1$H (CDCl$_3$): δ=2.41 (s, 3H, N—CH$_3$); 2.61 (dd, $^2J_{HP}$=6.3 Hz, $^2J_{HH}$=15.3 Hz, 1H, Hb); 3.12 (dd, $^2J_{HP}$=15.6 Hz, $^2J_{HH}$=15.6 Hz, 1H, Hb); 3.30-3.80 (m, 12H, —OMe); 4.05 (d, $^2J_{HP}$=23.9 Hz, 1H, Ha); 6.74 (d, $^3J_{HH}$=7.84 Hz, CH$_{arom}$, 2H); 7.17 (d, $^3J_{HH}$=7.85 Hz, CH$_{arom}$, 2H); 9.08 (broad s, 1H, —OH) ppm.

NMR $^{13}$C-{$^1$H} (CDCl$_3$): δ=42.3 (t, $^3J_{CP}$=6.3 Hz, N-Me); 49.2 (dd, $^1J_{CP}$=164.1 Hz, $^3J_{CP}$=10.1 Hz, CH$_2$); 53.0 (m, OMe); 65.2 (dd, $^1J_{CP}$=161.7 Hz, $^3J_{CP}$=13.5 Hz, CH); 115.4 (s, C$_2$); 120.9 (d, $^2J_{CP}$=3.5 Hz, C$_4$); 131.8 (d, $^3J_{CP}$=9.1 Hz, C$_3$); 157.8 (s, C$_1$) ppm.

Stage 4: Synthesis of First-Generation Dendrimer Derived from Amino-Methyl Bis-Phosphonate

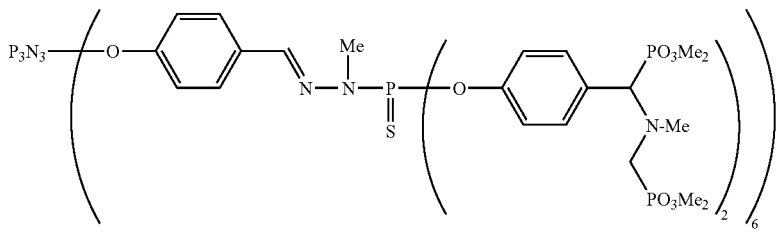

Cesium carbonate (1.2 mmol, 390 mg) is added to a solution of Gc$_1$ dendrimer (0.047 mmol, 87 mg) in anhydrous THF (2 mL) then phenol aza-bis-dimethyl-phosphonate derived from the methylamine of Stage 3 above is added (0.6 mmol, 220 mg). The mixture is left under stirring for 24 hours at room temperature then it is filtered on celite and the final mixture is centrifuged in order to separate the salts. Finally the final product is washed by precipitation in pentane and isolated with a yield of 75%.

NMR $^{31}$P-{$^1$H} (CDCl$_3$): δ=65.4 (s, P$_1$); 30.4 (s, P(O)(OMe)$_2$); 27.5 (s, P(O)(OMe)$_2$); 11.4 (s, P$_0$) ppm.

NMR $^1$H (CDCl$_3$): δ=2.46 (s, 36H, N—CH$_3$); 2.65 (dd, $^2J_{HP}$=7.4 Hz, $^2J_{HH}$=15.3 Hz, 12H, CH$_2$); 3.12 (dd, $^2J_{HP}$=15.5 Hz, $^2J_{HH}$=15.5 Hz, 12H, CH$_2$); 3.25 (d, $^3J_{HP}$=10.1 Hz, 18H, CH$_3$—N—P$_1$); 3.30-3.90 (m, 144H, —OMe); 4.2 (d, $^2J_{HP}$=23.4 Hz, 12H, CH); 6.7-7.6 (m, 78H, CH$_{arom}$, CH=N) ppm.

NMR $^{13}$C-{$^1$H} (CDCl$_3$): b=32.8 (d, $^2J_{CP}$=12.3 Hz, CH$_3$—N—P$_1$); 42.2 (t, $^3J_{CP}$=6.8 Hz, N-Me); 49.3 (dd, $^1J_{CP}$=164.0 Hz, $^3J_{CP}$=9.9 Hz, CH$_2$); 52.3-53.7 (m, OMe); 64.9 (dd, $^1J_{CP}$=138.1 Hz, $^3J_{CP}$=11.9 Hz, CH); 121.1 (broad s, C$_0^2$, C$_1^2$); 128.2 (s, C$_0^3$); 128.4 (d, $^2J_{CP}$=3.1 Hz, C$_1^4$); 131.8 (s, C$_0^4$); 131.8 (d, $^3J_{CP}$=8.2 Hz, C$_1^3$); 139.0 (d, $^3J_{CP}$=14.5 Hz, CH=N); 150.6 (d, $^2J_{CP}$=6.9 Hz, C$_1^1$); 151.2 (s, C$_0^1$) ppm.

Stage 5: Synthesis of First-Generation Dendrimer Derived from Amino-Methyl Bis-Phosphonic Acid

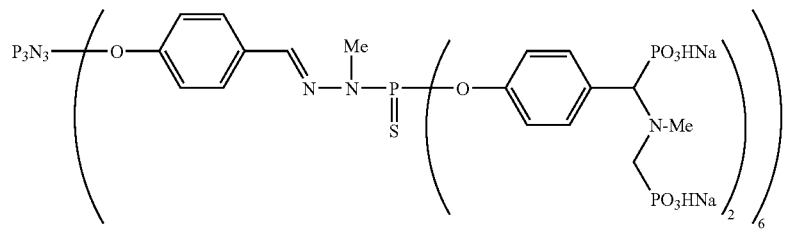

Bromotrimethylsilane (2.1 mmol; 280 μl) is slowly added to a solution of first-generation dendrimer with aza-bis-dimethyl-phosphonate ends derived from the methylamine of Stage 4 (3.97·10$^{-2}$ mmol, 230 mg) at 0° C. in acetonitrile (5 mL). Once the addition is finished the mixture is allowed to return to room temperature over 12 hours. The mixture is then evaporated to dryness then 1 ml of anhydrous methanol is added at room temperature and the mixture is left for one hour under stirring. After evaporation to dryness, the residue is washed several times with pure ether. As the product is totally insoluble in organic solvents it is converted to its monosodium salt in the presence of soda (3.1 ml of a soda solution, at 0.1955 mol·L$^{-1}$ for 130 mg of dendrimer phosphonic acid).

The resulting solution is lyophilized in order to produce the dendrimer in the form of a white powder. The final product is isolated with a yield of 58%.

NMR $^{31}$P-{$^{1}$H} (CD$_3$CN/D$_2$O): δ=66.09 (s, P$_1$ and P$_2$); 14.1 (s, P$_0$); 11.2 (s, PO$_3$HNa) ppm.

NMR $^{1}$H (CD$_3$CN/D$_2$O): b=2.5-3.8 (m, 90H, CH$_3$—N—P, N-Me, CH$_2$, CH); 6.5-8.0 (m, 78H, CH$_{arom}$, CH=N).

NMR $^{13}$C-{$^{1}$H} (CD$_3$CN/D$_2$O): δ=35.5 (broad s, CH$_3$—N—P$_1$); 44.8 (broad s, N-Me); 54.5 (d, $^{1}J_{CP}$=132.5 Hz, CH$_2$); 70.5 (d, $^{1}J_{CP}$=129.4 Hz, CH); 124.4 (broad s, C$_0^2$, C$_1^2$); 130.4 (broad s, C$_0^3$, C$_1^3$); 136.3 (broad s, C$_0^4$, C$_1^4$); 142.9 (broad s, CH=N); 153.9 (broad s, C$_0^1$, C$_1^1$) ppm.

Example 45

Synthesis of Second-Generation Dendrimer with a Cyclotriphosphazene Core Derived from Amino-Methyl Bis-Phosphonate Stage 1: Synthesis of Second-Generation Dendrimer Derived from Amino-Methyl Bis-Phosphonate

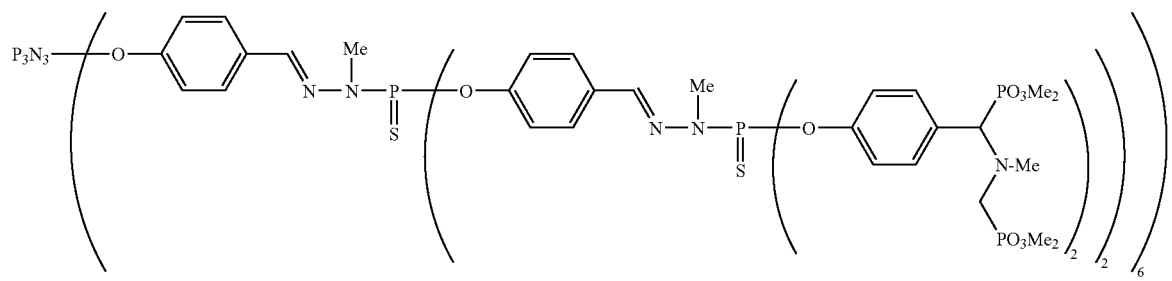

Cesium carbonate (1.3 mmol, 407 mg) is added to a solution of Gc$_2$ dendrimer (0.024 mmol, 119 mg) in anhydrous THF (2 mL) then phenol aza-bis-dimethyl-phosphonate derived from the methylamine of Stage 3 of Example 44 is added (0.67 mmol, 230 mg). The mixture is left under stirring for 24 hours at room temperature then filtered on celite and the final mixture is centrifuged in order to separate the salts. Finally the final product is washed by precipitation in pentane and isolated with a yield of 80%.

NMR $^{31}$P-{$^{1}$H} (CDCl$_3$): δ=66.1 (s, P$_1$); 65.4 (s, P$_2$); 30.4 (s, P(O)(OMe)$_2$); 27.5 (s, P(O)(OMe)$_2$); 11.6 (s, P$_0$) ppm.

NMR $^{1}$H (CDCl$_3$): δ=2.48 (s, 72H, N—CH$_3$); 2.67 (dd, $^{2}J_{HP}$=7.1 Hz, $^{2}J_{HH}$=15.3 Hz, 24H, CH$_2$); 3.14 (dd, $^{2}J_{HP}$=15.4 Hz, $^{2}J_{HH}$=15.4 Hz, 24H, CH$_2$); 3.31 (d, $^{3}J_{HP}$=10.9 Hz, 54H, CH$_3$—N—P$_1$, CH$_3$—N—P$_2$); 3.30-3.90 (m, 288H, —OMe); 4.2 (d, $^{2}J_{HP}$=23.2 Hz, 24H, CH); 7.0-7.7 (m, 186H, CH$_{arom}$, CH=N) ppm.

NMR $^{13}$C-{$^{1}$H} (CDCl$_3$): δ=32.9 (d, $^{2}J_{CP}$=12.4 Hz, CH$_3$—N—P$_1$, CH$_3$—N—P$_2$); 42.3 (t, $^{3}J_{CP}$=7.0 Hz, N-Me); 49.5 (dd, $^{1}J_{CP}$=163.7 Hz, $^{3}J_{CP}$=9.8 Hz, CH$_2$); 52.4-53.6 (m, OMe); 64.9 (dd, $^{1}J_{CP}$=160.2 Hz, $^{3}J_{CP}$=12.1 Hz, CH); 121.17 (s, C$_2^2$); 121.24 (s, C$_1^2$); 121.8 (s, C$_0^2$); 128.3 (broad s, C$_2^4$); 128.5 (broad s, C$_0^3$, C$_1^3$); 131.8 (broad d, $^{3}J_{CP}$=8.2 Hz, C$_1^4$, C$_2^3$); 132.3 (broad s, C$_0^4$); 138.9 (d, $^{3}J_{CP}$=13.8 Hz, CH=N); 150.7 (broad d, $^{2}J_{CP}$=7.2 Hz, C$_2^1$); 151.2 (broad s, C$_0^1$, C$_1^1$) ppm.

Stage 2: Synthesis of Second-Generation Dendrimer Derived from Amino-Methyl Bis-Phosphonic Acid

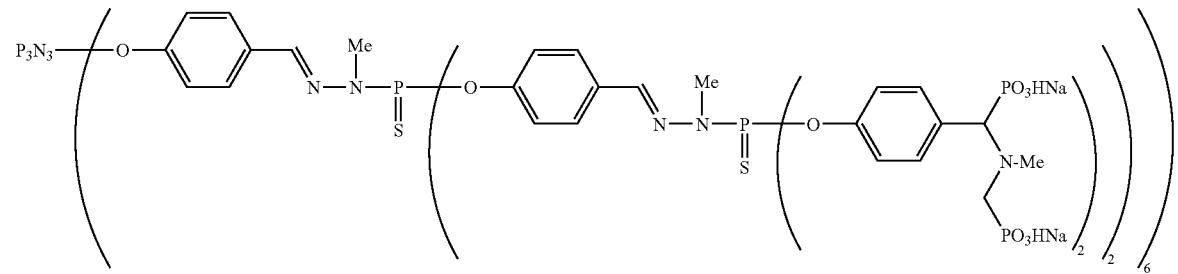

Bromotrimethylsilane (1.6 mmol; 210 μl) is slowly added to a solution of second-generation dendrimer with aza-bis-dimethyl-phosphonate ends derived from the methylamine of Stage 1 (1.49·10$^{-2}$ mmol, 190 mg) at 0° C. in acetonitrile (5 mL). Once the addition is finished the mixture is allowed to return to room temperature over 12 hours. The mixture is then evaporated to dryness then 1 ml of anhydrous methanol is added at room temperature and the mixture is left for one hour under stirring. After evaporation to dryness, the residue is washed several times with pure ether. As the product is totally insoluble in organic solvents it is converted to its monosodium salt in the presence of soda (3.01 ml of a soda solution, at 0.1955 mol·L$^{-1}$ for 140 mg of dendrimer phosphonic acid). The resulting solution is lyophilized in order to produce the dendrimer in the form of a white powder. The final product is isolated with a yield of 54%.

NMR $^{31}$P-{$^1$H} (CD$_3$CN/D$_2$O): δ=66.7 (s, P$_1$); 14.4 (s, P$_0$) 10.8 (s, PO$_3$HNa) ppm.

NMR $^1$H (CD$_3$CN/D$_2$O): δ=2.5-3.8 (m, 198H, CH$_3$—N—P$_1$, CH$_3$—N—P$_2$, N-Me, CH$_2$, CH); 6.5-8.0 (m, 186H, CH$_{arom}$, CH=N).

NMR $^{13}$C-{$^1$H} (CD$_3$CN/D$_2$O): δ=35.5 (broad s, CH$_3$—N—P$_1$, CH$_3$—N—P$_2$); 44.6 (broad s, N-Me); 55.6 (d, $^1$J$_{CP}$=102.7 Hz, CH$_2$); 71.0 (d, $^1$J$_{CP}$=128.2 Hz, CH); 124.4 (broad s, C$_0^2$, C$_1^2$, C$_2^2$); 130.4 (broad s, C$_0^3$, C$_1^3$, C$_2^3$); 136.3 (broad s, C$_0^4$, C$_1^4$, C$_2^4$); 142.9 (broad s, CH=N); 153.9 (s, C$_0^1$, C$_1^1$, C$_2^1$) ppm.

Example 46

Synthesis of Fourth-Generation Dendrimer with a Cyclotriphosphazene Core Derived from Amino-Methyl Bis-Phosphonate

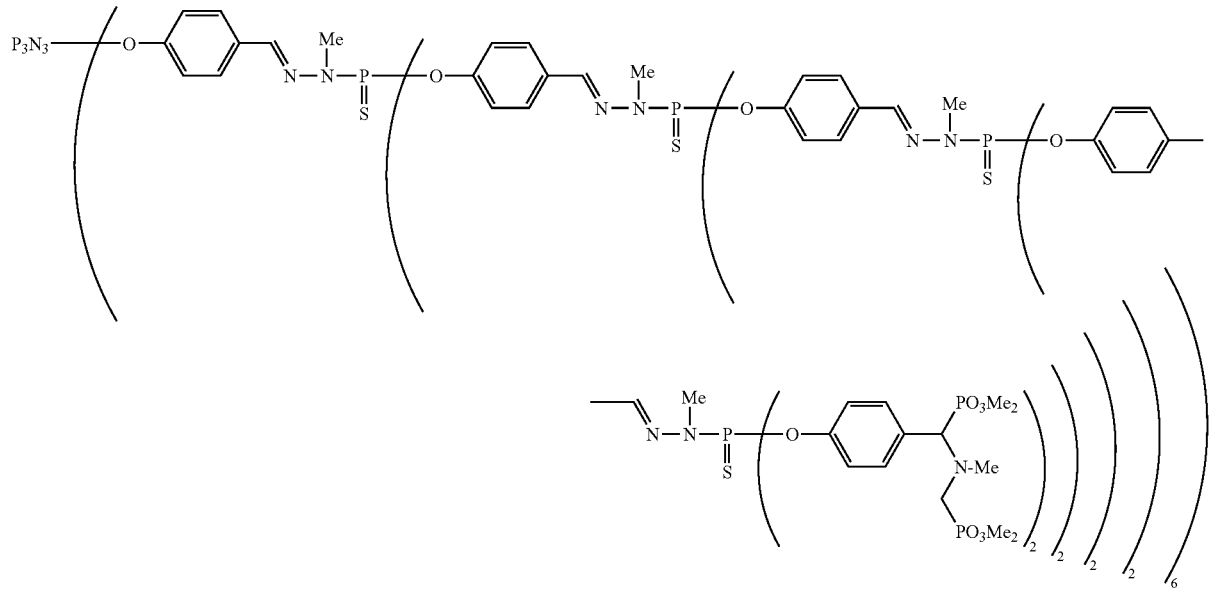

Cesium carbonate (0.71 mmol, 230 mg) is added to a solution of Gc$_4$ dendrimer (3.5·10$^{-3}$ mmol, 79.2 mg) in anhydrous THF (2 mL) then phenol aza-bis-dimethyl-phosphonate derived from the methylamine of Stage 3 of Example 44 is added (0.35 mmol, 130 mg). The mixture is left under stirring for 48 hours at room temperature then filtered on celite and the final mixture is centrifuged in order to separate the salts. Finally the final product is washed by precipitation in pentane and isolated with a yield of 84%.

NMR $^{31}$P-{$^1$H} (CDCl$_3$): δ=66.1 (broad s, P$_1$, P$_2$, P$_3$); 65.4 (s, P$_4$); 30.1 (s, P(O)(OMe)$_2$); 27.6 (s, P(O)(OMe)$_2$); 11.6 (s, P$_0$) ppm.

NMR $^1$H (CDCl$_3$): δ=2.48 (s, 288H, N—CH$_3$); 2.65 (dd, $^2$J$_{HP}$=7.2 Hz, $^2$J$_{HH}$=15.3 Hz, 96H, CH$_2$); 3.13 (dd, $^2$J$_{HP}$=15.2 Hz, $^2$J$_{HH}$=15.2 Hz, 96H, CH$_2$); 3.27 (broad s, 270H, CH$_3$—N—P$_1$, CH$_3$—N—P$_2$, CH$_3$—N—P$_3$, CH$_3$—N—P$_4$); 3.30-3.90 (m, 1152H, —OMe); 4.2 (d, $^2$J$_{HP}$=23.3 Hz, 96H, CH); 7.0-7.7 (m, 834H, CH$_{arom}$, CH=N) ppm.

NMR $^{13}$C-{$^1$H} (CDCl$_3$): δ=32.9 (d, $^2$J$_{CP}$=12.4 Hz, CH$_3$—N—P$_1$, CH$_3$—N—P$_2$, CH$_3$—N—P$_3$, CH$_3$—N—P$_4$); 42.3 (t, $^3$J$_{CP}$=7.0 Hz, N-Me); 49.5 (dd, $^1$J$_{CP}$=163.8 Hz, $^3$J$_{CP}$=9.9 Hz, CH$_2$); 52.4-53.9 (m, OMe); 65.1 (dd, $^1$J$_{CP}$=161.2 Hz, $^3$J$_{CP}$=12.3 Hz, CH); 121.45 (s, C$_3^2$); 122.1 (broad s, C$_2^2$, C$_1^2$, C$_0^2$); 128.5 (broad s, C$_0^3$ C$_1^3$ C$_2^3$); 128.7 (broad s, C$_3^3$); 132.1 (broad d, $^3$J$_{CP}$=8.2 Hz, C$_3^4$, C$_2^4$); 132.4 (broad s, C$_0^4$, C$_1^4$); 139.2 (d, $^3$J$_{CP}$=13.4 Hz, CH=N); 151.0 (broad d, $^2$J$_{CP}$=7.2 Hz, C$_3^1$); 151.6 (broad s, C$_2^1$, C$_1^1$); 151.7 (broad s, C$_0^1$) ppm.

Example 47

Synthesis of First-Generation Dendrimer with a Cyclotriphosphazene Core with a Surface Derived from Amino-Butyl Bis-Phosphonate

Stage 1: Synthesis of Imine Derived from Butylamine

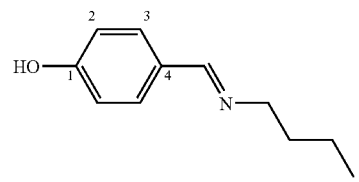

n-butylamine (43 mmol, 4.3 mL) and 4-hydroxybenzaldehyde (41 mmol, 5 g) are mixed without solvent and at room temperature with a 4 Å molecular sieve. The mixture is left under magnetic stirring for 24 hours then it is taken up with THF in order to be filtered on celite. The THF is evaporated under reduced pressure in order to obtain a thick and dark oil. This oil can be dissolved in a minimum amount of ether and is precipitated with pentane. A slightly pinkish powder is thus obtained with a yield of 80%.

NMR $^1$H (CDCl$_3$): δ=0.90 (t, $^3$J$_{HH}$=7.6 Hz, 3H, —CH$_3$); 1.33 (m, 2H, CH$_2$—CH$_2$—CH$_3$); 1.66 (m, 2H, CH$_2$—CH$_2$—CH$_3$); 3.59 (t, $^3$J$_{HH}$=7.4 Hz, 2H, N—CH$_2$—); 6.7 (d, $^3$J$_{HH}$=8.4 Hz, CH$_{arom}$, 2H); 7.5 (d, $^3$J$_{HH}$=8.4 Hz, 2H, CH$_{arom}$); 8.14 (s, 1H, CH=N); 8.81 (broad s, 1H, —OH) ppm.

NMR $^{13}$C-{$^1$H} (CDCl$_3$): δ=13.9 (s, CH$_3$); 20.3 (s, CH$_2$—CH$_3$); 32.7 (s, CH$_2$—CH$_2$—CH$_3$); 60.1 (s, N—CH$_2$—CH$_2$—CH$_2$—CH$_3$); 116.3 (s, C$_2$); 125.4 (s, Ca); 130.6 (s, C$_3$); 161.5 (s, C$_1$); 162.9 (s, CH=N) ppm.

Stage 2: Synthesis of Amino-Butyl Mono-Phosphonate

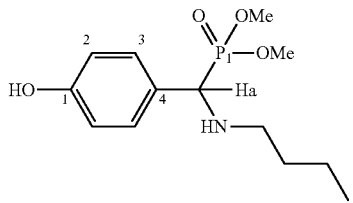

The phenol carrying the imine function of Stage 1 (16.9 mmol, 3 g) is mixed without solvent and at room temperature with triethylamine (16.9 mmol, 2.35 ml) as well as dimethylphosphite (16.9 mmol, 1.55 ml). The mixture is left for 12 hours at room temperature then it is evaporated to dryness. The powder obtained is placed in solution in acetone then passed over a silica "patch". Finally the eluent is evaporated in order to obtain the final product with a yield of 65%.

NMR $^{31}$P-{$^{1}$H} (CDCl$_3$): δ=29.8 (s, P$_1$) ppm.

NMR $^{1}$H (CDCl$_3$): δ=0.80 (t, $^{3}J_{HH}$=7.6 Hz, 3H, —CH$_3$); 1.20-1.55 (m, 4H, CH$_2$—CH$_2$); 2.41 (m, 2H, N—CH$_2$—); 3.6 (d, $^{3}J_{HP}$=10.4 Hz, 3H, —P$_1$OMe); 3.8 (d, $^{3}J_{HP}$=10.8 Hz, 3H, —P$_2$OMe); 4.0 (d, $^{2}J_{HP}$=26.0 Hz, 1H, Ha); 6.7 (d, $^{3}J_{HH}$=8.4 Hz, CH$_{arom}$, 2H); 7.2 (d, $^{3}J_{HH}$=8.4 Hz, CH$_{arom}$, 2H) ppm.

NMR $^{13}$C-{$^{1}$H} (CDCl$_3$): δ=13.9 (s, CH$_3$); 20.3 (s, CH$_2$—CH$_3$); 31.8 (s, CH$_2$—CH$_2$—CH$_3$); 47.4 (d, $^{3}J_{CP}$=17.6 Hz, N—CH$_2$—CH$_2$—CH$_2$—CH$_3$); 53.6 (d, $^{2}J_{CP}$=7.9 Hz, OMe); 53.9 (d, $^{2}J_{CP}$=6.2 Hz, OMe); 59.8 (d, $^{1}J_{CP}$=157.1 Hz, CH); 115.9 (s, C$_2$); 125.4 (s, C$_4$); 129.5 (s, C$_3$); 157.0 (s, C$_1$) ppm.

Stage 3: Synthesis of Amino-Butyl Bis-Phosphonate

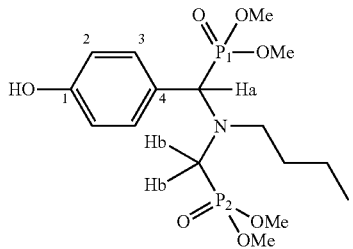

The secondary amine of Stage 2 (5.8 mmol, 1.67 g) is placed in solution at room temperature in formaldehyde in aqueous solution 37% (8.7 mmol, 657 µl) and dimethylphosphite (5.8 mmol, 530 µl). The mixture is left under magnetic stirring and at room temperature for 12 hours. Finally the excess of formaldehyde is eliminated under reduced pressure and the product is purified by chromatography on silica gel using ethyl acetate as solvent, the final product is isolated with a yield of 60%.

NMR $^{31}$P-{$^{1}$H} (CDCl$_3$): δ=28.3 (s, P$_1$); 30.9 (s, P$_2$) ppm.

NMR $^{1}$H (CDCl$_3$): δ=0.86 (t, $^{3}J_{HH}$=7.6 Hz, 3H, CH$_3$); 1.25-1.55 (m, 4H, CH$_2$—CH$_2$); 2.31 (m, 1H, N—CH$_2$—); 2.64 (dd, $^{2}J_{HP}$=3.2 Hz, $^{2}J_{HH}$=15.6 Hz, 1H, CH$_2$—P$_2$); 3.11 (m, 1H, N—CH$_2$—CH$_2$); 3.35 (ddd, $^{2}J_{HP}$=17.2 Hz, $^{2}J_{HH}$=17.0 Hz, $^{4}J_{HP}$=1.6 Hz, 1H, CH$_2$—P$_2$); 3.5 (d, $^{3}J_{HP}$=10.4 Hz, 3H, —P$_1$OMe); 3.7 (d, $^{3}J_{HP}$=10.8 Hz, 3H, —P$_2$OMe); 3.8 (d, $^{3}J_{HP}$=10.8 Hz, 3H, —P$_2$OMe); 3.9 (d, $^{3}J_{HP}$=10.8 Hz, 3H, —P$_1$OMe); 4.4 (d, $^{2}J_{HP}$=26.0 Hz, 1H, Ha); 6.84 (d, $^{3}J_{HH}$=8.4 Hz, CH$_{arom}$, 2H); 7.26 (d, $^{3}J_{HH}$=8.4 Hz, CH$_{arom}$, 2H); 9.1 (broad s, 1H, —OH) ppm.

NMR $^{13}$C-{$^{1}$H} (CDCl$_3$): δ=14.4 (s, CH$_3$); 20.4 (s, CH$_2$—CH$_3$); 30.6 (s, CH$_2$—CH$_2$—CH$_3$); 46.0 (dd, $^{1}J_{CP}$=166.8 Hz, $^{3}J_{CP}$=8.8 Hz, CH$_2$—P$_2$); 53.0 (d, $^{2}J_{CP}$=6.8 Hz, P$_2$OMe); 53.4 (d, $^{2}J_{CP}$=7.0 Hz, P$_1$OMe); 53.7 (d, $^{2}J_{CP}$=7.0 Hz, P$_2$OMe); 54.1 (d, $^{2}J_{CP}$=7.1 Hz, P$_1$OMe); 53.1 (t, $^{3}J_{CP}$=7.8 Hz, N—CH$_2$—CH$_2$—CH$_2$—CH$_3$); 61.3 (dd, $^{1}J_{CP}$=162.9 Hz, $^{3}J_{CP}$=10.0 Hz, CH); 115.9 (s, C$_2$); 121.5 (d, $^{2}J_{CP}$=6.0 Hz, C$_4$); 132.5 (d, $^{3}J_{CP}$=9.1 Hz, C$_3$); 158.1 (s, C$_1$) ppm.

Stage 4: Synthesis of First-Generation Dendrimer Derived from Amino-Butyl Bis-Phosphonate

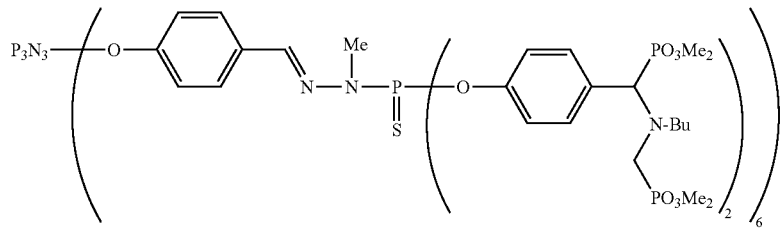

Cesium carbonate (1.4 mmol, 453 mg) is added to a solution of Gc$_1$ dendrimer (0.058 mmol, 106 mg) in anhydrous THF (3 mL) then phenol aza-bis-dimethyl-phosphonate derived from the butylamine of Stage 3 is added (0.73 mmol, 300 mg). The mixture is left under stirring for 24 hours at room temperature then filtered on celite and the final mixture is centrifuged in order to separate the salts. Finally the final product is washed by precipitation in pentane and isolated with a yield of 65%.

NMR $^{31}$P-{$^{1}$H} (CDCl$_3$): δ=65.4 (s, P$_1$); 30.8 (s, P(O)(OMe)$_2$); 28.3 (s, P(O)(OMe)$_2$); 11.4 (s, P$_0$) ppm.

NMR $^{1}$H (CDCl$_3$): δ=0.82 (t, $^{3}J_{HH}$=7.6 Hz, 36H, CH$_3$); 1.20-1.50 (m, 48H, CH$_2$—CH$_2$); 2.27 (m, 12H, N—CH$_2$—); 2.57 (dd, $^{2}J_{HP}$=3.4 Hz, $^{2}J_{HH}$=15.2 Hz, 12H, CH$_2$—P$_2$); 3.11 (m, 12H, N—CH$_2$—CH$_2$); 3.26 (d, $^{3}J_{HP}$=10.6 Hz, 18H, CH$_3$—N—P); 3.4 (d, $^{3}J_{HP}$=10.6 Hz, 36H, —P$_1$OMe); 3.6 (d, $^{3}J_{HP}$=10.7 Hz, 36H, —P$_2$OMe); 3.7 (d, $^{3}J_{HP}$=10.8 Hz, 36H, —P$_2$OMe); 3.8 (d, $^{3}J_{HP}$=10.6 Hz, 36H, —P$_1$OMe); 4.4 (d, $^{2}J_{HP}$=25.0 Hz, 12H, Ha); 6.9-7.8 (m, 78H, CH$_{arom}$, CH=N) ppm.

NMR $^{13}$C-{$^{1}$H} (CDCl$_3$): δ=14.0 (s, CH$_3$); 19.9 (s, CH$_2$—CH$_3$); 30.2 (s, CH$_2$—CH$_2$—CH$_3$); 32.8 (d, $^{2}J_{CP}$=11.5 Hz, CH$_3$—N—P$_1$); 46.0 (dd, $^{1}J_{CP}$=166.7 Hz, $^{3}J_{CP}$=8.6 Hz, CH$_2$—P$_2$); 52-54 (m, PO$_3$Me$_2$); 60.3 (dd, $^{1}J_{CP}$=163.9 Hz, $^{3}J_{CP}$=10.4 Hz, CH); 121.2 (broad s, C$_0{}^2$, C$_1{}^2$); 128.2 (s, C$_0{}^3$);

128.8 (d, $^3J_{CP}$=4.5 Hz, $C_1^3$); 131.9 (s, $C_1^4$); 132.1 (s, $C_0^4$); 139.1 (d, $^3J_{CP}$=13.9 Hz, CH=N); 150.6 (d, $^2J_{CP}$=6.9 Hz, $C_1^1$); 151.3 (s, $C_0^1$) ppm.

Stage 5: Synthesis of First-Generation Dendrimer Derived from Amino-Butyl Bis-Phosphonic Acid

Example 48

Synthesis of Second-Generation Dendrimer with a Cyclotriphosphazene Core with a Surface Derived from Amino-Butyl Bis-Phosphonate

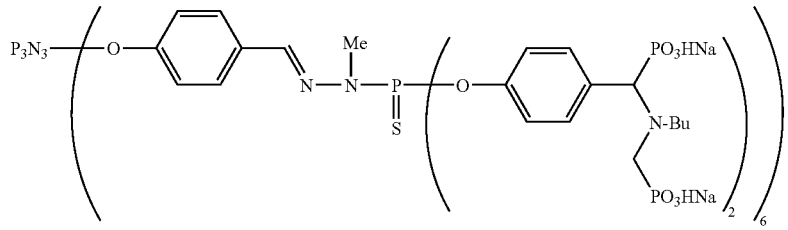

Bromotrimethylsilane (0.92 mmol, 123 μl) is slowly added to a solution of first-generation dendrimer with aza-bis-dimethyl-phosphonate ends derived from the butylamine of Stage 4 (1.75·10$^{-5}$ mmol, 110 mg) at 0° C. in acetonitrile (4 mL). Once the addition is finished the mixture is allowed to return to room temperature over 12 hours. The mixture is then

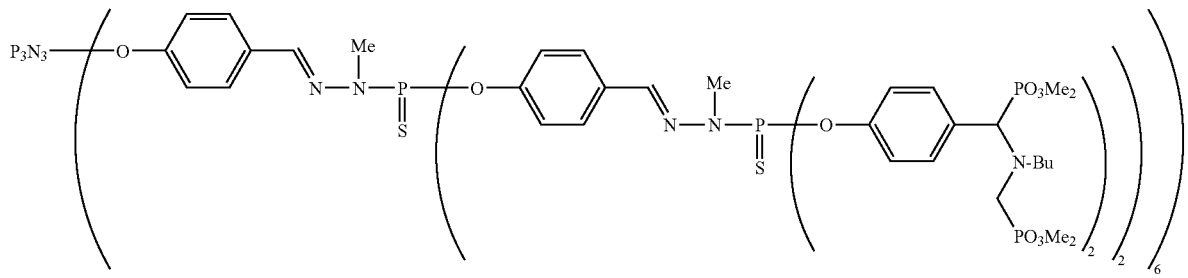

evaporated to dryness then 1 ml of anhydrous methanol is added at room temperature and the mixture is left for one hour under stirring. After evaporation to dryness, the residue is washed several times with pure ether. As the product is totally insoluble in organic solvents it is converted to its monosodium salt in the presence of soda (0.98 ml of a soda solution, at 0.1955 mol·L$^{-1}$ for 45 mg of phosphonic acid dendrimer). The resulting solution is lyophilized in order to produce the dendrimer in the form of a white powder. The final product is isolated with a yield of 55%.

NMR $^{31}$P-{$^1$H} (CD$_3$CN/D$_2$O): δ=69.3 (s, P$_1$); 15.3 (s, P$_0$); 13.5 (s, P(O)(OHNa)$_2$) ppm.

NMR $^1$H (CD$_3$CN/D$_2$O): δ=0.9 (broad s, 36H, CH$_3$); 1.20-1.50 (m, 48H, CH$_2$—CH$_2$); 2.5-3.8 (m, 78H, CH$_3$—N—P, N—CH$_2$, CH$_2$, CH); 6.5-8.0 (m, 78H, CH$_{arom}$, CH=N).

NMR $^{13}$C-{$^1$H} (CD$_3$CN/D$_2$O): δ=13.4 (s, CH$_3$); 19.6 (s, CH$_2$—CH$_3$); 26.2 (s, CH$_2$—CH$_2$—CH$_3$); 33.4 (broad s, CH$_3$—N—P$_2$, CH$_3$—N—P$_1$); 50.5 (d, $^1J_{CP}$=123.0 Hz, CH$_2$—P$_2$); 54.1 (broad s, N—CH$_2$—CH$_2$—CH$_2$—CH$_3$); 66.3 (dd, $^1J_{CP}$=126.9 Hz, CH); 121.0 (s, $C_0^2$); 121.9 (s, $C_1^2$); 128.6 (s, $C_0^3$); 129.0 (s, $C_1^3$); 132.8 (s, $C_0^4$); 134.1 (s, $C_1^4$); 141.5 (broad s, CH=N); 150.8 (s, $C_0^1$); 151.5 (d, $^2J_{CP}$=6.9 Hz, $C_1^1$) ppm.

Cesium carbonate (0.54 mmol, 176 mg) is added to a solution of Gc$_2$ dendrimer (0.0106 mmol, 51 mg) in anhydrous THF (2 mL) then phenol aza-bis-dimethyl-phosphonate derived from the butylamine of Stage 3 of Example 47 is added (0.27 mmol, 110 mg). The mixture is left under stirring for 36 hours at room temperature then filtered on celite and the final mixture is centrifuged in order to separate the salts. Finally the final product is washed by precipitation in pentane and isolated with a yield of 75%.

NMR $^{31}$P-{$^1$H} (CDCl$_3$): δ=66.1 (s, P$_1$); 65.3 (s, P$_2$); 30.8 (s, P(O)(OMe)$_2$); 28.3 (s, P(O)(OMe)$_2$); 11.4 (s, P$_0$) ppm.

NMR $^1$H (CDCl$_3$): δ=0.88 (t, $^3J_{HH}$=7.6 Hz, 72H, CH$_3$); 1.20-1.45 (m, 96H, CH$_2$—CH$_2$); 2.33 (m, 24H, N—CH$_2$—); 2.63 (dd, $^2J_{HP}$=3.4 Hz, $^2J_{HH}$=15.2 Hz, 24H, CH$_2$—P$_2$); 3.16 (m, 24H, N—CH$_2$—CH$_2$); 3.33 (m, 54H, CH$_3$—N—P); 3.44 (d, $^3J_{HP}$=12.0 Hz, 72H, —P$_1$OMe); 3.7 (d, $^3J_{HP}$=10.7 Hz, 72H, —P$_2$OMe); 3.8 (d, $^3J_{HP}$=10.6 Hz, 72H, —P$_2$OMe); 3.9 (d, $^3J_{HP}$=10.7 Hz, 72H, —P$_1$OMe); 4.5 (d, $^2J_{HP}$=25.5 Hz, 24H, Ha); 6.9-7.8 (m, 186H, CH$_{arom}$, CH=N) ppm.

NMR $^{13}$C-{$^1$H} (CDCl$_3$): δ=14.4 (s, CH$_3$); 20.3 (s, CH$_2$—CH$_3$); 30.6 (s, CH$_2$—CH$_2$—CH$_3$); 33.3 (d, $^2J_{CP}$=11.7 Hz, CH$_3$—N—P$_2$, CH$_3$—N—P$_1$); 46.5 (dd, $^1J_{CP}$=166.7 Hz, $^3J_{CP}$=8.6 Hz, CH$_2$—P$_2$); 52.5-54.1 (m, PO$_3$Me$_2$); "53.1 (t, $^3J_{CP}$=7.8 Hz, N—CH$_2$—CH$_2$—CH$_2$—CH$_3$) PB"; 61.3 (dd, $^1J_{CP}$=164.9 Hz, $^3J_{CP}$=10.9 Hz, CH); 121.6 (broad s, $C_1^2$, $C_2^2$); 122.2 (s, $C_0^2$); 128.7 (broad s, $C_2^3$); 129.3 (broad s, $C_0^3$, $C_1^3$); 132.5 (broad d, $^2J_{CP}$=7.5 Hz, $C_2^4$, $C_1^4$, $C_0^4$); 139.1 (broad s, CH=N); 151.0 (d, $^2J_{CP}$=6.9 Hz, $C_2^1$); 151.8 (broad s, $C_1^1$, $C_0^1$) ppm.

Example 49

Synthesis of Dendrimers with a Surface Derived from Dimethyl N-Allyl-N-(4-Hydroxy)-Benzyl-α-Amino-Phosphonate

Stage 1: Synthesis of a Phenol Monophosphonate

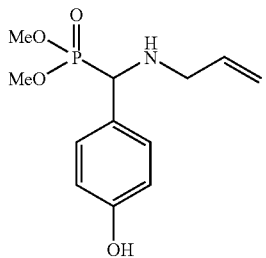 [SMILES: C=CCNC(c1ccc(O)cc1)P(=O)(OC)OC]

10 to 15 grains of MgSO$_4$ then allylamine (7.5 mL, 0.1 mol) at 0° C. are added to a solution of 4-hydroxyhenzaldehyde (11 g, 0.1 mol) in CH$_2$Cl$_2$ (25 mL). The reaction (exothermic) is maintained at room temperature and under vigorous stirring overnight and dimethyl phosphite (9 mL, 0.1 mole) is added and the reaction mixture is stirred at room temperature for 3 days. The progress of the reaction is monitored by $^1$H and $^{31}$P NMR. The reaction mixture is poured into 100 mL of water then extracted with 3 times 100 mL of CH$_2$Cl$_2$. The organic phase is dried over MgSO$_4$ and the solvent is eliminated under reduced pressure. The residue is washed twice with ether until a very viscous pale yellow oil is obtained with a yield of 90%.

NMR $^{31}$P{$^1$H} (CDCl$_3$, 81.01 MHz): δ=29.3 (s, P=O).

NMR $^1$H (CDCl$_3$, 200.13 MHz): δ=2.96 (dd, 1H, $^2J_{HH}$=14.0 Hz, $^3J_{HH}$=6.9 Hz, CHHCH$_2$=CH); 3.18 (dd, 1H, $^2J_{HH}$=14.0 Hz, $^3J_{HH}$=5.0 Hz, CHHCH$_2$=CH); 3.44 (d, 3H, $^3J_{HP}$=10.4 Hz, POMe); 3.65 (d, 3H, $^3J_{HP}$=10.5 Hz, POMe); 3.95 (d, 1H, $^2J_{HP}$=19.8 Hz, PCH); 5.01 (m, 2H, CH$_2$=CH); 5.72 (m, 1H, CH=); 6.74 (d, 2H, $^3J_{HH}$=8.1 Hz, C$^2$—H); 7.10 (d, 2H, $^3J_{HH}$=8.1 Hz, C$^3$—H).

Stage 2: Synthesis of a Phenol Bisphosphonate

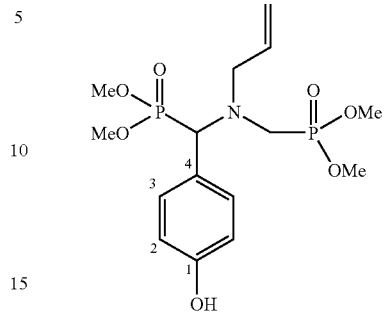

A 37% aqueous formaldehyde solution at (1.06 mL, 14.35 mmol, 4 eq.) is added to a solution of α-amino-phosphonate synthesized in the preceding stage (970 mg, 3.58 mmol) in THF (5 mL). After approximately 30 minutes dimethylphosphite (492 μL, 5.37 mmol, 1.5 eq.) is added. The solution is stirred for 72 hours. The progress of the reaction is monitored by $^{31}$P NMR. The reaction mixture is poured into 30 mL of water then extracted with CH$_2$Cl$_2$. The organic phase is dried over MgSO$_4$ and the solvent is eliminated under reduced pressure. The residue is washed twice with ether, dried under vacuum and the viscous oil is purified by chromatography on silica gel (eluent: AcOEt/MeOH, 95:5) with a yield of 28%.

NMR $^{31}$P{$^1$H} (CDCl$_3$, 81.01 MHz): δ=28.7 (s, P=O); 31.4 (s, P=O).

NMR $^1$H (CDCl$_3$, 200.13 MHz): δ=2.57 (dd, 1H, $^2J_{HH}$=15.5 Hz and $^2J_{HP}$=2.9 Hz, PCHH); 2.80 (dd, 1H, $^2J_{HH}$=13.8 Hz and $^3J_{HH}$=8.6 Hz, =CH—CHH); 3.43 (d, 3H, $^3J_{HP}$=10.5 Hz, POMe); 3.45 (dl, 1H, $^2J_{HH}$=16.0 Hz, PCHH); 3.69 (d, 3H, $^3J_{HP}$=10.7 Hz, POMe); 3.79 (d, 3H, $^3J_{HP}$=10.7 Hz, POMe); 3.86 (d, 3H, $^3J_{HP}$=10.6 Hz, POMe); 3.88 (dl, 1H, $^2J_{HH}$=14.0 Hz, =CH—CHH); 4.47 (d, 1H, $^2J_{HP}$=25.9 Hz, PCH); 5.20 (m, 2H, CH$_2$=CH); 5.79 (m, 1H, CH=CH$_2$); 6.82 (d, 2H, $^3J_{HH}$=8.4 Hz, C$^2$—H); 7.26 (d, 2H, $^3J_{HH}$=8.3 Hz, C$^3$—H); 9.02 (bs, OH).

NMR $^{13}$C{$^1$H} (CDCl$_3$, 50.32 MHz): δ=45.2 (dd, $^1J_{CP}$=165.8 and $^3J_{CP}$=8.0 Hz, PCH$_2$); 52.62 (d, $^2J_{CP}$=6.9 Hz, POMe); 53.0 (d, $^2J_{CP}$=7.1 Hz, POMe); 53.2 (d, $^2J_{CP}$=7.2 Hz, POMe); 53.9 (d, $^2J_{CP}$=7.0 Hz, POMe); 56.1 (t, $^3J_{CP}$=8.2 Hz, CH$_2$—CH=); 60.1 (dd, $^1J_{CP}$=163.0 Hz and $^3J_{CP}$=10.0 Hz, PCH); 115.6 (s, C$^2$); 118.7 (s, H$_2$C=); 120.7 (d, $^2J_{CP}$=5.4 Hz, C$^4$); 132.1 (d, $^3J_{CP}$=9.3 Hz, C$^3$); 135.6 (s, HC=); 157.6 (s, C$^1$).

Stage 3: Grafting on First-Generation Phosphorus-Containing Dendrimer

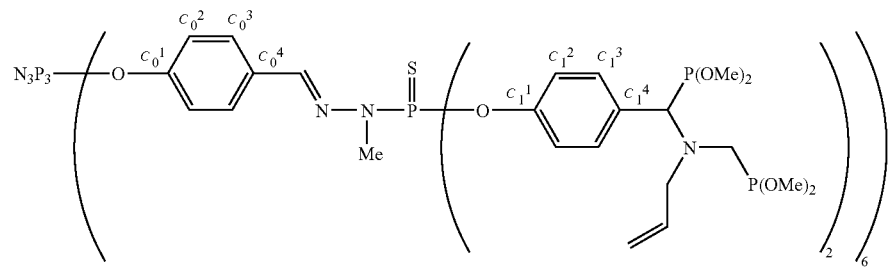

12.5 equivalents (600 mg, 1.53 mmol) of functionalized phenol (solubilized in acetonitrile or THF) are added to a solution of Gc1 dendrimer (223 mg, 0.122 mmol) with S=PCl$_2$ terminations in THF or acetonitrile. 15 equivalents (596 mg, 1.83 mmol) of Cs$_2$CO$_3$ are then added to the solution and the resulting suspension is stirred until the chlorines are completely substituted ($^{31}$P NMR monitoring). The mixture is decanted, the supernatant is collected and the residual solid is washed with THF. The supernatants are combined and centrifuged. The clear solution obtained is concentrated under reduced pressure. The residue is dissolved in a minimum amount of THF then precipitated with pentane. The solid obtained is purified by washing (THF/pentane and THF/Et$_2$O) with a yield of 76%.

NMR $^{31}$P{$^1$H} (CDCl$_3$, 81.01 MHz): δ=11.3 (s, N$_3$P$_3$); 27.9 (s, P=O); 30.7 (s, P=O); 65.3 (s, P=S).

NMR (CDCl$_3$, 250.13 MHz): δ=2.54 (dd, 12H, $^2J_{HH}$=15.7 Hz and $^2J_{HP}$=4.6 Hz, PCHH); 2.80 (dd, 12H, $^2J_{HH}$=13.4 Hz and $^3J_{HH}$=8.2 Hz, CHH—CH=); 3.29 (d, 18H, $^3J_{HP}$=9.9 Hz, NCH$_3$); 3.41 (d, 36H, $^3J_{HP}$=10.6 Hz, POMe); 3.42 (m, 12H, PCHH); 3.66 (d, 36H, $^3J_{HP}$=10.6 Hz, POMe); 3.76 (d, 36H, $^3J_{HP}$=10.7 Hz, POMe); 3.85 (d, 36H, $^3J_{HP}$=10.6 Hz, POMe); 3.87 (dl, 12H, $^2J_{HH}$=13.4 Hz, CHH—CH=); 4.57 (d, 12H, $^2J_{HP}$=25.2 Hz, PCH); 5.17 (m, 24H, CH$_2$=); 5.74 (m, 12H, CH=); 7.02 (d, 12H, $^3J_{HH}$=8.2 Hz, C$_o^2$—H); 7.18 (d, 24H, $^3J_{HH}$=8.4 Hz, C$_1^2$—H); 7.46 (d, 24H, $^3J_{HH}$=8.4 Hz, C$_1^3$—H); 7.61 (d, 12H, $^3J_{HH}$=8.2 Hz, C$_o^3$—H); 7.62 (s, 6H, CH=N).

NMR $^{13}$C{$^1$H} (CDCl$_3$, 62.89 MHz): δ=32.8 (d, $^2J_{CP}$=12.3 Hz, NCH$_3$); 45.1 (dd, $^1J_{CP}$=165.6 Hz and $^3J_{CP}$=8.2 Hz, PCH$_2$); 52.4 (d, $^2J_{CP}$=7.5 Hz, POMe); 52.7 (d, $^2J_{CP}$=6.1 Hz, POMe); 53.1 (d, $^2J_{CP}$=7.4 Hz, POMe); 53.9 (d, $^2J_{CP}$=7.5 Hz, POMe); 56.0 (t, $^3J_{CP}$=8.2 Hz, CH$_2$—CH=); 60.1 (dd, $^1J_{CP}$=161.7 and $^3J_{CP}$=9.2 Hz, PCH); 118.8 (s, H$_2$C=); 121.2 (dl, $^3J_{CP}$=4.6 Hz, C$_o^2$ and C$_1^2$); 128.3 (s, C$_o^3$); 128.4 (s, C$_1^4$); 132.0 (d, $^3J_{CP}$=8.6 Hz, C$_o^4$ and C$_1^3$); 135.5 (s, HC=); 139.2 (d, $^3J_{CP}$=14.6 Hz, CH=N); 150.7 (d, $^2J_{CP}$=7.4 Hz, C$_1^1$); 151.3 (bs, C$_o^1$).

Stage 4: First-Generation Phosphorus-Containing Dendrimer with Bisphosphonic Acid (Na Salt) Ends

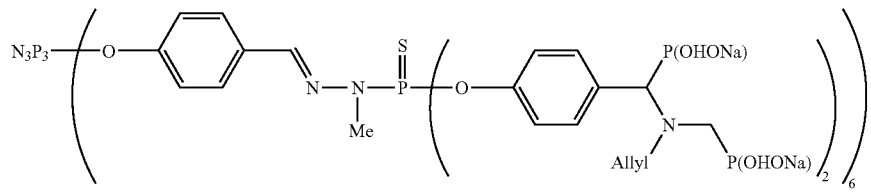

60 equivalents of bromo-trimethylsilane (260 μL, 1.964 mmol) is added at 0° C. under an argon flow to a solution of dendrimer with dimethyl phosphonate terminations synthesized in the preceding stage (200 mg, 32.7 μmol) in acetonitrile. The solution is stirred for 18 hours at room temperature then concentrated under reduced pressure. 5 mL of methanol are added and the mixture is vigorously stirred for 2 hours. The methanol is eliminated under reduced pressure and the residue is washed with distilled ether, then water and methanol. The solid is dried under reduced pressure until a powder is obtained. A soda solution (0.1966 M, 3.99 mL, 0.784 mmol, 24 eq.) is slowly added to the solid. The solution obtained is filtered then freeze-dried. The dendrimer with amino bis-phosphonic acid terminations is obtained in the form of a white powder with a yield of 79%.

NMR $^{31}$P{$^1$H} (D$_2$O/CD$_3$CN, 81.01 MHz): δ=11.0 (s, P=O); 11.3 (s, P=O); 12.7 (s, N$_3$P$_3$); 66.7 (s, P=S).

Example 50

Synthesis of Dendrimers with a Surface Derived from Dimethyl N-Benzyl-N-(4-Hydroxy)-Benzyl-α-Amino-Bis-Phosphonate Stage 1: Synthesis of a Phenol Monophosphonate

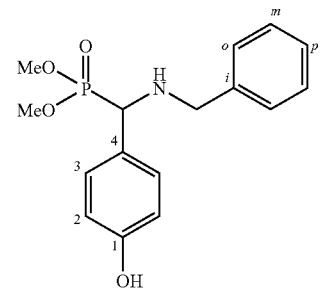 [SMILES: COP(=O)(OC)C(NCc1ccccc1)c1ccc(O)cc1]

Several grams of MgSO$_4$ then benzylamine (4.36 mL; 40 mmol) are added to a solution of 4-hydroxybenzaldehyde (4.4 g; 40 mmol) in THF (30 mL). The reaction (exothermic) is maintained at room temperature and under vigorous stirring for 2 hours. After decantation, the supernatant is canulated then concentrated (to approximately 50% of its initial volume) under reduced pressure. Dimethyl phosphite (3.66 mL; 40 mmol) is added and the reaction is heated under argon at 50° C. for 48 hours (or stirred at room temperature for 5 days). The progress of the reaction is monitored by $^1$H and $^{31}$P NMR. The reaction mixture is poured into a saturated solution of NaHCO$_3$ then extracted with 3 times 50 mL of CH$_2$Cl$_2$. The organic phase is dried over MgSO$_4$ and the solvent is eliminated under reduced pressure. The residue is washed twice with ether until a pale yellow solid is obtained with a yield of 77%.

NMR $^{31}$P{$^1$H} (CDCl$_3$, 121.4 MHz): δ=29.7 (s, P=O).

NMR $^1$H (CDCl$_3$, 200.13 MHz): δ=3.54 (d, 1H, $^2J_{HH}$=13.2 Hz, CHHPh); 3.58 (d, 3H, $^3J_{HP}$=10.5 Hz, POMe); 3.80 (d, 3H, $^3J_{HP}$=10.5 Hz, POMe); 3.81 (d, 1H, $^2J_{HH}$=13.2 Hz, CHHPh); 3.99 (d, 1H, $^2J_{HP}$=19.8 Hz, PCH); 6.77 (d, 2H, $^3J_{HH}$=8.4 Hz, C$^2$—H); 7.19 (d, 2H, $^3J_{HH}$=8.4 Hz, C$^3$—H); 7.28 (m, 5H, C$_6$H$_5$); 8.50 (bs, 1H, OH).

NMR $^{13}$C{$^1$H} (CDCl$_3$, 62.89 MHz): δ=50.8 (d, $^3J_{CP}$=17.5 Hz, CH$_2$N); 53.6 (d, $^2J_{CP}$=7.6 Hz, POMe); 54.1 (d, $^2J_{CP}$=7.8 Hz, POMe); 58.3 (d, $^1J_{CP}$=157.3 Hz, PCH); 116.1 (s, C$^2$); 125.1 (bs, C$^4$); 127.2 (s, C$_p$); 128.4 (s, C$_m$, C$_o$); 129.6 (d, $^2J_{CP}$=5.9 Hz, C$^3$); 139.1 (s, C$_i$); 157.1 (s, C$^1$).

Stage 2: Synthesis of a Bisphosphonate Phenol

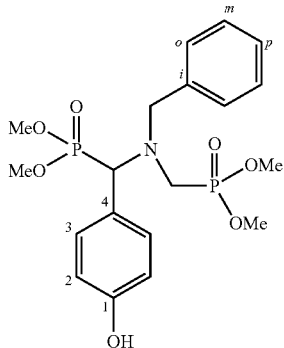 [SMILES: COP(=O)(CN(Cc1ccccc1)C(c1ccc(O)cc1)P(=O)(OC)OC)OC]

A 37% aqueous formaldehyde solution (870 μL; 11.7 mmol; 1.5 eq.) is added to a solution of α-aminophosphonate synthesized in the preceding stage (2.5 g; 7.79 mmol) in THF (50 mL). After 30 minutes dimethylphosphite is added (785 μL; 8.56 mmol; 1.1 eq). The solution is stirred for 24 hours and 600 μL of formaldehyde (37% aqueous solution) are added. The progress of the reaction is monitored by $^{31}$P NMR. After 96 hours of reaction, the reaction mixture is poured into a saturated solution of NaHCO$_3$ then extracted with CH$_2$Cl$_2$. The organic phase is dried over MgSO$_4$ and the solvent is eliminated under reduced pressure. The residue is washed twice with ether, twice with a THF/pentane mixture, dried under vacuum and it is purified by chromatography on silica gel (eluent: AcOEt/MeOH; 95:5) in order to produce a viscous oil with a yield of 65%.

NMR $^{31}$P{$^1$H}(CDCl$_3$, 81.01 MHz): δ=31.5 (s); 28.9 (s).

NMR $^1$H (CDCl$_3$, 200.13 MHz): δ=2.70 (dd, 1H, $^2J_{HH}$=15.5 Hz and $^2J_{HP}$=3.4 Hz, CHHP); 3.29 (d, 1H, $^2J_{HH}$=13.4 Hz, CHHPh); 3.44 (d, 3H, $^3J_{HP}$=10.5 Hz, POMe); 3.49 (dd, 1H, $^2J_{HH}$=15.5 Hz and $^2J_{HP}$=16 Hz, CHHP); 3.65 (d, 3H, $^3J_{HP}$=10.6 Hz, POMe); 3.74 (d, 3H, $^3J_{HP}$=10.7 Hz, POMe); 3.85 (d, 3H, $^3J_{HP}$=10.8 Hz, POMe); 4.42 (d, 1H, $^2J_{HP}$=25.6 Hz, PCH); 4.44 (d, 1H, $^2J_{HH}$=13.4 Hz, CHHPh); 6.85 (d, 2H, $^3J_{HH}$=8.4 Hz, C$^2$—H); 7.35 (m, 7H, H$_{arom}$); 8.80 (bs, 1H, OH).

NMR $^{13}$C{$^1$H} (CDCl$_3$, 62.89 MHz): δ=45.2 (dd, $^1J_{CP}$=165.3 Hz and $^3J_{CP}$=7.5 Hz, PCH$_2$); 52.3 (d, $^2J_{CP}$=6.2 Hz, POMe); 52.9 (d, $^2J_{CP}$=9.2 Hz, POMe); 53.1 (d, $^2J_{CP}$=8.2 Hz, POMe); 53.5 (d, $^2J_{CP}$=6.3 Hz, POMe); 57.1 (bs, CH$_2$Ph); 59.5 (dd, $^1J_{CP}$=163.4 Hz and $^3J_{CP}$=10.3 Hz, PCH); 115.5 (s, C$^2$); 120.4 (d, $^2J_{CP}$=4.3 Hz, C$^4$); 127.4 (s, C$_p$); 128.3 (s, C$_m$); 129.2 (s, C$_o$); 132.1 (d, $^3J_{CP}$=8.9 Hz, C$^3$); 138.2 (s, C$_i$); 157.9 (s, C$^1$).

Stage 3: Grafting on a First-Generation Phosphorus-Containing Dendrimer 12.6 equivalents (560 mg; 1.26 mmol) of the functionalized phenol obtained in the preceding stage (solubilized in acetonitrile or THF) are added to a solution of Gc$_1$ dendrimer with S=PCl$_2$ (181 mg; 99 μmol) terminations in THF or acetonitrile (10 mL). 15 equivalents (490 mg; 1.50 mmol) of Cs$_2$CO$_3$ are then added to the solution and the resulting suspension is stirred until the chlorines have been completely substituted (72 hours, $^{31}$P NMR monitoring). The mixture is decanted, the supernatant is collected and the residual solid is washed with THF. The supernatants are combined and centrifuged. The clear solution obtained is concentrated under reduced pressure. The residue is dissolved in a minimum amount of THF then precipitated with pentane and finally purified by washing (THF/pentane; THF/Et$_2$O; Et$_2$O) in order to produce a white solid with a yield of 90%.

NMR $^{31}$P{$^1$H} (CDCl$_3$, 101.2 MHz): δ=11.3 (s, N$_3$P$_3$); 28.2 (s, P=O); 30.6 (s, P=O); 65.3 (s, P=S).

NMR $^1$H (CDCl$_3$, 250.13 MHz): δ=2.64 (dd, 12H, $^2J_{HH}$=15.8 Hz and $^2J_{HP}$=3.4 Hz, CHHP); 3.27 (d, 12H, $^2J_{HH}$=12.5 Hz, CHHPh); 3.32 (d, 18H, $^3J_{HP}$=9.7 Hz, NMe); 3.39 (d, 36H, $^3J_{HP}$=10.6 Hz, POMe); 3.46 (m, 12H, PCHH); 3.58 (d, 36H, $^3J_{HP}$=10.7 Hz, POMe); 3.67 (d, 36H, $^3J_{HP}$=10.7 Hz, POMe); 3.83 (d, 36H, $^3J_{HP}$=10.7 Hz, POMe); 4.44 (d, 12H, $^2J_{HH}$=12.5 Hz, CHHPh); 4.52 (d, 12H, $^2J_{HP}$=24.9 Hz, CHP); 7.04 (d, 12H, $^3J_{HP}$=8.4 Hz, C$_0^2$—H); 7.28 (m, 84H, C$_6$H$_5$, C$_1^2$—H); 7.49 (d, 24H, $^3J_{HP}$=8.2 Hz, C$_1^3$—H); 7.63 (m, 18H, C$_0^3$—H and CH=N).

NMR $^{13}$C {$^1$H} (CDCl$_3$, 62.89 MHz): δ=32.8 (d, $^2J_{CP}$=11.4 Hz, NCH$_3$); 45.2 (dd, $^1J_{CP}$=164.6 and $^3J_{CP}$=8.4 Hz, PCH$_2$); 52.3 (d, $^2J_{CP}$=6.4 Hz, POMe); 52.7 (d, $^2J_{CP}$=5.8 Hz, POMe); 52.9 (d, $^2J_{CP}$=6.4 Hz, POMe); 53.6 (d, $^2J_{CP}$=7.6 Hz, POMe); 57.8 (t, $^3J_{CP}$=8.4 Hz, CH$_2$-Ph); 59.7 (dd, $^1J_{CP}$=160.8 and $^3J_{CP}$=9.4 Hz, PCH); 121.3 (d1, $^3J_{CP}$=3.3 Hz, C$_0^2$ and C$_1^2$); 127.5 (s, C$_p$); 128.4 (bs, C$_0^3$, C$_1^4$, C$_m$); 129.3 (s, C$_o$); 132.0 (s, C$_0^4$); 132.2 (d, $^3J_{CP}$=8.4 Hz, C$_1^3$); 138.2 (s, C$_i$); 139.1 (bs, CH=N); 150.8 (d, $^2J_{CP}$=7.2 Hz, C$_1^1$); 151.1 (bs, C$_0^1$).

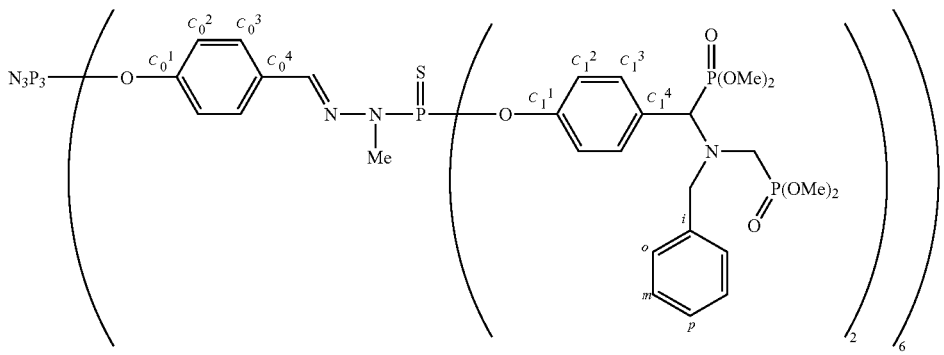

Stage 4: First-Generation Phosphorus-Containing Dendrimer with Amino Bis-Phosphonic Acid (Sodium Salt) Ends

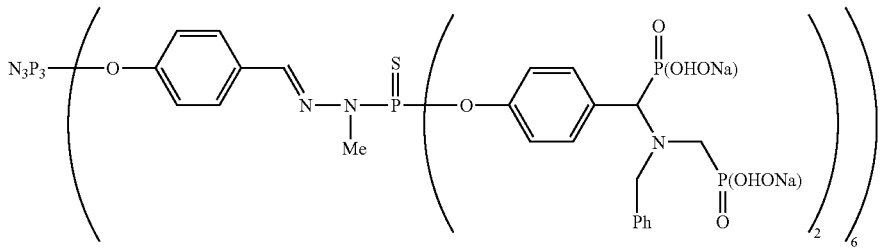

60 equivalents (190 μL; 1.430 mmol) of bromotrimethylsilane is added at 0° C. under an argon flow to a solution of dendrimer with dimethyl phosphonate terminations obtained in the preceding stage (160 mg; 23.8 mop in acetonitrile (5 mL). The solution is stirred for 16 hours at room temperature then concentrated under reduced pressure. 5 mL of methanol are added and the mixture is vigorously stirred for 2 hours. The methanol is eliminated under reduced pressure and the residue is washed with distilled ether, then water and methanol. The solid is dried under reduced pressure until a powder is obtained. A soda solution (0.1966 M, 2.07 mL, 24 eq.) is slowly added to the solid. The solution obtained is filtered then freeze-dried. The amino bis-phosphonic acid is obtained in the form of a white powder with a yield of 71%.

NMR $^{31}$P{$^1$H} (D$_2$O/CD$_3$CN, 81.01 MHz): δ=11.8 (bs, N$_3$P$_3$ and P=O), 67.1 (bs, P=S).

Example 51

Synthesis of Carboxylic Aza-Bis-Phosphonate Acids

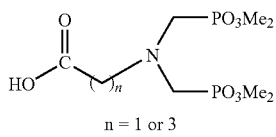

n = 1 or 3

(a) n=1

Synthesis of aminoacetic acid [bis-(dimethoxy-phosphorlmethyl)]

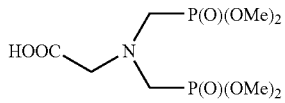

5 g of aminoacetic acid (66.6 mmol) are introduced into a flask and dissolved in 20 mL of THF. 3 equivalents of 37% aqueous formaldehyde solution are added at room temperature and stirred for 30 minutes. 4 equivalents of dimethylphosphite are then added. The mixture is maintained under magnetic stirring at room temperature for 12 h, 40 mL of distilled water are added to the reaction medium, the THF is eliminated under reduced pressure and the product is extracted with 3×100 mL of chloroform. The organic phase is dried over magnesium sulphate then evaporated. The amino bisphosphonate acetic acid is then purified by chromatography on a silica column in eluent with a CH$_2$Cl$_2$/MeOH mixture (95/5), and isolated in the form of an off-white powder with a yield of 37%.

Rf (CH$_2$Cl$_2$/MeOH: 95/5)=0.32
NMR $^{31}$P-{$^1$H} (CDCl$_3$) δ=30.0 ppm.
RMN $^1$H (CDCl$_3$) δ=3.22 (d, $^2$J$_{HP}$=10.1 Hz, 4H, CH$_2$—P), 3.61 (s, 2H, CH$_2$—CO), 3.68 (d, $^3$J$_{HP}$=10.6 Hz, 12H, O—CH$_3$), 10.8 (s, 1H, COOH) ppm.
RMN $^{13}$C-{$^1$H} (CDCl$_3$) δ=49.8 (dd, $^1$J$_{CP}$=162.1 Hz, $^3$J$_{CP}$=9.9 Hz, CH$_2$—P), 53.0 (d, $^2$J$_{CP}$=5.9 Hz, CH$_3$—O), 55.7 (t, $^3$J$_{CP}$=5.8 Hz, N—CH$_2$—CO), 171.9 (s, COOH) ppm.

(b) n=3

Synthesis of Aminobutyric Acid [Bis-(Dimethoxy-Phosnhorylmethyl)]

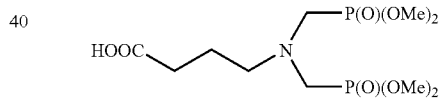

5 g of amino acid (48.5 mmol) are introduced into a flask and dissolved in 20 mL of THF, 3 equivalents of 37% aqueous formaldehyde solution are added at room temperature and stirred for 30 minutes. 4 equivalents of dimethylphosphite are then added. The mixture is maintained under magnetic stirring at room temperature for 12 h, 40 mL of distilled water are added to the reaction medium, the THF is eliminated under reduced pressure and the product is extracted with 3×100 mL of chloroform. The organic phase is dried over magnesium sulphate then evaporated. The product is then purified by chromatography on a silica column in eluent with a CH$_2$Cl$_2$/MeOH mixture (95/5), and isolated in the form of an off-white powder with a yield of 53%.

Rf (CH$_2$Cl$_2$/MeOH: 95/5)=0.35
NMR $^{31}$P-{$^1$H} (CDCl$_3$) δ=30.7 ppm.
RMN $^1$H (CDCl$_3$) δ=1.74 (quint, $^3$J$_{HH}$=7.1 Hz, 2H, CH$_2$—CH$_2$—CH$_2$), 2.36 (t, $^3$J$_{HH}$=7.1 Hz, 2H, HOOC—CH$_2$), 2.78 (t, $^3$J$_{HH}$=7.1 Hz, 2H, CH$_2$—CH$_2$—N), 3.10 (d, $^2$H$_{HP}$=8.8 Hz, 4H, CH$_2$—P), 3.74 (d, $^3$J$_{HP}$=10.7 Hz, 12H, O—CH$_3$) ppm. COOH proton not observed.
RMN $^{13}$C-{$^1$H} (CDCl$_3$) δ=22.6 (s, CH$_2$—CH$_2$—CH$_2$), 31.1 (s, HOOC—CH$_2$), 49.3 (dd, $^1$J$_{CP}$=158.0 Hz, $^3$J$_{CP}$=7.3

Hz, CH$_2$—P), 52.8 (d, $^2J_{CP}$=7.2 Hz, CH$_3$—O), 56.0 (t, $^3J_{CP}$=7.5 Hz, N—CH$_2$—CH$_2$), 176.1 (s, COOH) ppm.

Example 52

Cleavage of the Dimethylphosphonic Esters of Example 51 into Phosphonic Acids (a) n=1:

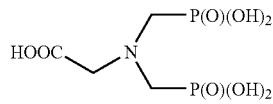

0.39 mmol of aza-bis-phosphonate compound are dissolved in 4 mL of acetonitrile and 2.33 mmol of BrTMS (5.5 equivalents) are added dropwise at 0° C. under an inert atmosphere. The mixture is stirred for 30 minutes at 0° C. then 15 h at room temperature. The acetonitrile is eliminated under reduced pressure then 3 mL of methanol are added. The mixture is stirred for 30 minutes then the solvent is evaporated. 5 mL of distilled water is added and stirring is continued for 1 hour at room temperature then the solution is freeze-dried. The dry residue is washed 3 times with ether. The product is obtained in the form of a yellow powder with a yield of 83%.

NMR $^{31}$P-{$^1$H} (D$_2$O) δ=10.6 ppm.

RMN $^{13}$C-{$^1$H} (CD$_3$OD) δ=51.9 (dd, $^1J_{CP}$=148.5 Hz, $^3J_{CP}$=13.2 Hz, CH$_2$—P), 55.9 (s, N—CH$_2$—CO), 168.1 (s, COOH) ppm.

(b) n=3:

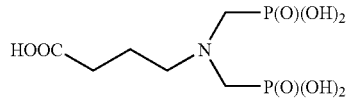

0.39 mmol of aza-bis-phosphonate compound are dissolved in 4 mL of acetonitrile and 2.33 mmol of BrTMS (5.5 equivalents) are added dropwise at 0° C. under an inert atmosphere. The mixture is stirred for 30 minutes at 0° C. then 15 h at room temperature. The acetonitrile is eliminated under reduced pressure then 3 mL of methanol are added. The mixture is stirred for 30 minutes then the solvent is evaporated. 5 mL of distilled water is added and stirring is continued for 1 hour at room temperature then the solution is freeze-dried. The dry residue is washed 3 times with ether. The product is obtained in the form of a yellow powder with a yield of 78%.

NMR $^{31}$P-{$^1$H} (D$_2$O) δ=11.3 ppm.

RMN $^{13}$C-{$^1$H} (D$_2$O) δ=21.4 (s, CH$_2$—CH$_2$—CH$_2$), 33.1 (s, CO—CH$_2$—), 53.8 (dd, $^1J_{CP}$=130.0 Hz, $^3J_{CP}$=4.1 Hz, CH$_2$—P), 58.8 (s, N—CH$_2$—CH$_2$), 179.4 (s, COOH) ppm.

Example 53

Synthesis of Amido-Tyramine-Azabis-Phosphonate Compounds

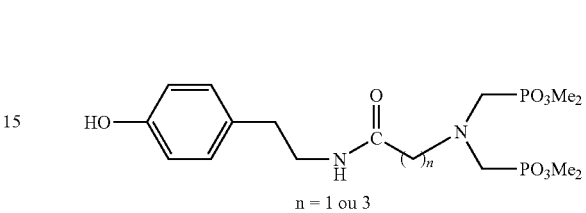

n = 1 ou 3

(a) n=1

Coupling of Aminoacetic Acid [Bis-(Dimethoxy-Phosphorylmethyl)] with Tyramine

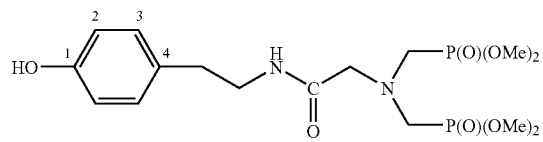

300 mg of carboxylic acid (0.94 mmol) obtained in Example 51 (n=1), are introduced into a flask under argon and dissolved in 5 mL of dry DMF. The solution is taken to 0° C., then 1.3 equivalents of HOBt are added to it, stirring is continued for 15 minutes at 0° C. then 1.3 equivalents of DCC are added. The mixture is stirred for 30 minutes at 0° C. then for 1 h at room temperature. The formation of a precipitate is observed. The mixture is again taken to 0° C. then tyramine (1.1 equivalents) is added followed by stirring for 30 minutes at 0° C. then 15 h at room temperature. The precipitate is eliminated on a 5μ Millipore filter and the solution is freeze-dried. The residual oil is purified by chromatography on a silica column in eluent by a CH$_2$Cl$_2$/MeOH mixture (90/10), Rf=0.47, the product is obtained with a yield of 42% in the form of an off-white powder.

NMR $^{31}$P-{$^1$H} (CDCl$_3$) δ=30.2 ppm.

RMN $^1$H (CDCl$_3$) δ=2.73 (t, $^3J_{HH}$=7.4 Hz, 2H, C$_6$H$_4$—CH$_2$), 3.13 (d, $^2J_{HP}$=9.0 Hz, 4H, CH$_2$—P), 3.33-3.52 (m, 4H, CO—CH$_2$—N, CH$_2$—NH), 3.74 (d, $^3J_{HP}$=10.7 Hz, 12H, CH$_3$—O), 6.75 (d, $^3J_{HH}$=8.4 Hz, 2H, HC$^2$), 7.00 (d, $^3J_{HH}$=8.4 Hz, 2H, HC$^3$), 7.46 (t, $^3J_{HH}$=5.8 Hz, 1H, NH) ppm.

RMN $^{13}$C-{$^1$H} (CDCl$_3$) δ=34.7 (s, C$_6$H$_4$—CH$_2$), 40.7 (s, CH$_2$—NH), 49.9 (dd, $^1J_{CP}$=158.9 Hz, $^3J_{CP}$=3.7 Hz, CH$_2$—P), 52.8 (d, $^2J_{CP}$=3.7 Hz, CH$_3$—O), 60.7 (t, $^3J_{CP}$=6.4 Hz, CO—CH$_2$—N), 115.4 (s, C$^2$), 129.7 (s, C$^3$, C$^4$), 155.4 (s, C$^1$), 169.7 (s, CONH) ppm.

(b) n=3

Coupling of Aminobutyric Acid
[Bis-(Dimethoxy-Phosphorylmethyl)] with Tyramine

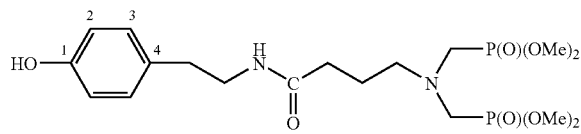

300 mg of carboxylic acid (0.86 mmol) obtained in Example 51 (n=3), are introduced into a flask under argon and dissolved in 5 mL of dry DMF. The solution is taken to 0° C., then 1.3 equivalents of HOBt is added to it, stirring is continued for 15 minutes at 0° C. then 1.3 equivalents of DCC is added. The mixture is stirred for 30 minutes at 0° C. then for 1 h at room temperature. The formation of a precipitate is observed. The mixture is again taken to 0° C. then tyramine (1.1 equivalents) is added followed by stirring for 30 minutes at 0° C. then 15 h at room temperature. The precipitate is eliminated on a 5µ Millipore filter and the solution is freeze-dried. The residual oil is purified by chromatography on a silica column in eluent by a $CH_2Cl_2$/MeOH mixture (95/5), Rf=0.52. The product is obtained with a yield of 51%.

NMR $^{31}P-\{^1H\}$ ($CDCl_3$) δ=30.6 ppm.

RMN $^1H$ ($CDCl_3$) δ=1.71 (quint, $^3J_{HH}$=6.8 Hz, 2H, $CH_2$—$\underline{CH_2}$—$CH_2$), 2.20 (t, $^3J_{HH}$=6.8 Hz, 2H, CO—C$\underline{H_2}$—$CH_2$—$CH_2$), 2.69 (m, 4H, CO—$CH_2$—$CH_2$—$\underline{CH_2}$, $C_6H_4$—$\underline{CH_2}$), 3.08 (d, $^2J_{HP}$=8.7 Hz, 4H, $CH_2$—P), 3.42 (dt, $^3J_{HH}$=7.1 Hz, 2H, $\underline{CH_2}$—NH), 3.75 (d, $^3J_{HP}$=10.5 Hz, 12H, $CH_3$—O), 6.67 (t, $^3J_{HH}$=7.1 Hz, 1H, NH), 6.76 (d, $^3J_{HH}$=8.4 Hz, 2H, $H_{Ar}$), 6.98 (d, $^3J_{HH}$=8.4 Hz, 2H, $H_{Ar}$), 8.34 (s, OH) ppm.

RMN $^{13}C-\{^1H\}$ ($CDCl_3$) δ=23.9 (s, $CH_2$—$\underline{CH_2}$—$CH_2$), 33.4 (s, CO—$\underline{CH_2}$—$CH_2$—$CH_2$), 34.6 (s, $C_6H_4$—$\underline{CH_2}$), 40.8 (s, $CH_2$—NH), 49.5 (dd, $^1J_{CP}$=159.4 Hz, $^3J_{CP}$=7.0 Hz, $CH_2$—P), 52.8 (d, $^2J_{CP}$=6.2 Hz, $CH_3$—O), 56.0 (t, $^3J_{CP}$=7.8 Hz, CO—$CH_2$—$CH_2$—$\underline{CH_2}$), 115.5 (s, $C^2$), 129.7 (s, $C^3$), 129.7 (s, $C^4$), 155.4 (s, $C^1$), 173.6 (s, CONH) ppm.

Example 54

Tyramines with [((Carbamoylmethyl-Amino)-Methyl]-Phosphonic Acid (Na Salt) Ends Obtained Using the Products of Example 53

(a) n=1:

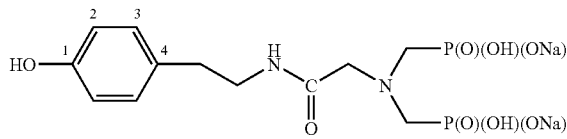

0.2 mmol of coupling product obtained in Example 53 part (a) are placed in solution at 0° C. in 3 mL of distilled acetonitrile. 5.5 equivalents of BrTMS are then added to the syringe. The stirring is continued for 15 minutes at 0° C. then overnight at room temperature. The mixture is then brought under vacuum and methanolyzed then hydrolyzed at room temperature. After freeze-drying the dry residue is washed three times with ether in order to produce the corresponding phosphonic acid. The sodium salt is prepared by adding 2 equivalents of an aqueous soda solution at 0.1955 N and isolated with a quantitative yield in the form of an off-white powder.

NMR $^{31}P-\{^1H\}$ ($D_2O$/THFd8) δ=19.9 ppm.

RMN $^{13}C-\{^1H\}$ ($D_2O$/THFd8) δ=36.7 (s, $C_6H_4$—$\underline{CH_2}$), 44.1 (s, $CH_2$—NH), 58.1 (dd, $^1J_{CP}$=147.2 Hz, $^3J_{CP}$=14.5 Hz, $CH_2$—P), 63.3 (t, $^3J_{CP}$=8.7 Hz, CO—$\underline{CH_2}$—N), 121.4 (s, $C^2$), 127.6 (s, $C^4$), 132.5 (s, $C^3$), 167.0 (s, $C^1$), 177.4 (s, CONH) ppm.

(b) n=3:

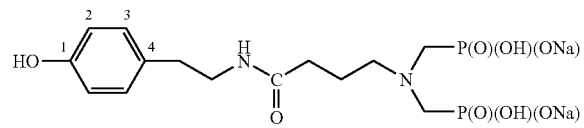

0.2 mmol of coupling product obtained in Example 53 part (b) are placed in solution at 0° C. in 3 mL of distilled acetonitrile. 5.5 equivalents of BrTMS is then added to the syringe. The stirring is continued for 15 minutes at 0° C. then overnight at room temperature. The mixture is then brought under vacuum and methanolyzed then hydrolyzed at room temperature. After freeze-drying the dry residue is washed three times with ether in order to produce the corresponding phosphonic acids. The sodium salt is prepared by adding 2 equivalents of an aqueous soda solution at 0.1955 N and isolated with a quantitative yield in the form of an off-white powder.

NMR $^{31}P-\{^1H\}$ ($D_2O$) δ=10.9 ppm.

RMN $^{13}C-\{^1H\}$ ($D_2O$) δ=22.6 (s, $CH_2$—$\underline{CH_2}$—$CH_2$), 35.1 (s, CO—$\underline{CH_2}$—$CH_2$—$CH_2$), 36.2 (s, $C_6H_4$—$\underline{CH_2}$), 43.3 (s, $CH_2$—NH), 54.1 (d, $^1J_{CP}$=136.5 Hz, $CH_2$—P), 59.0 (s, CO—$CH_2$—$CH_2$—$\underline{CH_2}$), 118.1 (s, $C^2$), 133.0 (s, $C^3$), 133.8 (s, $C^4$), 156.6 (s, $C^1$), 177.0 (s, CONH) ppm.

Example 55

Synthesis of DAB Dendrimer Models with Aza-Bis-Phosphonic Ends Derived from Glycine Stage 1: Coupling of Aminoacetic Acid [Bis-(Dimethoxy-Phosphorylmethyl)] with Tris-(2-Aminoethylamine) (DAB Dendrimer Model)

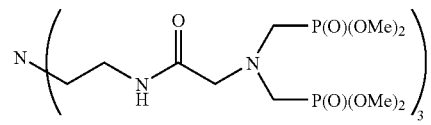

1.57 mmol of aza-bis-phosphonate carboxylic acid obtained in Example 51 (n=1) are introduced into a flask under argon and dissolved in 5 mL of dry DMF. The solution is taken to 0° C., then 1.1 equivalents of 1-hydroxybenzotriazole (HOBt) is added to it, stirring is continued for 15 minutes at 0° C. then 1.1 equivalents of 1.3-dicyclohexylcarbodiimide (DCC) is added. The mixture is stirred for 30 minutes at 0° C. then for 1 h at room temperature. The formation of a precipitate is observed. 0.4 mmol of tris-(2-aminoethylamine) in solution in 1 mL of dry DMF at 0° C. is then added, stirring is continued for 15 minutes at 0° C. then overnight at room temperature. The precipitate is eliminated by filtration on a 5µ

Millipore syringe filter then the solution is freeze-dried. The product is purified by dissolution in a minimum volume of $CH_2Cl_2$ and precipitation in a large volume of diethylether. These precipitations are repeated three times in order to eliminate the traces of HOBt. The product is obtained with a yield of 55% in the form of an off-white powder.

NMR $^{31}P-\{^1H\}$ (CDCl$_3$) δ=30.3 ppm.

RMN $^1H$ (CDCl$_3$) δ=2.67 (bs, 6H, N—CH$_2$), 3.20 (d, $^2J_{HP}$=9.3 Hz, 12H, P—CH$_2$), 3.28 (bs, 6H, CH$_2$—NHCO), 3.47 (s, 6H, N—CH$_2$—CO), 3.73 (d, $^3J_{HP}$=10.6 Hz, 36H, O—CH$_3$), 7.65 (bs, 3H, CONH) ppm.

RMN $^{13}C-\{^1H\}$ (CDCl$_3$) δ=36.9 (s, N—CH$_2$—CH$_2$), 49.8 (dd, $^1J_{CP}$=158.2 Hz, $^3J_{CP}$=6.3 Hz, CH$_2$—P), 52.7 (d, $^2J_{CP}$=3.4 Hz, CH$_3$—O), 53.7 (s, N—CH$_2$—CH$_2$), 59.9 (t, $^3J_{CP}$=6.4 Hz, N—CH$_2$—CO), 170.1 (s, CONH) ppm.

Stage 2: Synthesis of the DAB Dendrimer Model with Aza-Bis-Phosphonic Acid Ends Derived from Glycine

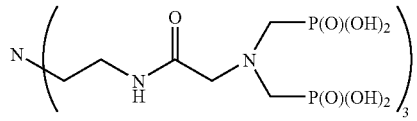

0.25 mmol of DAB azabis-phosphonate model compound of Stage 1 are placed in solution in 3 mL of acetonitrile and taken to 0° C. then 3.75 mmol of BrTMS is added dropwise under an inert atmosphere. After 30 minutes of stirring at 0° C. the ice bath is removed and stirring is continued for 15 h at room temperature. The solvent is eliminated under reduced pressure and 3 mL of MeOH are added to the dry residue. The mixture is stirred for 30 minutes then the solvent is eliminated under vacuum and 3 mL of distilled water is added. After 1 hour of stirring the mixture is freeze-dried. The dry residue is washed 3 times with dry ether. The product is obtained in the form of a beige powder.

NMR $^{31}P-\{^1H\}$ (D$_2$O, THFd8) δ=11.2 ppm.

Stage 3: DAB Dendrimer Model with [(Carbamoylmethyl-Amino)-Methyl]-Phosphoric Acid (Na Salt) Ends

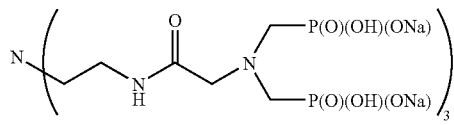

The sodium salt is obtained by adding 1 equivalent of an aqueous soda solution at 0.1955 N per —PO$_3$H$_2$ group present in the molecule obtained in Stage 2. The product is isolated in the form of an off-white powder after freeze-drying with a yield of 67%.

NMR $^{31}P-\{^1H\}$ (D$_2$O/THFd8) δ=17.8 ppm.

RMN $^{13}C-\{^1H\}$ (D$_2$O/THFd8) δ=36.3 (s, N—CH$_2$—CH$_2$), 54.2 (s, N—CH$_2$—CH$_2$), 57.2 (dd, $^1J_{CP}$=149.0 Hz, $^3J_{CP}$=9.8 Hz, CH$_2$—P), 62.6 (bs, N—CH$_2$—CO), 174.8 (s, CONH) ppm.

Example 56

Synthesis of DAB Dendrimer Models with Aza-Bis-Phosphonic Ends Derived from Aminobutyric Acid Stage 1: Coupling of Aminobutyric Acid [Bis-(Dimethoxy-Phosphorylmethyl)] with Tris-(2-Aminoethylamine) (DAB Dendrimer Model)

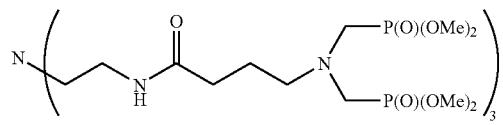

1.57 mmol of aza-bis-phosphonate carboxylic acid obtained in Example 51 (n=3) are introduced into a flask under argon and dissolved in 5 mL of dry DMF. The solution is taken to 0° C., then 1.1 equivalents of 1-hydroxybenzotriazole (HOBt) is added to it, stirring is continued for 15 minutes at 0° C. then 1.1 equivalents of 1.3-dicyclohexylcarbodiimide (DCC) is added. The mixture is stirred for 30 minutes at 0° C. then for 1 h at room temperature. The formation of a precipitate is observed. 0.4 mmol of tris-(2-aminoethylamine) in solution in 1 mL of dry DMF is then added at 0° C., stirring is continued for 15 minutes at 0° C. then overnight at room temperature. The precipitate is eliminated by filtration on a 5 II Millipore syringe filter then the solution is freeze-dried. The product is purified by dissolution in a minimum volume of $CH_2Cl_2$ and precipitation in a large volume of diethylether. These precipitations are repeated three times in order to eliminate the traces of HOBt. The product is obtained in the form of an off-white powder with a yield of 66%.

NMR $^{31}P-\{^1H\}$ (CDCl$_3$) δ=30.5 ppm.

RMN $^1H$ (CDCl$_3$) δ=1.16 (quint, $^3J_{HH}$=7.0 Hz, 6H, CH$_2$—CH$_2$—CH$_2$), 2.24 (t, $^3J_{HH}$=7.0 Hz, 6H, CO—CH$_2$), 2.72 (t, $^3J_{HH}$=7.0 Hz, 6H, CH$_2$—N—CH$_2$—P), 2.86 (bs, 6H, N—CH$_2$—CH$_2$—NH), 3.08 (d, $^2J_{HP}$=8.9 Hz, 12H, P—CH$_2$), 3.36 (bs, 6H, CH$_2$—NHCO), 3.71 (d, $^3J_{HP}$=10.5 Hz, 36H, O—CH$_3$), 7.65 (bs, 3H, CONH) ppm.

RMN $^{13}C-\{^1H\}$ (CDCl$_3$) δ=23.6 (s, CH$_2$—CH$_2$—CH$_2$), 33.1 (s, NHCO—CH$_2$), 36.4 (s, NH—CH$_2$), 49.4 (dd, $^1J_{CP}$=157.8 Hz, $^3J_{CP}$=7.7 Hz, CH$_2$—P), 52.7 (d, $^2J_{CP}$=6.0 Hz, CH$_3$—O), 54.0 (s, N—CH$_2$—CH$_2$—NH), 56.2 (t, $^3J_{CP}$=6.7 Hz, P—CH$_2$—N—CH$_2$), 174.1 (s, CONH) ppm.

Stage 2: Synthesis of the DAB Dendrimer Model with Aza-Bis-Phosphonic Acid Ends Derived from Aminobutyric Acid

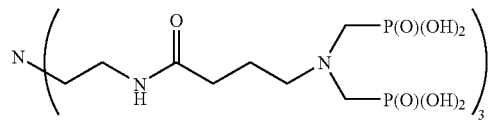

0.25 mmol of DAB azabis-phosphonate model compound of Stage 1 are placed in solution in 3 mL of acetonitrile and taken to 0° C. then 3.75 mmol of BrTMS is added dropwise under an inert atmosphere. After 30 minutes of stirring at 0° C. the ice bath is removed and stirring is continued for 15 h at room temperature. The solvent is eliminated under reduced pressure and 3 mL of MeOH are added to the dry residue. The mixture is stirred for 30 minutes then the solvent is eliminated under vacuum and 3 mL of distilled water is added. After 1 hour of stirring the mixture is freeze-dried. The dry residue is washed 3 times with dry ether. The product is obtained in the form of a beige powder.

NMR $^{31}$P-{$^{1}$H} (D$_2$O, THFd8) δ=11.0 ppm.

Stage 3: DAB Dendrimer Model with [(Carbamoylpropyl-Amino)-Methyl]-Phosphonic Acid (Na Salt) Ends

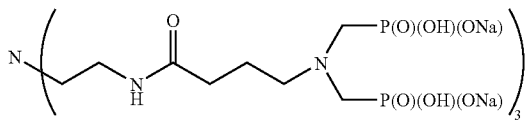

The sodium salt is obtained by adding 1 equivalent of an aqueous soda solution at 0.1955 N per —PO$_3$H$_2$ group present in the molecule obtained in Stage 2. The product is isolated in the form of an off-white powder after freeze-drying with a yield of 70%.

NMR $^{31}$P-{$^{1}$H} (D$_2$O/THFd8) δ=11.4 ppm.
RMN $^{13}$C-{$^{1}$H} (D$_2$O/THFd8) δ=22.1 (s, CH$_2$—CH$_2$—CH$_2$), 35.0 (s, NHCO—CH$_2$), 37.0 (s, NH—CH$_2$), 53.8 (dl, $^{1}J_{CP}$=136.8 Hz, CH$_2$—P), 55.1 (s, N—CH$_2$—CH$_2$—NH), 59.2 (bs, P—CH$_2$—N—CH$_2$), 178.4 (s, CONH) ppm.

Example 57

Synthesis of Generation 1 DAB-Type Dendrimers Having 4 Azabis-Phosphonic Groups Derived from Glycine

Stage 1: Coupling of [Bis-(Dimethoxy-Phosphorylmethyl)] Aminoacetic Acid with the First Generation of DAB Dendrimer

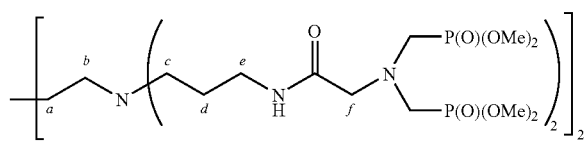

4 mL of dry DMF is added under an inert atmosphere to 2 mmol of aza-bis-phosphonate carboxylic acid obtained in Example 51 (n=1). The solution is taken to 0° C. then 2.6 mmol of HOBt is added and stirring is continued at 0° C. for 30 minutes, 2.6 mmol of DCC is added. After 30 minutes at 0° C. the mixture is allowed to return to room temperature and stirring is continued for an additional 1 hour, the progressive formation of a precipitate is observed. The suspension is again taken to 0° C. then 0.33 mmol of first-generation DAB dendrimer is added. After 30 minutes at 0° C. stirring is continued at room temperature for 20 h. The precipitate is eliminated on 5μ Millipore filters then the DMF is freeze-dried. The product is treated three times by dissolution in a minimum volume of dichloromethane and precipitation in a large volume of diethylether so as to eliminate the excess of reagents. The dendrimer is obtained in the form of an off-white powder with a yield of 73%.

NMR $^{31}$P-{$^{1}$H} (CDCl$_3$) δ=30.2 ppm.
RMN $^{1}$H (CDCl$_3$) δ=1.67 (bs, 4H, Ha), 1.86 (bs, 8H, Hd), 2.97 (bs, 12H, Hb and Hc), 3.20 (d, $^{2}J_{HP}$=9.2 Hz, 16H, CH$_2$P), 3.28 (bs, 8H, He), 3.47 (bs, 8H, Hf), 3.73 (d, $^{3}J_{HP}$=10.6 Hz, 48H, OMe), 7.98 (bs, 4H, CONH) ppm.
RMN $^{13}$C-{$^{1}$H} (CDCl$_3$) δ=21.9 (s, Ca), 24.4 (s, Cd), 36.5 (s, Ce), 49.8 (dd, $^{1}J_{CP}$=157.6 Hz, $^{3}J_{CP}$=6.3 Hz, CH$_2$P), 50.5 (s, Cc), 52.4 (s, Cb), 52.7 (d, $^{2}J_{CP}$=5.9 Hz, OMe), 60.3 (t, $^{3}J_{CP}$=6.5 Hz, Cf), 170.3 (s, CONH) ppm.

Stage 2: Synthesis of Generation 1 DAB-Type Dendrimer Having 4 Azabis-Phosphonic Acid Groups Derived from Glycine at the Surface

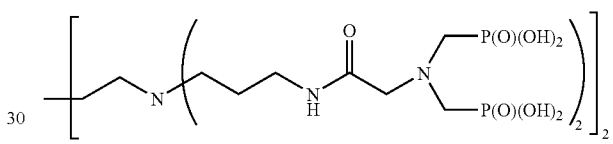

4 mL of freshly distilled acetonitrile is added under an inert atmosphere to 0.2 mmol of generation 1 DAB-type dendrimer with azabis-phosphonate ends of Stage 1, and the mixture is cooled to 0° C. 6.4 mmol of BrTMS (or 32 equivalents) is then added dropwise. The mixture is maintained at 0° C. for 30 minutes then under stirring at room temperature for another 15 hours. The acetonitrile is eliminated under reduced pressure then the mixture is methanolyzed and hydrolyzed as in the preceding cases. The dry residue is then washed twice with a THF/diethylether mixture (1/9). The powder is then dried under vacuum in order to produce the pure product with a yield of 79%.

NMR $^{31}$P-{$^{1}$H} (D$_2$O, THFd8) δ=11.5 ppm.

Stage 3: First-Generation DAB Dendrimer with (Carbamoylmethyl-Amino)-Methyl]-Phosphonic Acid (Na Salt) Ends

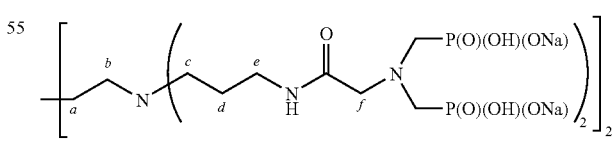

The sodium salt is obtained by adding 1 equivalent of an aqueous soda solution at 0.1955 N per —PO$_3$H$_2$ group present in the molecule obtained in Stage 2. The dendrimer is isolated in the form of a beige powder with a yield of 68% after freeze-drying.

NMR $^{31}$P-{$^{1}$H} (D$_2$O/CD$_3$COCD$_3$) δ=19.9 ppm.

RMN $^{13}$C-{$^1$H} (CDCl$_3$) δ=23.7 (s, Ca), 26.0 (s, Cd), 38.8 (s, Ce), 54.4 (d, $^1J_{CP}$=159.6 Hz, CH$_2$P), 54.6 (s, Cc), 58.1 (s, Cb), 63.1 (bs, Cf), 175.8 (s, CONH) ppm.

Example 58

Synthesis of Generation 1 DAB-Type Dendrimers Having 4 Azabis-Phosphonic Groups Derived from Aminobutyric Acid Stage 1: Coupling of [Bis-(Dimethoxy-Phosphorylmethyl)] Aminobutyric Acid with the First Generation of DAB Dendrimer

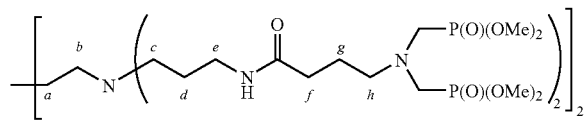

4 mL of dry DMF is added under an inert atmosphere to 2 mmol of aza-bis-phosphonate carboxylic acid obtained in Example 51 (n=3) (ex. A3). The solution is taken to 0° C. then 2.6 mmol of HOBt are added and stirring is continued at 0° C. for 30 minutes, 2.6 mmol of DCC are added. After 30 minutes at 0° C. the mixture is allowed to return to room temperature and stirring is continued for another hour, the progressive formation of a precipitate is observed. The suspension is again taken to 0° C. then 0.33 mmol of first-generation DAB dendrimer is added. After 30 minutes at 0° C. stirring is continued at room temperature for 20 h. The precipitate is eliminated on 5μ Millipore filters then the DMF is freeze-dried. The product is treated three times by dissolution in a minimum volume of dichloromethane and precipitation in a large volume of diethylether so as to eliminate the excess of reagents. The dendrimer is obtained in the form of an off-white powder with a yield of 69%.

NMR $^{31}$P-{$^1$H} (CDCl$_3$) δ=30.4 ppm.

RMN $^1$H (CDCl$_3$) δ=1.70-1.83 (m, 20H, Ha, Hd and Hg), 2.23 (t, $^3J_{HH}$=6.9 Hz, 8H, Hf), 2.72 (m, 8H, Hh), 2.97 (m, 12H, Hb and Hc), 3.09 (d, $^3J_{HH}$=6.9 Hz, 16H, CH$_2$P), 3.24 (m, 8H, He), 3.72 (d, $^3J_{HP}$=10.5 Hz, 48H, OMe), 7.83 (m, 4H, CONH) ppm.

RMN $^{13}$C-{$^1$H} (CDCl$_3$) δ=21.5 (5, Ca), 23.6 (s, Cg), 23.9 (s, Cd), 33.2 (s, Cf), 36.4 (s, Ce), 49.4 (dd, $^1J_{CP}$=151.7 Hz, $^3J_{CP}$=6.5 Hz, CH$_2$P), 50.5 (s, Cc), 52.2 (s, Cb), 52.7 (d, $^2J_{CP}$=5.5 Hz, OMe), 56.2 (t, $^3J_{CP}$=6.5 Hz, Ch), 173.9 (s, CONH) ppm.

Stage 2: Synthesis of Generation 1 DAB-Type Dendrimer Having 4 Azabis-Phosphonic Acid Groups Derived from Aminobutyric Acid

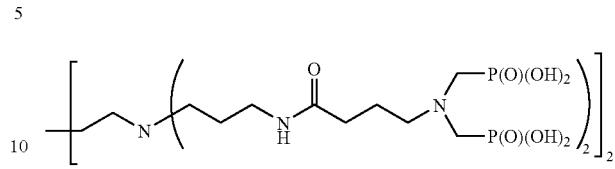

4 mL of freshly distilled acetonitrile is added under an inert atmosphere to 0.2 mmol of generation 1 DAB-type dendrimer with azabis-phosphonate ends of Stage 1, and the mixture is cooled to 0° C. 6.4 mmol of BrTMS (or 32 equivalents) is then added dropwise. The mixture is maintained at 0° C. for 30 minutes then under stirring at room temperature for another 15 hours. The acetonitrile is eliminated under reduced pressure then the mixture is methanolyzed and hydrolyzed as in the preceding cases. The dry residue is then washed twice with a THF/diethylether mixture (1/9). The powder is then dried under vacuum in order to produce the pure product with a yield of 68%

NMR $^{31}$P-{$^1$H} (D$_2$O, CD$_3$COCD$_3$) δ=11.0 ppm.

Stage 3: First-Generation DAB Dendrimer with [(Carbamoylpropyl-Amino)-Methyl]-Phosphonic Acid (Na Salt) Ends

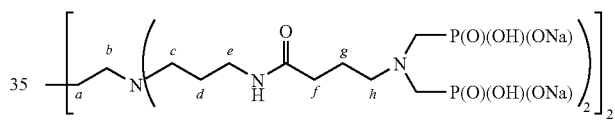

The sodium salt is obtained by adding 1 equivalent of an aqueous soda solution at 0.1955 N per —PO$_3$H$_2$ group present in the molecule obtained in Stage 2. The dendrimer is isolated in the form of an off-white powder with a yield of 69% after freeze-drying.

NMR $^{31}$P-{$^1$H} (D$_2$O/CD$_3$COCD$_3$) δ=10.2 ppm.

RMN $^{13}$C-{$^1$H} (D$_2$O/CD$_3$COCD$_3$) δ=22.7 (s, Cg), 23.3 (s, Ca), 26.0 (s, Cd), 35.2 (s, Cf), 39.0 (s, Ce), 52.9 (s, Cc), 55.0 (d, $^1J_{CP}$=130.7 Hz, CH$_2$P), 54.4 (s, Cb), 58.8 (s, Ch), 177.6 (s, CONH) ppm.

Example 59

Synthesis of Generation 2 DAB-Type Dendrimers Having 8 Azabis-Phosphonic Groups Derived from Glycine Stage 1: Coupling of Aminoacetic Acid [Bis-(Dimethoxy-Phosphorylmethyl)] with the Second-Generation of DAB Dendrimer

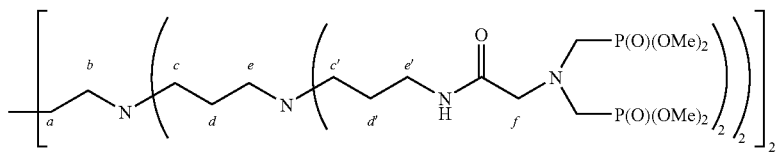

4 mL of dry DMF is added under an inert atmosphere to 2 mmol of aza-bis-phosphonate carboxylic acid obtained in Example 51 (n=1). The solution is taken to 0° C. then 2.6 mmol of HOBt are added and stirring is continued at 0° C. for 30 minutes, 2.6 mmol of DCC are added. After 30 minutes at 0° C. the mixture is allowed to return to room temperature and stirring is continued for another hour, the progressive formation of a precipitate is observed. The suspension is again taken to 0° C. then 0.17 mmol of second-generation DAB dendrimer is added. After 30 minutes at 0° C. stirring is continued at room temperature for 20 h. The precipitate is eliminated on 5 Millipore filters then the DMF is freeze-dried. The product is treated three times by dissolution in a minimum volume of dichloromethane and precipitation in a large volume of diethylether so as to eliminate the excess of reagents. The dendrimer is obtained in the form of an off-white powder with a yield of 64%.

NMR $^{31}$P-$\{^{1}$H$\}$ (CDCl$_3$) $\delta$=30.3 ppm.

Stage 2: Synthesis of the Generation 2 DAB-Type Dendrimer Having 8 Azabis-Phosphonic Acid Groups Derived from Glycine at the Surface

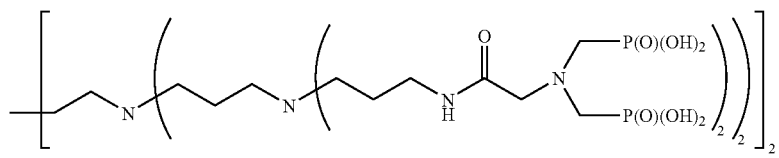

4 mL of freshly distilled acetonitrile is added under an inert atmosphere to 0.2 mmol of generation 2 DAB-type dendrimer with azabis-phosphonate ends of Stage 1, and the mixture is cooled to 0° C. 12.8 mmol of BrTMS (or 64 equivalents) is then added dropwise. The mixture is maintained at 0° C. for 30 minutes then under stirring at room temperature for another 15 hours. The acetonitrile is eliminated under reduced pressure then the mixture is methanolyzed and hydrolyzed as in the preceding cases. The dry residue is then washed twice with a THF/diethylether mixture (1/9). The powder is then dried under vacuum in order to produce the pure product with a yield of 68%.

NMR $^{31}$P-$\{^{1}$H$\}$ (D$_2$O, CD$_3$COCD$_3$) $\delta$=10.6 ppm.

Stage 3: Second-Generation DAB Dendrimer with (Carbamoylmethyl-Amino)-Methyl]-Phosphonic Acid (Na Salt) Ends

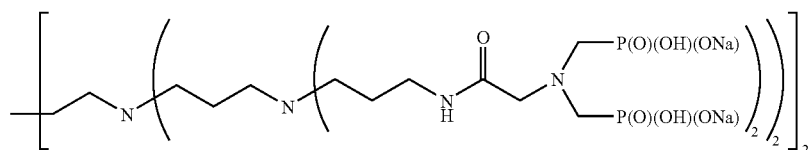

The sodium salt is obtained by adding 1 equivalent of an aqueous soda solution at 0.1955 N per —PO$_3$H$_2$ group present in the molecule obtained in Stage 2. The dendrimer is isolated in the form of a beige powder with a yield of 68% after freeze-drying.

NMR $^{31}$P-{$^1$H} (D$_2$O, CD$_3$COCD$_3$) δ=18.6 ppm.

Example 60

Synthesis of Generation 2 DAB-Type Dendrimers Having 8 Azabis-Phosphonic Groups Derived from Aminobutyric Acid Stage 1: Coupling of Aminobutyric Acid [bis-(Dimethoxy-Phosphorylmethyl)] with the Second Generation of DAB Dendrimer RMN $^1$H (CDCl$_3$) δ=1.62-1.91 (m, 44H, Ha, Hd, Hof and Hg), 2.16 (bs, 24H, Hc and Hc'), 2.72 (bs, 24H, He and He'), 2.88-3.25 (m, 68H, Hb, Hf, Hh and CH$_2$P), 3.69 (d, $^3$J$_{HP}$=10.5 Hz, 96H, OMe), 7.80 (m, 8H, CONH) ppm.

RMN $^{13}$C-{$^1$H} (CDCl$_3$) δ=20.8 (s, Ca), 23.6 (s, Cg), 24.4 (s, Cd and Cd'), 33.2 (s, Cf), 36.6 (s, Ce'), 49.3 (dd, $^1$J$_{CP}$=158.1 Hz, $^3$J$_{CP}$=6.8 Hz, CH$_2$P), 50.5 (s, Cc and Cc'), 52.4 (s, Cb and Ce), 52.7 (d, $^2$J$_{CP}$=5.8 Hz, OMe), 56.2 (t, $^3$J$_{CP}$=6.5 Hz, Ch), 173.7 (s, CONH) ppm.

Stage 2: Synthesis of Generation 2 DAB-Type Dendrimer Having 8 Azabis-Phosphonic Acid Groups Derived from Aminobutyric Acid at the Surface

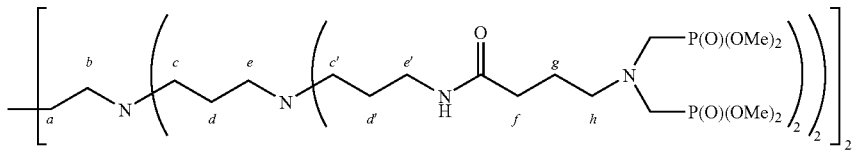

4 mL of dry DMF is added under an inert atmosphere to 2 mmol of aza-bis-phosphonate carboxylic acid obtained in Example 51 (n=3). The solution is taken to 0° C. then 2.6 mmol of HOBt is added and stirring is continued at 0° C. for 30 minutes, 2.6 mmol of DCC is added. After 30 minutes at 0°

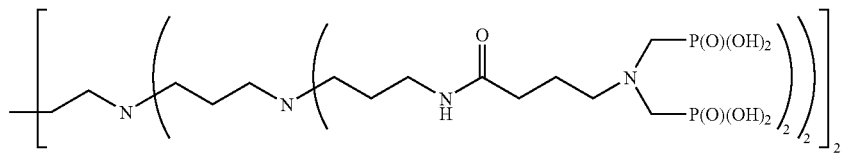

C. the mixture is allowed to return to room temperature and stirring is continued for another hour, the progressive formation of a precipitate is observed. The suspension is again taken to 0° C. then 0.17 mmol of second-generation DAB dendrimer is added. After 30 minutes at 0° C. stirring is continued at room temperature for 20 h. The precipitate is eliminated on 5µ Millipore filters then the DMF is freeze-dried. The product is treated three times by dissolution in a minimum volume of dichloromethane and precipitation in a large volume of diethylether so as to eliminate the excess of reagents. The dendrimer is obtained in the form of an off-white powder with a yield of 75%.

NMR $^{31}$P-{$^1$H} (CDCl$_3$) δ=30.4 ppm.

4 mL of freshly distilled acetonitrile is added under an inert atmosphere to 0.2 mmol of generation 1 or 2 DAB-type dendrimer with azabis-phosphonate ends of Stage 1 and the mixture is cooled to 0° C. 12.8 mmol of BrTMS (or 64 equivalents) is then added dropwise. The mixture is maintained at 0° C. for 30 minutes then under stirring at room temperature for another 15 hours. The acetonitrile is eliminated under reduced pressure then the mixture is methanolyzed and hydrolyzed as in the preceding cases. The dry residue is then washed twice with a THF/diethylether mixture (1/9). The powder is then dried under vacuum in order to produce the pure product with a yield of 74%.

NMR $^{31}$P-{$^1$H} (D$_2$O, CD$_3$COCD$_3$) δ=10.9 ppm.

Stage 3: Second-Generation DAB Dendrimer with [(Carbamoylpropyl-Amino)-Methyl]-Phosphonic Acid (Na Salt) Ends

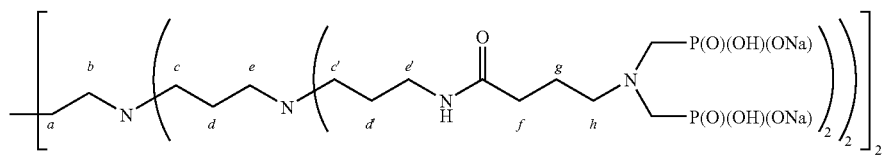

The sodium salt is obtained by adding 1 equivalent of an aqueous soda solution at 0.1955 N per —PO$_3$H$_2$ group present in the molecule obtained in Stage 2. The dendrimer is isolated in the form of an off-white powder with a yield of 72% after freeze-drying.

NMR $^{31}$P-{$^1$H} (D$_2$O/CD$_3$COCD$_3$) δ=10.1 ppm.

RMN $^{13}$C-{$^1$H} (D$_2$O/CD$_3$COCD$_3$) δ=21.7 (s, Ca), 22.8 (s, Cg), 25.8 (s, Cd and Cd'), 35.2 (s, Cf), 39.1 (s, Ce'), 55.2 (d, $^1J_{CP}$=129.4 Hz, CH$_2$P), 52.4 (s, Cc and Cc'), 52.9 (s, Cb and Ce), 58.8 (s, Ch), 177.7 (s, CONH) ppm.

Example 61

PAMAM Dendrimer Model with an Azabis-Phosphonic Group Derived from Glycine

Stage 1: Coupling of [Bis-(Dimethoxy-Phosphorylmethyl)] Aminoacetic Acid with N-(2-Aminoethyl)-Acetamide

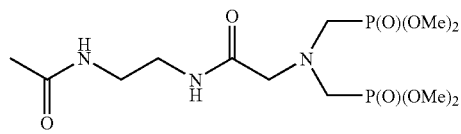

1.58 mmol of aza-bis-phosphonate carboxylic acid obtained in Example 51 (n=1), are placed in solution in 5 mL of dry DMF at 0° C. 1.74 mmol of HOBt is then added followed by stirring for 15 minutes at 0° C. then 1.74 mmol of DCC is added and stirring is continued for 30 minutes at 0° C. and 1 hour at room temperature. A precipitate forms, the mixture is taken to 0° C. and 1.58 mmol of N-(2-aminoethyl)-acetamide is added at 0° C. The mixture is stirred for 15 minutes at 0° C. then overnight at room temperature. The coupling product is purified on a silica chromatography column using as eluent pure CH$_2$Cl$_2$ then producing a gradient up to 10% MeOH. It is obtained with a yield of 43% in the form of an off-white powder.

Rf=0.19 (CH$_2$Cl$_2$/MeOH: 95/5).

NMR $^{31}$P-{$^1$H} (CDCl$_3$) δ=30.0 ppm.

RMN $^1$H (CDCl$_3$) δ=1.93 (s, 3H, COCH$_3$), 3.15 (d, $^2J_{HP}$=9.3 Hz, 4H, P—CH$_2$), 3.36-3.42 (m, 6H, N—CH$_2$—CO, NH—CH$_2$—CH$_2$—NH), 3.76 (d, $^3J_{HP}$=10.7 Hz, 12H, O—CH$_3$), 7.55 (bs, 1H, CONH), 7.78 (bs, 1H, CONH) ppm.

RMN $^{13}$C-{$^1$H} (CDCl$_3$) δ=23.0 (s, COCH$_3$), 39.3 (s, NH—CH$_2$), 39.4 (s, NH—CH$_2$), 50.7 (dd, $^1J_{CP}$=160.1 Hz, $^3J_{CP}$=6.5 Hz, CH$_2$—P), 52.8 (d, $^2J_{CP}$=4.4 Hz, CH$_3$—O), 61.5 (t, $^3J_{CP}$=7.0 Hz, N—CH$_2$—CO), 170.1 (s, CONH), 170.7 (s, CONH) ppm.

Stage 2: PAMAM Dendrimer Model with [(Carbamoylmethyl-Amino)-Methyl]-Phosphonic Acid (Na Salt) Ends

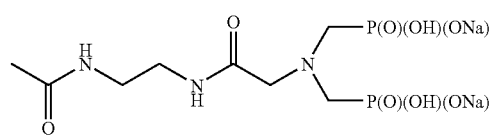

0.5 mmol of the PAMAM aza-bis-phosphonate model of Stage 1 are placed in solution in 5 mL of distilled acetonitrile, then 1.1 equivalent of BrTMS per equivalent of P-OMe bond present in the starting molecule is added dropwise at 0° C. using a syringe. The stirring is continued for 30 minutes at 0° C. then overnight at room temperature. The mixture is brought under vacuum and 5 mL of methanol are added to the dry residue. After 1 hour of stirring at room temperature, the solution is brought under vacuum and 3 mL of distilled water is added. After 1 hour at room temperature, the solution is freeze-dried. The dry residue is washed with ether distilled three times. The sodium salt is obtained by adding 1 equivalent of an aqueous soda solution at 0.1955 N per —PO$_3$H$_2$ group present in the molecule. The model is obtained after freeze-drying in the form of an off-white powder and with a yield of 68%.

NMR $^{31}$P-{$^{1H}$} (D$_2$O/THFd8) δ=18.0 ppm.

Example 62

PAMAM Dendrimer Model with an Azabis-Phosphonic Group Derived from Butyric Acid

Stage 1: Coupling of Aminobutyric Acid [Bis-(Dimethoxy-Phosphorylmethyl)] with N-(2-Aminoethyl)-Acetamide

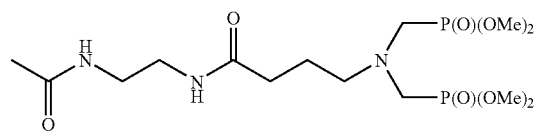

1.58 mmol of aza-bis-phosphonate carboxylic acid obtained in Example 51 (n=3), are placed in solution in 5 mL of dry DMF at 0° C. 1.74 mmol of HOBt is then added followed by stirring for 15 minutes at 0° C. then 1.74 mmol of DCC is added and stirring is continued for 30 minutes at 0° C. and 1 hour at room temperature. A precipitate forms, the mixture is taken to 0° C. and 1.58 mmol of N-(2-aminoethyl)-acetamide is added at 0° C. The mixture is stirred for 15 minutes at 0° C. then overnight at room temperature. The coupling product is thus obtained, which is purified on a chromatographic silica column using as eluent pure $CH_2Cl_2$ then producing a gradient up to 10% of MeOH. It is obtained with a yield of 52%, in the form of an off-white powder.

Rf=0.43 ($CH_2Cl_2$/MeOH: 90/10).

NMR $^{31}P$-{$^1H$} (CDCl$_3$) δ=30.0 ppm.

RMN $^1H$ (CDCl$_3$) δ=1.68 (quint, $^3J_{HH}$=6.6 Hz, 2H, $CH_2$—$CH_2$—$CH_2$), 1.87 (s, 3H, $COCH_3$), 2.20 (t, $^3J_{HH}$=6.6 Hz, 2H, N—$CH_2$—CO), 2.69 (t, $^3J_{HH}$=6.6 Hz, 2H, $CH_2$—N), 3.02 (d, $^2J_{HP}$=8.7 Hz, 4H, P—$CH_2$), 3.23-3.29 (m, 4H, NH—$CH_2$—$CH_2$—NH), 3.69 (d, $^3J_{HP}$=10.6 Hz, 12H, O—$CH_3$), 7.26 (bs, 1H, CONH), 7.37 (bs, 1H, CONH) ppm.

RMN $^{13}C$-{$^1H$} (CDCl$_3$) δ=22.9 (s, $COCH_3$), 23.8 (s, $CH_2$—$CH_2$—$CH_2$), 33.2 (s, NHCO—$CH_2$), 39.3 (s, NH—$CH_2$), 40.0 (s, NH—$CH_2$), 49.5 (dd, $^1J_{CP}$=159.4 Hz, $^3J_{CP}$=7.2 Hz, $CH_2$—P), 52.6 (d, $^2J_{CP}$=5.4 Hz, $CH_3$—O), 55.9 (t, $^3J_{CP}$=7.1 Hz, N—$CH_2$—$CH_2$), 170.9 (s, CONH), 174.3 (s, CONH) ppm.

Stage 2: PAMAM Dendrimer Model with [(Carbamoylpropyl-Amino)-Methyl]-Phosphonic Acid (Na Salt) Ends

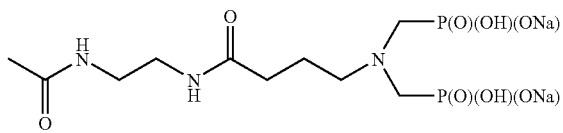

0.5 mmol of the aza-bis-phosphonate compound of Stage 1 is placed in solution in 5 mL of distilled acetonitrile, then 1.1 equivalent of BrTMS per equivalent of P-OMe bond present in the starting molecule is added dropwise at 0° C. using a syringe. The stirring is continued for 30 minutes at 0° C. then overnight at room temperature. The mixture is brought under vacuum and 5 mL of methanol are added to the dry residue. After 1 hour of stirring at room temperature, the solution is brought under vacuum and 3 mL of distilled water is added. After 1 hour at room temperature, the solution is freeze-dried. The dry residue is washed with distilled ether three times. The sodium salt is obtained by adding 1 equivalent of an aqueous soda solution at 0.1955 N per —$PO_3H_2$ group present in the molecule. The product is obtained in the form of an off-white powder with a yield of 71% after freeze-drying.

NMR $^{31}P$-{$^1H$} (D$_2$O) δ=10.7 ppm.

RMN $^{13}C$-{$^1H$} (D$_2$O) δ=22.5 (s, $COCH_3$), 24.7 (s, $CH_2$—$CH_2$—$CH_2$), 35.5 (s, NHCO-$CH_2$), 41.3 (s, NH—$CH_2$), 41.4 (s, NH—$CH_2$), 54.2 (dl, $^1J_{CP}$=134.1 Hz, $CH_2$—P), 58.9 (bs, N—$CH_2$—$CH_2$), 177.1 (s, CONH), 177.6 (s, CONH) ppm.

Example 63

Synthesis of the Generation 1 PAMAM-Type Dendrimer Having 4 Azabis-Phosphonate Groups Derived from Glycine at the Surface Stage 1: Coupling of [Bis-(Dimethoxy-Phosphorylmethyl)] Aminoacetic Acid with the First-Generation of PAMAM Dendrimer

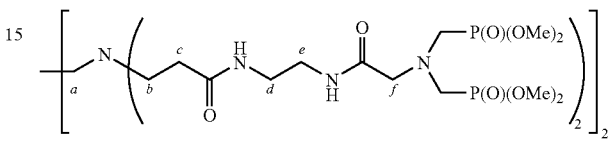

4 mL of dry DMF is added under an inert atmosphere to 2 mmol of carboxylic acid aza-bis-phosphonate obtained in Example 51 (n=1). The solution is taken to 0° C. then 2.6 mmol of HOBt is added and stirring is continued at 0° C. for 30 minutes, 2.6 mmol of DCC is added. After 30 minutes at 0° C. the mixture is allowed to return to room temperature and stirring is continued for another hour, the progressive formation of a precipitate is observed. The suspension is again taken to 0° C. then 0.33 mmol of first-generation PAMAM dendrimer is added. After 30 minutes at 0° C. stirring is continued at room temperature for 20 h. The precipitate is eliminated on 5μ Millipore filters then the DMF is freeze-dried. The product is treated three times by dissolution in a minimum volume of dichloromethane and precipitation in a large volume of diethylether so as to eliminate the excess of reagents. The dendrimer is isolated in the form of an off-white powder with a yield of 67%.

NMR $^{31}P$-{$^1H$} (CDCl$_3$) δ=30.1 ppm.

RMN $^1H$ (CDCl$_3$) δ=2.48 (bs, 12H, Ha and Hc), 2.98 (m, 8H, Hb), 3.18 (d, $^2J_{HP}$=9.4 Hz, 16H, $CH_2P$), 3.29 (bs, 16H, Hd and He), 3.41 (bs, 8H, Hf), 3.72 (d, $^3J_{HP}$=10.6 Hz, 48H, OMe), 7.77 (bs, 4H, CONH), 8.17 (bs, 4H, CONH) ppm.

RMN $^{13}C$-{$^1H$} (CDCl$_3$) δ=31.6 (s, Cc), 38.9 (s, Ce), 39.2 (s, Cd), 48.8 (s, Cb), 49.7 (s, Ca), 50.2 (dd, $^1J_{CP}$=159.2 Hz, $^3J_{CP}$=6.5 Hz, $CH_2P$), 52.8 (d, $^2J_{CP}$=5.0 Hz, OMe), 60.7 (t, $^3J_{CP}$=6.6 Hz, CO, 170.3 (s, CONH), 171.4 (s, CONH) ppm.

Stage 2: Synthesis of Generation 1 PAMAM Dendrimer Having 4 Azabis-Phosphonic Acid Groups Derived from Glycine at the Surface

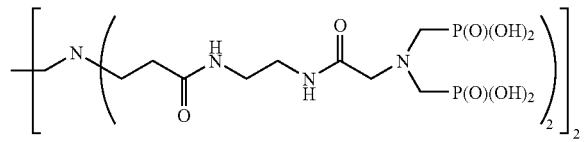

4 mL of freshly distilled acetonitrile is added under an inert atmosphere to 0.2 mmol of generation 1 PAMAM-type dendrimer with azabis-phosphonate ends of Stage 1 and the mixture is cooled to 0° C. 6.4 mmol of BrTMS (or 32 equivalents) is then added dropwise. The mixture is maintained at 0° C. for 30 minutes then under stirring at room temperature for another 15 hours. The acetonitrile is eliminated under reduced pressure then the mixture is methanolyzed and hydrolyzed as in the preceding cases. The dry residue is then washed twice with a THF/diethylether mixture (1/9). The powder is then dried under vacuum in order to produce the pure product with a yield of 65%

NMR $^{31}$P-$\{^1$H$\}$ (D$_2$O, THFd8) δ=10.9 ppm.

Stage 3: First-Generation PAMAM Dendrimer with [(Carbamoylmethyl-Amino)-Methyl]-Phosphonic Acid (Na Salt) Ends

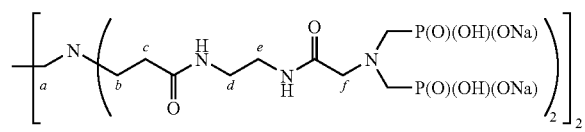

The sodium salt is obtained by adding 1 equivalent of an aqueous soda solution at 0.1955 N per —PO$_3$H$_2$ group present in the molecule obtained in Stage 2. The product is isolated with a yield of 72% after freeze-drying in the form of an off-white powder.

NMR $^{31}$P-$\{^1$H$\}$ (D$_2$O/CD$_3$COCD$_3$) δ=19.6 ppm.

Example 64

Synthesis of the Generation 1 PAMAM-Type Dendrimer Having 4 Azabis-Phosphonate Groups Derived from Aminobutyric Acid at the Surface

Stage 1: Coupling of [bis-(Dimethoxy-Phosphorylmethyl)] Aminobutyric Acid with the First Generation of PAMAM Dendrimer

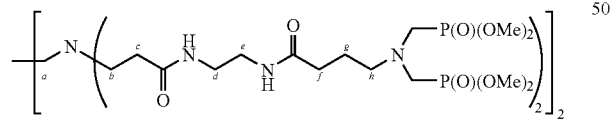

4 mL of dry DMF is added under an inert atmosphere to 2 mmol of aza-bis-phosphonate carboxylic acid obtained in Example 51 (n=3). The solution is taken to 0° C. then 2.6 mmol of HOBt is added and stirring is continued at 0° C. for 30 minutes, 2.6 mmol of DCC are added. After 30 minutes at 0° C. the mixture is allowed to return to room temperature and stirring is continued for another hour, the progressive formation of a precipitate is observed. The suspension is again taken to 0° C. then 0.33 mmol of first-generation PAMAM dendrimer is added. After 30 minutes at 0° C. stirring is continued at room temperature for 20 h. The precipitate is eliminated on 5μ Millipore filters then the DMF is freeze-dried. The product is treated three times by dissolution in a minimum volume of dichloromethane and precipitation in a large volume of diethylether so as to eliminate the excess of reagents. It is isolated in the form of an off-white powder with a yield of 61%.

NMR $^{31}$P-$\{^1$H$\}$ (CDCl$_3$) δ=30.4 ppm.

RMN $^1$H (CDCl$_3$) δ=1.72 (quint, $^3J_{13H}$=6.3 Hz, 8H, Hg), 2.21 (t, $^3J_{HH}$=6.3 Hz, 8H, Hf), 2.55 (m, 12H, Ha and Hc), 2.73 (t, $^3J_{HH}$=6.3 Hz, 8H, Hh), 2.93 (m, 8H, Hb), 3.09 (d, $^2J_{HP}$=9.1 Hz, 16H, CH$_2$P), 3.28 (bs, 16H, Hd and He), 3.73 (d, $^3J_{HP}$=10.6 Hz, 48H, OMe), 7.65 (bs, 4H, CONH), 8.21 (bs, 4H, CONH) ppm.

RMN $^{13}$C-$\{^1$H$\}$ (CDCl$_3$) δ=23.5 (s, Cg), 32.1 (s, Cc), 33.3 (s, Cf), 39.2 (s, Ce), 39.6 (s, Cd), 49.2 (s, Cb), 49.5 (dd, $^1J_{CP}$=157.9 Hz, $^3J_{CP}$=7.2 Hz, CH$_2$P), 50.1 (s, Ca), 52.6 (d, $^2J_{CP}$=4.6 Hz, OMe), 56.1 (t, $^3J_{CP}$=6.7 Hz, Ch), 171.7 (s, CONH), 173.7 (s, CONH) ppm.

Stage 2: Synthesis of Generation 1 PAMAM Dendrimer Having 4 Azabis-Phosphonic Acid Groups Derived from Butyric Acid at the Surface

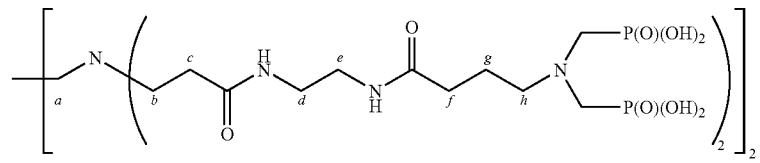

4 mL of freshly distilled acetonitrile is added under an inert atmosphere to 0.2 mmol of generation 0 or 1 PAMAM-type dendrimer with azabis-phosphonate ends of Stage 1, and the mixture is cooled to 0° C. 6.4 mmol of BrTMS (or 32 equivalents) is then added dropwise. The mixture is maintained at 0° C. for 30 minutes then under stirring at room temperature for another 15 hours. The acetonitrile is eliminated under reduced pressure then the mixture is methanolyzed and hydrolyzed as in the preceding cases. The dry residue is then washed twice with a THF/diethylether mixture (1/9). The powder is then dried under vacuum in order to produce the pure product with a yield of 71%

NMR $^{31}$P-{$^1$H} (D$_2$O, CD$_3$COCD$_3$) δ=11.1 ppm.

Stage 3: First-Generation PAMAM Dendrimer with [(Carbamoylpropyl-Amino)-Methyl]-Phosphonic Acid (Na Salt) Ends

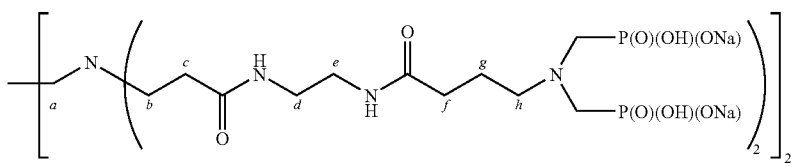

The sodium salt is obtained by adding 1 equivalent of an aqueous soda solution at 0.1955 N per —PO$_3$H$_2$ group present in the molecule obtained in Stage 2. The product is isolated with a yield of 73% after freeze-drying in the form of an off-white powder.

NMR $^{31}$P-{$^1$H} (D$_2$O/CD$_3$COCD$_3$) δ=10.2 ppm.

RMN $^{13}$C-{$^1$H} (D$_2$O/CD$_3$COCD$_3$) δ=22.8 (s, Cg), 33.4 (s, Cc), 35.2 (s, Cf), 41.3 (s, Ce), 41.4 (s, Cd), 51.3 (s, Cb), 51.7 (s, Ca), 55.1 (d, $^1J_{CP}$=130.0 Hz, CH$_2$P), 58.9 (bs, Ch), 175.9 (s, CONH), 177.5 (s, CONH) ppm.

Example 65

Synthesis of Generation 2 PAMAM-Type Dendrimer Having 8 Azabis-Phosphonate Groups Derived from Glycine at the Surface Stage 1: Coupling of Aminoacetic Acid [Bis-(Dimethoxy-Phosphorylmethyl)] with the Second Generation of PAMAM Dendrimer

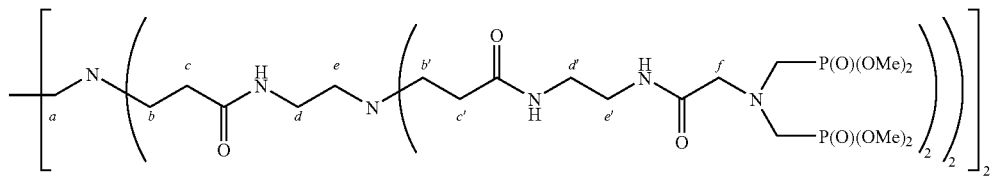

4 mL of dry DMF is added under an inert atmosphere to 2 mmol of aza-bis-phosphonate carboxylic acid obtained in Example 51 (n=1). The solution is taken to 0° C. then 2.6 mmol of HOBt is added and stirring is continued at 0° C. for 30 minutes, 2.6 mmol of DCC are added. After 30 minutes at 0° C. the mixture is allowed to return to room temperature and stirring is continued for another hour, the progressive formation of a precipitate is observed. The suspension is again taken to 0° C. then 0.17 mmol of second-generation PAMAM dendrimer is added. After 30 minutes at 0° C. stirring is continued at room temperature for 20 h. The precipitate is eliminated on 5µ Millipore filters then the DMF is freeze-dried. The product is treated three times by dissolution in a minimum volume of dichloromethane and precipitation in a large volume of diethylether so as to eliminate the excess of reagents. The dendrimer is isolated in the form of an off-white powder with a yield of 63%.

NMR $^{31}$P-{$^1$H} (CDCl$_3$) δ=30.2 ppm.

Stage 2: Synthesis of Generation 2 PAMAM Dendrimer Having 8 Azabis-Phosphonic Acid Groups Derived from Glycine at the Surface

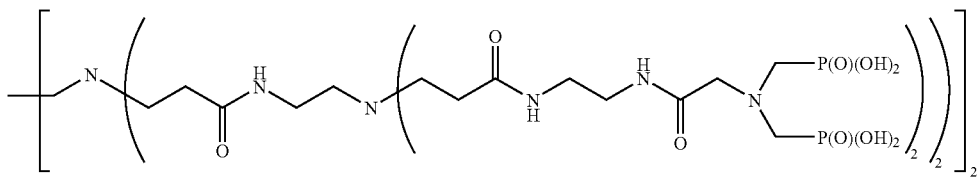

4 mL of freshly distilled acetonitrile is added under an inert atmosphere to 0.2 mmol of generation 0 or 1 PAMAM-type dendrimer with azabis-phosphonate ends of Stage 1, and the mixture is cooled to 0° C. 12.8 mmol of BrTMS (or 64 equivalents) is then added dropwise. The mixture is maintained at 0° C. for 30 minutes then under stirring at room temperature for another 15 hours. The acetonitrile is eliminated under reduced pressure then the mixture is methanolyzed and hydrolyzed as in the preceding cases. The dry residue is then washed twice with a THF/diethylether mixture (1/9). The powder is then dried under vacuum in order to produce the pure product with a yield of 73%

NMR $^{31}$P-$\{^{1}$H$\}$ (D$_2$O, CD$_3$COCD$_3$) δ=11.0 ppm.

Stage 3: Second-Generation PAMAM Dendrimer with [(Carbamoylmethyl-Amino)-Methyl]-Phosphonic Acid (Na Salt) Ends

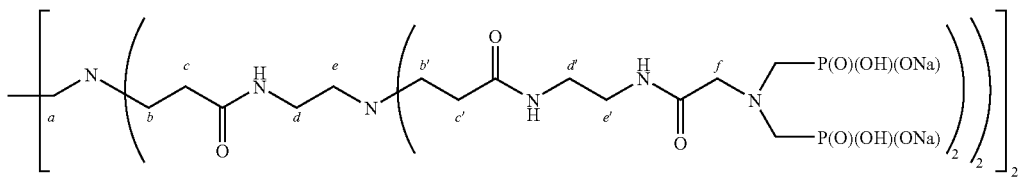

The sodium salt is obtained by adding 1 equivalent of an aqueous soda solution at 0.1955 N per —PO$_3$H$_2$ group present in the molecule obtained in Stage 2. The product is isolated with a yield of 69% after freeze-drying in the form of an off-white powder.

NMR $^{31}$P-$\{^{1}$H$\}$ (D$_2$O, CD$_3$COCD$_3$) δ=18.5 ppm.

Example 66

Synthesis of Generation 2 PAMAM-Type Dendrimer Having 8 Azabis-Phosphonate Groups Derived from Aminobutyric Acid at the Surface Stage 1: Coupling of Aminobutyric Acid [bis-(Dimethoxy-Phosphorylmethyl)] with the Second Generation of PAMAM Dendrimer

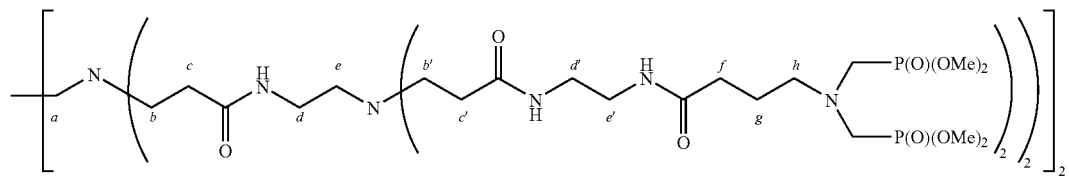

4 mL of dry DMF is added under an inert atmosphere to 2 mmol of aza-bis-phosphonate carboxylic acid obtained in Example 51 (n=3). The solution is taken to 0° C. then 2.6 mmol of HOBt is added and stirring is continued at 0° C. for 30 minutes, 2.6 mmol of DCC is added. After 30 minutes at 0° C. the mixture is allowed to return to room temperature and stirring is continued for an additional 1 hour, the progressive formation of a precipitate is observed. The suspension is again taken to 0° C. then 0.17 mmol of the second-generation PAMAM dendrimer is added. After 30 minutes at 0° C. stirring is continued at room temperature for 20 h. The precipitate is eliminated on 5μ Millipore filters then the DMF is freeze-dried. The product is treated three times by dissolution in a minimum volume of dichloromethane and precipitation in a large volume of diethylether so as to eliminate the excess of reagents. The dendrimer is obtained in the form of an off-white powder with a yield of 63%.

NMR $^{31}P-\{^1H\}$ (CDCl$_3$) δ=30.4 ppm.

RMN $^1H$ (CDCl$_3$) δ=1.69 (quint1, $^3J_{HH}$=5.9 Hz, 16H, Hg), 2.17 (t1, $^3J_{HP}$=5.9 Hz, 16H, Hf), 2.21-2.93 (m, 76H, Ha, Hb, Hc, He, Hh, Hb', Hc'), 3.06 (d, $^2J_{HP}$=9.1 Hz, 32H, CH$_2$P), 3.25 (bs, 40H, Hd, Hof and He'), 3.69 (d, $^3J_{HP}$=10.5 Hz, 96H, OMe), 7.70 (bs, 8H, CONH), 8.07 (bs, 8H, CONH), 8.28 (bs, 4H, CONH) ppm.

RMN $^{13}C-\{^1H\}$ (CDCl$_3$) δ=23.7 (s, Cg), 33.5 (s, Cc and Cc'), 39.7 (s, Cd, Ce' and CO, 48.8 (s, Cd'), 49.6 (dd, $^1J_{CP}$=158.1 Hz, $^3J_{CP}$=7.0 Hz, CH$_2$P), 50.4 (s, Ca, Cb and Cb'), 52.4 (s, Ce), 53.0 (bs, OMe), 56.3 (t, $^3J_{CP}$=8.2 Hz, Ch), 171.6 (s, CONH), 172.7 (s, CONH), 174.1 (s, CONH) ppm.

Stage 2: Synthesis of Generation 2 PAMAM Dendrimer Having 8 Azabis-Phosphonic Acid Groups Derived from Butyric Acid at the Surface 4 mL of freshly distilled acetonitrile is added under an inert atmosphere to 0.2 mmol of generation 0 or 1 PAMAM-type dendrimer with azabis-phosphonate ends of Stage 1, and the mixture is cooled to 0° C. 12.8 mmol of BrTMS (or 64 equivalents) is then added dropwise. The mixture is maintained at 0° C. for 30 minutes then under stirring at room temperature for another 15 hours. The acetonitrile is eliminated under reduced pressure then the mixture is methanolyzed and hydrolyzed as in the preceding cases. The dry residue is then washed twice with a THF/diethylether mixture (1/9). The powder is then dried under vacuum in order to produce the pure product with a yield of 67%.

NMR $^{31}P-\{^1H\}$ (D$_2$O, CD$_3$COCD$_3$) δ=11.3 ppm.

Stage 3: Second-Generation PAMAM Dendrimer with [(Carbamoylpropyl-Amino)-Methyl]-Phosphonic Acid (Na Salt) Ends

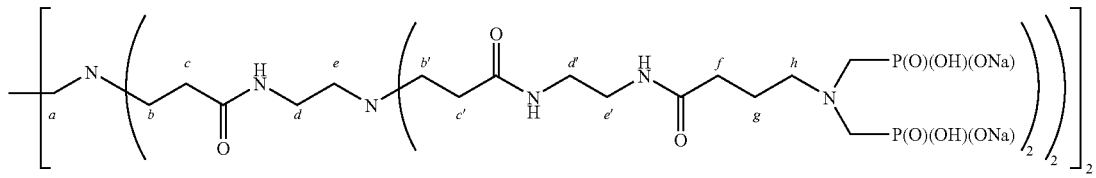

The sodium salt is obtained by adding 1 equivalent of an aqueous soda solution at 0.1955 N per —PO$_3$H$_2$ group present in the molecule obtained in Stage 2. The product is isolated with a yield of 71% after freeze-drying in the form of an off-white powder.

NMR $^{31}P-\{^1H\}$ (D$_2$O/CD$_3$COCD$_3$) δ=10.1 ppm.

RMN $^{13}C-\{^1H\}$ (D$_2$O/CD$_3$COCD$_3$) δ=22.8 (s, Cg), 32.0 (s, Cc and Cc'), 35.2 (s, Cd), 41.3 (s, Ce' or Cf), 41.6 (s, Ce' or Cf), 51.1 (s, Cd'), 52.4 (s, Cb and Cb'), 54.4 (s, Ce), 55.3 (d, $^1J_{CP}$=132.6 Hz, CH$_2$P), 58.9 (s, Ch), 174.7 (s, CONH), 176.5 (s, CONH), 177.7 (s, CONH) ppm.

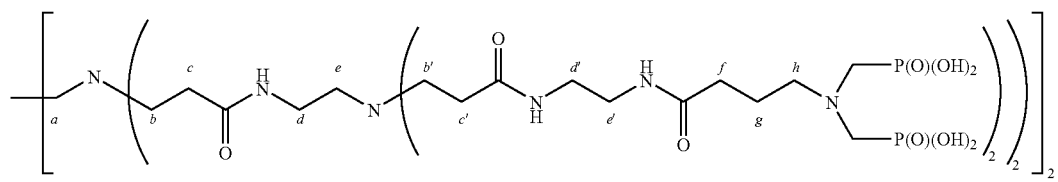

Example 67

Synthesis of Phosphorus-Containing Dendrimers of Gc Type Having 12 Amido-Azabis-Phosphonic Ends Derived from Glycine at the Surface Stage 1: Coupling of the Phenol with [Carbamoyl-Methyl-Amino-Methyl]Dimethylesterphoshonic Ends with the First-Generation Phosphorus-Containing Dendrimer

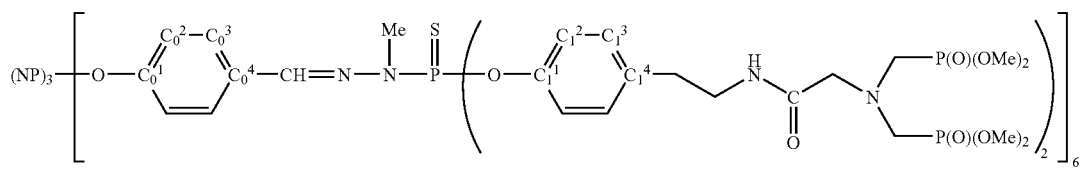

0.017 mmol of generation 1 phosphorus-containing dendrimer (12 Cl ends) are placed in solution in 3 mL of dry THF. 5.04 mmol of cesium carbonate then 0.23 mmol of tyramine-amido-azabis-phosphonate compound obtained in Example 53 (n=1) in solution in 3 mL of dry THF are successively added to this solution. The mixture is stirred overnight at room temperature then filtered on celite. The reaction medium is evaporated under reduced pressure then the dry residue is dissolved in a minimum volume of dichloromethane. The product is then precipitated in a large volume of ether. This operation is repeated three times in order to eliminate the slight excess of starting phenol. The product is obtained in the form of an off-white powder with a yield of 88%.

NMR $^{31}$P-$\{^{1}$H$\}$ (CDCl$_3$) δ=11.7 (s, N$_3$P$_3$), 30.1 (s, PO$_3$Me$_2$), 66.6 (s, P=S) ppm.

RMN $^{1}$H (CDCl$_3$) δ=2.77 (t, $^3J_{HH}$=6.8 Hz, 24H, C$\underline{H}_2$—CH$_2$—N), 3.13 (d, $^3J_{HP}$=9.4 Hz, 48H, P—CH$_2$), 3.23 (d, $^3J_{HP}$=10.1 Hz, 18H, N—CH$_3$), 3.41-3.48 (m, 48H, C$\underline{H}_2$—NH, CO—CH$_2$—N), 3.72 (d, $^2$hp=10.7 Hz, 144H, OMe), 6.97-7.15, 7.50-7.64 (m, 90H, H$_{Ar}$, CH=N, NH) ppm.

RMN $^{13}$C-$\{^{1}$H$\}$ (CDCl$_3$) δ=33.0 (d, $^2J_{CP}$=12.0 Hz, CH$_3$—N), 35.0 (s, C$_6$H$_4$—$\underline{C}$H$_2$), 40.4 (s, CH$_2$—NH), 49.9 (dd, $^1J_{CP}$=158.4 Hz, $^3J_{CP}$=6.0 Hz, CH$_2$P), 52.8 (s, OMe), 60.8 (bs, CO—$\underline{C}$H$_2$—N), 121.3 (s, C$_0^2$, C$_1^2$), 128.3 (s, C$_0^3$), 129.8 (s, C$_1^3$), 132.2 (s, C$_0^4$), 136.2 (s, C$_1^4$), 138.8 (d, $^3J_{CP}$=11.1 Hz, CH=N), 149.9 (d, $^2J_{CP}$=6.0 Hz, C$_1^1$), 151.2 (bs, C$_0^1$), 169.6 (s, CONH) ppm.

Stage 2: Synthesis of Gc-Type Phosphorus-Containing Dendrimer Having 12 Amido-Azabis-Phosphonic Acid Ends Derived from Glycine at the Surface

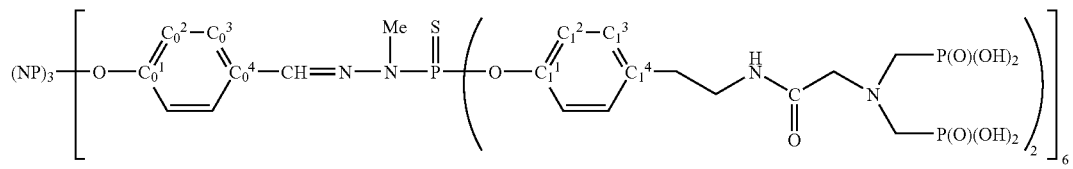

0.015 mmol of dendrimer with amido-azabis-phosphonate ends previously described in Stage 1 are placed in solution under an inert atmosphere in 3 mL of distilled acetonitrile. The solution is taken to 0° C. then 48 equivalents of BrTMS (0.73 mmol) are added dropwise under argon. The mixture is stirred for 30 minutes at 0° C. then overnight at room temperature. After methanolysis and hydrolysis as described in the customary protocol (i.e. DAB and PAMAM), the dry residue is washed with dry ether in order to produce the pure product with a yield of 63%.

NMR $^{31}$P-$\{^{1}$H$\}$ (D$_2$O, THFd8) δ=11.9 (s, PO$_3$H$_2$), 12.8 (s, N$_3$P$_3$), 66.5 (s, P=S) ppm.

Stage 3: First-Generation Phosphorus-Containing Dendrimer with [(Carbamoylmethyl-Amino)-Methyl]-Phosphonic Acid (Na Salt) Ends

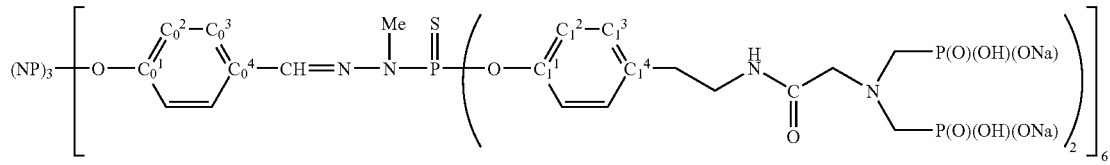

The sodium salt is obtained by reaction of 24 equivalents of soda solution at 0.1955N on one equivalent of dendrimer obtained in Stage 2, in order to produce after one hour of stirring at room temperature and freeze-drying the expected product with a yield of 70%.

NMR $^{31}$P-{$^1$H} (D$_2$O/THFd8) δ=12.8 (s, N$_3$P$_3$), 16.5 (s, PO$_3$HNa), 66.8 (s, P=S) ppm.

RMN $^{13}$C-{$^1$H} (D$_2$O/THFd8) δ=33.2 (bs, CH$_3$—N), 37.0 (s, C$_6$H$_4$—CH$_2$), 43.6 (s, CH$_2$—NH), 58.1 (d, $^1J_{CP}$=140.7 Hz, CH$_2$—P=O), 62.0 (bs, CO—CH$_2$—N), 121.7 (s, C$_0^2$, C$_1^2$), 123.6 (s, C$_1^3$), 130.9 (s, C$_0^3$), 132.8 (s, C$_1^4$), 136.5 (s, C$_0^4$), 139.6 (bs, CH=N), 151.5 (bs, C$_1^1$), 153.4 (bs, C$_0^1$), 172.8 (s, CONH) ppm.

Example 68

Synthesis of Gc-Type Phosphorus-Containing Dendrimers Having 12 Amido-Azabis-Phosphonic Ends Derived from Butyric Acid at the Surface Stage 1: Coupling of the Phenol with [Carbamoyl Propyl-Amino-Methyl]Dimethylesterphoshonic Ends with the First-Generation Phosphorus-Containing Dendrimer 0.017 mmol of generation 1 phosphorus-containing dendrimer (12 Cl ends) are placed in solution in 3 mL of dry THF. 5.04 mmol of cesium carbonate then 0.23 mmol of tyramine-amido-azabis-phosphonate compound obtained in Example 53 (n=3) in solution in 3 mL of dry THF are successively added to this solution. The mixture is stirred overnight at room temperature then filtered on celite. The reaction medium is evaporated under reduced pressure then the dry residue is dissolved in a minimum volume of dichloromethane. The product is then precipitated in a large volume of ether. This operation is repeated three times in order to eliminate the slight excess of starting phenol. The product is obtained in the form of an off-white powder with a yield of 85%.

NMR $^{31}$P-{$^1$H} (CDCl$_3$) δ=11.9 (s, N$_3$P$_3$), 30.5 (s, PO$_3$Me$_2$), 66.5 (s, P=S) ppm.

RMN $^1$H (CDCl$_3$) δ=1.67 (quint, $^3J_{HH}$=6.2 Hz, 24H, CH$_2$—CH$_2$—CH$_2$), 2.19 (t, $^3J_{HH}$=6.2 Hz, 24H, CO—CH$_2$—CH$_2$—CH$_2$), 2.67-2.70 (m, 48H, CO—CH$_2$—CH$_2$—CH$_2$, C$_6$H$_4$—CH$_2$), 3.04 (d, $^2J_{HP}$=8.9 Hz, 48H, P—CH$_2$), 3.18 (d, $^3J_{HP}$=10.2 Hz, 18H, N—CH$_3$), 3.33-3.42 (m, 24H, CH$_2$—NH), 3.70 (d, $^3J_{HP}$=10.5 Hz, 144H, CH$_3$—O), 6.91-7.04 (m, 7211, NHCO, H$_{Ar}$), 7.56-7.61 (m, 18H, H$_{Ar}$, CH=N) ppm.

RMN $^{13}$C-{$^1$H} (CDCl$_3$) δ=24.1 (s, CH$_2$—CH$_2$—CH$_2$), 33.0 (d, $^2J_{CP}$=11.8 Hz, CH$_3$—N), 33.4 (s, CO—CH$_2$), 34.9 (s, C$_6$H$_4$—CH$_2$), 40.5 (s, CH$_2$—NH), 49.5 (dd, $^1J_{CP}$=159.3 Hz, $^3J_{CP}$=6.9 Hz, CH$_2$P), 52.7 (d, $^2J_{CP}$=4.9 Hz, OCH$_3$), 56.1 (t, $^3J_{CP}$=6.9 Hz, CO—CH$_2$—N), 121.1 (s, C$_0^2$), 121.2 (s, C$_1^2$), 128.3 (s, C$_0^3$), 129.8 (s, C$_1^3$), 132.2 (s, C$_0^4$), 136.5 (s, C$_1^4$),

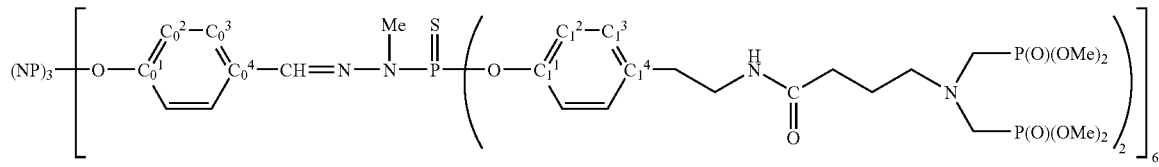

138.7 (d, $^3J_{CP}$=13.9 Hz, CH=N), 148.9 (d, $^2J_{CP}$=6.9 Hz, C$_1^1$), 151.2 (bs, C$_0^1$), 173.4 (s, CONH) ppm.

Stage 2: Synthesis of the Gc-Type Phosphorus-Containing Dendrimer Having 12 Amido-Azabis-Phosphonic Acid Ends Derived from Butyric Acid at the Surface

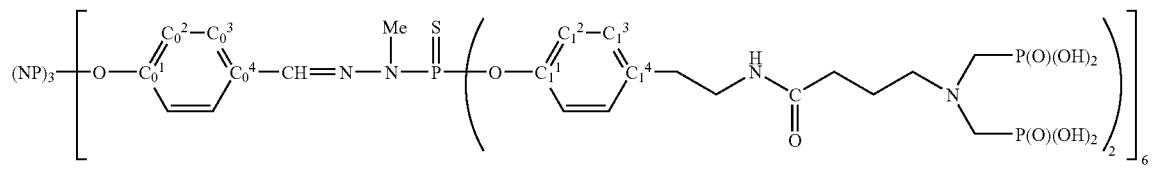

0.015 mmol of dendrimers with amido-azabis-phosphonate ends previously described in Stage 1 are placed in solution under an inert atmosphere in 3 mL of distilled acetonitrile. The solution is taken to 0° C. then 48 equivalents of BrTMS (0.73 mmol) are added dropwise under argon. The mixture is stirred for 30 minutes at 0° C. then overnight at room temperature. After methanolysis and hydrolysis as described in the customary protocol (i.e. DAB and PAMAM), the dry residue is washed with dry ether in order to produce the pure product with a yield of 58%.

NMR $^{31}$P-{$^{1}$H} (D$_2$O, THFd8) δ=12.1 (s, PO$_3$H$_2$), 12.8 (s, N$_3$P$_3$), 66.5 (s, P=S) ppm.

Stage 3: First-Generation Phosphorus-Containing Dendrimer with [(Carbamoylpropyl-Amino)-Methyl]-Phosphonic Acid (Na Salt) Ends The product with aza-bis-phosphonic ends thus obtained in Stage 2 is introduced into 24 equivalents of soda solution at 0.1955N in order to obtain the corresponding sodium salt with a yield of 72% after one hour of stirring at room temperature and freeze-drying.

NMR $^{31}$P-{$^{1}$H} (D$_2$O/THFd8) δ=10.3 (s, PO$_3$HNa), 66.8 (s, P=S) (N$_3$P$_3$ not observed) ppm RMN $^{13}$C-{$^{1}$H} (D$_2$O/THFd8) δ=22.8 (s, CH$_2$—$\underline{C}$H$_2$—CH$_2$), 35.0 (bs, CH$_3$—N, CO—$\underline{C}$H$_2$), 36.8 (s, C$_6$H$_4$—$\underline{C}$H$_2$), 43.4 (s, CH$_2$—NH), 53.4 (s, CO—$\underline{C}$H$_2$—N), 57.4 (d, $^{1}$J$_{CP}$=146.6 Hz, CH$_2$P), 121.9 (bs, C$_0^2$, C$_1^2$), 123.7 (s, C$_1^3$), 131.0 (s, C$_0^3$), 132.6 (s, C$_1^4$), 136.1 (s, C$_0^4$), 139.3 (s, CH=N), 151.5 (bs, C$_1^1$), 153.6 (s, C$_0^1$), 176.6 (s, CONH) ppm.

Example 69

Polyarylether-Type Dendrimers with Phosphonic Acid Ends Derived From Glycine

Stage 1: Coupling of [Bis-(Dimethoxy-Phosphorylmethyl)] Aminoacetic

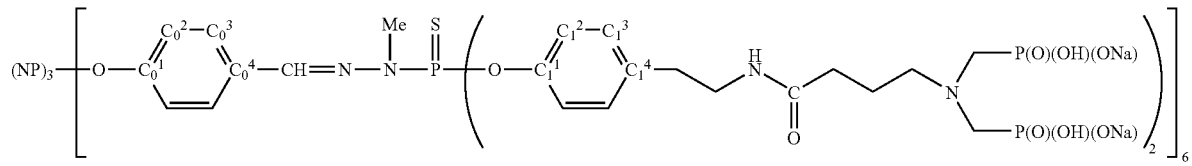

Acid with a Second-Generation Dendrimer of the Polyarylether Type

The polyarylether-type dendrimers (PAE) with hydrazine terminations were prepared according to the procedure described in the literature [K. Kono, M. Liu, J. M. J. Frechet, *Bioconjugate Chem.* 1999, 10, 1115-1121].

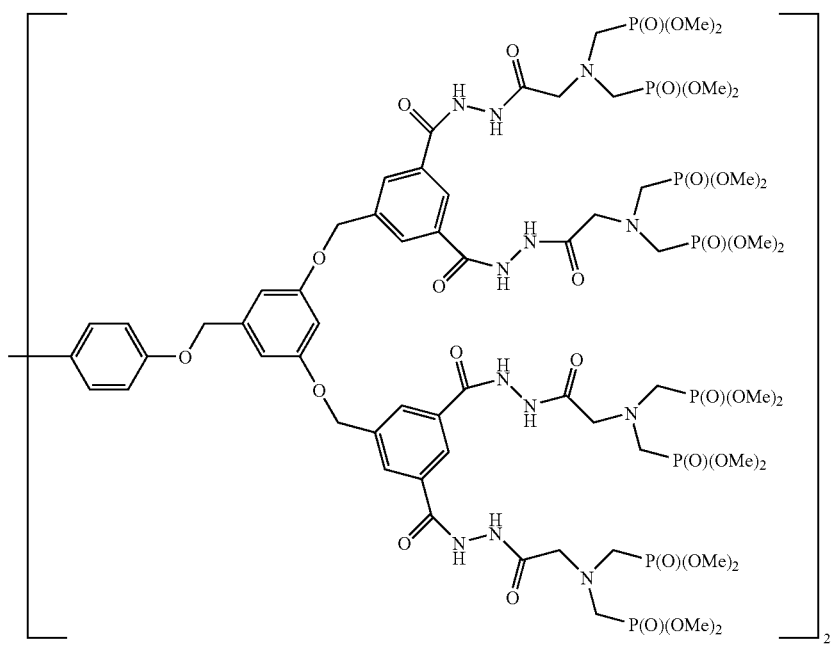

2 mmol of azabis-phosphonate carboxylic acid obtained in Example 51 (n=1) are placed in solution in 4 mL of dry DMF at 0° C. 1.2 equivalents of HOBt is then added and stirring is continued at 0° C. for 30 minutes. 1.2 equivalents of DCC are added and the mixture is stirred for 30 minutes at 0° C. then for 1 hour at room temperature. The mixture is again taken to 0° C. and 225 mg (0.18 mmol) of PAE dendrimer possessing 8 hydrazide ends in solution in 2 mL of dry DMF are added. The stirring is continued for 30 minutes at 0° C. then for 24 hours at room temperature. The precipitate is eliminated on a Millipore filter (5μ) then the DMF is freeze-dried. The product is treated three times by the following process: dissolution in a minimum volume of dichloromethane then precipitation in a large volume of diethylether. The dendrimer is obtained with a yield of 63%.

NMR $^{31}$P-$\{^{1}$H$\}$ (CDCl$_3$) δ=29.9 ppm.

Stage 2: Second-Generation PAE Dendrimer with [(Carbamoylmethyl-Amino)-Methyl]-Phosphonic Acid (Na Salt) Ends 4 mL of freshly distilled acetonitrile is added under an inert atmosphere to 0.11 mmol of PAE dendrimer with aza-bis-phosphonate ends of Stage 1 and the mixture is cooled to 0° C. 3.87 mmol of BrTMS (or 35.2 equivalents) is then added dropwise. The mixture is maintained at 0° C. for 30 minutes then under stirring at room temperature for another 15 hours. The acetonitrile is eliminated under reduced pressure then the mixture is methanolyzed and hydrolyzed. After freeze-drying, the dry residue is washed with a THF/ether mixture (1/9). The addition of 1 equivalent of NaOH (0.1955N in aqueous solution) per PO$_3$H$_2$ surface function leads to the corresponding sodium salt. After freeze-drying, the product is obtained with a yield of 75%.

NMR $^{31}$P-$\{^{1}$H$\}$ (D$_2$O/CD$_3$COCD$_3$) δ=19.1 ppm.

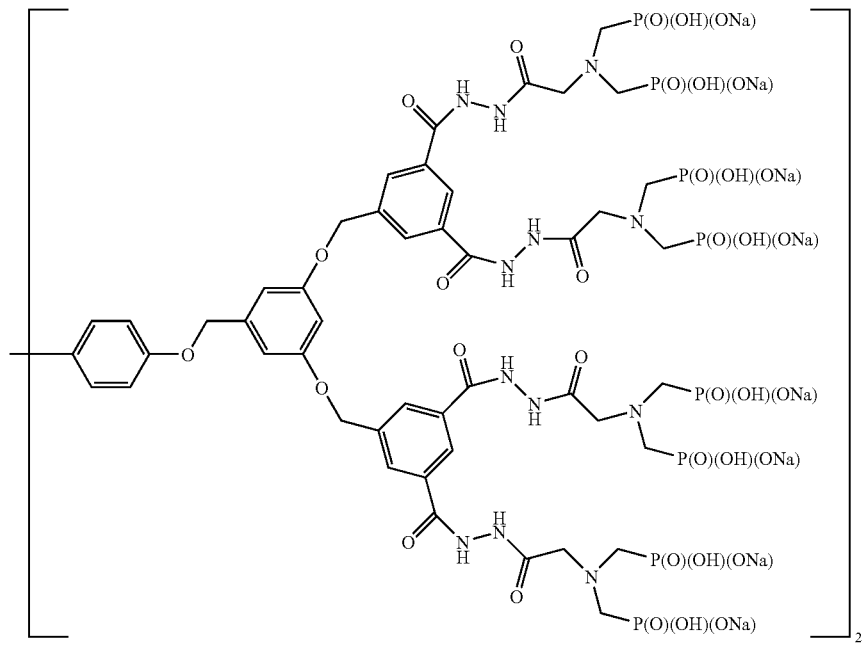

Example 70

Polyarylether-Type Dendrimers with Phosphonic Acid Ends Derived From Butyric Acid Stage 1: Coupling of [Bis-(Dimethoxy-Phosphorylmethyl)] Aminobutyric Acid with a Second-Generation Dendrimer of the Polyarylether Type

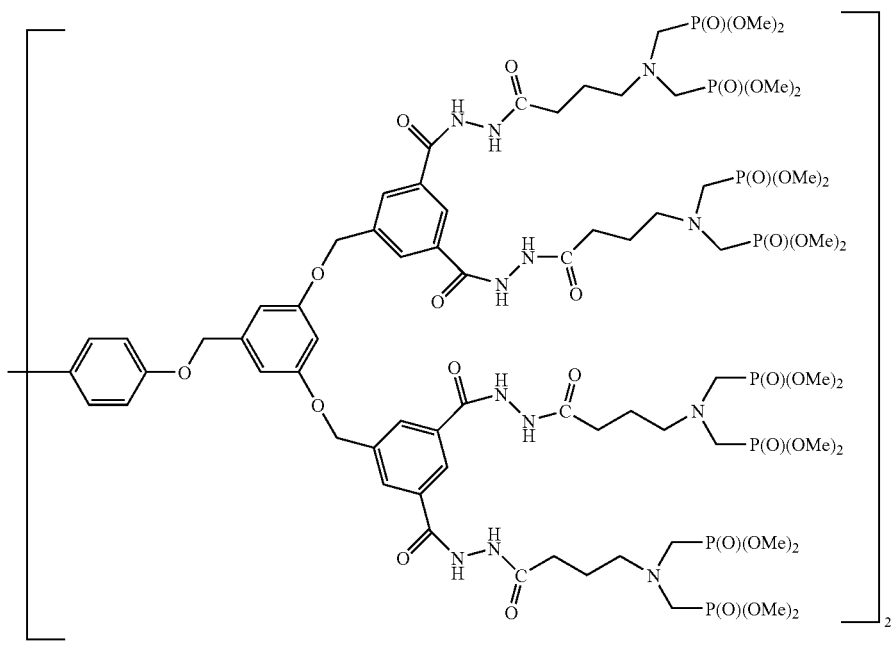

2 mmol of aza-bis-phosphonate carboxylic acid obtained in Example 51 (n=3) are placed in solution in 4 mL of dry DMF at 0° C. 1.2 equivalents of HOBt is then added and stirring is continued at 0° C. for 30 minutes. 1.2 equivalents of DCC are added and the mixture is stirred for 30 minutes at 0° C. then for 1 hour at room temperature. The mixture is again taken to 0° C. and 225 mg (0.18 mmol) of PAE dendrimer possessing 8 hydrazide ends in solution in 2 mL of dry DMF are added. The stirring is continued for 30 minutes at 0° C. then for 24 hours at room temperature. The precipitate is eliminated on a Millipore filter (5µ) then the DMF is freeze-dried. The product is treated three times by the following process: dissolution in a minimum volume of dichloromethane then precipitation in a large volume of diethyl-ether. The dendrimer is isolated with a yield of 68%.

NMR $^{31}$P-$\{^{1}$H$\}$ (CDCl$_3$) δ=30.2 ppm.

Stage 2: Second-Generation PAE Dendrimer with [(Carbamoylpropyl-Amino)-Methyl]-Phosphonic Acid (Na Salt) Ends

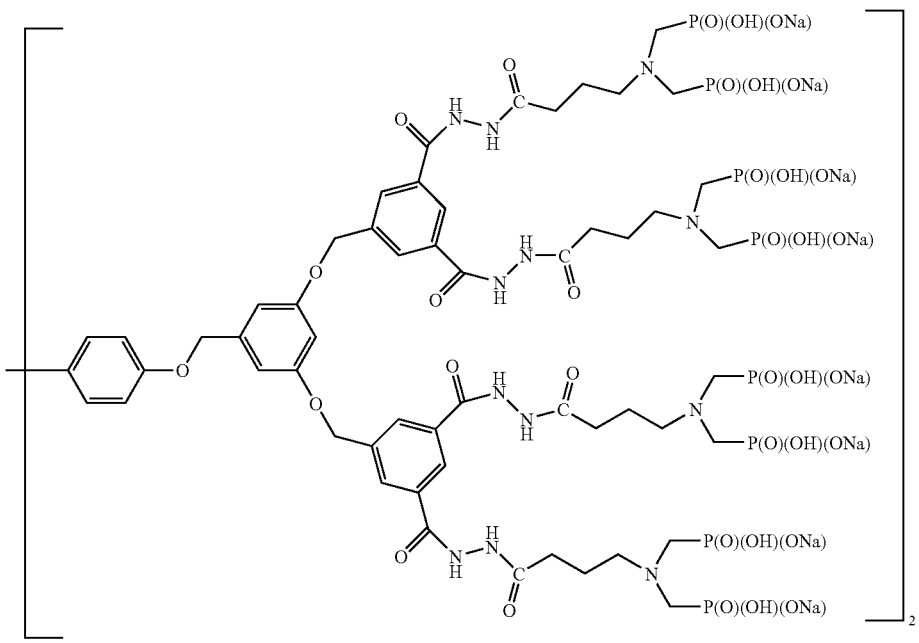

4 mL of freshly distilled acetonitrile is added under an inert atmosphere to 0.11 mmol of dendrimer with aza-bis-phosphonate ends of Stage 1 and the mixture is cooled to 0° C. 3.87 mmol of BrTMS (or 35.2 equivalents) is then added dropwise. The mixture is maintained at 0° C. for 30 minutes then under stirring at room temperature for another 15 hours. The acetonitrile is eliminated under reduced pressure then the mixture is methanolyzed and hydrolyzed. After freeze-drying, the dry residue is washed with a THF/ether mixture (1/9). The addition of 1 equivalent of NaOH (0.1955N in aqueous solution) per $PO_3H_2$ surface function leads to the corresponding sodium salt. After freeze-drying, the product is obtained with a yield of 71%.

NMR $^{31}$P-$\{^1H\}$ ($D_2O/CD_3COCD_3$) δ=10.4 ppm.

Example 71

Synthesis of a Dendrimer with a Tyrosine Aza-Bis-Phosphonate Surface

Stage 1: Tyrosine Bis Phosphonate Derivative

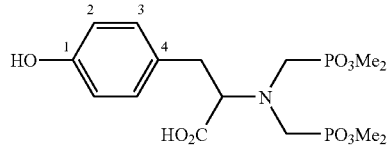

Aqueous formaldehyde (2.5 mL, 30.8 mmol, 2.8 eq.) and dimethyl phosphite (3 mL, 32.7 mmol, 2.96 eq.) are added to a suspension of (D-L) tyrosine (2 g, 11.05 mmol) in 4 mL of THF. The suspension is stirred overnight at room temperature and the resulting homogeneous solution is concentrated under reduced pressure. The residue is washed with twice 15 mL of AcOEt and twice 15 mL of $CH_2Cl_2$. The solid is then dried under reduced pressure. The phenol bisphosphonate is obtained in the form of a white powder with a yield of 85%.

NMR $^{31}$P$\{^1H\}$ ($CD_3OD$, 81.01 MHz): δ=31.0 (s, P=O).

NMR $^1$H ($CD_3OD$, 200.13 MHz): δ=2.81 (dd, 2H, $^2J_{HH}$=14.1 Hz, $^3J_{HH}$=7.4 Hz, CHHCH); 3.04 (dd, 2H, $^2J_{HH}$=14.1 Hz, $^3J_{HH}$=7.2 Hz, CHHCH); 3.22-3.51 (m, 4H, $PCH_2$); 3.70 (d, 6H, $^3J_{HP}$=8.1 Hz, POMe); 3.76 (d, 6H, $^3J_{HP}$=8.1 Hz, POMe); 4.21 (t, $^3J_{HP}$=7.3 Hz, CH); 6.70 (d, 2H, $^3J_{HH}$=8.5 Hz, $C^2$—H); 7.13 (d, 2H, $^3J_{HP}$=8.5 Hz, $C^3$—H).

NMR $^{13}$C—$\{^1H\}$ ($CD_3OD$, 62.89 MHz): δ=35.0 (s, $CH_2$); 47.3 (dd, $^1J_{CP}$=167.3 and $^3J_{HP}$=9.3 Hz, $PCH_2$); 52.9 (d, $^2J_{CP}$=7.0 Hz, POMe); 53.3 (d, $^2J_{CP}$=7.0 Hz, POMe); 66.6 (t, $^3J_{CP}$=6.9 Hz, CH); 115.4 (s, $C^2$); 129.2 (s, $C^4$); 130.9 (s, $C^3$); 156.4 (s, $C^1$); 173.8 (COOH).

Stage 2: Methylation of the Acid

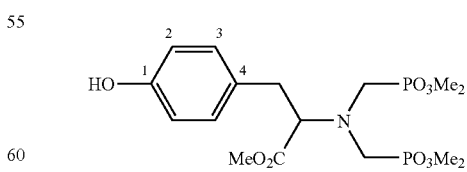

A solution of tyrosine bis-phosphonate synthesized in the preceding stage (760 mg, 1.79 mmol) in 12 mL of methanol is heated at reflux for 36 hours in the presence of a catalytic quantity of para-toluene sulphonic acid. After cooling the solution is filtered then concentrated under reduced pressure.

The residual oil is washed with an ether/pentane mixture then precipitated in a THF/Et$_2$O/pentane mixture with a yield of 93%.

NMR $^{31}$P{$^1$H} (CDCl$_3$, 121.5 MHz): δ=29.6 (s, P=O).

NMR (CDCl$_3$, 200.13 MHz): δ=2.87 (dd, 2H, $^2J_{HH}$=13.7 Hz and $^3J_{HH}$=8.0 Hz, CHHPh); 3.17 (dd, 2H, $^2J_{HH}$=16.0 Hz and $^2J_{HP}$=5.7 Hz, CHHP); 3.29 (t, 2H, $^2J_{HH}$=$^2J_{HP}$=16.0 Hz, CHHP); 3.59 (s, 3H, COOMe); 3.69 (d, 6H, $^3J_{HP}$=11.8 Hz, POMe); 3.70 (d, 6H, $^3J_{HP}$=10.6 Hz, POMe); 4.38 (t, 1H, $^3J_{HH}$=7.0 Hz, CH); 6.76 (d, 2H, $^3J_{HH}$=8.3 Hz, C$^2$—H); 7.08 (d, 2H, $^3J_{HH}$=8.3 Hz, C$^3$—H); 8.50 (bs, OH).

NMR $^{13}$C{$^1$H} (CDCl$_3$, 75.5 MHz): δ=35.6 (s, CH$_2$Ph); 47.6 (dd, $^1J_{CP}$=166.8 Hz and $^3J_{CP}$=9.8 Hz, PCH$_2$); 51.8 (s, OMe); 53.9 (d, $^3J_{CP}$=6.8 Hz, POMe); 53.8 (d, $^3J_{CP}$=6.8 Hz, POMe); 66.5 (t, $^3J_{CP}$=6.8 Hz, CH); 115.7 (s, C$^2$); 128.2 (s, C$^4$); 130.7 (s, C$^3$); 156.2 (s, C$^1$); 172.6 (s, CO$_2$Me).

Stage 3: Grafting on Dendrimer

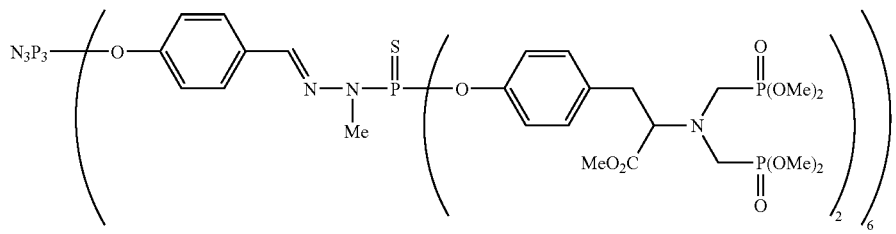

12.2 equivalents of phenol synthesized in the preceding stage (420 mg, 0.956 mmol) and 15 equivalents of Cs$_2$CO$_3$ (383 mg, 1.175 mmol) are added to a solution of dendrimer Gc 1 (143 mg, 78.3 μmol) with an S=PCl$_2$ termination in THF. The resulting suspension is stirred (26 hours) until the chlorines have been completely substituted ($^{31}$P NMR monitoring). The mixture is decanted, the supernatant is collected and the residual solid is washed with THF. The supernatants are combined and centrifuged. The clear solution obtained is concentrated under reduced pressure. The residue is dissolved in a minimum amount of THF then precipitated with pentane. The solid obtained is purified by washing (THF/Et$_2$O and CH$_2$Cl$_2$/pentane) with a yield of 73%.

NMR $^{31}$P{$^1$H} (CDCl$_3$, 121.5 MHz): δ=11.5 (s, N$_3$P$_3$); 29.6 (s, P=O); 66.4 (s, P=S).

NMR $^1$H (CDCl$_3$, 400.13 MHz): δ=2.82-3.10 (m, 24H, CH$_2$Ar); 3.10-3.50 (m, 66H, PCH$_2$ and NCH$_3$); 3.62 (d, 72H, $^3J_{HP}$=10.6 Hz, POMe); 3.68 (d, 72H, $^3J_{HP}$=10.6 Hz, POMe); 3.75 (s, 36H, COOMe); 4.41 (t, 12H, $^3J_{HH}$=6.9 Hz, CH); 7.05 (m, 36H, C$_0^2$—H and C$_1^2$—H); 7.24 (m, 24H, C$_1^3$—H); 7.61 (m, 18H, C$_1^3$—H and CH=N).

NMR $^{13}$C{$^1$H} (CDCl$_3$, 62.89 MHz): δ=32.8 (d, $^2J_{CP}$=11.9 Hz, NCH$_3$); 35.2 (s, CH$_2$Ph); 46.9 (dd, $^1J_{CP}$=165.5 and $^3J_{CP}$=9.18 Hz, PCH$_2$); 51.5 (s, OMe); 52.4 (d, $^2J_{CP}$=7.4 Hz, POMe); 53.1 (d, $^2J_{CP}$=6.3 Hz, POMe); 65.2 (s, CH); 121.1 (s, C$_0^2$ and C$_1^2$); 128.2 (s, C$_0^3$); 130.5 (s, C$_1^3$); 132.0 (s, C$_0^4$); 134.6 (s, C$_1^4$); 138.8 (d, $^3J_{CP}$=14.0 Hz, CH=N); 149.1 (d, $^2J_{CP}$=6.5 Hz, C$_1^1$); 151.2 (bs, C$_0^1$); 171.8 (s, CO$_2$Me).

Stage 4: First-Generation Phosphorus-Containing Dendrimer with Bisphosphonic Acid (Na Salt) Ends

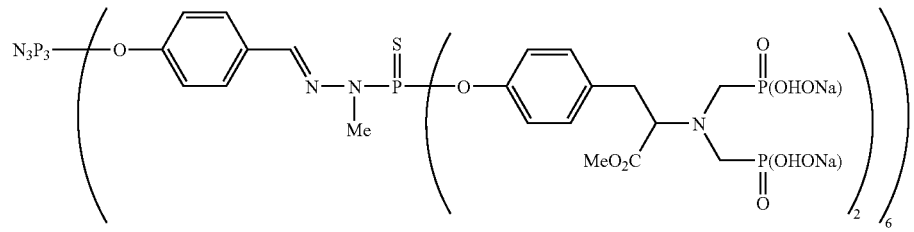

75 equivalents (222 μL, 1.68 mmol) of bromotrimethylsilane are added at 0° C. under an argon flow to a solution of dendrimer with dimethyl phosphonate terminations synthesized in the preceding stage (150 mg, 22.5 μmol) in acetonitrile. The solution is stirred overnight at room temperature then concentrated under reduced pressure. 5 mL of methanol are added and the mixture is vigorously stirred for 2 hours. The methanol is eliminated under reduced pressure and the residue is washed with distilled ether, then water and methanol. The solid is dried under reduced pressure until a powder is obtained. A soda solution (0.1966 M, 2.72 mL, 24 eq.) is slowly added to the solid. The solution obtained is filtered then freeze-dried. The dendrimer with bis-phosphonic amino acid terminations is obtained in the form of a white powder with a yield of 91%.

NMR $^{31}$P{$^1$H} (D$_2$O/CD$_3$CN 81.01 MHz): δ=12.6 (s, N$_3$P$_3$); 20.9 (s, P=O); 67.5 (bs, P=S).

Example 72

Synthesis of a Dendrimer with a Benzyl-Aza-Bis-Phosphonate Surface

Stage 1: Phenol Azabisphosphonate

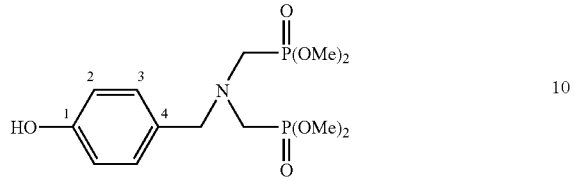

An aqueous solution of formaldehyde (37% in water, 990 µL, 12.19 mmol, 3 eq.) is added to a solution of 4-hydroxybenzylamine (500 mg, 4.06 mmol) in THF (7 mL). After 30 minutes of stirring, 3 equivalents (1.12 mL, 12.2 mmol) of dimethyl phosphite are added. The solution is stirred at room temperature for 48 hours then poured into 150 mL of AcOEt. The organic phase is washed with a solution of $NaHCO_3$ and salt water then dried over $MgSO_4$ and concentrated under reduced pressure. The residue is subjected to column chromatography with silica gel (eluent: acetone/MeOH; 95:5) with a yield of 72%.

NMR $^{31}P\{^1H\}$ ($CDCl_3$, 81.01 MHz): δ=31.2 (s, P=O).

Stage 2: Grafting on First-Generation Phosphorus-Containing Dendrimer

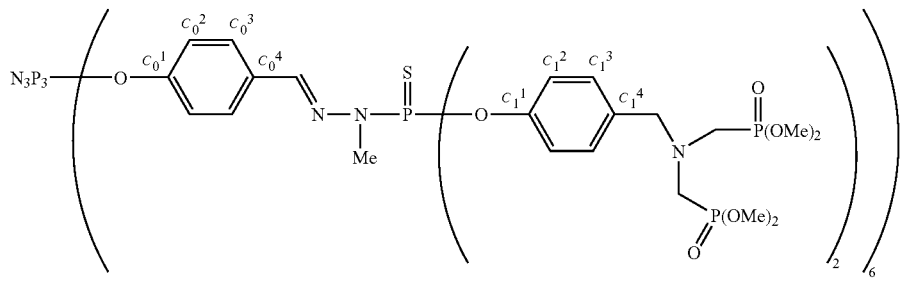

13 equivalents (275 mg, 0.75 mmol) of phenol synthesized in the preceding stage (solubilized in THF) and 15 equivalents (281 mg, 0.864 mmol) of $Cs_2CO_3$ are added to a solution of Gel dendrimer (105 mg, 57.6 µmol) with an S=$PCl_2$ termination in THF. The resulting suspension is stirred until the chlorines are completely substituted ($^{31}P$ NMR monitoring). The mixture is decanted, the supernatant is collected and the residual solid is washed with THF. The supernatants are combined and centrifuged. The clear solution obtained is concentrated under reduced pressure. The residue is dissolved in a minimum amount of THF then precipitated with pentane. The solid obtained is purified by washing (THF/pentane and THF/$Et_2O$) with a yield of 90%.

NMR $^{31}P\{^1H\}$ ($CDCl_3$, 81.01 MHz): δ=11.3 (s, $N_3P_3$); 31.0 (s, P=O); 65.6 (s, P=S).

Stage 3: First-Generation Phosphorus-Containing Dendrimer with Bisphosphonic Acid (Na Salt) Ends

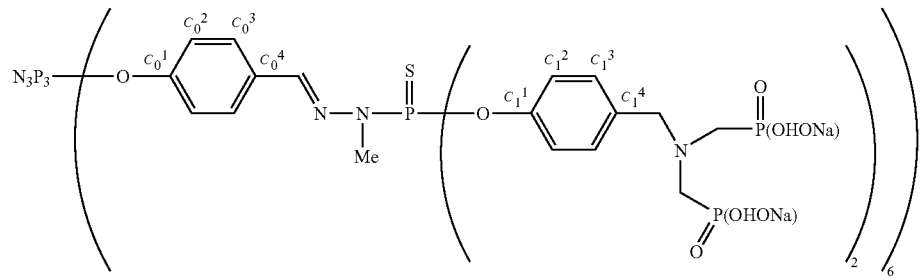

60 equivalents (245 μL, 1.86 mmol) of bromotrimethylsilane are added at 0° C. under an argon flow to a solution of dendrimer with dimethyl phosphonate terminations synthesized in the preceding stage (180 mg, 31 μmol) in acetonitrile. The solution is stirred overnight at room temperature then concentrated under reduced pressure. 5 mL of methanol are added and the mixture is vigorously stirred for 2 hours. The methanol is eliminated under reduced pressure and the residue is washed with distilled ether, then water and methanol. The solid is dried under reduced pressure until a powder is obtained. A soda solution (0.1966 M, 3.78 mL, 24 eq.) is slowly added to the solid. The solution obtained is filtered then freeze-dried. The bis-phosphonic amino acid is obtained in the form of a white powder with a yield of 92%.

NMR $^{31}P\{^{1}H\}$ (D$_2$O/CD$_3$CN, 81.01 MHz): δ=10.8 (bs, P=O); 11.1 (bs, N$_3$P$_3$); 65.2 (s, P=S).

Example 73

Synthesis of the Cyclotetraphosphazene Octaaldehyde Core

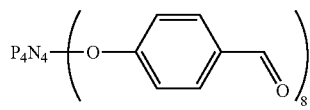

Octachlorocyclotetraphosphazene (2.15 mmol, 1 g) and sodium hydride (18.9 mmol, 454 mg) are added to 100 mL of tetrahydrofuran, the mixture is taken to −20° C. with magnetic stirring. Then 4-hydroxybenzaldehyde (18.9 mmol, 2.31 g) in solution in THF (20 mL) is added dropwise. After addition the mixture slowly rises to room temperature then is left under stirring for 48 hours. After filtration on celite, the product is washed several times with cold methanol in order to remove the excess of 4-hydroxybenzaldehyde sodium salt. The product is obtained in the form of a white powder with a yield of 90%.

NMR $^{31}P$-$\{^{1}H\}$ (CDCl$_3$): δ=−10.5 (s, P) ppm.
NMR $^{1}H$ (CDCl$_3$): δ=7.04 (d, $^{3}J_{HH}$=8.4 Hz, 16H, CH$_{arom}$); 7.56 (d, $^{3}J_{HH}$=8.6 Hz, 16H, CH$_{arom}$); 9.68 (s, 8H, CH=O) ppm.

NMR $^{13}C$-$\{^{1}H\}$ (CDCl$_3$): δ=121.9 (s, C$_0^2$); 132.1 (s, C$_0^3$); 134.6 (s, C$_0^4$); 155.7 (s, C$_0^1$); 191.5 (s, CHO) ppm.

Example 74

Synthesis of a Dendrimer with a Cyclotetraphosphazene Core and with a Dichloro-Thio-Phosphorhydrazide Surface

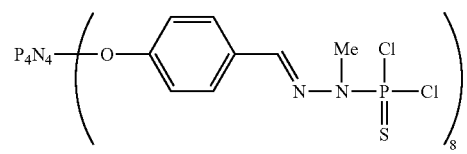

The cyclotetraphosphazene octaaldehyde core obtained in Example 73 (0.87 mmol, 1 g) is placed without solvent into a flask. Dichloro-thio-phosphorhydrazide (7.66 mmol, 33.3 mL) in solution in chloroform at 0.23 mol·L$^{-1}$ is added to this powder rapidly and at −20° C. Once the addition is finished the mixture is maintained under magnetic stirring and at room temperature for 12 hours. The solvent is evaporated from the reaction mixture then the product is taken up three times in a minimum amount of tetrahydrofuran in order to precipitate it in pentane. The product is isolated in the form of a white powder with a yield of 86%.

NMR $^{31}P$-$\{^{1}H\}$ (CDCl$_3$): δ=65.7 (s, P$_1$); −10.0 (s, P$_0$) ppm.
NMR $^{1}H$ (CDCl$_3$): δ=3.47 (d, $^{3}J_{HP}$=14.0 Hz, 24H, CH$_3$—N—P$_1$); 7.04 (d, $^{3}J_{HH}$=8.4 Hz, 16H, CH$_{arom}$); 7.56 (broad d, $^{4}J_{HP}$=$^{3}J_{HH}$=8.6 Hz, 24H, CH$_{arom}$, CH=N) ppm.
NMR $^{13}C$-$\{^{1}H\}$ (CDCl$_3$): δ=31.9 (d, $^{2}J_{CP}$=12.9 Hz, CH$_3$—N—P)); 121.2 (s, C$_0^2$); 128.5 (s, C$_0^3$); 130.8 (s, C$_0^4$); 140.7 (d, $^{3}J_{CP}$=18.8 Hz, CH=N); 152.3 (s, C$_0^1$) ppm.

Example 75

Synthesis of a Dendrimer with a Cyclotetraphosphazene Core and with an Aza-Bis-Dimethyl-Phosphonate Surface Derived from Tyramine

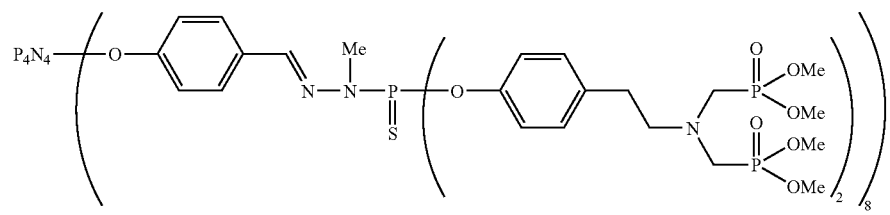

Cesium carbonate (14.4 mmol, 4.68 g) and phenol aza-bis-dimethyl-phosphonate derived from the tyramine obtained in Example 31 (7.23 mmol, 2.8 g) are added to a solution of dendrimer with a cyclotetraphosphazene core and with a dichloro-thio-phosphorhydrazide surface obtained in Example 74 (0.41 mmol, 1 g) in anhydrous THF (10 mL). The mixture is left under stirring for 24 hours at room temperature then the final mixture is filtered on celite with THF so as to separate the salts. Finally the final product is washed by precipitation in a pentane/ether mixture 1/1, the final product is isolated in the form of a white powder with a yield of 80%.

NMR $^{31}$P-{$^1$H} (CDCl$_3$): δ=66.8 (s, P$_1$); 30.2 (s, P(O)(OMe)$_2$); −9.4 (s, P$_0$) ppm.

NMR $^1$H (CDCl$_3$): δ=2.67 (broad t, $^3J_{HH}$=6.5 Hz, 32H, C$\underline{H}_2$—CH$_2$—N); 2.96 (broad t, $^3J_{HH}$=6.5 Hz, 32H, CH$_2$—C$\underline{H}_2$—N); 3.10 (d, $^2J_{HP}$=9.57 Hz, 64H, —C$\underline{H}_2$—P(O)(OCH$_3$)$_2$); 3.14 (d, $^3J_{HP}$=11.8 Hz, 24H, CH$_3$—N—P$_1$); 3.64 (d, $^3J_{HP}$=10.5 Hz, 192H, —P(O)(O—C$\underline{H}_3$)$_2$); 6.8-7.8 (m, 104H, CH$_{arom}$, CH=N) ppm.

NMR $^{13}$C-{$^1$H} (CDCl$_3$): δ=32.9 (broad s, CH$_3$—N—P$_1$); 32.9 (broad s, C$\underline{H}_2$—CH$_2$—N) 49.3 (dd, $^1J_{CP}$=157.6 Hz, $^3J_{CP}$=6.7 Hz, —C$\underline{H}_2$—P(O)(OCH$_3$)$_2$); 52.6 (d, $^2J_{CP}$=4.1 Hz, —P(O)(O—C$\underline{H}_3$)$_2$); 58.1 (t, $^3J_{CP}$=7.8 Hz, CH$_2$—C$\underline{H}_2$—N); 121.2 (s, C$_0^2$); 121.2 (d, $^3J_{CP}$=3.6 Hz, C$_1^2$); 128.2 (s, C$_0^3$); 129.9 (s, C$_1^3$); 131.7 (s, C$_0^4$); 136.6 (s, C$_1^4$); 138.9 (d, $^3J_{CP}$=16.0 Hz, CH=N); 148.9 (d, $^2J_{CP}$=6.1 Hz, C$_1^1$); 151.8 (broad s, C$_0^1$) ppm.

Example 76

Synthesis of a Dendrimer with a Cyclotetraphosphazene Core and with an Aza-Bis-Phosphonic Surface Derived from Tyramine Bromotrimethylsilane (5.82 mmol, 777 μl) is added slowly to a solution of first-generation dendrimer with aza-bis-dimethyl-phosphonate ends derived from tyramine and with a cyclotetraphosphazene core obtained in Example 75 (8.27·10$^{-2}$ mmol, 570 mg) at 0° C. in acetonitrile (5 mL). Once the addition is finished the mixture is allowed to return to room temperature over 12 hours. The mixture is then evaporated to dryness then 1 ml of anhydrous methanol is added at room temperature and the mixture is left for one hour under stirring. The product is then evaporated to dryness and the same operation is carried out with 1 mL of water. After freeze-drying, the residue is washed several times with ether. As the product is totally insoluble in organic solvents it is converted to its monosodium salt in the presence of a solution of titrated sodium hydroxide. The resulting solution is lyophilized in order to produce the dendrimer in the form of a white powder. The final product is isolated with a yield of 52%.

NMR $^{31}$P-{$^1$H} (CD$_3$CN/D$_2$O): δ=67.7 (s, P$_1$); 10.1 (broad s, P(O)(OH)(ONa)); 8.7 (broad s, P(O)(OH)(ONa)); −9.5 (s, P$_0$) ppm.

NMR $^1$H (CD$_3$CN/D$_2$O): δ=2.5-4.2 (m, 152H, CH$_2$—C$\underline{H}_2$—N, C$\underline{H}_2$—CH$_2$—N, —C$\underline{H}_2$—P(O)(OH)(ONa), CH$_3$—N—P$_1$)); 4.84 (broad s, 32H, —P(O)(OH)(ONa)); 6.7-8.1 (m, 104H, CH$_{arom}$, CH=N) ppm.

NMR $^{13}$C-{$^1$H} (CD$_3$CN/D$_2$O): δ=31.4 (broad s, C$\underline{H}_2$—CH$_2$—N); 35.1 (broad s, CH$_3$—N—P$_1$); 55.5 (d, $^1J_{CP}$=169.2 Hz, —C$\underline{H}_2$—P(O)(OH)(ONa)); 59.9 (broad s, CH$_2$—C$\underline{H}_2$—N); 121.6 (broad s, C$_0^2$, C$_1^2$); 123.9 (broad s, C$_1^3$); 130.8 (broad s, C$_0^3$); 133.2 (broad s, C$_1^4$); 136.8 (broad s, C$_0^4$); 142.7 (broad s, CH=N); 151.7 (broad s, C$_1^1$); 153.8 (broad s, C$_0^1$) ppm.

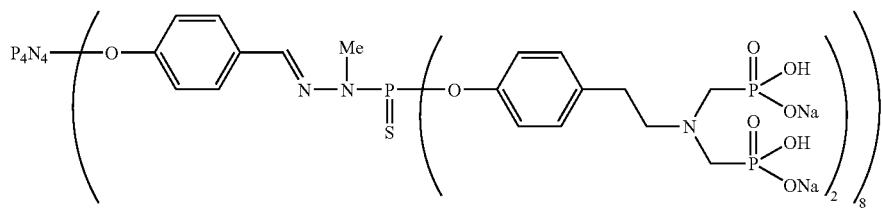

Example 77
Synthesis of 6-2-5-2-Type Dendrimer with a Dichlorothiophosphorhydrazide Surface
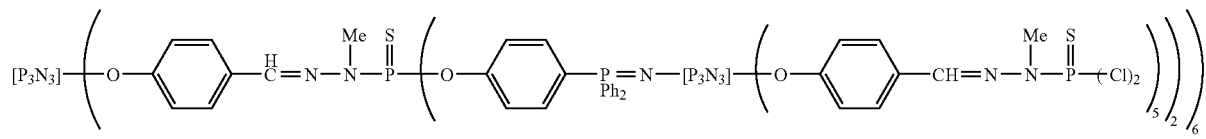
The 6-2-5, 6-5-2, 6-5-5 type hyperdense dendrimers used and defined below have been described in V. Maraval et al. *Angew. Chem. Int. Ed.* (2003) 42, 1822.

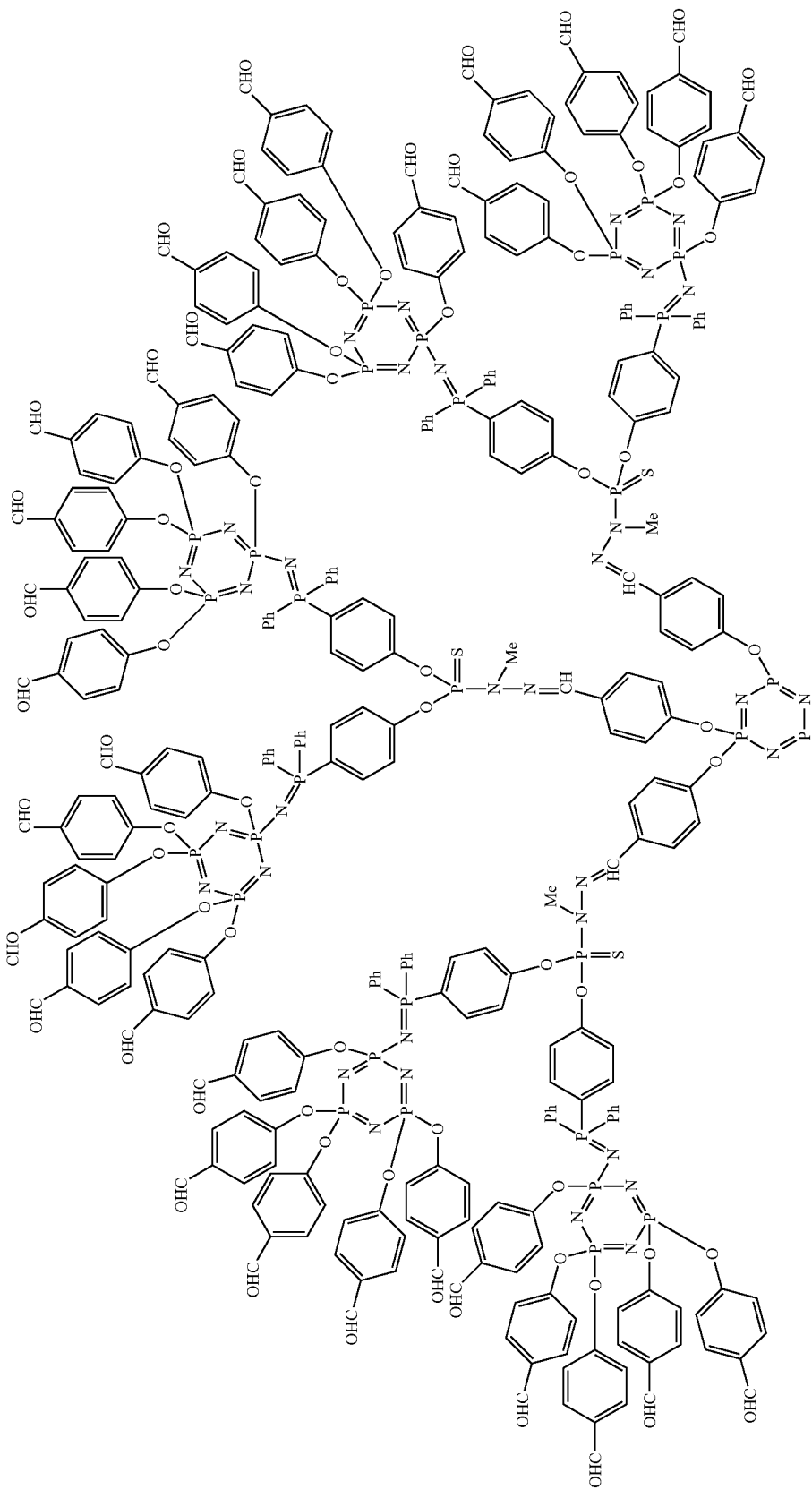

-continued
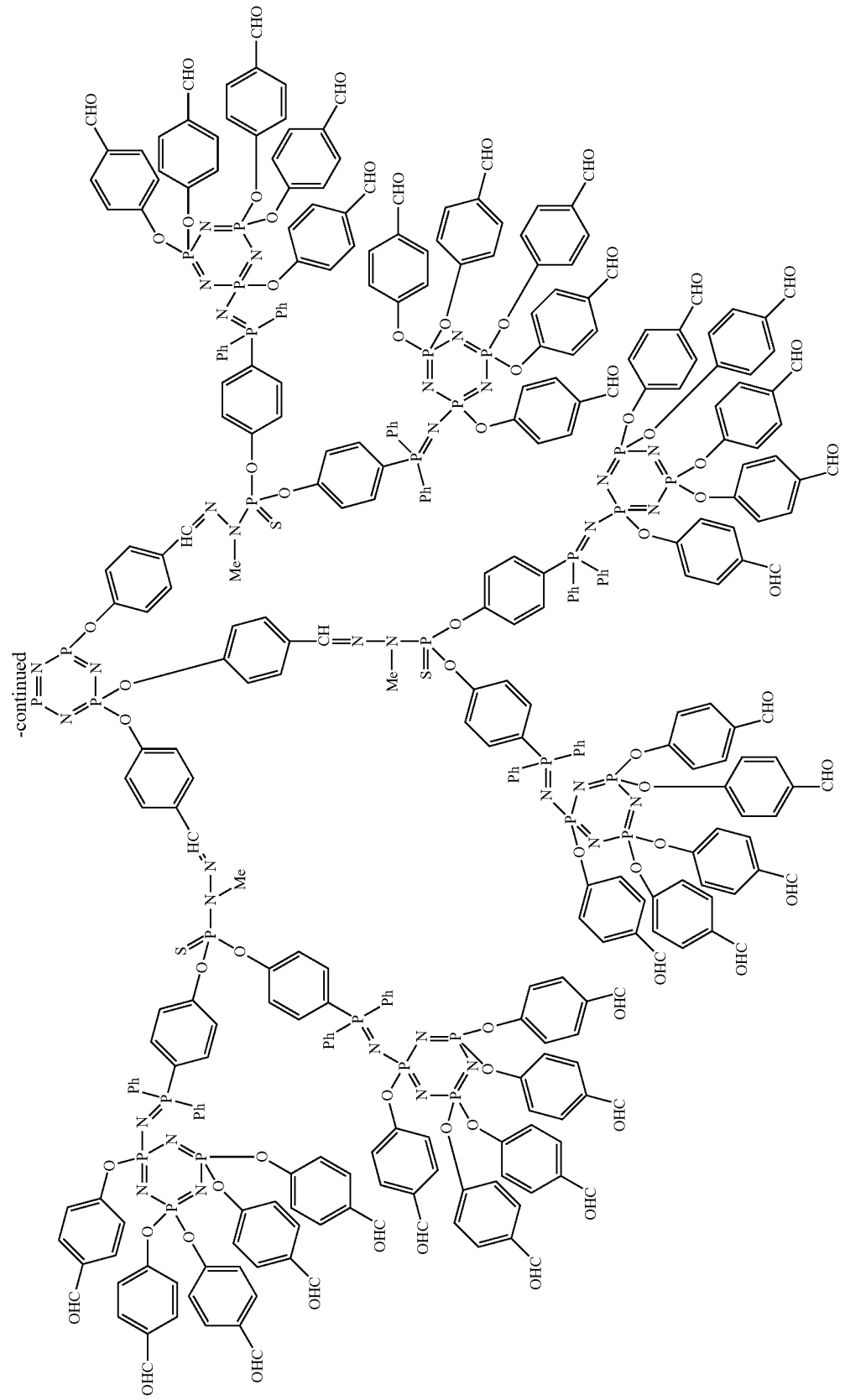

-continued
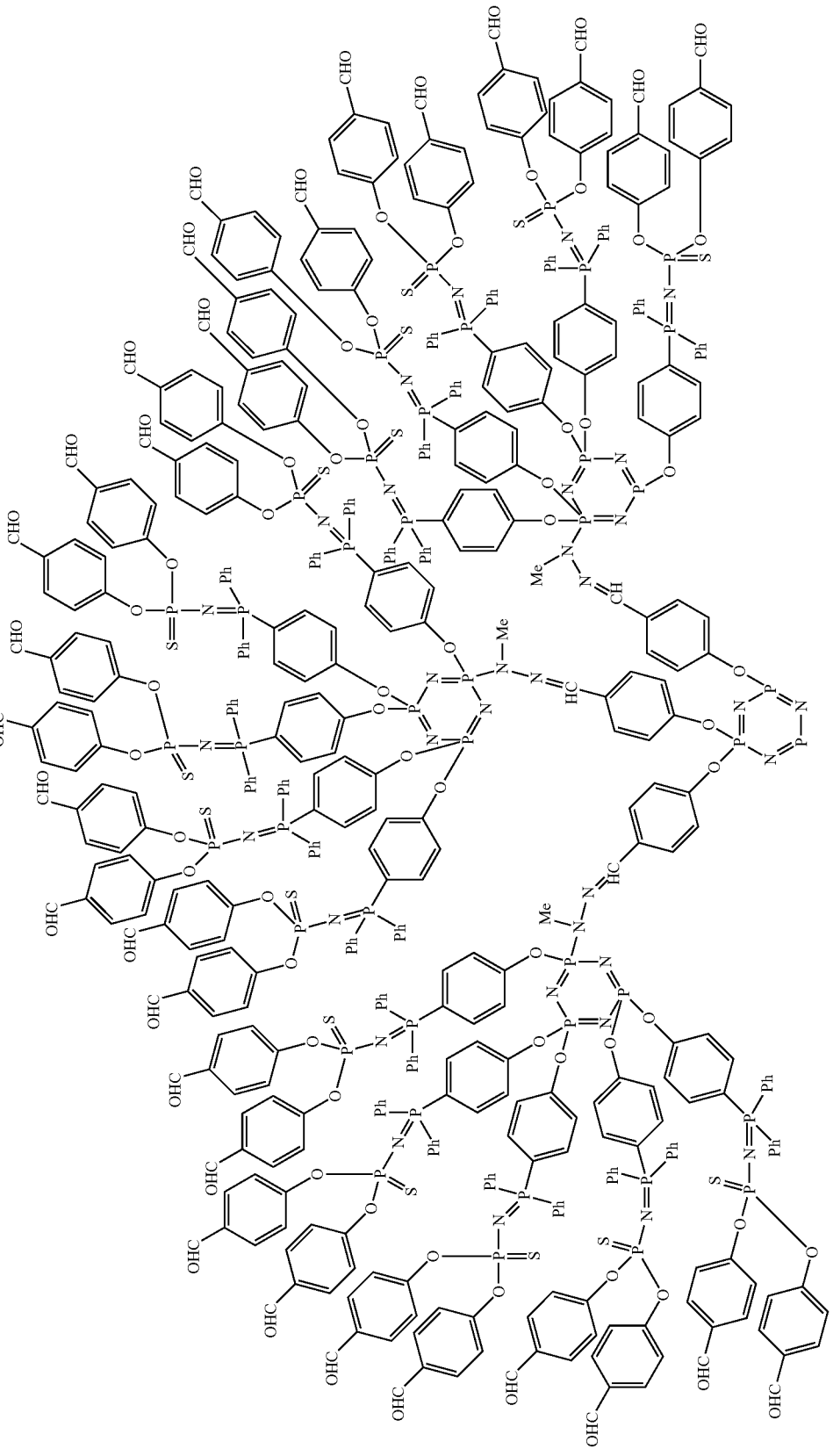

-continued
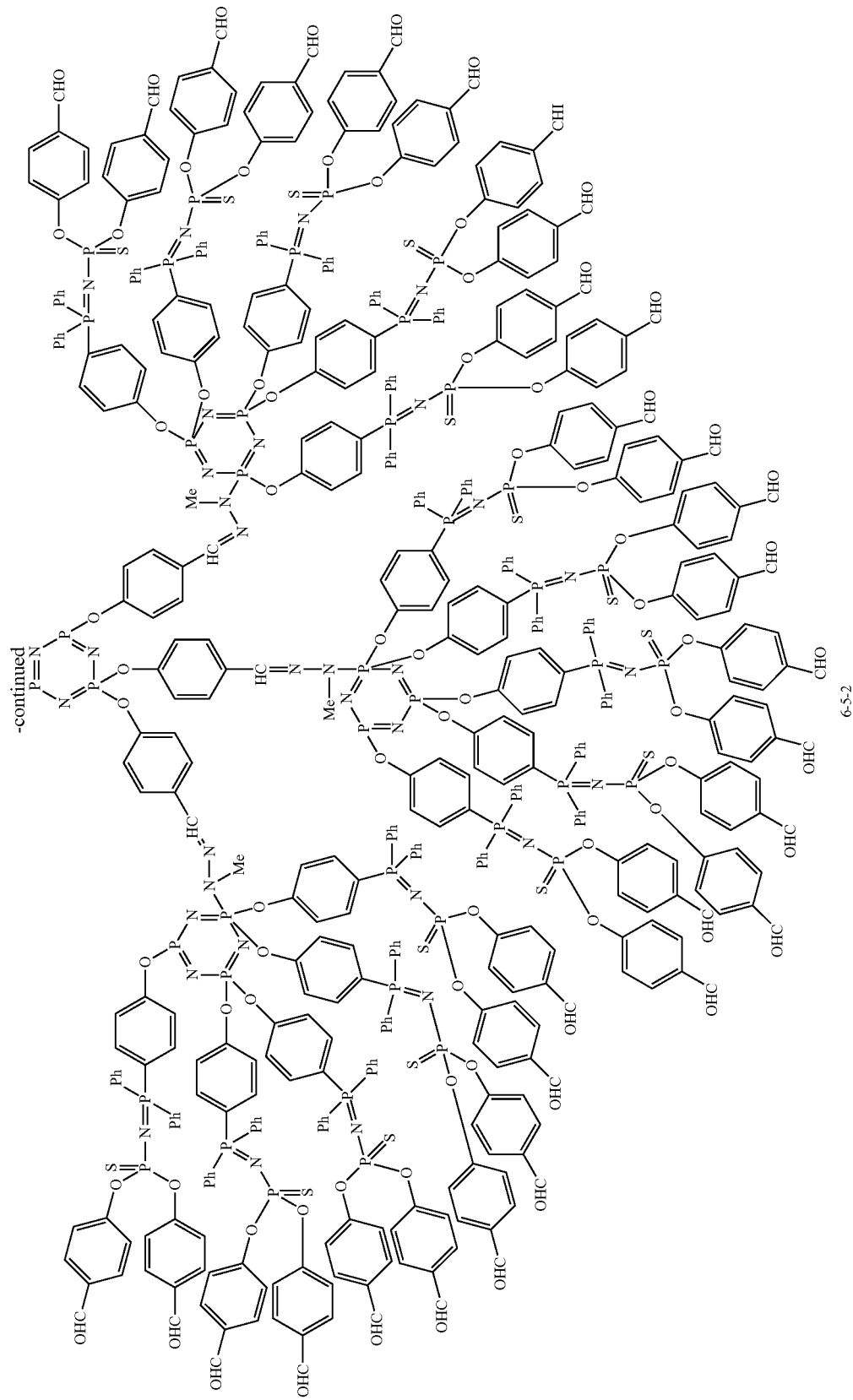

-continued
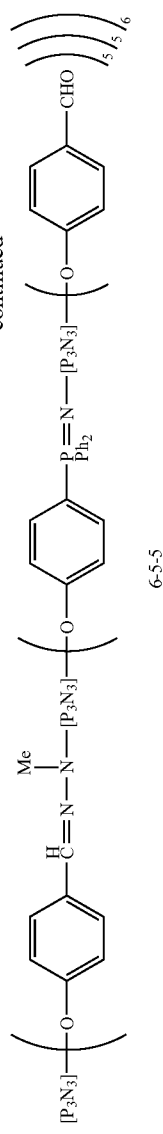
6-5-5
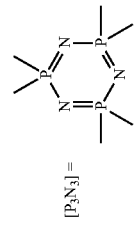
[P₃N₃] =

A slight excess (1.1 equivalents per aldehyde function) of a solution of N-methyl-dichlorothiophosphorhydrazide at 0.2 M in chloroform is added at −30° C. to a solution of 6-2-5 type dendrimer with aldehyde ends (250 mg, 18.1·10$^{-3}$ mmol) in 2 mL of chloroform. After stirring for 5 to 60 minutes at a temperature comprised between −30 and 0° C. the mixture is filtered on celite then precipitated by addition of pentane. The powder obtained is dissolved in the minimum amount of THF then precipitated with pentane and finally dried in order to be isolated with a final yield of 92%.

Example 78

Synthesis of the 6-2-5-2-Type Dendrimer with an Aza-Bis-Dimethyl-Phosphonate Surface Derived from Tyramine

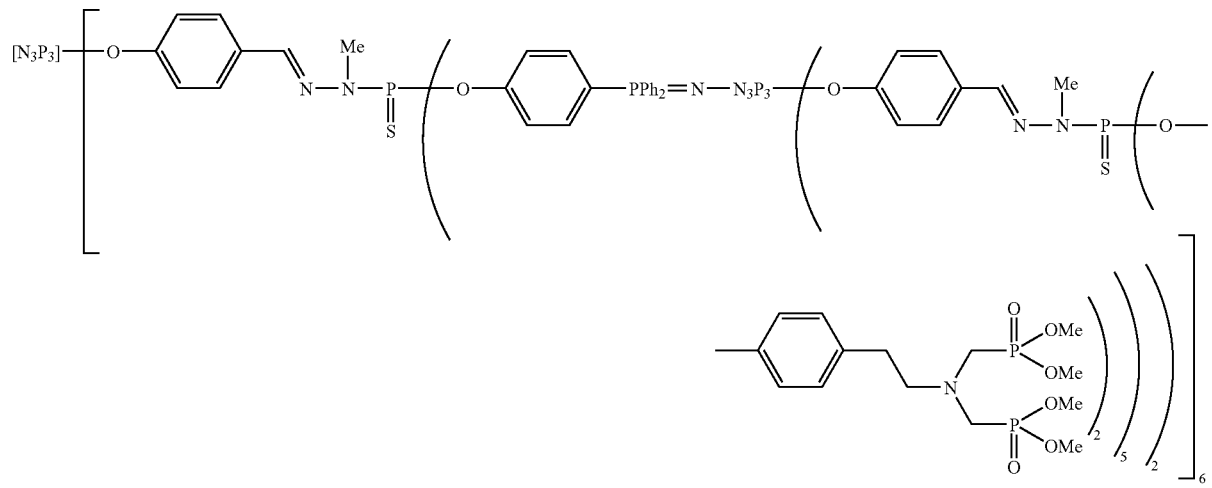

Cesium carbonate (1.019 mmol, 0.332 g) is added to a solution of 6-2-5-2-type dendrimer (200 mg, 8.5·10$^{-3}$ mmol) with a dichlorothiophosphorhydrazide surface obtained in Example 31 in THF (2 mL) then phenol aza-bis-dimethyl-phosphonate derived from tyramine is added (0.510 mmol, 195 mg). The mixture is left under stirring for 24 hours at room temperature then the final mixture is filtered on celite in order to separate the salts. Finally the final product is washed by precipitation in pentane and isolated with a yield of 85%.

Example 79

Synthesis of the 6-2-5-2-Type Dendrimer with an Aza-Bis-Dimethyl-Phosphonic Surface Derived from Tyramine

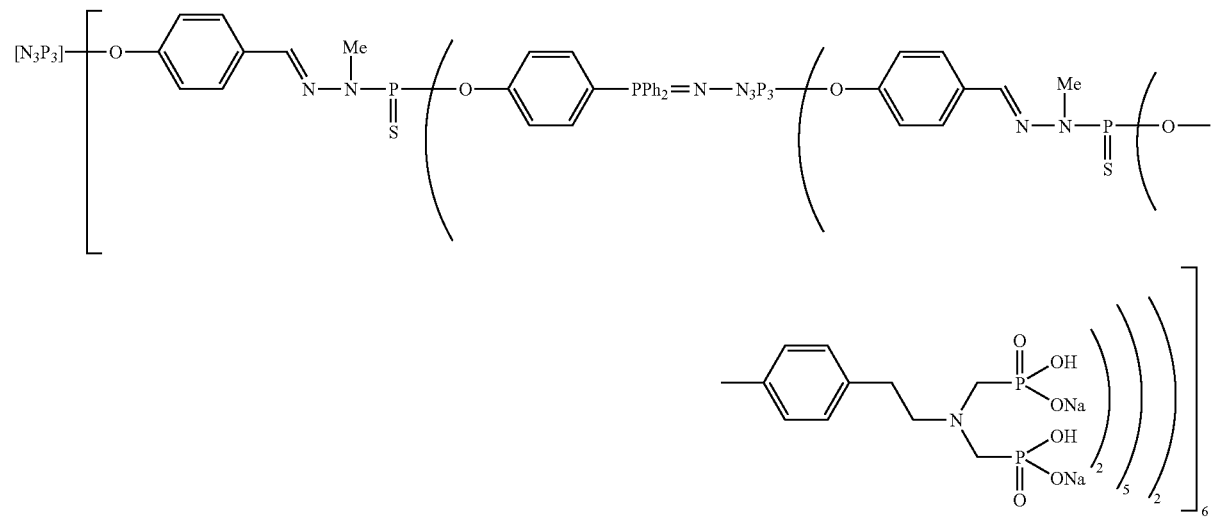

Bromotrimethylsilane (1.1 equivalents per methoxy group) is slowly added to a solution of 6-2-5-2-type dendrimer (200 mg, 3.08·10⁻³ mmol) with an aza-bis-dimethyl-phosphonate surface derived from the tyramine obtained in Example 78 at 0° C. in acetonitrile (5 mL). Once the addition is finished the mixture is allowed to return to room temperature over 12 hours. The mixture is then evaporated to dryness then 1 mL of anhydrous methanol is added at room temperature and the mixture is left for one hour under stirring. After evaporation to dryness, the residue is washed several times with pure ether. The product is then converted to its monosodium salt in the presence of soda (1 equivalent of NaOH per phosphonic acid termination). The resulting solution is lyophilized in order to produce the dendrimer in the form of a white powder. The final product is isolated with a yield of 52%.

Example 80

Synthesis of the 6-5-2-2-Type Dendrimer with a Dichlorothiophosphorhydrazide Surface

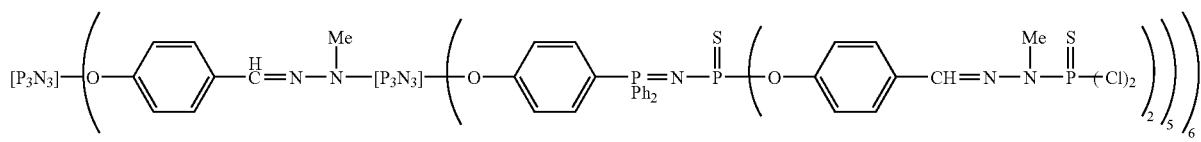

A slight excess (1.1 equivalents per aldehyde function) of a 0.2 M solution of N-methyl-dichlorothiophosphorhydrazide in chloroform is added at −30° C. to a solution of 6-5-2-type dendrimer (250 mg) in 2 mL of chloroform. After stirring for 5 to 60 minutes at a temperature comprised between −30 and 0° C. the mixture is filtered on celite then precipitated by addition of pentane. The powder obtained is dissolved in the minimum amount of THF then precipitated with pentane and finally dried in order to be isolated with a final yield of 90%.

Example 81

Synthesis of the 6-5-2-2-Type Dendrimer with an Aza-Bis-Dimethyl-Phosphonate Surface Derived from Tyramine

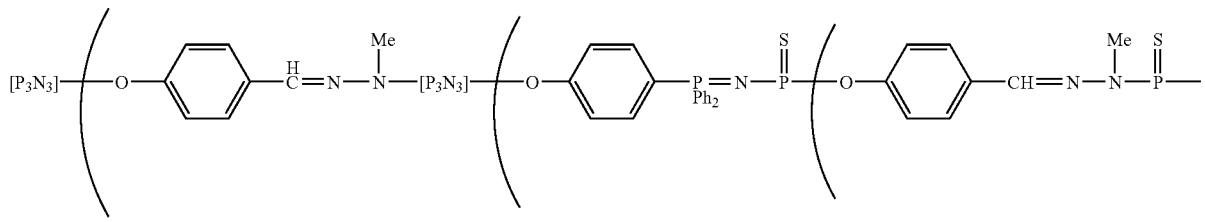

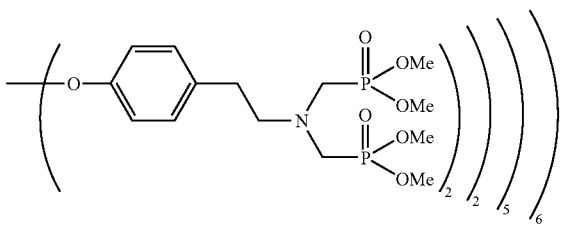

Cesium carbonate (2.05 equivalents per terminal chlorine) is added to a solution of 6-5-2-2-type dendrimer (200 mg) with a dichlorothiophosphorhydrazide surface in THF (2 mL) then the phenol aza-bis-dimethyl-phosphonate derived from the tyramine obtained in Example 31 is added (1.03 equivalents per chlorine terminal). The mixture is left under stirring for 24 hours at room temperature then the final mixture is filtered on celite in order to separate the salts. Finally the final product is washed by precipitation in pentane and isolated with a yield of 88%.

Example 82

Synthesis of the 6-5-2-2-Type Dendrimer with an Aza-Bis-Dimethyl-Phosphonic Surface Derived from Tyramine

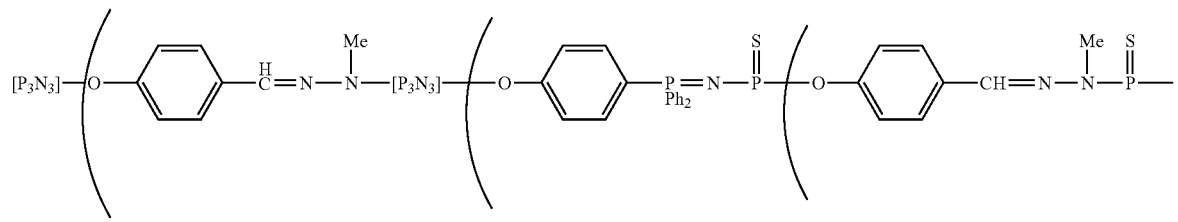

Bromotrimethylsilane (1.1 equivalents per methoxy group) is slowly added to a solution of 6-5-2-2-type dendrimer (200 mg) with an aza-bis-dimethyl-phosphonate surface derived from the tyramine obtained in Example 81 at 0° C. in acetonitrile (5 mL). Once the addition is finished the mixture is allowed to return to room temperature over 12 hours. The mixture is then evaporated to dryness then 1 mL of anhydrous methanol is added at room temperature and the mixture is left for one hour under stirring. After evaporation to dryness, the residue is washed several times with pure ether. The product is then converted to its monosodium salt in the presence of soda (1 equivalent of NaOH per phosphonic acid termination). The resulting solution is lyophilized in order to produce the dendrimer in the form of a white powder. The final product is isolated with a yield of 61%.

Example 83

Synthesis of the 6-5-5-2-Type Dendrimer with a Dichlorothiophosphorhydrazide Surface

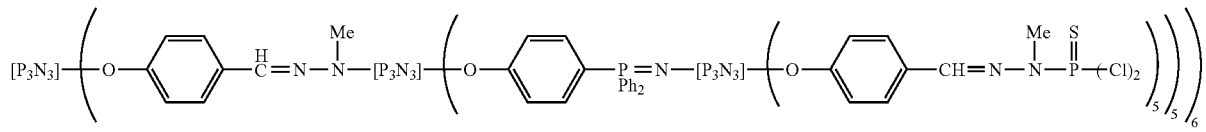

2A slight excess (1.1 equivalents per aldehyde function) of a 0.2 M solution of N-methyl-dichlorothiophosphorhydrazide in chloroform is added at −30° C. to a solution of 6-5-5-type dendrimer (250 mg) in 2 mL of chloroform. After stirring for 5 to 60 minutes at a temperature comprised between −30 and 0° C. the mixture is filtered on celite then precipitated by addition of pentane. The powder obtained is dissolved in the minimum amount of THF then precipitated with pentane and finally dried in order to be isolated with a final yield of 93%.

Example 84

Synthesis of the 6-5-5-2-Type Dendrimer with an Aza-Bis-Dimethyl-Phosphonate Surface Derived from Tyramine

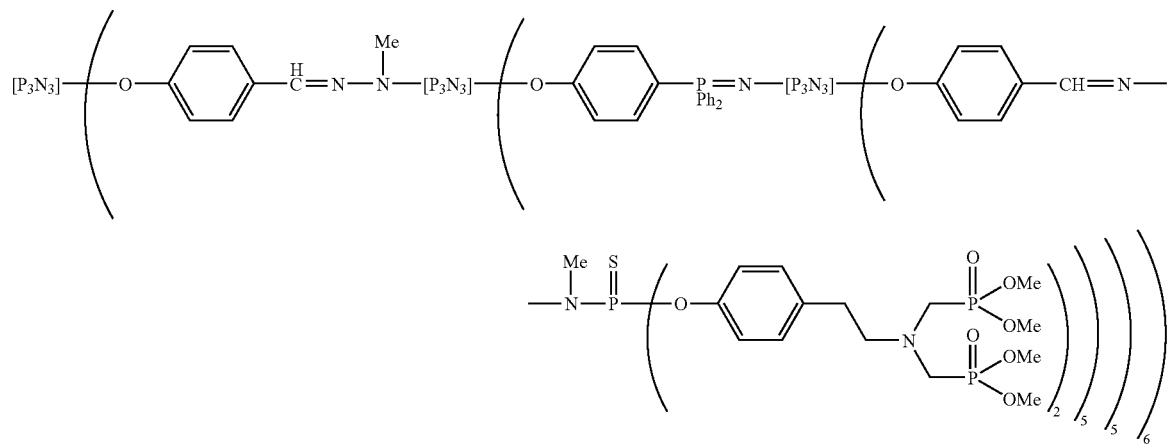

Cesium carbonate (2.05 equivalents per chlorine terminal) is added to a solution of 6-5-5-2-type dendrimer (250 mg) with a dichlorothiophosphorhydrazide surface in THF (2 mL) then phenol aza-bis-dimethyl-phosphonate derived from the tyramine obtained in Example 31 is added (1.03 equivalents per terminal chlorine). The mixture is left under stirring for 24 hours at room temperature then the final mixture is filtered on celite in order to separate the salts. Finally the final product is washed by precipitation in pentane and isolated with a yield of 83%.

Example 85

Synthesis of the 6-5-5-2-Type Dendrimer with an Aza-Bis-Dimethyl-Phosphonic Surface Derived from Tyramine

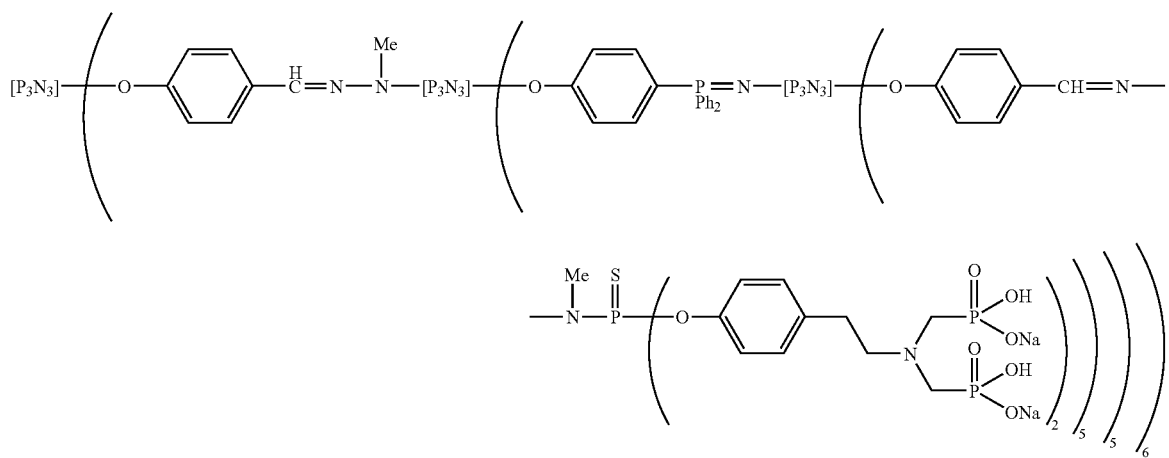

Bromotrimethylsilane (1.1 equivalents per methoxy group) is added slowly to a solution of 6-5-5-2-type dendrimer (250 mg) with an aza-bis-dimethyl-phosphonate surface derived from the tyramine obtained in Example 84 at 0° C. in acetonitrile (5 mL). Once the addition is finished the mixture is allowed to return to room temperature over 12 hours. The mixture is then evaporated to dryness then 1 mL of anhydrous methanol is added at room temperature and the mixture is left for one hour under stirring. After evaporation to dryness, the residue is washed several times with pure ether. The product is then converted to its monosodium salt in the presence of soda (1 equivalent of NaOH per phosphonic acid termination). The resulting solution is lyophilized in order to produce the dendrimer in the form of a white powder. The final product is isolated with a yield of 66%.

Example 86

Synthesis of a Hyperdense Dendrimer with an $N_3P_3$ Core and Carrying 30 Aza-Bis-Phosphonic Acid Ends Derived from Tyramine Stage 1: Synthesis of Hexa(N-Methylhydrazino) Cyclotriphosphazene

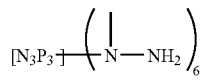

This molecule has been described by J. P. Majoral et al. in *Angew. Chem. Int. Ed. Engl.* 1993, 32, 1477 and *Inorg. Chem.* 1994, 33, 6351.

Stage 2: Synthesis of Pentachloro-(4-Formylphenoxy)Cyclotriphosphazene

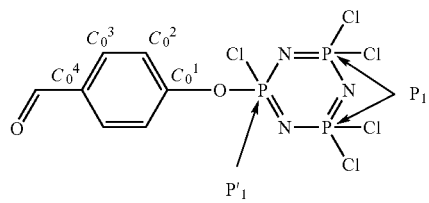

500 mg of 4-hydroxybenzaldehyde sodium salt (3.47 mmol) is added at 0° C. and under an inert atmosphere to a solution containing 4.8 g of hexachlorocyclotriphosphazene (13.8 mmol) in THF (200 mL). The reaction medium is stirred for 12 hours while the temperature is left to gradually return to room temperature. The crude reaction product is evaporated to dryness then purified by "flash" chromatography on a silica column. The product is isolated in the form of a translucent oil with a yield of 75%.

NMR $^{31}P\{^1H\}$ (CDCl$_3$, 81 MHz): $\delta$=15.2 (t, $^2J_{PP}$=62.0 Hz, P$_1$); 26.0 (d, $^2J_{PP}$=62.0 Hz, P$_1$) ppm.

NMR (CDCl$_3$): $\delta$=7.43 (d, $^3J_{HH}$=7.5 Hz, 2H, $C_0^2$—H); 7.95 (d, $^3J_{HH}$=7.5 Hz, 2H, $C_0^3$—H); 10.00 (s, 1H, CHO) ppm.

Stage 3: Synthesis of the Dendrimer Carrying 30 Chlorinated Ends

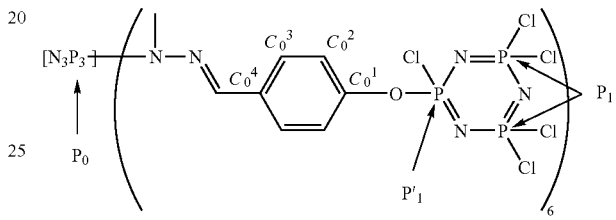

61 mg of hexa(N-methylhydrazino)cyclotriphosphazene (0.15 mmol) is added at room temperature to a solution containing 655 mg of pentachloro-(4-formylphenoxy)cyclotriphosphazene (1.51 mmol) in chloroform (10 mL). The reaction mixture is stirred for two and a half hours. The crude reaction product is evaporated to dryness then purified by "flash" chromatography on a silica column. The product is isolated in the form of a white solid with a yield of 97%.

NMR $^{31}P\{^1H\}$ (CDCl$_3$, 81 MHz): $\delta$=15.6 (t, $^2J_{PP}$=60.0 Hz, P'$_1$); 21.7 (s, P$_0$); 26.0 (d, $^2J_{PP}$=60.0 Hz, P$_1$) ppm.

NMR $^1H$ (CDCl$_3$, 200.13 MHz): $\delta$=3.31 (s, 18H, CH$_3$—N); 7.17 (d, $^3J_{HH}$=7.8 Hz, 12H, $C_0^2$—H); 7.52 (s, 6H, CH=N); 7.62 (d, $^3J_{HH}$=8.3 Hz, 12H, $C_0^3$—H) ppm.

NMR $^{13}C\{^1H\}$ (CDCl$_3$, 50.32 MHz): $\delta$=32.4 (s, CH$_3$—N); 121.4 (d, $^3J_{CP}$=5.2 Hz, $C_0^2$); 127.9 (d, $^4J_{CP}$=1.2 Hz, $C_0^3$); 134.7 (dl, $^4J_{CP}$=2.3 Hz, $C_0^4$); 135.2 (bs, CH=N); 149.0 (d, $^2J_{CP}$=10.2 Hz, $C_0^1$) ppm.

Stage 4: Synthesis of the Dendrimer with Phenol Aza-Bis-Dimethyl-Phosphonate Ends Derived from Tyramine

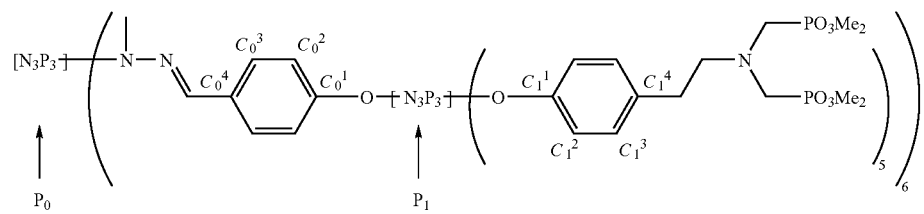

150 mg of the dendrimer carrying 30 chlorinated ends (0.05 mmol), then 1.11 g of cesium carbonate (3.42 mmol) are added at room temperature to a solution of 597 mg of phenol aza-bis-dimethyl-phosphonate derived from the tyramine obtained in Example 31 (1.55 mmol) in THF (8 mL). The reaction medium is stirred for 12 hours. The cesium salts are removed by dilution (20 mL of THF) and centrifugation of the crude reaction product. THF/pentane washings make it possible to isolate the product in the form of an oil with a yield of 70%.

NMR $^{31}P\{^1H\}$ (acetone $d_6$, 81 MHz): δ=12.9 (bs, $P_1$); 20.7 (s, $P_0$); 30.2 (s, $PO_3Me_2$); 30.3 (s, $PO_3Me_2$) ppm.

NMR $^1H$ (acetone $d_6$, 500.33 MHz): δ=2.79 (deformed t, $^3J_{HH}$=6.5 Hz, 24H, $\underline{CH_2}$—$CH_2$—N); 2.87 (deformed t, $^3J_{HH}$=6.5 Hz, 36H, $\underline{CH_2}$—$CH_2$—N); 3.07 (deformed t, $^3J_{HH}$=6.5 Hz, 24H, $CH_2$—$\underline{CH_2}$—N); 3.10 (deformed t, $^3J_{HH}$=6.5 Hz, 36H, $CH_2$—$\underline{CH_2}$—N); 3.22 (d, $^2J_{HP}$=9.7 Hz, 48H, N—$CH_2$—P); 3.27 (d, $^2J_{HP}$=9.7 Hz, 72H, N—$CH_2$—P); 3.44 (bs, 18H, $CH_3$—N); 3.68 (d, $^3J_{HP}$=10.4 Hz, 144H, $P(O)(OCH_3)$); 3.72 (d, $^3J_{HP}$=10.4 Hz, 72H, $P(O)(OCH_3)$); 3.73 (d, $^3J_{HP}$=10.4 Hz, 144H, $P(O)(OCH_3)$); 6.85 (d, $^3J_{HH}$=8.1 Hz, 24H, $C_1^2$—H); 6.89 (d, $^3J_{HH}$=8.1 Hz, 12H, $C_1^2$—H); 6.90 (d, $^3J_{HH}$=8.1 Hz, 24H, $C_1^2$—H); 7.01 (d, $^3J_{HH}$=8.1 Hz, 12H, $C_0^2$—H); 7.20 (d, $^3J_{HH}$=8.1 Hz, 24H, $C_1^3$—H); 7.24 (d, $^3J_{HH}$=8.1 Hz, 36H, $C_1^3$—H); 7.67 (d, $^3J_{HH}$=8.1 Hz, 12H, $C_0^3$—H); 7.84 (bs, 6H, CH=N) ppm.

NMR $^{13}C\{^1H\}$ (acetone $d_6$, 125.81 MHz): δ=32.3 (bs, $CH_3$—N, $\underline{CH_2}$—$CH_2$—N); 49.1 (dd, $^1J_{CP}$=156.0 Hz, $^3J_{CP}$=7.6 Hz, N—$CH_2$—P); 52.0 (s, $P(O)(OCH_3)$); 58.2 (m, $CH_2$—$\underline{CH_2}$—N); 58.3 (m, $CH_2$—$\underline{CH_2}$—N); 120.6 (s, $C_1^2$); 120.7 (s, $C_1^2$); 120.9 (bs, $C_0^2$); 127.6 (s, $C_0^3$); 130.0 (s, $C_1^3$); 133.7 (s, $C_0^4$); 136.1 (bs, CH=N); 136.9 (s, $C_1^4$); 137.0 (s, $C_1^4$); 149.0 (bs, $C_1^1$); 150.7 (d, $^2J_{CP}$=10.2 Hz, $C_0^1$) ppm.

Stage 5: Synthesis of the Dendrimer with Aza-Bisphosphonic Acid Sodium Salt Ends Derived from Tyramine

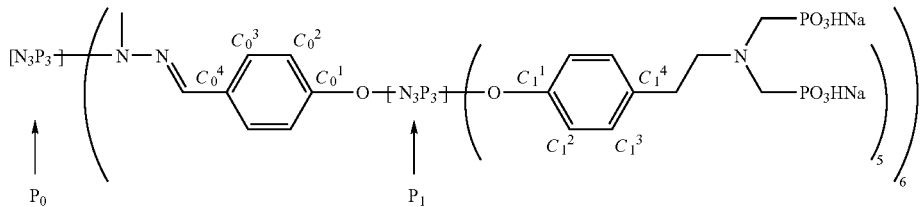

132 μl of bromotrimethylsilane (0.997 mmol) is slowly added to a solution containing 100 mg of the dendrimer carrying 30 aza-bisphosphonic acid ends derived from tyramine (0.008 mmol) in 3 mL of acetonitrile at 0° C. under an inert atmosphere. At the end of the addition, the reaction medium is stirred at room temperature for 12 hours. The reaction medium is then evaporated to dryness then 2.5 mL of methanol are added at room temperature. The reaction medium is stirred for 1 hour then evaporated to dryness. This methanolysis operation is repeated a second time then the product is washed several times with diethyl ether.

The resulting product, for the purposes of NMR analysis, is then converted to its sodium salt. The product is firstly introduced into water (1 mL) then 2.30 mL of aqueous soda are added (0.1966 N). After total dissolution of the dendrimer, the solution is freeze-dried, which allows the dendrimer to be obtained in the form of a white powder with a yield of 70%.

NMR $^{31}P\{^1H\}$ ($D_2O/CD_3CN$, 81 MHz): δ=10.7 (s, P(O)(OH)(ONa)); 12.5 (bs, $P_1$); 20.9 (s, $P_0$) ppm.

Example 87

Synthesis of a Hyperdense Dendrimer with an $N_3P_3$ Core and Carrying 30 Alpha-Hydroxy-Phosphonic Acid Ends Stage 1: Synthesis of the Dendrimer with Aldehyde Ends

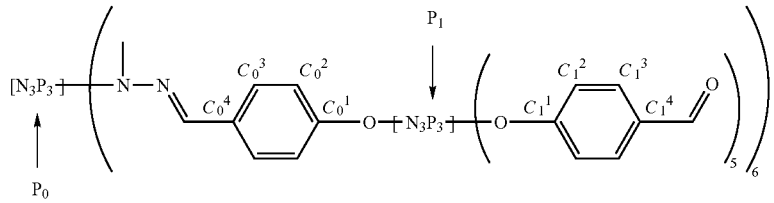

300 mg of 4-hydroxybenzaldehyde sodium salt (2.1 mmol) is added at room temperature to a solution containing 200 mg of dendrimer carrying 30 chlorinated ends obtained in Stage 3 of Example 86 (0.07 mmol) in THF (8 mL). The reaction medium is stirred for 12 hours. The sodium salts are removed by dilution and centrifugation of the crude reaction product. Acetone/pentane washings make it possible to isolate the product in the form of an off-white solid with a yield of 70%.

NMR $^{31}P\{^1H\}$ (acetone $d_6$, 81 MHz): δ=11.7 (broad s, $P_1$); 21.3 (s, $P_0$) ppm.

NMR $^1H$ (acetone $d_6$, 500.33 MHz): δ=3.51 (s, 18H, $CH_3$—N); 6.91 (d, $^3J_{HH}$=8.4 Hz, 12H, $C_0^2$—H); 7.13 (d, $^3J_{HH}$=8.6 Hz, 24H, $C_1^2$—H); 7.21 (d, $^3J_{HH}$=8.6 Hz, 12H, $C_1^2$—H); 7.23 (d, $^3J_{HH}$=8.6 Hz, 24H, $C_1^2$—H); 7.53 (d, $^3J_{HH}$=8.4 Hz, 12H, $C_0^3$—H); 7.75 (s, 6H, CH=N); 7.76 (d, $^3J_{HH}$=8.6 Hz, 24H, $C_1^3$—H); 7.80 (d, $^3J_{HH}$=8.6 Hz, 12H, $C_1^3$—H); 7.81 (d, $^3J_{HH}$=8.6 Hz, 24H, $C_1^3$—H); 9.94 (s, 6H, CHO); 9.96 (s, 24H, CHO) ppm.

NMR $^{13}$C{$^1$H} (acetone d$_6$, 125.81 MHz): δ=32.2 (m, CH$_3$—N); 120.9 (bs, C$_0^2$); 121.2 (s, C$_1^2$); 121.3 (s, C$_1^2$); 121.4 (s, C$_1^2$); 127.6 (s, C$_0^3$); 131.3 (s, C$_1^3$); 131.4 (s, C$_1^3$); 134.0 (s, C$_1^4$); 134.1 (s, C$_1^4$); 134.2 (s, C$_0^4$); 135.7 (m, CH=N); 149.6 (m, C$_0^1$); 154.3 (m, C$_1^1$); 154.4 (m, C$_1^1$); 154.5 (m, C$_1^1$); 190.6 (s, CHO); 190.9 (s, CHO) ppm.

Stage 2: Synthesis of the Dendrimer with Dimethyl α-Hydroxyphosphonate Ends

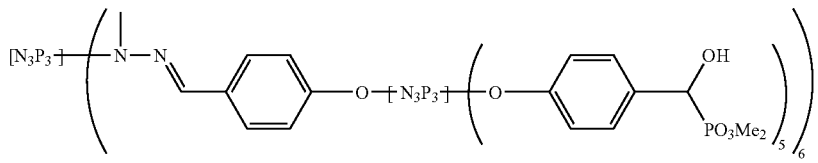

111 μmL of dimethylphosphite (1.21 mmol) then one drop of triethylamine are added at room temperature to a solution containing 200 mg of the dendrimer carrying 30 benzaldehyde ends (0.037 mmol) in THF (1 mL). The reaction medium is stirred for 12 hours. The reaction medium which has become viscous is then washed with diethyl ether, which makes it possible to isolate the product in the form of a white solid with a yield of 70%.

NMR $^{31}$P{$^1$H} (DMSO d$_6$, 81 MHz): δ=11.8 (s, P$_1$); 20.6 (s, P$_0$); 27.2 (s, P(O)(OCH$_3$)$_2$) ppm.

NMR $^1$H (DMSO d$_6$, 500.33 MHz): δ=2.21 (m, 18H, CH$_3$—N); 3.45-3.68 (m, 180H, P(O)(OCH$_3$)); 5.03 (m, 30H, P—CH); 6.31 (broad d, $^3J_{HP}$=14.6 Hz, 30H, CH-OH); 6.91 (m, 72H, C$_0^2$—H, C$_1^2$—H); 7.35 (m, 60H, C$_1^3$—H); 7.54 (m, 12H, C$_0^3$—H); 7.73 (broad s, 6H, CH=N) ppm.

Stage 3: Synthesis of the Dendrimer with α-Hydroxyphosphonic Acid Sodium Salt Ends

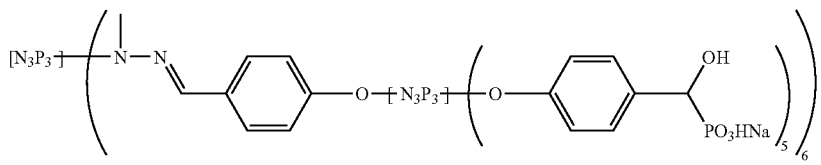

99 μl of bromotrimethylsilane (0.753 mmol) is added slowly to a solution of 3 mL of acetonitrile at 0° C. under an inert atmosphere containing 100 mg of the dendrimer carrying 30 dimethyl α-hydroxyphosphonate ends (0.011 mmol). At the end of the addition, the reaction medium is stirred at room temperature for 12 hours. The reaction medium is then evaporated to dryness then 2.5 mL of methanol are added at room temperature. The reaction medium is stirred for 1 hour then evaporated to dryness. This methanolysis operation is repeated a second time then the product is washed several times with diethyl ether.

The resulting product, for NMR analysis purposes, is then converted to its sodium salt. The product is firstly introduced into water (1 mL) then 1.74 mL of aqueous soda is added (0.1966 N). After total dissolution of the dendrimer, the solution is freeze-dried, which makes it possible to obtain the dendrimer in the form of a white powder with a yield of 70%.

NMR $^{31}$P{$^1$H} (D$_2$O/CD$_3$CN, 81 MHz): δ=12.6 (bs, P$_1$); 19.7 (s, P$_0$); 20.1 (s, P(O)(OH)(ONa)) ppm.

Example 88

Synthesis of the First-Generation Dendrimer with an Aza-Bis-Dimethyl-Phosphonate Surface Derived from Tyramine and with a Fluorescent Core a. Synthesis of the Fluorescent Phenol Derived from Diphenyl-Maleic Anhydride

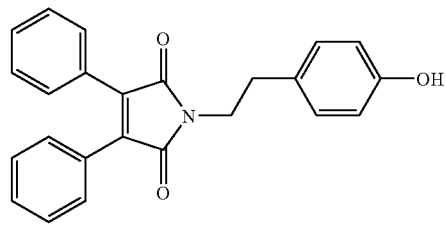 [SMILES: O=C1C(c2ccccc2)=C(c2ccccc2)C(=O)N1CCc1ccc(O)cc1]

Diphenyl-maleic anhydride (20 mmol, 5 g), tyramine (40 mmol, 5.48 g), N,N diisopropylethylamine (14 mmol, 32 ml), 50 g of phenol used as solvent, and 50 g of 4 Å molecular sieve are introduced into a 250 mL flask at room temperature. The mixture is taken to 150° C. for one and a half hours then cooled to room temperature. The product is then diluted in 1.2 l of dichloromethane, filtered on celite and washed with 1.6 l of 4% aqueous hydrochloric acid. The organic phase is dried with magnesium sulphate and concentrated. The phenol used as solvent is eliminated by sublimation at 70° C. Finally the product is purified by chromatography on silica gel using as eluent a gradient: chloroform then ether. The final product is isolated with a yield of 20%.

NMR $^1$H (CDCl$_3$): δ=2.93 (t, $^3J_{HH}$=7.8 Hz, 2H, CH$_2$—CH$_2$—N); 3.86 (t, $^3J_{HH}$=7.8 Hz, 2H, CH$_2$—CH$_2$—N); 5.38 (broad s, 1H, OH); 6.7-7.5 (m, 14H, CH$_{arom}$) ppm.

b. Synthesis of Cyclotriphosphazene Monosubstituted by the Fluorescent Phenol Derived from Diphenyl-Maleic Anhydride

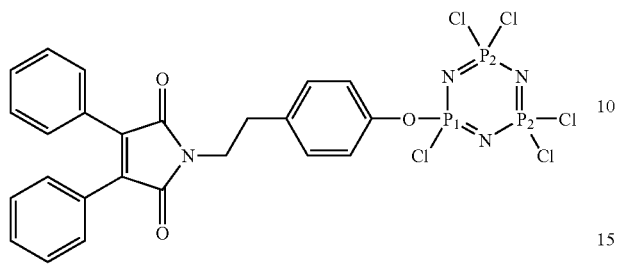

Hexachlorocyclotriphosphazene (0.403 mmol, 140 mg) is placed in solution in 20 mL of toluene at room temperature with triethylamine (0.54 mmol, 100 µl) and the fluorescent phenol (0.277 mmol, 100 mg) obtained in Stage a. The mixture is left under stirring at room temperature for 72 hours then filtered on celite and concentrated. Finally the product is purified by chromatography on silica gel. For this purpose a solvent gradient is used: firstly pure hexane then a hexane/ether mixture 1/1. The final product is isolated with a yield of 40%.

NMR $^{31}P-\{^{1}H\}$ (CDCl$_3$): δ=15.6 (t, P$_1$); 25.8 (d, P$_2$) ppm.

NMR $^{1}H$ (CDCl$_3$): δ=3.03 (t, $^3J_{HH}$=7.8 Hz, 2H, $\underline{CH_2}$—CH$_2$—N); 3.91 (t, $^3J_{HH}$=7.8 Hz, 2H, CH$_2$—$\underline{CH_2}$—N); 7.2-7.5 (m, 14H, CH$_{arom}$) ppm.

c. Synthesis of the Penta Aldehyde Core Monosubstituted by the Fluorescent Phenol Derived from Diphenyl-Maleic Anhydride

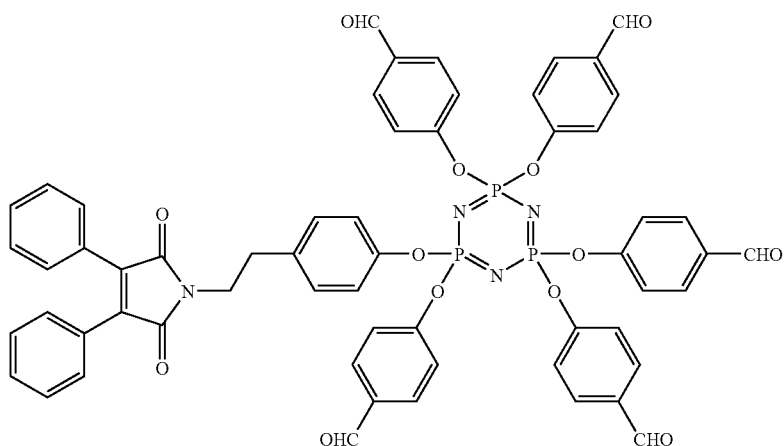 [SMILES: O=Cc1ccc(OP2(Oc3ccc(C=O)cc3)=NP(Oc3ccc(C=O)cc3)(Oc3ccc(C=O)cc3)=NP(Oc3ccc(C=O)cc3)(Oc3ccc(CCN4C(=O)C(c5ccccc5)=C(c5ccccc5)C4=O)cc3)=N2)cc1]

The cyclotriphosphazene mono-substituted by the fluorescent group, derived from diphenyl-maleic anhydride, (1.07 mmol, 730 mg) obtained during Stage b, is placed in solution in anhydrous THF (5 mL) with cesium carbonate (11.8 mmol, 3.85 g) and 4-hydroxy-benzaldehyde (5.57 mmol, 680 mg). The mixture is left under stirring for 12 hours at room temperature. The final product is placed in solution in a minimum amount of THF and washed by precipitation in pentane. It is isolated with a yield of 80%.

NMR $^{31}P-\{^{1}H\}$ (CDCl$_3$): δ=11.7 (s, P) ppm.

NMR $^{1}H$ (CDCl$_3$): δ=2.96 (t, $^3J_{HH}$=7.8 Hz, 2H, $\underline{CH_2}$—CH$_2$—N); 3.83 (t, $^3J_{HH}$=7.8 Hz, 2H, CH$_2$—$\underline{CH_2}$—N); 6.9-7.8 (m, 34H, CH$_{arom}$); 9.92 (s, 5H, CHO) ppm.

d. Synthesis of the First-Generation Dendrimer with a Dichlorothiophosphine Surface and a Fluorescent Core

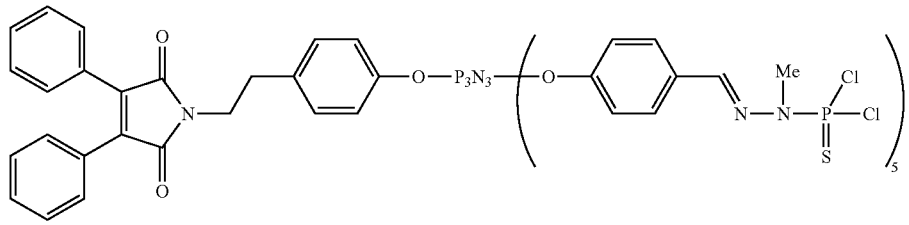

Hydrazino-dichloro-thiophosphine (7 mL, 0.24 mol·L$^{-1}$) in solution in chloroform is added at 0° C. to a penta-functional core carrying the fluorescent group, derived from the diphenyl-maleic anhydride, (0.279 mmol, 310 mg), obtained during Stage c, in powder. The mixture is left under magnetic stirring and at room temperature for 8 hours then evaporated. Finally the powder obtained is washed three times by precipitation in a dichloromethane pentane 1/5 mixture. The final product is isolated with a yield of 76%.

NMR $^{31}$P-{$^1$H} (CDCl$_3$): δ=66.00 (s, P$_1$); 65.91 (s, P$_1$); 11.9 (m, P$_0$) ppm.

NMR $^1$H (CDCl$_3$): δ=2.93 (t, $^3J_{HH}$=7.8 Hz, 2H, C$\underline{H_2}$—CH$_2$—N); 3.42 (d, $^3J_{HP}$=8.9 Hz, 9H, CH$_3$—N—P$_1$); 3.48 (d, $^3J_{HP}$=8.7 Hz, 6H, CH$_3$—N—P$_1$); 3.78 (t, $^3J_{HH}$=7.8 Hz, 2H, CH$_2$—C$\underline{H_2}$—N); 6.7-7.7 (m, 34H, CH$_{arom}$) ppm.

e. Synthesis of the First-Generation Dendrimer with an Azabisphosphonate Surface and a Fluorescent Core dendrimer carrying the fluorescent group, derived from diphenyl-maleic anhydride, (0.198 mmol, 380 mg), obtained during Stage d, in anhydrous THF (5 mL). The mixture is left under stirring for 24 hours at room temperature then the final mixture is filtered on celite in order to separate the salts. Finally the final product is washed by precipitation in pentane and isolated with a yield of 70%.

NMR $^{31}$P-{$^1$H} (CDCl$_3$): δ=66.58 (s, P$_1$); 30.19 (s, PO$_3$Me$_2$); 11.8 (s, P$_0$) ppm.

NMR $^1$H (CDCl$_3$): δ=2.70 (broad s, 22H, C$\underline{H_2}$—CH$_2$—N); 3.00 (broad s, 22H, CH$_2$—C$\underline{H_2}$—N); 3.13 (d, $^2J_{HP}$=9.2 Hz, 40H, —C$\underline{H_2}$—P(O)(OCH$_3$)$_2$); 3.20 (d, $^3J_{HP}$=11.8 Hz, 15H, CH$_3$—N—P$_1$); 3.68 (d, $^3J_{HP}$=10.4 Hz, 96H, —P(O)(O—C$\underline{H_3}$)$_2$); 6.6-7.7 (m, 79H, CH=N) ppm.

Example 89

Synthesis of the First-Generation Dendrimer with an Aza-Bis-Phosphonic Surface Derived from Tyramine and with a Fluorescent Core

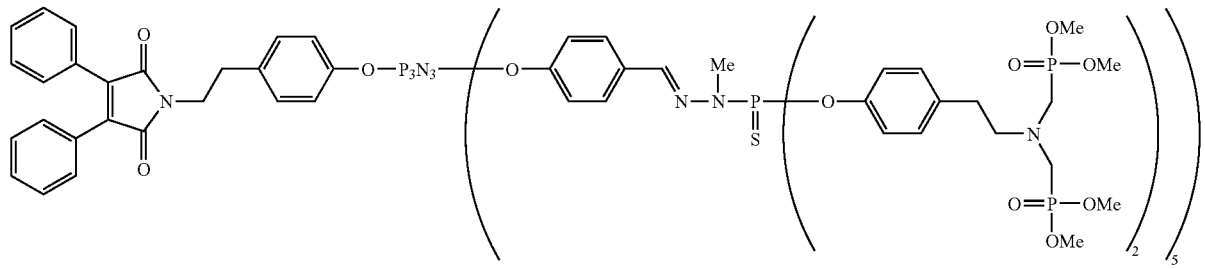

Finally, cesium carbonate (4.16 mmol, 1.35 g) and the phenol aza-bis-dimethyl-phosphonate derived from tyramine (2.08 mmol, 736 mg) is added to a solution of first-generation

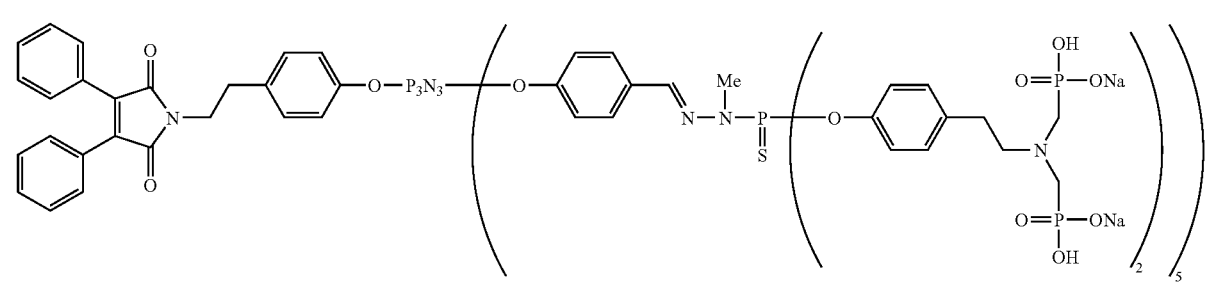

Bromotrimethylsilane (4.3 mmol, 578 μl) is added dropwise at 0° C. to a solution of first-generation dendrimer carrying the fluorescent group, derived from diphenyl-maleic anhydride, and with an aza-bis-dimethyl-phosphonate surface (0.098 mmol, 500 mg), obtained in Example 88, in acetonitrile (10 ml). Once the addition is finished the mixture is allowed to return to room temperature over 12 hours. The mixture is then evaporated to dryness then 1 ml of anhydrous methanol is added at room temperature and the mixture is left for one hour under stirring. After evaporation to dryness, the residue is washed several times with pure ether. As the product is totally insoluble in organic solvents it is converted to its monosodium salt in the presence of an aqueous soda solution (8.6 ml at 0.1955 mol·L$^{-1}$, for 380 mg of dendrimer). The resulting solution is lyophilized in order to produce the dendrimer in the form of a white-yellow powder. The final product is isolated with a yield of 51%.

NMR $^{31}$P-{$^1$H} (CD$_3$CN/D$_2$O): δ=66.58 (s, P$_1$); 14.2 (s, P(O)(ONa)(OH)); 11.8 (s, P$_0$) ppm.

Example 90

Synthesis of a First-Generation Phosphorus-Containing Dendrimer Carrying a Fluorescent Marker Derived from Julolidine with Aza-Bis-Phosphonic Acid Ends Derived from Tyramine Stage 1: Synthesis of 2,3,6,7-Tetrahydro-1H,5H-3-Formyl-Benzo(ij)Quinolizine (or Para-Formylated Julolidine)

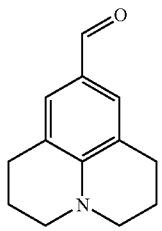 [SMILES: O=Cc1cc2c3c(c1)CCCN3CCC2]

The synthesis of this molecule was carried out according to the procedure described by M. A. Haidekk et al. *Chemistry and Biology* 2001, 8, 123-131.

Stage 2: Synthesis of 2-cyano-N-[2-(4-hydroxy-phenyl)-ethyl]-acetamide

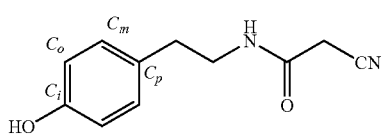

1.28 g (9.33 mmol) of tyramine is added to a solution containing 1.00 g (8.84 mmol) of ethyl cyanoacetate in 13 mL of dimethylformamide under an inert atmosphere. The mixture is stirred at 110° C. for 4 hours, then at room temperature for 12 h. The reaction medium is then diluted in 100 mL of ethyl acetate and washed with 50 mL of an aqueous acid solution at pH=3. The aqueous phase is again extracted with 50 mL of ethyl acetate. The organic phases are combined, dried over magnesium sulphate, filtered and the solvent is evaporated under reduced pressure. The resulting viscous brown solid is then dissolved several times in toluene and the toluene azeotrope/DMF is evaporated. Finally, the solid is washed with dichloromethane and ether. The product is isolated in the form of a pale brown solid with a yield of 65%.

NMR $^1$H (acetone d$_6$, 200.13 MHz): δ=2.71 (t, $^3$J$_{HH}$=7.0 Hz, 2H, C̲H$_2$—C$_6$H$_4$); 3.41 (m, 2H, HN—C̲H$_2$); 3.56 (s, 2H, C̲H$_2$—CN); 6.76 (d, $^3$J$_{HH}$=8.3 Hz, 2H, C$_o$—H); 7.05 (d, $^3$J$_{HH}$=8.2 Hz, 2H, C$_m$—H); 7.52 (bs, 1H, OH); 8.21 (bs, 1H, NH) ppm.

NMR $^{13}$C{$^1$H} (acetone d$_6$, 50.32 MHz): δ=26.1 (s, C̲H$_2$—CN); 35.1 (s, C̲H$_2$—C$_6$H$_4$); 42.3 (s, HN—C̲H$_2$); 116.0 (s, C$_o$ and CN); 130.4 (s, C$_m$ and C$_p$); 156.6 (s, C$_i$); 162.7 (s, CO) ppm.

Stage 3: Synthesis of 2-Cyano-N-[2-(4-Hydroxy-Phenyl)-Ethyl]-3-(2,3,6,7-Tetrahydro-1H,5H-3-Formyl-Benzo(ij)Quinolizine)-Acrylamide

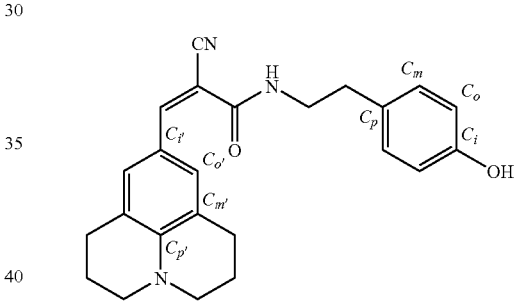

198 mg (0.969 mmol) of 2-cyano-N-[2-(4-hydroxy-phenyl)-ethyl]-acetamide and 360 μL (2.580 mmol) of triethylamine are added to a solution of 130 mg (0.646 mmol) of formylated julolidine in 14 mL of THF. The reaction mixture is refluxed for 18 hours. The solvent is then evaporated under reduced pressure and the residue is purified by chromatography on a silica column (eluent: dichloromethane containing 2% methanol). The product obtained (Rf=0.29) is isolated in the form of an orange solid with a yield of 67%.

NMR $^1$H (DMSO d$_6$, 500.33 MHz): δ=1.86 (m, 4H, C̲H$_2$—CH$_2$—N); 2.64 (m, 6H, C̲H$_2$—CH$_2$—CH$_2$—N, HN—CH$_2$—C̲H$_2$); 3.31 (m, 6H, CH$_2$—CH$_2$—C̲H$_2$—N, HN—C̲H$_2$—CH$_2$); 6.66-7.01 (m, 4H, C$_m$—H, C$_o$—H); 7.42 (s, 2H, C$_{o'}$—H); 7.79 (s, 1H, H̲C=C—CN); 7.97 (t, $^3$J$_{HH}$=7.5 Hz, 1H, NH); 9.18 (s, 1H, OH) ppm.

NMR $^{13}$C{$^1$H} (DMSO d$_6$, 125.81 MHz): δ=21.1 (s, C̲H$_2$—CH$_2$—N); 27.6 (s, C̲H$_2$—CH$_2$—CH$_2$—N); 34.8 (s, C̲H$_2$—CH$_2$—NH); 42.0 (s, CH$_2$—NH); 49.8 (s, CH$_2$—N); 95.2 (s, C̲—CN); 115.6 (s, C$_o$); 118.1 (s, C$_i$); 119.0 (s, CN); 120.9 (s, C$_{m'}$); 129.9 (s, C$_m$, C$_p$); 130.6 (s, C$_{o'}$); 147.1 (s, C$_{p'}$); 150.6 (s, H̲C=C—CN); 156.1 (s, C$_i$); 162.7 (s, CO) ppm.

Stage 4: Synthesis of Penta(4-Formylphenoxy)-Chlorocyclotriphosphazene

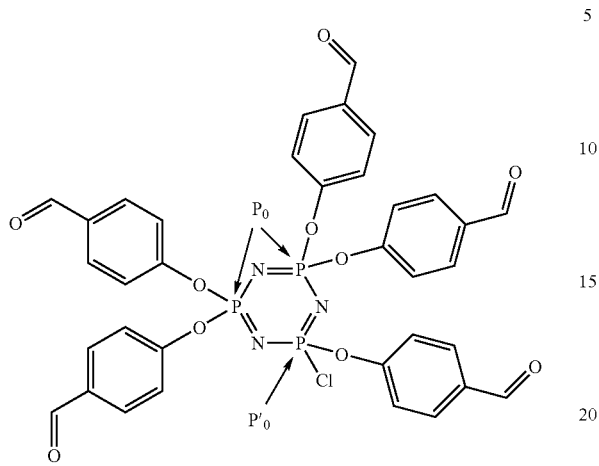

2591 mg of 4-hydroxybenzaldehyde sodium salt (18 mmol) are added at 0° C. and under an inert atmosphere to a solution containing 1.2 g of hexachlorocyclotriphosphazene (3.45 mmol) in THF (300 mL). The reaction medium is stirred for 12 hours while the temperature is allowed to gradually return to room temperature. The crude reaction product is evaporated to dryness then purified by "flash" chromatography on a silica column. The product is isolated in the form of a translucent oil with a yield of 70%.

NMR $^{31}P\{^{1}H\}$ (CDCl$_3$, 81 MHz): δ=9.2 (d, $^2J_{PP}$=86.6 Hz, P'$_0$); 24.3 (t, $^2J_{PP}$=86.6 Hz, P'$_0$) ppm.

Stage 5: Synthesis of an ABS-Type Dendritic Core Carrying a Fluorophore Derived from Julolidine and 5 Aldehyde Functions

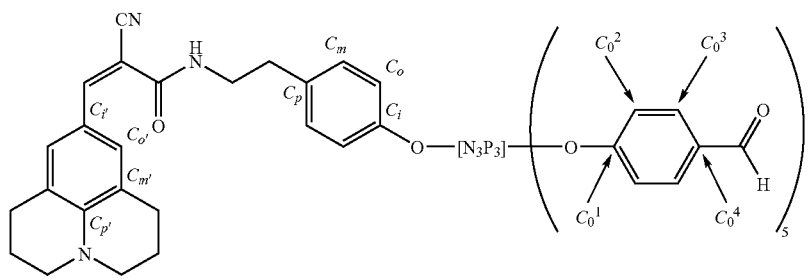

184 mg (237 mmol) of penta(4-formylphenoxy)-chlorocyclotri-phosphazene described in the preceding stage then 155 mg (475 mmol) of cesium carbonate are added to a solution containing 92 mg (237 mmol) of 2-cyano-N-[2-(4-hydroxyphenyl)-ethyl]-3-(2,3,6,7-tetrahydro-1H,5H-3-formyl-benzo(ij)quinolizine)-acrylamide in 10 mL of THF. The reaction medium is stirred at room temperature for 12 hours. The cesium salts are eliminated by centrifugation, and after evaporation of the solvent under reduced pressure the crude residue is purified by chromatography on a silica column (eluent: ethyl acetate/pentane, 1:1). The product (Rf=0.26) is isolated in the form of an orange oil.

NMR $^{31}P\{^{1}H\}$ (CDCl$_3$, 81.02 MHz): δ=10.9 (bs) ppm.

NMR $^{1}H$ (acetone d$_6$, 200.13 MHz): δ=1.90 (m, 4H, C$\underline{H}_2$—CH$_2$—N); 2.67 (t, $^3J_{HH}$=6.3 Hz, 4H, C$\underline{H}_2$—CH$_2$—CH$_2$—N); 2.84 (deformed t, $^3J_{HH}$=6.9 Hz, 2H, HN—CH$_2$—C$\underline{H}_2$); 3.25 (t, $^3J_{HH}$=6.0 Hz, 4H, C$\underline{H}_2$—N); 3.58 (t, $^3J_{HH}$=6.0 Hz, 2H, HN—C$\underline{H}_2$); 6.37 (t, $^3J_{HH}$=5.4 Hz, 1H, NH); 6.92 (d, $^3J_{HH}$=8.4 Hz, 2H, C$_o$—H); 7.10 (m, 12H, C$_m$—H and C$_o^2$—H); 7.36 (s, 2H, C$_{o'}$—H), 7.69 (d, $^3J_{HH}$=8.6 Hz, 10H, C$_o^3$—H); 7.95 (s, 1H, $\underline{H}$C=C—CN); 9.90 (s; 3H, CHO), 9.92 (s; 2H, CHO) ppm.

Stage 6: Synthesis of Fluorescent Dendrimer with a PSCl₂ Termination

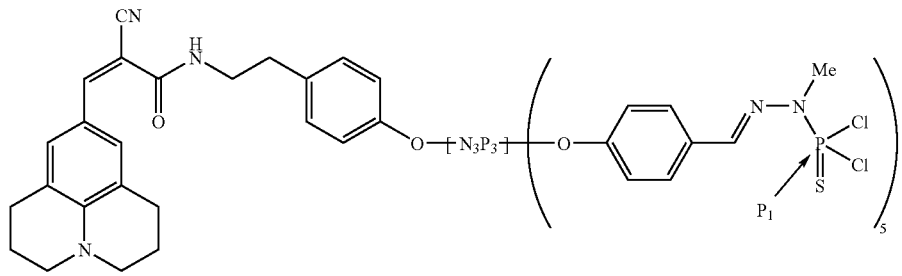

100 mg of the compound obtained in Stage 5 (0.05 mmol) is added at 0° C. to a solution of dichlorothiophospho-(N-methyl)-hydrazide (0.3 mmol) in chloroform (1.5 mL). The reaction mixture is stirred for 12 hours. After evaporation of the reaction solvent, the product is diluted in a minimum amount of dichloromethane and precipitated by addition of a large volume of pentane. This treatment is carried out three times. The product is isolated with a yield of 90%.

NMR $^{31}P\{^1H\}$ (CDCl₃, 81.02 MHz): δ=11.8 (bs, N₃P₃); 65.9 (s, P₁); 66.0 (s, P₁); 66.1 (s, P₁) ppm.

amount of THF and precipitated by addition of a large volume of pentane. The product is isolated with a yield of 70%.

NMR $^{31}P\{^1H\}$ (CDCl₃, 81.02 MHz): δ=11.9 (s, N₃P₃); 30.3 (s, PO₃Me₂); 30.6 (s, PO₃Me₂); 66.7 (s, P₁); 66.8 (s, P₁) ppm.

Stage 7: Synthesis of the Fluorescent Dendrimer with Aza-Bis-Dimethyl-Phosphonate Ends Derived from Tyramine

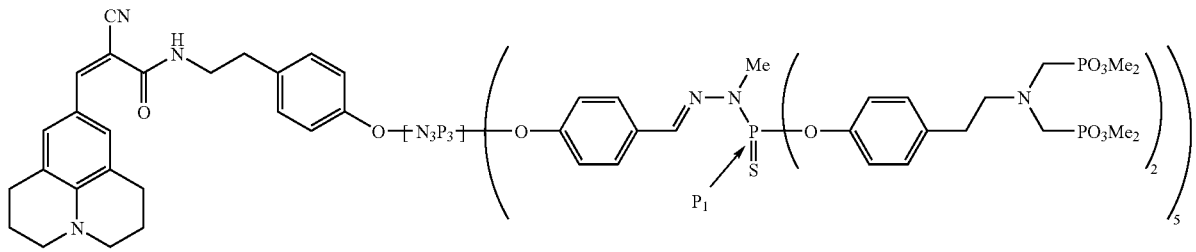

339 mg of cesium carbonate (1.04 mmol) and 198 mg of phenol aza-bis-dimethyl-phosphonate derived from the Stage 8: Synthesis of the Fluorescent Dendrimer with Aza-Bis-Phosphonic Acid Derived from Tyramine Sodium Salt Ends

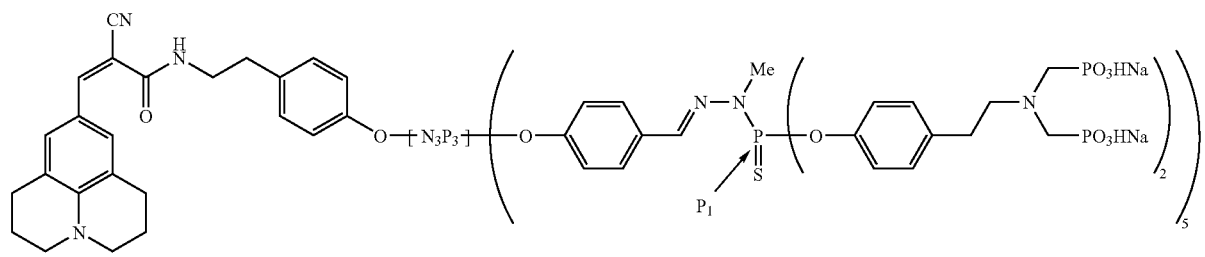

tyramine obtained in Example 31 (0.520 mmol) are added to a solution containing 100 mg of fluorescent dendrimer with a PSCl₂ termination (0.052 mmol) in 5 mL of THF. The mixture is stirred for 12 hours at room temperature then the salts formed are eliminated by centrifugation. After evaporation of the reaction solvent, the product is diluted in a minimum 110 μL of bromotrimethylsilane (0.838 mmol) are added slowly to a solution containing 100 mg of fluorescent dendrimer with aza-bis-dimethyl-phosphonate ends derived from tyramine obtained in the preceding stage (0.019 mmol) in acetonitrile (5 mL) at 0° C. under an inert atmosphere. At the end of the addition, the reaction medium is stirred at room temperature for 12 hours. The reaction medium is then evaporated to dryness then 2.5 mL of methanol are added at room temperature. The reaction medium is stirred for 1 hour then evaporated to dryness. This methanolysis operation is repeated a second time then the product is washed several times with diethyl ether. The resulting product, for NMR analysis purposes, is then converted to its sodium salt. The product is firstly introduced into water (1 mL) then 4.8 mL of aqueous soda (0.1966 N) are added. After total dissolution of the dendrimer, the solution is freeze-dried, which makes it possible to obtain the dendrimer in the form of a white powder with a yield of 75%.

NMR $^{31}P\{^1H\}$ (D$_2$O/CD$_3$CN, 81.02 MHz): δ=10.3 (bs, PO$_3$HNa); 13.1 (s, N$_3$P$_3$); 64.5 (s, P$_1$) ppm.

Example 91

Synthesis of Dendrimer with a Cyclotriphosphazene Core and with An Aza-Bis-Phosphonic Surface Derived from Tyramine, Having One Missing Branch Stage 1: Monosubstitution Reaction on Cyclotriphosphazene 140 mg of hexachlorocyclotriphosphazene, 0.1 mL of triethylamine and 1 equivalent of phenol are placed under stirring at RT in 15 mL of toluene for 72 hours. The reaction mixture is then filtered and then concentrated under reduced pressure. The crude residue is purified by chromatography on silica gel with an ether/hexane 1:1 mixture as eluent. The final product is obtained in the form of a paste with a yield of 65%.

The product obtained corresponds to the following formula:

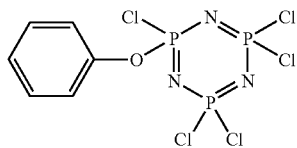 [SMILES: ClP1(Cl)=NP(Cl)(Cl)=NP(Cl)(Oc2ccccc2)=N1]

NMR $^{31}P\{^1H\}$ (CDCl$_3$, 81 MHz): δ=15.7 (d, $^2J_{CP}$=60 Hz, PCl(OPh)), 25.9 (d, $^2J_{CP}$=60 Hz, PCl$_2$).

A dendrimer is then constructed using methods well known to a person skilled in the art, in particular described in "A general synthetic strategy for neutral phosphorus containing dendrimers" Launay N., Caminade A. M., Lahana R., Majoral J. P., *Angew. Chem.* 1994, 106, 1682. *Angew. Chem. Int. Ed. Engl.* 1994, 33, 1589 and in «Synthesis of bowl-shaped dendrimers from generation 1 to generation 8" Launay N., Caminade A. M., Majoral J. P., *J. Organomet. Chem.* 1997, 529, 51. Then the phenol bisphosphonate is grafted at the surface according to the method used for the symmetrical dendrimers of the preceding examples.

In particular, the following may be carried out:

Stage 2: Grafting of Hydroxybenzaldehyde

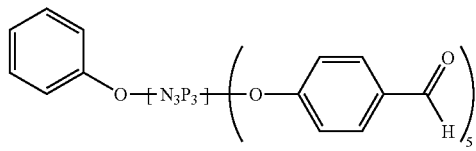

1170 mg of 4-hydroxybenzaldehyde and 6800 mg of cesium carbonate are added to a solution containing 650 mg of dendritic core obtained in the preceding stage in 20 mL of THF. The mixture is stirred at RT overnight, and the salts are eliminated by centrifugation. The resulting solution is then concentrated under reduced pressure and precipitated with an ether/pentane mixture (1/1) in order to produce a white powder with a yield of 82%.

NMR $^{31}P\{^1H\}$ (CDCl$_3$, 81 MHz): δ=12.1 (bs, N$_3$P$_3$).

Stage 3: Condensation of Phosphorhydrazide: First Generation of the Dendrimer

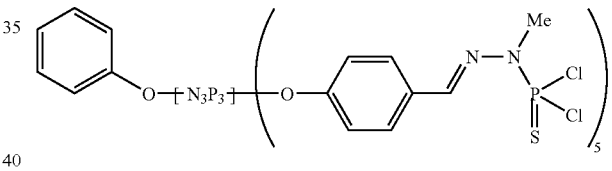

30 mL of dichlorothiophosphorhydrazide freshly synthesized at 0.24M in CHCl$_3$ are added to a solution containing 1000 mg of dendritic core obtained in the preceding stage in 20 mL of CHCl$_3$. The solution is stirred at RT overnight then the crude reaction product is concentrated under reduced pressure and precipitated by addition of pentane. The white powder obtained is then purified by chromatography on silica gel (eluent CH$_2$Cl$_2$/pentane, 1/1) with a yield of 76%.

NMR $^{31}P\{^1H\}$ (CDCl$_3$, 81 MHz): δ=11.7 (bs, N$_3$P$_3$), 65.9 (s, P=S), 66.0 (s, P=S).

Stage 4: Grafting of Phenol Aminobisphosphonate Derived from Tyramine

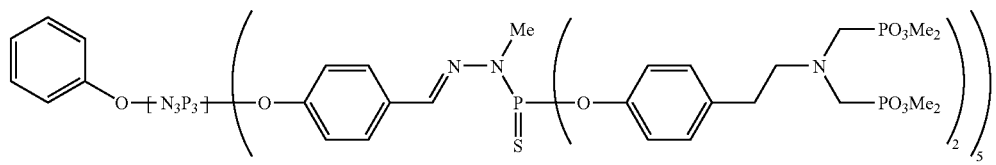

279 mg of aminobisphosphonate phenol derived from the tyramine obtained in Example 31 and 516 mg of cesium carbonate are added to a solution containing 120 mg of dendrimer obtained in the preceding stage in 20 mL of THF. The suspension is stirred at RT overnight and the salts are eliminated by centrifugation. The resulting solution is then concentrated under reduced pressure and precipitated with an ether/pentane mixture (1/1) in order to produce a white powder with a yield of 86%.

NMR $^{31}P\{^{1}H\}$ (CDCl$_3$, 81 MHz): δ=11.9 (s1, N$_3$P$_3$), 30.3 (s, P=O), 66.7 (s, P=S).

Stage 5: First-Generation Dendrimer with One Missing Branch and with Na Salt Ends

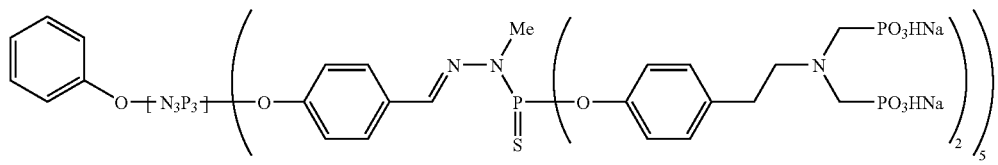

52 equivalents of BrTMS are added to a solution containing 100 mg of dendrimer obtained in the preceding stage in 5 mL of acetonitrile at 0° C. under an inert atmosphere. At the end of the addition, the reaction medium is stirred at room temperature for 12 hours. The reaction medium is then evaporated to dryness then 2.5 mL of methanol are added at room temperature. The reaction medium is stirred for 1 hour then evaporated to dryness. This methanolysis operation is repeated a second time then the product is washed several times with diethyl ether. The resulting product, for NMR analysis purposes, is then converted to its sodium salt. The product is firstly introduced into water (1 mL) then 10 equivalents of aqueous soda (0.1966 N) are added. After total dissolution of the dendrimer, the solution is freeze-dried, which makes it possible to obtain the dendrimer in the form of a white powder with a yield of 79%.

NMR $^{31}P\{^{1}H\}$ (CDCl$_3$, 81 MHz): δ=9.9 (s, P=O), 11.8 (bs, N$_3$P$_3$), 66.3 (s, P=S).

Example 92

Synthesis of a First-Generation Dendrimer Having Two Core Functions Blocked by a Biphenol and with Aza-Bis-Phosphonic Acid Ends Derived from Tyramine Stage 1: Synthesis of Tetrachloro-(2.2'-Dihydroxybiphenyl)Cyclotriphosphazene

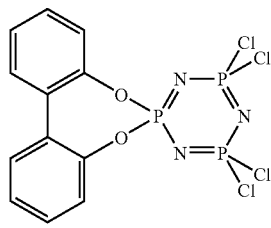 [SMILES: ClP1(Cl)=NP(Cl)(Cl)=NP2(=N1)Oc1ccccc1-c1ccccc1O2]

The synthesis of this molecule was carried out according to the procedure described by R. Pelc et al. *Phosphorus, Sulfur and Silicon* 1990, 47, 375-382.

Stage 2: Synthesis of Tetra(4-Formylphenoxy)(2,2'-Dihydroxybiphenyl)Cyclotriphosphazene

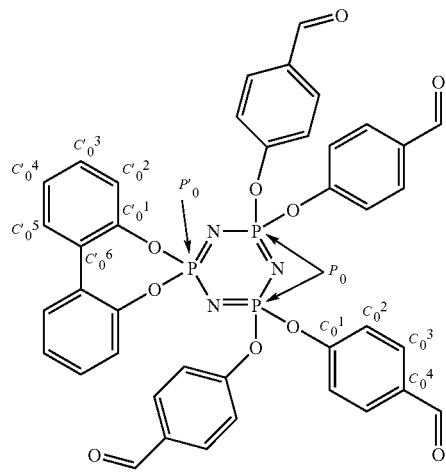

1.640 mg (11.39 mmol) of 4-hydroxybenzaldehyde sodium salt are added to a solution containing 1.270 mg (2.76 mmol) of tetrachloro-(2,2'-dihydroxybiphenyl) cyclotriphosphazene in 4 mL of THF. The reaction mixture is stirred for 12 hours. After dilution of the reaction medium with 20 mL of THF, the sodium salts are removed by centrifugation. After evaporation to dryness, the product is washed twice with methanol. The product is isolated with a yield of 90%.

NMR $^{31}P\{^{1}H\}$ (CDCl$_3$, 81 MHz): δ=11.5 (d, $^2J_{PP}$=94.8 Hz, P$_0$); 27.5 (t, $^2J_{PP}$=94.8 Hz, P'$_0$) ppm.

NMR $^1H$ (CDCl$_3$, 200.13 MHz): δ=6.78 (m, 2H, C'$_0^2$—H); 7.37 (m, 12H, C'$_0^3$—H, C'$_0^5$—H, C$_0^2$—H); 7.55 (m, 2H, C'$_0^4$—H); 7.82 (m, 8H, C$_0^3$—H); 9.95 (s, 4H, CHO) ppm.

NMR $^{13}C\{^{1}H\}$ (CDCl$_3$, 50.32 MHz): δ=121.3 (d, $^3J_{CP}$=4.6 Hz, C'$_0^2$); 121.5 (d, $^3J_{CP}$=7.3 Hz, C$_0^2$); 126.5 (d, $^4J_{CP}$=1.6 Hz, C'$_0^5$); 128.4 (d, $^3J_{CP}$=1.4 Hz, C'$_0^6$); 129.9 (s, C'$_0^3$, C'$_0^4$); 131.4 (s, C$_0^3$); 133.7 (s, C$_0^4$); 147.5 (d, $^2J_{CP}$=9.3 Hz, C'$_0^1$); 154.8 (t, $^2J_{CP}$=3.7 Hz, C$_0^1$); 190.6 (s, CHO) ppm.

Stage 3: Synthesis of the Dendrimer with Chlorinated Ends

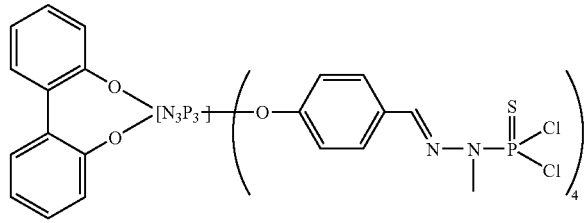

3 mL (0.66 mmol) of a solution of dichlorothiophospho-N-methylhydrazide at 0.22 mol.l$^{-1}$ are added at 0° C. to a solution containing 129 mg (0.16 mmol) of tetra(4-formylphenoxy)(2.2'-dihydroxy biphenyl)cyclotriphosphazene in 2 mL of THF. The reaction mixture is stirred at 0° C. for 2 hours. The product is purified by THF/pentane washings and isolated in the form of a white solid with a yield of 95%.

NMR $^{31}$P{$^1$H} (CDCl$_3$, 81 MHz): δ=11.5 (d, $^2J_{PP}$=96 Hz, P$_0$); 27.2 (t, $^2J_{PP}$=96 Hz, P'$_0$); 66.3 (s, P$_1$) ppm.

Stage 4: Synthesis of Dendrimer with Aza-Bis-Dimethyl-Phosphonate Ends Derived from Tyramine

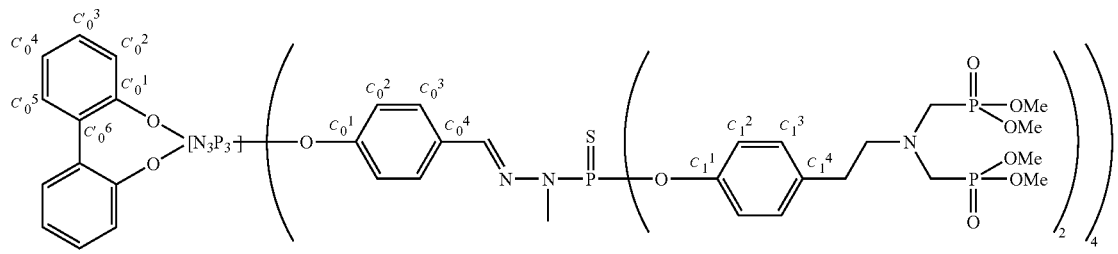

500 mg (1.31 mmol) of phenol aza-bis-dimethyl-phosphonate derived from the tyramine obtained in Example 31, then 750 mg (2.3 mmol) of cesium carbonate are added at room temperature to a solution containing 206 mg (0.14 mmol) dendrimer with chlorinated ends of the preceding stage in 4 mL of THF. The reaction mixture is stirred for 12 hours, diluted with 20 mL of THF and the cesium salts are removed by centrifugation. After evaporation of the volatiles, the residue is diluted in the minimum amount of THF and precipitated with a large excess of pentane. The expected product is thus obtained in the form of a viscous solid with a yield of 90%.

NMR $^{31}$P{$^1$H} (CDCl$_3$, 81 MHz): δ=11.5 (d, $^2J_{PP}$=96 Hz, P$_0$); 27.5 (t, $^2J_{PP}$=96 Hz, P'$_0$); 29.8 (s, PO$_3$Me$_2$); 65.9 (s, P$_1$) ppm.

NMR $^1$H (CDCl$_3$, 200.13 MHz): δ=2.74 (deformed t, $^3J_{HH}$=7.4 Hz, 16H, CH$_2$—CH$_2$—N); 3.04 (deformed t, $^3J_{HH}$=7.4 Hz, 16H, CH$_2$—CH$_2$—N); 3.18 (d, $^2J_{HP}$=9.1 Hz, 32H, N—CH$_2$—P); 3.72 (d, $^3J_{HP}$=10.5 Hz, 96H, P(O)(OMe)); 6.78-7.69 (m, 60H, H$_{arom}$ and CH=N) ppm.

Stage 5: Synthesis of Dendrimer with Aza-Bisphosphonic Acid Sodium Salt Ends Derived from Tyramine

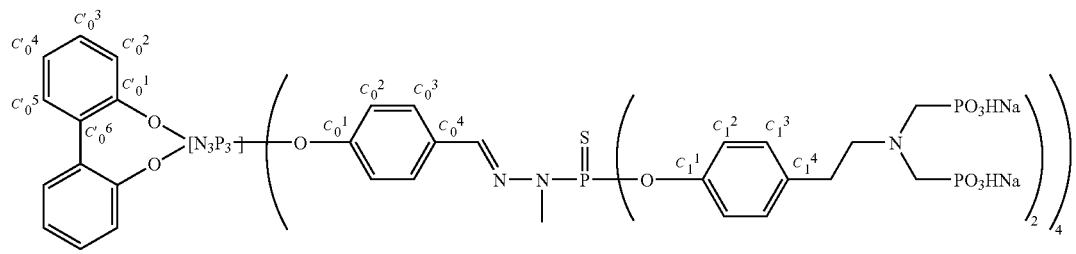

35 equivalents of bromotrimethylsilane are added slowly to a solution of 3 mL of acetonitrile maintained at 0° C. under an inert atmosphere containing 200 mg of the compound of the preceding stage. At the end of the addition, the reaction medium is stirred at room temperature for 12 hours. The reaction medium is then evaporated to dryness then 1 mL of methanol is added at room temperature. The reaction medium is stirred for 1 hour then evaporated to dryness. This methanolysis operation is repeated a second time then the crude residue is washed several times with diethyl ether. The resulting product, for the purposes of NMR analysis, is then converted to its sodium salt. The product is firstly placed in the presence of water (1 mL) then 16 equivalents of aqueous soda (0.1966 N) are added. The resulting solution is freeze-dried, which makes it possible to obtain the compound in the form of a white powder with a yield of 82%.

NMR $^{31}$P{$^1$H} (CDCl$_3$, 81 MHz): δ=9.5 (bs, PO$_3$HNa); 11.0 (d, $^2J_{PP}$=95 Hz, P$_0$); 27.1 (t, $^2J_{PP}$=95 Hz, P'$_0$); 65.7 (s, P$_1$) ppm.

Example 93

Synthesis of a Generation 1 Dendron with Aza-Bis-Dimethyl-Phosphonate Ends Derived from Tyramine By dendron is meant a dendrimer having one or more missing linkage chains said missing linkage chains being replaced by a reactive group.

Stage 1: Synthesis of Dichlorothiophospho-(N-Methyl)-(4-Methoxyphenyl)-Hydrazone Para-anisaldehyde (2.71 mmol, 330 μL) is added at 0° C. to a solution of dichlorothiophospho-N-methylhydrazide (4.4 mmol) in chloroform (22 mL). The reaction mixture is stirred for 12 hours. After evaporation of the reaction solvent, the product is washed with ether then purified by chromatography. The product is isolated in the form of a white powder with a yield of 90%.

NMR $^{31}$P{$^1$H} (CDCl$_3$, 81 MHz): δ=66.9 (s, P$_1$) ppm.

NMR $^1$H (CDCl$_3$, 200.13 MHz): δ=3.50 (d, $^3$J$_{HP}$=14.1 Hz, 3H, CH$_3$—N); 3.87 (s, 3H, CH$_3$—O); 6.96 (d, $^3$J$_{HH}$=8.1 Hz, 2H, C$_0^2$—H); 7.66 (s, CH=N); 7.68 (d, $^3$J$_{HH}$=8.2 Hz, 2H, C$_0^3$—H) ppm.

NMR $^{13}$C{$^1$H} (CDCl$_3$, 50.32 MHz): δ=31.8 (d, $^2$J$_{CP}$=13.1 Hz, CH$_3$—N); 55.4 (s, CH$_3$—O); 114.2 (s, C$_0^2$); 126.9 (s, C$_0^4$); 128.9 (s, C$_0^3$); 141.3 (d, $^3$J$_{CP}$=18.7 Hz, CH=N); 161.2 (s, C$_0^1$) ppm.

Stage 2: Synthesis of a Generation 0 Dendron with Aza-Bis-Dimethyl-Phosphonate Ends Derived from Tyramine 195 mg of dichlorothiophospho-(N-methyl)-(4-methoxyphenyl)-hydrazone (0.66 mmol), then 881 mg of cesium carbonate (2.70 mmol) are added at room temperature to a solution containing 596 mg of phenol aza-bis-dimethyl-phosphonate derived from the tyramine obtained in Example 31 (1.49 mmol) in 5 mL of acetone. The reaction mixture is stirred for 12 hours, diluted with 20 mL of THF and the cesium salts are removed by centrifugation. After evaporation of the volatiles, the residue is diluted in the minimum amount of THF and precipitated with a large excess of pentane. The expected product is thus obtained in the form of a viscous solid with a yield of 94%.

NMR $^{31}$P{$^1$H} (CDCl$_3$, 81 MHz): δ=30.3 (s, PO$_3$Me$_2$); 66.6 (s, P$_1$) ppm.

NMR $^1$H (CDCl$_3$, 200.13 MHz): δ=2.73 (deformed t, $^3$J$_{HH}$=7.1 Hz, 4H, CH$_2$—CH$_2$—N); 3.03 (deformed t, $^3$J$_{HH}$=7.1 Hz, 4H, CH$_2$—CH$_2$—N); 3.16 (d, $^3$J$_{HP}$=9.0 Hz, 8H, N—CH$_2$—P); 3.30 (d, $^3$J$_{HP}$=11.1 Hz, 3H, CH$_3$—N), 3.71 (d, $^3$J$_{HP}$=10.4 Hz, 24H, P(O)(OCH$_3$)$_2$); 3.84 (s, 3H, CH$_3$—O); 6.92 (d, $^3$J$_{HH}$=8.8 Hz, 2H, C$_0^2$—H); 7.13 (m, 8H, C$_1^2$—H, C$_1^3$—H); 7.59 (s, CH=N); 7.66 (d, $^3$J$_{HH}$=8.7 Hz, 2H, C$_0^3$—H) ppm.

NMR $^{13}$C{$^1$H} (CDCl$_3$, 50.32 MHz): δ=32.8 (s, CH$_2$—CH$_2$—N); 33.0 (s, CH$_3$—N); 49.4 (dd, $^1$J$_{CP}$=157.4 Hz, $^3$J$_{CP}$=7.1 Hz, N—CH$_2$—P); 52.6 (d, $^2$J$_{CP}$=5.2 Hz, PO$_3$Me$_2$); 55.4 (s, CH$_3$—O); 58.1 (t, $^3$J$_{CP}$=7.4 Hz, CH$_2$—CH$_2$—N); 114.1 (s, C$_0^2$); 121.3 (d, $^3$J$_{CP}$=4.4 Hz, C$_1^2$); 127.7 (s, C$_0^4$); 128.4 (s, C$_0^3$); 129.8 (s, C$_1^3$); 136.3 (s, C$_1^4$); 139.4 (d, $^3$J$_{CP}$=4.5 Hz, CH=N); 149.0 (d, $^2$J$_{CP}$=6.6 Hz, C$_1^1$); 160.6 (s, C$_0^1$) ppm.

Stage 3: Synthesis of Generation 0 Dendron with Aza-Bis-Phosphonic Acid Sodium Salt Ends Derived from Tyramine 0.396 mL of bromotrimethylsilane (3.0 mmol) is added slowly to a solution containing 286 mg of the compound of Stage 2 (0.29 mmol) in 3 mL of acetonitrile maintained at 0° C. under an inert atmosphere. At the end of the addition, the reaction medium is stirred at room temperature for 12 hours. The reaction medium is then evaporated to dryness then 1 mL of methanol is added at room temperature. The reaction medium is stirred for 1 hour then evaporated to dryness. This methanolysis operation is repeated a second time then the crude residue is washed several times with diethyl ether.

The resulting product, for the purposes of NMR analysis, is then converted to its sodium salt. The product is firstly introduced into water (1 mL) then 4.60 mL of aqueous soda is added (0.1966 N). The resulting solution is freeze-dried, which makes it possible to obtain the dendron in the form of a white powder with a yield of 80%.

NMR $^{31}$P{$^{1}$H} (CD$_3$CN/D$_2$O, 81 MHz): δ=10.1 (s, PO$_3$HNa); 68.4 (s, P$_1$) ppm.

NMR $^{1}$H (CD$_3$CN/D$_2$O, 500.33 MHz): δ=2.99 (deformed t, $^{3}J_{HH}$=7.5 Hz, 4H, CH$_2$—CH$_2$—N); 3.19 (d, $^{3}J_{HP}$=10.6 Hz, 3H, CH$_3$—N); 3.34 (d, $^{2}J_{HP}$=11.7 Hz, 8H, N—CH$_2$—P); 3.56 (deformed t, $^{3}J_{HH}$=7.5 Hz, 4H; CH$_2$—CH$_2$—N); 3.73 (s, 3H, CH$_3$—O); 6.90 (d, $^{3}J_{HH}$=8.7 Hz, 2H, C$_0^2$—H); 7.09 (d, $^{3}J_{HH}$=8.1 Hz, 4H, C$_1^2$—H); 7.23 (d, $^{3}J_{HH}$=8.1 Hz, 4H, C$_1^3$—H); 7.55 (d, $^{3}J_{HH}$=8.5 Hz, 2H, C$_0^3$—H); 7.76 (s, 1H, CH=N) ppm.

NMR $^{13}$C{$^{1}$H} (CD$_3$CN/D$_2$O, 125.86 MHz): δ=28.9 (s, CH$_2$—CH$_2$—N); 32.6 (d, $^{2}J_{CP}$=11.3 Hz, CH$_3$—N); 52.3 (d, $^{1}J_{CP}$=130.8 Hz, N—CH$_2$—P); 55.4 (s, CH$_3$—O); 57.5 (s, CH$_2$—CH$_2$—N); 114.3 (s, C$_0^1$); 121.5 (d, $^{3}J_{CP}$=5.0 Hz: C$_1^2$); 127.3 (s, C$_0^4$); 128.8 (s, C$_0^3$); 130.5 (s, C$_1^3$); 134.0 (s, C$_1^4$); 143.0 (d, $^{3}J_{CP}$=3.8 Hz, CH=N); 148.9 (d; $^{2}J_{CP}$=6.3 Hz, C$_1^1$); 160.2 (s, C$_0^1$) ppm.

Example 94

Synthesis of a Generation 0 Dendrimer with a PS Core and with Aza-Bis-Phosphonic Acid Ends Derived from Tyramine Stage 1: Synthesis of Generation 0 Dendrimer with a PS Core and with Aza-Bis-Dimethyl-Phosphonate Ends Derived from Tyramine

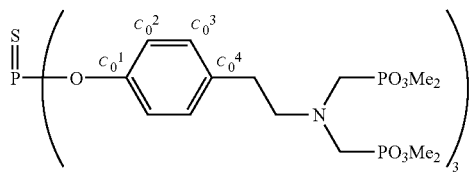

0.058 mL of trichlorothiophosphore (0.57 mmol), then 1.140 g of cesium carbonate (3.50 mmol) are added at 0° C. and under an inert atmosphere to a solution containing 700 mg of phenol aza-his-dimethyl-phosphonate derived from the tyramine obtained in Example 31 (1.75 mmol) in 8 mL of acetonitrile. The mixture is stirred for 12 hours at room temperature then the salts formed are eliminated by centrifugation. After evaporation of the reaction solvent, the product is diluted in a minimum amount of THF and precipitated by addition of a large volume of pentane. These washings by precipitation make it possible to isolate the product in the form of an oil with a yield of 98%.

NMR $^{31}$P{$^{1}$H} (CDCl$_3$, 81 MHz): δ=30.3 (s, P(O)(OCH$_3$)$_2$); 57.0 (s, P$_0$) ppm.

NMR (CDCl$_3$, 300.13 MHz): δ=2.79 (deformed t, $^{3}J_{HH}$=7.3 Hz, 6H, CH$_2$—CH$_2$—N); 3.05 (deformed t, $^{3}J_{HH}$=7.3 Hz, 6H, CH$_2$—CH$_2$—N); 3.18 (d, $^{2}J_{HP}$=9.0 Hz, 12H, N—CH$_2$—P); 3.72 (d, $^{3}J_{HP}$=10.5 Hz, 36H, P(O)(OCH$_3$)$_2$); 7.11 (d, $^{3}J_{HH}$=8.0 Hz, 6H, C$_0^2$—H); 7.22 (d, $^{3}J_{HH}$=8.0 Hz, 6H, C$_0^3$—H) ppm.

Stage 2: Synthesis of the Generation 0 Dendrimer with a PS Core and with Aza-Bis-Phosphonic Acid Sodium Salt Ends Derived from Tyramine

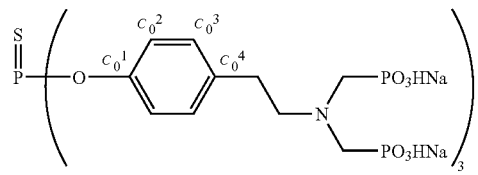

492 µl of bromotrimethylsilane (3.7 mmol) are added slowly at 0° C. under an inert atmosphere to a solution containing 325 mg of generation 0 dendrimer with aza-bis-dimethyl-phosphonate ends derived from the tyramine (0.27 mmol) obtained in the preceding stage in 3 mL of acetonitrile. At the end of the addition, the reaction medium is stirred at room temperature for 12 hours. The reaction medium is then evaporated to dryness then 2.5 mL of methanol are added at room temperature. The reaction medium is stirred for 1 hour then evaporated to dryness. This methanolysis operation is repeated a second time then the product is washed several times with diethyl ether.

The resulting product, for the purposes of NMR analysis, is then converted to its sodium salt. The product is firstly introduced into water (1 mL) then 6.22 mL of aqueous soda is added (0.1966 N). After total dissolution of the dendrimer, the solution is freeze-dried, which makes it possible to obtain the dendrimer in the form of a white powder with a yield of 75%.

NMR $^{31}$P{$^{1}$H} (D$_2$O/CD$_3$CN, 81 MHz): δ=10.2 (s, PO$_3$HNa); 58.5 (s, P$_0$) ppm.

NMR $^{1}$H (D$_2$O/CD$_3$CN, 200.13 MHz): δ=3.01-4.30 (m, 24H, CH$_2$); 7.51-7.63 (m, 12H, C$_0^2$—H, C$_0^3$—H) ppm.

NMR $^{13}$C{$^{1}$H} (D$_2$O/CD$_3$CN, 50.32 Mz); S=31.8 (s, CH$_2$—CH$_2$—N); 55.5 (d, $^{1}J_{CP}$=128.3 Hz, N—CH$_2$—P); 60.6 (s, CH$_2$—CH$_2$—N); 124.2 (d, $^{3}J_{CP}$=4.48 Hz, C$_0^2$); 133.7 (s, C$_0^3$); 137.5 (s, C$_0^4$); 152.1 (d, $^{2}J_{CP}$=8.7 Hz, C$_0^1$) ppm.

Example 95

Synthesis of Salamonczyk-Type Phosphorus-Containing Dendrimers

Stage 1: Synthesis of a Diphenoxyamino Phosphine Derived from Tyramine

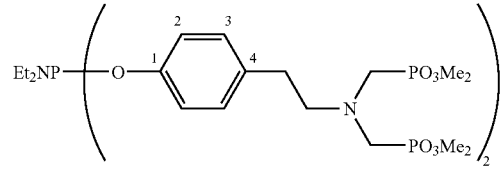

The experimental protocol used for preparing this molecule was inspired by that used by Salamonczyk in order to create his dendrimers (*Tetrahedron Lett.* 2000, 41, 1643). The aza bis phosphonate tyramine derivative obtained in Example 31 is weighed in a Schlenk tube under argon (2.3 g) and dissolved in 10 mL of distilled THF. The diethylaminodichlorophosphine is introduced into another Schlenk tube (0.5 mL) and placed in solution in 5 mL of distilled THF. The two Schlenk tubes are taken to −70° C. 1.4 mL of triethylamine are then added to the dichlorophosphine solution then the tyramine aza bis phosphonate solution is cannulated onto the mixture still at −70° C. The stirring is continued for half an hour at a low temperature then for 4 hours at room temperature. The mixture is then filtered on celite under argon then the solvent is eliminated under reduced pressure. The dry residue is kept under argon at a low temperature and used without other treatment in the rest of the synthesis.

$^3J_{CP}$=7.6 Hz, CH$_2$CH$_2$N); 64.4 (d, $^2J_{CP}$=3.7 Hz, P(S)O CH$_2$CH$_2$CH$_2$); 65.5 (d, $^2J_{CP}$=5.2 Hz, CH$_2$OP(S)OC$_6$H$_4$); 120.8 (d, $^3J_{CP}$=5.0 Hz, C$^2$); 130.0 (s, C$^3$); 136.6 (s, C$^4$); 148.9 (d, $^2J_{CP}$=7.2 Hz, C$^1$) ppm.

Stage 3: Synthesis of the Generation 0 of Salamonczyk-Type Dendrimers with Azabisphosphonic Acid Sodium Salt Ends Derived from Tyramine

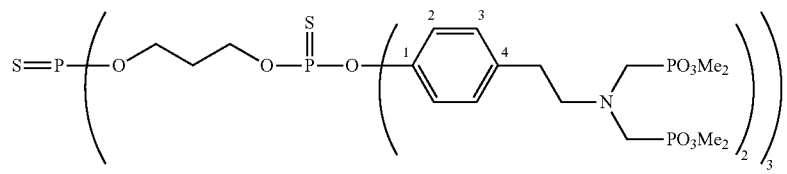

NMR $^{31}$P{$^1$H} (CDCl$_3$): δ=30.4 (s, PO$_3$Me$_2$); 144.5 (s, Et$_2$NP) ppm.

NMR $^1$H (CDCl$_3$): δ=1.00 (t, $^3J_{HH}$=7.2 Hz, 6H, CH$_3$CH$_2$); 2.70 (m, 4H, N—CH$_2$CH$_2$); 3.00 (m, 4H, CH$_2$CH$_2$P); 3.11-3.23 (m, 12H, CH$_2$P, CH$_3$CH$_2$); 3.69 (d, $^3J_{HP}$=6.9 Hz, 24H, CH$_3$O); 6.90 (d, $^3J_{HH}$=8.4 Hz, 4H, C$^2$H); 6.97 (d, $^3J_{HH}$=8.4 Hz, 4H, C$^3$H) ppm.

Stage 2: Coupling with a Generation 0 Salamonczyk-Type Dendrimer

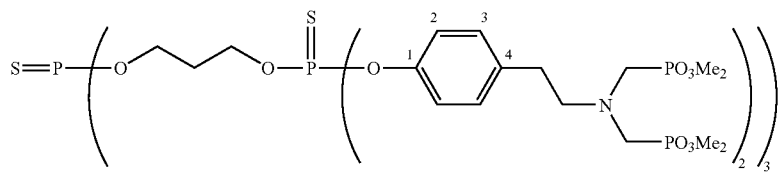

2.95 g of diethylaminophosphine obtained in Stage 1 are placed in solution in 10 mL of dichloromethane under argon. A solution of 219 mg of (S)P(O—(CH$_2$)$_3$(OH))$_3$ (synthesized as described in G. M. Salamonczyk, *Tetrahedron Lett.* 2000, 41, 1643) in 10 mL of dichloromethane is added to it at room temperature. This mixture is added to a solution of 400 mg of tetrazole in 5 mL of acetonitrile. The solution thus obtained is stirred for 3 hours at room temperature under argon then a spatula tip's worth of sulphur is added to it and stirring is continued at RT until all the phosphines are sulphur-containing ($^{31}$P NMR control), that is approximately 5 days. The mixture is filtered then the solvent evaporated. The dry residue is then subjected to chromatography on silica gel with a mixture of eluent CHCl$_3$/MeOH (90/10). Rf=0.41.

NMR $^{31}$P{$^1$H} (CDCl$_3$): δ=30.3 (s, PO$_3$Me$_2$); 62.3 (s, P$_1$); 71.7 (s, P0) ppm.

NMR $^1$H (CDCl$_3$): δ=2.08 (q, $^3J_{HH}$=5.7 Hz, 6H, CH$_2$CH$_2$CH$_2$); 2.75 (m, 12H, CH$_2$C$_6$H$_4$); 3.04 (m, 12H, NCH$_2$); 3.19 (d, $^2J_{HP}$=9.2 Hz, 24H, CH$_2$P); 3.73 (d, $^3J_{HP}$=10.5 Hz, 72H, CH$_3$O); 4.18 (dt, $^3J_{HH}$=5.7 Hz, $^3J_{HP}$=8.7 Hz, 6H, CH$_2$OP(S)); 4.33 (dt, $^3J_{HH}$=6.2 Hz, $^3J_{HP}$=9.2 Hz, 6H, CH$_2$OP(S)), 7.05 (d, $^3J_{HH}$=7.8 Hz, 12H, C$^2$H); 7.18 (d, $^3J_{HH}$=7.8 Hz, 12H, C$^3$H) ppm.

NMR $^{13}$C{$^1$H} (CDCl$_3$): δ=30.6 (dd, $^3J_{CP}$=$^3J_{CP}$=7.6 Hz, CH$_2$CH$_2$CH$_2$); 33.0 (s, CH$_2$C$_6$H$_4$); 49.4 (dd, $^1J_{CP}$=159.0 Hz, $^3J_{CP}$=7.7 Hz, NCH$_2$P); 52.8 (d, $^2J_{CP}$=7.4 Hz, OCH$_3$); 58.2 (t, 350 mg of dendrimer with azabisphosphonate ends are placed in solution in 5 mL of dry acetonitrile; then 0.420 mL of BrTMS (or 1.05 equivalents of BrTMS per P-Ome bond) is added to it at 0° C. dropwise using a syringe. After 30 minutes at 0° C. the ice bath is removed and stirring is continued overnight at RT. The mixture is brought under vacuum. 5 mL of MeOH is added to the dry residue and the mixture is stirred for one hour. After being brought under vacuum the dry residue is hydrolyzed for one hour at RT with 5 mL of distilled water. After freeze-drying the powder is washed twice with 10 mL of ether. The product is obtained with a yield of 83%. 6.4 mL of a 0.1966 M NaOH solution is added in order to form the monosodium salt and make the product hydrosoluble. After freeze-drying the product is obtained in a quantitative manner and does not require additional purification.

NMR $^{31}$P{$^1$H} (D$_2$O/CD$_3$CN): δ=10.5 (s, PO$_3$HNa); 62.8 (s, P1); 70.8 (s, P0) ppm.

NMR $^{13}$C{$^1$H} (D$_2$O/CD$_3$CN): δ=31.9 (s, CH$_2$C$_6$H$_4$); 33.0 (dl, $^3J_{CP}$=9.0 Hz, CH$_2$CH$_2$CH$_2$); 54.9 (dl, $^1J_{CP}$=130.9 Hz, NCH$_2$P); 60.6 (bs, CH$_2$CH$_2$N); 67.6 (bs, P(S)O CH$_2$CH$_2$CH$_2$); 69.0 (bs, CH$_2$OP(S)OC$_6$H$_4$); 124.3 (d, $^3J_{CP}$=3.4 Hz, C$^2$); 133.6 (s, C$^3$); 137.2 (s, C$^4$); 152.2 (d, $^2J_{CP}$=7.4 Hz, C$^1$) ppm.

Example 96

Synthesis of Carbosilane-Type Dendrimers with a Bis-Phosphonate Surface

Stage 1: Synthesis of an Allyl Aminobisphosphonate

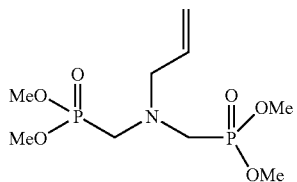 [SMILES: C=CCN(CP(=O)(OC)OC)CP(=O)(OC)OC]

Aqueous formaldehyde (3.27 mL, 2.2 equivalents, 44 mmol) is added slowly to a solution of allylamine (1.5 mL, 20 mmol) in THF (6 mL). After 15 minutes of stirring, dimethyl phosphite (4.03 mL, 2.2 equivalents, 44 mmol) is added and the solution is vigorously stirred for 20 hours at room temperature. 1.6 mL of formaldehyde are added and after 15 hours of stirring the solution is diluted with 15 mL of water then extracted with 100 mL of $CH_2Cl_2$. The organic phase is dried over $MgSO_4$, filtered then concentrated under reduced pressure. The oil obtained is washed with twice 30 mL of ether then dried. The yield is 76%.

NMR $^{31}P$ {$^1H$} ($CDCl_3$, 81.01 MHz): δ=30.5 (s, P=O).

NMR $^1H$ ($CDCl_3$); 200.13 MHz: δ=3.01 (d, 4H, $^2J_{HP}$=9.1 Hz, $PCH_2$); 3.26 (m, 2H, $CH_2$—CH); 3.63 (d, 12H, $^3J_{HP}$=10.6, POMe); 5.10 (m, 2H, $CH_2$=); 5.67 (m, 1H, CH=).

Stage 2: Synthesis of a Carbosilane Dendrimer with Azabisphosphonate Terminations

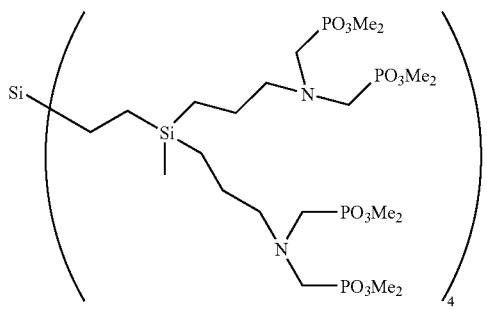

The first-generation dendrimer having 8 Si—Cl bonds at the periphery was prepared according to the procedure described in the literature [L.-L. Thou, J. Roovers *Macromolecules* 1993, 26, 963]. The transition to the Si—H bonds is achieved with $LiAlH_4$/Ether according to the procedure described [D. Seyferth, D. Y. Son *Organometallics* 1994, 13, 2682]. 500 mg (1.55 mmol) of dendrimer possessing 8 Si—H bonds at the periphery are mixed with 8.4 equivalents of N-allyl-aza-bis-phosphonate obtained in Stage 1 (or 13.64 mmol) and two drops of platinum catalyst in solution in isopropanol ($H_2PtCl_6$, $nH_2O$). The mixture is stirred for 12 h at 70° C. then overnight at room temperature. The solvent is eliminated and the dry residue is washed with hexane. The product is then purified by silica column chromatography and obtained with a yield of 65%.

NMR $^{31}P${$^1H$} ($CDCl_3$) δ=30.1 ppm.

Stage 3: Carbosilane Dendrimers with Aza-Bis-Phosphonic Acid (Na Salt) Terminations

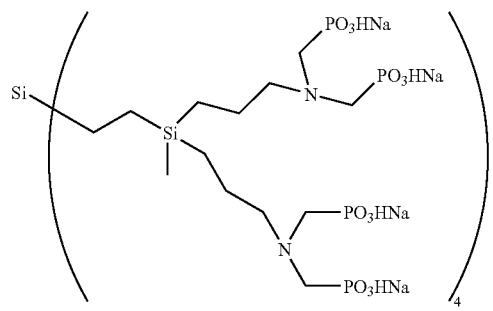

400 mg (0.15 mmol) of carbosilane dendrimer having 8 aza-bis-phosphonate groups at the periphery are dissolved in 4 mL of freshly distilled acetonitrile and placed at 0° C. 8.4 equivalents of BrTMS (or 1.28 mmol) are then added dropwise using a syringe. After 30 minutes at 0° C. and overnight at room temperature the mixture is brought under vacuum and the dry residue is methanolyzed then hydrolyzed. After freeze-drying the solid is washed with ether. The addition of 1 equivalent of NaOH (0.1955N in aqueous solution) per $PO_3H_2$ surface function leads to the corresponding sodium salt with a yield of 68%.

NMR $^{31}P${$^1H$} ($D_2O$/$CD_3COCD_3$) δ=10.9 ppm.

Example 97

Poly-L-Lysine Dendrimer with an Amino Bisphosphonic Acid Surface Derived from Glycine Stage 1: Deprotection and Grafting of the [Bis-(Dimethoxy-Phosphorylmethyl)] Amino Acid

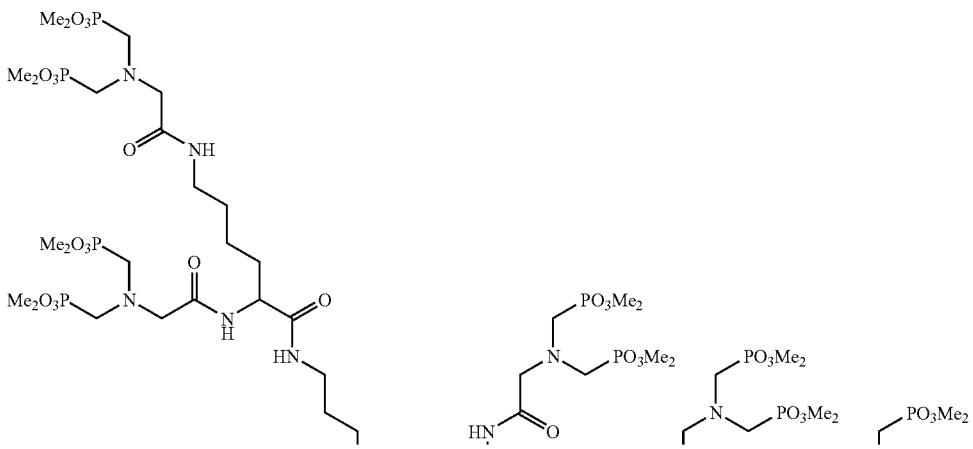

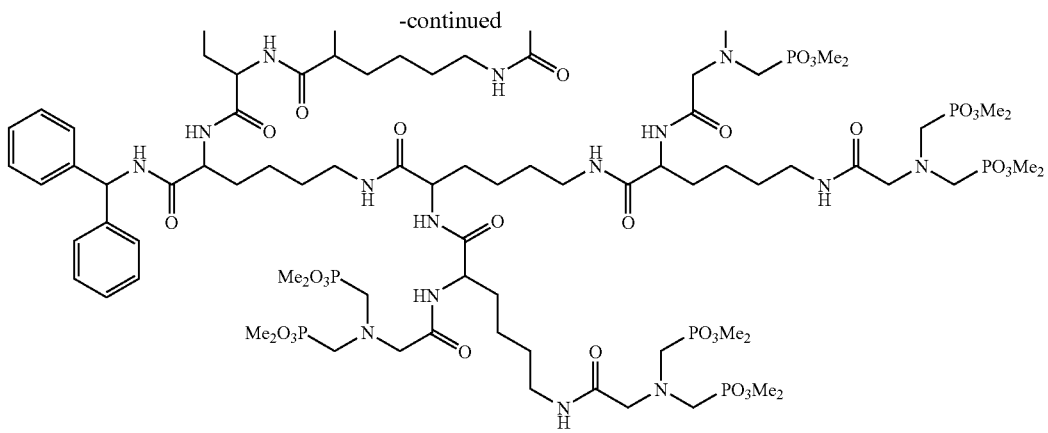

100 mg of generation 1 BHA-Lysine-100% BOC (Aldrich) dendrimer are placed in solution in 20 mL of dichloromethane containing 30% trifluoroacetic acid for three hours at 25° C. After evaporation of the volatiles, the crude product is dried overnight under reduced pressure, then placed in solution in 1 mL of dry DMF at 0° C. with 8 equivalents of triethylamine. 8.8 equivalents of aza-bis-phosphonate carboxylic acid obtained in Example 51 (n=1) are introduced into another flask under argon and dissolved in 5 mL of dry DMF at 0° C. 8.8 equivalents of 1-hydroxybenzotriazole (HOBt) is then added under argon, stirring is continued for 15 minutes at 0° C. then 8.8 equivalents of 1.3-dicyclohexylcarbodiimide (DCC) is added. The mixture is stirred for 30 minutes at 0° C. then for 1 h at room temperature. The formation of a precipitate is observed. The deprotected first-generation poly-L-lysine dendrimer solution in 1 mL of dry DMF is then added at 0° C., stirring is continued for 15 minutes at 0° C. then overnight at room temperature. The precipitate is eliminated by filtration on a 5μ Millipore syringe filter then the solution is freeze-dried. The product is purified by dissolution in a minimum volume of $CH_2Cl_2$ and precipitation in a large volume of diethylether. These precipitations are repeated three times in order to eliminate the traces of HOBt. The product is obtained with a yield of 65% in the form of an off-white powder.

NMR $^{31}P\text{-}\{^1H\}$ ($CDCl_3$) δ=30.2 ppm.

Stage 2: Phosphonic Acid Ends

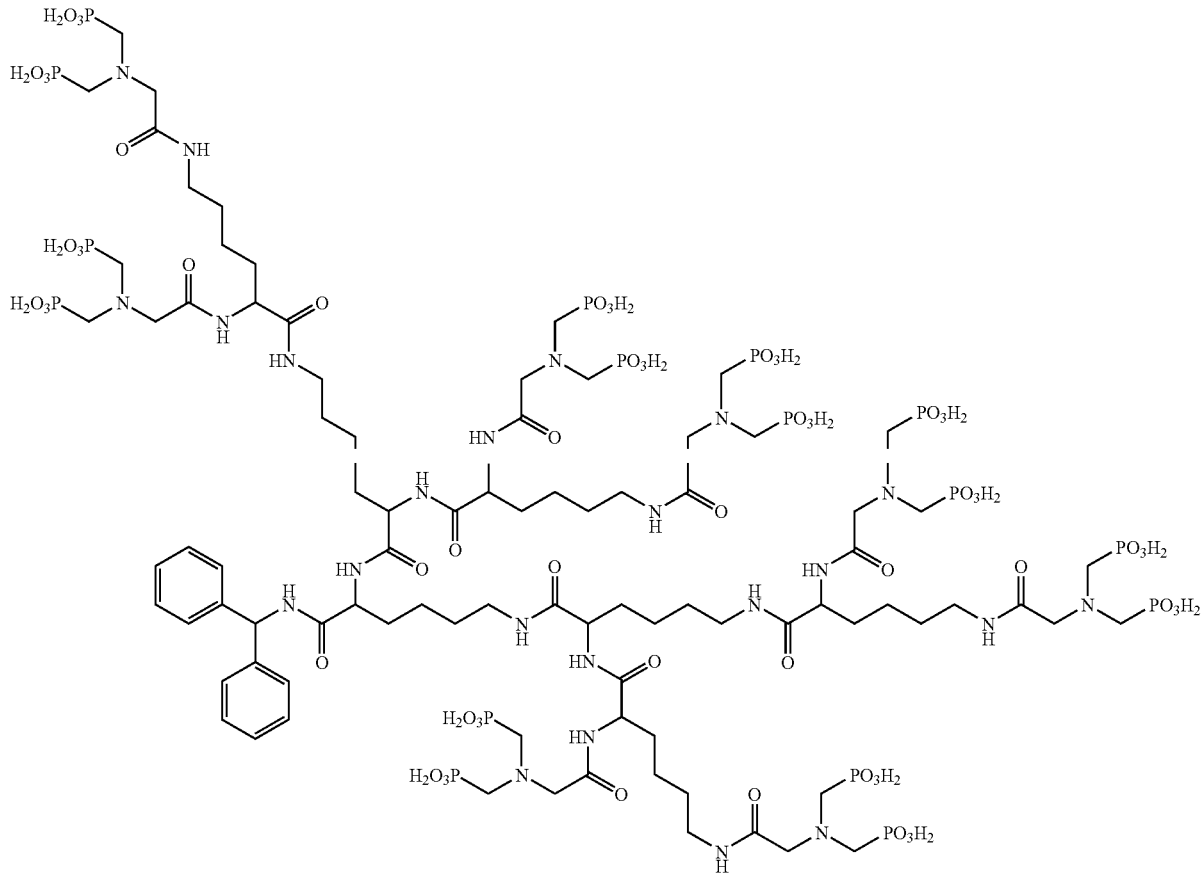

4 mL of freshly distilled acetonitrile is added under an inert atmosphere to 0.2 mmol of generation 1 poly-L-lysine-type dendrimer with azabis-phosphonate ends of the preceding stage, and the mixture is cooled to 0° C. 12.8 mmol of BrTMS (or 64 equivalents) is then added dropwise. The mixture is maintained at 0° C. for 30 minutes then under stirring at room temperature for another 15 hours. The acetonitrile is eliminated under reduced pressure then the mixture is methanolyzed and hydrolyzed as in the preceding cases. The dry residue is then washed twice with a THF/diethylether mixture (1/9). The powder is then dried under vacuum in order to produce the pure product with a yield of 68%.

NMR $^{31}$P-{$^{1}$H} (D$_2$O, CD$_3$COCD$_3$) δ=10.6 ppm.

Stage 3: Na Salt

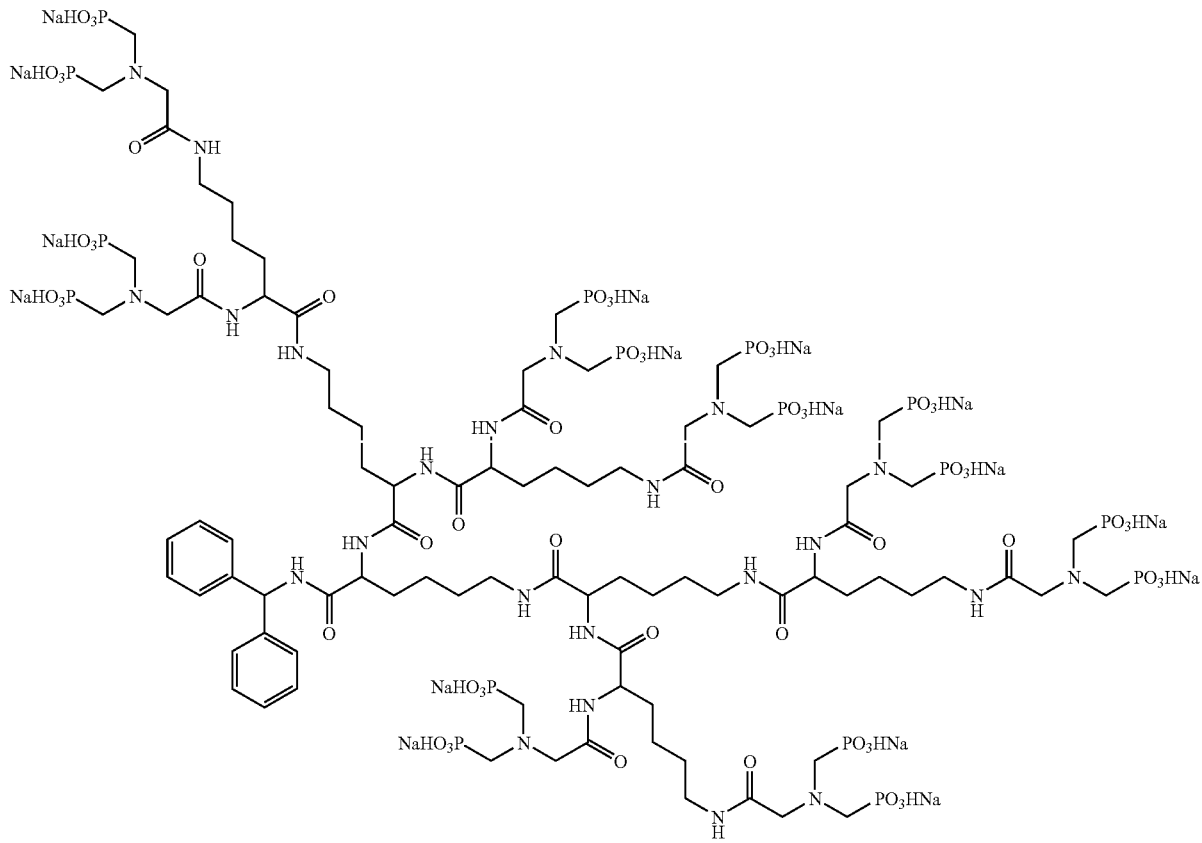

The sodium salt is obtained by adding 1 equivalent of an aqueous soda solution at 0.1955 N per —PO$_3$H$_2$ group present in the molecule obtained in the preceding stage. The dendrimer is isolated in the form of a white powder with a yield of 86% after freeze-drying.

NMR $^{31}$P-{$^{1}$H} (D$_2$O, CD$_3$COCD$_3$) δ=18.5 ppm.

Example 98

Use of Dendrimers with an Aza-Bis-Phosphonic Surface for the Culture of Cells

GC1 dendrimeric compound with an aza-bis-phosphonic surface (Example 36) in its sodium salt form has principally been used for the culture of peripheral blood mononuclear cells:

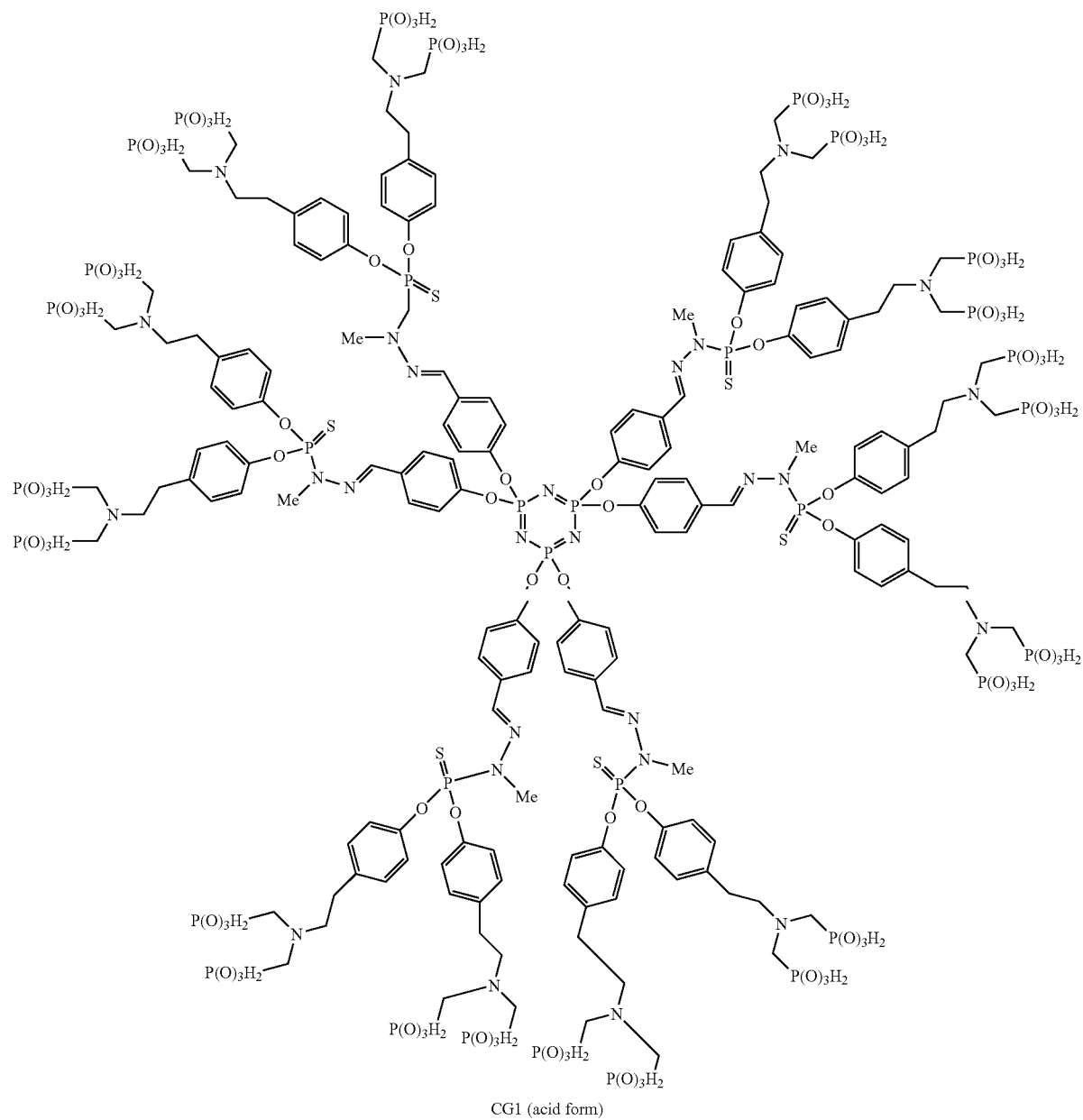
CG1 (acid form)

-continued

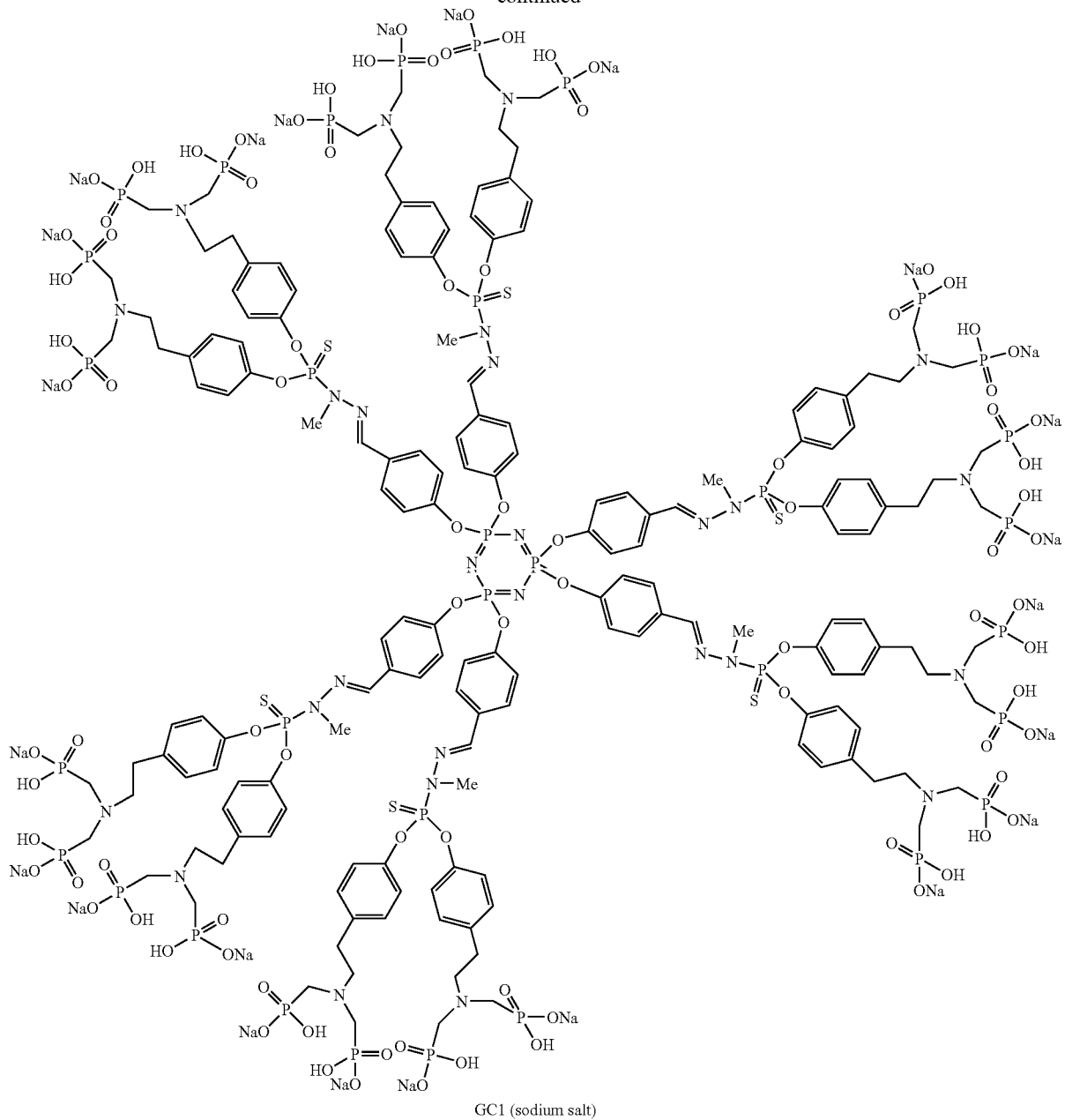

GC1 (sodium salt)

This compound is soluble in saline solutions such as PBS buffers at concentrations less than or equal to 1 mg/ml. Stock solutions of GC1 are prepared in sterile non-pyrogenic PBS (Cambrex Bio Science, Verviers, BELGIUM), for example at a concentration of 2 mM (approximately 1 mg/ml), or 100×, which is then sterilized by filtration on micromembrane at 0.2 μm or irradiation; these solutions are kept at 4° C.

Method of Cell Culture with Dendrimer, for Example GC1

Peripheral blood mononuclear cells (PBMC) obtained from a healthy adult human donor by centrifugation over a density gradient (Ficoll-Hypaque, Amersham Pharmacia Biotech, Upsalla, SWEDEN) are cultured in sterile cell culture flasks at a concentration of 1.5 million cells per ml of culture medium of the RPMI 1640 type, 25 mM Hepes/ Ultraglutamine 1 (Cambrex Bio Science, Verviers, BELGIUM) supplemented with:

i) 1 mM sodium pyruvate (Invitrogen Corporation, Paisley, UNITED KINGDOM)
ii) 100 μg/ml of streptomycin and 100 U/ml of penicillin (Cambrex Bio Science, Verviers, BELGIUM);
iii) 10% by volume of foetal calf serum (Invitrogen Corporation, Paisley, UNITED KINGDOM) decomplemented for 30 minutes at 56° C. (FCS);
iv) 20 μM of GC1 dendrimer solubilized at a concentration of 2 mM in sterile non-pyrogenic PBS;
v) 200 U/ml of human recombinant IL2 (Sanofi-Synthelabo, Paris, FRANCE) is added to the culture medium thus produced.

The culture takes place over several days in an incubator at 37° C., at constant humidity and in an atmosphere of 5% $CO_2$ in air. The culture medium is regularly changed during the culture period, for example by thirds or half of the volume, for example every 3 days at the start, then every 2 days and even every day when the cells are in exponential multiplication phase. As the amplification of the number of cells proceeds, the culture volume is increased in order to maintain the cell concentration between 0.7 and 1.5 million per ml. The renewed culture medium is supplemented with 10% FCS, GC1 dendrimer at 20 µM and human recombinant IL2 at 200 U/ml of the total culture volume. These in vitro cultures last from 15 to 25 days.

Activation and Maintenance in Culture of Monocytes, Purified Starting with PBMCs, Under the Action of GC1 Dendrimer (FIG. 14)

The monocytes purified starting with PBMCs (tri magnetic positive on a column of $CD14^+$ cells, Miltenyi Biotech or StemCell Technologies Inc. systems) are placed in culture under the conditions described previously, but without IL2.

Within 3 to 6 days, the presence of GC1 (20 µM) in the monocyte culture medium leads to morphological modifications (for example enlargement of the monocytes, FIG. 14A) and phenotypic modifications of the cells (for example reduction in the expression of the markers HLA-A, B and C; CD14; HLA-DR measured by flow cytometry using the antibodies anti-HLA A, B and C-PC5: clone G46-2.6, BD Biosciences; anti-CD14-PE: clone RMO52 and anti-HLA DR-FITC: clone Immu-357, Beckman-Coulter) (FIG. 14B).

These morphological and phenotypic modifications lead to an activation of the monocytes in culture in the presence of GC1.

For example, induction of the increase in the phagocytic capacities of monocytes is observed, demonstrated for example by internalization of bacteria (*Mycobacterium bovis* BCG) rendered fluorescent by transfection of a plasmid encoding the Green Fluorescent Protein (GFP) (infection of the monocytes with an Infection Multiplicity of 200 bacteria for one monocyte). The internalization is quantified by flow cytometry (detection of the GFP). The activation of the monocytes is also shown by an increase of the nuclear translocation of the NF-κB transcription factor in the presence of the GC1 dendrimer in the culture medium. The nuclear extracts are prepared with the "Nuclear Extract" kit (Active Motif), the protein concentration of the extracts is measured with the "Micro BCA Protein Assay Reagent Kit" kit (Pierce Biotechnology), the quantification of NF-κB in the protein nuclear extracts is carried out with the "TransAM NF-κB p50 Chemi" kit (Active Motif) by luminometry (Mithras LB940, Berthold Biotechnologies) (FIG. 14C).

This activation of the monocytes in culture with the GC1 dendrimer finally results in a maintenance of the monocytes in culture: the count of the monocytes in culture with the GC1 dendrimer is always greater than that of the monocytes in culture without the GC1 dendrimer. This maintenance of the monocytes in culture under the action of GC1 correlates with the reduction in the percentage of monocytes in apoptosis in the culture (measured by the percentage of annexin V-positive cells in flow cytometry, "Annexin V-FITC Detection Kit I", BD Biosciences) (FIG. 14D). The GC1 dendrimer has an anti-apoptotic effect on the human monocytes in culture in vitro.

Phenotype of the Cells Amplified by Culture with the GC1 Dendrimer (FIGS. 1A-1G)

During the culture (t0) then after two weeks of culture with the GC1 dendrimer, the phenotyping of the cells is carried out by immunological marking and revealed by flow cytometry (XL Epics cytometer, Beckman-Coulter-Immunotech, Marseille, FRANCE). In the cultures with the GC1 dendrimer it is observed with all the donors tested that the cells in culture become mainly NK cells, which only represent a minority at the start of the culture. The example presented comprises 23% NK cells at the start and 76% NK cells after two weeks of in vitro culture with GC1. These cells are identified by their $CD3^-CD16^+CD56^+$ phenotype (antibodies anti-CD3-FITC/anti-CD56-PC5: clones UCHT1/NKH-1, anti-CD16-PE: clone 3G8, Beckman-Coulter-Immunotech, Marseille, FRANCE). Their identification is confirmed by the presence of NCR NKp30 and NKp44 and of NKR NKG2D and CD85j (antibodies anti-NKp30: clone Z25, anti-NKp44-PE: clone Z231, anti-NKG2D: clone ON72, anti-CD85j (ILT2): clone HPF1, Beckman-Coulter-Immunotech, Marseille, FRANCE), various specific markers of human NK cells. Moreover, these NK cells amplified with GC1 unexpectedly express the Toll-like receptor-2 (TLR2) detected by flow cytometry with an anti-TLR2-PE antibody (clone TL2.1, BioLegend, San Diego, Calif., USA).

Lymphocyte Compositions after Fifteen Days of In Vitro Culture of PBMC with the GC1 Dendrimer (FIGS. 2A-2D)

The PBMCs obtained from a healthy adult human donor are cultured for 15 days with GC1 then counted by total counting of the living cells ($N_{tot}$). The total population of each culture is composed of various sub-populations identified by flow cytometry: only NK cells, γδ T and $CD8^+$ αβ T lymphocytes (antibodies anti-TCR-Vγ9-FITC: clone IMMU 360, anti-CD8-PE: clone B9.11, Beckman-Coulter-Immunotech, Marseille, FRANCE), in varying proportions according to the donors. The number of cells of each sub-type is obtained by the following calculation:

[number of cells in each sub-population=$N_{tot}$×% of the sub-population in this culture]

The counts for the sub-populations constituting the cell lines obtained with GC1 are compared with the same counts carried out at the start of the culture (D1) and in the cultures produced under the same conditions without GC1 dendrimer. Using the cells from all the donors tested, the lymphocyte culture with GC1 favours the proliferation of living NK cells.

These results demonstrate that the GC1 dendrimer has general immuno-stimulant properties for human lymphocytes.

Figure 1A:
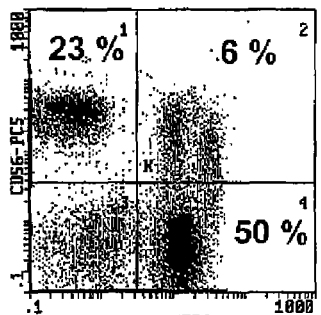
FIG. 1A, FIG. 1B, FIG. 1C, FIG. 1D, FIG. 1E, FIG. 1F, FIG. 1G
Figure 1B:
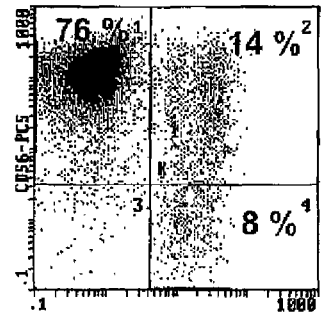
Figure 1C:
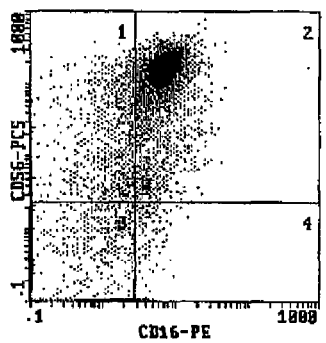
Figure 1D:
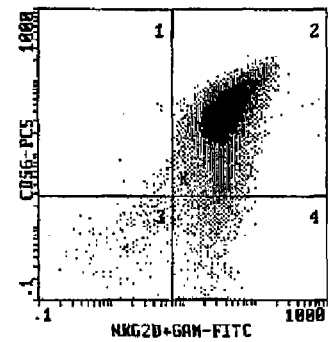
Figure 1E:
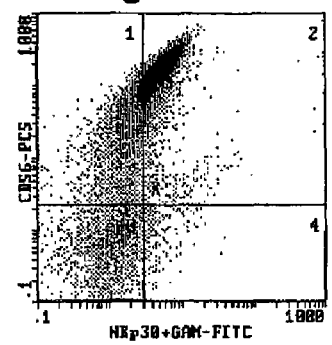
Figure 1F:
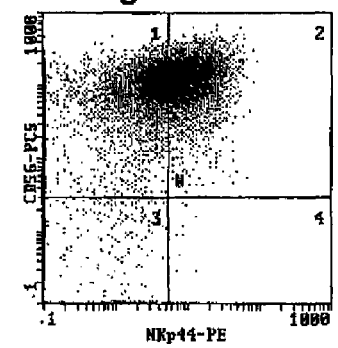
Figure 1G:
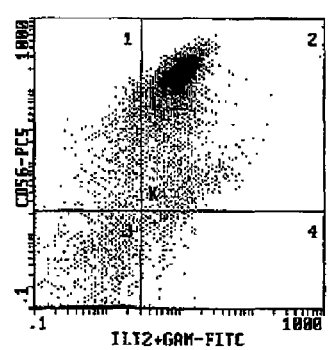
Figure 3:
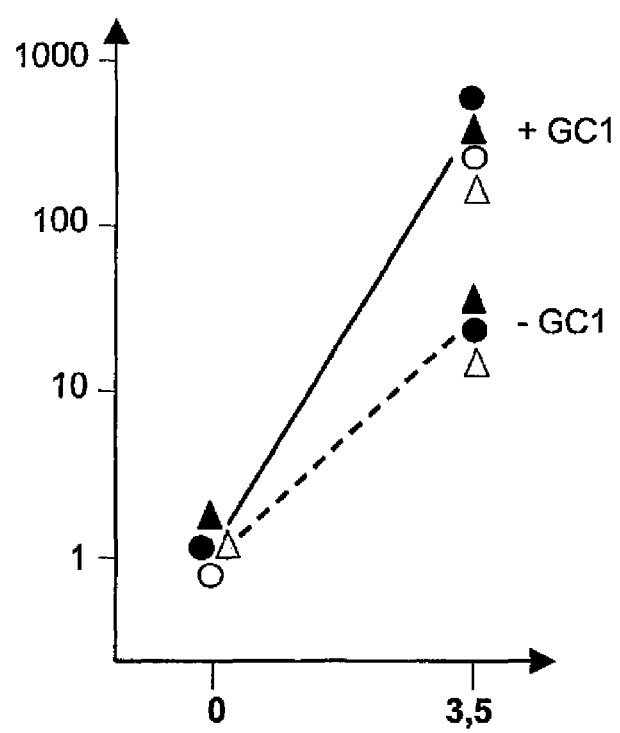
FIG. 3

Amplification of NK Cells Starting with PBMCs Cultivated In Vitro with the GC1 Dendrimer (FIG. 3)

The NK cells obtained starting with PBMCs from healthy donors cultured under the conditions described previously are counted, at the start of the experiment then at the end of 3.5 weeks of culture. The amplification of the number of NK cells is compared with that of the NK cells obtained starting with PBMCs cultured under the same conditions but without GC1 dendrimer (each point represents a different donor). These results demonstrate that GC1 dendrimer has immuno-stimulant properties for human NK cells.

Amplification of NK Cells by In Vitro Culture with the GC1 Dendrimer Starting with PBMCs from Cancer Patients (FIG. 11)

Moreover, similar results were obtained starting with PBMCs from cancer patients suffering from multiple myeloma cultured under the conditions described previously at the end of 2.5 weeks of culture. The amplification of the number of NK cells in the presence of GC1 (full circle) is compared with that obtained starting with PBMCs cultured under the same conditions but without dendrimer (empty circle) in the case of 14 healthy donors and 14 cancer patients.

Amplification of NK Cells Starting with PBMCs Cultured In Vitro with the GC1 Dendrimer in the Presence of Different Cytokines (FIGS. 12A, 12B)

The results obtained above were confirmed by combining the addition of GC1 with various cytokines. Thus, the NK cells obtained starting with PBMCs from healthy donors were cultured with GC1 in the presence: of IL2 (200 U/ml or 8 ng/ml), of IL15 (10 ng/ml), or of a mixture of IL2 (200 U/ml or 8 ng/ml) and of IL15: (10 ng/ml)).

The results obtained, representative of 4 donors, demonstrate that IL15 alone, like IL2 alone, or IL15 and IL2 combined allow an amplification of the NKs in the presence of GC1.

Figure 4A:
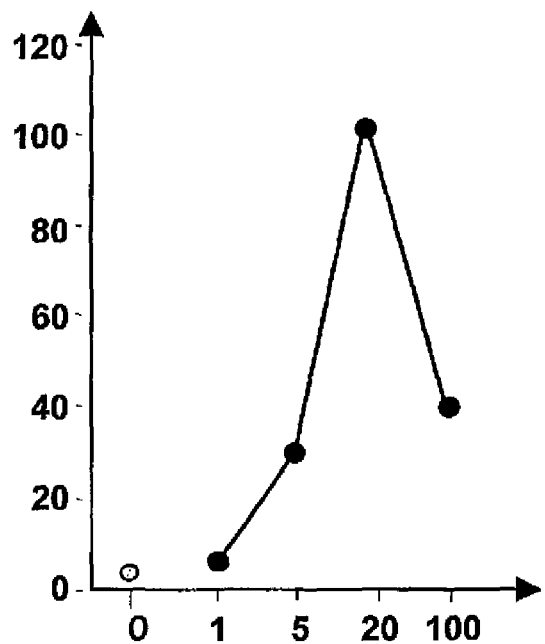
FIG. 4A, FIG. 4B
Figure 4B:
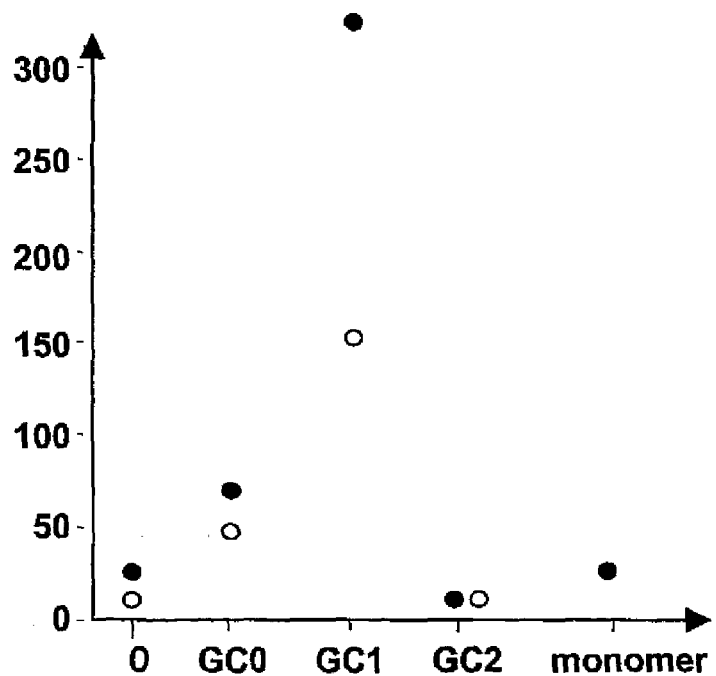

Bioactivities of Different Dendrimers on Lymphoid Cells, in Particular Human NK (FIGS. 4A-4B)

The titration of the active concentrations of GC1 dendrimer tested on the in vitro amplification of human NK cells in a range of concentrations from 1 to 100 µM shows an optimum at 20 µM (FIG. 4A). The dendrimers carrying the same azabisphosphonic functions at the surface, but of successive generation (GC0<GC1<GC2) have the same immunostimulant properties as GC1 (FIG. 4B), in particular at a concentration of 20 µM, on the in vitro amplification of human NK cells (culture conditions described previously). The phenolazabisphosphonic monomer derived from tyramine is inactive in the same tests.

Other dendrimers, in particular those of Examples 5, 15, 26, 49, 71 and 76 have been tested compared with the GC1 dendrimer (Example 36), under the conditions described previously, and with the culture medium without dendrimer (point 0 in FIG. 13). The percentage and the total number of NK cells obtained after 2.5 weeks of culture have been determined for each of the dendrimers tested (FIG. 13).

Figure 5A:
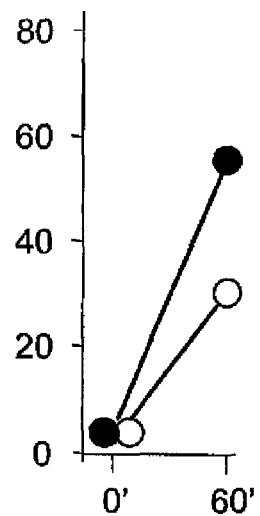
FIG. 5A, FIG. 5B, FIG. 5C
Figure 5B:
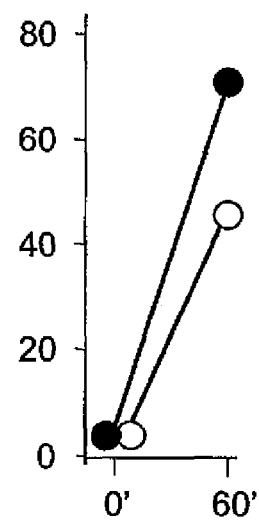
Figure 5C:
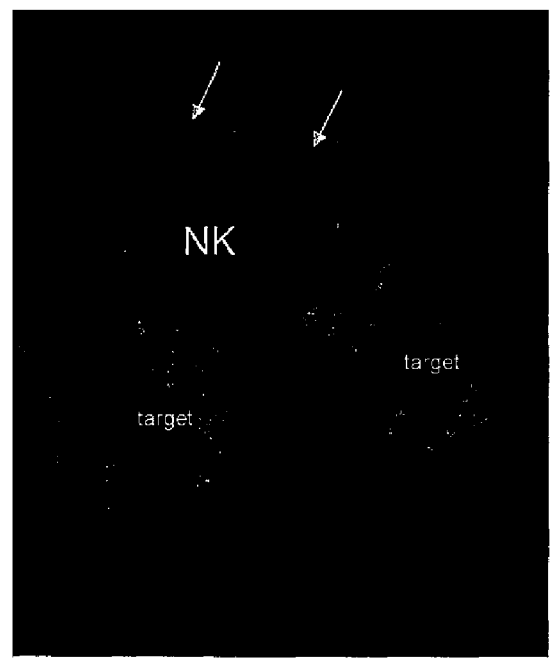

Functionality of the NK Cells Obtained with the GC1 Dendrimer:

1. Intact Capacity to Establish Interactions Between Cells (Trogocytosis) (FIGS. 5A-5C)

Normal lymphoid cells actively attach to the surface of their target (phenomenon called trogocytosis) before any effector response. The NK cells obtained in vitro thanks to GC1 dendrimer and labelled with the intracellular stain CMTMR (Molecular Probes, Eugene, Oreg., USA) (incubate 5 million cells for 30 minutes at 37° C. in 1 ml of supplemented RPMI 1640 medium to which 1 µl of CMTMR is added, then rinsed 5 times with 10 ml of supplemented RPMI 1640 medium) are incubated with target cancer cells (B cell lymphoma (FIG. 5A) and colic carcinoma (FIG. 5B)) having incorporated the fluorescent green membrane marker PKH 67 (Sigma-Aldrich, Saint-Louis, Mo., USA) (incubate 5 million cells for 5 minutes at room temperature in 250 µl of C Sigma-Aldrich diluent to which PKH 67 is added at 1/500, then add 250 µl of FCS, leave to incubate for 1 minute at room temperature, then rinse 3 times with 10 ml of supplemented RPMI 1640 medium). At the end of one hour of incubation at 37° C. in a multi-well plate (96 wells with a round bottom) ($6\times10^5$ cells of each sort in 100 µl of supplemented RPMI 1640, with 10% of FCS; the multi-well plate is centrifuged for 2 minutes at 800 rpm) in an incubator at 37° C., at constant humidity and in a atmosphere of 5% $CO_2$ in air, the complexed cells are separated by washing with PBS containing 0.5 mM of EDTA then the acquisition of the PKH 67 marker (trogocytosis or synaptic transfer) by the NK cells is measured by flow cytometry (FACSCalibur and CellQuest Software, BD Biosciences, Mountain View, Calif., USA) (measurement of the average green fluorescence intensity of all the NK cells at time 0 then at the end of 60 minutes of incubation). The NK cells obtained with the GC1 dendrimer have a functional trogocytosis such as that of the normal NK cells on two distinct types of cancer cells (B cell lymphoma, carcinoma).

After the synaptic transfer, the cells are resuspended delicately, deposited on a glass plate covered with poly-L-lysine (Sigma-Aldrich, Saint-Louis, Mo., USA) for an incubation of 5 minutes at 37° C. After fixation by PBS containing 4% para-formaldehyde, the cells are washed and covered with PBS containing 90% glycerol and 2% 1-4-diazabicyclo (2.2.2) octane (DABCO, Sigma-Aldrich, Saint-Louis, Mo., USA) and cover slipped. The confocal microscopy image obtained with a LSM410 device (Zeiss, Jena, GERMANY) (arrows, FIG. 5C) shows the trogocytosis of (target) green cancer cells by the NK cells obtained with the GC1 dendrimer (cytoplasm in red) during their interaction.

These results demonstrate that the culture with the GC1 dendrimer does not affect the interaction capacity of the NK cells obtained.

Figure 6A:
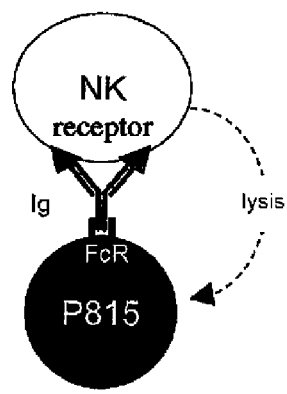
FIG. 6A, FIG. 6B
Figure 6B:
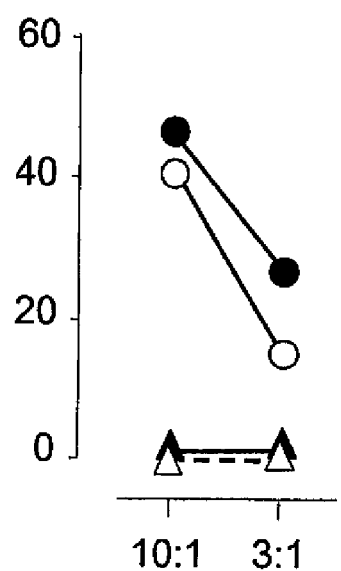

Functionality of the NK Cells Obtained with GC1 Dendrimer:

2. Functionality of the NKp30 and NKG2D Activator Receptors (Redirected Lysis) (FIG. 6A-6B)

The functionality of the principle lysis activator receptors expressed at the surface of the NK cells produced with the GC1 dendrimer is tested by the standard redirected lysis test. Briefly, this test involves triggering the killing activity of the NK cells by means of antibodies specific to these activator receptors (FIG. 6A), the killing activity then takes place on specific cells: P815 murine mastocytoma (cultured in RPMI 1640, 25 mM Hepes/Ultraglutamine 1 supplemented with 1 mM sodium pyruvate, 100 µg/ml streptomycin and 100 U/ml penicillin, 10% by volume FCS) which are not killed if the NK cells are not activated. The P815 target cells are charged with $^{51}Cr$ (chromium sulphate—$^{51}Cr$ at 10 mCi/ml, ICN Biomedicals, Costa Mesa, Calif., USA) (2 million cells are incubated with 20 µl of chromium sulphate, 1 h at 37° C., then rinsed 3 times with 1 ml of culture medium). Then, 3000 charged target cells are brought together, for 4 hours (in an incubator at 37° C., at constant humidity and in an atmosphere of 5% $CO_2$ in air), with human NK cells and the following antibodies: no antibodies, non-specific antibodies: 4 µg/ml control isotype (mouse IgG1: clone 679.1Mc7, Beckman-Coulter-Immunotech, Marseille, FRANCE), 4 µg/ml anti-NKG2D (clone ON72, Beckman-Coulter-Immunotech, Marseille, FRANCE), 4 µg/ml anti-NKp30 (clone AZ20, Innate Pharma, Marseille, FRANCE). The incubation takes place in a multi-well plate (96 wells with a round bottom) in a total volume of 200 µl, after having centrifuged for 2 minutes at 800 rpm.

The ratios of effector cells to target cells (E:T) are 10 to 1 here (i.e. 30000 effectors and 3000 targets) and 3 to 1 (or 9000 effectors and 3000 targets), respectively.

In each test the release of $^{51}Cr$ from the targets is measured in 100 µl of culture medium, finding the average of 3 identical experiments. For each experimental condition (antibody used) the following radioactivity (cpm) is measured:
 the MR: total quantity of $^{51}Cr$ incorporated by the target cells alone;
 the SR: spontaneous release of $^{51}Cr$ by the targets alone;
 X: release of $^{51}Cr$ measured in the test.

The percentage of specific lysis in each experiment is obtained using the following formula:

$$[\text{specific lysis (\%)} = (X-SR)/(MR-SR)]$$

The results presented (FIG. 6B) demonstrate the functionality of the NKG2D and NKp30 activator receptors expressed by an NK line obtained with GC1.

Figure 7A:
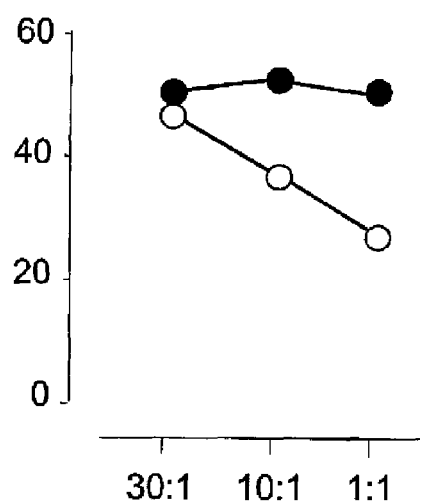
FIG. 7A, FIG. 7B, FIG. 7C
Figure 7B:
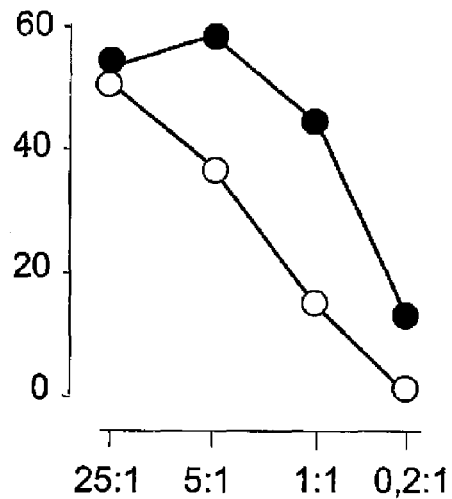
Figure 7C:
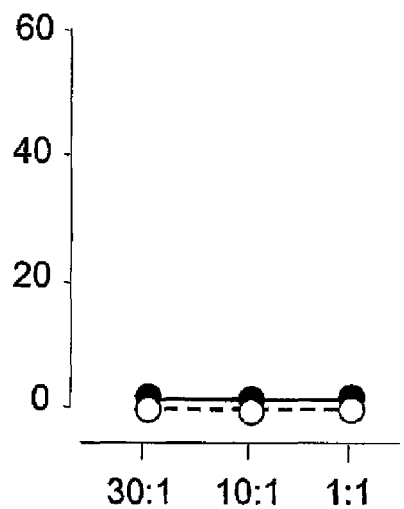

Functionality of the NK Cells Obtained with the GC1 Dendrimer:

3. Unchanged Control of their Cytolytic Activity (FIGS. 7A-7C)

The NK cells obtained with the GC1 dendrimer normally control their direct cytotoxic activity vis-à-vis potential target cells: they do not lyse the autologous lymphocytes at rest (identical CMH haplotype cells of class I), but very effectively lyse the standard K562 and Daudi targets (cells of chronic myeloid leukemia and Burkitt's lymphoma, respectively, both deficient in class I CMH molecules). The direct lysis (without another addition of antibodies) of the specified target cells (Burkitt's Daudi lymphoma, LMC K562 or autologous PBMCs of the NKs) is measured as in the preceding test, with E:T ratios comprised between 30:1 and 0.2:1. The results presented demonstrate that the culture with the GC1 dendrimer does not affect the cytolytic capacity of the NK cells obtained.

Functionality of the NK Cells Obtained with GC1 Dendrimer:

4. Broad Spectrum of Antitumour Activity (FIG. 8)

The NK cells obtained with GC1 exert their cytotoxicity vis-à-vis a broad spectrum of target cancer cells divided into leukemias and carcinomas. The lysis of the target cells is measured as described previously by release of $^{51}Cr$ with E:T ratios of 1:1 (white bars) and 10:1 (grey bars) and it is expressed as a percentage of specific lysis. These results demonstrate that the culture with the GC1 dendrimer does not affect the cytolytic capacity of the NK cells obtained vis-à-vis a broad spectrum of cancer cells.

Example 99

Evaluation of the In Vivo Toxicity of Dendrimers with an Aza-Bis-Phosphonic Surface A suspension of GC1 at 1 mg/ml was carried out in non-pyrogenic PBS and the solution obtained was sterilized by filtration on a membrane with a 0.22 µm pore size.

The suspension was administered by intravenous route at a rate of 0 (control), 10, 100 or 1000 µg per animal every three days over 120 days respectively to 4 groups of 5 BALB/c mice.

No toxicity was observed.

Example 100

Use of NK Cells Amplified by Dendrimers with an Aza-Bis-Phosphonic Surface for the Treatment of Cancers The animal model chosen is that of immunodeficient mice having received a xenograft of human tumour cells.

Male and female immunodeficient mice, more than 3 months old, were raised in a strictly sterile environment, in an isolator ventilated with filtered and sterilized air, at 22° C. and 40% humidity, in a day-12 h/night-12 h cycle. The cages, drinking tubes and water were sterilized in an autoclave at 120° C. for 30 minutes and the food as well as the bedding was treated by γ-irradiation. All handling took place in an aseptic manner under a laminar flow hood.

The mice were subjected to a general anesthesia by i.p. injection of 0.3 to 0.4 ml of hypnomidate at 2 mg/ml. $1\times10^7$ K 562 leukemia tumour cells in suspension in 200 µl of PBS were then injected sub-cutaneously, into the back of the mice. When the tumour reaches approximately 1 cm in length (approximately 2 to 3 weeks after the injection), human NK cells obtained using human PBMCs cultured in the presence of GC1 compound as described in Example 49 were administered by intravenous route close to the tumour at a rate of 0 (control), $10^4$, $10^6$ or $10^8$ cells per animal respectively to 4 groups of 5 mice. The procedure was repeated 3 to 5 weeks after the first administration of cells.

The volume of the tumour was measured regularly.

The first results obtained indicate that the administration of the NK cells prepared using the GC1 compound is capable of inhibiting the tumour growth.

Example 101

Use of Dendrimers with an Aza-Bis-Phosphonic Surface for the Treatment of Cancers The animal model chosen is that of immunodeficient mice having received a xenograft of human tumour cells.

Male and female immunodeficient mice, more than 3 months old, were raised in a strictly sterile environment, in an isolator ventilated with filtered and sterilized air, at 22° C. and 40% humidity, in a day-12 h/night-12 h cycle. The cages, drinking tubes and water were sterilized in an autoclave at 120° C. for 30 minutes and the food as well as the bedding are treated by γ-irradiation. All handling took place in an aseptic manner under a laminar flow hood.

The mice were subjected to a general anesthesia by i.p. injection of 0.3 to 0.4 ml of hypnomidate at 2 mg/ml. $1\times10^7$ K 562 leukemia tumour cells in suspension in 200 µl of PBS were then injected sub-cutaneously, into the back of the mice. On the 10th day from grafting the length of the tumour reaches approximately 1 cm.

A suspension of GC1 at 1 mg/nil was carried out in non-pyrogenic PBS and the solution obtained was sterilized by filtration on a membrane with a 0.22 µm pore size.

On the tenth day from the grafting, the suspension was administered by intravenous route at a rate of 0 (control), 10, 100 or 1000 µg per animal every three days over 120 days respectively to 4 groups of 5 mice.

The volume of the tumour was measured regularly.

The first results obtained indicate that the administration of GC1 is capable of inhibiting the tumour growth.

Example 102

Use of Fluorescent Dendrimers with an Aza-Bis-Phosphonic Surface for the Marking of Lymphocytes The fluorescent dendrimer of Example 89 (GC1F) was introduced into an in vitro culture of total lymphocytes and the mixture was incubated for 4 h, 24 h or 15 days. The cells were then analyzed by flow cytometry: the lymphocytes were selected on the basis of their morphology (FIG. 10A), then analyzed for their fluorescence due to the fluorescent dendrimer (FIG. 10B).

The comparison of the fluorescence of lymphocytes maintained in the presence of IL2 alone, of IL2+GC1F, or of IL2+GC1 (non-fluorescent) (FIG. 10B) indicates an acquisition of the fluorescence associated with the dendrimers on the lymphocytes after fifteen days of culture, whereas no signal was detected after four hours of coincubation, and a only very small shift could be observed after twenty four hours of coincubation.

The invention claimed is:
1. A method for activating or stimulating growth of peripheral blood mononuclear cell (PBMC) cultures originating from differentiation of hematopoietic stem cells in culture, comprising administering to said culture dendrimers having monophosphonic or bisphosphonic terminations, said terminations comprising a terminal group being represented by the formula:

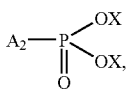

wherein,
A$_2$ represents a single bond or a linear, branched or cyclic hydrocarbon chain with 1 to 6 members; and
X represents —H, -alkyl, -aryl, -alkaryl, or -aralkyl radical, or a corresponding salt, said salt being formed by a combination of a monophosphonic or bisphosphonic termination and a cation.

2. The method according to claim 1, wherein the dendrimers are of generation n and include a central core § having a valency of m, which can establish m−2 bonds when m is greater than 2, or m−1 bonds when m is greater than 1, or m bonds with linkage chains, identical to each other, m representing an integer from 1 to 20, and n representing an integer from 0 to 12, said linkage chains comprising:

generation chains attached in a tree-like structure around the core on each of the bonds, and when n is greater than or equal to 1, then a generation chain of a given generation is linked to:
a generation chain of the generation immediately below the given generation, or to the core when the given generation is 1, and to
at least 2 generation chains of the generation immediately above the given generation, or optionally to at least one intermediate chain when the given generation is n,
a terminal group being attached to the end of each generation chain of generation n, or optionally to the end of each intermediate chain; or
intermediate chains attached around the core on each of the bonds, and when n is 0, then a terminal group is attached to an end of each intermediate chain,
said terminal group being represented by the formula:

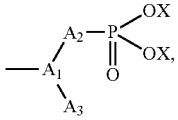

where
A$_1$ represents N, a P=Y group, where Y represents O, S, or any atom, an N—R group, or a C—R group, R representing H or a linear, branched or cyclic hydrocarbon chain with 1 to 16 members, optionally containing one or more heteroatoms, said heteroatoms being selected from the group consisting of oxygen, sulphur, nitrogen, phosphorus, silicon and one or more double or triple bonds, each of said members being optionally substituted by at least one substituent selected from the group consisting of a hydroxyl group, an —NR'R" group, an alkoxy group of 1 to 16 carbon atoms, an alkyl group of 1 to 16 carbon atoms, a halogen atom, an —NO$_2$ group, a —CN group, a —CF$_3$ group, an aryl group of 6 to 24 carbon atoms, and an aralkyl group of 7 to 16 carbon atoms, R' and R" representing independently of each other H or an alkyl group of 1 to 16 carbon atoms, an aryl group of 6 to 24 carbon atoms or an aralkyl group of 7 to 16 carbon atoms;
A$_2$ represents a single bond or a linear, branched or cyclic hydrocarbon chain with 1 to 6 members, each of said members optionally comprising one or more heteroatoms, said heteroatoms being selected from the group consisting of a sulphur, oxygen, phosphorus and nitrogen atom, and being optionally substituted by at least one substituent being selected from the group consisting of H, an alkyl group of 1 to 16 carbon atoms, a halogen, an —NO$_2$ group, an —NRR' group, a —CN group, a —CF$_3$ group, a hydroxyl group, an alkoxy group of 1 to 16 carbon atoms, an aryl or heteroaryl group of 1 to 24 carbon atoms, the heteroelement being selected from the group consisting of oxygen, nitrogen and sulphur, and an aralkyl group of 7 to 16 carbon atoms, R and R' representing independently of each other H or a linear, branched or cyclic hydrocarbon chain with 1 to 16 members, optionally comprising one or more heteroatoms, said heteroatoms being selected from the group consisting of oxygen, sulphur, nitrogen, phosphorus, silicon and one or more double or triple bonds, each of said members being optionally substituted by at least one substituent selected from the group consisting of a hydroxyl group, an —NR"R"' group, an alkoxy group of 1 to 16 carbon atoms, an alkyl group of 1 to 16 carbon atoms, a halogen atom, an —NO$_2$ group, a —CN group, a —CF$_3$ group, an aryl group of 6 to 24 carbon atoms, and an aralkyl group of 7 to 16 carbon atoms, R" and R"' representing independently of each other H or an alkyl group of 1 to 16 carbon atoms, an aryl group of 6 to 24 carbon atoms or an aralkyl group of 7 to 16 carbon atoms;
A$_3$ represents H, or a linear, branched or cyclic hydrocarbon chain with 1 to 6 members, each of said members optionally comprising a heteroatom, said heteroatom being selected from the group consisting of sulphur, nitrogen, phosphorus and silicon, each member being able to be optionally substituted by at least one group selected from the group consisting of a hydroxyl group, an —NR"R"' group, an alkoxy group of 1 to 16 carbon atoms, an alkyl group of 1 to 16 carbon atoms, a halogen atom, an —NO$_2$ group, a —CN group, a —CF$_3$ group, an aryl group of 6 to 24 carbon atoms, and an aralkyl group of 7 to 16 carbon atoms, R" and R"' representing independently of each other H, an alkyl group of 1 to 16 carbon atoms, an aryl group of 6 to 24 carbon atoms, an aralkyl group of 7 to 16 carbon atoms or

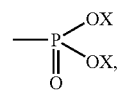

or
A$_3$ represents

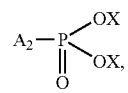

each A$_2$ being identical or different, each OX, identical or different for each phosphonic group, represents OH, Oalkyl, where the alkyl group comprises from 1 to 16 carbon atoms, Oaryl, where the aryl group comprises from 6 to 24 carbon atoms, Oaralkyl, where the aralkyl group comprises from 7 to 24 carbon atoms, Oalkylaryl, where the alkylaryl group comprises from 7 to 24 carbon atoms, OSiR'$_1$R'$_2$R'$_3$, where R'$_1$, R'$_2$ and R'$_3$, identical or different, represent an alkyl group of 1 to 16 carbon atoms, $O^-M^+$, where $M^+$ is a cation of elements of group IA, IB, IIA, IIB or IIIA, IIIB of the periodic table of elements, $M^+$ is selected from the group consisting of cations of sodium, potassium, copper, calcium, barium, zinc, magnesium, lithium and aluminium atoms, hydrocarbon groups of 1 to 100 carbon atoms, nitrogenous groups of 0 to 100 carbon atoms, $NR_1R_2R_3R_4^+$, where independently of each other $R_1$, $R_2$, $R_3$ and $R_4$ represent H or a linear, branched or cyclic hydrocarbon chain with 1 to 16 members, optionally comprising one or more heteroatoms, said heteroatoms being selected from the group consisting of oxygen, sulphur, nitrogen, phosphorus, silicon and one or more double or triple bonds, each of said members being optionally substituted by at least one substituent selected from the group consisting of a hydroxyl group, an —NR"R'" group, an alkoxy group of 1 to 16 carbon atoms, an alkyl group of 1 to 16 carbon atoms, a halogen atom, an —$NO_2$ group, a —CN group, a —$CF_3$ group, an aryl group of 6 to 24 carbon atoms, and an aralkyl group of 7 to 16 carbon atoms, R" and R'" representing independently of each other H or an alkyl group of 1 to 16 carbon atoms, an aryl group of 6 to 24 carbon atoms or an aralkyl group of 7 to 16 carbon atoms;

said central core § representing a group comprising from 1 to 500 atoms, and optionally comprising one or more heteroatoms, said heteroatoms being selected from the group consisting of oxygen, sulphur, nitrogen, phosphorus and silicon.

3. The method according to claim 2, wherein the core § establishes m bonds with m identical linkage chains comprising:

either generation chains attached in a tree-like structure around the core on each of the bonds, an end of each chain generation furthest from a central core being attached either to a terminal group or to an intermediate chain, an end of each intermediate chain being attached to a terminal group, or intermediate chains attached around the core on each of the bonds, an end of each intermediate chain being attached to a terminal group.

4. The method according to claim 2, wherein the core establishes m−2 or m−1 bonds, m representing an integer from 3 to 20, with respectively m−2 or m−1 identical linkage chains comprising:

either generation chains attached in a tree-like structure around the core on each of the bonds, an end of each chain generation furthest from a central core being attached either to a terminal group or to an intermediate chain, and an end of each intermediate chain being attached to a terminal group, or intermediate chains attached around the core on each of the bonds, an end of each intermediate chain being attached to a terminal group; and one or two remaining bonds being attached to linkage groups, identical or different, optionally linked together, by means of a covalent bond, comprising:

either part of the linkage chains defined above, or a hydrogen atom, or hydrocarbon groups comprising from 1 to 500 carbon atoms, said hydrocarbon groups comprising H or a linear, branched or cyclic hydrocarbon chain having 1 to 200 members, optionally comprising one or more double or triple bonds, each of said members being optionally selected from the group consisting of a heteroatom, said heteroatom being selected from the group consisting of a nitrogen, oxygen, phosphorus, silicon and sulphur atom, an aryl group of 6 to 24 carbon atoms, a heteroaryl group of 1 to 24 carbon atoms, a carboxyl group, a >C=NR group, each member optionally substituted by at least one substituent selected from the group consisting of a hydroxyl group, an —NR"R'" group, an alkoxy group of 1 to 16 carbon atoms, an alkyl group of 1 to 16 carbon atoms, a halogen atom, an —$NO_2$ group, a —CN group, a —$CF_3$ group, an aryl group of 6 to 24 carbon atoms, and an aralkyl group of 7 to 16 carbon atoms, R" and R'" representing independently of each other H or an alkyl group of 1 to 16 carbon atoms, an aryl group of 6 to 24 carbon atoms or an aralkyl group of 7 to 16 carbon atoms, the first member of said hydrocarbon chain being oxygen or nitrogen.

5. The method according to claim 2, wherein the generation chains are selected from the group consisting of a linear, branched or cyclic hydrocarbon chain having 1 to 12 members, optionally comprising one or more double or triple bonds, each of said members being optionally selected from the group consisting of a heteroatom, said heteroatom being selected from the group consisting of nitrogen, oxygen, sulphur, phosphorus and silicon, an aryl group of 6 to 24 carbon atoms, a heteroaryl group of 1 to 24 carbon atoms, the heteroelement being selected from the group consisting of oxygen, nitrogen and sulphur, a carboxyl group, a >C=NR group, each member being optionally substituted by at least one substituent selected from the group consisting of an alkyl group of 1 to 16 carbon atoms, a halogen atom, an —$NO_2$ group, an —NRR' group, a —CN group, a —$CF_3$ group, a hydroxyl group, an alkoxy group of 1 to 16 carbon atoms, an aryl group of 6 to 24 carbon atoms, and an aralkyl group of 7 to 16 carbon atoms, R and R' representing independently of each other H or an alkyl group of 1 to 16 carbon atoms, an aryl group of 6 to 24 carbon atoms, or an aralkyl group of 7 to 16 carbon atoms.

6. The method according to claim 2, wherein the intermediate chains are groups corresponding to the formula:

-J-K-L-, where,

J represents an oxygen or sulphur atom, or an —NR— group;

K represents an aryl group of 6 to 24 carbon atoms, a heteroaryl group of 1 to 24 carbon atoms, the heteroelement being selected from the group consisting of oxygen, nitrogen and sulphur, an alkyl group of 1 to 16 carbon atoms, each being able to be optionally substituted by a halogen atom or an —$NO_2$, —NRR', —CN, —$CF_3$, —OH group, an alkyl group of 1 to 16 carbon atoms, an aryl group of 6 to 24 carbon atoms, or an aralkyl group of 7 to 16 carbon atoms; and L represents a linear, branched or cyclic hydrocarbon chain with 0 to 10 members, optionally comprising one or more double or triple bonds, each of said members optionally being able to be a heteroatom, said heteroatom being selected from the group consisting of oxygen, sulphur, nitrogen, phosphorus and silicon, each member being able to be optionally substituted by at least one substituent selected from the group consisting of an alkyl group of 1 to 16 carbon atoms, a halogen, an oxygen atom, —$NO_2$, —NRR', —CN, —$CF_3$, —OH, an alkoxy group of 1 to 16 carbon atoms, an aryl group of 6 to 24 carbon atoms, and an aralkyl group of 7 to 16 carbon atoms, R and R' representing independently of each other H, an alkyl group of 1 to 16 carbon atoms, an aryl group of 6 to 24 carbon atoms, or an aralkyl group of 7 to 16 carbon atoms.

7. The method according to claim 2, wherein the core is selected from the group consisting of:

a nitrogen or silicon atom;

a group of formula

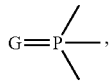

wherein G represents an oxygen, nitrogen, sulphur, selenium, tellurium atom or an =NR group, R representing H or an alkyl group of 1 to 16 carbon atoms, an aryl group of 6 to 24 carbon atoms, an aralkyl group of 7 to 16 carbon atoms, a thiophosphoryl group of formula

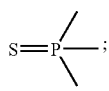

a bis-phenyloxy group of formula

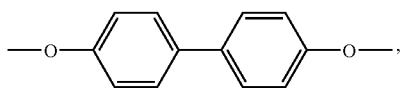

a 1,2-diamino-ethane group of formula

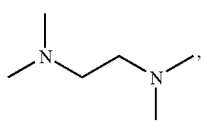

a 1,4-diamino-butane group of formula

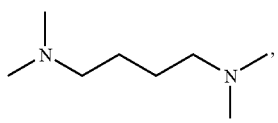

a cyclotriphosphazene group of formula

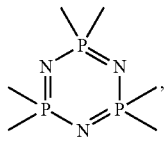

also denoted $N_3P_3$ or $P_3N_3$, and a cyclotetraphosphazene group of formula

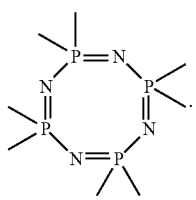

also denoted $N_4P_4$ or $P_4N_4$.

8. The method according to claim 1, wherein the dendrimers correspond to a structure PAMAM, DAB or PMMH.

9. The method according to claim 5, wherein the dendrimers with monophosphonic or bisphosphonic terminations correspond to the following general formula (1a):

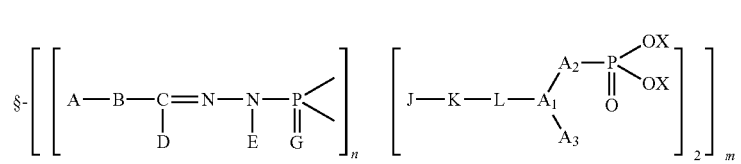

(1a)

where n represents an integer from 0 to 3, and:

when n=0, formula (1a) corresponds to the following formula (2a),

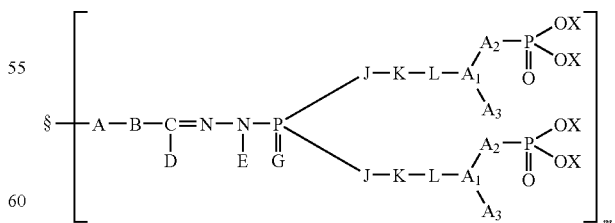

(2a)

when n=1, formula (1a) corresponds to the following formula (3a),

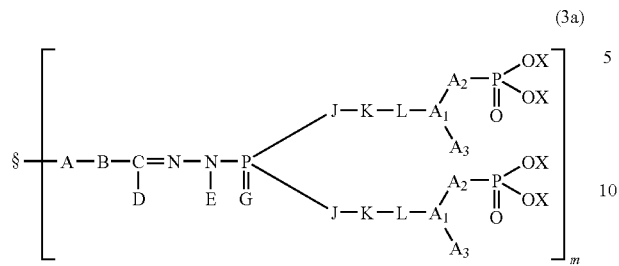
(3a)
when n=2, formula (1a) corresponds to the following formula (4a),
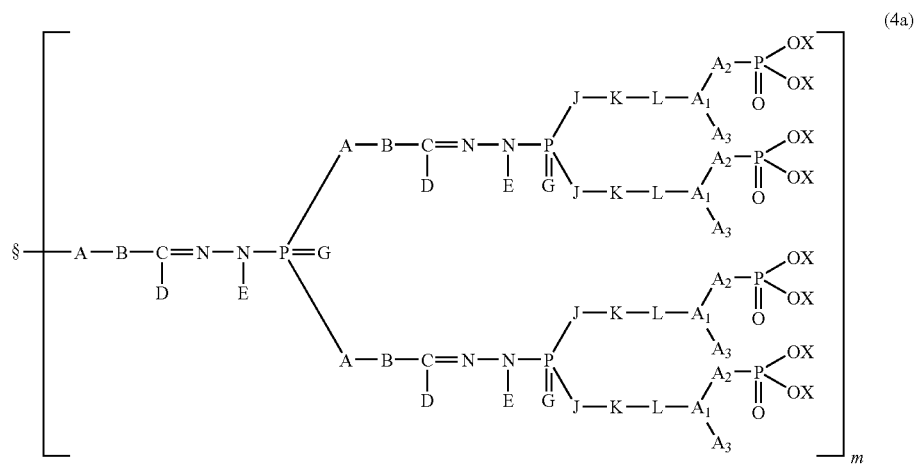
and when n=3, formula (1a) corresponds to the following formula (5a),
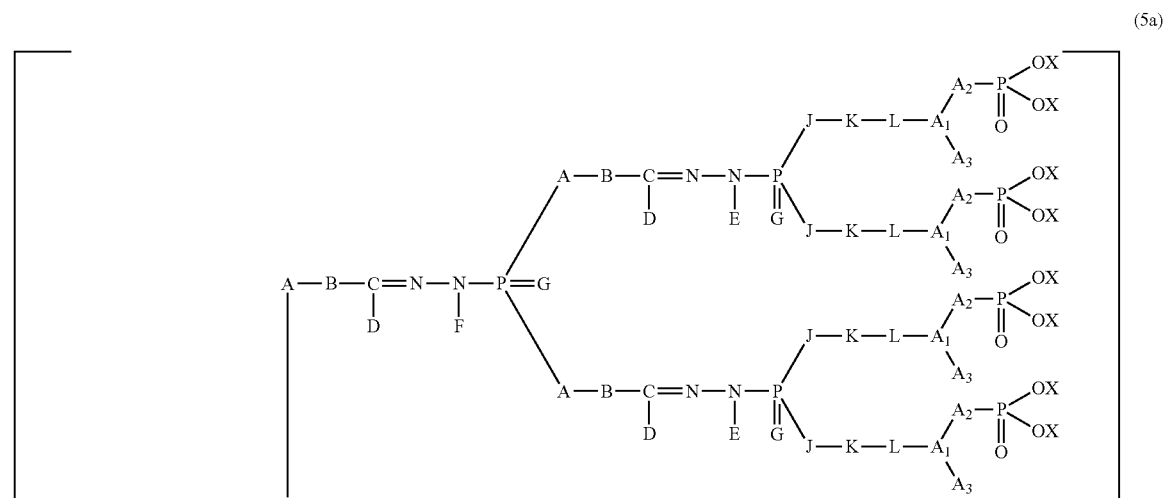

-continued

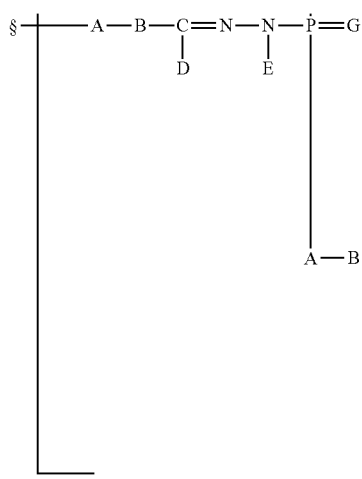
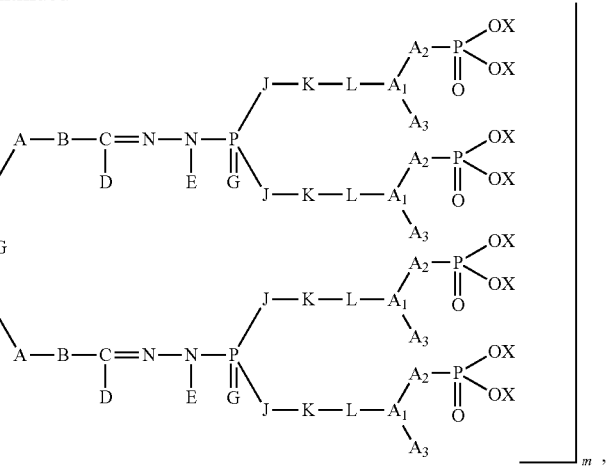

and wherein:

the central core § is chosen from the following groups:

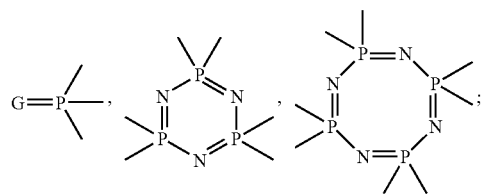

m represents 3, 6 or 8;

the generation chain corresponds to the formula:

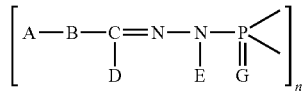

where

A represents an oxygen, sulphur, phosphorus atom or an —NR— group,

B represents an aryl group of 6 to 24 carbon atoms, a heteroaryl group of 1 to 24 carbon atoms, an alkyl group of 1 to 16 carbon atoms, each being able to be optionally substituted by a halogen atom or an —NO$_2$, —NRR', —CN, —CF$_3$, —OH group, an alkyl group of 1 to 16 carbon atoms, an aryl group of 6 to 24 carbon atoms, an aralkyl group of 7 to 16 carbon atoms, D represents a hydrogen atom, an alkyl group of 1 to 16 carbon atoms, an alkoxy group of 1 to 16 carbon atoms, an aryl group of 6 to 24 carbon atoms, an aralkyl group of 7 to 16 carbon atoms, each being able to be optionally substituted by a halogen atom or an —NO$_2$, —NRR', —CN, —CF$_3$, —OH group, an alkyl group of 1 to 16 carbon atoms, an aryl group of 6 to 24 carbon atoms, an aralkyl group of 7 to 16 carbon atoms, E represents a hydrogen atom, an alkyl group of 1 to 16 carbon atoms, an alkoxy group of 1 to 16 carbon atoms, an aryl group of 6 to 24 carbon atoms, an aralkyl group of 7 to 16 carbon atoms, each being able to be optionally substituted by a halogen atom or an —NO$_2$, —NRR', —CN, —CF$_3$, —OH group, an alkyl group of 1 to 16 carbon atoms, an aryl group of 6 to 24 carbon atoms, an aralkyl group of 7 to 16 carbon atoms, and G represents an oxygen, nitrogen, sulphur, selenium, tellurium atom or an =NR group, R and R' representing independently of each other H or an alkyl group of 1 to 16 carbon atoms, an aryl group of 6 to 24 carbon atoms, or an aralkyl group of 7 to 16 carbon atoms;

the intermediate chain corresponds to the formula:

where

J represents an oxygen, sulphur atom, or an —NR— group,

K represents an aryl group of 6 to 24 carbon atoms, a heteroaryl group of 1 to 24 carbon atoms, the heteroelement being selected from the group consisting of oxygen, nitrogen and sulphur, an alkyl group of 1 to 16 carbon atoms, each being able to be optionally substituted by a halogen atom or an —NO$_2$, —NRR', —CN, —CF$_3$, —OH group, an alkyl group of 1 to 16 carbon atoms, an aryl group of 6 to 24 carbon atoms, an aralkyl group of 7 to 16 carbon atoms, and L represents a linear, branched or cyclic hydrocarbon chain with 0 to 10 members, optionally containing one or more double or triple bonds, each of said members being able to be optionally a heteroatom, said heteroatom being selected from the group consisting of oxygen, sulphur, nitrogen, phosphorus and silicon, each member being able to be optionally substituted by at least one substituent selected from the group consisting of an alkyl group of 1 to 16 carbon atoms, a halogen, an oxygen atom, —NO$_2$, —NRR', —CN, —CF$_3$, —OH, an alkoxy group of 1 to 16 carbon atoms, an aryl group of 6 to 24 carbon atoms, and an aralkyl group of 7 to 16 carbon atoms, R and R' representing independently of each other H or an alkyl group of 1 to 16 carbon atoms, an aryl group of 6 to 24 carbon atoms, or an aralkyl group of 7 to 16 carbon atoms; and the terminal group corresponds to the formula:

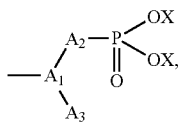

where $A_1$, $A_3$ and X have been defined previously, each X being identical or different.

10. The method according to claim 9, wherein the dendrimer corresponds to the general formula (1a) and $A_3$ represents:

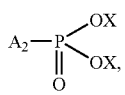

said general formula (1a) then corresponding to the following general formula (1):

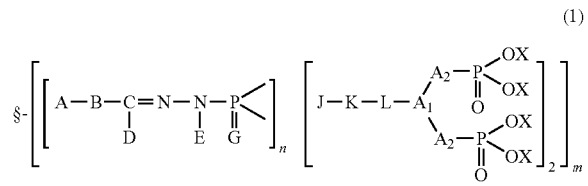

§, A, B, C, D, E, G, J, K, L, $A_1$, $A_2$, X, m and n being as previously defined.

11. The method according to claim 10, wherein the dendrimer corresponds to the general formula (1) of structure PMMH, and § represents

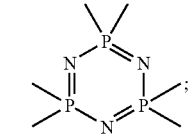

m represents 6;
n represents 0, 1, or 2;
A represents an oxygen atom;
B represents a benzene group;
D represents hydrogen;
E represents a methyl group;
G represents a sulphur atom;
J represents an oxygen atom;
K represents a benzene group;
L represents a non-substituted linear saturated hydrocarbon chain with two carbon atoms;
$A_1$ represents a nitrogen atom;
$A_2$ represents a $CH_2$ group; and
X represents a methyl group, or a hydrogen or sodium atom;
said dendrimer being designated GCn, n being defined above.

12. The method according to claim 2, wherein the dendrimers are selected from the group consisting of compounds of the following formulae:

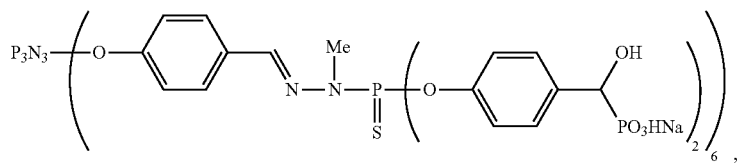

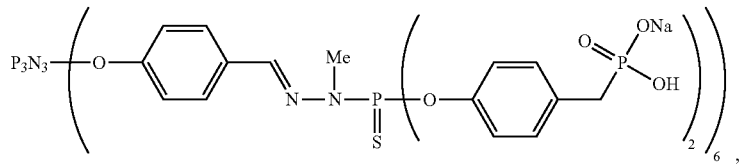

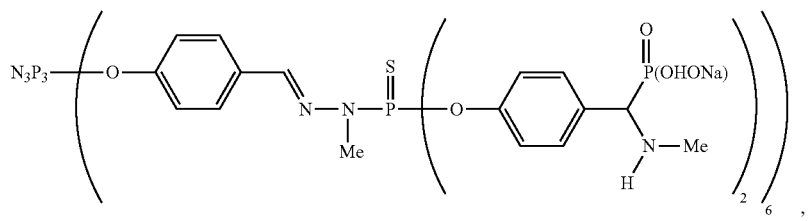

-continued
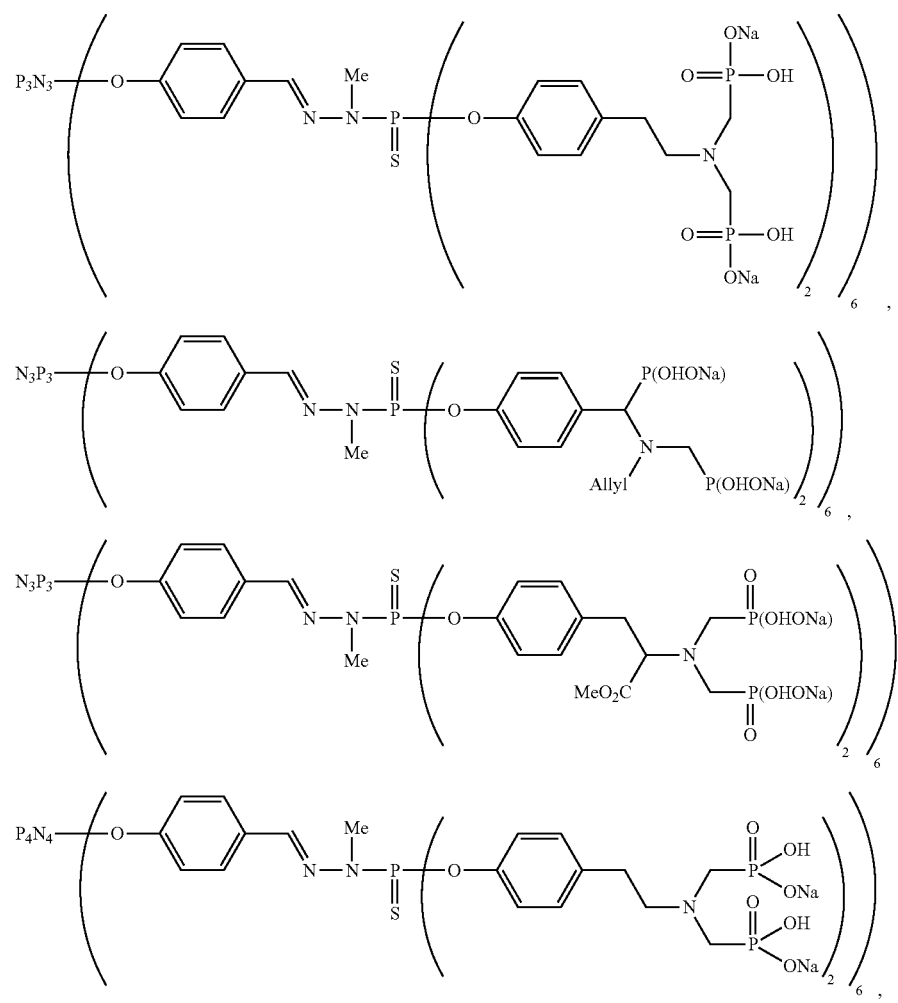
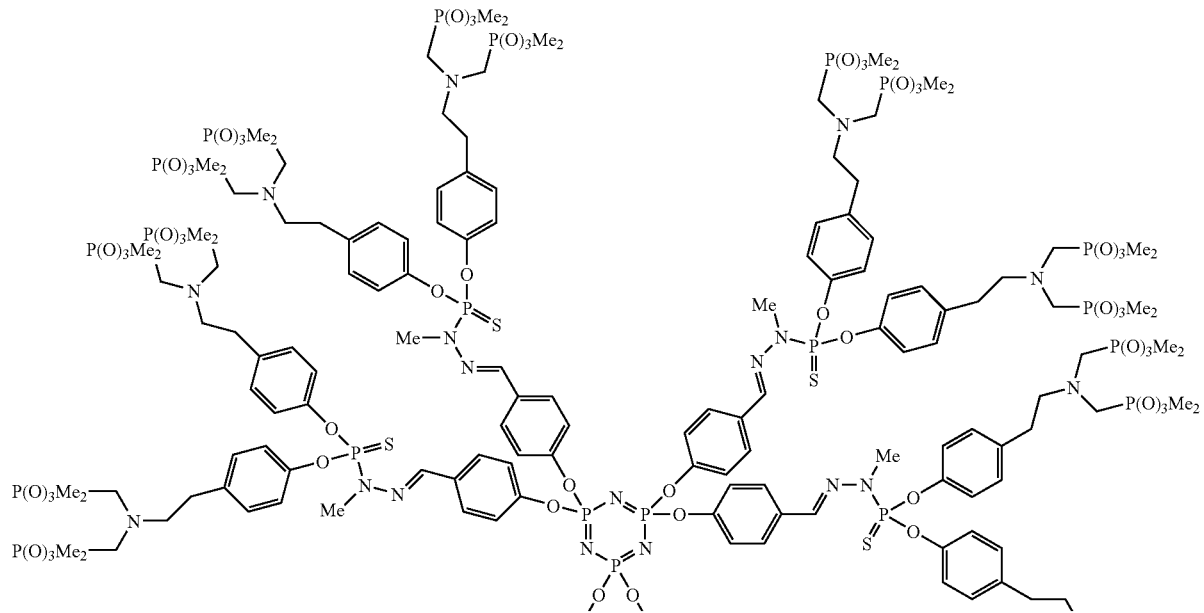

411 412
-continued
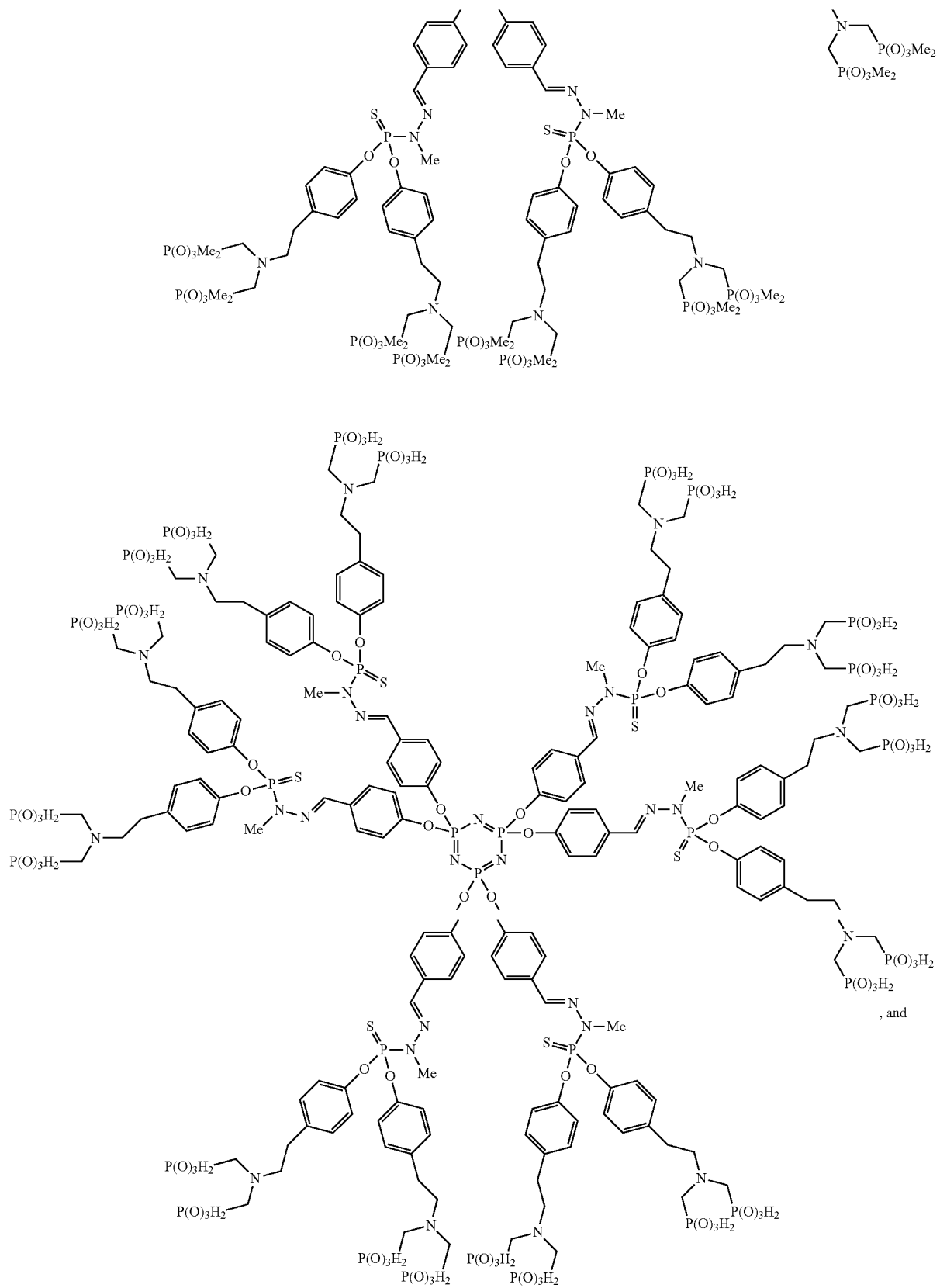
, and

-continued

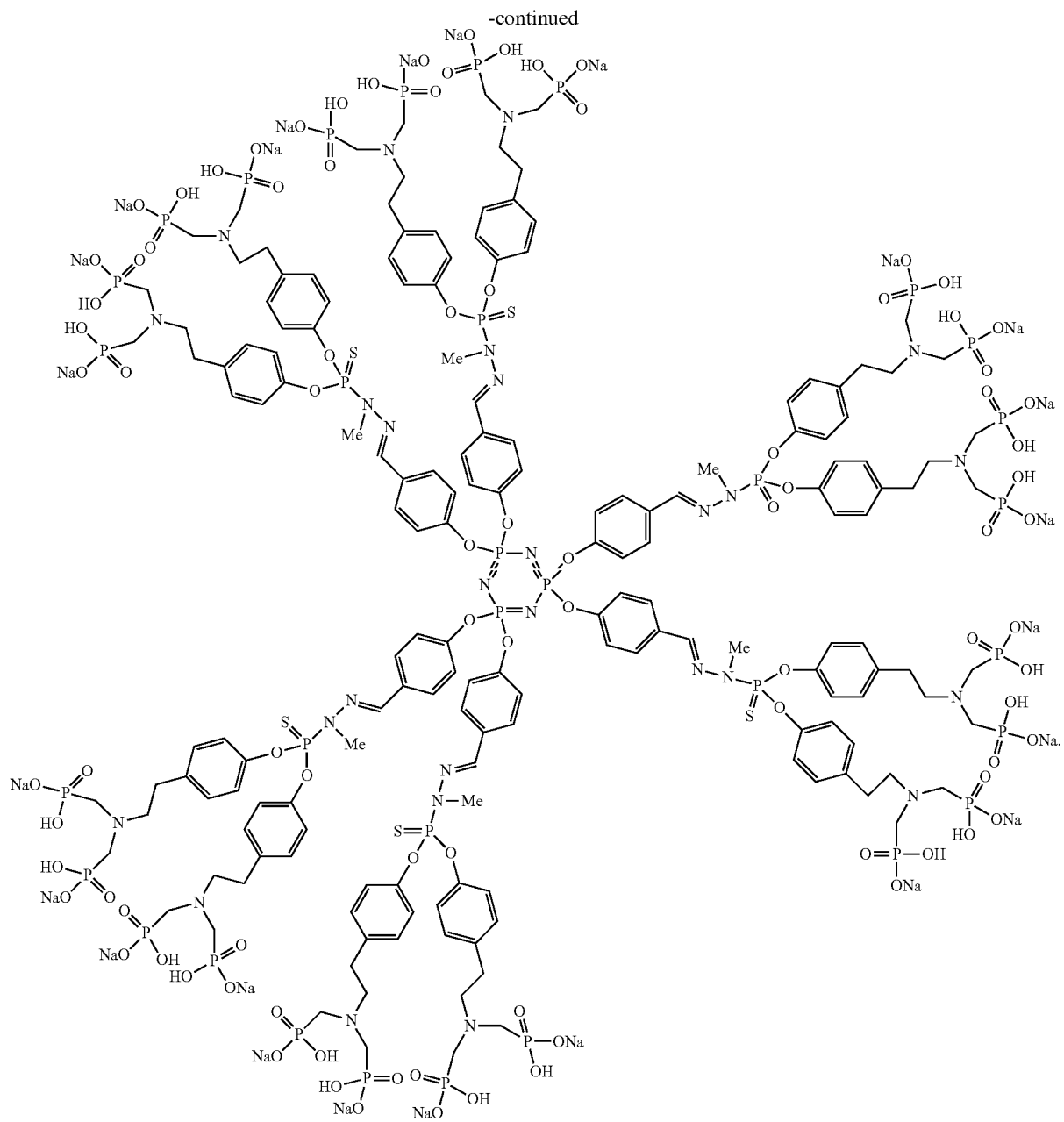

50

13. The method according to claim 1, wherein the peripheral blood mononuclear cells are of a lymphoid line expressing a receptor NKG2D and are derived from NK cells, CD8+ αβ T lymphocytes or γδ lymphocytes.

14. The method according to claim 1, wherein the peripheral blood mononuclear cells in culture are activated by the dendrimers with monophosphonic or bisphosphonic terminations, the activation of the cells corresponding to:
- an increase in size of the activated cells compared with non-activated cells, and/or
- a reduction in expression of MHC class I and class II molecules, or of a molecule CD14 compared with non-activated cells, and/or
- an increase in nuclear translocation of a factor NFκB.

15. The method according to claim 14, wherein the peripheral blood mononuclear cells in culture exhibit reduced apoptosis compared with cells cultured in the absence of dendrimers with monophosphonic or bisphosphonic terminations.

16. The method according to claim 1, wherein the dendrimers have bisphosphonic terminations.

17. The method according to claim 16, wherein the terminations consist of bisphosphonic terminations.

18. The method according to claim 16, wherein X represents H, alkyl comprising 1-16 carbon atoms, aryl comprising 6-24 carbon atoms, araalkyl comprising 7-24 carbon atoms, or alkylaryl comprising 7-24 carbon atoms.

* * * * *